US007825233B2

(12) United States Patent
Steward et al.

(10) Patent No.: US 7,825,233 B2
(45) Date of Patent: Nov. 2, 2010

(54) OPTIMIZING EXPRESSION OF ACTIVE BOTULINUM TOXIN TYPE E

(75) Inventors: Lance E. Steward, Irvine, CA (US); Marcella A. Gilmore, Santa Ana, CA (US); Ester G. Fernandez-Salas, Fullerton, CA (US); Shengwen Li, Irvine, CA (US); Ronald G. Miller, Pueblo West, CO (US); Kei Roger Aoki, Coto de Caza, CA (US)

(73) Assignee: Allergan, Inc., Irvine, CA (US)

( * ) Notice: Subject to any disclaimer, the term of this patent is extended or adjusted under 35 U.S.C. 154(b) by 484 days.

(21) Appl. No.: 11/568,834

(22) PCT Filed: Jun. 9, 2005

(86) PCT No.: PCT/US2005/020578

§ 371 (c)(1), (2), (4) Date: Jan. 11, 2007

(87) PCT Pub. No.: WO2005/011966

PCT Pub. Date: Feb. 2, 2006

(65) Prior Publication Data

US 2008/0138893 A1 Jun. 12, 2008

Related U.S. Application Data

(60) Provisional application No. 60/584,378, filed on Jun. 30, 2004, provisional application No. 60/599,132, filed on Aug. 4, 2004.

(51) Int. Cl.
*C12N 5/06* (2006.01)
*C07H 21/04* (2006.01)

(52) U.S. Cl. ...................................... 536/23.7; 435/325

(58) Field of Classification Search ....................... None
See application file for complete search history.

(56) References Cited

U.S. PATENT DOCUMENTS

| | | | |
|---|---|---|---|
| 6,114,148 A | 9/2000 | Seed et al. | |
| 6,121,014 A | 9/2000 | Koziel et al. | |
| 6,153,377 A | 11/2000 | Devare et al. | |
| 6,214,602 B1 | 4/2001 | Zdanovsky | |
| 6,218,188 B1 | 4/2001 | Cardineau et al. | |
| 6,277,622 B1 | 8/2001 | Weiss | |
| 6,319,505 B1 * | 11/2001 | Aoki et al. | 424/236.1 |
| 6,399,857 B1 | 6/2002 | Kloti | |
| 6,538,127 B1 | 3/2003 | Devare et al. | |
| 6,733,994 B2 | 5/2004 | Weiner et al. | |
| 7,037,680 B2 | 5/2006 | Smith et al. | |
| 2003/0009025 A1 | 1/2003 | Smith et al. | |
| 2004/0092009 A1 | 5/2004 | Draghia-Akli et al. | |

FOREIGN PATENT DOCUMENTS

| | | |
|---|---|---|
| WO | WO 00/12728 | 3/2000 |
| WO | WO 00/67700 | 11/2000 |
| WO | WO 02/36758 | 5/2002 |
| WO | WO 02/089834 | 11/2002 |

OTHER PUBLICATIONS

Bork (Genome Research, 2000,10:398-400).*
Bowie et al (Science, 1990, 257:1306-1310).*
Smith et al, "*Light Chain of Botulinum a Neurotoxin Expressed as an Inclusion Body from a Synthetic Gene is Catalytically and Functionally Active*", 19 J. Protein Chem. 475-487, (2000).
Byrne et al, "*Fermentation, Purification, and Efficacy of a Recombinant Vaccine Candidate Against Botulinum Neurotoxin Type F from Pichia pastoris*", 18 Protein Expr. Purif. 327-337, (2000).
Karlin et al, "Codon usages in different gene classes of the *Escherichia coli* genome", Molecular Microbilogy (1998) 29(6), 1341-1355.
Lin et al, The use of synthetic genes for the expression of ciliate proteins in heterologous systems, Gene 288 (2002) 85-94.
Madzak et al, "Heterologous protein expression and secretion in the non-conventional yeast Yarowia lipolytica: a review", Journal of Biotechnology 109 (2004) 63-81.
Makoff et al., *Expression of Tetanus Toxin Fragment C in E. coli: High Level Expression by Removing Rare Codons*, 17 Nucleic Acids Res. 10191-10202, (1989).
Pellizzari et al, "Tetanus and botulinum neurotoxins: mechanism of action and therapeutic uses", BiolSci Feb. 28, 1999; 354 (1381):259-268.
Potter et al., *Production and Purification of the Heavy-Chain Fragment C of Botulinum Neurotoxin, Serotype A, Expressed in the Methylotrophic Yeast Pichia pastoris*, 19 Protein Expr. Purif. 393-402, (2000).
Potter et al., *Production and Purification of the Heavy-Chain Fragment C of Botulinum Neurotoxin, Serotype B, Expressed in the Methylotrophic Yeast Pichia pastoris*, 13 Protein Expr. Purif. 357-365, (1998).
Leonard A. Smith, *Development of Recombinant Vaccines for Botulinum Neurotoxin*, 36 TOXICON 1539-1548, (1998).
Chen et al, "Sequencing the Botulinum Neurotoxin Gene and Related Genes in Clostridium botulinum Type E Strains Reveals . . ." Journal of Bacteriology, vol. 189, No. 23, p. 8643-8650, Dec. 2007.

* cited by examiner

*Primary Examiner*—Robert A Zeman
(74) *Attorney, Agent, or Firm*—Dean G. Stathakis; Debra Condino

(57) ABSTRACT

Nucleic acid molecules that comprise modified open reading frames providing increased expression of the encoded active BoNT/E in a heterologous cell, expression constructs and cells comprising such nucleic acid molecules and methods useful for expressing the encoding active BoNT/E from such nucleic acid molecules, expression constructs and cells.

5 Claims, 17 Drawing Sheets

OPTIMIZING EXPRESSION OF ACTIVE BOTULINUM TOXIN TYPE E

This is a national stage application under 35 U.S.C. §371 of PCT application PCT/US 2005/020578, filed 9 Jun., 2005 which claims priority pursuant to 35 U.S.C. §119(e) to provisional patent application Ser. No. 60/584,378 filed Jun. 30, 2004 and provisional patent application Ser. No. 60/599,132 filed Aug. 4, 2004, which are all hereby incorporated by reference in their entirety.

All of the publications cited in this application are hereby incorporated by reference in their entirety. All GeneBank sequence listings cited this application, as identified by their GenBank accession numbers, are available from the National Center for Biotechnological Information and are all hereby incorporated by reference in their entirety. All URL addresses cited in this application are hereby incorporated by reference in their entirety.

The myorelaxant properties of Botulinum neurotoxins (BoNTs), such as, e.g., BoNT/A and BoNT/E, are being exploited in a wide variety of therapeutic and cosmetic applications, see e.g., William J. Lipham, Cosmetic and Clinical Applications of Botulinum Toxin (Slack, Inc., 2004). As an example, BOTOX® is currently approved in one or more countries for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder. In addition, BoNTs therapies, including BoNT/A and BoNT/E therapies, are proposed for treating neuromuscular disorders, see e.g., Kei Roger Aoki et al., Method for Treating Neuromuscular Disorders and Conditions with Botulinum Toxin Types A and B, U.S. Pat. No. 6,872,397 (Mar. 29, 2005); Rhett M. Schiffman, Methods for Treating Uterine Disorders, U.S. Patent Publication No. 2004/0175399 (Sep. 9, 2004); and Richard L. Barron, Methods for Treating Ulcers and Gastroesophageal Reflux Disease, U.S. Patent Publication No. 2004/0086531 (May 7, 2004); and Kei Roger Aoki, et al., *Method for Treating Dystonia with Botulinum Toxin C to G*, U.S. Pat. No. 6,319,505 (Nov. 20, 2001); eye disorders, see e.g., Eric R. First, Methods and Compositions for Treating Eye Disorders, U.S. Patent Publication No. 2004/0234532 (Nov. 25, 2004); Kei Roger Aoki et al., Botulinum Toxin Treatment for Blepharospasm, U.S. Patent Publication No. 2004/0151740 (Aug. 5, 2004); and Kei Roger Aoki et al., Botulinum Toxin Treatment for Strabismus, U.S. Patent Publication No. 2004/0126396 (Jul. 1, 2004); pain, see e.g., Kei Roger Aoki et al., Pain Treatment by Peripheral Administration of a Neurotoxin, U.S. Pat. No. 6,869,610 (Mar. 22, 2005); Stephen Donovan, Clostridial Toxin Derivatives and Methods to Treat Pain, U.S. Pat. No. 6,641,820 (Nov. 4, 2003); Kei Roger Aoki, et al., *Method for Treating Pain by Peripheral Administration of a Neurotoxin*, U.S. Pat. No. 6,464,986 (Oct. 15, 2002); Kei Roger Aoki and Minglei Cui, Methods for Treating Pain, U.S. Pat. No. 6,113,915 (Sep. 5, 2000); Martin Voet, Botulinum Toxin Therapy for Fibromyalgia, U.S. Patent Publication No. 2004/0062776 (Apr. 1, 2004); and Kei Roger Aoki et al., Botulinum Toxin Therapy for Lower Back Pain, U.S. Patent Publication No. 2004/0037852 (Feb. 26, 2004); muscle injuries, see e.g., Gregory F. Brooks, *Methods for Treating Muscle Injuries*, U.S. Pat. No. 6,423,319 (Jul. 23, 2002); headache, see e.g., Martin Voet, Methods for Treating Sinus Headache, U.S. Pat. No. 6,838,434 (Jan. 4, 2005); Kei Roger Aoki et al., Methods for Treating Tension Headache, U.S. Pat. No. 6,776,992 (Aug. 17, 2004); and Kei Roger Aoki et al., Method for Treating Headache, U.S. Pat. No. 6,458,365 (Oct. 1, 2002); cardiovascular diseases, see e.g., Gregory F. Brooks and Stephen Donovan, Methods for Treating Cardiovascular Diseases with Botulinum Toxin, U.S. Pat. No. 6,767,544 (Jul. 27, 2004); neurological disorders, see e.g., Stephen Donovan, Parkinson's Disease Treatment, U.S. Pat. No. 6,620,415 (Sep. 16, 2003); and Stephen Donovan, Method for Treating Parkinson's Disease with a Botulinum Toxin, U.S. Pat. No. 6,306,403 (Oct. 23, 2001); neuropsychiatric disorders, see e.g., Stephen Donovan, Botulinum toxin therapy for neuropsychiatric disorders, U.S. Patent Publication No. 2004/0180061 (Sep. 16, 2004); and Steven Donovan, Therapeutic Treatments for Neuropsychiatric Disorders, U.S. Patent Publication No. 2003/0211121 (Nov. 13, 2003); endocrine disorders, see e.g., Stephen Donovan, Method for Treating Endocrine Disorders, U.S. Pat. No. 6,827,931 (Dec. 7, 2004); Stephen Donovan, Method for Treating Thyroid Disorders with a Botulinum Toxin, U.S. Pat. No. 6,740,321 (May 25, 2004); Kei Roger Aoki et al., Method for Treating a Cholinergic Influenced Sweat Gland, U.S. Pat. No. 6,683,049 (Jan. 27, 2004); Stephen Donovan, Neurotoxin Therapy for Diabetes, U.S. Pat. No. 6,416,765 (Jul. 9, 2002); Stephen Donovan, Methods for Treating Diabetes, U.S. Pat. No. 6,337,075 (Jan. 8, 2002); Stephen Donovan, Method for Treating a Pancreatic Disorder with a Neurotoxin, U.S. Pat. No. 6,261,572 (Jul. 17, 2001); Stephen Donovan, Methods for Treating Pancreatic Disorders, U.S. Pat. No. 6,143,306 (Nov. 7, 2000); cancers, see e.g., Stephen Donovan, Methods for Treating Bone Tumors, U.S. Pat. No. 6,565,870 (May 20, 2003); Stephen Donovan, Method for Treating Cancer with a Neurotoxin to Improve Patient Function, U.S. Pat. No. 6,368,605 (Apr. 9, 2002); Stephen Donovan, Method for Treating Cancer with a Neurotoxin, U.S. Pat. No. 6,139,845 (Oct. 31, 2000); and Mitchell F. Brin and Stephen Donovan, Methods for treating diverse cancers, U.S. Patent Publication No. 2005/0031648 (Feb. 10, 2005); otic disorders, see e.g., Stephen Donovan, Neurotoxin therapy for inner ear disorders, U.S. Pat. No. 6,358,926 (Mar. 19, 2002); and Stephen Donovan, Method for Treating Otic Disorders, U.S. Pat. No. 6,265,379 (Jul. 24, 2001); as well as other disorders, see e.g., Stephen Donovan, Use of a Clostridial Toxin to Reduce Appetite, U.S. Patent Publication No. 2004/40253274 (Dec. 16, 2004); and Howard I. Katz and Andrew M. Blumenfeld, Botulinum Toxin Dental Therapies and Procedures, U.S. Patent Publication No. 2004/0115139 (Jun. 17, 2004); Kei Roger Aoki, et al., *Treatment of Neuromuscular Disorders and Conditions with Different Botulinum*, U.S. Patent Publication No. 2002/0010138 (Jan. 24, 2002); and Kei Roger Aoki, et al., *Use of Botulinum Toxins for Treating Various Disorders and Conditions and Associated Pain*, U.S. Patent Publication No. 2004/0013692 (Jan. 22, 2004). In addition, the expected use of BoNTs, such as, e.g., BoNT/A and BoNT/E, in both therapeutic and cosmetic treatments of humans is anticipated to expand to an ever widening range of diseases and aliments that can benefit from the myorelaxant properties of these toxins.

The increasing use of BoNTs therapies, such as, e.g., BoNT/A and BoNT/E, in treating a wider range of human afflictions necessitates increasing the efficiency with which these toxins are produced. However, meeting the needs for this ever increasing demand for such BoNT treatments may become difficult. One outstanding problem is that methods previously described to express BoNTs using heterologous organisms have failed to achieve optimal levels of BoNTs in commercial quantities. This inefficiency is a problem not only because the amount of BoNTs, such as, e.g., BoNT/A and BoNT/E, anticipated for future therapies is increasing, but also because this inefficiency leads to higher overall production costs. Furthermore, this difficulty is exacerbated for BoNTs that require in vitro activation by an exogenous protease, such as, e.g., BoNT/E, since the loss of toxin associated with the activation procedure require even larger amounts of starting material. Therefore, the poor yields using previously described methods is a significant obstacle to the overall commercial production of these BoNTs and is thus a major problem since active forms of these toxins are needed for scientific, therapeutic and cosmetic applications.

BRIEF DESCRIPTION OF THE DRAWINGS

FIG. 1 shows a schematic of the current paradigm of neurotransmitter release and Clostridial toxin intoxication in a central and peripheral neuron.

FIG. 6 shows IMAC purified BoNT/E expressed from modified open reading frames.

DETAILED DESCRIPTION

Figure 1A:
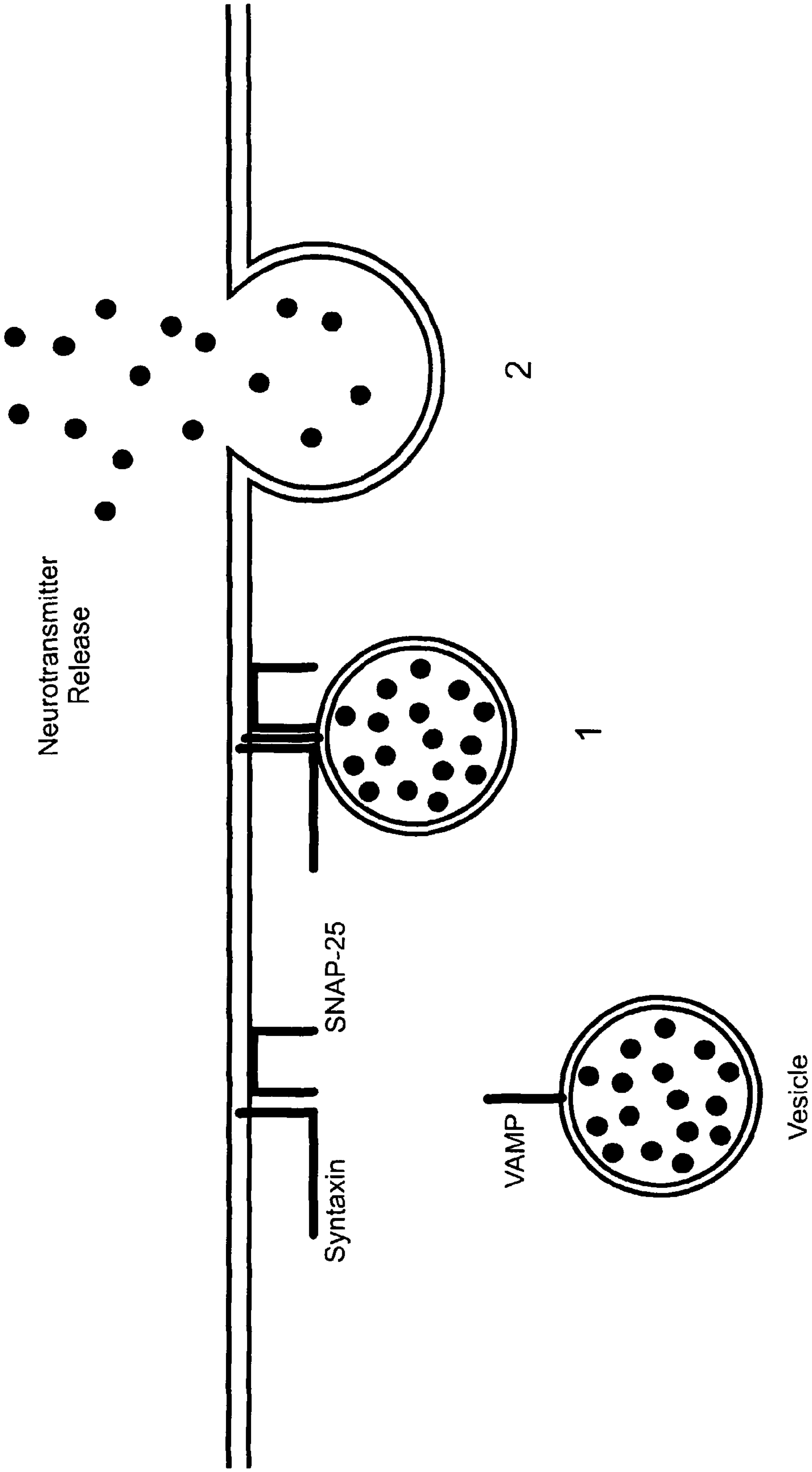
FIG. 1*a* shows a schematic for the neurotransmitter release mechanism of a central and peripheral neuron. The release process can be described as comprising two steps: 1) vescle docking, where the vescicle-bound SNARE protein of a vescicle containing neurotransmitter molecules associates with the membrane-bound SNARE proteins located at the plasma membrane; and 2) neurotransmitter release, where the vesicle fuses with the plasma membrane and the neurotransmitter molecules are exocytosed.

The present invention recognizes the need for the high-level, commercial production of active clostridial toxins using heterologous organisms. All clostridial toxins useful for scientific, therapeutic and cosmetic applications are envisioned including, without limitation, BoNTs, such as, e.g., BoNT/A, BoNT/B, BoNT/C, BoNT/D, BoNT/E, BoNT/F and BoNT/G, and TeNT. Furthermore, BoNTs that require in vitro activation, such as e.g., BoNT/E and BoNT/G, can also benefit from the present invention. High-level production of a clostridial toxin is achieved by using modified nucleic acid molecules which allows for increased expression of the encoded toxin in a heterologous cell and thus higher protein yields. In aspects of the present invention, nucleic acid molecules encoding a clostridial toxin comprise modified open reading frames designed to 1) contain codons typically present in the open reading frames of native nucleic acid molecules found in the heterologous cell selected to express that molecule; 2) contain a G+C content that more closely matches the average G+C content of open reading frames of native nucleic acid molecules found in the heterologous cell selected to express that molecule; 3) reduce polymononucleotide regions found within the open reading frame encoding an active clostridial toxin; and/or 4) eliminate internal regulatory or structural sites found within the open reading frame encoding an active clostridial toxin. Because a large number of production factors can influence the selection of a specific heterologous cell, nucleic acid molecules disclosed in the present specification are directed toward a wide range of prokaryotic and eukaryotic cell including, without limitation, bacteria strains, yeast strains, plant cells and cell lines derived from plants, insect cells and cell lines derived from insects and mammalian cells and cell lines derived from mammals. Aspects of the present invention also provide for expression constructs and cell compositions useful for expressing modified nucleic acid molecules disclosed in the present specification. In addition, aspects of the present invention provide methods for producing Clostridial toxins using the disclosed nucleic acid molecules.

Aspects of the present invention provide nucleic acid molecules comprising a modified open reading frame providing increased expression of the encoded active BoNT/E. The modified open reading frame includes at least one nucleotide change as compared to the unmodified open reading frame encoding the same active BoNT/E. Increased active BoNT/E expression from a modified open reading frame in a heterologous cell is determined by comparing the expression level from an unmodified open reading frame encoding the same active BoNT/E from an otherwise identical nucleic acid molecule in the same type of heterologous cell. A nucleotide change may alter a synonymous codon within the open reading frame in order to agree with the endogenous codon usage found in the heterologous cell selected to express the molecule disclosed in the present specification. Additionally, a nucleotide change may alter the G+C content within the open reading frame to better match the average G+C content of open reading frames found in endogenous nucleic acid molecules present in the heterologous cell. A nucleotide change may also alter a polymononucleotide region or an internal regulatory or structural site found within the native nucleic acid molecule. A wide variety of modified nucleic acid molecules are envisioned including, without limitation, molecules comprising a modified open reading frame providing increased expression of the encoded active BoNT/E in a prokaryotic cell; molecules comprising a modified open reading frame providing increased expression of the encoded active BoNT/E in a yeast cell; molecules comprising a modified open reading frame providing increased expression of the encoded active BoNT/E in an insect cell; and molecules comprising a modified open reading frame providing increased expression of the encoded active BoNT/E in a mammalian cell.

Other aspects of the present invention provide expression constructs comprising a nucleic acid molecule disclosed in the present specification, operably-linked to an expression vector useful for expressing the nucleic acid molecule in a heterologous cell. A wide variety of expression vectors are envisioned, including, without limitation, a prokaryotic expression vector useful for expressing a nucleic acid molecule comprising a modified open reading frame providing increased expression of the encoded active BoNT/E in a prokaryotic cell; a yeast expression vector useful for expressing a nucleic acid molecule comprising a modified open reading frame providing increased expression of the encoded active BoNT/E in a yeast cell; an insect expression vector useful for expressing a nucleic acid molecule comprising a modified open reading frame providing increased expression of the encoded active BoNT/E in an insect cell; a mammalian expression vector useful for expressing a nucleic acid molecule comprising a modified open reading frame providing increased expression of the encoded active BoNT/E in a mammalian cell.

Aspects of the present invention further provide heterologous cells comprising an expression construct disclosed in the present specification. It is envisioned that a cell can include, without limitation, a prokaryotic cell containing a prokaryotic expression construct useful for expressing a nucleic acid molecule comprising a modified open reading frame providing increased expression of the encoded active BoNT/E in a prokaryotic cell; a yeast cell containing a yeast expression construct useful for expressing a nucleic acid molecule comprising a modified open reading frame providing increased expression of the encoded active BoNT/E in a yeast cell; an insect cell containing an insect expression construct useful for expressing a nucleic acid molecule comprising a modified open reading frame providing increased expression of the encoded active BoNT/E in an insect cell; and a mammalian cell containing a mammalian expression construct useful for expressing a nucleic acid molecule comprising a modified open reading frame providing increased expression of the encoded active BoNT/E in a mammalian cell.

Other aspects of the present invention provide methods of producing an active BoNT/E comprising the step of expressing a nucleic acid molecule in a heterologous cell, the nucleic acid molecule comprising a modified open reading frame encoding the active BoNT/E. Aspects of these methods use nucleic acid molecules, expression constructs and cells disclosed in the present specification. It is envisioned that both cell-free and cell-based expression systems can be used to produce an active BoNT/E disclosed in the present specification according to this method.

Aspects of the present invention provide, in part, nucleic acid molecules comprising a modified open reading frame encoding active BoNT/E in a heterologous cell. As used herein, the term "open reading frame" is synonymous with "ORF" and means any nucleotide sequence that is potentially able to encode a protein, or a portion of a protein. An open reading frame usually begins with a start codon (represented as, e.g. AUG for an RNA molecule and ATG in a DNA molecule in the standard code) and is read in codon-triplets until the frame ends with a STOP codon (represented as, e.g. UAA, UGA or UAG for an RNA molecule and TAA, TGA or TAG in a DNA molecule in the standard code). As used herein, the term "codon" means a sequence of three nucleotides in a nucleic acid molecule that specifies a particular amino acid during protein synthesis; also called a triplet or codon-triplet. For example, of the 64 possible codons in the standard genetic code, two codons, GAA and GAG encode the amino acid Glutamine whereas the codons AAA and AAG specify the amino acid Lysine. In the standard genetic code three codons are stop codons, which do not specify an amino acid. As used herein, the term "synonymous codon" means any and all of the codons that code for a single amino acid. Except for Methionine (Met) and Tryptophan (Trp), amino acids are coded by two to six synonymous codons (see e.g., Table 1). For example, in the standard genetic code the four synonymous codons that code for the amino acid Alanine are GCA, GCC, GCG and GCU, the two synonymous codons that specify Glutamine are GAA and GAG and the two synonymous codons that encode Lysine are AAA and AAG (for other non-limiting examples see Table 1).

Thus in an embodiment, a modified open reading frame that encodes an active BoNT/E is changed by altering the nucleotide sequence of native *Clostridia botulinum* codons to better match the synonymous codons used by the heterologous cell selected to express nucleic acid molecules disclosed in the present specification. The *C. botulinum* strain that expresses BoNT/E exhibits a specific preference or bias for one synonymous codon over the others and there is a direct correlation between this *C. botulinum* strain-specific codon usage and the cellular concentration of the corresponding isoacceptor tRNA. This unequal presence of synonymous codons in a known or predicted open reading frame in an organism-, cell-, or functional class-specific manner is a phenomenon called codon bias or codon preference. Thus, it can be said that a heterologous cell has a bias for one synonymous codon over another synonymous codon, or that a heterologous cell prefers one synonymous codon over another synonymous codon. In addition, the synonymous codon to which the most abundant isoacceptor tRNA equates is often different between organisms, and, in some cases, between cells comprising different tissue types of the same organism, or between functional classes of proteins of the same organism, e.g., proteins expressed during exponential growth phase of a bacterium relative to proteins expressed during stationary growth phase of a bacterium. Different codon bias may also occur through the length of the open reading frame, such as, e.g., codons from the 5' third of the open reading frame may use different codons relative the the remaining 3' two-thirds of the same open reading frame. For example, as mentioned above, GCA, GCC, GCG and GCU are the four synonymous codons that encode Alanine (Ala). While the most abundant Ala isoacceptor representative in *C. botulinum* recognizes the GCA codon, the bacterium *Escherichia coli* recognizes GCG, the yeast *Pichia pastoris* recognizes GCT and most multicellular eukaryotes appear to recognizes GCC (see e.g., Table 1). Thus, certain codons that are normally used in the *Clostridia botulinum* strain that expresses BoNT/E may be rarely present in heterologous cells commonly used in the commercial expression of BoNT/E. Because these heterologous organisms do not produce the corresponding isoacceptor tRNAs at a concentration sufficient to support high-level BoNT/E expression, optimal protein yields are not achieved. Therefore, a modified open reading frame comprising nucleotide changes that increase the number of synonymous codons preferred by a heterologous cell will provide increased expression of the encoded active BoNT/E as compared to an unmodified open reading frame encoding the same active BoNT/E. A synonymous codon of the open reading frame can be changed by substituting a nucleotide at the third position of a codon with a different nucleotide, while still retaining the identity of the amino acid coded by that codon. As a non-limiting example, a 5'-AAATACTTA-3' (SEQ ID NO: 126) open reading frame encoding the tripeptide $NH_2$-lysine-tyrosine-leucine-COOH can be changed to 5'-AAGTATCTG-3' (SEQ ID NO: 127) and still encode the tripeptide $NH_2$-lysine-tyrosine-leucine-COOH.

Thus, in an aspect of this embodiment, at least one nucleotide change is made to a nucleic acid molecule that substitutes a codon in the open reading frame for a synonymous codon providing increased expression of the encoded active BoNT/E in a heterologous cell. In another aspect of this embodiment, a plurality of nucleotide changes are made to a nucleic acid molecule that substitutes a plurality of codons in the open reading frame for a plurality of synonymous codon providing increased expression of the encoded active BoNT/E in a heterologous cell. Thus, aspects of this embodiment can include a modified open reading frame comprises nucleotide changes that alter, e.g., at least 10 synonymous codons, at least 25 synonymous codons, at least 50 synonymous codons, at least 75 synonymous codons, at least 100 synonymous codons, at least 200 synonymous codons, at least 300 synonymous codons, at least 400 synonymous codons, at least 500 synonymous codons, at least 600 synonymous codons, at least 700 synonymous codons, at least 800 synonymous codons, at least 900 synonymous codons, at least 1000 synonymous codons, at least 1100 synonymous codons or at least 1200 synonymous codons. In other aspects of this embodiment a modified open reading frame comprises nucleotide changes that alter, e.g., at most 10 synonymous codons, at most 25 synonymous codons, at most 50 synonymous codons, at most 75 synonymous codons, at most 100 synonymous codons, at most 200 synonymous codons, at most 300 synonymous codons, at most 400 synonymous codons, at most 500 synonymous codons, at most 600 synonymous codons, at most 700 synonymous codons, at most 800 synonymous codons, at most 900 synonymous codons, at most 1000 synonymous codons, at most 1100 synonymous codons or at most 1200 synonymous codons.

In another embodiment, a modified open reading frame encoding an active BoNT/E is changed by altering the native Clostridial botulinum G+C content to better match the G+C content found in the heterologous cell selected to express nucleic acid molecules disclosed in the present specification. The average guanine and cytosine content (referred to as the G+C content) of the C. botulinum nucleic acid molecule comprising the open reading frame encoding BoNT/E is approximately 25%. This very low G+C content is in contrast to the approximately 50% G+C content of endogenous nucleic acid molecules encoding proteins found in heterologous cells commonly used in the commercial expression of BoNT/E (see e.g. Table 2). This unequal G+C content in a known or predicted open reading frame in an organism-specific manner is a phenomenon called G+C content bias or G+C content preference. Thus, it can be said that a heterologous cell has a bias for a certain G+C content level as compared to a different G+C content level, or that a heterologous cell prefers a certain G+C content level as compared to a different G+C content. The low G+C content of the open reading frame encoding BoNT/E conversely results in higher regions of adenine and thymidine content (A+T content). Higher A+T content appears to disrupt protein expression in a heterologous cell because these regions may, for example, mimic regulatory signals that could terminate transcriptional or translational expression, form secondary structures that could hinder transcriptional or translational read-through, or comprise repetitive sequences that could promote transcriptional or translational slippage. Thus, the average G+C content of the open reading frame can influence the expression levels of BoNT/E in a heterologous cell. Therefore, a modified open reading frame comprising nucleotide changes that increase the total G+C content to a level preferred by a heterologous cell will provide increased expression of the encoded active BoNT/E as compared to an unmodified open reading frame encoding the same active BoNT/E. The G+C content of the sequence can be increased by substituting an adenine or thymidine at the third position of a codon with a guanine or cytosine, while still retaining the same amino acid coded by that codon. As a non-limiting example, a 5'-AAATATTTA-3' (SEQ ID NO: 128) region in frame with the open reading frame could be changed to 5'-AAGTACCTG-3' (SEQ ID NO: 129) and still code for the tripeptide NH2-lysine-tyrosine-leucine-COOH. Conversely, the G+C content of the sequence can be decreased by substituting a guanine or cytosine at the third position of a codon with an adenine or thymidine, while still retaining the same amino acid coded by that codon. As a non-limiting example, a 5'-AAGTACCTG-3' (SEQ ID NO: 129) open reading frame encoding NH2-lysine-tyrosine-leucine-COOH can be changed to 5'-AAATATTTA-3' (SEQ ID NO: 128) and still encode the tripeptide NH2-lysine-tyrosine-leucine-COOH.

Thus in an aspect of this embodiment, at least one nucleotide change is made to a nucleic acid molecule that alters the G+C content of an open reading frame providing increased expression of the encoded active BoNT/E in a heterologous cell. In another aspect of this embodiment, a plurality of nucleotide substitutions are made to a nucleic acid molecule that alters the G+C content of an open reading frame providing increased expression of the encoded active BoNT/E in a heterologous cell. Therefore, aspects of this embodiment include a modified open reading frame comprising nucleotide changes that increase the total G+C content level to, e.g., at least 30% total G+C content, at least 40% total G+C content, at least 50% total G+C content, at least 60% total G+C content or at least 70% total G+C content. Other aspects of this embodiment include a modified open reading frame comprising nucleotide changes that increase the total G+C content level to, e.g., at most 30% total G+C content, at most 40% total G+C content, at most 50% total G+C content, at most 60% total G+C content or at most 70% total G+C content. Furthermore, such an open reading frame can include altering the total G+C content to any 50 consecutive nucleotides by, e.g., at least 30% total G+C content, at least 40% total G+C content, at least 50% total G+C content, at least 60% total G+C content or at least 25% total G+C content. In other aspects, a modified open reading frame can include altering the total G+C content to any 75 consecutive nucleotides by, e.g., at least 30% total G+C content, at least 40% total G+C content, at least 50% total G+C content, at least 60% total G+C content or at least 25% total G+C content. In yet other aspects, a modified open reading frame can include altering the total G+C content to any 100 consecutive nucleotides by, e.g., at least 30% total G+C content, at least 40% total G+C content, at least 50% total G+C content, at least 60% total G+C content or at least 25% total G+C content.

In another embodiment, a modified open reading frame encoding an active BoNT/E is changed by altering a polymononucleotide region. Polymononucleotide regions (i.e., polyadenine, polyA; polythymidine, polyT; polyguanine, polyG; and polycytosine, polyC) can be detrimental to protein synthesis, especially if these regions are composed of five or more nucleotides. These regions can, for example, 1) contribute to translational staling which reduces the rate of protein synthesis as well as increase the numbers of incomplete/partial peptides synthesized; and 2) participate in translational skipping where the translational apparatus becomes misaligned with the open reading frame thereby producing aberrant proteins that are, e.g., truncated or contain a different amino acid sequence due to a frame shift. A polymononucleotide region can be changed by substituting a nucleotide different from the one contained in the polymononucleotide region at the third position of a codon that interrupts the region while still maintaining the same amino acid coded by the codon. As a non-limiting example, a polyA region containing nine adenosines (i.e., 5'-AAAAAAAAA-3'; SEQ ID NO: 130) encoding the tripeptide $NH_2$-lysine-lysine-lysine-COOH can be eliminated by changing the sequence to 5'-AAGAAGAAG-3' (SEQ ID NO: 131) and still encode the tripeptide $NH_2$-lysine-lysine-lysine-COOH.

Thus in an aspect of this embodiment, at least one nucleotide change may be made to a nucleic acid molecule that alters a polymononucleotide region found in an open reading frame providing increased expression of the encoded active BoNT/E. In another aspect of this embodiment, a plurality of nucleotide changes are made to a nucleic acid molecule that alter a plurality of polymononucleotide regions in an open reading frame providing increased expression of the encoded active BoNT/E. In aspects of this embodiment an open reading frame can include, e.g., at least one nucleotide change, at least two nucleotide changes, at least three nucleotide changes, at least four nucleotide changes, at least five nucleotide changes, at least 10 nucleotide, at least 20 nucleotide, or at least 30 nucleotide changes. In other aspects of this embodiment an open reading frame can include, e.g., at most one nucleotide change, at most two nucleotide changes, at most three nucleotide changes, at most four nucleotide changes, at most five nucleotide changes, at most 10 nucleotide changes, at most 20 nucleotide changes, or at most 30 nucleotide changes.

In another embodiment, a modified open reading frame is changed by altering the nucleotide sequence that alters an internal regulatory or structural site. Internal regulatory or structural sites, include, without limitation, internal or cryptic translational start sites, RNase cleavage sites, out-of-frame stop codons, methylation sites and hairpin-loop structures Internal translational start sites can misdirected the translational apparatus to an incorrect start site, thereby increasing the number of incomplete/partial or abnormal proteins synthesized. The presence of out-of-frame stop codons in the second and third reading frames of an open reading frame can increase translational efficiency and thus protein yields. For example, if the translational apparatus shifts to a reading frame not encoding the desired protein, time, resources and energy will be wasted translating defective proteins. The presence of out-of-frame stop codons reduces the cellular efforts expended in translating these aberrant peptides. RNases are enzymes that cleave RNA molecules, thereby destroying transcripts encoding a protein of interest and reducing yields. Hairpin-loop structures can physically block or disrupt the translational apparatus, thereby preventing protein synthesis or increasing the number of incomplete/partial or abnormal peptides synthesized. An internal regulatory or structural site can be changed by substituting a nucleotide different from the one contained in the consensus sequence, altering the nucleotide identity to the consensus sequence while still maintaining the same amino acid coded by the codon present in the in-frame reading frame.

In an aspect of this embodiment, a modified open reading frame is changed by altering the nucleotide sequence that alters an internal translational start site. An internal translational start site can be changed by substituting a nucleotide different from the one contained in the consensus sequence at the third position of a codon, reducing the nucleotide identity to the consensus sequence while still maintaining the same amino acid coded by the codon. As a non-limiting example, the typical translational start site in the insect *Drosophila melanogaster* is 5'-ACAACCAAAATG-3', (SEQ ID NO: 132) and is present within an open reading frame would encode the peptide $NH_2$-threonine-threonine-lysine-methionine-COOH (SEQ ID NO: 133). This translational start site can be eliminated by changing the sequence to 5'-ACGACTAAGATG-3' (SEQ ID NO: 134) and still encode the peptide $NH_2$-threonine-threonine-lysine-methionine-COOH (SEQ ID NO: 133). In another aspect of this embodiment, at least one nucleotide change may be made to a nucleic acid molecule altering the consensus sequence of an internal translational start site found in an open reading frame providing increased expression of the encoded active BoNT/E. In another aspect of this embodiment, a plurality of nucleotide changes are made to a nucleic acid molecule altering one or more internal translational start sites of an open reading frame providing increased expression of the encoded active BoNT/E. Therefore, aspects of this embodiment an open reading frame can include, e.g., at least one nucleotide change, at least two nucleotide changes, at least three nucleotide changes, at least four nucleotide changes, at least five nucleotide changes or at least 10 nucleotide. In other aspects of this embodiment an open reading frame can include, e.g., at most one nucleotide change, at most two nucleotide changes, at most three nucleotide changes, at most four nucleotide changes, at most five nucleotide changes, or at most 10 nucleotide changes.

In another aspect of this embodiment, a modified open reading frame is changed by altering the nucleotide sequence that alters a RNase cleavage site. A RNase cleavage site can be changed by substituting a nucleotide different from the one contained in the consensus sequence at the third position of a codon, reducing the nucleotide identity to the consensus sequence while still maintaining the same amino acid coded by the codon. As a non-limiting example, the typical RNase E cleavage site is 5'-GGTAATTGC-3' (SEQ ID NO: 135) is present within an open reading frame and encodes the peptide $NH_2$-glycine-isoleucine-cysteine-COOH. This RNase cleavage site can be eliminated by changing the sequence to 5'-GGCAACTGC-3' (SEQ ID NO: 136) and still encode the peptide $NH_2$-threonine-threonine-lysine-methionine-COOH. In another aspect of this embodiment, at least one nucleotide change may be made to a nucleic acid molecule altering the consensus sequence of a RNase cleavage site found in an open reading frame providing increased expression of the encoded active BoNT/E. In another aspect of this embodiment, a plurality of nucleotide changes are made to a nucleic acid molecule altering one or more RNase cleavage sites of an open reading frame providing increased expression of the encoded active BoNT/E. Therefore, aspects of this embodiment an open reading frame can include, e.g., at least one nucleotide change, at least two nucleotide changes, at least three nucleotide changes, at least four nucleotide changes, at least five nucleotide changes or at least 10 nucleotide. In other aspects of this embodiment an open reading frame can include, e.g., at most one nucleotide change, at most two nucleotide changes, at most three nucleotide changes, at most four nucleotide changes, at most five nucleotide changes, or at most 10 nucleotide changes.

In another aspect of this embodiment, a modified open reading frame is changed by altering the nucleotide sequence to add a stop codon to an out-of-frame reading frame. A stop codon in an out-of-frame reading frame can be added by substituting a nucleotide different from the one contained in the consensus sequence of the stop codon, reducing the nucleotide identity to the consensus sequence while still maintaining the same amino acid coded by the in-frame codon. As a non-limiting example, the in-frame open reading frame of the nucleotide sequence 5'-GGCAACTGC-3' (SEQ ID NO: 137) encodes the peptide $NH_2$-glycine-isoleucine-cysteine-COOH. An out of frame stop codon can be added by changing the sequence to 5'-GGTAACTGC-3' (SEQ ID NO: 138) (underlined sequence) and still encode the peptide $NH_2$-glycine-isoleucine-cysteine-COOH. In another aspect of this embodiment, at least one nucleotide change may be made to a nucleic acid molecule adding a stop codon to an out-of-frame reading frame providing increased expression of the encoded active BoNT/E. In another aspect of this embodiment, a plurality of nucleotide changes are made to a nucleic acid molecule adding one or more stop codons to an out-of-frame reading frame providing increased expression of the encoded active BoNT/E. Therefore, aspects of this embodiment an out of frame reading frame can include, e.g., at least one nucleotide change, at least two nucleotide changes, at least three nucleotide changes, at least four nucleotide changes, at least five nucleotide changes, at least 10 nucleotide, at least 20 nucleotide, or at least 30 nucleotide changes. In other aspects of this embodiment an out of frame reading frame can include, e.g., at most one nucleotide change, at most two nucleotide changes, at most three nucleotide changes, at most four nucleotide changes, at most five nucleotide changes, at most 10 nucleotide changes, at most 20 nucleotide changes, or at most 30 nucleotide changes.

In another aspect of this embodiment, a modified open reading frame is changed by altering the nucleotide sequence that alters a hairpin-loop structure. A hairpin-loop structure can be changed by substituting a nucleotide different from the one contained in the consensus sequence at the third position of a codon, reducing the nucleotide identity to the consensus sequence while still maintaining the same amino acid coded by the codon. As a non-limiting example, the hairpin-loop structure 5'-GCTTGGCCAAGC-3' (SEQ ID NO: 139) is present within an open reading frame and encodes the peptide $NH_2$-alanine-tryptophan-proline-serine-COOH. This hairpin-loop structure can be eliminated by changing the sequence to 5'-GCATGGCCTAGC-3' (SEQ ID NO: 140) and still encode the peptide $NH_2$-alanine-tryptophan-proline-serine-COOH. In another aspect of this embodiment, at least one nucleotide change may be made to a nucleic acid molecule altering the consensus sequence of a hairpin-loop structure found in an open reading frame providing increased expression of the encoded active BoNT/E. In another aspect of this embodiment, a plurality of nucleotide changes are made to a nucleic acid molecule altering the consensus sequence of a hairpin-loop structure found in an open reading frame providing increased expression of the encoded active BoNT/E. Therefore, aspects of this embodiment an open reading frame can include , e.g., at least one nucleotide change, at least two nucleotide changes, at least three nucleotide changes, at least four nucleotide changes, at least five nucleotide changes, at least 10 nucleotide, at least 20 nucleotide, or at least 30 nucleotide changes. In other aspects of this embodiment an open reading frame can include, e.g., at most one nucleotide change, at most two nucleotide changes, at most three nucleotide changes, at most four nucleotide changes, at most five nucleotide changes, at most 10 nucleotide changes, at most 20 nucleotide changes, or at most 30 nucleotide changes.

In yet another embodiment, a modified open reading frame is changed, as compared to the open reading frame of SEQ ID NO: 3, altering synonymous codons, G+C content, polymononucleotide regions and internal regulatory or structural sites, or any combination thereof, providing increased expression of the encoded active BoNT/E.

In an aspect of this embodiment, at least one nucleotide change is made to a nucleic acid molecule that substitutes a codon in the open reading frame for a synonymous codon and alters the G+C content of an open reading frame providing increased expression of the encoded active BoNT/E. In another aspect of this embodiment, a plurality of nucleotide changes are made to a nucleic acid molecule that substitutes a plurality of codons in the open reading frame for a plurality of synonymous codon and alters the G+C content of an open reading frame providing increased expression of the encoded active BoNT/E. In another aspect of this embodiment, at least one nucleotide change is made to a nucleic acid molecule that substitutes a codon in the open reading frame for a synonymous codon and alters a polymononucleotide region found in an open reading frame providing increased expression of the encoded active BoNT/E. In another aspect of this embodiment, a plurality of nucleotide changes are made to a nucleic acid molecule that substitutes a plurality of codons in the open reading frame for a plurality of synonymous codon and alters a plurality of polymononucleotide region found in an open reading frame providing increased expression of the encoded active BoNT/E. In a further aspect of this embodiment, at least one nucleotide change is made to a nucleic acid molecule that substitutes a codon in the open reading frame for a synonymous codon and alters an internal regulatory or structural site found in an open reading frame providing increased expression of the encoded active BoNT/E. In another aspect of this embodiment, a plurality of nucleotide changes are made to a nucleic acid molecule that substitutes a plurality of codons in the open reading frame for a plurality of synonymous codon and alters a plurality of internal regulatory or structural sites found in an open reading frame providing increased expression of the encoded active BoNT/E.

In still another aspect of this embodiment, at least one nucleotide change is made to a nucleic acid molecule that substitutes a codon in the open reading frame for a synonymous codon, alters the G+C content of an open reading frame and alters a polymononucleotide region providing increased expression of the encoded active BoNT/E. In another aspect of this embodiment, a plurality of nucleotide changes are made to a nucleic acid molecule that substitutes a plurality of codons in the open reading frame for a plurality of synonymous codon, alters the G+C content of an open reading frame and alters a plurality of polymononucleotide region providing increased expression of the encoded active BoNT/E. In yet another aspect of this embodiment, at least one nucleotide change is made to a nucleic acid molecule that substitutes a codon in the open reading frame for a synonymous codon, alters the G+C content of an open reading frame and alters an internal regulatory or structural site providing increased expression of the encoded active BoNT/E. In another aspect of this embodiment, a plurality of nucleotide changes are made to a nucleic acid molecule that substitutes a plurality of codons in the open reading frame for a plurality of synonymous codon, alters the G+C content of an open reading frame and alters a plurality of internal regulatory or structural sites providing increased expression of the encoded active BoNT/E.

In an aspect of this embodiment, at least one nucleotide change is made to a nucleic acid molecule that substitutes a codon in the open reading frame for a synonymous codon, alters the G+C content of an open reading frame, alters a polymononucleotide region and alters an internal regulatory or structural site providing increased expression of the encoded active BoNT/E. In another aspect of this embodiment, a plurality of nucleotide changes are made to a nucleic acid molecule that substitutes a plurality of codons in the open reading frame for a plurality of synonymous codon, alters the G+C content of an open reading frame, alters a plurality of polymononucleotide region and alters a plurality of internal regulatory or structural sites providing increased expression of the encoded active BoNT/E.

Non-limiting examples of nucleic acid molecules disclosed in the present specification include the nucleic acid sequence molecules comprising SEQ ID NO: 4 through SEQ ID NO: 97, SEQ ID NO: 117, SEQ ID NO: 122 and SEQ ID NO: 124.

It is envisioned that any of a variety of additional nucleotide modifications can be done to assist in the making and using of a nucleic acid molecule and the active BoNT/E encoded by such molecules. In one embodiment, a nucleic acid molecule disclosed in the present specification can be modified to add at least one nucleotide sequence region comprising a restriction endonuclease binding site. In another aspect of this embodiment, a molecule disclosed in the present specification can include a plurality of restriction endonuclease binding sites. Therefore, aspects of this embodiment can include a nucleic acid molecule that includes a nucleic acid region comprising one or more restriction endonuclease binding sites, two or more restriction endonuclease sites, three or more restriction endonuclease sites, four or more restriction endonuclease sites, or five or more restriction endonuclease enzyme sites. It is envisioned that the location of a nucleic acid region comprising a restriction endonuclease binding site can be at the 5' end of a molecule, the 3' end of the molecule, within the molecule, or any combination thereof. In another aspect of this embodiment, regions comprising restriction endonuclease sites are added to both the 5' and 3' ends of the open reading frame contained in a nucleic acid molecule. In another aspect of this embodiment, restriction endonuclease sites flank each end of an open reading frame encoding the BoNT/E of SEQ ID NO: 1. Any of a wide variety of restriction endonuclease binding sites can be used with nucleic acid molecules disclosed in the present specification. The selection, making and use of restriction endonuclease binding sites are routine procedures well within the scope of one skilled in the art and from the teaching herein.

In another embodiment, nucleic acid molecules disclosed in the present specification can include at least one nucleotide change that eliminates a restriction endonuclease binding site from within an open reading frame. In another aspect of this embodiment, a molecule disclosed in the present specification can include a plurality of nucleotide substitutions that eliminate a restriction endonuclease binding site from within an open reading frame. Therefore, aspects of this embodiment can include a nucleic acid molecule that alters the recognition sequence of a restriction endonuclease binding site found within an open reading frame by one or more nucleotides, two or more nucleotides, three or more nucleotides, or four or more nucleotides. A restriction endonuclease binding site can be altered by substituting a nucleotide different from the one contained in the palindrome recognition sequence of that enzyme at the third position of a codon that interrupted the site while still maintaining the same amino acid coded by the codon. As a non-limiting example, an EcoRI recognition site of 5'-GAATTC-3', found in the open reading frame, encoding for the dipeptide $NH_2$-glutamate-phenylalanine-COOH can be changed to 5'-GAGTTC-3' to eliminate the EcoRI recognition site and still code for the dipeptide $NH_2$-glutamate-phenylalanine-COOH. In yet another aspect of this embodiment, a nucleic acid molecule disclosed in the present specification can include the elimination of at least one restriction endonuclease site from an open reading frame. In yet another aspect of this embodiment, a molecule disclosed in the present specification can include the elimination of a plurality of restriction endonuclease binding sites from an open reading frame. Thus, aspects of this embodiment can eliminate one or more restriction endonuclease binding sites from an open reading frame, two or more restriction endonucleases binding site from an open reading frame, three or more restriction endonucleases binding site from an open reading frame, or four or more restriction endonucleases binding site from an open reading frame.

In yet another embodiment, nucleic acid molecules disclosed in the present specification can include at least one nucleic acid region encoding a binding peptide. Such a binding peptide is operably-linked in-frame to an open reading frame encoding a BoNT/E as a fusion protein. In another aspect of this embodiment, a nucleic acid molecule disclosed in the present specification can include a plurality of nucleic acid regions encoding multiple operably-linked binding peptides. Therefore, aspects of this embodiment can include a nucleic acid molecule including a one nucleic acid region encoding one or more operably-linked binding peptides, two or more operably-linked binding peptides, three or more operably-linked binding peptides, four or more operably-linked binding peptides, or five or more operably-linked binding peptides. In another aspect of this embodiment, nucleic acid regions comprising multiple binding peptides can encode multiple copies of the same binding peptide, different binding peptides, or any combination thereof. The location of a nucleic acid region encoding a binding peptide may be in various positions, including, without limitation, before the amino terminus of the BoNT/E, within the BoNT/E, or after the carboxy terminus of the BoNT/E and a binding peptide. Examples of binding peptides that can be encoded by a nucleic acid region disclosed in the present specification include, without limitation, epitope-binding peptides such as FLAG, Express™, human Influenza virus hemagluttinin (HA), human p62$^{c\text{-}Myc}$ protein (c-MYC), Vesicular Stomatitis Virus Glycoprotein (VSV-G), glycoprotein-D precursor of Herpes simplex virus (HSV), V5, and AU1; affinity-binding peptides such as polyhistidine (HIS), streptavidin binding peptide (strep), and biotin; and peptide-binding domains such as the glutathione binding domain of glutathione-S-transferase, the calmodulin binding domain of the calmodulin binding protein, and the maltose binding domain of the maltose binding protein. Non-limiting examples of specific protocols for selecting, making and using an appropriate binding peptide are described in, e.g., Molecular Cloning A Laboratory Manual (Joseph Sambrook & David W. Russell eds., Cold Spring Harbor Laboratory Press, 3$^{rd}$ ed. 2001); Antibodies: A Laboratory Manual (Edward Harlow & David Lane, eds., Cold Spring Harbor Laboratory Press, 2$^{nd}$ ed. 1998); and Using Antibodies: A Laboratory Manual: Portable Protocol No. I (Edward Harlow & David Lane, Cold Spring Harbor Laboratory Press, 1998), which are hereby incorporated by reference. In addition, non-limiting examples of binding peptides as well as well-characterized reagents, conditions and protocols are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; and Stratagene, La Jolla, Calif. These protocols are routine procedures within the scope of one skilled in the art and from the teaching herein.

In yet another embodiment, a nucleic acid molecules disclosed in the present specification can include at least one nucleic acid region encoding a protease cleavage site. Such a protease cleavage site is operably-linked in-frame to an open reading frame encoding an active BoNT/E and a binding peptide as a fusion protein. In another aspect of this embodiment, a molecule disclosed in the present specification can comprise a plurality of one nucleic acid regions encoding multiple protease cleavage sites. It is further envisioned that in a molecule containing two or more one nucleic acid regions, these regions may encode the same protease cleavage sites or may encode for different protease cleavage sites. The location of the one nucleic acid region encoding the cleavage site may be in various positions, including, without limitation, between a binding peptide and the amino terminus of the active BoNT/E or between the carboxy terminus of the active BoNT/E and a binding peptide element. Examples of protease cleavage sites that can be encoded by a nucleic acid region disclosed in the present specification include, without limitation, an enterokinase cleavage site, a thrombin cleavage site, a Factor Xa cleavage site, a tobacco etch virus (TEV) protease cleavage site, a dipeptidyl aminopeptidase cleavage site and a small ubiquitin-like modifier (SUMO)/ubiquitin-like protein-1 (ULP-1) protease cleavage site. Non-limiting examples of protease cleavage site as well as well-characterized reagents, conditions and protocols are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; and Stratagene, La Jolla, Calif. The selection, making and use of an appropriate protease cleavage site are routine procedures within the scope of one skilled in the art and from the teaching herein.

It is envisioned that any of a variety of means can be used to identify appropriate nucleotides to change in order to make a modified open reading frame providing increased expression of an active BoNT/E. Appropriate nucleotide changes can be identified manually using published codon usage tables, see e.g., Codon Usage Database, supra, (2004), or codon usage tables developed by one skilled in the art. In addition, computer programs designed to assist in the selection of nucleotide changes. Non-limiting examples of such software include eCodonOpt, Gregory L. Moore and Costas D. Maranas, eCodonOpt: A Systematic Computational Framework for Optimizing Codon Usage in Directed Evolution Experiments, 30(11) Nucleic Acids Res. 2407-2416 (2002); DNA Works, see, e.g., David M. Hoover and Jacek Lubkowski, DNAWorks: An Automated Method for Designing Oligonucleotides for PCR-Based Gene Synthesis, 30(10) Nucleic Acids Res. E43 (2002); DNA2.0, see, e.g., Claes Gustafsson et al., Codon Bias and Heterologous Protein Expression, 22(7) Trends Biotechnol. 346-353 (2004); GeMS, see, e.g., Sarah J. Kodumal et al., Total Synthesis of Long DNA Sequences: Synthesis of a Contiguous 32-Kb Polyketide Synthase Gene Cluster, 101(44) Proc. Natl. Acad. Sci. U.S.A. 15573-15578 (2004); CAD PAM, see, e.g., Lance Stewart and Alex B. Burgin, supra, 2005; and Gene Composer, see, e.g., Lance Stewart and Alex B. Burgin, supra, 2005. In addition, publicly available internet sites useful for identifying codon bias are available, such as, Graphical Codon User Analyzer at gcua.schoedl.de, see, e.g., Markus Fuhrmann et al., Monitoring Dynamic Expression of Nuclear Genes in Chlamydomonas Reinhardtii by Using a Synthetic Luciferase Reporter Gene, 55(6) Plant Mol. Biol. 869-881 (2004); and UpGene at URL address vectorcore.pitt.edu/upgene/upgene.html, see, e.g., Wentao Gao et al., *UpGene: Application of a Web-based DNA Codon Optimization Algorithm,* 20 Biotechnol. Prog. 443-448, (2004). Alternatively, a variety of commercial vendors provide nucleotide optimization services including, but not limited, to Aptagen, Inc. (Herndon, Va.); BLUEHERON® Biotechnology (Bothell, Wash.); deCODE Biostructures, Inc. (Bainbridge Island, Wash.); DNA 2.0 (Menlo Park, Calif.); Entelechon, GmbH. (Regensburg, Germany); Genscript Corp. (Piscataway, N.J.); Modular Genetics, Inc. (Woburn, Mass.); and QIAGEN, Inc. (Valencia, Calif.). The identification of appropriate nucleotide changes to make in a modified open reading frame disclosed in the present specification is a routine procedure within the scope of one skilled in the art and from the teachings herein.

A variety of methods can be used to make a nucleic acid molecule comprising a modified open reading frame disclosed in the present specification, see, e.g., Lance Stewart and Alex B. Burgin, supra, 2005. Non-limiting examples of methods include, oligonucleotide ligation methods, in vivo repair methods and PCR-based methods. The synthesis of nucleic acid molecules is a routine procedure within the scope of one skilled in the art and from the teachings herein.

Nucleic acid synthesis by sequential assembly of complementary oligonucleotides is a solid phase method involving the sequential hybridization of overlapping complementary oligonucleotides to a starting oligonucleotide that is chemically coupled to an insert support, see, e.g., Zdenek Hostomsky and Jiri Smrt, Solid-phase assembly of DNA duplexes from synthetic oligonucleotides, 18 Nucleic Acids Symp Ser. 241-244 (1987); and K L. Beattie and R. F. Fowler, Solid-phase gene assembly, 352(6335) Nature 548-549 (1991). In this oligonucleotide ligation method, oligonucleotide building blocks of approximately 30 nucleotides in length that correspond to the top and bottom strands of the entire gene are individually denatured and purified by denaturing polyacrylamide gel elctrophoresis. These purified oligonucleotides are phosphorylation of the 5' end, divided into subgroups and then hybridized to form subassemblies on the solid-phase support. Sequential rounds of sub assembly hybridizations to the solid-phase support extend the attached DNA molecule until the full-length gene is constructed.

Nucleic acid synthesis by the FokI method utilizes the *E. coli* in vivo repair mechanism of DNA synthesis to construct a synthetic gene from oligonucleotides, see e.g., Wlodek Mandecki & Timothy J. Boiling, FokI *Method of Gene Synthesis,* 68(1) GENE 101-107, (1988), The method is based on the observation that large (approx. 100 bp long) inserts can be cloned into a plasmid using a technique of oligodeoxynucleotide (oligo)-directed double-strand break repair. The method involves transforming a denatured mixture of oligonucleotides of approximately 40 to 90 nucleotides in length and a linearized plasmid into *E. coli*. The oligonucleotides are designed with terminal sequences which contain a FokI restriction endonuclease site and complement the ends of the linearized plasmid, which also has sites for FokI. The nucleotide (nt) sequences are inserted between the two FokI sites of the plasmid. FokI is a class IIs endonuclease which makes a staggered double strand break at a site 9 and 13 nucleotides away from its recognition site. Upon cleavage of the plasmid DNA with FokI, a restriction fragment is liberated that by design contains unique four nucleotide FokI 5'-overhang sequences that can serve as cohesive ends for subsequent assembly of larger fragments of synthetic DNA until the gene of interest is constructed.

Nucleic acid synthesis by polymerase cycling assembly (PCA) or assembly PCR uses the polymerase chain reaction to construct a gene from oligonucleotides instead of methods involving the ligation of overlapping oligonucleotide, see e.g., Patrick J. Dillon & Craig A. Rosen, *A Rapid Method for the Construction of Synthetic Genes Using the Polymerase Chain Reaction,* 9(3) BIOTECHNIQUES 298-300, (1990); and Willem P. Stemmer et al., *Single-Step Assembly of a Gene and Entire Plasmid from Large Numbers of Oligodeoxyribonucleotides,* 164(1) GENE 49-53, (1995). In this method, overlapping, complementary oligonucleotides of approximately 40 to 60 nucleotides in length that correspond to the top and bottom strands of the entire gene are pooled and subjected to multiple cycles of denaturation, renaturation and polymerization. The resulting PCR products are then subjected to PCR amplification using outside flanking primers containing restriction endonuclease sites that facilitate cloning of the final PCR product.

Alternatively, a variety of commercial vendors provide nucleic acid synthesis services through the use of high throughput gene synthesis platforms including, but not limited, to Aptagen, Inc. (Herndon, VA); BLUEHERON® Biotechnology (Bothell, WA); DNA 2.0 (Menlo Park, CA); Entelechon, GmbH. (Regensburg, Germany); Genscript Corp. (Piscataway, NJ); Modular Genetics, Inc. (Woburn, MA); and QIAGEN, Inc. (Valencia, CA). A method of nucleic acid synthesis is illustrated in Example 3. The synthesis of a modified open reading frame disclosed in the present specification is a routine procedure within the scope of one skilled in the art and from the teachings herein.

Seven antigenically-distinct types of Botulinum toxins (BoNTs) have been identified by investigating botulism outbreaks in man (BoNT/A, /B, /E and /F), animals (BoNT/C1 and /D), or isolated from soil (BoNT/G). BoNTs possess approximately 35% amino acid identity with each other and share the same functional domain organization and overall structural architecture. The amino acid sequences of eight Clostridial toxin serotypes have been derived from the corresponding genes (Niemann, "Molecular Biology of Clostridial Neurotoxins" in Sourcebook of Bacterial Protein Toxins Alouf and Freer (Eds.) pp. 303-348 London: Academic Press 1991). It is recognized by those of skill in the art that within each type of Clostridial toxin there can be various strains differing somewhat in their amino acid sequence, and also in the nucleic acids encoding these proteins. While all seven BONT serotypes have similar structure and pharmacological properties, each also displays heterogeneous bacteriological characteristics. In contrast, tetanus toxin (TeNT) is produced by a uniform group of *C. tetani*. Two other species of clostridia, *C. baratii* and *C. butyricum*, also produce toxins similar to BoNT/F and BoNT/E, respectively.

Clostridia toxins (CoNTs) are each translated as a single chain polypeptide of approximately 150 kDa that is subsequently cleaved by proteolytic scission within a disulphide loop by bacterial or tissue proteases. This posttranslational processing yields a di-chain molecule comprising an approximately 50 kDa light chain (LC) and an approximately 100 kDa heavy chain ($H_C$) held together by a single disulphide bond and noncovalent interactions. Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus; 2) a translocation domain contained within the amino-terminal half of the HC($H_N$) that facilitates release of the toxin from intracellular vesicles into the cytoplasm of the target cell; and 3) a binding domain found within the carboxy-terminal half of the HC ($H_C$) that determines the binding activity and binding specificity of the toxin to the receptor complex located at the surface of the target cell.

Figure 1B:
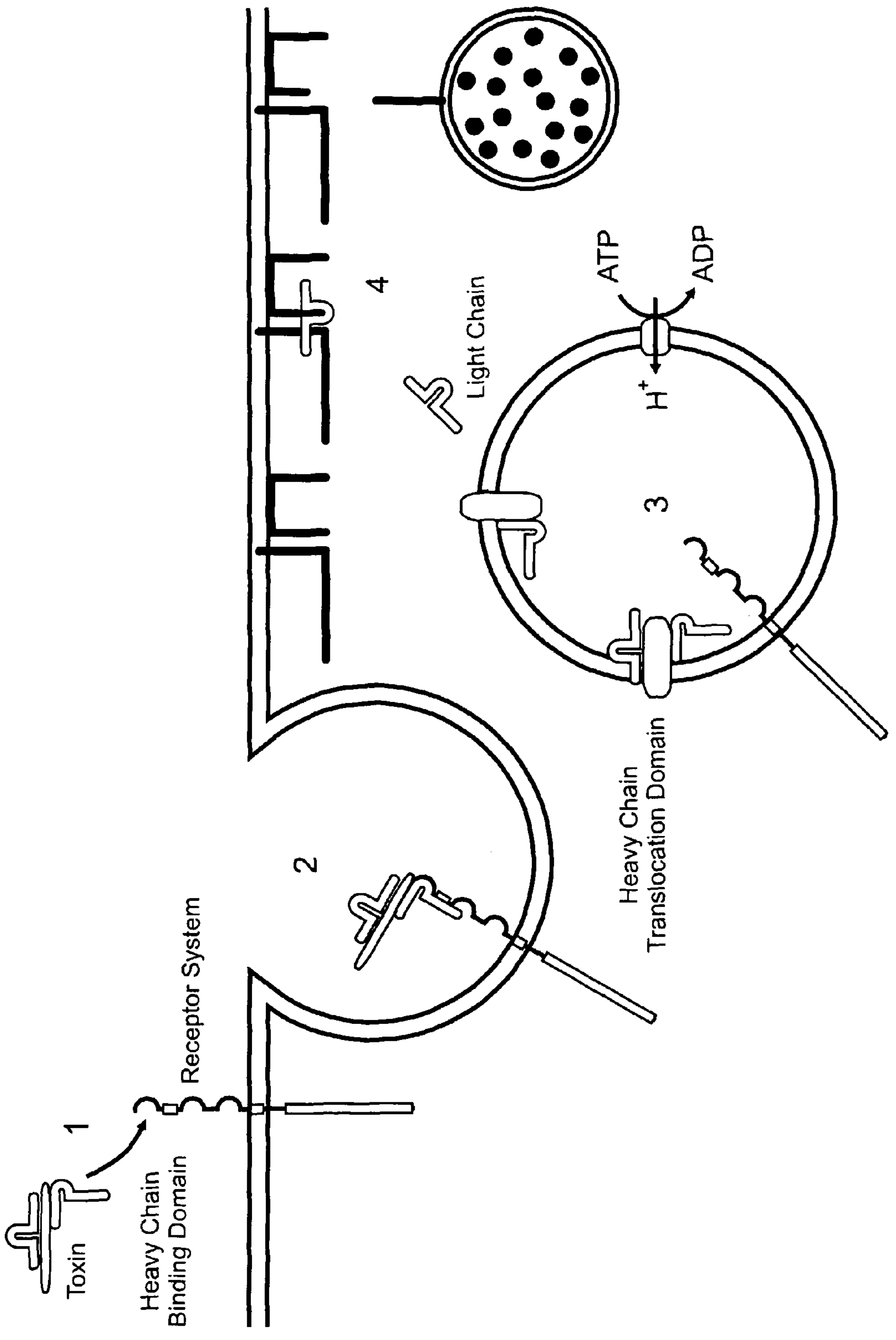
FIG. 1*b* shows a schematic of the intoxication mechanism for tetanus and botulinum toxin activity in a central and peripheral neuron. This intoxication process can be described as comprising four steps: 1) receptor binding, where a Clostridial toxin binds to a Clostridial receptor system and initiates the intoxication process; 2) complex internalization, where after toxin binding, a vesicle containing the toxin/receptor system complex is endocytosed into the cell; 3) light chain translocation, where multiple events are thought to occur, including changes in the internal pH of the vesicle, formation of a channel pore comprising the $H_N$ domain of Clostridial toxin heavy chain, separation of the Clostridial toxin light chain from the heavy chain, enzymatic activation of the light chain; and release of the activated light chain and 4) enzymatic target modification, where the activated light chain of Clostridial toxin proteolytically cleaves its target SNARE substrates, such as, e.g., SNAP-25, VAMP or Syntaxin, thereby preventing vescle docking and neurotransmitter release.

The binding, translocation and enzymatic activity of these three functional domains are all necessary for toxicity. While all details of this process are not yet precisely known, the overall cellular intoxication mechanism whereby CoNTs enter a neuron and inhibit neurotransmitter release is similar, regardless of type. Although the applicants have no wish to be limited by the following description, the intoxication mechanism can be described as comprising at least four steps: 1) receptor binding, 2) complex internalization, 3) light chain translocation, and 4) enzymatic target modification (see FIG. 1). The process is initiated when the Hc domain of a CoNT binds to CoNT-specific receptor complex located on the plasma membrane surface of a target cell. The binding specificity of a receptor complex is thought to be achieved, in part, by specific combinations of gangliosides and protein receptors that appear to distinctly comprise each Clostridial toxin receptor complex. Once bound, the CoNT/receptor complexes are internalized by endocytosis and the internalized vesicles are sorted to specific intracellular routes. The translocation step appears to be triggered by the acidification of the vesicle compartment. This process seems to initiate two important pH-dependent structural rearrangements that increase hydrophobicity and promote enzymatic activation of the toxin. Once activated, light chain endopeptidase of the toxin is released from the intracellular vesicle into the cytosol where it specifically targets one of three known core components of the neurotransmitter release apparatus. These core proteins, vesicle-associated membrane protein (VAMP)/synaptobrevin, synaptosomal-associated protein of 25 kDa (SNAP-25) and Syntaxin, are necessary for synaptic vesicle docking and fusion at the nerve terminal and constitute members of the soluble N-ethylmaleimide-sensitive factor-attachment protein-receptor (SNARE) family. BoNT/A and BoNT/E cleave SNAP-25 in the carboxy-terminal region, releasing a nine or twenty-six amino acid segment, respectively, and BoNT/C1 also cleaves SNAP-25 near the carboxy-terminus. The botulinum serotypes BoNT/B, BoNT/D, BoNT/F and BoNT/G, and tetanus toxin, act on the conserved central portion of VAMP, and release the amino-terminal portion of VAMP into the cytosol. BoNT/C1 cleaves syntaxin at a single site near the cytosolic membrane surface. The selective proteolysis of synaptic SNAREs accounts for the total block of neurotransmitter release caused by Clostridial toxins in vivo. The SNARE protein targets of Clostridial toxins are common to exocytosis in a variety of non-neuronal types; in these cells, as in neurons, light chain peptidase activity inhibits exocytosis, see, e.g., Yann Humeau et al., *How Botulinum and Tetanus Neurotoxins Block Neurotransmitter Release,* 82(5) Biochimie. 427-446 (2000); Kathryn Turton et al., *Botulinum and Tetanus Neurotoxins: Structure, Function and Therapeutic Utility,* 27(11) Trends Biochem. Sci. 552-558. (2002); M. Zouhair Atassi, *Basic and Therapeutic Aspects of Botulinum and Tetanus Toxins*, (Dirk W. Dressler & Joseph J. Jankovic eds., 2003); Giovanna Lalli et al., *The Journey of Tetanus and Botulinum Neurotoxins in Neurons,* 11 (9) Trends Microbiol. 431-437, (2003) which are hereby incorporated by reference.

Aspects of the present invention provide, in part, an active BoNT/E. As used herein, the term "active BoNT/E" means any protein, or fragment thereof, that can execute the overall cellular mechanism whereby BoNT/E enter a neuron and inhibit neurotransmitter release and encompasses the binding of a BoNT/E to a low or high affinity receptor complex, the internalization of the toxin/receptor complex, the translocation of the BoNT/E light chain into the cytoplasm and the enzymatic modification of a BoNT/E substrate. Thus, active BoNT/E encompass without limitation, naturally occurring active BoNT/E variants, such as, e.g., active BoNT/E isoforms, non-naturally occurring active BoNT/E variants, such as, e.g., conservative BoNT/E variants, non-conservative BoNT/E variants and active BoNT/E fragments thereof, or any combination thereof. As used herein, the term "BoNT/E variant," whether naturally-occurring or non-naturally-occurring, means an active BoNT/E that has at least one amino acid change from the corresponding region of SEQ ID NO: 1 and can be described in percent identity to the corresponding region of SEQ ID NO: 1. As a non-limiting example, an active BoNT/E variant comprising amino acids 1-1252 of SEQ ID NO: 1 will have at least one amino acid difference, such as, e.g., an amino acid substitution, deletion or addition, as compared to the amino acid region 1-1252 of SEQ ID NO: 1. As another non-limiting example, an active BoNT/E variant comprising amino acids 15-1240 of SEQ ID NO: 1 will have at least one amino acid difference, such as, e.g., an amino acid substitution, deletion or addition, as compared to the amino acid region 15-1240 of SEQ ID NO: 1.

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art and from the teaching herein.

Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: improving the sensitivity of progressive multiple sequence alignment through sequence weighting, position-specific gap penalties and weight matrix choice, 22(22) Nucleic Acids Research 4673-4680 (1994); and iterative refinement, see, e.g., Osamu Gotoh, Significant improvement in accuracy of multiple protein sequence alignments by iterative refinement as assessed by reference to structural alignments, 264(4) J. Mol. Biol. 823-838 (1996).

Local methods align sequences by identifying one or more conserved motifs shared by all of the input sequences. Non-limiting methods include, e.g., Match-box, see, e.g., Eric Depiereux and Ernest Feytmans, Match-box: a fundamentally new algorithm for the simultaneous alignment of several protein sequences, 8(5) CABIOS 501-509 (1992); Gibbs sampling, see, e.g., C. E. Lawrence et al., Detecting subtle sequence signals: a gibbs sampling strategy for multiple alignment, 262(5131) Science 208-214 (1993); Align-M, see, e.g., Ivo Van Walle et al., Align-m—a new algorithm for multiple alignment of highly divergent sequences, 20(9) Bioinformatics: 1428-1435 (2004).

Hybrid methods combine functional aspects of both global and local alignment methods. Non-limiting methods include, e.g., segment-to-segment comparison, see, e.g., Burkhard Morgenstern et al., Multiple DNA and protein sequence alignment based on segment-to-segment comparison, 93(22) Proc. Natl. Acad. Sci. U.S.A. 12098-12103 (1996); T-Coffee, see, e.g., Cédric Notredame et al., T-Coffee: a novel algorithm for multiple sequence alignment, 302(1) J. Mol. Biol. 205-217 (2000); MUSCLE, see, e.g., Robert C. Edgar, MUSCLE: Multiple sequence alignment with high score accuracy and high throughput, 32(5) Nucleic Acids Res. 1792-1797 (2004); and DIALIGN-T, see, e.g., Amarendran R Subramanian et al., DIALIGN-T: An improved algorithm for segment-based multiple sequence alignment, 6(1) BMC Bioinformatics 66 (2005).

As used herein, the term "naturally occurring BoNT/E variant" means any active BoNT/E produced without the aid of any human manipulation, including, without limitation, BoNT/E isoforms produced from alternatively-spliced transcripts and BoNT/E isoforms produced by spontaneous mutation. As used herein, the term "non-naturally occurring BoNT/E variant" means any active BoNT/E produced with the aid of human manipulation, including, without limitation, active BoNT/E produced by genetic engineering using random mutagenesis or rational designed and active BoNT/E produced by chemical synthesis.

As used herein, the term "conservative BoNT/E variant" means an active BoNT/E that has at least one amino acid substituted by another amino acid or an amino acid analog that has at least one property similar to that of the original amino acid. Examples of properties include, without limitation, similar size, topography, charge, hydrophobicity, hydrophilicity, lipophilicity covalent-bonding capacity, hydrogen-bonding capacity, a physicochemically property, of the like, or any combination thereof. A conservative BoNT/E variant can function in substantially the same manner as the active BoNT/E on which the conservative BoNT/E variant is based, and can be substituted for the active BoNT/E in any aspect of the present invention. A conservative BoNT/E variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the active BoNT/E on which the DAGL conservative variant is based. A conservative BoNT/E variant can also substitute at least 10 contiguous amino acids, at least 15 contiguous amino acids, at least 20 contiguous amino acids, or at least 25 contiguous amino acids from the active BoNT/E on which the conservative BoNT/E variant is based, that possess at least 50% amino acid identity, 65% amino acid identity, 75% amino acid identity, 85% amino acid identity or 95% amino acid identity to the active BoNT/E on which the conservative BoNT/E variant is based.

As used herein, the term "non-conservative BoNT/E variant" means an active BoNT/E in which 1) at least one amino acid is deleted from the active BoNT/E on which the non-conservative BoNT/E variant is based; 2) at least one amino acid added to the active BoNT/E on which the non-conservative BoNT/E variant is based; or 3) at least one amino acid is substituted by another amino acid or an amino acid analog that does not share any property similar to that of the original amino acid. A non-conservative BoNT/E variant can function in substantially the same manner as the active BoNT/E on which the non-conservative BoNT/E variant is based, and can be substituted for the active BoNT/E in any aspect of the present invention. A non-conservative BoNT/E variant can delete one or more amino acids, two or more amino acids, three or more amino acids, four or more amino acids, five or more amino acids, and ten or more amino acids from the active BoNT/E on which the non-conservative BoNT/E variant is based. A non-conservative BoNT/E variant can add one or more amino acids, two or more amino acids, three or more amino acids, four or more amino acids, five or more amino acids, and ten or more amino acids to the active BoNT/E on which the non-conservative BoNT/E variant is based. A non-conservative BoNT/E variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the active BoNT/E on which the non-conservative BoNT/E variant is based. A non-conservative BoNT/E variant can also substitute at least 10 contiguous amino acids, at least 15 contiguous amino acids, at least 20 contiguous amino acids, or at least 25 contiguous amino acids from the active BoNT/E on which the non-conservative BoNT/E variant is based, that possess at least 50% amino acid identity, 65% amino acid identity, 75% amino acid identity, 85% amino acid identity or 95% amino acid identity to the active BoNT/E on which the non-conservative BoNT/E variant is based.

It is also envisioned that any of a variety of active BoNT/E fragments can be useful in aspects of the present invention with the proviso that these active fragments can execute the overall cellular mechanism whereby an active BoNT/E proteolytically cleaves a substrate. Thus, aspects of this embodiment can include active BoNT/E fragments having a length of, e.g., at least 300 amino acids, at least 400 amino acids, at least 500 amino acids, at least 600 amino acids, at least 700 amino acids, at least 800 amino acids, at least 900 amino acids, at least 1000 amino acids, at least 1100 amino acids and at least 1200 amino acids. Other aspects of this embodiment, can include active BoNT/E fragments having a length of, e.g., at most 300 amino acids, at most 400 amino acids, at most 500 amino acids, at most 600 amino acids, at most 700 amino acids, at most 800 amino acids, at most 900 amino acids, at most 1000 amino acids, at most 1100 amino acids and at most 1200 amino acids.

Thus, in an embodiment, a nucleic acid molecule comprising a modified open reading frame disclosed in the present specification encodes an active BoNT/E. Other aspects of this embodiment include, without limitation, naturally occurring BoNT/E variants, such as, e.g., BoNT/E isoforms, non-naturally occurring BoNT/E variants, such as, e.g., conservative BoNT/E variants, non-conservative BoNT/E variants and active BoNT/E fragments, or any combination thereof. In another embodiment, a nucleic acid molecule comprising a modified open reading frame disclosed in the present specification encodes an active BoNT/E comprising SEQ ID NO:1. Other aspects of this embodiment include, without limitation, naturally occurring BoNT/E variants of SEQ ID NO: 1, such as, e.g., BoNT/E isoforms of SEQ ID NO: 1, non-naturally occurring BoNT/E variants of SEQ ID NO: 1, such as, e.g., conservative BoNT/E variants of SEQ ID NO: 1, non-conservative BoNT/E variants of SEQ ID NO: 1 and active BoNT/E fragments of SEQ ID NO: 1, or any combination thereof.

In still other aspects of this embodiment, an active BoNT/E has, e.g., at least 70% amino acid identity with SEQ ID NO:1, at least 75% amino acid identity with the SEQ ID NO:1, at least 80% amino acid identity with SEQ ID NO:1, at least 85% amino acid identity with SEQ ID NO:1, at least 90% amino acid identity with SEQ ID NO:1 or at least 95% amino acid identity with SEQ ID NO:1. In yet other aspects of this embodiment, an active BoNT/E has, e.g., at most 70% amino acid identity with SEQ ID NO:1, at most 75% amino acid identity with the SEQ ID NO:1, at most 80% amino acid identity with SEQ ID NO:1, at most 85% amino acid identity with SEQ ID NO:1, at most 90% amino acid identity with SEQ ID NO:1 or at most 95% amino acid identity with SEQ ID NO:1.

In other aspects of this embodiment, an active BoNT/E has, e.g., at most one, two, three, four, five, six, seven, eight, nine, 10, 20, 30, 40 or 50 non-contiguous amino acid substitutions relative to SEQ ID NO:1. In other aspects of this embodiment, an active BoNT/E has, e.g., at least one, two, three, four, five, six, seven, eight, nine, 10, 20, 30, 40 or 50 non-contiguous amino acid substitutions relative to SEQ ID NO:1. In yet other aspects of this embodiment, an active BoNT/E has, e.g., at most one, two, three, four, five, six, seven, eight, nine, 10, 20, 30, 40 or 50 non-contiguous amino acid deletions relative to SEQ ID NO:1. In other aspects of this embodiment, an active BoNT/E has, e.g., at least one, two, three, four, five, six, seven, eight, nine, 10, 20, 30, 40 or 50 non-contiguous amino acid deletions relative to SEQ ID NO:1. In still other aspects of this embodiment, an active BoNT/E has, e.g., at most one, two, three, four, five, six, seven, eight, nine, 10, 20, 30, 40 or 50 non-contiguous amino acid additions relative to SEQ ID NO:1. In other aspects of this embodiment, an active BoNT/E has, e.g., at least one, two, three, four, five, six, seven, eight, nine, 10, 20, 30, 40 or 50 non-contiguous amino acid additions relative to SEQ ID NO:1.

In other aspects of this embodiment, an active BoNT/E has, e.g., at most one, two, three, four, five, six, seven, eight, nine, 10, 20, 30, 40 or 50 contiguous amino acid substitutions relative to SEQ ID NO:1. In other aspects of this embodiment, an active BoNT/E has, e.g., at least one, two, three, four, five, six, seven, eight, nine, 10, 20, 30, 40 or 50 contiguous amino acid substitutions relative to SEQ ID NO:1. In yet other aspects of this embodiment, an active BoNT/E has, e.g., at most one, two, three, four, five, six, seven, eight, nine, 10, 20, 30, 40 or 50 contiguous amino acid deletions relative to SEQ ID NO:1. In other aspects of this embodiment, an active BoNT/E has, e.g., at least one, two, three, four, five, six, seven, eight, nine, 10, 20, 30, 40 or 50 contiguous amino acid deletions relative to SEQ ID NO:1. In still other aspects of this embodiment, an active BoNT/E has, e.g., at most one, two, three, four, five, six, seven, eight, nine, 10, 20, 30, 40 or 50 contiguous amino acid additions relative to SEQ ID NO:1. In other aspects of this embodiment, an active BoNT/E has, e.g., at least one, two, three, four, five, six, seven, eight, nine, 10, 20, 30, 40 or 50 contiguous amino acid additions relative to SEQ ID NO:1.

Aspects of the present invention provide, in part, a heterologous cell. As used herein, the term "heterologous cell" means any cell other than the native strain of *Clostridium* from which the Clostridial toxin was discovered. that expresses, or can be engineered to express an active BoNT/E disclosed in the present specification. Thus, for example, a heterologous cell that expresses a nucleic acid molecule comprising a modified open reading frame encoding an active BoNT/E would be any prokaryotic or eukaryotic cell other than the *C. botulinum* strain that produces the E serotype. The term heterologous cell encompasses cells from a variety of organisms, including, without limitation, bacteria strains, yeast strains, plant cells and cell lines derived from plants, insect cells and cell lines derived from insects and mammalian cells and cell lines derived from mammals. It is understood that cells useful in aspects of the invention can included, without limitation, primary cells; cultured cells; established cells; normal cells; transformed cells; tumor cells; infected cells; proliferating and terminally differentiated cells; and stably or transiently transfected cells, including stably and transiently transfected cells. It is further understood that cells useful in aspects of the invention can be in any state such as proliferating or quiescent; intact or permeabilized such as through chemical-mediated transfection such as, e.g., calcium phosphate-mediated, diethyl-laminoethyl (DEAE) dextran-mediated, lipid-mediated, polyethyleneimine (PEI)-mediated and polybrene-mediated; physical-mediated tranfection, such as, e.g., biolistic particle delivery, microinjection and electroporation; and viral-mediated transfection, such as, e.g., retroviral-mediated transfection. It is further understood that cells useful in aspects of the invention may include those which express an active BoNT/E under control of a constitutive, tissue-specific, cell-specific or inducible promoter element, enhancer element or both.

Because a wide variety of factors could influence the selection of a specific heterologous cell, nucleic acid molecules comprising a modified open reading frame providing increased expression of the encoded active BoNT/E can be designed to be expressed in a range of prokaryotic and eukaryotic cells. Codon usage tables and G+C content information for prokaryotic and eukaryotic organisms are publicly maintained by the Codon Usage Database, The First Laboratory for Plant Gene Research, Kazusa DNA Research Institute (2004).

Thus in an embodiment, nucleic acid molecules comprising a modified open reading frame providing increased expression of the encoded active BoNT/E are expressed in a prokaryotic cell. Non-limiting examples of prokaryotic cells include strains of aerobic, microaerophilic, capnophilic, facultative, anaerobic, gram-negative and gram-positive bacterial cells such as those derived from, e.g., *Escherichia coli, Salmonella typhimurium, Bacillus subtilis, Bacillus lichenifonnis, Bacteroides fragilis, Clostridia perfringens, Clostridia difficile, Caulobacter crescentus, Lactococcus lactis, Methylobacterium extorquens, Neisseria meningirulls* and *Neisseria meningitidis*. In an aspect of this embodiment, a nucleic acid molecule disclosed in the present specification is expressed in an *E. coli* strain. In other aspects of this embodiment, a nucleic acid molecule is expressed in an *E. coli* strain comprises, e.g., the open reading frame of SEQ ID NO: 4, SEQ ID NO: 5, SEQ ID NO: 6, SEQ ID NO: 7, SEQ ID NO: 117, SEQ ID NO: 122 or SEQ ID NO: 124. In an aspect of this embodiment, a nucleic acid molecule disclosed in the present specification is expressed in a *B. fragilis* strain. In other aspects of this embodiment, a nucleic acid molecule expressed in a *B. fragilis* strain comprises, e.g., the open reading frame of SEQ ID NO: 8, SEQ ID NO: 9 or SEQ ID NO: 10. In an aspect of this embodiment, a nucleic acid molecule disclosed in the present specification is expressed in a *B. licheniformis* strain. In other aspects of this embodiment, a nucleic acid molecule expressed in a *B. licheniformis* strain comprises, e.g., the open reading frame of SEQ ID NO: 11, SEQ ID NO: 12 or SEQ ID NO: 13. In an aspect of this embodiment, a nucleic acid molecule disclosed in the present specification is expressed in a *B. subtilis* strain. In other aspects of this embodiment, a nucleic acid molecule expressed in an *B. subtilis* strain comprises, e.g., the open reading frame of SEQ ID NO: 14, SEQ ID NO: 15 or SEQ ID NO: 16. In an aspect of this embodiment, a nucleic acid molecule disclosed in the present specification is expressed in a *C. difficile* strain. In another aspect of this embodiment, a nucleic acid molecule expressed in a *C. difficile* strain comprises, e.g., the open reading frame of SEQ ID NO: 17, SEQ ID NO: 18 or SEQ ID NO: 19. In an aspect of this embodiment, a nucleic acid molecule disclosed in the present specification is expressed in a *C. perfringens* strain. In other aspects of this embodiment, a nucleic acid molecule expressed in a *C. perfringens* strain comprises, e.g., the open reading frame of SEQ ID NO: 20, SEQ ID NO: 21 or SEQ ID NO: 22. In an aspect of this embodiment, a nucleic acid molecule disclosed in the present specification is expressed in a *C. crescentus* strain. In other aspects of this embodiment, a nucleic acid molecule expressed in a *C. crescentus* strain comprises, e.g., the open reading frame of SEQ ID NO: 23, SEQ ID NO: 24 or SEQ ID NO: 25. In an aspect of this embodiment, a nucleic acid molecule disclosed in the present specification is expressed in a *L. lactis* strain. In another aspect of this embodiment, a nucleic acid molecule expressed in a *L. lactis* strain comprises, e.g., the open reading frame of SEQ ID NO: 26, SEQ ID NO: 27 or SEQ ID NO: 28. In an aspect of this embodiment, a nucleic acid molecule disclosed in the present specification is expressed in a *M. extorquens* strain. In another aspect of this embodiment, a nucleic acid molecule expressed in a *M. extorquens* strain comprises, e.g., the open reading frame of SEQ ID NO: 29, SEQ ID NO: 30 or SEQ ID NO: 31. In an aspect of this embodiment, a nucleic acid molecule disclosed in the present specification is expressed in an *N. meningirulls* strain. In an aspect of this embodiment, a nucleic acid molecule disclosed in the present specification is expressed in a *S. typhimurium* strain. In other aspects of this embodiment, a nucleic acid molecule expressed in a *S. typhimurium* strain comprises, e.g., the open reading frame of SEQ ID NO: 32, SEQ ID NO: 33 or SEQ ID NO: 34.

In another embodiment, nucleic acid molecules comprising a modified open reading frame providing increased expression of the encoded active BoNT/E is expressed in an eukaryotic cell or cell line derived from an eukaryotic cell. In aspects of this embodiment, a nucleic acid molecule expressed in an eukaryotic cell or cell line derived from an eukaryotic cell comprises, e.g., any one of the open reading frames of SEQ ID NO: 35 through SEQ ID NO: 97.

In yet another embodiment, nucleic acid sequence molecules comprising a modified open reading frame providing increased expression of the encoded active BoNT/E is expressed in a yeast strain. Non-limiting examples of yeast strains include those derived from, e.g., *Pichia pastoris, Pichia methanolica, Pichia angusta, Schizosaccharomyces pombe, Saccharomyces cerevisiae* and *Yarrowia lipolytica*. In an aspect of this embodiment, a nucleic acid molecule disclosed in the present specification is expressed in a *P. pastoris* strain. In other aspects of this embodiment, a nucleic acid molecule expressed in a *P. pastoris* strain comprises, e.g., the open reading frame of SEQ ID NO: 35, SEQ ID NO: 36 or SEQ ID NO: 37. In an aspect of this embodiment, a nucleic acid molecule disclosed in the present specification is expressed in a *P. methanolica* strain. In other aspects of this embodiment, a nucleic acid molecule expressed in a *P. methanolica* strain comprises, e.g., the open reading frame of SEQ ID NO: 35, SEQ ID NO: 36 or SEQ ID NO: 37. In an aspect of this embodiment, a nucleic acid molecule disclosed in the present specification is expressed in a *P. angusta* strain. In other aspects of this embodiment, a nucleic acid molecule expressed in a *P. angusta* strain comprises, e.g., the open reading frame of SEQ ID NO: 35, SEQ ID NO: 36 or SEQ ID NO: 37. In an aspect of this embodiment, a nucleic acid molecule disclosed in the present specification is expressed in a *S. cerevisiae* strain. In other aspects of this embodiment, a nucleic acid molecule expressed in a *S. cerevisiae* strain comprises, e.g., the open reading frame of SEQ ID NO: 38, SEQ ID NO: 39 or SEQ ID NO: 40. In an aspect of this embodiment, a nucleic acid molecule disclosed in the present specification is expressed in a *S. pombe* strain. In other aspects of this embodiment, a nucleic acid molecule expressed in a *S. pombe* strain comprises, e.g., the open reading frame of SEQ ID NO: 41, SEQ ID NO: 42 or SEQ ID NO: 43. In an aspect of this embodiment, a nucleic acid molecule disclosed in the present specification is expressed in a *Y. lipolytica* strain. In other aspects of this embodiment, a nucleic acid molecule expressed in a *Y. lipolytica* strain comprises, e.g., the open reading frame of SEQ ID NO: 44, SEQ ID NO: 45 or SEQ ID NO: 46.

In yet another embodiment, nucleic acid sequence molecules comprising a modified open reading frame providing increased expression of the encoded active BoNT/E is expressed in a slime mold strain. Non-limiting examples of slime mold strains include those derived from, e.g., *Dictyostelium discoideum*. In an aspect of this embodiment, a nucleic acid molecule disclosed in the present specification is expressed in a *D. discoideum* strain. In other aspects of this embodiment, a nucleic acid molecule expressed in a *D. discoideum* strain comprises, e.g., the open reading frame of SEQ ID NO: 47, SEQ ID NO: 48 or SEQ ID NO: 49.

In yet another embodiment, nucleic acid sequence molecules comprising a modified open reading frame providing increased expression of the encoded active BoNT/E is expressed in a plant cell. Non-limiting examples of plant cells and cell lines derived from plant cells include those derived from, e.g., species of monocots, such as, e.g., *Zea mays* and species of dicots, such as, e.g., *Arabidopsis thaliana, Lemna gibba* and *Lemna minor*. In an aspect of this embodiment, a nucleic acid molecule disclosed in the present specification is expressed in a monocot cell or cell line derived from a monocot cell. In an aspect of this embodiment, a nucleic acid molecule disclosed in the present specification is expressed in a dicot cell or cell line derived from a dicot cell. In an aspect of this embodiment, a nucleic acid molecule disclosed in the present specification is expressed in a *Z. mays* cell or cell line derived from a *Z. mays* cell. In other aspects of this embodiment, a nucleic acid molecule expressed in a *Z. mays* cell or cell line derived from a *Z. mays* cell comprises, e.g., the open reading frame of SEQ ID NO: 50, SEQ ID NO: 51 or SEQ ID NO: 52. In an aspect of this embodiment, a nucleic acid molecule disclosed in the present specification is expressed in an *A. thaliana* cell or cell line derived from an *A. thaliana* cell. In other aspects of this embodiment, a nucleic acid molecule expressed in an *A. thaliana* cell or cell line derived from an *A. thaliana* cell comprises, e.g., the open reading frame of SEQ ID NO: 53, SEQ ID NO: 54 or SEQ ID NO: 55.

In yet another embodiment, nucleic acid sequence molecules comprising a modified open reading frame providing increased expression of the encoded active BoNT/E is expressed in an insect cell or a cell line derived from insects. Non-limiting examples of insect cells and cell lines derived from insects such as those derived from, e.g., *Spodoptera frugiperda, Trichoplusia ni, Drosophila melanogaster* and *Manduca sexta*. In an aspect of this embodiment, a nucleic acid molecule disclosed in the present specification is expressed in a *D. melanogaster* cell or a cell line derived from *D. melanogaster*. In other aspects of this embodiment, a nucleic acid molecule expressed in a *D. melanogaster* cell or a cell line derived from *D. melanogaster* comprises, e.g., the open reading frame of SEQ ID NO: 56, SEQ ID NO: 57 or SEQ ID NO: 58. In an aspect of this embodiment, a nucleic acid molecule disclosed in the present specification is expressed in a *S. frugiperda* strain or a cell line derived from *S. frugiperda*. In other aspects of this embodiment, a nucleic acid molecule expressed in a *S. frugiperda* cell or a cell line derived from *S. frugiperda* comprises, e.g., the open reading frame of SEQ ID NO: 59, SEQ ID NO: 60 or SEQ ID NO: 61. In an aspect of this embodiment, a nucleic acid molecule disclosed in the present specification is expressed in a *T. ni* cell or a cell line derived from *T. ni*. In other aspects of this embodiment, a nucleic acid molecule expressed in a *T. ni* cell or a cell line derived from *T. ni* comprises, e.g., the open reading frame of SEQ ID NO: 59, SEQ ID NO: 60 or SEQ ID NO: 61. In an aspect of this embodiment, a nucleic acid molecule disclosed in the present specification is expressed in a *M. sexta* strain or a cell line derived from *M. sexta*. In an aspect of this embodiment, a nucleic acid molecule disclosed in the present specification is expressed in a Sf9 cell line. In other aspects of this embodiment, a nucleic acid molecule expressed in a Sf9 cell line comprises, e.g., the open reading frame of SEQ ID NO: 59, SEQ ID NO: 60 or SEQ ID NO: 61. In an aspect of this embodiment, a nucleic acid molecule disclosed in the present specification is expressed in a Sf21 cell line. In other aspects of this embodiment, a nucleic acid molecule expressed in a Sf21 cell line comprises, e.g., the open reading frame of SEQ ID NO: 59, SEQ ID NO: 60 or SEQ ID NO: 61. In an aspect of this embodiment, a nucleic acid molecule disclosed in the present specification is expressed in a High-Five cell line. In other aspects of this embodiment, a nucleic acid molecule expressed in a High-Five cell line comprises, e.g., the open reading frame of SEQ ID NO: 59, SEQ ID NO: 60 or SEQ ID NO: 61. In an aspect of this embodiment, a nucleic acid molecule disclosed in the present specification is expressed in a Schneider's *Drosophila* line 2 (S2) cell line. In other aspects of this embodiment, a nucleic acid molecule expressed in a Schneider's *Drosophila* line 2 (S2) cell line comprises, e.g., the open reading frame of SEQ ID NO: 56, SEQ ID NO: 57 or SEQ ID NO: 58. In an aspect of this embodiment, a nucleic acid molecule disclosed in the present specification is expressed in a Kc cell line. In other aspects of this embodiment, a nucleic acid molecule expressed in a Kc cell line comprises, e.g., the open reading frame of SEQ ID NO: 56, SEQ ID NO: 57 or SEQ ID NO: 58.

In yet another embodiment, nucleic acid sequence molecules comprising a modified open reading frame providing increased expression of the encoded active BoNT/E is expressed in a fish cell or a cell line derived from a fish cell. Non-limiting examples of fish cells and cell lines derived from fish cells include those derived from, e.g., Danio rerio. In an aspect of this embodiment, a nucleic acid molecule disclosed in the present specification is expressed in a *D. rerio* cell or a cell line derived from *D. rerio*. In other aspects of this embodiment, a nucleic acid molecule expressed in a *D. rerio* cell or a cell line derived from *D. rerio* comprises, e.g., the open reading frame of SEQ ID NO: 62, SEQ ID NO: 63 or SEQ ID NO: 64.

In yet another embodiment, nucleic acid sequence molecules comprising a modified open reading frame providing increased expression of the encoded active BoNT/E is expressed in an amphibian cell. Non-limiting examples of amphibian cells and cell lines derived from amphibian cells include those derived from, e.g., *Xenopus*. In an aspect of this embodiment, a nucleic acid molecule disclosed in the present specification is expressed in a *X. laevis* cell or a cell line derived from *X. laevis*. In other aspects of this embodiment, a nucleic acid molecule expressed in a *X. laevis* cell or a cell line derived from *X. laevis* comprises, e.g., the open reading frame of SEQ ID NO: 65, SEQ ID NO: 66 or SEQ ID NO: 67. In another aspect of this embodiment, a nucleic acid molecule disclosed in the present specification is expressed in a *X. tropicalis* cell or a cell line derived from *X. tropicalis*. In other aspects of this embodiment, a nucleic acid molecule expressed in a *X. tropicalis* cell or a cell line derived from *X. tropicalis* comprises, e.g., the open reading frame of SEQ ID NO: 68, SEQ ID NO: 69 or SEQ ID NO: 70.

In yet another embodiment, nucleic acid sequence molecules comprising a modified open reading frame providing increased expression of the encoded active BoNT/E is expressed in a bird cell. Non-limiting examples of bird cells and cell lines derived from bird cells include those derived from, e.g., *Gallus gallus*. In an aspect of this embodiment, a nucleic acid molecule disclosed in the present specification is expressed in a *G. gallus* cell or a cell line derived from *G. gallus*. In other aspects of this embodiment, a nucleic acid molecule expressed in a *G. gallus* cell or a cell line derived from *G.gallus* comprises, e.g., the open reading frame of SEQ ID NO: 71, SEQ ID NO: 72 or SEQ ID NO: 73.

In yet another embodiment, nucleic acid sequence molecules comprising a modified open reading frame providing increased expression of the encoded active BoNT/E is expressed in a mammalian cell. Non-limiting examples of mammalian cells and cell lines derived from mammalian cells include those derived from, e.g., mouse, rat, hamster, porcine, bovine, equine, primate and human. In an aspect of this embodiment, a nucleic acid molecule disclosed in the present specification is expressed in a mouse cell or a cell line derived from mouse. In other aspects of this embodiment, a nucleic acid molecule expressed in a mouse cell or a cell line derived from mouse comprises, e.g., the open reading frame of SEQ ID NO: 74, SEQ ID NO: 75 or SEQ ID NO: 76. In yet another aspect of this embodiment, a nucleic acid molecule disclosed in the present specification is expressed in a *Mus musculus* cell or a cell line derived from *M. musculus*. In yet other aspects of this embodiment, a nucleic acid molecule expressed in a *M. musculus* cell or a cell line derived from *M. musculus* comprises, e.g., the open reading frame of SEQ ID NO: 74, SEQ ID NO: 75 or SEQ ID NO: 76. In an aspect of this embodiment, a nucleic acid molecule disclosed in the present specification is expressed in a 10T1/2 cell line. In other aspects of this embodiment, a nucleic acid molecule expressed in a 10T1/2cell line comprises, e.g., the open reading frame of SEQ ID NO: 74, SEQ ID NO: 75 or SEQ ID NO: 76. In another aspect of this embodiment, a nucleic acid molecule disclosed in the present specification is expressed in a BALB/3T3 cell line. In yet other aspects of this embodiment, a nucleic acid molecule expressed in a BALB/3T3 cell line comprises, e.g., the open reading frame of SEQ ID NO: 74, SEQ ID NO: 75 or SEQ ID NO: 76. In another aspect of this embodiment, a nucleic acid molecule disclosed in the present specification is expressed in a L-M cell line. In yet other aspects of this embodiment, a nucleic acid molecule expressed in a L-M cell line comprises, e.g., the open reading frame of SEQ ID NO: 74, SEQ ID NO: 75 or SEQ ID NO: 76. In another aspect of this embodiment, a nucleic acid molecule disclosed in the present specification is expressed in a NB4 cell line. In yet other aspects of this embodiment, a nucleic acid molecule expressed in a NB4 cell line comprises, e.g., the open reading frame of SEQ ID NO: 74, SEQ ID NO: 75 or SEQ ID NO: 76. In another aspect of this embodiment, a nucleic acid molecule disclosed in the present specification is expressed in a 1A3 cell line. In yet other aspects of this embodiment, a nucleic acid molecule expressed in a 1A3 cell line comprises, e.g., the open reading frame of SEQ ID NO: 74, SEQ ID NO: 75 or SEQ ID NO: 76. In another aspect of this embodiment, a nucleic acid molecule disclosed in the present specification is expressed in a NIE-115 cell line. In yet other aspects of this embodiment, a nucleic acid molecule expressed in a NIE-115 cell line comprises, e.g., the open reading frame of SEQ ID NO: 74, SEQ ID NO: 75 or SEQ ID NO: 76. In another aspect of this embodiment, a nucleic acid molecule disclosed in the present specification is expressed in a NG108-15 cell line. In yet other aspects of this embodiment, a nucleic acid molecule expressed in a NG108-15 cell line comprises, e.g., the open reading frame of SEQ ID NO: 74, SEQ ID NO: 75 or SEQ ID NO: 76. In another aspect of this embodiment, a nucleic acid molecule disclosed in the present specification is expressed in a NIH3T3 cell line. In yet other aspects of this embodiment, a nucleic acid molecule expressed in a NIH3T3 cell line comprises, e.g., the open reading frame of SEQ ID NO: 74, SEQ ID NO: 75 or SEQ ID NO: 76. In another aspect of this embodiment, a nucleic acid molecule disclosed in the present specification is expressed in a NCTC cell line. In yet other aspects of this embodiment, a nucleic acid molecule expressed in a NCTC cell line comprises, e.g., the open reading frame of SEQ ID NO: 74, SEQ ID NO: 75 or SEQ ID NO: 76. In another aspect of this embodiment, a nucleic acid molecule disclosed in the present specification is expressed in a Neuro-2A cell line. In yet other aspects of this embodiment, a nucleic acid molecule expressed in a Neuro-2A cell line comprises, e.g., the open reading frame of SEQ ID NO: 74, SEQ ID NO: 75 or SEQ ID NO: 76.

In an aspect of this embodiment, a nucleic acid molecule disclosed in the present specification is expressed in a rat cell or a cell line derived from rat. In other aspects of this embodiment, a nucleic acid molecule expressed in a rat cell or a cell line derived from rat comprises, e.g., the open reading frame of SEQ ID NO: 77, SEQ ID NO: 78 or SEQ ID NO: 79. In yet another aspect of this embodiment, a nucleic acid molecule disclosed in the present specification is expressed in a *Rattus norvegicus* cell or a cell line derived from *R. norvegicus*. In yet another aspect of this embodiment, a nucleic acid molecule expressed in a *R. norvegicus* cell or a cell line derived from *R. norvegicus* comprises, e.g., the open reading frame of SEQ ID NO: 77, SEQ ID NO: 78 or SEQ ID NO: 79. In an aspect of this embodiment, a nucleic acid molecule disclosed in the present specification is expressed in a PC12 cell line. In other aspects of this embodiment, a nucleic acid molecule expressed in a PC12 cell line comprises, e.g., the open reading frame of SEQ ID NO: 77, SEQ ID NO: 78 or SEQ ID NO: 79. In another aspect of this embodiment, a nucleic acid molecule disclosed in the present specification is expressed in a GH1 cell line. In yet other aspects of this embodiment, a nucleic acid molecule expressed in a GH1 cell line comprises, e.g., the open reading frame of SEQ ID NO: 77, SEQ ID NO: 78 or SEQ ID NO: 79. In another aspect of this embodiment, a nucleic acid molecule disclosed in the present specification is expressed in a GH3 cell line. In yet other aspects of this embodiment, a nucleic acid molecule expressed in a GH3 cell line comprises, e.g., the open reading frame of SEQ ID NO: 77, SEQ ID NO: 78 or SEQ ID NO: 79. In another aspect of this embodiment, a nucleic acid molecule disclosed in the present specification is expressed in a C6 cell line. In yet other aspects of this embodiment, a nucleic acid molecule expressed in a C6 cell line comprises, e.g., the open reading frame of SEQ ID NO: 77, SEQ ID NO: 78 or SEQ ID NO: 79. In another aspect of this embodiment, a nucleic acid molecule disclosed in the present specification is expressed in a L2 cell line. In yet other aspects of this embodiment, a nucleic acid molecule expressed in a L2 cell line comprises, e.g., the open reading frame of SEQ ID NO: 77, SEQ ID NO: 78 or SEQ ID NO: 79.

In an aspect of this embodiment, a nucleic acid molecule disclosed in the present specification is expressed in a hamster cell or a cell line derived from hamster. In other aspects of this embodiment, a nucleic acid molecule expressed in a hamster cell or a cell line derived from hamster comprises, e.g., the open reading frame of SEQ ID NO: 80, SEQ ID NO: 81 or SEQ ID NO: 82. In yet another aspect of this embodiment, a nucleic acid molecule disclosed in the present specification is expressed in a *Cricetulus griseus* cell or a cell line derived from *C. griseus*. In yet other aspects of this embodiment, a nucleic acid molecule expressed in a *C. griseus* cell or a cell line derived from *C. griseus* comprises, e.g., the open reading frame of SEQ ID NO: 80, SEQ ID NO: 81 or SEQ ID NO: 82. In an aspect of this embodiment, a nucleic acid molecule disclosed in the present specification is expressed in a CHO cell line. In other aspects of this embodiment, a nucleic acid molecule expressed in a CHO cell line comprises, e.g., the open reading frame of SEQ ID NO: 80, SEQ ID NO: 81 or SEQ ID NO: 82. In another aspect of this embodiment, a nucleic acid molecule disclosed in the present specification is expressed in a 6E6 cell line. In yet other aspects of this embodiment, a nucleic acid molecule expressed in a 6E6 cell line comprises, e.g., the open reading frame of SEQ ID NO: 80, SEQ ID NO: 81 or SEQ ID NO: 82.

In an aspect of this embodiment, a nucleic acid molecule disclosed in the present specification is expressed in a porcine cell or a cell line derived from porcine. In other aspects of this embodiment, a nucleic acid molecule expressed in a porcine cell or a cell line derived from porcine comprises, e.g., the open reading frame of SEQ ID NO: 83, SEQ ID NO: 84 or SEQ ID NO: 85. In yet another aspect of this embodiment, a nucleic acid molecule disclosed in the present specification is expressed in a *Sus scrofa* cell or a cell line derived from *S. scrofa*. In yet other aspects of this embodiment, a nucleic acid molecule expressed in a *S. scrofa* cell or a cell line derived from *S. scrofa* comprises, e.g., the open reading frame of SEQ ID NO: 83, SEQ ID NO: 84 or SEQ ID NO: 85. In an aspect of this embodiment, a nucleic acid molecule disclosed in the present specification is expressed in a PK15 cell line. In other aspects of this embodiment, a nucleic acid molecule expressed in a PK15 cell line comprises, e.g., the open reading frame of SEQ ID NO: 83, SEQ ID NO: 84 or SEQ ID NO: 85. In another aspect of this embodiment, a nucleic acid molecule disclosed in the present specification is expressed in a LLC-PK1 cell line. In yet other aspects of this embodiment, a nucleic acid molecule expressed in a LLC-PK1 cell line comprises, e.g., the open reading frame of SEQ ID NO: 83, SEQ ID NO: 84 or SEQ ID NO: 85. In another aspect of this embodiment, a nucleic acid molecule disclosed in the present specification is expressed in a ST cell line. In yet other aspects of this embodiment, a nucleic acid molecule expressed in a ST cell line comprises, e.g., the open reading frame of SEQ ID NO: 83, SEQ ID NO: 84 or SEQ ID NO: 85. In another aspect of this embodiment, a nucleic acid molecule disclosed in the present specification is expressed in a ESK-4 cell line. In yet other aspects of this embodiment, a nucleic acid molecule expressed in a ESK-4 cell line comprises, e.g., the open reading frame of SEQ ID NO: 83, SEQ ID NO: 84 or SEQ ID NO: 85.

In an aspect of this embodiment, a nucleic acid molecule disclosed in the present specification is expressed in a bovine cell or a cell line derived from bovine. In other aspects of this embodiment, a nucleic acid molecule expressed in a bovine cell or a cell line derived from bovine comprises, e.g., the open reading frame of SEQ ID NO: 86, SEQ ID NO: 87 or SEQ ID NO: 88. In yet another aspect of this embodiment, a nucleic acid molecule disclosed in the present specification is expressed in a *Bos taurus* cell or a cell line derived from *B. taurus*. In yet other aspects of this embodiment, a nucleic acid molecule expressed in a *B. taurus* cell or a cell line derived from *B. taurus* comprises, e.g., the open reading frame of SEQ ID NO: 86, SEQ ID NO: 87 or SEQ ID NO: 88. In an aspect of this embodiment, a nucleic acid molecule disclosed in the present specification is expressed in a CPAE cell line. In other aspects of this embodiment, a nucleic acid molecule expressed in a CPAE cell line comprises, e.g., the open reading frame of SEQ ID NO: 86, SEQ ID NO: 87 or SEQ ID NO: 88. In another aspect of this embodiment, a nucleic acid molecule disclosed in the present specification is expressed in a BT cell line. In yet other aspects of this embodiment, a nucleic acid molecule expressed in a BT cell line comprises, e.g., the open reading frame of SEQ ID NO: 86, SEQ ID NO: 87 or SEQ ID NO: 88. In another aspect of this embodiment, a nucleic acid molecule disclosed in the present specification is expressed in a SBAC cell line. In yet other aspects of this embodiment, a nucleic acid molecule expressed in a SBAC cell line comprises, e.g., the open reading frame of SEQ ID NO: 86, SEQ ID NO: 87 or SEQ ID NO: 88. In another aspect of this embodiment, a nucleic acid molecule disclosed in the present specification is expressed in a FB2 cell line. In yet other aspects of this embodiment, a nucleic acid molecule expressed in a FB2 cell line comprises, e.g., the open reading frame of SEQ ID NO: 86, SEQ ID NO: 87 or SEQ ID NO: 88.

In an aspect of this embodiment, a nucleic acid molecule disclosed in the present specification is expressed in a equine cell or a cell line derived from equine. In other aspects of this embodiment, a nucleic acid molecule expressed in a equine cell or a cell line derived from equine comprises, e.g., the open reading frame of SEQ ID NO: 89, SEQ ID NO: 90 or SEQ ID NO: 91. In yet another aspect of this embodiment, a nucleic acid molecule disclosed in the present specification is expressed in a *Equus caballus* cell or a cell line derived from *E. caballus*. In yet other aspects of this embodiment, a nucleic acid molecule expressed in a *E. caballus* cell or a cell line derived from *E. caballus* comprises, e.g., the open reading frame of SEQ ID NO: 89, SEQ ID NO: 90 or SEQ ID NO: 91.

In an aspect of this embodiment, a nucleic acid molecule disclosed in the present specification is expressed in a NBL-6 cell line. In other aspects of this embodiment, a nucleic acid molecule expressed in a NBL-6 cell line comprises, e.g., the open reading frame of SEQ ID NO: 89, SEQ ID NO: 90 or SEQ ID NO: 91.

In an aspect of this embodiment, a nucleic acid molecule disclosed in the present specification is expressed in a primate cell or a cell line derived from primate. In other aspects of this embodiment, a nucleic acid molecule expressed in a primate cell or a cell line derived from primate comprises, e.g., the open reading frame of SEQ ID NO: 92, SEQ ID NO: 93 or SEQ ID NO: 94. In yet another aspect of this embodiment, a nucleic acid molecule disclosed in the present specification is expressed in a *Cercopithecus aethiops* cell or a cell line derived from *C. aethiops*. In yet other aspects of this embodiment, a nucleic acid molecule expressed in a *C. aethiops* cell or a cell line derived from *C. aethiops* comprises, e.g., the open reading frame of SEQ ID NO: 92, SEQ ID NO: 93 or SEQ ID NO: 94. In an aspect of this embodiment, a nucleic acid molecule disclosed in the present specification is expressed in a COS-1 cell line. In other aspects of this embodiment, a nucleic acid molecule expressed in a COS-1 cell line comprises, e.g., the open reading frame of SEQ ID NO: 92, SEQ ID NO: 93 or SEQ ID NO: 94. In another aspect of this embodiment, a nucleic acid molecule disclosed in the present specification is expressed in a COS-7 cell line. In yet other aspects of this embodiment, a nucleic acid molecule expressed in a COS-7 cell line comprises, e.g., the open reading frame of SEQ ID NO: 92, SEQ ID NO: 93 or SEQ ID NO: 94. In another aspect of this embodiment, a nucleic acid molecule disclosed in the present specification is expressed in a VV-1 cell line. In yet other aspects of this embodiment, a nucleic acid molecule expressed in a VV-1 cell line comprises, e.g., the open reading frame of SEQ ID NO: 92, SEQ ID NO: 93 or SEQ ID NO: 94.

In an aspect of this embodiment, a nucleic acid molecule disclosed in the present specification is expressed in a human cell or a cell line derived from human. In another aspect of this embodiment, a nucleic acid molecule expressed in a human cell or a cell line derived from human comprises, e.g., the open reading frame of SEQ ID NO: 95, SEQ ID NO: 96 or SEQ ID NO: 97. In yet another aspect of this embodiment, a nucleic acid molecule disclosed in the present specification is expressed in a *Homo sapiens* cell or a cell line derived from *H. sapiens*. In another aspect of this embodiment, a nucleic acid molecule expressed in a *H. sapiens* cell or a cell line derived from *H. sapiens* comprises, e.g., the open reading frame of SEQ ID NO: 95, SEQ ID NO: 96 or SEQ ID NO: 97. In an aspect of this embodiment, a nucleic acid molecule disclosed in the present specification is expressed in a SH-SY5Y cell line. In other aspects of this embodiment, a nucleic acid molecule expressed in a SH-SY5Y cell line comprises, e.g., the open reading frame of SEQ ID NO: 95, SEQ ID NO: 96 or SEQ ID NO: 97. In another aspect of this embodiment, a nucleic acid molecule disclosed in the present specification is expressed in a SK-N-DZ cell line. In yet other aspects of this embodiment, a nucleic acid molecule expressed in a SK-N-DZ cell line comprises, e.g., the open reading frame of SEQ ID NO: 95, SEQ ID NO: 96 or SEQ ID NO: 97. In another aspect of this embodiment, a nucleic acid molecule disclosed in the present specification is expressed in a SK-N-SH cell line. In yet other aspects of this embodiment, a nucleic acid molecule expressed in a SK-N-SH cell line comprises, e.g., the open reading frame of SEQ ID NO: 95, SEQ ID NO: 96 or SEQ ID NO: 97. In another aspect of this embodiment, a nucleic acid molecule disclosed in the present specification is expressed in a BE(2)-C cell line. In yet other aspects of this embodiment, a nucleic acid molecule expressed in a BE(2)-C cell line comprises, e.g., the open reading frame of SEQ ID NO: 95, SEQ ID NO: 96 or SEQ ID NO: 97. In another aspect of this embodiment, a nucleic acid molecule disclosed in the present specification is expressed in a HeLa cell line. In yet other aspects of this embodiment, a nucleic acid molecule expressed in a HeLa cell line comprises, e.g., the open reading frame of SEQ ID NO: 95, SEQ ID NO: 96 or SEQ ID NO: 97. In another aspect of this embodiment, a nucleic acid molecule disclosed in the present specification is expressed in a HEK 293 cell line. In yet other aspects of this embodiment, a nucleic acid molecule expressed in a HEK 293 cell line comprises, e.g., the open reading frame of SEQ ID NO: 95, SEQ ID NO: 96 or SEQ ID NO: 97. In another aspect of this embodiment, a nucleic acid molecule disclosed in the present specification is expressed in a MCF-7 cell line. In yet other aspects of this embodiment, a nucleic acid molecule expressed in a MCF-7 cell line comprises, e.g., the open reading frame of SEQ ID NO: 95, SEQ ID NO: 96 or SEQ ID NO: 97. In another aspect of this embodiment, a nucleic acid molecule disclosed in the present specification is expressed in a HepG2 cell line. In yet other aspects of this embodiment, a nucleic acid molecule expressed in a HepG2 cell line comprises, e.g., the open reading frame of SEQ ID NO: 95, SEQ ID NO: 96 or SEQ ID NO: 97. In another aspect of this embodiment, a nucleic acid molecule disclosed in the present specification is expressed in a HL-60 cell line. In yet other aspects of this embodiment, a nucleic acid molecule expressed in a HL-60 cell line comprises, e.g., the open reading frame of SEQ ID NO: 95, SEQ ID NO: 96 or SEQ ID NO: 97. In another aspect of this embodiment, a nucleic acid molecule disclosed in the present specification is expressed in a IMR-32 cell line. In yet other aspects of this embodiment, a nucleic acid molecule expressed in a IMR-32 cell line comprises, e.g., the open reading frame of SEQ ID NO: 95, SEQ ID NO: 96 or SEQ ID NO: 97. In another aspect of this embodiment, a nucleic acid molecule disclosed in the present specification is expressed in a SW-13 cell line. In yet other aspects of this embodiment, a nucleic acid molecule expressed in a SW-13 cell line comprises, e.g., the open reading frame of SEQ ID NO: 95, SEQ ID NO: 96 or SEQ ID NO: 97. In another aspect of this embodiment, a nucleic acid molecule disclosed in the present specification is expressed in a CHP3 cell line. In yet other aspects of this embodiment, a nucleic acid molecule expressed in a CHP3 cell line comprises, e.g., the open reading frame of SEQ ID NO: 95, SEQ ID NO: 96 or SEQ ID NO: 97.

The nucleic acid molecules disclosed in the present specification include, in part, a modified open reading frame providing increased expression of an encoded active BoNT/E. Increased expression of an active BoNT/E is determined by comparing the amount of an active BoNT/E expressed from a modified open reading frame with the amount of the same active BoNT/E expressed from an unmodified open reading frame in an otherwise identical nucleic acid molecule. As used herein, the term "modified open reading frame" means an open reading frame that contains at least one nucleotide change providing increased expression of the encoded active BoNT/E. As used herein, the term "unmodified open reading frame" means an open reading frame that does not contain any nucleotide changes providing increased expression of the encoded active BoNT/E. As a non-limiting example, SEQ ID NO: 3 and SEQ ID NO: 98 are unmodified open reading frames that will not provide increased expression of the encoded active BoNT/E in a heterologous cell and SEQ ID NO: 4 through SEQ ID NO: 97, SEQ ID NO: 117, SEQ ID NO: 122 and SEQ ID NO: 124 are modified open reading frames that can provide increased expression of the encoded active BoNT/E in the appropriate heterologous cell. It is further understood by one skilled in the art that the methods and procedures used to express the nucleic acid molecules comprising the modified open reading frame should be the same or similar to the methods and procedures used to express the nucleic acid molecules comprising the unmodified open reading frame to ensure accurate and consistent comparisons.

A wide variety of well-established methods can be used to compare the amount of expressed active BoNT/E from a modified open reading frame to the amount of the same active BoNT/E expressed from an unmodified open reading frame in an otherwise identical nucleic acid molecule. Comparisons of amounts of an active BoNT/E expressed can be either qualitative or quantitative.

Active BoNT/E amounts can be measured using any procedure that can separate and visualize proteins from a cell lystae, such as, e.g., procedures involving gel electrophoresis and protein staining, western blotting, protein-labeling, as well as, other procedures involving protein separation and visualization. Thus, amounts of active BoNT/E can be appraised by labeling active BoNT/E using a radioactive amino acid tracer and visualizing expression by autoradiography after gel electrophoresis. Likewise, incorporation of radiolabeled amino acids into active BoNT/E can be measured by scintillation counting after Trichloroacetic Acid (TCA) precipitation. Amounts of active BoNT/E can also be assessed by staining proteins separated by gel electrophoresis using, e.g., dye staining procedures like Coomassie Brilliant Blue and Colloidal Coomassie Brilliant Blue; fluorescence staining procedures like SYPRO® Ruby and ruthenium II; or silver staining procedures. Amounts of active BoNT/E can likewise be determined by antibody staining after Western blot analysis. Furthermore, functional assays that measure the biological activity of active BoNT/E can be used to compare amounts of active BoNT/E expressed from a modified open reading frame to the amount of the same active BoNT/E expressed from an unmodified open reading frame in an otherwise identical nucleic acid molecule, such as, e.g., SNAP25 cleavage assay and the GFP-SNAP25 Fluorescence Release Assay. Non-limiting examples of specific procedures to separate and visualize protein amounts, as well as well-characterized reagents, conditions and protocols are readily available from commercial vendors that include, without limitation, Amersham Biosciences, Piscataway, N.J.; Bio-Rad Laboratories, Hercules, Calif.; Pierce Biotechnology, Inc., Rockford, Ill.; Promega Corporation, Madison, Wis., and Stratagene, La Jolla, Calif. In addition, non-limiting examples of specific protocols necessary to separate, visualize and quantify a protein are described in e.g., MOLECULAR CLONING A LABORATORY MANUAL, supra, (2001); and CURRENT PROTOCOLS IN MOLECULAR BIOLOGY, supra, (2004). These protocols are routine procedures within the scope of one skilled in the art and from the teaching herein.

Active BoNT/E amounts can be measured after one or more purification steps using, without limitation, gel electrophoresis and protein staining, western blotting, protein-labeling, UV absorbance, the Lowry assay, the biuret assay, the Smith copper/bicinchoninic (BCA) assay, and the Bradford dye assay, see e.g., Christine V. Sapan et al., *Colorimetric Protein Assay Techniques,* 29(2) BIOTECHNOL. APPL. BIOCHEM. 99-108, (1999). Any of a variety of methods can be used for purifying an active BoNT/E disclosed in the present specification. Examples of purification methods include, without limitation, ammonium sulfate or ethanol precipitation, acid extraction, ion exchange chromatography, phosphocellulose chromatography, lectin chromatography, affinity chromatography, hydrophobic interaction chromatography, size exclusion chromatography, gel-filtration chromatography, adsorption chromatography, hydroxyapatite chromatography, fast performance liquid chromatography (FPLC), and high performance liquid (HPLC) chromatography. Binding moieties of the target peptide of interest may be attached to any of a variety of substances including, without limitation resins, agarose, and magnetic beads. In addition, any of a variety of processing techniques can be used including, without limitation, batch-wise processing, and gravity-feed columns. Protein refolding steps may also be necessary to ensure recovery of a functionally active BoNT/E encoded by nucleic acid molecules disclosed in the specification. Non-limiting examples of specific protocols for purifying and recovering proteins are described in, e.g., John Abelson et al., GUIDE TO PROTEIN PURIFICATION, (Academic Press, 1990), PROTEIN PURIFICATION: PRINCIPLES AND PRACTICE, (Robert K. Scopes et al. eds., Springer Verlag, 3rd ed. 1994), PROTEIN PURIFICATION TECHNIQUES: A PRACTICAL APPROACH, (Simon Roe ed., Oxford University Press, 2nd ed. 2001), MOLECULAR CLONING A LABORATORY MANUAL, supra, (2001), Ian M. Rosenberg, PROTEIN ANALYSIS & PURIFICATION: BENCHTOP TECHNIQUES, (Springer Verlag, 2002). These protocols are routine procedures within the scope of one skilled in the art and from the teaching herein.

Thus, in an embodiment, the amount of an active BoNT/E expressed from a modified open reading frame is increased as compared to the amount of the same active BoNT/E expressed from an unmodified open reading frame in an otherwise identical nucleic acid molecule. In aspects of this embodiment, the amount of an active BoNT/E expressed from a modified open reading frame is, e.g., increased at least 1.5-fold as compared to the amount of the same BoNT/E expressed from an unmodified open reading frame in an otherwise identical nucleic acid molecule; increased at least 2-fold as compared to the amount of the same BoNT/E expressed from an unmodified open reading frame in an otherwise identical nucleic acid molecule; increased at least 3-fold as compared to the amount of the same BoNT/E expressed from an unmodified open reading frame in an otherwise identical nucleic acid molecule; increased at least 4-fold as compared to the amount of the same BoNT/E expressed from an unmodified open reading frame in an otherwise identical nucleic acid molecule; increased at least 5-fold as compared to the amount of the same BoNT/E expressed from an unmodified open reading frame in an otherwise identical nucleic acid molecule; increased at least 10-fold as compared to the amount of the same BoNT/E expressed from an unmodified open reading frame in an otherwise identical nucleic acid molecule; increased at least 25-fold as compared to the amount of the same BoNT/E expressed from an unmodified open reading frame in an otherwise identical nucleic acid molecule; increased at least 50-fold as compared to the amount of the same BoNT/E expressed from an unmodified open reading frame in an otherwise identical nucleic acid molecule; increased at least 100-fold as compared to the amount of the same BoNT/E expressed from an unmodified open reading frame in an otherwise identical nucleic acid molecule; or increased at least 200-fold as compared to the amount of the same BoNT/E expressed from an unmodified open reading frame in an otherwise identical nucleic acid molecule.

In aspects of this embodiment, the amount of an active BoNT/E expressed from a modified open reading frame is, e.g., increased at most 1.5-fold as compared to the amount of the same BoNT/E expressed from an unmodified open reading frame in an otherwise identical nucleic acid molecule;

increased at most 2-fold as compared to the amount of the same BoNT/E expressed from an unmodified open reading frame in an otherwise identical nucleic acid molecule; increased at most 3-fold as compared to the amount of the same BoNT/E expressed from an unmodified open reading frame in an otherwise identical nucleic acid molecule; increased at most 4-fold as compared to the amount of the same BoNT/E expressed from an unmodified open reading frame in an otherwise identical nucleic acid molecule; increased at most 5-fold as compared to the amount of the same BoNT/E expressed from an unmodified open reading frame in an otherwise identical nucleic acid molecule; increased at most 10-fold as compared to the amount of the same BoNT/E expressed from an unmodified open reading frame in an otherwise identical nucleic acid molecule; increased at most 25-fold as compared to the amount of the same BoNT/E expressed from an unmodified open reading frame in an otherwise identical nucleic acid molecule; increased at most 50-fold as compared to the amount of the same BoNT/E expressed from an unmodified open reading frame in an otherwise identical nucleic acid molecule; increased at most 100-told as compared to the amount of the same BoNT/E expressed from an unmodified open reading frame in an otherwise identical nucleic acid molecule; or increased at most 200-fold as compared to the amount of the same BoNT/E expressed from an unmodified open reading frame in an otherwise identical nucleic acid molecule.

Other aspects of the present invention provide expression constructs comprising a nucleic acid molecule disclosed in the present specification, operably-linked to an expression vector useful for expressing the nucleic acid molecule in a heterologous cell. A wide variety of expression vectors are envisioned, including, without limitation, a prokaryotic expression vector useful for expressing a nucleic acid molecule comprising a modified open reading frame providing increased expression of the encoded active BoNT/E in a prokaryotic cell; a yeast expression vector useful for expressing a nucleic acid molecule comprising a modified open reading frame providing increased expression of the encoded active BoNT/E in a yeast cell; an insect expression vector useful for expressing a nucleic acid molecule comprising a modified open reading frame providing increased expression of the encoded active BoNT/E in an insect cell; a mammalian expression vector useful for expressing a nucleic acid molecule comprising a modified open reading frame providing increased expression of the encoded active BoNT/E in a mammalian cell.

The expression constructs disclosed in the present specification include, in part, a nucleic acid molecule. In is envisioned that any and all nucleic acid molecules disclosed in the present specification can be used. Thus, aspects of this embodiment include, without limitation, nucleic acid molecules comprising a modified open reading frame providing increased expression of the encoded active BoNT/E in a prokaryotic cell; nucleic acid molecules comprising a modified open reading frame providing increased expression of the encoded active BoNT/E in a yeast cell; nucleic acid molecules comprising a modified open reading frame providing increased expression of the encoded active BoNT/E in an slime mold cell; nucleic acid molecules comprising a modified open reading frame providing increased expression of the encoded active BoNT/E in a plant cell or cell line derived from a plant cell; nucleic acid molecules comprising a modified open reading frame providing increased expression of the encoded active BoNT/E in an insect cell or cell line derived from an insect cell; nucleic acid molecules comprising a modified open reading frame providing increased expression of the encoded active BoNT/E in an fish cell or cell line derived from a fish cell; nucleic acid molecules comprising a modified open reading frame providing increased expression of the encoded active BoNT/E in an amphibian cell or cell line derived from an amphibian cell; nucleic acid molecules comprising a modified open reading frame providing increased expression of the encoded active BoNT/E in a bird cell or cell line derived from a bird cell; and nucleic acid molecules comprising a modified open reading frame providing increased expression of the encoded active BoNT/E in a mammalian cell or cell line derived from a mammalian cell, such as, e.g., mouse, rat, hamster, porcine, bovine, equine, primate and human.

The expression constructs disclosed in the present specification include, in part, a heterologous cell. In is envisioned that any and all heterologous cells disclosed in the present specification can be used. Thus, aspects of this embodiment include, without limitation, prokaryotic cells prokaryotic cells including, without limitation, strains of aerobic, microaerophilic, capnophilic, facultative, anaerobic, gram-negative and gram-positive bacterial cells such as those derived from, e.g., *Escherichia coli, Salmonella typhimurium, Bacillus subtilis, Bacillus licheniformis, Clostridia perfringens, Clostridia difficile, Bacteroides fragilis, Caulobacter crescentus, Methylobacterium extorquens, Lactococcus lactis* and *Neisseria meningirulls*; and eukaryotic cells including, without limitation, yeast strains, such as, e.g., those derived from *Pichia pastoris, Pichia methanolica, Pichia angusta, Schizosaccharomyces pombe, Saccharomyces cerevisiae* and *Yarrowia lipolytica*; slime mold strains, such as, e.g., those derived from, e.g., *Dictyostelium discoideum*; plant cells and cell lines derived from plant cells, such as, e.g., those derived from species of monocots, species of dicots, *Zea mays* and *Arabidopsis thaliana*; insect cells and cell lines derived from insects, such as, e.g., those derived from *Spodoptera frugiperda, Trichoplusia ni, Drosophila melanogaster* and *Manduca sexta*; fish cells and cell lines derived from fish cells, such as, e.g., those derived from *Denio renia*; amphibian cells and cell lines derived from amphibian cells, such as, e.g., those derived from *Xenopus laevis* and *Xenopus tropicalis*; bird cells and cell lines derived from bird cells, such as, e.g., those derived from *Gallus gallus*; mammalian cells and cell lines derived from mammalian cells, such as, e.g., those derived from mouse, rat, hamster, porcine, bovine, equine, primate and human.

The expression constructs disclosed in the present specification include, in part, a nucleic acid molecule disclosed in the present specification, operably-linked to an expression vector. As used herein, the term "operably linked" means any of a variety of cloning methods that can join a nucleic acid molecule disclosed in the present specification to an expression vector such that a peptide encoded by the nucleic acid molecule is expressed when introduced into a heterologous cell. Well-established molecular biology techniques that may be necessary to make an expression construct disclosed in the present specification including, but not limited to, procedures involving polymerase chain reaction (PCR) amplification restriction enzyme reactions, agarose gel electrophoresis, nucleic acid ligation, bacterial transformation, nucleic acid purification, nucleic acid sequencing are routine procedures well within the scope of one skilled in the art and from the teaching herein. Non-limiting examples of specific protocols necessary to make an expression construct are described in e.g., MOLECULAR CLONING A LABORATORY MANUAL, supra, (2001); and CURRENT PROTOCOLS IN MOLECULAR BIOLOGY (Frederick M. Ausubel et al., eds. John Wiley & Sons, 2004), which are hereby incorporated by reference. These protocols are routine procedures well within the scope of one skilled in the art and from the teaching herein.

A wide variety of expression vectors can be employed for expressing an open reading frame encoding an active BoNT/E and include without limitation, viral expression vectors, prokaryotic expression vectors and eukaryotic expression vectors including yeast, insect, plant and mammalian expression vectors. Non-limiting examples of expression vectors, along with well-established reagents and conditions for making and using an expression construct from such expression vectors are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; EMD Biosciences-Novagen, Madison, Wis.; QIAGEN, Inc., Valencia, Calif.; and Stratagene, La Jolla, Calif. The selection, making and use of an appropriate expression vector are routine procedures well within the scope of one skilled in the art and from the teachings herein.

It is envisioned that any of a variety of expression systems may be useful for expressing constructs disclosed in the present specification. An expression system encompasses both cell-based systems and cell-free expression systems. Cell-based systems include, without limited, viral expression systems, prokaryotic expression systems, yeast expression systems, baculoviral expression systems, insect expression systems and mammalian expression systems. Cell-free systems include, without limitation, wheat germ extracts, rabbit reticulocyte extracts and *E. coli* extracts and generally are equivalent to the method disclosed herein. Expression using an expression system can include any of a variety of characteristics including, without limitation, inducible expression, non-inducible expression, constitutive expression, viral-mediated expression, stably-integrated expression, and transient expression. Expression systems that include well-characterized vectors, reagents, conditions and cells are well-established and are readily available from commercial vendors that include, without limitation, Ambion, Inc. Austin, Tex.; BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; Roche Applied Science, Indianapolis, Ind.; and Stratagene, La Jolla, Calif. Non-limiting examples on the selection and use of appropriate heterologous expression systems are described in e.g., PROTEIN EXPRESSION. A PRACTICAL APPROACH (S. J. Higgins and B. David Hames eds., Oxford University Press, 1999); Joseph M. Fernandez & James P. Hoeffler, GENE EXPRESSION SYSTEMS. USING NATURE FOR THE ART OF EXPRESSION (Academic Press, 1999); and Meena Rai & Harish Padh, *Expression Systems for Production of Heterologous Proteins,* 80(9) CURRENT SCIENCE 1121-1128, (2001), which are hereby incorporated by reference. These protocols are routine procedures well within the scope of one skilled in the art and from the teaching herein.

Thus, in an embodiment disclosed in the present invention, a nucleic acid molecule disclosed in the present specification is operably linked to control sequences from a viral expression vector useful for expressing an encoded active BoNT/E in a viral expression system. Non-limiting examples of viral expression vector include lentivirus vectors, fowl pox virus, pseudorabies virus, retrovirus vectors, semliki forest virus vectors, sindbis virus vectors, vaccinia virus vectors, and adenovirus vectors. In an aspect of this embodiment, an expression construct comprises a viral expression vector operably linked to a modified open reading frame providing increased expression of an encoded active BoNT/E in a mammalian cell.

In another embodiment disclosed in the present invention, a nucleic acid molecule disclosed in the present specification is operably linked to control sequences from a prokaryotic expression vector useful for expressing an encoded active BoNT/E in a prokaryotic cell. Non-limiting examples of prokaryotic expression vectors include an *Escherichia coli* expression vector, a *Salmonella typhimurium* expression vector, a *Caulobacter crescentus* expression vector, a *Methylobacterium extorquens* expression vector, a *Lactococcus lactis* expression vector, a *Neisseria meningirulls* expression vector, a *Bacillus subtilis* expression vector and a *Bacillus licheniformis* expression vector. In an aspect of this embodiment, an expression construct comprises a prokaryotic expression vector operably linked to a modified open reading frame providing increased expression of an encoded active BoNT/E in a prokaryotic cell. In an aspect of this embodiment, an expression construct comprises a pET28 expression vector and a modified open reading frame providing increased expression of an encoded active BoNT/E in an *E. coli* cell. In another aspect of this embodiment, an expression construct comprises a pET28 expression vector operably linked to a modified open reading frame of SEQ ID NO: 4 providing increased expression of the encoded active BoNT/E in an *E. coli* cell. In another aspect of this embodiment, an expression construct comprises a pET28 expression vector operably linked to a modified open reading frame of SEQ ID NO: 5 providing increased expression of the encoded active BoNT/E in an *E. coli* cell. In another aspect of this embodiment, an expression construct comprises a pET28 expression vector operably linked to a modified open reading frame of SEQ ID NO: 6 providing increased expression of the encoded active BoNT/E in an *E. coli* cell. In another aspect of this embodiment, an expression construct comprises a pET28 expression vector operably linked to a modified open reading frame of SEQ ID NO: 7 providing increased expression of the encoded active BoNT/E in an *E. coli* cell. In another aspect of this embodiment, an expression construct comprises a pET29 expression vector operably linked to a modified open reading frame of SEQ ID NO: 4 providing increased expression of the encoded active BoNT/E in an *E. coli* cell. In another aspect of this embodiment, an expression construct comprises a pET29 expression vector operably linked to a modified open reading frame of SEQ ID NO: 5 providing increased expression of the encoded active BoNT/E in an *E. coli* cell. In another aspect of this embodiment, an expression construct comprises a pET29 expression vector operably linked to a modified open reading frame of SEQ ID NO: 6 providing increased expression of the encoded active BoNT/E in an *E. coli* cell. In another aspect of this embodiment, an expression construct comprises a pET29 expression vector operably linked to a modified open reading frame of SEQ ID NO: 7 providing increased expression of the encoded active BoNT/E in an *E. coli* cell. In another aspect of this embodiment, an expression construct comprises a pRSET expression vector operably linked to a modified open reading frame of SEQ ID NO: 4 providing increased expression of the encoded active BoNT/E in an *E. coli* cell. In another aspect of this embodiment, an expression construct comprises a pRSET expression vector operably linked to a modified open reading frame of SEQ ID NO: 5 providing increased expression of the encoded active BoNT/E in an *E. coli* cell. In another aspect of this embodiment, an expression construct comprises a pRSET expression vector operably linked to a modified open reading frame of SEQ ID NO: 6 providing increased expression of the encoded active BoNT/E in an *E. coli* cell. In another aspect of this embodiment, an expression construct comprises a pRSET expression vector operably linked to a modified open reading frame of SEQ ID NO: 7 providing increased expression of the encoded active BoNT/E in an *E. coli* cell.

In yet another embodiment disclosed in the present invention, expression constructs disclosed in the present specification are operably linked to control sequences from a eukaryotic expression vector useful for expressing an encoded active BoNT/E in an eukaryotic cell. In an aspect of this embodiment, a nucleic acid molecule disclosed in the present specification is operably linked to control sequences from a yeast expression vector useful for expressing an encoded BoNT/E in a yeast cell. Non-limiting examples of yeast expression vectors include a *Pichia pastoris* expression vector, a *Pichia methanolica* expression vector, a *Pichia angusta* expression vector, a *Schizosaccharomyces pombe* expression vector, a *Saccharomyces cerevisiae* expression vector and a *Yarrowia lipolytica* expression vector. In an aspect of this embodiment, an expression construct comprises a yeast expression vector operably linked to a modified open reading frame providing increased expression of an encoded active BoNT/E in a yeast cell. In an aspect of this embodiment, an expression construct comprises a pPICZ A expression vector and a modified open reading frame providing increased expression of an encoded active BoNT/E in a *P. pastoris* cell. In another aspect of this embodiment, an expression construct comprises a pPICZ A expression vector operably linked to a modified open reading frame of SEQ ID NO: 35 providing increased expression of the encoded active BoNT/E in a *P. pastoris* cell. In another aspect of this embodiment, an expression construct comprises a pPICZ A expression vector operably linked to a modified open reading frame of SEQ ID NO: 36 providing increased expression of the encoded active BoNT/E in a *P. pastoris* cell. In another aspect of this embodiment, an expression construct comprises a pPICZ A expression vector operably linked to a modified open reading frame of SEQ ID NO: 37 providing increased expression of the encoded active BoNT/E in a *P. pastoris* cell.

In yet another aspect of this embodiment, a nucleic acid molecule disclosed in the present specification is operably linked to control sequences from an insect expression vector useful for expressing an encoded active BoNT/E in an insect cell. Non-limiting examples of an insect expression vector include a *Spodoptera frugiperda* expression vector, a *Trichoplusia ni* expression vector, a *Drosophila melanogaster* expression vector and a *Manduca sexta* expression vector. In an aspect of this embodiment, an expression construct comprises an insect expression vector operably linked to a modified open reading frame providing increased expression of an encoded active BoNT/E in an insect cell or cell line derived from an insect cell. In an aspect of this embodiment, an expression construct comprises a pFastBac™HT expression vector and a modified open reading frame providing increased expression of an encoded active BoNT/E in an insect cell line, such as, e.g., Sf9, Sf21 and High-Five. In another aspect of this embodiment, an expression construct comprises a pFastBac™HT expression vector operably linked to a modified open reading frame of SEQ ID NO: 59 providing increased expression of the encoded active BoNT/E in an insect cell line, such as, e.g., Sf9, Sf21 and High-Five. In another aspect of this embodiment, an expression construct comprises a pFastBac™HT expression vector operably linked to a modified open reading frame of SEQ ID NO: 60 providing increased expression of the encoded active BoNT/E in an insect cell line, such as, e.g., Sf9, Sf21 and High-Five. In another aspect of this embodiment, an expression construct comprises a pFastBac™HT expression vector operably linked to a modified open reading frame of SEQ ID NO: 61 providing increased expression of the encoded active BoNT/E in an insect cell line, such as, e.g., Sf9, Sf21 and High-Five.

In an aspect of this embodiment, an expression construct comprises a pMT/BiP-V5-His/GFP expression vector and a modified open reading frame providing increased expression of an encoded active BoNT/E in an insect cell line, such as, e.g., Schneider's *Drosophila* line 2 (S2) and Kc. In another aspect of this embodiment, an expression construct comprises a pMT/BiP-V5-His/GFP expression vector operably linked to a modified open reading frame of SEQ ID NO: 56 providing increased expression of the encoded active BoNT/E in an insect cell line, such as, e.g., Schneider's *Drosophila* line 2 (S2) and Kc. In another aspect of this embodiment, an expression construct comprises a pMT/BiP-V5-His/GFP expression vector operably linked to a modified open reading frame of SEQ ID NO: 57 providing increased expression of the encoded active BoNT/E in an insect cell line, such as, e.g., Schneider's *Drosophila* line 2 (S2) and Kc. In another aspect of this embodiment, an expression construct comprises a pMT/BiP-V5-His/GFP expression vector operably linked to a modified open reading frame of SEQ ID NO: 58 providing increased expression of the encoded active BoNT/E in an insect cell line, such as, e.g., Schneider's *Drosophila* line 2 (S2) and Kc.

In yet another aspect of this embodiment, a nucleic acid molecule disclosed in the present specification is operably linked to control sequences from a mammalian expression vector useful for expressing an encoded active BoNT/E in a mammalian cell or cell line derived from a mammalian cell. Non-limiting examples of mammalian expression vectors include a mouse expression vector, a rat expression vector, a hamster expression vector, a porcine expression vector, a bovine expression vector, an equine expression vector, a primate expression vector and a human expression vector. In an aspect of this embodiment, an expression construct comprises a mammalian expression vector operably linked to a modified open reading frame providing increased expression of an encoded active BoNT/E in a mammalian cell or cell line derived from a mammalian cell.

In an aspect of this embodiment, an expression construct comprises a mouse expression vector operably linked to a modified open reading frame providing increased expression of an encoded active BoNT/E in a mouse cell or cell line derived from a mouse cell. In an aspect of this embodiment, an expression construct comprises a pQBI25fC1 expression vector and a modified open reading frame providing increased expression of an encoded active BoNT/E in a mouse cell line, such as, e.g., 10T1/2, BALB/3T3, L-M, NB4 1A3, NIE-115, NG108-15, NIH3T3, NCTC and Neuro 2A. In another aspect of this embodiment, an expression construct comprises a pQBI25fC1 expression vector operably linked to a modified open reading frame of SEQ ID NO: 74 providing increased expression of the encoded active BoNT/E in a mouse cell line, such as, e.g., 10T1/2, BALB/3T3, L-M, NB4 1A3, NIE-115, NG108-15, NIH3T3, NCTC and Neuro 2A. In another aspect of this embodiment, an expression construct comprises a pQBI25fC1 expression vector operably linked to a modified open reading frame of SEQ ID NO: 75 providing increased expression of the encoded active BoNT/E in a mouse cell line, such as, e.g., 10T1/2, BALB/3T3, L-M, NB4 1A3, NIE-115, NG108-15, NIH3T3, NCTC and Neuro 2A. In another aspect of this embodiment, an expression construct comprises a pQBI25fC1 expression vector operably linked to a modified open reading frame of SEQ ID NO: 76 providing increased expression of the encoded active BoNT/E in a mouse cell line, such as, e.g., 10T1/2, BALB/3T3, L-M, NB4 1A3, NIE-115, NG108-15, NIH3T3, NCTC and Neuro 2A.

In an aspect of this embodiment, an expression construct comprises a rat expression vector operably linked to a modified open reading frame providing increased expression of an encoded active BoNT/E in a rat cell or cell line derived from a rat cell. In an aspect of this embodiment, an expression construct comprises a pQBI25fC1 expression vector and a modified open reading frame providing increased expression of an encoded active BoNT/E in a rat cell line, such as, e.g., PC12, GH1, GH3, C6 and L2. In another aspect of this embodiment, an expression construct comprises a pQBI25fC1 expression vector operably linked to a modified open reading frame of SEQ ID NO: 77 providing increased expression of the encoded active BoNT/E in a rat cell line, such as, e.g., PC12, GH1, GH3, C6 and L2. In another aspect of this embodiment, an expression construct comprises a pQBI25fC1 expression vector operably linked to a modified open reading frame of SEQ ID NO: 78 providing increased expression of the encoded active BoNT/E in a rat cell line, such as, e.g., PC12, GH1, GH3, C6 and L2. In another aspect of this embodiment, an expression construct comprises a pQBI25fC1 expression vector operably linked to a modified open reading frame of SEQ ID NO: 79 providing increased expression of the encoded active BoNT/E in a rat cell line, such as, e.g., PC12, GH1, GH3, C6 and L2.

In an aspect of this embodiment, an expression construct comprises a hamster expression vector operably linked to a modified open reading frame providing increased expression of an encoded active BoNT/E in a hamster cell or cell line derived from a hamster cell. In an aspect of this embodiment, an expression construct comprises a pQBI25fC1 expression vector and a modified open reading frame providing increased expression of an encoded active BoNT/E in a hamster cell line, such as, e.g., CHO and 6E6. In another aspect of this embodiment, an expression construct comprises a pQBI25fC1 expression vector operably linked to a modified open reading frame of SEQ ID NO: 80 providing increased expression of the encoded active BoNT/E in a hamster cell line, such as, e.g., CHO and 6E6.

In another aspect of this embodiment, an expression construct comprises a pQBI25fC1 expression vector operably linked to a modified open reading frame of SEQ ID NO: 81 providing increased expression of the encoded active BoNT/E in a hamster cell line, such as, e.g., CHO and 6E6. In another aspect of this embodiment, an expression construct comprises a pQBI25fC1 expression vector operably linked to a modified open reading frame of SEQ ID NO: 82 providing increased expression of the encoded active BoNT/E in a hamster cell line, such as, e.g., CHO and 6E6.

In an aspect of this embodiment, an expression construct comprises a primate expression vector operably linked to a modified open reading frame providing increased expression of an encoded active BoNT/E in a primate cell or cell line derived from a primate cell. In an aspect of this embodiment, an expression construct comprises a pQBI25fC1 expression vector and a modified open reading frame providing increased expression of an encoded active BoNT/E in a primate cell line, such as, e.g., COS-1, COS-7 and VV-1. In another aspect of this embodiment, an expression construct comprises a pQBI25fC1 expression vector operably linked to a modified open reading frame of SEQ ID NO: 92 providing increased expression of the encoded active BoNT/E in a primate cell line, such as, e.g., COS-1, COS-7 and VV-1. In another aspect of this embodiment, an expression construct comprises a pQBI25fC1 expression vector operably linked to a modified open reading frame of SEQ ID NO: 93 providing increased expression of the encoded active BoNT/E in a primate cell line, such as, e.g., COS-1, COS-7 and VV-1. In another aspect of this embodiment, an expression construct comprises a pQBI25fC1 expression vector operably linked to a modified open reading frame of SEQ ID NO: 94 providing increased expression of the encoded active BoNT/E in a primate cell line, such as, e.g., COS-1, COS-7 and VV-1.

In an aspect of this embodiment, an expression construct comprises a human expression vector operably linked to a modified open reading frame providing increased expression of an encoded active BoNT/E in a human cell or cell line derived from a human cell. In an aspect of this embodiment, an expression construct comprises a pQBI25fC1 expression vector and a modified open reading frame providing increased expression of an encoded active BoNT/E in a primate cell line, such as, e.g., SH-SY5Y, SK-N-DZ, SK-N-F1, SK-N-SH, BE (2)-C, HeLa, HEK 293, MCF-7, HepG2, HL-60, IMR-32, SW-13 and CHP3. In another aspect of this embodiment, an expression construct comprises a pQBI25fC1 expression vector operably linked to a modified open reading frame of SEQ ID NO: 95 providing increased expression of the encoded active BoNT/E in a primate cell line, such as, e.g., SH-SY5Y, SK-N-DZ, SK-N-F1, SK-N-SH, BE (2)-C, HeLa, HEK 293, MCF-7, HepG2, HL-60, IMR-32, SW-13 and CHP3. In another aspect of this embodiment, an expression construct comprises a pQBI25fC1 expression vector operably linked to a modified open reading frame of SEQ ID NO: 96 providing increased expression of the encoded active BoNT/E in a primate cell line, such as, e.g., SH-SY5Y, SK-N-DZ, SK-N-F1, SK-N-SH, BE (2)-C, HeLa, HEK 293, MCF-7, HepG2, HL-60, IMR-32, SW-13 and CHP3. In another aspect of this embodiment, an expression construct comprises a pQBI25fC1 expression vector operably linked to a modified open reading frame of SEQ ID NO: 97 providing increased expression of the encoded active BoNT/E in a primate cell line, such as, e.g., SH-SY5Y, SK-N-DZ, SK-N-F1, SK-N-SH, BE (2)-C, HeLa, HEK 293, MCF-7, HepG2, HL-60, IMR-32, SW-13 and CHP3.

Aspects of the present invention further provide cells comprising an expression construct disclosed in the present specification. It is envisioned that a cell can include, without limitation, a prokaryotic cell containing a prokaryotic expression construct useful for expressing a nucleic acid molecule comprising a modified open reading frame providing increased expression of the encoded active BoNT/E in a prokaryotic cell; a yeast cell containing a yeast expression construct useful for expressing a nucleic acid molecule comprising a modified open reading frame providing increased expression of the encoded active BoNT/E in a yeast cell; an insect cell containing an insect expression construct useful for expressing a nucleic acid molecule comprising a modified open reading frame providing increased expression of the encoded active BoNT/E in an insect cell; and a mammalian cell containing a mammalian expression construct useful for expressing a nucleic acid molecule comprising a modified open reading frame providing increased expression of the encoded active BoNT/E in a mammalian cell.

The cells disclosed in the present specification include, in part, an expression construct. In is envisioned that any and all expression constructs disclosed in the present specification can be used. Thus, aspects of this embodiment include, without limitation, cells comprising a viral expression vector operably linked to a modified open reading frame providing increased expression of an encoded active BoNT/E in a mammalian cell; a prokaryotic expression vector operably linked to a modified open reading frame providing increased expression of an encoded active BoNT/E in a prokaryotic cell; cells comprising a yeast expression vector operably linked to a modified open reading frame providing increased expression of an encoded active BoNT/E in a yeast cell; cells comprising a slime mold expression vector operably linked to a modified open reading frame providing increased expression of an encoded active BoNT/E in an slime mold cell; cells comprising a plant expression vector operably linked to a modified open reading frame providing increased expression of an encoded active BoNT/E in a plant cell or cell line derived from a plant cell; cells comprising an insect expression vector operably linked to a modified open reading frame providing increased expression of the encoded active BoNT/E in an insect cell or cell line derived from an insect cell; cells comprising a fish expression vector operably linked to a modified open reading frame providing increased expression of an encoded active BoNT/E in an fish cell or cell line derived from a fish cell; cells comprising an amphibian expression vector operably linked to a modified open reading frame providing increased expression of an encoded active BoNT/E in an amphibian cell or cell line derived from an amphibian cell; cells comprising a bird expression vector operably linked to a modified open reading frame providing increased expression of an encoded active BoNT/E in a bird cell or cell line derived from a bird cell; and cells comprising a mammalian expression vector operably linked to a modified open reading frame providing increased expression of an encoded active BoNT/E in a mammalian cell or cell line derived from a mammalian cell, such as, e.g., mouse, rat, hamster, porcine, bovine, equine, primate and human. Other aspects of this embodiment include, without limitation, expression constructs comprising a modified open reading frame that comprises any one of SEQ ID NO: 4 through SEQ ID NO: 97, SEQ ID NO: 117, SEQ ID NO: 122 or SEQ ID NO: 124.

The cells disclosed in the present specification include, in part, a heterologous cell. In is envisioned that any and all heterologous cells disclosed in the present specification can be used. Thus, aspects of this embodiment include, without limitation, prokaryotic cells prokaryotic cells including, without limitation, strains of aerobic, microaerophilic, capnophilic, facultative, anaerobic, gram-negative and gram-positive bacterial cells such as those derived from, e.g., *Escherichia coli, Salmonella typhimurium, Bacillus subtilis, Bacillus licheniformis, Clostridia perfringens, Clostridia difficile, Bacteroides fragilis, Caulobacter crescentus, Methylobacterium extorquens, Lactococcus lactis*and *Neisseria Meningirulls*; and eukaryotic cells including, without limitation, yeast strains, such as, e.g., those derived from *Pichia pastoris, Pichia methanolica, Pichia angusta, Schizosaccharomyces pombe, Saccharomyces cerevisiae*and *Yarrowia lipolytica*; slime mold strains , such as, e.g., those derived from, e.g., *Dictyostelium discoideum*; plant cells and cell lines derived from plant cells, such as, e.g., those derived from species of monocots, species of dicots, *Zea mays* and *Arabidopsis thaliana*; insect cells and cell lines derived from insects, such as, e.g., those derived from *Spodoptera frugiperda, Trichoplusia ni, Drosophila melanogaster* and *Manduca sexta*; fish cells and cell lines derived from fish cells, such as, e.g., those derived from *Denio renia*; amphibian cells and cell lines derived from amphibian cells, such as, e.g., those derived from *Xenopus laevis* and *Xenopus tropicalis*; bird cells and cell lines derived from bird cells, such as, e.g., those derived from *Gallus gallus*; mammalian cells and cell lines derived from mammalian cells, such as, e.g., those derived from mouse, rat, hamster, porcine, bovine, equine, primate and human. Cell lines may be obtained from the American Type Culture Collection (2004); European Collection of Cell Cultures (2004); and the German Collection of Microorganisms and Cell Cultures (2004). Non-limiting examples of specific protocols for selecting, making and using an appropriate cell line are described in e.g., Insect Cell Culture Engineering (Mattheus F. A. Goosen et al. eds., Marcel Dekker, 1993); Insect Cell Cultures: Fundamental and Applied Aspects (J. M. Vlak et al. eds., Kluwer Academic Publishers, 1996); Maureen A. Harrison & Ian F. Rae, General Techniques of Cell Culture (Cambridge University Press, 1997); Cell and Tissue Culture: Laboratory Procedures (Alan Doyle et al eds., John Wiley and Sons, 1998); R. Ian Freshney, Culture of Animal Cells: A Manual of Basic Technique (Wiley-Liss, 4th ed. 2000); Animal Cell Culture: A Practical Approach (John R. W. Masters ed., Oxford University Press, 3rd ed. 2000); Molecular Cloning A Laboratory Manual, supra, (2001); Basic Cell Culture: A Practical Approach (John M. Davis, Oxford Press, 2nd ed. 2002); and Current Protocols in Molecular Biology, supra, (2004). These protocols are routine procedures within the scope of one skilled in the art and from the teaching herein.

It is envisioned that any and all methods for introducing an expression construct disclosed in the present specification into a cell can be used. A cell disclosed in the present specification can maintain an expression construct transiently or stably. Stably-maintained constructs may be extra-chromosomal and replicate autonomously, or they may be integrated into the chromosomal material of the cell and replicate non-autonomously. Methods useful for introducing a nucleic acid molecule into a cell including, without limitation, calcium phosphate-mediated, DEAE dextran-mediated, lipid-mediated, polybrene-mediated, polylysine-mediated, viral-mediated, microinjection, protoplast fusion, biolistic, and electroporation, see, e.g., Introducing Cloned Genes into Cultured Mammalian Cells, pp. 16. 1-16. 62 (Sambrook & Russell, eds., Molecular Cloning A Laboratory Manual, Vol. 3, 3rd ed. 2001). One skilled in the art understands that selection of a specific method to introduce an expression construct into a cell will depend, in part, on whether the cell will transiently contain an expression construct or whether the cell will stably contain an expression construct. These protocols are routine procedures within the scope of one skilled in the art and from the teaching herein.

In an aspect of this embodiment, a chemical-mediated method, termed transfection, is used to introduce a construct expressing an active BoNT/E into a heterologous cell. In chemical-mediated methods of transfection the chemical reagent forms a complex with the nucleic acid that facilitates its uptake into the cells. Such chemical reagents include, without limitation, calcium phosphate-mediated, see, e.g., Martin Jordan & Florian Worm, Transfection of adherent and suspended cells by calcium phosphate, 33(2) Methods 136-143 (2004); diethy-laminoethyl (DEAE) dextran-mediated, lipid-mediated, cationic polymer-mediated like polyethyleneimine (PEI)-mediated and polylysine-mediated and polybrene-mediated, see, e.g., Chun Zhang et al., Polyethylenimine strategies for plasmid delivery to brain-derived cells, 33(2) Methods 144-150 (2004). Such chemical-mediated delivery systems can be prepared by standard methods and are commercially available, see, e.g., CellPhect Transfection Kit, a DEAE-Dextran reagent, (Amersham Biosciences, Piscataway, N.J.); Mammalian Transfection Kit, Calcium phosphate and DEAE Dextran, (Stratagene, Inc., La Jolla, Calif.);-LIPOFECTAMINE™ Transfection Reagent, a cationic liposome based reagent, (Invitrogen, Inc., Carlsbad, Calif.); EXGEN™ 500 Transfection kit, a 22 kDa linear polyethylenimine (PEI) reagent, (Fermentas, Inc., Hanover, MD), and SUPERFECT®, an activated-dendrimer reagent, and EFFECTENE™, a non-liposomal lipid reagent, Transfection Kits (Qiagen, Inc., Valencia, Calif.).

In another aspect of this embodiment, a physical-mediated method is used to introduce a construct expressing an active BoNT/E into a heterologous cell. Physical reagents include, without limitation, electroporation, biolistic and microinjection. Biolistics and microinjection techniques perforate the cell wall in order to introduce the nucleic acid molecule into the cell, see, e.g., Jeike E. Biewenga et al., Plasmid-mediated gene transfer in neurons using the biolistics technique, 71 (1) J. Neurosci. Methods. 67-75 (1997); and John O'Brien & Sarah C. R. Lummis, Biolistic and diolistic transfection: using the gene gun to deliver DNA and lipophilic dyes into mammalian cells, 33(2) Methods 121-125 (2004). Electroporation, also termed electropermeabilization, uses brief, high-voltage, electrical pulses to create transient pores in the membrane through which the nucleic acid molecules enter and be used effectively for stable and transient transfections of all cell types, see, e.g., M. Golzio et al., In vitro and in vivo electric field-mediated permeabilization, gene transfer, and expression, 33(2) Methods 126-135 (2004); and Oliver Greschet al., New non-viral method for gene transfer into primary cells, 33(2) Methods 151-163 (2004).

In another aspect of this embodiment, a viral-mediated method, termed transduction, is used to introduce a construct expressing an active BoNT/E into a heterologous cell. In viral-mediated methods of transient transduction, the process by which viral particles infect and replicate in a host cell has been manipulated in order to use this mechanism to introduce a nucleic acid molecule into the cell. Viral-mediated methods have been developed from a wide variety of viruses including, without limitation, retroviruses, adenoviruses, adeno-associated viruses, herpes simplex viruses, picornaviruses, alphaviruses and baculoviruses, see, e.g., Armin Blesch, Lentiviral and MLV based retroviral vectors for ex vivo and in vivo gene transfer, 33(2) Methods 164-172 (2004); and Maurizio Federico, From lentiviruses to lentivirus vectors, 229 Methods Mol. Biol. 3-15 (2003); E. M. Poeschla, Non-primate lentiviral vectors, 5(5) Curr. Opin. Mol. Ther. 529-540 (2003); Karim Benihoud et al, Adenovirus vectors for gene delivery, 10(5) Curr. Opin. Biotechnol. 440-447 (1999); H. Bueler, Adeno-associated viral vectors for gene transfer and gene therapy, 380(6) Biol. Chem. 613-622 (1999); Chooi M. Lai et al., Adenovirus and adeno-associated virus vectors, 21(12) DNA Cell Biol. 895-913 (2002); Edward A. Burton et al., Gene delivery using herpes simplex virus vectors, 21(12) DNA Cell Biol. 915-936 (2002); Paola Grandi et al., Targeting HSV amplicon vectors, 33(2) Methods 179-186 (2004); Ilya Frolov et al., Alphavirus-based expression vectors: strategies and applications, 93(21) Proc. Natl. Acad. Sci. U.S.A. 11371-11377 (1996); Markus U. Ehrengruber, Alphaviral gene transfer in neurobiology, 59(1) Brain Res. Bull. 13-22 (2002); Thomas A. Kost & J. Patrick Condreay, Recombinant baculoviruses as mammalian cell gene-delivery vectors, 20(4) Trends Biotechnol. 173-180 (2002); and A. Huser & C. Hofmann, Baculovirus vectors: novel mammalian cell gene-delivery vehicles and their applications, 3(1) Am. J. Pharmacogenomics 53-63 (2003).

Adenoviruses, which are non-enveloped, double-stranded DNA viruses, are often selected for mammalian cell transduction because adenoviruses handle relatively large nucleic acid molecules of about 36 kd, are produced at high titer, and can efficiently infect a wide variety of both dividing and non-dividing cells, see, e.g., Wim T. J. M. C. Hermens et al., Transient gene transfer to neurons and glia: analysis of adenoviral vector performance in the CNS and PNS, 71(1) J. Neurosci. Methods 85-98 (1997); and Hiroyuki Mizuguchi et al., Approaches for generating recombinant adenovirus vectors, 52(3) Adv. Drug Deliv. Rev. 165-176 (2001). Transduction using adenoviral-based system do not support prolonged protein expression because the nucleic acid molecule is carried from an episome in the cell nucleus, rather than being integrated into the host cell chromosome. Adenovirual vector systems and specific protocols for how to use such vectors are disclosed in, e.g., VIRAPOWER™ Adenoviral Expression System, a E1 and E3-deleted, pDEST-based expression vector controlled by a human cytomegalovirus (CMV) promoter, (Invitrogen, Inc., Carlsbad, Calif.) and VIRAPOWER™ Adenoviral Expression System Instruction Manual 25-0543 version A, Invitrogen, Inc., (Jul. 15, 2002); and ADEASY™ Adenoviral Vector System, an Ad5 virus-based expression vector, (Stratagene, Inc., La Jolla, Calif.) and ADEASY™ Adenoviral Vector System Instruction Manual 064004f, Stratagene, Inc.

Nucleic acid molecule delivery can also use single-stranded RNA retroviruses viruses, such as, e.g., oncoretroviruses and lentiviruses. Retroviral-mediated transduction often produce transduction efficiencies close to 100%, can easily control the proviral copy number by varying the multiplicity of infection (MOI), and can be used to either transiently or stably transduce cells, see, e.g., Tiziana Tonini et al., Transient production of retroviral- and lentiviral-based vectors for the transduction of Mammalian cells, 285 Methods Mol. Biol. 141-148 (2004); Armin Blesch, Lentiviral and MLV based retroviral vectors for ex vivo and in vivo gene transfer, 33(2) Methods 164-172 (2004); Felix Recillas-Targa, Gene transfer and expression in mammalian cell lines and transgenic animals, 267 Methods Mol. Biol. 417-433 (2004); and Roland Wolkowicz et al., Lentiviral vectors for the delivery of DNA into mammalian cells, 246 Methods Mol. Biol. 391-411 (2004). Retroviral particles consist of an RNA genome packaged in a protein capsid, surrounded by a lipid envelope. The retrovirus infects a host cell by injecting its RNA into the cytoplasm along with the reverse transcriptase enzyme. The RNA template is then reverse transcribed into a linear, double stranded cDNA that replicates itself by integrating into the host cell genome. Viral particles are spread both vertically (from parent cell to daughter cells via the provirus) as well as horizontally (from cell to cell via virions). This replication strategy enables long-term persist expression since the nucleic acid molecules of interest are stably integrated into a chromosome of the host cell, thereby enabling long-term expression of the protein. For instance, animal studies have shown that lentiviral vectors injected into a variety of tissues produced sustained protein expression for more than 1 year, see, e.g., Luigi Naldini et al., In vivo gene delivery and stable transduction of non-dividing cells by a lentiviral vector, 272(5259) Science 263-267 (1996). The Oncoretroviruses-derived vector systems, such as, e.g., Moloney murine leukemia virus (MoMLV), are widely used and infect many different non-dividing cells. Lentiviruses can also infect many different cell types, including dividing and non-dividing cells and possess complex envelope proteins, which allows for highly specific cellular targeting.

Retroviral vectors and specific protocols for how to use such vectors are disclosed in, e.g., U.S. Pat. Nos. Manfred Gossen & Hermann Bujard, Tight control of gene expression in eukaryotic cells by tetracycline-responsive promoters, U.S. Pat. No. 5,464,758 (Nov. 7, 1995) and Hermann Bujard & Manfred Gossen, Methods for regulating gene expression, U.S. Pat. No. 5,814,618 (Sep. 29, 1998) David S. Hogness, Polynucleotides encoding insect steroid hormone receptor polypeptides and cells transformed with same, U.S. Pat. No. 5,514,578 (May 7, 1996) and David S. Hogness, Polynucleotide encoding insect ecdysone receptor, U.S. Pat. No. 6,245,531 (Jun. 12, 2001); Elisabetta Vegeto et al., Progesterone receptor having C. terminal hormone binding domain truncations, U.S. Pat. No. 5,364,791 (Nov. 15, 1994), Elisabetta Vegeto et al., Mutated steroid hormone receptors, methods for their use and molecular switch for gene therapy, U.S. Pat. No. 5,874,534 (Feb. 23, 1999) and Elisabetta Vegeto et al., Mutated steroid hormone receptors, methods for their use and molecular switch for gene therapy, U.S. Pat. No. 5,935,934 (Aug. 10, 1999). Furthermore, such viral delivery systems can be prepared by standard methods and are commercially available, see, e.g., BD™ Tet-Off and Tet-On Gene Expression Systems, a tetracycline-inducible mammalian adenovirus-based expression vector, (BD Biosciences-Clonetech, Palo Alto, Calif.) and BD™ Tet-Off and Tet-On Gene Expression Systems User Manual, PT3001-1, BD Biosciences Clonetech, (Mar. 14, 2003), GENESWITCH™ System, an inducible mammalian adenovirus-based expression vector, (Invitrogen, Inc., Carlsbad, Calif.) and GENESWITCH™ System A Mifepristone-Regulated Expression System for Mammalian Cells version D, 25-0313, Invitrogen, Inc., (Nov. 4, 2002); VIRAPOWER™ Lentiviral Expression System, a replication-incomplete, HIV-1-based lentivirus expression vector, (Invitrogen, Inc., Carlsbad, Calif.) and VIRAPOWER™ Lentiviral Expression System Instruction Manual 25-0501 version E, Invitrogen, Inc., (Dec. 8, 2003); and COMPLETE CONTROL® Retroviral Inducible Mammalian Expression System, an ecdysone-inducible lentivirus-based mammalian expression vector, (Stratagene, La Jolla, Calif.) and COMPLETE CONTROL® Retroviral Inducible Mammalian Expression System Instruction Manual, 064005e.

Thus, in an embodiment, a cell comprises a mammalian cell comprising an expression construct operably linked to a nucleic acid molecule comprising a modified open reading frame providing increased expression of the encoded active BoNT/E in a mammalian cell. In an aspect of this embodiment, a cell comprises a mammalian cell transiently containing an expression construct operably linked to a nucleic acid molecule comprising a modified open reading frame providing increased expression of the encoded active BoNT/E in a mammalian cell. In another aspect of this embodiment, a cell comprises a mammalian cell stably containing an expression construct operably linked to a nucleic acid molecule comprising a modified open reading frame providing increased expression of the encoded active BoNT/E in a mammalian cell. In yet another aspect of this embodiment, an expression construct is a viral expression construct. In further aspect of this embodiment, a viral expression construct is a lentivirus expression construct, a fowl pox virus expression construct, a pseudorabies virus expression construct, a retrovirus expression construct, a semliki forest virus expression construct, a sindbis virus expression construct, a vaccinia virus expression construct, or an adenovirus expression construct. In yet other aspect of this embodiment, a nucleic acid molecule comprises any of the modified open reading frames of SEQ ID NO: 56 through SEQ ID NO: 97.

Thus, in an embodiment, a cell comprises a prokaryotic cell comprising an expression construct operably linked to a nucleic acid molecule comprising a modified open reading frame providing increased expression of the encoded active BoNT/E in a prokaryotic cell. In an aspect of this embodiment, a cell comprises a prokaryotic cell transiently containing an expression construct operably linked to a nucleic acid molecule comprising a modified open reading frame providing increased expression of the encoded active BoNT/E in a prokaryotic cell. In another aspect of this embodiment, a cell comprises a prokaryotic cell stably containing an expression construct operably linked to a nucleic acid molecule comprising a modified open reading frame providing increased expression of the encoded active BoNT/E in a prokaryotic cell. In a further aspect of this embodiment, a prokaryotic cell is derived from an aerobic bacterium, a microaerophilic bacterium, a capnophilic bacterium, a facultative bacterium, an anaerobic bacterium, a gram-negative bacterium or a gram-positive bacterium. In a further aspect of this embodiment, a prokaryotic cell is a prokaryotic strain derived from *Escherichia coli, Salmonella typhimurium, Bacillus subtilis, Bacillus licheniformis, Clostridia perfringens, Clostridia difficile, Bacteroides fragilis, Caulobacter crescentus, Methylobacterium extorquens, Lactococcus lactis* or *Neisseria meningirulls*. In yet another aspect of this embodiment, an expression construct is a prokaryotic expression construct. In yet another aspect of this embodiment, a nucleic acid molecule comprises any of the modified open reading frames of SEQ ID NO: 4 through SEQ ID NO: 34, SEQ ID NO: 117, SEQ ID NO: 122 and SEQ ID NO: 124.

In an embodiment, a cell comprises an eukaryotic cell comprising an expression construct operably linked to a nucleic acid molecule comprising a modified open reading frame providing increased expression of the encoded active BoNT/E in an eukaryotic cell. In an aspect of this embodiment, a cell comprises an eukaryotic cell transiently containing an expression construct operably linked to a nucleic acid molecule comprising a modified open reading frame providing increased expression of the encoded active BoNT/E in an eukaryotic cell. In another aspect of this embodiment, a cell comprises an eukaryotic cell stably containing an expression construct operably linked to a nucleic acid molecule comprising a modified open reading frame providing increased expression of the encoded active BoNT/E in an eukaryotic cell. In yet another aspect of this embodiment, an expression construct is an eukaryotic expression construct. In yet other aspect of this embodiment, a nucleic acid molecule comprises any of the modified open reading frames of SEQ ID NO: 35 through SEQ ID NO: 97.

In an embodiment, a cell comprises a yeast cell comprising an expression construct operably linked to a nucleic acid molecule comprising a modified open reading frame providing increased expression of the encoded active BoNT/E in a yeast cell. In an aspect of this embodiment, a cell comprises a yeast cell transiently containing an expression construct operably linked to a nucleic acid molecule comprising a modified open reading frame providing increased expression of the encoded active BoNT/E in a yeast cell. In another aspect of this embodiment, a cell comprises a yeast cell stably containing an expression construct operably linked to a nucleic acid molecule comprising a modified open reading frame providing increased expression of the encoded active BoNT/E in a yeast cell. In a further aspect of this embodiment, a yeast cell is a yeast strain derived from *Pichia pastoris, Pichia methanolica, Pichia angusta, Schizosaccharomyces pombe, Saccharomyces cerevisiae* or *Yarrowia lipolytica*. In yet another aspect of this embodiment, an expression construct is a yeast expression construct. In yet another aspect of this embodiment, a nucleic acid molecule comprises any of the modified open reading frames of SEQ ID NO: 35 through SEQ ID NO: 46.

In an embodiment, a cell comprises a slime mold cell comprising an expression construct operably linked to a nucleic acid molecule comprising a modified open reading frame providing increased expression of the encoded active BoNT/E in a slime mold cell. In an aspect of this embodiment, a cell comprises a slime mold cell transiently containing an expression construct operably linked to a nucleic acid molecule comprising a modified open reading frame providing increased expression of the encoded active BoNT/E in a slime mold cell. In another aspect of this embodiment, a cell comprises a slime mold cell stably containing an expression construct operably linked to a nucleic acid molecule comprising a modified open reading frame providing increased expression of the encoded active BoNT/E in a slime mold cell. In a further aspect of this embodiment, a slime mold cell is a slime mold strain derived from Dictyostelium discoideum. In yet another aspect of this embodiment, an expression construct is a slime mold expression construct. In yet another aspect of this embodiment, a nucleic acid molecule comprises any of the modified open reading frames of SEQ ID NO: 47 through SEQ ID NO: 49.

In an embodiment, a cell comprises a plant cell comprising an expression construct operably linked to a nucleic acid molecule comprising a modified open reading frame providing increased expression of the encoded active BoNT/E in a plant cell. In an aspect of this embodiment, a cell comprises a plant cell transiently containing an expression construct operably linked to a nucleic acid molecule comprising a modified open reading frame providing increased expression of the encoded active BoNT/E in a plant cell. In another aspect of this embodiment, a cell comprises a plant cell stably containing an expression construct operably linked to a nucleic acid molecule comprising a modified open reading frame providing increased expression of the encoded active BoNT/E in a plant cell. In a further aspect of this embodiment, a plant cell is derived from a monocot cell or cell line derived from a monocot cell or a dicot cell or cell line derived from a dicot cell. In a further aspect of this embodiment, a plant cell or cell line derived from a plant cell is from *Zea mays* or *Arabidopsis thaliana*. In yet another aspect of this embodiment, an expression construct is a plant expression construct. In yet another aspect of this embodiment, a nucleic acid molecule comprises any of the modified open reading frames of SEQ ID NO: 50 through SEQ ID NO: 55.

In an embodiment, a cell comprises an insect cell comprising an expression construct operably linked to a nucleic acid molecule comprising a modified open reading frame providing increased expression of the encoded active BoNT/E in an insect cell. In an aspect of this embodiment, a cell comprises an insect cell transiently containing an expression construct operably linked to a nucleic acid molecule comprising a modified open reading frame providing increased expression of the encoded active BoNT/E in an insect cell. In another aspect of this embodiment, a cell comprises an insect cell stably containing an expression construct operably linked to a nucleic acid molecule comprising a modified open reading frame providing increased expression of the encoded active BoNT/E in an insect cell. In a further aspect of this embodiment, an insect cell is an insect strain derived from *Spodoptera frugiperda, Trichoplusia ni, Drosophila melanogaster* or *Manduca sexta*. In a further aspect of this embodiment, an insect cell is an insect cell line derived from Sf9, Sf21, High-five, S2 and Kc. In yet another aspect of this embodiment, an expression construct is an insect expression construct. In yet another aspect of this embodiment, a nucleic acid molecule In yet another aspect of this embodiment, a nucleic acid molecule comprises any of the modified open reading frames of SEQ ID NO: 56 through SEQ ID NO: 61. In additional aspects of this embodiment, a Sf9 cell line contains an expression construct operably linked to a nucleic acid molecule comprising a modified open reading frame of SEQ ID NO: 59, SEQ ID NO: 60 or SEQ ID NO: 61; a Sf21 cell line contains an expression construct operably linked to a nucleic acid molecule comprising a modified open reading frame of SEQ ID NO: 59, SEQ ID NO: 60 or SEQ ID NO: 61; a High-Five cell line contains an expression construct operably linked to a nucleic acid molecule comprising a modified open reading frame of SEQ ID NO: 59, SEQ ID NO: 60 or SEQ ID NO: 61; a S2 cell line contains an expression construct operably linked to a nucleic acid molecule comprising a modified open reading frame of SEQ ID NO: 56, SEQ ID NO: 57 or SEQ ID NO: 58; or a Kc cell line contains an expression construct operably linked to a nucleic acid molecule comprising a modified open reading frame of SEQ ID NO: 56, SEQ ID NO: 57 or SEQ ID NO: 58.

In an embodiment, a cell comprises a fish cell comprising an expression construct operably linked to a nucleic acid molecule comprising a modified open reading frame providing increased expression of the encoded active BoNT/E in a fish cell. In an aspect of this embodiment, a cell comprises a fish cell transiently containing an expression construct operably linked to a nucleic acid molecule comprising a modified open reading frame providing increased expression of the encoded active BoNT/E in a fish cell. In another aspect of this embodiment, a cell comprises a fish cell stably containing an expression construct operably linked to a nucleic acid molecule comprising a modified open reading frame providing increased expression of the encoded active BoNT/E in a fish cell. In a further aspect of this embodiment, a fish cell is a fish cell or cell line derived from a fish cell from *Denio renia*. In yet another aspect of this embodiment, an expression construct is a fish expression construct. In yet another aspect of this embodiment, a nucleic acid molecule comprises any of the modified open reading frames of SEQ ID NO: 62 through SEQ ID NO: 64.

In an embodiment, a cell comprises an amphibian cell comprising an expression construct operably linked to a nucleic acid molecule comprising a modified open reading frame providing increased expression of the encoded active BoNT/E in an amphibian cell. In an aspect of this embodiment, a cell comprises an amphibian cell transiently containing an expression construct operably linked to a nucleic acid molecule comprising a modified open reading frame providing increased expression of the encoded active BoNT/E in an amphibian cell. In another aspect of this embodiment, a cell comprises an amphibian cell stably containing an expression construct operably linked to a nucleic acid molecule comprising a modified open reading frame providing increased expression of the encoded active BoNT/E in an amphibian cell. In a further aspect of this embodiment, an amphibian cell is an amphibian cell or cell line derived from an amphibian cell from *Xenopus laevis*. In a further aspect of this embodiment, an amphibian cell is an amphibian cell or cell line derived from an amphibian cell from *Xenopus tropicalis*. In yet another aspect of this embodiment, an expression construct is an amphibian expression construct. In yet another aspect of this embodiment, a nucleic acid molecule comprises any of the modified open reading frames of SEQ ID NO: 65 through SEQ ID NO: 70.

In an embodiment, a cell comprises a bird cell comprising an expression construct operably linked to a nucleic acid molecule comprising a modified open reading frame providing increased expression of the encoded active BoNT/E in a bird cell. In an aspect of this embodiment, a cell comprises a bird cell transiently containing an expression construct operably linked to a nucleic acid molecule comprising a modified open reading frame providing increased expression of the encoded active BoNT/E in a bird cell. In another aspect of this embodiment, a cell comprises a bird cell stably containing an expression construct operably linked to a nucleic acid molecule comprising a modified open reading frame providing increased expression of the encoded active BoNT/E in a bird cell. In a further aspect of this embodiment, a bird cell is a bird cell or cell line derived from a bird cell from *Gallus gallus*. In yet another aspect of this embodiment, an expression construct is a bird expression construct. In yet another aspect of this embodiment, a nucleic acid molecule comprises any of the modified open reading frames of SEQ ID NO: 71 through SEQ ID NO: 73.

In an embodiment, a cell comprises a mammalian cell comprising an expression construct operably linked to a nucleic acid molecule comprising a modified open reading frame providing increased expression of the encoded active BoNT/E in a mammalian cell. In an aspect of this embodiment, a cell comprises a mammalian cell transiently containing an expression construct operably linked to a nucleic acid molecule comprising a modified open reading frame providing increased expression of the encoded active BoNT/E in a mammalian. In another aspect of this embodiment, a cell comprises a mammalian cell stably containing an expression construct operably linked to a nucleic acid molecule comprising a modified open reading frame providing increased expression of the encoded active BoNT/E in a mammalian cell. In a further aspect of this embodiment, a mammalian cell is a mammalian cell or cell line derived from a mammalian cell from a mouse, a rat, a hamster, a porcine, a bovine, an equine, a primate or a human. In yet another aspect of this embodiment, an expression construct is a mammalian expression construct. In yet another aspect of this embodiment, a nucleic acid molecule comprises any of the modified open reading frames of SEQ ID NO: 74 through SEQ ID NO: 97.

In an embodiment, a cell comprises a mouse cell comprising an expression construct operably linked to a nucleic acid molecule comprising a modified open reading frame providing increased expression of the encoded active BoNT/E in a mouse cell. In an aspect of this embodiment, a cell comprises a mouse cell transiently containing an expression construct operably linked to a nucleic acid molecule comprising a modified open reading frame providing increased expression of the encoded active BoNT/E in a mouse cell. In another aspect of this embodiment, a cell comprises a mouse cell stably containing an expression construct operably linked to a nucleic acid molecule comprising a modified open reading frame providing increased expression of the encoded active BoNT/E in a mouse cell. In further aspect of this embodiment, a mouse cell is a mouse cell or cell line derived from a mouse cell from *M musculus*. In a further aspect of this embodiment, a mouse cell is a mouse cell line derived from 10T1/2, BALB/3T3, L-M, NB4 1A3, NIE-115, NG108-15, NIH3T3, NCTC or Neuro 2A. In yet another aspect of this embodiment, an expression construct is a mouse expression construct. In yet another aspect of this embodiment, a nucleic acid molecule comprises any of the modified open reading frames of SEQ ID NO: 74 through SEQ ID NO: 76. In additional aspects of this embodiment, a Neuro 2A cell line contains an expression construct operably linked to a nucleic acid molecule comprising a modified open reading frame of SEQ ID NO: 74, SEQ ID NO: 75 or SEQ ID NO: 76; a 10T1/2 cell line contains an expression construct operably linked to a nucleic acid molecule comprising a modified open reading frame of SEQ ID NO: 74, SEQ ID NO: 75 or SEQ ID NO: 76; a BALB/3T3 cell line contains an expression construct operably linked to a nucleic acid molecule comprising a modified open reading frame of SEQ ID NO: 74, SEQ ID NO: 75 or SEQ ID NO: 76; a NG108-15 cell line contains an expression construct operably linked to a nucleic acid molecule comprising a modified open reading frame of SEQ ID NO: 74, SEQ ID NO: 75 or SEQ ID NO: 76; or a NIE-115 cell line contains an expression construct operably linked to a nucleic acid molecule comprising a modified open reading frame of SEQ ID NO: 74, SEQ ID NO: 75 or SEQ ID NO: 76.

In an embodiment, a cell comprises a rat cell comprising an expression construct operably linked to a nucleic acid molecule comprising a modified open reading frame providing increased expression of the encoded active BoNT/E in a rat cell. In an aspect of this embodiment, a cell comprises a rat cell transiently containing an expression construct operably linked to a nucleic acid molecule comprising a modified open reading frame providing increased expression of the encoded active BoNT/E in a rat cell.

In another aspect of this embodiment, a cell comprises a rat cell stably containing an expression construct operably linked to a nucleic acid molecule comprising a modified open reading frame providing increased expression of the encoded active BoNT/E in a rat cell. In further aspect of this embodiment, a rat cell is a rat cell or cell line derived from a rat cell from R norvegicus. In a further aspect of this embodiment, a rat cell is a rat cell line derived from PC12, GH1, GH3, C6 or L2. In yet another aspect of this embodiment, an expression construct is a rat expression construct. In yet another aspect of this embodiment, a nucleic acid molecule comprises any of the modified open reading frames of SEQ ID NO: 77 through SEQ ID NO: 79. In additional aspects of this embodiment, a PC12 cell line contains an expression construct operably linked to a nucleic acid molecule comprising a modified open reading frame of SEQ ID NO: 77, SEQ ID NO: 78 or SEQ ID NO: 79; a GH1 cell line contains an expression construct operably linked to a nucleic acid molecule comprising a modified open reading frame of SEQ ID NO: 77, SEQ ID NO: 78 or SEQ ID NO: 79; a GH3 cell line contains an expression construct operably linked to a nucleic acid molecule comprising a modified open reading frame of SEQ ID NO: 77, SEQ ID NO: 78 or SEQ ID NO: 79; a C6 cell line contains an expression construct operably linked to a nucleic acid molecule comprising a modified open reading frame of SEQ ID NO: 77, SEQ ID NO: 78 or SEQ ID NO: 79; or a L2 cell line contains an expression construct operably linked to a nucleic acid molecule comprising a modified open reading frame of SEQ ID NO: 77, SEQ ID NO: 78 or SEQ ID NO: 79.

In an embodiment, a cell comprises a hamster cell comprising an expression construct operably linked to a nucleic acid molecule comprising a modified open reading frame providing increased expression of the encoded active BoNT/E in a hamster cell. In an aspect of this embodiment, a cell comprises a hamster cell transiently containing an expression construct operably linked to a nucleic acid molecule comprising a modified open reading frame providing increased expression of the encoded active BoNT/E in a hamster cell. In another aspect of this embodiment, a cell comprises a hamster cell stably containing an expression construct operably linked to a nucleic acid molecule comprising a modified open reading frame providing increased expression of the encoded active BoNT/E in a hamster cell. In further aspect of this embodiment, a hamster cell is a hamster cell or cell line derived from a hamster cell from C griseus. In a further aspect of this embodiment, a hamster cell is a hamster cell line derived from CHO or 6E6. In yet another aspect of this embodiment, an expression construct is a hamster expression construct. In yet another aspect of this embodiment, a nucleic acid molecule comprises any of the modified open reading frames of SEQ ID NO: 80 through SEQ ID NO: 81. In additional aspects of this embodiment, a CHO cell line contains an expression construct operably linked to a nucleic acid molecule comprising a modified open reading frame of SEQ ID NO: 80, SEQ ID NO: 81 or SEQ ID NO: 82; or a 6E6 cell line contains an expression construct operably linked to a nucleic acid molecule comprising a modified open reading frame of SEQ ID NO: 80, SEQ ID NO: 81 or SEQ ID NO: 82.

In an embodiment, a cell comprises a porcine cell comprising an expression construct operably linked to a nucleic acid molecule comprising a modified open reading frame providing increased expression of the encoded active BoNT/E in a porcine cell. In an aspect of this embodiment, a cell comprises a porcine cell transiently containing an expression construct operably linked to a nucleic acid molecule comprising a modified open reading frame providing increased expression of the encoded active BoNT/E in a porcine cell. In another aspect of this embodiment, a cell comprises a porcine cell stably containing an expression construct operably linked to a nucleic acid molecule comprising a modified open reading frame providing increased expression of the encoded active BoNT/E in a porcine cell. In further aspect of this embodiment, a porcine cell is a porcine cell or cell line derived from a porcine cell from *S. scrofa*. In a further aspect of this embodiment, a porcine cell is a porcine cell line derived from PK15, LLC-PK1, ST or ESK-4. In yet another aspect of this embodiment, an expression construct is a porcine expression construct. In yet another aspect of this embodiment, a nucleic acid molecule comprises any of the modified open reading frames of SEQ ID NO: 83 through SEQ ID NO: 85.

In an embodiment, a cell comprises a bovine cell comprising an expression construct operably linked to a nucleic acid molecule comprising a modified open reading frame providing increased expression of the encoded active BoNT/E in a bovine cell. In an aspect of this embodiment, a cell comprises a bovine cell transiently containing an expression construct operably linked to a nucleic acid molecule comprising a modified open reading frame providing increased expression of the encoded active BoNT/E in a bovine cell. In another aspect of this embodiment, a cell comprises a bovine cell stably containing an expression construct operably linked to a nucleic acid molecule comprising a modified open reading frame providing increased expression of the encoded active BoNT/E in a bovine cell. In further aspect of this embodiment, a bovine cell is a bovine cell or cell line derived from a bovine cell from *B. taurus*. In a further aspect of this embodiment, a bovine cell is a bovine cell line derived from CPAE, BT, SBAC or FB2. In yet another aspect of this embodiment, an expression construct is a bovine expression construct. In yet another aspect of this embodiment, a nucleic acid molecule comprises any of the modified open reading frames of SEQ ID NO: 86 through SEQ ID NO: 88.

In an embodiment, a cell comprises an equine cell comprising an expression construct operably linked to a nucleic acid molecule comprising a modified open reading frame providing increased expression of the encoded active BoNT/E in an equine cell. In an aspect of this embodiment, a cell comprises an equine cell transiently containing an expression construct operably linked to a nucleic acid molecule comprising a modified open reading frame providing increased expression of the encoded active BoNT/E in an equine cell. In another aspect of this embodiment, a cell comprises an equine cell stably containing an expression construct operably linked to a nucleic acid molecule comprising a modified open reading frame providing increased expression of the encoded active BoNT/E in an equine cell. In further aspect of this embodiment, an equine cell is an equine cell or cell line derived from an equine cell from *E. caballus*. In a further aspect of this embodiment, an equine cell is an equine cell line derived from NBL-6. In yet another aspect of this embodiment, an expression construct is an equine expression construct. In yet another aspect of this embodiment, a nucleic acid molecule comprises any of the modified open reading frames of SEQ ID NO: 89 through SEQ ID NO: 92.

In an embodiment, a cell comprises a primate cell comprising an expression construct operably linked to a nucleic acid molecule comprising a modified open reading frame providing increased expression of the encoded active BoNT/E in a primate cell. In an aspect of this embodiment, a cell comprises a primate cell transiently containing an expression construct operably linked to a nucleic acid molecule comprising a modified open reading frame providing increased expression of the encoded active BoNT/E in a primate cell. In another aspect of this embodiment, a cell comprises a primate cell stably containing an expression construct operably linked to a nucleic acid molecule comprising a modified open reading frame providing increased expression of the encoded active BoNT/E in a primate cell. In further aspect of this embodiment, a primate cell is a primate cell or cell line derived from a primate cell from *C. aethiops*. In a further aspect of this embodiment, a primate cell is a primate cell line derived from COS-1, COS-7 or VV-1. In yet another aspect of this embodiment, a nucleic acid molecule comprises any of the modified open reading frames of SEQ ID NO: 92 through SEQ ID NO: 94. In additional aspects of this embodiment, a COS-1 cell line contains an expression construct operably linked to a nucleic acid molecule comprising a modified open reading frame of SEQ ID NO: 92, SEQ ID NO: 93 or SEQ ID NO: 94; a COS-7 cell line contains an expression construct operably linked to a nucleic acid molecule comprising a modified open reading frame of SEQ ID NO: 92, SEQ ID NO: 93 or SEQ ID NO: 94; or a VV-1 cell line contains an expression construct operably linked to a nucleic acid molecule comprising a modified open reading frame of SEQ ID NO: 92, SEQ ID NO: 93 or SEQ ID NO: 94.

In an embodiment, a cell comprises a human cell comprising an expression construct operably linked to a nucleic acid molecule comprising a modified open reading frame providing increased expression of the encoded active BoNT/E in a human cell. In an aspect of this embodiment, a cell comprises a human cell transiently containing an expression construct operably linked to a nucleic acid molecule comprising a modified open reading frame providing increased expression of the encoded active BoNT/E in a human cell. In another aspect of this embodiment, a cell comprises a human cell stably containing an expression construct operably linked to a nucleic acid molecule comprising a modified open reading frame providing increased expression of the encoded active BoNT/E in a human cell. In further aspect of this embodiment, a human cell is a human cell or cell line derived from a human cell from *H. sapiens*. In a further aspect of this embodiment, a human cell is a human cell line derived from SH-SY5Y, SK-N-DZ, SK-N-F1, SK-N-SH, BE (2)-C, HeLa, HEK 293, MCF-7, HepG2, HL-60, IMR-32, SW-13 or CHP3. In yet another aspect of this embodiment, an expression construct is a human expression construct. In yet another aspect of this embodiment, a nucleic acid molecule comprises any of the modified open reading frames of SEQ ID NO: 95 through SEQ ID NO: 97. In additional aspects of this embodiment, a SH-SY5Y cell line contains an expression construct operably linked to a nucleic acid molecule comprising a modified open reading frame of SEQ ID NO: 95, SEQ ID NO: 96 or SEQ ID NO: 97; a SK-N-DZ cell line contains an expression construct operably linked to a nucleic acid molecule comprising a modified open reading frame of SEQ ID NO: 95, SEQ ID NO: 96 or SEQ ID NO: 97; a SK-N-F1 cell line contains an expression construct operably linked to a nucleic acid molecule comprising a modified open reading frame of SEQ ID NO: 95, SEQ ID NO: 96 or SEQ ID NO: 97; a SK-N-SH cell line contains an expression construct operably linked to a nucleic acid molecule comprising a modified open reading frame of SEQ ID NO: 95, SEQ ID NO: 96 or SEQ ID NO: 97; a BE (2)-C cell line contains an expression construct operably linked to a nucleic acid molecule comprising a modified open reading frame of SEQ ID NO: 95, SEQ ID NO: 96 or SEQ ID NO: 97; a HeLa cell line contains an expression construct operably linked to a nucleic acid molecule comprising a modified open reading frame of SEQ ID NO: 95, SEQ ID NO: 96 or SEQ ID NO: 97; a HEK 293 cell line contains an expression construct operably linked to a nucleic acid molecule comprising a modified open reading frame of SEQ ID NO: 95, SEQ ID NO: 96 or SEQ ID NO: 97; a MCF-7 cell line contains an expression construct operably linked to a nucleic acid molecule comprising a modified open reading frame of SEQ ID NO: 95, SEQ ID NO: 96 or SEQ ID NO: 97; a HepG2 cell line contains an expression construct operably linked to a nucleic acid molecule comprising a modified open reading frame of SEQ ID NO: 95, SEQ ID NO: 96 or SEQ ID NO: 97; a HepG2 cell line contains an expression construct operably linked to a nucleic acid molecule comprising a modified open reading frame of SEQ ID NO: 95, SEQ ID NO: 96 or SEQ ID NO: 97; a HL-60 cell line contains an expression construct operably linked to a nucleic acid molecule comprising a modified open reading frame of SEQ ID NO: 95, SEQ ID NO: 96 or SEQ ID NO: 97; a IMR-32 cell line contains an expression construct operably linked to a nucleic acid molecule comprising a modified open reading frame of SEQ ID NO: 95, SEQ ID NO: 96 or SEQ ID NO: 97; a SW-13 cell line contains an expression construct operably linked to a nucleic acid molecule comprising a modified open reading frame of SEQ ID NO: 95, SEQ ID NO: 96 or SEQ ID NO: 97; or a CHP3 cell line contains an expression construct operably linked to a nucleic acid molecule comprising a modified open reading frame of SEQ ID NO: 95, SEQ ID NO: 96 or SEQ ID NO: 97.

Another aspect of the present invention provides a method of producing an active BoNT/E comprising the step of expressing an expression construct comprising a modified open reading frame providing increased expression of an encoded active BoNT/E in a heterologous cell. In another aspect of the present invention provides a method of producing an active BoNT/E comprising the steps of introducing an expression construct comprising a modified open reading frame providing increased expression of an encoded active BoNT/E into a heterologous cell and expressing the expression construct in the heterologous cell.

The methods disclosed in the present specification include, in part, an active BoNT/E. In is envisioned that any and all active BoNT/E disclosed in the present specification can be produced using the methods disclosed in the present specification. Thus, aspects of this embodiment include producing, without limitation, active BoNT/E, naturally occurring active BoNT/E variants, such as, e.g., BoNT/E isoforms, non-naturally occurring active BoNT/E variants, such as, e.g., conservative BoNT/E variants, non-conservative BoNT/E variants and active BoNT/E fragments thereof, or any combination thereof. Other aspects of this embodiment include, without limitation, active BoNT/E of SEQ ID NO:1, naturally occurring active BoNT/E variants of SEQ ID NO: 1, such as, e.g., active BoNT/E isoforms of SEQ ID NO: 1, non-naturally occurring active BoNT/E variants of SEQ ID NO: 1, such as, e.g., conservative BoNT/E variants of SEQ ID NO: 1, non-conservative BoNT/E variants of SEQ ID NO: 1 and active BoNT/E fragments of SEQ ID NO: 1, or any combination thereof.

The methods disclosed in the present specification include, in part, an expression construct. In is envisioned that any and all expression constructs disclosed in the present specification can be used. Thus, aspects of this embodiment include, without limitation, cells comprising a viral expression vector operably linked to a modified open reading frame providing increased expression of an encoded active BoNT/E in a mammalian cell; a prokaryotic expression vector operably linked to a modified open reading frame providing increased expression of an encoded active BoNT/E in a prokaryotic cell; cells comprising a yeast expression vector operably linked to a modified open reading frame providing increased expression of an encoded active BoNT/E in a yeast cell; cells comprising a slime mold expression vector operably linked to a modified open reading frame providing increased expression of an encoded active BoNT/E in an slime mold cell; cells comprising a plant expression vector operably linked to a modified open reading frame providing increased expression of an encoded active BoNT/E in a plant cell or cell line derived from a plant cell; cells comprising an insect expression vector operably linked to a modified open reading frame providing increased expression of the encoded active BoNT/E in an insect cell or cell line derived from an insect cell; cells comprising a fish expression vector operably linked to a modified open reading frame providing increased expression of an encoded active BoNT/E in an fish cell or cell line derived from a fish cell; cells comprising an amphibian expression vector operably linked to a modified open reading frame providing increased expression of an encoded active BoNT/E in an amphibian cell or cell line derived from an amphibian cell; cells comprising a bird expression vector operably linked to a modified open reading frame providing increased expression of an encoded active BoNT/E in a bird cell or cell line derived from a bird cell; and cells comprising a mammalian expression vector operably linked to a modified open reading frame providing increased expression of an encoded active BoNT/E in a mammalian cell or cell line derived from a mammalian cell, such as, e.g., mouse, rat, hamster, porcine, bovine, equine, primate and human. Other aspects of this embodiment include, without limitation, expression constructs comprising a modified open reading frame that comprises any one of SEQ ID NO: 4 through SEQ ID NO: 97, SEQ ID NO: 117, SEQ ID NO: 122 or SEQ ID NO: 124.

The methods disclosed in the present specification include, in part, a heterologous cell. In is envisioned that any and all heterologous cells disclosed in the present specification can be used. Thus, aspects of this embodiment include, without limitation, prokaryotic cells prokaryotic cells including, without limitation, strains of aerobic, microaerophilic, capnophilic, facultative, anaerobic, gram-negative and gram-positive bacterial cells such as those derived from, e.g., *Escherichia coli, Salmonella typhimurium, Bacillus subtilis, Bacillus licheniformis, Clostridia perfringens, Clostridia difficile, Bacteroides fragilis, Caulobacter crescentus, Methylobacterium extorquens, Lactococcus lactis* and *Neisseria Meningirulls*; and eukaryotic cells including, without limitation, yeast strains, such as, e.g., those derived from *Pichia pastoris, Pichia methanolica, Pichia angusta, Schizosaccharomyces pombe, Saccharomyces cerevisiae* and *Yarrowia lipolytica*; slime mold strains , such as, e.g., those derived from, e.g., *Dictyostelium discoideum*; plant cells and cell lines derived from plant cells, such as, e.g., those derived from species of monocots, species of dicots, *Zea mays* and *Arabidopsis thaliana*; insect cells and cell lines derived from insects, such as, e.g., those derived from *Spodoptera frugiperda, Trichoplusia ni, Drosophila melanogaster* and *Manduca sexta*; fish cells and cell lines derived from fish cells, such as, e.g., those derived from *Denio renia*; amphibian cells and cell lines derived from amphibian cells, such as, e.g., those derived from *Xenopus laevis* and *Xenopus tropicalis*; bird cells and cell lines derived from bird cells, such as, e.g., those derived from *Gallus gallus*; mammalian cells and cell lines derived from mammalian cells, such as, e.g., those derived from mouse, rat, hamster, porcine, bovine, equine, primate and human. Cell lines may be obtained from the American Type Culture Collection (2004); European Collection of Cell Cultures (2004); and the German Collection of Microorganisms and Cell Cultures (2004). Non-limiting examples of specific protocols for selecting, making and using an appropriate cell line are described in e.g., Insect Cell Culture Engineering (Mattheus F. A. Goosen et al. eds., Marcel Dekker, 1993); Insect Cell Cultures: Fundamental and Applied Aspects (J. M. Vlak et al. eds., Kluwer Academic Publishers, 1996); Maureen A. Harrison & Ian F. Rae, General Techniques of Cell Culture (Cambridge University Press, 1997); Cell and Tissue Culture: Laboratory Procedures (Alan Doyle et al eds., John Wiley and Sons, 1998); R. Ian Freshney, Culture of Animal Cells: A Manual of Basic Technique (Wiley-Liss, 4$^{th}$ ed. 2000); Animal Cell Culture: A Practical Approach (John R. W. Masters ed., Oxford University Press, 3$^{rd}$ ed. 2000); Molecular Cloning A Laboratory Manual, supra, (2001); Basic Cell Culture: A Practical Approach (John M. Davis, Oxford Press, 2$^{nd}$ ed. 2002); and Current Protocols in Molecular Biology, supra, (2004). These protocols are routine procedures within the scope of one skilled in the art and from the teaching herein.

The methods disclosed in the present specification include, in part, introducing an expression construct into a heterologous cell. It is envisioned that any and all methods for introducing an expression construct disclosed in the present specification into a cell can be used. A cell disclosed in the present specification can maintain an expression construct transiently or stably. Stably-maintained constructs may be extra-chromosomal and replicate autonomously, or they may be integrated into the chromosomal material of the cell and replicate non-autonomously. Methods useful for introducing a nucleic acid molecule into a cell including, without limitation, calcium phosphate-mediated, DEAE dextran-mediated, lipid-mediated, polybrene-mediated, polylysine-mediated, viral-mediated, microinjection, protoplast fusion, biolistic, and electroporation, see, e.g., Introducing Cloned Genes into Cultured Mammalian Cells, pp. 16. 1-16. 62 (Sambrook & Russell, eds., Molecular Cloning A Laboratory Manual, Vol. 3, 3$^{rd}$ ed. 2001). One skilled in the art understands that selection of a specific method to introduce an expression construct into a cell will depend, in part, on whether the cell will transiently contain an expression construct or whether the cell will stably contain an expression construct. These protocols are routine procedures within the scope of one skilled in the art and from the teaching herein.

It is envisioned that both cell-free and cell-based procedures can be used to produce an active BoNT/E using methods disclosed in the present specification. These procedures involve the use of well-characterized vectors, reagents, conditions and cells that are readily available from commercial vendors including, without limitation, BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; Roche Applied Science, Indianapolis, Ind.; and Stratagene, La Jolla, Calif. The selection and use of appropriate procedures to produce an active BoNT/E are described in e.g., Protein Expression. A Practical Approach, supra, (1999) and Fernandez & Hoeffler, supra, (1999). These protocols are routine procedures within the scope of one skilled in the art and from the teaching herein.

One procedure of producing active BoNT/E employs a cell-free expression system such as, without limitation, prokaryotic extracts and eukaryotic extracts. Non-limiting examples of prokaryotic cell extracts include the RTS 100 *E. coli* HY Kit (Roche Applied Science, Indianapolis, Ind.), the ACTIVEPRO™ In Vitro Translation Kit (Ambion, inc., Austin, Tex.), a prokaryotic S30-based in vitro translation and translation, the ECOPRO™ System, a prokaryotic S30-based in vitro translation and translation, (EMD Biosciences-Novagen, Madison, Wis.) and the EXPRESSWAY™ Plus Expression System, a prokaryotic S30-based in vitro translation and translation, (Invitrogen, Inc., Carlsbad, Calif.). Eukaryotic cell extract include, without limitation, the RTS 100 Wheat Germ CECF Kit (Roche Applied Science, Indianapolis, Ind.), the TnT® Coupled Wheat Germ Extract Systems, an eukaryotic wheat germ extract-based in vitro translation and translation, (Promega Corp., Madison, Wis.), the WHEAT GERM IVT™ Kit, an eukaryotic wheat germ extract-based in vitro translation and translation, (Ambion, Austin, Tex.), the RETIC LYSATE IVT™ Kit, an eukaryotic rabbit reticulocyte extract-based in vitro translation and translation, (Ambion, Inc., Austin, Tex.), the PROTEIN-SCRIPT® II System, an eukaryotic ITV-based in vitro translation and translation, (Ambion, inc., Austin, Tex.) and the TnT® Coupled Reticulocyte Lysate Systems, an eukaryotic rabbit reticulocyte extract-based in vitro translation and translation, (Promega Corp., Madison, Wis.).

It is also envisioned that any of a variety of cell-based expression procedures are useful for expressing nucleic acid molecules encoding an active BoNT/E disclosed in the present specification. Examples included, without limitation, viral expression systems, prokaryotic expression systems, baculoviral expression systems, insect expression systems and mammalian expression systems. Viral expression systems include, without limitation, the VIRAPOWER™ Lentiviral, a replication-incomplete, HIV-1-based lentivirus expression vector, (Invitrogen, Inc., Carlsbad, Calif.), the Adenoviral Expression Systems, a E1 and E3-deleted, pDEST-based expression vector controlled by a human cytomegalovirus (CMV) promoter, (Invitrogen, Inc., Carlsbad, Calif.), the ADEASY™ XL Adenoviral Vector System, an Ad5 virus-based expression vector, (Stratagene, La Jolla, Calif,) and the VIRAPORT® Retroviral Gene Expression System, a mammalian retrovirus expression vector, (Stratagene, La Jolla, Calif.). Non-limiting examples of prokaryotic expression systems include the CHAMPION™ pET Expression System, a prokaryotic expression vector, (EMD Biosciences-Novagen, Madison, Wis.), the TRIEX™ Bacterial Expression Systems, a prokaryotic expression vector, (EMD Biosciences-Novagen, Madison, Wis.), the QIAEX-PRESS® Expression System, a prokaryotic expression vector, (QIAGEN, Inc.), and the AFFINITY® Protein Expression and Purification System, a prokaryotic expression vector, (Stratagene, La Jolla, Calif.). Yeast expression systems include, without limitation, the EASYSELECT™ Pichia Expression Kit, a yeast expression vector, (Invitrogen, Inc., Carlsbad, Calif.), the YES-ECHO™ Expression Vector Kits, a yeast expression vector, (Invitrogen, Inc., Carlsbad, Calif.) and the SPECTRA™ *S. pombe* Expression System, a yeast expression vector, (Invitrogen, Inc., Carlsbad, Calif.). Non-limiting examples of baculoviral expression systems include the BACULODIRECT™, a baculovirus-based expression vector, (Invitrogen, Inc., Carlsbad, Calif.), the BAC-TO-BAC®, a baculovirus-based expression vector, (Invitrogen, Inc., Carlsbad, Calif.), and the BD BACUL- OGOLD™, a baculovirus-based expression vector, (BD Biosciences-Pharmigen, San Diego, Calif.). Insect expression systems include, without limitation, the *Drosophila* Expression System (DES®) (Invitrogen, Inc., Carlsbad, Calif.), INSECTSELECT™ System, an insect expression vector, (Invitrogen, Inc., Carlsbad, Calif. A) and INSECTDIRECTTM System, an insect expression vector, (EMD Biosciences-Novagen, Madison, Wis.). Non-limiting examples of mammalian expression systems include the T-REX™ (Tetracycline-Regulated Expression) System, a tetracycline-inducible mammalian expression vector, (Invitrogen, Inc., Carlsbad, Calif.), the FLP-IN™ T-REX™ System, a tetracycline-inducible mammalian expression vector, (Invitrogen, Inc., Carlsbad, Calif.), the pcDNA™ system, a constitutive mammalian expression vector, (Invitrogen, Inc., Carlsbad, Calif.), the EXCHANGER® System, INTERPLAY™ mammalian TAP System, a mammalian expression vector, (Stratagene, La Jolla, Calif.), COMPLETE CONTROL® Inducible Mammalian Expression System, an ecdysone-inducible mammalian expression vector, (Stratagene, La Jolla, Calif.) and LACSWITCH® II Inducible Mammalian Expression System, a IPTG-inducible mammalian expression vector, (Stratagene, La Jolla, Calif.).

Aspects of the present invention can also be described as follows:

1. A nucleic acid molecule comprising a modified open reading frame encoding an active BoNT/E, wherein the modified open reading frame comprises nucleotide changes that increase the number of synonymous codons preferred by a prokaryotic cell as compared to an unmodified open reading frame encoding the same active BoNT/E; and wherein the modified open reading frame provides increased expression of the encoded active BoNT/E in the prokaryotic cell as compared to an expression level of the same active BoNT/E in the prokaryotic cell from an unmodified open reading frame in an otherwise identical nucleic acid molecule.
2. The molecule according to 1, wherein the modified open reading frame comprises nucleotide changes that alter at least 500 synonymous codons.
3. The molecule according to 1, wherein the modified open reading frame comprises nucleotide changes that alter at least 700 synonymous codons.
4. The molecule according to 1, wherein the modified open reading frame comprises nucleotide changes that alter at least 1000 synonymous codons.
5. The molecule according to 1, wherein the active BoNT/E comprises SEQ ID NO: 1, SEQ ID NO: 123 or SEQ ID NO: 125.
6. The molecule according to 1, wherein the prokaryotic cell comprises a *Bacteroides fragilis* strain, a *Bacillus licheniformis* strain, a *Bacillus subtilis* strain, a *Caulobacter crescentus* strain, a *Clostridia difficile* strain, a *Clostridia perfringens* strain, an *Escherichia coli* strain, a *Lactococcus lactis* strain, a *Methylobacterium extorquens* strain, a *Neisseria meningirulls* strain or a *Salmonella typhimurium* strain.
7. The molecule according to 1, wherein the prokaryotic cell is a strain of *Escherichia coli.*
8. The molecule according to 1, wherein the increased expression of the active BoNT/E from the modified open reading frame is at least two-fold higher as compared to the expression level of the same active BoNT/E from the unmodified open reading frame.
9. The molecule according to 1, wherein the increased expression of the active BoNT/E from the modified open reading frame is at least five-fold higher as compared to the expression level of the same active BoNT/E from the unmodified open reading frame.
10. The molecule according to 1, wherein the increased expression of the active BoNT/E from the modified open reading frame is at least ten-fold higher as compared to the expression level of the same active BoNT/E from the unmodified open reading frame.
11. A nucleic acid molecule comprising a modified open reading frame encoding an active BoNT/E, wherein the modified open reading frame comprises nucleotide changes that increase total G+C content to a level preferred by a prokaryotic cell as compared to an unmodified open reading frame encoding the same active BoNT/E; and wherein the modified open reading frame provides increased expression of the encoded active BoNT/E in the prokaryotic cell as compared to the expression level of the same active BoNT/E in the prokaryotic cell from the unmodified open reading frame in an otherwise identical nucleic acid molecule.
12. The molecule according to 11, wherein the modified open reading frame comprises nucleotide changes that increase the total G+C content to at least 30%.
13. The molecule according to 11, wherein the modified open reading frame comprises nucleotide changes that increase the total G+C content to at least 40%.
14. The molecule according to 11, wherein the modified open reading frame comprises nucleotide changes that increase the total G+C content to at least 50%.
15. The molecule according to 11, wherein the active BoNT/E comprises SEQ ID NO: 1, SEQ ID NO: 123 or SEQ ID NO: 125.
16. The molecule according to 11, wherein the prokaryotic cell comprises a *Bacteroides fragilis* strain, a *Bacillus licheniformis* strain, a *Bacillus subtilis* strain, a *Caulobacter crescentus* strain, a *Clostridia difficile* strain, a *Clostridia perfringens* strain, an *Escherichia coli* strain, a *Lactococcus lactis* strain, a *Methylobacterium extorquens* strain, a *Neisseria meningirulls* strain or a *Salmonella typhimurium* strain.
17. The molecule according to 11, wherein the prokaryotic cell is a strain of Escherichia coli.
18. The molecule according to 11, wherein the increased expression of the active BoNT/E from the modified open reading frame is at least two-fold higher as compared to the expression level of the same active BoNT/E from the unmodified open reading frame.
19. The molecule according to 11, wherein the increased expression of the active BoNT/E from the modified open reading frame is at least five-fold higher as compared to the expression level of the same active BoNT/E from the unmodified open reading frame.
20. The molecule according to 11, wherein the increased expression of the active BoNT/E from the modified open reading frame is at least ten-fold higher as compared to the expression level of the same active BoNT/E from the unmodified open reading frame.
21. A nucleic acid molecule comprising a modified open reading frame comprises SEQ ID NO: 4, SEQ ID NO: 5, SEQ ID NO: 6 SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO:

30, SEQ ID NO: 31, SEQ ID NO: 32, SEQ ID NO: 33 or SEQ ID NO: 34, SEQ ID NO: 117, SEQ ID NO: 122 or SEQ ID NO: 124.

22. The molecule according to 21, wherein the modified open reading frame comprises SEQ ID NO: 4.

23. The molecule according to 21, wherein the modified open reading frame comprises SEQ ID NO: 117.

24. The molecule according to 21, wherein the unmodified open reading frame comprises SEQ ID NO: 3.

25. The molecule according to 21, wherein the molecule comprises an expression construct.

26. A prokaryotic cell comprising an expression construct, the expression construct comprising i) a modified open reading frame encoding an active BoNT/E; and ii) an expression vector; wherein the modified open reading frame comprises nucleotide changes that increase the number of synonymous codons preferred by the prokaryotic cell as compared to an unmodified open reading frame encoding the same active BoNT/E; and wherein the modified open reading frame provides increased expression of the encoded active BoNT/E in the prokaryotic cell as compared to an expression level of the same active BoNT/E in the prokaryotic cell from an unmodified open reading frame in an otherwise identical nucleic acid molecule.

27. The cell according to 26, wherein the prokaryotic cell comprises a *Bacteroides fragilis* strain, a *Bacillus licheniformis* strain, a *Bacillus subtilis* strain, a *Caulobacter crescentus* strain, a *Clostridia difficile* strain, a *Clostridia perfringens* strain, an *Escherichia coli* strain, a *Lactococcus lactis* strain, a *Methylobacterium extorquens* strain, a *Neisseria meningirulls* strain or a *Salmonella typhimurium* strain.

28. The cell according to 26, wherein the prokaryotic cell is a strain of *Escherichia coli*.

29. The cell according to 26, wherein the expression construct is transiently contained in the prokaryotic cell.

30. The cell according to 26, wherein the expression construct is stably contained in the prokaryotic cell.

31. The cell according to 26, wherein the modified open reading frame comprises nucleotide changes that alter at least 500 synonymous codons.

32. The cell according to 26, wherein the modified open reading frame comprises nucleotide changes that alter at least 700 synonymous codons.

33. The cell according to 26, wherein the modified open reading frame comprises nucleotide changes that alter at least 1000 synonymous codons.

34. The cell according to 26, wherein the active BoNT/E comprises SEQ ID NO: 1, SEQ ID NO: 123 or SEQ ID NO: 125.

35. The cell according to 26, wherein the expression vector is a prokaryotic expression vector.

36. The cell according to 26, wherein the increased expression of the active BoNT/E from the modified open reading frame is at least two-fold higher as compared to the expression level of the same active BoNT/E from the unmodified open reading frame.

37. The cell according to 26, wherein the increased expression of the active BoNT/E from the modified open reading frame is at least five-fold higher as compared to the expression level of the same active BoNT/E from the unmodified open reading frame.

38. The cell according to 26, wherein the increased expression of the active BoNT/E from the modified open reading frame is at least ten-fold higher as compared to the expression level of the same active BoNT/E from the unmodified open reading frame.

39. A prokaryotic cell comprising an expression construct, the expression construct comprising i) a modified open reading frame encoding an active BoNT/E; and ii) an expression vector; wherein the modified open reading frame comprises nucleotide changes that increase total G+C content to a level preferred by a prokaryotic cell as compared to an unmodified open reading frame encoding the same active BoNT/E; and wherein the modified open reading frame provides increased expression of the encoded active BoNT/E in the prokaryotic cell as compared to an expression level of the same active BoNT/E in the prokaryotic cell from an unmodified open reading frame in an otherwise identical nucleic acid molecule.

40. The cell according to 39, wherein the prokaryotic cell comprises a *Bacteroides fragilis* strain, a *Bacillus licheniformis* strain, a *Bacillus subtilis* strain, a *Caulobacter crescentus* strain, a *Clostridia difficile* strain, a *Clostridia perfringens* strain, an *Escherichia coli* strain, a *Lactococcus lactis* strain, a *Methylobacterium extorquens* strain, a *Neisseria meningirulls* strain or a *Salmonella typhimurium* strain.

41. The cell according to 39, wherein the prokaryotic cell is a strain of *Escherichia coli*.

42. The cell according to 39, wherein the expression construct is transiently contained in the prokaryotic cell.

43. The cell according to 39, wherein the expression construct is stably contained in the prokaryotic cell.

44. The cell according to 39, wherein the modified open reading frame comprises nucleotide changes that increase the total G+C content to at least 30%.

45. The cell according to 39, wherein the modified open reading frame comprises nucleotide changes that increase the total G+C content to at least 40%.

46. The cell according to 39, wherein the modified open reading frame comprises nucleotide changes that increase the total G+C content to at least 50%.

47. The cell according to 39, wherein the active BoNT/E comprises SEQ ID NO: 1, SEQ ID NO: 123 or SEQ ID NO: 125.

48. The cell according to 39, wherein the expression vector is a prokaryotic expression vector.

49. The cell according to 39, wherein the increased expression of the active BoNT/E from the modified open reading frame is at least two-fold higher as compared to the expression level of the same active BoNT/E from the unmodified open reading frame.

50. The cell according to 39, wherein the increased expression of the active BoNT/E from the modified open reading frame is at least five-fold higher as compared to the expression level of the same active BoNT/E from the unmodified open reading frame.

51. The cell according to 39, wherein the increased expression of the active BoNT/E from the modified open reading frame is at least ten-fold higher as compared to the expression level of the same active BoNT/E from the unmodified open reading frame.

52. A nucleic acid molecule comprising a modified open reading frame encoding an active BoNT/E, wherein the modified open reading frame comprises nucleotide changes that increase the number of synonymous codons preferred by a yeast cell as compared to an unmodified open reading frame encoding the same active BoNT/E; and wherein the modified open reading frame provides increased expression of the encoded active BoNT/E in the yeast cell as compared to an expression level of the same active BoNT/E in the yeast cell from an unmodified open reading frame in an otherwise identical nucleic acid molecule.

53. The molecule according to 52, wherein the modified open reading frame comprises nucleotide changes that alter at least 500 synonymous codons.

54. The molecule according to 52, wherein the modified open reading frame comprises nucleotide changes that alter at least 700 synonymous codons.

55. The molecule according to 52, wherein the modified open reading frame comprises nucleotide changes that alter at least 1000 synonymous codons.

56. The molecule according to 52, wherein the active BoNT/E comprises SEQ ID NO: 1, SEQ ID NO: 123 or SEQ ID NO: 125.

57. The molecule according to 52, wherein the yeast cell comprises a *Pichia pastoris* strain, a *Pichia methanolica strain*, a *Pichia angusta strain*, a *Schizosaccharomyces pombe* strain, a *Saccharomyces cerevisiae* strain or a *Yarrowia lipolytica* strain.

58. The molecule according to 52, wherein the yeast cell is a strain of Pichia pastoris.

59. The molecule according to 52, wherein the increased expression of the active BoNT/E from the modified open reading frame is at least two-fold higher as compared to the expression level of the same active BoNT/E from the unmodified open reading frame.

60. The molecule according to 52, wherein the increased expression of the active BoNT/E from the modified open reading frame is at least five-fold higher as compared to the expression level of the same active BoNT/E from the unmodified open reading frame.

61. The molecule according to 52, wherein the increased expression of the active BoNT/E from the modified open reading frame is at least ten-fold higher as compared to the expression level of the same active BoNT/E from the unmodified open reading frame.

62. A nucleic acid molecule comprising a modified open reading frame encoding an active BoNT/E, wherein the modified open reading frame comprises nucleotide changes that increase total G+C content to a level preferred by a yeast cell as compared to an unmodified open reading frame encoding the same active BoNT/E; and wherein the modified open reading frame provides increased expression of the encoded active BoNT/E in the yeast cell as compared to the expression level of the same active BoNT/E in the yeast cell from the unmodified open reading frame in an otherwise identical nucleic acid molecule.

63. The molecule according to 62, wherein the modified open reading frame comprises nucleotide changes that increase the total G+C content to at least 30%.

64. The molecule according to 62, wherein the modified open reading frame comprises nucleotide changes that increase the total G+C content to at least 40%.

65. The molecule according to 62, wherein the modified open reading frame comprises nucleotide changes that increase the total G+C content to at least 50%.

66. The molecule according to 62, wherein the active BoNT/E comprises SEQ ID NO: 1, SEQ ID NO: 123 or SEQ ID NO: 125.

67. The molecule according to 62, wherein the yeast cell comprises a *Pichia pastoris* strain, a *Pichia methanolica* strain, a *Pichia angusta* strain, a *Schizosaccharomyces pombe* strain, a *Saccharomyces cerevisiae* strain or a *Yarrowia lipolytica* strain.

68. The molecule according to 62, wherein the yeast cell is a strain of Pichia pastoris.

69. The molecule according to 62, wherein the increased expression of the active BoNT/E from the modified open reading frame is at least two-fold higher as compared to the expression level of the same active BoNT/E from the unmodified open reading frame.

70. The molecule according to 62, wherein the increased expression of the active BoNT/E from the modified open reading frame is at least five-fold higher as compared to the expression level of the same active BoNT/E from the unmodified open reading frame.

71. The molecule according to 62, wherein the increased expression of the active BoNT/E from the modified open reading frame is at least ten-fold higher as compared to the expression level of the same active BoNT/E from the unmodified open reading frame.

72. A nucleic acid molecule comprising a modified open reading frame comprises SEQ ID NO: 35, SEQ ID NO: 36, SEQ ID NO: 37 SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45 or SEQ ID NO: 46.

73. The molecule according to 72, wherein the modified open reading frame comprises SEQ ID NO: 37.

74. The molecule according to 72, wherein the unmodified open reading frame comprises SEQ ID NO: 3.

75. The molecule according to 72, wherein the molecule comprises an expression construct.

76. A yeast cell comprising an expression construct, the expression construct comprising i) a modified open reading frame encoding an active BoNT/E; and ii) an expression vector; wherein the modified open reading frame comprises nucleotide changes that increase the number of synonymous codons preferred by the yeast cell as compared to an unmodified open reading frame encoding the same active BoNT/E; and wherein the modified open reading frame provides increased expression of the encoded active BoNT/E in the yeast cell as compared to an expression level of the same active BoNT/E in the yeast cell from an unmodified open reading frame in an otherwise identical nucleic acid molecule.

77. The cell according to 76, wherein the yeast cell comprises a *Pichia pastoris* strain, a *Pichia methanolica* strain, a *Pichia angusta* strain, a *Schizosaccharomyces pombe* strain, a *Saccharomyces cerevisiae* strain or a *Yarrowia lipolytica* strain.

78. The cell according to 76, wherein the yeast cell is a strain of *Pichia pastoris*.

79. The cell according to 76, wherein the expression construct is transiently contained in the yeast cell.

80. The cell according to 76, wherein the expression construct is stably contained in the yeast cell.

81. The cell according to 76, wherein the modified open reading frame comprises nucleotide changes that alter at least 500 synonymous codons.

82. The cell according to 76, wherein the modified open reading frame comprises nucleotide changes that alter at least 700 synonymous codons.

83. The cell according to 76, wherein the modified open reading frame comprises nucleotide changes that alter at least 1000 synonymous codons.

84. The cell according to 76, wherein the active BoNT/E comprises SEQ ID NO: 1, SEQ ID NO: 123 or SEQ ID NO: 125.

85. The cell according to 76, wherein the expression vector is a yeast expression vector.

86. The cell according to 76, wherein the increased expression of the active BoNT/E from the modified open reading frame is at least two-fold higher as compared to the expression level of the same active BoNT/E from the unmodified open reading frame.

87. The cell according to 76, wherein the increased expression of the active BoNT/E from the modified open reading frame is at least five-fold higher as compared to the expression level of the same active BoNT/E from the unmodified open reading frame.

88. The cell according to 76, wherein the increased expression of the active BoNT/E from the modified open reading frame is at least ten-fold higher as compared to the expression level of the same active BoNT/E from the unmodified open reading frame.

89. A yeast cell comprising an expression construct, the expression construct comprising, i) a modified open reading frame encoding an active BoNT/E; and ii) an expression vector; wherein the modified open reading frame comprises nucleotide changes that increase total G+C content to a level preferred by the yeast cell as compared to an unmodified open reading frame encoding the same active BoNT/E; and wherein the modified open reading frame provides increased expression of the encoded active BoNT/E in the yeast cell as compared to an expression level of the same active BoNT/E in the yeast cell from an unmodified open reading frame in an otherwise identical nucleic acid molecule.

90. The cell according to 89, wherein the prokaryotic cell comprises a *Pichia pastoris* strain, a *Pichia methanolica* strain, a *Pichia angusta* strain, a *Schizosaccharomyces pombe* strain, a *Saccharomyces cerevisiae* strain or a *Yarrowia lipolytica* strain.

91. The cell according to 89, wherein the yeast cell is a strain of *Pichia pastoris.*

92. The cell according to 89, wherein the expression construct is transiently contained in the yeast cell.

93. The cell according to 89, wherein the expression construct is stably contained in the yeast cell.

94. The cell according to 89, wherein the modified open reading frame comprises nucleotide changes that increase the total G+C content to at least 30%.

95. The cell according to 89, wherein the modified open reading frame comprises nucleotide changes that increase the total G+C content to at least 40%.

96. The cell according to 89, wherein the modified open reading frame comprises nucleotide changes that increase the total G+C content to at least 50%.

97. The cell according to 89, wherein the active BoNT/E comprises SEQ ID NO: 1, SEQ ID NO: 123 or SEQ ID NO: 125.

98. The cell according to 89, wherein the expression vector is a yeast expression vector.

99. The cell according to 89, wherein the increased expression of the active BoNT/E from the modified open reading frame is at least two-fold higher as compared to the expression level of the same active BoNT/E from the unmodified open reading frame.

100. The cell according to 89, wherein the increased expression of the active BoNT/E from the modified open reading frame is at least five-fold higher as compared to the expression level of the same active BoNT/E from the unmodified open reading frame.

101. The cell according to 89, wherein the increased expression of the active BoNT/E from the modified open reading frame is at least ten-fold higher as compared to the expression level of the same active BoNT/E from the unmodified open reading frame.

102. A nucleic acid molecule comprising a modified open reading frame encoding an active BoNT/E, wherein the modified open reading frame comprises nucleotide changes that increase the number of synonymous codons preferred by an insect cell as compared to an unmodified open reading frame encoding the same active BoNT/E; and wherein the modified open reading frame provides increased expression of the encoded active BoNT/E in the insect cell as compared to an expression level of the same active BoNT/E in the insect cell from an unmodified open reading frame in an otherwise identical nucleic acid molecule.

103. The molecule according to 102, wherein the modified open reading frame comprises nucleotide changes that alter at least 500 synonymous codons.

104. The molecule according to 102, wherein the modified open reading frame comprises nucleotide changes that alter at least 700 synonymous codons.

105. The molecule according to 102, wherein the modified open reading frame comprises nucleotide changes that alter at least 1000 synonymous codons.

106. The molecule according to 102, wherein the active BoNT/E comprises SEQ ID NO: 1, SEQ ID NO: 123 or SEQ ID NO: 125.

107. The molecule according to 102, wherein the insect cell comprises a *Spodoptera frugiperda* strain, a *Trichoplusia ni* strain, a *Drosophila melanogaster* strain or a *Manduca sexta* strain.

108. The molecule according to 102, wherein the insect cell comprises a *Spodoptera frugiperda* cell line, a *Trichoplusia ni* cell line, a *Drosophila melanogaster* cell line or a *Manduca sexta* cell line.

109. The molecule according to 102, wherein the increased expression of the active BoNT/E from the modified open reading frame is at least two-fold higher as compared to the expression level of the same active BoNT/E from the unmodified open reading frame.

110. The molecule according to 102, wherein the increased expression of the active BoNT/E from the modified open reading frame is at least five-fold higher as compared to the expression level of the same active BoNT/E from the unmodified open reading frame.

111. The molecule according to 102, wherein the increased expression of the active BoNT/E from the modified open reading frame is at least ten-fold higher as compared to the expression level of the same active BoNT/E from the unmodified open reading frame.

112. A nucleic acid molecule comprising a modified open reading frame encoding an active BoNT/E, wherein the modified open reading frame comprises nucleotide changes that increase total G+C content to a level preferred by an insect cell as compared to an unmodified open reading frame encoding the same active BoNT/E; and wherein the modified open reading frame provides increased expression of the encoded active BoNT/E in the insect cell as compared to the expression level of the same active BoNT/E in the insect cell from the unmodified open reading frame in an otherwise identical nucleic acid molecule.

113. The molecule according to 112, wherein the modified open reading frame comprises nucleotide changes that increase the total G+C content to at least 30%.

114. The molecule according to 112, wherein the modified open reading frame comprises nucleotide changes that increase the total G+C content to at least 40%.

115. The molecule according to 112, wherein the modified open reading frame comprises nucleotide changes that increase the total G+C content to at least 50%.

116. The molecule according to 112, wherein the active BoNT/E comprises SEQ ID NO: 1, SEQ ID NO: 123 or SEQ ID NO: 125.

117. The molecule according to 112, wherein the insect cell comprises a *Spodoptera frugiperda* strain, a *Trichoplusia ni* strain, a *Drosophila melanogaster* strain or a *Manduca sexta* strain.

118. The molecule according to 112, wherein the insect cell comprises a *Spodoptera frugiperda* cell line, a *Trichoplusia ni* cell line, a *Drosophila melanogaster* cell line or a *Manduca sexta* cell line.

119. The molecule according to 112, wherein the increased expression of the active BoNT/E from the modified open reading frame is at least two-fold higher as compared to the expression level of the same active BoNT/E from the unmodified open reading frame.

120. The molecule according to 112, wherein the increased expression of the active BoNT/E from the modified open reading frame is at least five-fold higher as compared to the expression level of the same active BoNT/E from the unmodified open reading frame.

121. The molecule according to 112, wherein the increased expression of the active BoNT/E from the modified open reading frame is at least ten-fold higher as compared to the expression level of the same active BoNT/E from the unmodified open reading frame.

122. A nucleic acid molecule comprising a modified open reading frame comprises SEQ ID NO: 56, SEQ ID NO: 57, SEQ ID NO: 58 SEQ ID NO: 59, SEQ ID NO: 60 or SEQ ID NO: 61.

123. The molecule according to 122, wherein the modified open reading frame comprises SEQ ID NO: 61.

124. The molecule according to 122, wherein the unmodified open reading frame comprises SEQ ID NO: 3.

125. The molecule according to 122, wherein the molecule comprises an expression construct.

126. An insect cell comprising an expression construct, the expression construct comprising, i) a modified open reading frame encoding an active BoNT/E; and ii) an expression vector; wherein the modified open reading frame comprises nucleotide changes that increase the number of synonymous codons preferred by the insect cell as compared to an unmodified open reading frame encoding the same active BoNT/E; and wherein the modified open reading frame provides increased expression of the encoded active BoNT/E in the insect cell as compared to an expression level of the same active BoNT/E in the insect cell from an unmodified open reading frame in an otherwise identical nucleic acid molecule.

127. The cell according to 126, wherein the insect cell comprises a *Spodoptera frugiperda* strain, a *Trichoplusia ni* strain, a *Drosophila melanogaster* strain or a *Manduca sexta* strain.

128. The cell according to 126, wherein the insect cell comprises a *Spodoptera frugiperda* cell line, a *Trichoplusia ni* cell line, a *Drosophila melanogaster* cell line or a *Manduca sexta* cell line.

129. The cell according to 126, wherein the expression construct is transiently contained in the insect cell.

130. The cell according to 126, wherein the expression construct is stably contained in the insect cell.

131. The cell according to 126, wherein the modified open reading frame comprises nucleotide changes that alter at least 500 synonymous codons.

132. The cell according to 126, wherein the modified open reading frame comprises nucleotide changes that alter at least 700 synonymous codons.

133. The cell according to 126, wherein the modified open reading frame comprises nucleotide changes that alter at least 1000 synonymous codons.

134. The cell according to 126, wherein the active BoNT/E comprises SEQ ID NO: 1, SEQ ID NO: 123 or SEQ ID NO: 125.

135. The cell according to 126, wherein the expression vector is an insect expression vector.

136. The cell according to 126, wherein the increased expression of the active BoNT/E from the modified open reading frame is at least two-fold higher as compared to the expression level of the same active BoNT/E from the unmodified open reading frame.

137. The cell according to 126, wherein the increased expression of the active BoNT/E from the modified open reading frame is at least five-fold higher as compared to the expression level of the same active BoNT/E from the unmodified open reading frame.

138. The cell according to 126, wherein the increased expression of the active BoNT/E from the modified open reading frame is at least ten-fold higher as compared to the expression level of the same active BoNT/E from the unmodified open reading frame.

139. An insect cell comprising an expression construct, the expression construct comprising i) a modified open reading frame encoding an active BoNT/E; and ii) an expression vector; wherein the modified open reading frame comprises nucleotide changes that increase total G+C content to a level preferred by the insect cell as compared to an unmodified open reading frame encoding the same active BoNT/E; and wherein the modified open reading frame provides increased expression of the encoded active BoNT/E in the insect cell as compared to an expression level of the same active BoNT/E in the insect cell from an unmodified open reading frame in an otherwise identical nucleic acid molecule.

140. The cell according to 139, wherein the insect cell comprises a *Spodoptera frugiperda* strain, a *Trichoplusia ni* strain, a *Drosophila melanogaster* strain or a *Manduca sexta* strain.

141. The cell according to 139, wherein the insect cell comprises a *Spodoptera frugiperda* cell line, a *Trichoplusia ni* cell line, a *Drosophila melanogaster* cell line or a *Manduca sexta* cell line.

142. The cell according to 139, wherein the expression construct is transiently contained in the insect cell.

143. The cell according to 139, wherein the expression construct is stably contained in the insect cell.

144. The cell according to 139, wherein the modified open reading frame comprises nucleotide changes that increase the total G+C content to at least 30%.

145. The cell according to 139, wherein the modified open reading frame comprises nucleotide changes that increase the total G+C content to at least 40%.

146. The cell according to 139, wherein the modified open reading frame comprises nucleotide changes that increase the total G+C content to at least 50%.

147. The cell according to 139, wherein the active BoNT/E comprises SEQ ID NO: 1, SEQ ID NO: 123 or SEQ ID NO: 125.

148. The cell according to 139, wherein the expression vector is an insect expression vector.

149. The cell according to 139, wherein the increased expression of the active BoNT/E from the modified open reading frame is at least two-fold higher as compared to the expression level of the same active BoNT/E from the unmodified open reading frame.

150. The cell according to 139, wherein the increased expression of the active BoNT/E from the modified open reading frame is at least five-fold higher as compared to the expression level of the same active BoNT/E from the unmodified open reading frame.

151. The cell according to 139, wherein the increased expression of the active BoNT/E from the modified open reading frame is at least ten-fold higher as compared to the expression level of the same active BoNT/E from the unmodified open reading frame.

152. A nucleic acid molecule comprising a modified open reading frame encoding an active BoNT/E, wherein the modified open reading frame comprises nucleotide changes that increase the number of synonymous codons preferred by a mammalian cell as compared to an unmodified open reading frame encoding the same active BoNT/E; and wherein the modified open reading frame provides increased expression of the encoded active BoNT/E in the mammalian cell as compared to an expression level of the same active BoNT/E in the mammalian cell from an unmodified open reading frame in an otherwise identical nucleic acid molecule.

153. The molecule according to 152, wherein the modified open reading frame comprises nucleotide changes that alter at least 500 synonymous codons.

154. The molecule according to 152, wherein the modified open reading frame comprises nucleotide changes that alter at least 700 synonymous codons.

155. The molecule according to 152, wherein the modified open reading frame comprises nucleotide changes that alter at least 1000 synonymous codons.

156. The molecule according to 152, wherein the active BoNT/E comprises SEQ ID NO: 1, SEQ ID NO: 123 or SEQ ID NO: 125.

157. The molecule according to 152, wherein the mammalian cell comprises a mouse cell, a rat cell, a hamster cell, a porcine cell, a bovine cell, an equine cell, a primate cell or a human cell.

158. The molecule according to 152, wherein the mammalian cell comprises a mouse cell line, a rat cell line, a hamster cell line, a porcine cell line, a bovine cell line, an equine cell line, a primate cell line or a human cell line.

159. The molecule according to 152, wherein the increased expression of the active BoNT/E from the modified open reading frame is at least two-fold higher as compared to the expression level of the same active BoNT/E from the unmodified open reading frame.

160. The molecule according to 152, wherein the increased expression of the active BoNT/E from the modified open reading frame is at least five-fold higher as compared to the expression level of the same active BoNT/E from the unmodified open reading frame.

161. The molecule according to 152, wherein the increased expression of the active BoNT/E from the modified open reading frame is at least ten-fold higher as compared to the expression level of the same active BoNT/E from the unmodified open reading frame.

162. A nucleic acid molecule comprising a modified open reading frame encoding an active BoNT/E, wherein the modified open reading frame comprises nucleotide changes that increase total G+C content to a level preferred by a mammalian cell as compared to an unmodified open reading frame encoding the same active BoNT/E; and wherein the modified open reading frame provides increased expression of the encoded active BoNT/E in the mammalian cell as compared to the expression level of the same active BoNT/E in the mammalian cell from the unmodified open reading frame in an otherwise identical nucleic acid molecule.

163. The molecule according to 162, wherein the modified open reading frame comprises nucleotide changes that increase the total G+C content to at least 30%.

164. The molecule according to 162, wherein the modified open reading frame comprises nucleotide changes that increase the total G+C content to at least 40%.

165. The molecule according to 162, wherein the modified open reading frame comprises nucleotide changes that increase the total G+C content to at least 50%.

166. The molecule according to 162, wherein the active BoNT/E comprises SEQ ID NO: 1, SEQ ID NO: 123 or SEQ ID NO: 125.

167. The molecule according to 162, wherein the mammalian cell comprises a mouse cell, a rat cell, a hamster cell, a porcine cell, a bovine cell, an equine cell, a primate cell or a human cell.

168. The molecule according to 162, wherein the mammalian cell comprises a mouse cell line, a rat cell line, a hamster cell line, a porcine cell line, a bovine cell line, an equine cell line, a primate cell line or a human cell line.

169. The molecule according to 162, wherein the increased expression of the active BoNT/E from the modified open reading frame is at least two-fold higher as compared to the expression level of the same active BoNT/E from the unmodified open reading frame.

170. The molecule according to 162, wherein the increased expression of the active BoNT/E from the modified open reading frame is at least five-fold higher as compared to the expression level of the same active BoNT/E from the unmodified open reading frame.

171. The molecule according to 162, wherein the increased expression of the active BoNT/E from the modified open reading frame is at least ten-fold higher as compared to the expression level of the same active BoNT/E from the unmodified open reading frame.

172. A nucleic acid molecule comprising a modified open reading frame comprises SEQ ID NO: 74, SEQ ID NO: 75, SEQ ID NO: 76 SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88 SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96 or SEQ ID NO: 97.

173. The molecule according to 172, wherein the modified open reading frame comprises SEQ ID NO: 97.

174. The molecule according to 172, wherein the unmodified open reading frame comprises SEQ ID NO: 3.

175. The molecule according to 172, wherein the molecule comprises an expression construct.

176. A mammalian cell comprising an expression construct, the expression construct comprising i) a modified open reading frame encoding an active BoNT/E; and ii) an expression vector; wherein the modified open reading frame comprises nucleotide changes that increase the number of synonymous codons preferred by the mammalian cell as compared to an unmodified open reading frame encoding the same active BoNT/E; and wherein the modified open reading frame provides increased expression of the encoded active BoNT/E in the mammalian cell as compared to an expression level of the same active BoNT/E in the mammalian cell from an unmodified open reading frame in an otherwise identical nucleic acid molecule.

177. The cell according to 176, wherein the mammalian cell comprises a mouse cell, a rat cell, a hamster cell, a porcine cell, a bovine cell, an equine cell, a primate cell or a human cell.
178. The cell according to 176, wherein the mammalian cell comprises a mouse cell line, a rat cell line, a hamster cell line, a porcine cell line, a bovine cell line, an equine cell line, a primate cell line or a human cell line.
179. The cell according to 176, wherein the expression construct is transiently contained in the mammalian cell.
180. The cell according to 176, wherein the expression construct is stably contained in the mammalian cell.
181. The cell according to 176, wherein the modified open reading frame comprises nucleotide changes that alter at least 500 synonymous codons.
182. The cell according to 176, wherein the modified open reading frame comprises nucleotide changes that alter at least 700 synonymous codons.
183. The cell according to 176, wherein the modified open reading frame comprises nucleotide changes that alter at least 1000 synonymous codons.
184. The cell according to 176, wherein the active BoNT/E comprises SEQ ID NO: 1, SEQ ID NO: 123 or SEQ ID NO: 125.
185. The cell according to 176, wherein the expression vector is a mammalian expression vector.
186. The cell according to 176, wherein the increased expression of the active BoNT/E from the modified open reading frame is at least two-fold higher as compared to the expression level of the same active BoNT/E from the unmodified open reading frame.
187. The cell according to 176, wherein the increased expression of the active BoNT/E from the modified open reading frame is at least five-fold higher as compared to the expression level of the same active BoNT/E from the unmodified open reading frame.
188. The cell according to 176, wherein the increased expression of the active BoNT/E from the modified open reading frame is at least ten-fold higher as compared to the expression level of the same active BoNT/E from the unmodified open reading frame.
189. A mammalian cell comprising an expression construct, the expression construct comprising, i) a modified open reading frame encoding an active BoNT/E; and ii) an expression vector; wherein the modified open reading frame comprises nucleotide changes that increase total G+C content to a level preferred by the mammalian cell as compared to an unmodified open reading frame encoding the same active BoNT/E; and wherein the modified open reading frame provides increased expression of the encoded active BoNT/E in the mammalian cell as compared to an expression level of the same active BoNT/E in the mammalian cell from an unmodified open reading frame in an otherwise identical nucleic acid molecule.
190. The cell according to 189, wherein the mammalian cell comprises a mouse cell, a rat cell, a hamster cell, a porcine cell, a bovine cell, an equine cell, a primate cell or a human cell.
191. The cell according to 189, wherein the mammalian cell comprises a mouse cell line, a rat cell line, a hamster cell line, a porcine cell line, a bovine cell line, an equine cell line, a primate cell line or a human cell line.
192. The cell according to 189, wherein the expression construct is transiently contained in the mammalian cell.
193. The cell according to 189, wherein the expression construct is stably contained in the mammalian cell.
194. The cell according to 189, wherein the modified open reading frame comprises nucleotide changes that increase the total G+C content to at least 30%.
195. The cell according to 189, wherein the modified open reading frame comprises nucleotide changes that increase the total G+C content to at least 40%.
196. The cell according to 189, wherein the modified open reading frame comprises nucleotide changes that increase the total G+C content to at least 50%.
197. The cell according to 189, wherein the active BoNT/E comprises SEQ ID NO: 1, SEQ ID NO: 123 or SEQ ID NO: 125.
198. The cell according to 189, wherein the expression vector is a mammalian expression vector.
199. The cell according to 189, wherein the increased expression of the active BoNT/E from the modified open reading frame is at least two-fold higher as compared to the expression level of the same active BoNT/E from the unmodified open reading frame.
200. The cell according to 189, wherein the increased expression of the active BoNT/E from the modified open reading frame is at least five-fold higher as compared to the expression level of the same active BoNT/E from the unmodified open reading frame.
201. The cell according to 189, wherein the increased expression of the active BoNT/E from the modified open reading frame is at least ten-fold higher as compared to the expression level of the same active BoNT/E from the unmodified open reading frame.

EXAMPLES

The following non-limiting examples are provided for illustrative purposes only in order to facilitate a more complete understanding of disclosed embodiments and are in no way intended to limit any of the embodiments disclosed in the present specification.

Example 1

Selection of Nucleotide Alterations for an Open Reading Frame Providing Increased Expression of the Encoded Active BoNT/E in a Heterologous Cell 1. Manual Selection of Nucleotide Alterations To determine codon use of a particular heterologous cell and how it compares to the codon usage found in *C. botulinum*, codon usage for *C. botulinum* and selected heterologous cells were tabulated using information obtained from the publicly maintained Codon Usage Database to facilitate comparisons among organisms (Table 1).

TABLE 1

Codon Usage Frequency

| Amino Acid | Codon | Codon Usage Frequency (%) *Clostridia botulinum* | *Escherichia coli* K12 | *Pichia pastoris* | *Yarrowia lipolytica* | *Spodoptera frugiperda* | *Drosophila melanogaster* | *Mus musculus* |
|---|---|---|---|---|---|---|---|---|
| Gly | GGG | 0.10 | 0.15 | 0.10 | 0.05 | 0.05 | 0.07 | 0.23 |
| Gly | GGA | 0.50 | 0.11 | 0.32 | 0.29 | 0.28 | 0.28 | 0.26 |
| Gly | GGT | 0.33 | 0.34 | 0.44 | 0.32 | 0.37 | 0.21 | 0.18 |
| Gly | GGC | 0.07 | 0.40 | 0.14 | 0.34 | 0.31 | 0.43 | 0.33 |
| Glu | GAG | 0.17 | 0.31 | 0.43 | 0.77 | 0.59 | 0.67 | 0.60 |
| Glu | GAA | 0.83 | 0.69 | 0.57 | 0.23 | 0.41 | 0.33 | 0.40 |
| Asp | GAT | 0.90 | 0.63 | 0.58 | 0.34 | 0.37 | 0.53 | 0.44 |
| Asp | GAC | 0.10 | 0.37 | 0.42 | 0.66 | 0.63 | 0.47 | 0.56 |
| Val | GTG | 0.07 | 0.37 | 0.19 | 0.33 | 0.35 | 0.47 | 0.46 |
| Val | GTA | 0.47 | 0.15 | 0.15 | 0.05 | 0.15 | 0.11 | 0.12 |
| Val | GTT | 0.45 | 0.26 | 0.42 | 0.25 | 0.20 | 0.18 | 0.17 |
| Val | GTC | 0.02 | 0.22 | 0.23 | 0.37 | 0.30 | 0.24 | 0.25 |
| Ala | GCG | 0.04 | 0.35 | 0.06 | 0.08 | 0.17 | 0.19 | 0.10 |
| Ala | GCA | 0.46 | 0.21 | 0.24 | 0.11 | 0.15 | 0.17 | 0.23 |
| Ala | GCT | 0.45 | 0.16 | 0.45 | 0.35 | 0.36 | 0.19 | 0.29 |
| Ala | GCC | 0.06 | 0.27 | 0.26 | 0.46 | 0.31 | 0.45 | 0.38 |
| Arg | AGG | 0.12 | 0.02 | 0.15 | 0.04 | 0.21 | 0.11 | 0.22 |
| Arg | AGA | 0.73 | 0.04 | 0.47 | 0.13 | 0.16 | 0.09 | 0.21 |
| Ser | AGT | 0.30 | 0.15 | 0.15 | 0.07 | 0.11 | 0.14 | 0.15 |
| Ser | AGC | 0.06 | 0.28 | 0.09 | 0.11 | 0.17 | 0.25 | 0.24 |
| Lys | AAG | 0.19 | 0.23 | 0.54 | 0.85 | 0.69 | 0.71 | 0.61 |
| Lys | AAA | 0.81 | 0.77 | 0.46 | 0.15 | 0.31 | 0.29 | 0.39 |
| Asn | AAT | 0.90 | 0.45 | 0.47 | 0.17 | 0.29 | 0.44 | 0.43 |
| Asn | AAC | 0.10 | 0.55 | 0.53 | 0.83 | 0.71 | 0.56 | 0.57 |
| Met | ATG | 1.00 | 1.00 | 1.00 | 1.00 | 1.00 | 1.00 | 1.00 |
| Ile | ATA | 0.52 | 0.07 | 0.18 | 0.03 | 0.12 | 0.19 | 0.16 |
| Ile | ATT | 0.43 | 0.51 | 0.50 | 0.44 | 0.29 | 0.34 | 0.34 |
| Ile | ATC | 0.05 | 0.42 | 0.32 | 0.53 | 0.60 | 0.47 | 0.51 |
| Thr | ACG | 0.04 | 0.27 | 0.11 | 0.11 | 0.16 | 0.26 | 0.11 |
| Thr | ACA | 0.44 | 0.13 | 0.24 | 0.13 | 0.21 | 0.19 | 0.29 |
| Thr | ACT | 0.46 | 0.17 | 0.40 | 0.26 | 0.27 | 0.17 | 0.25 |
| Thr | ACC | 0.06 | 0.43 | 0.25 | 0.50 | 0.36 | 0.38 | 0.35 |
| Trp | TGG | 1.00 | 1.00 | 1.00 | 1.00 | 1.00 | 1.00 | 1.00 |
| End | TGA | 0.03 | 0.29 | 0.18 | 0.15 | 0.16 | 0.26 | 0.50 |
| Cys | TGT | 0.80 | 0.45 | 0.66 | 0.45 | 0.35 | 0.29 | 0.48 |
| Cys | TGC | 0.20 | 0.55 | 0.34 | 0.55 | 0.65 | 0.71 | 0.52 |
| End | TAG | 0.23 | 0.07 | 0.28 | 0.39 | 0.16 | 0.33 | 0.23 |
| End | TAA | 0.74 | 0.64 | 0.54 | 0.46 | 0.69 | 0.41 | 0.27 |
| Tyr | TAT | 0.90 | 0.57 | 0.44 | 0.17 | 0.25 | 0.37 | 0.42 |
| Tyr | TAC | 0.10 | 0.43 | 0.56 | 0.83 | 0.75 | 0.63 | 0.58 |
| Leu | TTG | 0.10 | 0.13 | 0.33 | 0.09 | 0.20 | 0.18 | 0.13 |
| Leu | TTA | 0.65 | 0.13 | 0.15 | 0.01 | 0.07 | 0.05 | 0.06 |
| Phe | TTT | 0.88 | 0.57 | 0.54 | 0.37 | 0.24 | 0.37 | 0.43 |
| Phe | TTC | 0.12 | 0.43 | 0.46 | 0.63 | 0.76 | 0.63 | 0.57 |
| Ser | TCG | 0.02 | 0.15 | 0.09 | 0.16 | 0.13 | 0.20 | 0.05 |
| Ser | TCA | 0.28 | 0.12 | 0.19 | 0.08 | 0.15 | 0.09 | 0.14 |
| Ser | TCT | 0.30 | 0.15 | 0.29 | 0.28 | 0.19 | 0.08 | 0.19 |
| Ser | TCC | 0.04 | 0.15 | 0.20 | 0.31 | 0.25 | 0.24 | 0.22 |
| Arg | CGG | 0.01 | 0.10 | 0.05 | 0.11 | 0.05 | 0.15 | 0.19 |
| Arg | CGA | 0.04 | 0.06 | 0.11 | 0.55 | 0.07 | 0.15 | 0.12 |
| Arg | CGT | 0.09 | 0.38 | 0.16 | 0.10 | 0.26 | 0.16 | 0.09 |
| Arg | CGC | 0.01 | 0.40 | 0.05 | 0.07 | 0.24 | 0.33 | 0.18 |
| Gln | CAG | 0.14 | 0.65 | 0.39 | 0.82 | 0.60 | 0.70 | 0.75 |
| Gln | CAA | 0.86 | 0.35 | 0.61 | 0.18 | 0.40 | 0.30 | 0.25 |
| His | CAT | 0.87 | 0.57 | 0.54 | 0.32 | 0.32 | 0.40 | 0.40 |
| His | CAC | 0.13 | 0.43 | 0.46 | 0.68 | 0.68 | 0.60 | 0.60 |
| Leu | CTG | 0.01 | 0.50 | 0.16 | 0.38 | 0.31 | 0.43 | 0.40 |
| Leu | CTA | 0.10 | 0.04 | 0.11 | 0.05 | 0.07 | 0.09 | 0.08 |
| Leu | CTT | 0.13 | 0.10 | 0.16 | 0.18 | 0.13 | 0.10 | 0.13 |
| Leu | CTC | 0.01 | 0.10 | 0.08 | 0.29 | 0.22 | 0.15 | 0.20 |
| Pro | CCG | 0.03 | 0.52 | 0.09 | 0.09 | 0.16 | 0.29 | 0.10 |
| Pro | CCA | 0.44 | 0.19 | 0.40 | 0.10 | 0.23 | 0.25 | 0.28 |
| Pro | CCT | 0.46 | 0.16 | 0.35 | 0.32 | 0.30 | 0.13 | 0.30 |
| Pro | CCC | 0.07 | 0.13 | 0.15 | 0.49 | 0.31 | 0.33 | 0.31 |

| Amino Acid | Codon | Codon Usage Frequency (%) *Rattus norvegicus* | *Cricetulus griseus* | *Sus scrofa* | *Bos taurus* | *Equus caballus* | *Cercopithecus aethiops* | *Homo sapiens* |
|---|---|---|---|---|---|---|---|---|
| Gly | GGG | 0.24 | 0.21 | 0.26 | 0.25 | 0.24 | 0.26 | 0.25 |
| Gly | GGA | 0.25 | 0.25 | 0.23 | 0.24 | 0.23 | 0.24 | 0.25 |

TABLE 1-continued

| Codon Usage Frequency | | | | | | | | |
|---|---|---|---|---|---|---|---|---|
| Gly | GGT | 0.17 | 0.20 | 0.14 | 0.16 | 0.17 | 0.15 | 0.16 |
| Gly | GGC | 0.34 | 0.34 | 0.37 | 0.35 | 0.37 | 0.35 | 0.34 |
| Glu | GAG | 0.61 | 0.60 | 0.64 | 0.60 | 0.64 | 0.62 | 0.58 |
| Glu | GAA | 0.39 | 0.40 | 0.36 | 0.40 | 0.36 | 0.38 | 0.42 |
| Asp | GAT | 0.42 | 0.47 | 0.39 | 0.42 | 0.41 | 0.42 | 0.46 |
| Asp | GAC | 0.58 | 0.53 | 0.61 | 0.58 | 0.59 | 0.58 | 0.54 |
| Val | GTG | 0.48 | 0.46 | 0.51 | 0.49 | 0.50 | 0.46 | 0.47 |
| Val | GTA | 0.11 | 0.12 | 0.08 | 0.10 | 0.08 | 0.08 | 0.12 |
| Val | GTT | 0.16 | 0.18 | 0.14 | 0.16 | 0.14 | 0.17 | 0.18 |
| Val | GTC | 0.26 | 0.24 | 0.27 | 0.26 | 0.28 | 0.29 | 0.24 |
| Ala | GCG | 0.10 | 0.07 | 0.12 | 0.11 | 0.12 | 0.10 | 0.11 |
| Ala | GCA | 0.22 | 0.24 | 0.18 | 0.20 | 0.18 | 0.19 | 0.23 |
| Ala | GCT | 0.28 | 0.33 | 0.24 | 0.26 | 0.25 | 0.26 | 0.26 |
| Ala | GCC | 0.40 | 0.37 | 0.46 | 0.43 | 0.44 | 0.45 | 0.40 |
| Arg | AGG | 0.21 | 0.19 | 0.20 | 0.21 | 0.22 | 0.20 | 0.21 |
| Arg | AGA | 0.19 | 0.19 | 0.19 | 0.20 | 0.20 | 0.16 | 0.21 |
| Ser | AGT | 0.15 | 0.16 | 0.12 | 0.14 | 0.13 | 0.14 | 0.15 |
| Ser | AGC | 0.25 | 0.22 | 0.27 | 0.25 | 0.26 | 0.26 | 0.24 |
| Lys | AAG | 0.63 | 0.61 | 0.63 | 0.61 | 0.63 | 0.61 | 0.57 |
| Lys | AAA | 0.37 | 0.39 | 0.37 | 0.39 | 0.37 | 0.39 | 0.43 |
| Asn | AAT | 0.40 | 0.45 | 0.39 | 0.40 | 0.39 | 0.41 | 0.47 |
| Asn | AAC | 0.60 | 0.55 | 0.61 | 0.60 | 0.61 | 0.59 | 0.53 |
| Met | ATG | 1.00 | 1.00 | 1.00 | 1.00 | 1.00 | 1.00 | 1.00 |
| Ile | ATA | 0.14 | 0.14 | 0.13 | 0.14 | 0.13 | 0.12 | 0.16 |
| Ile | ATT | 0.32 | 0.35 | 0.29 | 0.33 | 0.29 | 0.30 | 0.36 |
| Ile | ATC | 0.54 | 0.51 | 0.57 | 0.53 | 0.58 | 0.58 | 0.48 |
| Thr | ACG | 0.12 | 0.08 | 0.15 | 0.13 | 0.13 | 0.18 | 0.12 |
| Thr | ACA | 0.28 | 0.29 | 0.22 | 0.25 | 0.22 | 0.27 | 0.28 |
| Thr | ACT | 0.23 | 0.26 | 0.20 | 0.22 | 0.22 | 0.22 | 0.24 |
| Thr | ACC | 0.37 | 0.37 | 0.43 | 0.39 | 0.43 | 0.34 | 0.36 |
| Trp | TGG | 1.00 | 1.00 | 1.00 | 1.00 | 1.00 | 1.00 | 1.00 |
| End | TGA | 0.49 | 0.49 | 0.55 | 0.49 | 0.42 | 0.48 | 0.49 |
| Cys | TGT | 0.44 | 0.47 | 0.39 | 0.42 | 0.43 | 0.39 | 0.45 |
| Cys | TGC | 0.56 | 0.53 | 0.61 | 0.58 | 0.57 | 0.61 | 0.55 |
| End | TAG | 0.23 | 0.26 | 0.19 | 0.23 | 0.23 | 0.32 | 0.23 |
| End | TAA | 0.28 | 0.25 | 0.25 | 0.29 | 0.35 | 0.20 | 0.28 |
| Tyr | TAT | 0.40 | 0.44 | 0.36 | 0.39 | 0.35 | 0.41 | 0.44 |
| Tyr | TAC | 0.60 | 0.56 | 0.64 | 0.61 | 0.65 | 0.59 | 0.56 |
| Leu | TTG | 0.12 | 0.15 | 0.11 | 0.12 | 0.11 | 0.12 | 0.13 |
| Leu | TTA | 0.06 | 0.06 | 0.05 | 0.06 | 0.05 | 0.06 | 0.07 |
| Phe | TTT | 0.41 | 0.47 | 0.38 | 0.41 | 0.39 | 0.40 | 0.46 |
| Phe | TTC | 0.59 | 0.53 | 0.62 | 0.59 | 0.61 | 0.60 | 0.54 |
| Ser | TCG | 0.06 | 0.05 | 0.06 | 0.06 | 0.06 | 0.05 | 0.06 |
| Ser | TCA | 0.14 | 0.14 | 0.12 | 0.13 | 0.12 | 0.13 | 0.15 |
| Ser | TCT | 0.19 | 0.22 | 0.17 | 0.18 | 0.18 | 0.19 | 0.19 |
| Ser | TCC | 0.23 | 0.22 | 0.26 | 0.23 | 0.25 | 0.23 | 0.22 |
| Arg | CGG | 0.20 | 0.20 | 0.21 | 0.20 | 0.18 | 0.22 | 0.21 |
| Arg | CGA | 0.12 | 0.14 | 0.10 | 0.11 | 0.10 | 0.11 | 0.11 |
| Arg | CGT | 0.09 | 0.11 | 0.07 | 0.08 | 0.10 | 0.08 | 0.08 |
| Arg | CGC | 0.19 | 0.17 | 0.22 | 0.20 | 0.20 | 0.22 | 0.19 |
| Gln | CAG | 0.76 | 0.77 | 0.78 | 0.76 | 0.76 | 0.73 | 0.74 |
| Gln | CAA | 0.24 | 0.23 | 0.22 | 0.24 | 0.24 | 0.27 | 0.26 |
| His | CAT | 0.38 | 0.44 | 0.35 | 0.36 | 0.38 | 0.36 | 0.42 |
| His | CAC | 0.62 | 0.56 | 0.65 | 0.64 | 0.62 | 0.64 | 0.58 |
| Leu | CTG | 0.42 | 0.40 | 0.45 | 0.43 | 0.46 | 0.41 | 0.40 |
| Leu | CTA | 0.07 | 0.08 | 0.05 | 0.06 | 0.06 | 0.06 | 0.07 |
| Leu | CTT | 0.12 | 0.13 | 0.11 | 0.12 | 0.11 | 0.15 | 0.13 |
| Leu | CTC | 0.21 | 0.19 | 0.23 | 0.21 | 0.22 | 0.20 | 0.20 |
| Pro | CCG | 0.11 | 0.08 | 0.14 | 0.13 | 0.11 | 0.11 | 0.11 |
| Pro | CCA | 0.27 | 0.28 | 0.24 | 0.25 | 0.23 | 0.33 | 0.27 |
| Pro | CCT | 0.30 | 0.32 | 0.26 | 0.27 | 0.30 | 0.24 | 0.28 |
| Pro | CCC | 0.32 | 0.32 | 0.37 | 0.35 | 0.35 | 0.33 | 0.33 |

To determine G+C content of a particular heterologous cell and how it compares to the codon usage found in *C. botulinum*, G+C content for *C. botulinum* and selected heterologous cells were tabulated using information obtained from the publicly maintained Codon Usage Database to facilitate comparisons among organisms (Table 2).

TABLE 2

G + C content

| Organism | Total G + C Content (%) | First Codon Position G + C Content (%) | Second Codon Position G + C Content (%) | Third Codon Position G + C Content (%) |
|---|---|---|---|---|
| *Clostridium botulinum* | 25.29 | 33.44 | 28.38 | 14.04 |
| *Escherichia coli* | 51.80 | 58.89 | 40.72 | 55.79 |
| *Pichia pastoris* | 42.99 | 49.16 | 37.49 | 42.32 |
| *Yarrowia lipolytica* | 54.69 | 58.17 | 41.18 | 64.71 |
| *Zea mays* | 54.60 | 57.46 | 43.03 | 63.31 |
| *Spodoptera frugiperda* | 51.44 | 53.92 | 39.52 | 60.88 |
| *Drosophila melanogaster* | 53.99 | 55.90 | 41.51 | 64.57 |
| *Mus musculus* | 52.33 | 55.57 | 42.19 | 59.24 |
| *Rattus norvegicus* | 52.82 | 55.64 | 41.64 | 61.19 |
| *Cricetulus griseus* | 51.26 | 55.29 | 40.43 | 58.07 |
| *Sus scrofa* | 54.68 | 56.47 | 41.95 | 65.63 |
| *Bos taurus* | 53.14 | 55.43 | 41.46 | 62.53 |
| *Equus caballus* | 53.63 | 55.96 | 40.71 | 64.21 |
| *Cercopithecus aethiops* | 52.81 | 53.80 | 42.36 | 62.26 |
| *Homo sapiens* | 52.54 | 56.10 | 42.55 | 58.99 |

Using Tables 1 and 2, one skilled in the art can manually select which nucleotides to alter to the open reading frame of SEQ ID NO: 3 so that the open reading frame now provides synonymous codons preferred by the heterologous cell selected to express this open reading frame and increase the G+C content to better match the G+C content of this heterologous cell.

2. Computer-Assisted Selection of Nucleotide Alterations

To alter the open reading frame of SEQ ID NO: 3 in order to provide increased expression of the encoded BoNT/E in a heterologous cell, synonymous codon usage for each organism was determined using the publicly available Backtranslate Tool, version 2 (Entelechon, GmbH, Regensburg, Germany, at URL address entelechon. com/eng/backtranslation). The active BoNT/E amino acid sequence of SEQ ID NO: 1 was submitted to this web-based program and prospective modified open reading frames were generated. These modified sequences were subsequently analyzed for G+C content, and substitutions that better matched the G+C content of a specific heterologous cell were made. This procedure resulted in the modified open reading frames SEQ ID NO: 5 through SEQ ID NO: 97, each encoding an active BoNT/E of SEQ ID NO: 1, but optimized to be expressed in a heterologous cell.

Example 2

Synthesis of a Nucleic Acid Molecule

A nucleic acid molecule of SEQ ID NO: 98 encoding a BoNT/E was modified so that particular synonymous codons preferred by *E. coli* were incorporated and the G+C content was increased from about 25% to approximately 40%. Initially, an algorithm generated the modified open reading frame of SEQ ID NO: 98 that encoded the BoNT/E of SEQ ID NO: 2 (BLUEHERON® Biotechnology, Bothell Wash.). This program 1) reduced the mRNA secondary structure (based on a free energy calculation) of the nucleic acid molecule and 2) altered the synonymous codon usage of the open reading frame of the nucleic acid molecule to an overall codon usage preferred by *E. coli*. The algorithm uses a statistical model to search for improved solutions (i. e., combinations of representative codon usage and lower free energy) through an iterative process. This sequence was then modified by one skilled in the art at Allergan, Inc. to add unique restriction endonuclease sites at the 5'-termini (e.g., EcoRV, BamHI, EcoRI, SacI and NdeI) and 3'-termini (e.g., SalI, HindIII, NotI, EagI, XhoI and AvaI) of the nucleic acid molecule in order to facilitate cloning into expression vectors, reduce polymononucleotide regions and remove internal regulatory or structural site sequences.

Based on this sequence information above, BLUEHERON® Biotechnology synthesized a nucleic acid molecule of SEQ ID NO: 98, designated BoNT/E (8m). Oligonucleotides of 20 to 50 bases in length were synthesized using standard phosphoramidite synthesis. These oligonucleotides were hybridized into double stranded duplexes that were ligated together to assemble the full-length nucleic acid molecule. This nucleic acid molecule was cloned using standard molecular biology methods into a pUCBHB1 vector at the SmaI site to generate pUCBHB1-BoNT/E (8m). The synthesized nucleic acid molecule was verified by sequencing using BIG DYE TERMINATOR™ Chemistry 3.1, a fluorescently-labeled dideoxynucleotide chain-terminator sequencing method, (Applied Biosystems, Foster City, Calif.) and an ABI 3100 sequencer (Applied Biosystems, Foster City, Calif.).

Example 3

Construction of pET28a/His-BoNT/E (8m)

To construct pET28a/His-BoNT/E (8m), a pUCBHB1/BoNT/E (8m) construct was digested with NdeI and HinIII at 37° C. for 2.5 hours to excise the BoNT/E (8m) insert. The resulting restriction fragment was purified by the QIAquick Gel Extraction Kit (QIAGEN, Inc., Valencia, Calif.), and the fragment containing the entire open reading frame was subcloned into the pET28a vector (EMD Biosciences-Novagen, Madison, Wis.) that had been digested with restriction endonucleases NdeI and HindIII. The fragment and vector were ligated using T4 DNA ligase protocol to yield pET28a/His-BoNT/E (8m). Both 1 μL and 2 μL samples from this ligation mixture were transformed by a standard heat-shock protocol into two separate vials of competent TOP10 cells (Invitrogen, Inc, Carlsbad, Calif.), plated onto 1.5% Luria-Bertani agar plates (pH 7.0) containing 50 μg/mL of Kanamycin, and placed in a 37° C. incubator for overnight growth. Candidate expression constructs were selected as Kanamycin-resistant colonies. Resistant colonies were used to inoculate 2 mL of Luria-Bertani media containing 50 μg/mL of Kanamycin that were then grown in a 37° C. incubator, shaking at 250 rpm, for 5 hours. The bacteria cells were harvested by microcentrifugation and the plasmid DNA was isolated using QIAGEN miniprep kits (QIAGEN, Inc., Valencia, Calif.). Candidate expression constructs were screened by restriction digestion with NdeI and HindIII to determine the presence and orientation of the correct insert fragment. Cultures containing the desired expression construct were used to inoculate 1 L baffled flasks containing 200 mL of Luria-Bertani media containing 50 μg/mL of Kanamycin and placed in a 37° C. incubator, shaking at 250 rpm, for overnight growth. Purified plasmid DNA corresponding to an expression construct was isolated using the QIAGEN Maxi-prep method (QIAGEN, Inc., Valencia, Calif.) and sequenced to verify that the correct expression construct was made (service contract with Sequetech Corp., Mountain View, Calif.). This cloning strategy yielded a prokaryotic expression construct encoding a BoNT/E (8m) peptide containing an amino-terminal thrombin cleavable polyhistidine affinity binding peptide.

To test for enzymatic activity of His-BoNT/E (8m), the light chain from His-BoNT/E (8m) was tested using a SNAP-25 Cleavage Assay. Because of regulatory and safety considerations, initial activity assays were performed using pQBI25/GFP-LC-BoNT/E (8m), a construct comprising amino acids 3 to 422 of SEQ ID NO: 2, the light chain of BoNT/E (8m), operationally linked to an amino-terminal Green Fluorescent Protein (GFP). To test for enzymatic activity using a SNAP-25 Cleavage Assay, about $1.0\times10^6$ SH-SY5Y cells were plated in a 60 mm tissue culture dish containing 5 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 1× MEM non-essential amino acids solution (Invitrogen, Inc, Carlsbad, Calif.), and grown in a 37° C. incubator under 5% carbon dioxide until cells reach a density of about $5\times10^6$ cells/ml (6-16 hours). A 500 μL transfection solution is prepared by adding 250 μL of OPTI-MEM Reduced Serum Medium containing 15 μL of LIPOFECTAMINE 2000, a cationic liposome based reagent, (Invitrogen, Carlsbad, Calif.) incubated at room temperature for 5 minutes to 250 μL of OPTI-MEM Reduced Serum Medium containing 5 μg of pQBI25/GFP-LC-BoNT/E. This transfection was incubated at room temperature for approximately 20 minutes. The complete, supplemented DMEM media was replaced with 2 mL of OPTI-MEM Reduced Serum Medium and the 500 μL transfection solution was added to the SH-SY5Y cells and the cells incubated in a 37° C. incubator under 5% carbon dioxide for approximately 6 to 18 hours. Transfection media was replaced with 3 mL of fresh complete, supplemented DMEM and incubate cells in a 37° C. incubator under 5% carbon dioxide for an additional 24 hours. Cells were harvest by rinsing cells once with 3.0 mL of 100 mM phosphate-buffered saline, pH 7.4 and rinsed cells were lysed with 500 μL of Lysis Buffer containing 50 mM N-(2-hydroxyethyl) piperazine-N'-(2-ethanesulfonic acid) (HEPES), 150 mM sodium chloride, 1.5 mM magnesium chloride, 1 mM ethylene glycol bis(β-aminoethyl ether) N, N, N', N'-tetraacetic acid (EGTA), 10% (v/v) glycerol and 1% (v/v) TRITON-X® 100 (4-octylphenol polyethoxylate) at 4° C. with rotation for 60 minutes. Lysed cells were centrifuged (5000 rpm at 4° C. for 10 min) to pellet debris and the supernatant was transferred to fresh siliconized tubes.

The protein concentration of a sample was measured by a Bradford dye assay and 1× LDS Sample Buffer was added to bring the protein concentration to 1 mg/ml. Protein samples were then added to 2× LDS Sample Buffer (Invitrogen, Inc, Carlsbad, Calif.) and separated by MOPS polyacrylamide gel electrophoresis using NUPAGE® Novex 4-12% Bis-Tris precast polyacrylamide gels (Invitrogen, Inc, Carlsbad, Calif.) under denaturing, reducing conditions. Separated peptides were transferred from the gel onto polyvinylidene fluoride (PVDF) membranes (Invitrogen, Inc, Carlsbad, Calif.) by Western blotting using a TRANS-BLOT® SD semi-dry electrophoretic transfer cell apparatus (Bio-Rad Laboratories, Hercules, Calif.). PVDF membranes were blocked by incubating at room temperature for 2 hours in a solution containing 25 mM Tris-Buffered Saline (25 mM 2-amino-2-hydroxymethyl-1,3-propanediol hydrochloric acid (Tris-HCl), pH 7.4, 137 mM sodium chloride, 2.7 mM potassium chloride), 0.1% TWEEN-20®, polyoxyethylene (20) sorbitan monolaureate, 2% (w/v) bovine serum albumin, 5% (w/v) nonfat dry milk. Blocked membranes were incubated at 4° C. for overnight in Tris-Buffered Saline TWEEN-20® (25 mM Tris-Buffered Saline, 0.1% TWEEN-20®, polyoxyethylene (20) sorbitan monolaureate) containing the following primary antibodies as a probe: a 1:50,000 dilution of mouse monoclonal anti-BoNT/E SMI-81 antibody (Sternberger Monoclonals, Lutherville, Md). Primary antibody probed blots were washed three times for 15 minutes each time in Tris-Buffered Saline TWEEN-20®. Washed membranes were incubated at room temperature for 2 hours in Tris-Buffered Saline TWEEN-20® containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) as a secondary antibody. Secondary antibody-probed blots were washed three times for 15 minutes each time in Tris-Buffered Saline TWEEN-20®. Signal detection of labeled His-iBoNT/E was visualized using the ECL Plus™ Western Blot Detection System (Amersham Biosciences, Piscataway, N.J.) and imaged with a Typhoon 9410 Variable Mode Imager (Amersham Biosciences, Piscataway, N.J.) for quantification of peptide expression levels.

Unexpectedly, this initial analysis revealed that while the positive controls showed significant protease activity, GFP-LC-BoNT/E expressed at the same level as the controls from modified nucleic acid molecules derived from SEQ ID NO: 98 did not exhibit appreciable levels of enzymatic activity. Sequence alignment of the full-length BoNT/E revealed eight non-conserved amino acid polymorphisms that were unique to the native *C. botulinum* sequence deposited in GenBank as accession # X62089 (SEQ ID NO: 2) relative to another native *C. botulinum* sequence deposited as accession # X62683 (SEQ ID NO: 1). There were three amino acid substitutions located in the LC, while four substitutions and a single amino acid deletion were present in the HC. The amino acid changes that were unique to the Genbank *C. botulinum* (accession # X62089; SEQ ID NO: 2) are summarized in Table 3.

Using a SNAP-25 Cleavage Assay as described above, the presence of either G177 or A340 in the LC resulted in enzymatic inactivity of the His-BoNT/E (8m). Furthermore, any combination of the two LC amino acid mutations from SEQ ID NO: 2 inactivated the BoNT/E (i. e., G177/S198, G177/A340, S198/A340). Thus, the nucleic acid molecule of SEQ ID NO: 98 encodes an inactive BoNT/E (SEQ ID NO: 2) containing eight mutations and is referred to as: BoNT/E (G177R/S198C/A340R/L7731/L963F/Q964E/A967R/AN1196) or BoNT/E (8m).

TABLE 3

Eight mutations found in BoNT/E

| Position | BoNT/E SEQ ID NO: 1 | BoNT/E SEQ ID NO: 2 | Abbreviation | Conserved |
|---|---|---|---|---|
| 177 (LC) | Glycine | Arginine | G177R | No |
| 198 (LC) | Serine | Cysteine | S198C | Weak |
| 340 (LC) | Alanine | Arginine | A340R | No |
| 773 (HC) | Leucine | Isoleucine | L773I | Strong |
| 963 (HC) | Leucine | Phenylalanine | L963F | No |
| 964 (HC) | Glutamine | Glutamate | Q964E | Weak |
| 967 (HC) | Alanine | Arginine | A967R | No |
| 1196 (HC) | Asparagine | Deleted | ΔN1196 | No |

Example 4

Construction of pET28a/His-iBoNT/E (H216Y) and pET28a/His-iBoNT/E (E213Q)

Because of regulatory and safety considerations, initial expression of a construct comprising a modified open reading frame encoding BoNT/E was performed using enzymatically inactive BoNT/E (iBoNT/E). These initial expression attempts allowed development of the protocols and strategies necessary for expressing the constructs encoding an active BoNT/E. Several iBoNT/Es were designed based on the knowledge that mutation of the zinc binding motif within the LC disrupts enzymatic activity. Substitution of residue Histidine-227 in BoNT/A with tyrosine (H227Y) is inactivating, see, e.g., Zhou et al., supra, (1995). Since the zinc binding motif of the BoNT light chain endopeptidases is absolutely conserved, the equivalent BoNT/E point mutation was designed to yield iBoNT/E (H216Y) (numbering based on the native BoNT/E sequence without any affinity binding peptide). A second point mutation, one in which glutamine replaces Glutamate-213 (E213Q), was also constructed. Unlike the H216Y mutant, in which a zinc binding residue is mutated, the E213Q mutation replaces the residue responsible for coordinating and activating the nucleophilic water molecule that adds to the scissile peptide bond. Both of these inactivating mutations are within the highly conserved zinc binding motif (Table 4).

TABLE 4

Zinc-binding motif inactivating mutations

| Consensus motif: | HExxH |
|---|---|
| Native BoNT/E: | HELIH |
| iBoNT/E(H216Y) | HELIY |
| iBoNT/E(E213Q) | HQLIH |

The pET28a/His-BoNT/E (8m) of Example 3 was used as the starting construct for a series of site-directed in vitro mutagenesis experiments that resulted in the construction of the prokaryotic expression constructs pET28a/His-iBoNT/E (H216Y) and pET28a/His-iBoNT/E (E213Q). These experiments both corrected the eight mutations discussed in Example 3 and introduced one of the two zinc binding motif mutations. A 50 μL reaction was assembled with the pET28a/His-BoNT/E (8m) expression construct as a template, primers specified below and reagents included with the QuickChange® II XL Site-Directed Mutagenesis kit (Stratagene, La Jolla, Calif.). The polymerase chain reaction (PCR) mix contained 5 μL of 10× Buffer, 1 μL of deoxyribonucleotides (dNTPs), 1 μL of PfuUltra™ High Fidelity DNA polymerase (2.5 units/μL), 125 ng of each primer, 100 ng of template DNA, and nuclease-free water to a final volume of 50 μL. The thermocycler conditions were: one cycle of 95° C. for 60 seconds; 16 cycles of 95° C. for 30 seconds, 55° C. for 60 seconds, and 72° C. for 10 minutes; one cycle of 72° C. for 5 minutes; and 4° C. to hold. Following thermocycling, 1 μL of DpnI restriction enzyme (Stratagene, La Jolla, Calif.) was added to the reaction and incubated for 1 hour at 37° C. to digest the template DNA. The reaction was purified by QIAquick kit (QIAGEN, Inc., Valencia, Calif.) and analysis by agarose gel electrophoresis showed that the reaction produced full-length plasmid. The mutagenesis products were transformed into chemically competent *E. coli* DH5α cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Candidate mutagenesis constructs were isolated as Ampicillin resistant colonies and analyzed using an alkaline lysis plasmid mini-preparation procedure to isolate the expression construct and restriction endonuclease digests to determine the presence of the insert. The incorporation of the point mutation was determined by sequence analysis (service contract with Sequetech Corp., Mountain View, Calif.) of candidate plasmid constructs.

In the initial round of site-directed mutagenesis the following oligonucleotide primer pairs were used to alter the nucleic acid molecule encoding iBoNT/E (H216Y): R177G Primer Pair, sense oligonucleotide, 5'-TATATGCCGTCGAACCAT <u>G</u>GCTTTGGCTCAATCGCAATTG-3' (SEQ ID NO: 99) and antisense oligonucleotide, 5'-CAATTGCGATTGAGCCAAAGC<u>C</u>ATGGTTCGACGGCATATA-3' (SEQ ID NO: 100); C198S Primer Pair, sense oligonucleotide, 5'-CGTTTTAACGACAAC<u>A</u>GCATGAATGAATTTAT CC-3' (SEQ ID NO: 101) and antisense oligonucleotide, 5'-GGATAAATTCATTCATGC<u>T</u>GTTGTCGTTAA ACG-3' (SEQ ID NO: 102); R340A Primer Pair, sense oligonucleotide, 5'-CCTTCACCGAATTTGA TTTG<u>GC</u>CACCAA ATTCCAGGT CAA-3' (SEQ ID NO: 103) and antisense oligonucleotide, 5'-TTGACCTGGAATT TGGTG <u>GC</u>CAAATCAAATTCGGTGAAGG-3' (SEQ ID NO: 104); 1773L Primer Pair, sense oligonucleotide, 5'-CTATTTCCTATTTGATGAAA<u>C</u>TTATCAATGAAGTCAAA-3' (SEQ ID NO: 105) and antisense, 5'-TTTGACTTCATTGATAA <u>G</u>TTTCATCAAATAGGAAATAG-3' (SEQ ID NO: 106); F963L/E964Q/R967A Primer Pair, sense primer, 5'-TATCTGGA CT<u>C</u>TT<u>C</u>AGGACAAT <u>GC</u>TGGTATCAACCAAAA ATTAGC-3' (SEQ ID NO: 107) and antisense oligonucleotide 5'-GCTAATTTTTGGTTGATACCA<u>GC</u>ATTG TCCT<u>G</u>AA<u>G</u>AGTCCAGATA-3' (SEQ ID NO: 108); +N1196 Primer Pair, sense oligonucleotide, 5'-GTTAT GAACTCGGTCGGC <u>AAC</u>AATTGTACTATGAAT-3' (SEQ ID NO: 109) and antisense oligonucleotide, 5'-ATTCATAGTACAATT <u>GTT</u>GCCGACCGAGTTCATAAC-3' (SEQ ID NO: 110) The nucleotides that were changed to correct the coding sequence are shown in bold and underlined. Sequence analysis of the resulting plasmid revealed that three corrections (C198S, R340A and Δ1196N) were incorporated to yield pET28a/His-iBoNT/E (G 177R/L7731/L963F/Q964E/A967R).

In the second round of site-directed mutagenesis the zinc-binding residue, His-216, was mutated to tyrosine using the following oligonucleotide primer pair to yield pET28a/His-iBoNT/E (G177R/H216Y/L7731/L963F/Q964E/A967R): H216Y Primer Pair, sense oligonucleotide, 5'-GCTGACTTTGATGCATGAA CTGATC <u>T</u>ATAGCTTGCACGGCCTG-3' (SEQ ID NO: 111) and antisense oligonucleotide, 5'-CAGGCCG TGCAAGCTAT <u>A</u>GATCAGTTCATGCATCAAAGTCAGC-3' (SEQ ID NO: 112). The nucleotides that were mutated are shown in bold and underlined.

In a third round of site-directed mutagenesis, the 1773L primer pair (SEQ ID NO: 105 and SEQ ID NO: 106) and the F963UE964Q/R967A primer pair (SEQ ID NO: 107 and SEQ ID NO: 108) were utilized to yield pET28a/His-iBoNT/E (G177R/H216Y). In the final round of site-directed mutagenesis, the R177G primer pair (SEQ ID NO: 99 and SEQ ID NO: 100) was used to correct the G177R substitution and produce the expression construct pET28a/His-iBoNT/E (H216Y), containing the modified nucleic acid sequence of SEQ ID NO: 118 encoding iBoNT/E (H216Y).

The plasmid coding for a second iBoNT/E, iBoNT/E (E213Q), was prepared by site-directed mutagenesis of pET28a/His-iBoNT/E (H216Y) using the procedure as described above. Correction of the inactivating H216Y mutation and incorporation of the inactivating E2130 mutation were accomplished in a single site-directed mutagenesis step using the procedure described above and the following two oligonucleotides to yield pET28a/His-iBoNT/E (E213Q): E213Q Primer Pair, sense oligonucleotide, 5'-GCTGACTTTGATGCATCAACTGATCCATAGCTTGCAC GGCCTG-3' (SEQ ID NO: 113) and antisense oligonucleotide, 5'-CAGGCCGTGCAAGCTATGGATCAGTT GATGCATCAAAGTCAGC-3' (SEQ ID NO: 114). The amino acid numbering corresponds to native sequence lacking an amino-terminal polyhistidine tag. The nucleotides that were changed to correct H216Y are shown in bold and nucleotides that were mutated to produce E213Q are shown in bold and underlined. The nucleic acid molecule of SEQ ID NO: 119 encodes a iBoNT/E (E213Q).

Example 5

Expression of pET28a/His-iBoNT/E (E213Q)

The following example illustrates a procedure useful for expressing a BoNT/E from an expression construct disclosed in the present specification. An pET28a/His-iBoNT/E (E213Q) expression construct was introduced into chemically competent *E. coli* BL21 (DE3) cells (Invitrogen, Inc, Carlsbad, Calif.) using a heat-shock transformation protocol. The heat-shock reaction was plated onto 1.5% Luria-Bertani agar plates (pH 7.0) containing 50 μg/mL of Kanamycin and placed in a 37° C. incubator for overnight growth. Kanamycin-resistant colonies of transformed *E. coli* containing pET28a/His-iBoNT/E (E213Q) were used to inoculate baffled flask containing 3.0 mL of PA-0.5 G media containing 50 μg/mL of Kanamycin which was then placed in a 37° C. incubator, shaking at 250 rpm, for overnight growth. The resulting overnight starter culture was in turn used to inoculate a 3 L baffled flask containing ZYP-5052 autoinducing media containing 50 μg/mL of Kanamycin at a dilution of 1:1000. Culture volumes ranged from about 600 mL (20% flask volume) to about 750 mL (25% flask volume). These cultures were grown in a 37° C. incubator shaking at 250 rpm for approximately 5.5 hours until mid-log phase was reached ($OD_{600}$ of about 0.6-0.8). Cultures were then transferred to a 16° C. incubator shaking at 250 rpm for overnight expression. Cells were harvested by centrifugation (4,000 rpm at 4° C. for 20-30 minutes) and used immediately, or stored dry at −80° C. until needed.

Example 6

Purification and Quantification of His-iBoNT/E (E213Q)

The following example illustrates methods useful for purification and quantification of BoNT/E disclosed in the present specification. For immobilized metal affinity chromatography (IMAC) protein purification, *E. coli* BL21 (DE3) cell pellets used to express His-iBoNT/E (E213Q), as described in Example 5, were resuspended in Column Binding Buffer (25 mM N-(2-hydroxyethyl) piperazine-N'-(2-ethanesulfonic acid) (HEPES), pH 7.8; 500 mM sodium chloride; 10 mM imidazole; 2× Protease Inhibitor Cocktail Set III (EMD Biosciences-Calbiochem, San Diego Calif.); 5 units/mL of Benzonase (EMD Biosciences-Novagen, Madison, Wis.); 0.1% (v/v) TRITON-X® 100, 4-octylphenol polyethoxylate; 10% (v/v) glycerol), and then transferred to a cold Oakridge centrifuge tube. The cell suspension was sonicated on ice (10-12 pulses of 10 seconds at 40% amplitude with 60 seconds cooling intervals on a Branson Digital Sonifier) in order to lyse the cells and release the His-iBoNT/E, and then centrifuged (16,000 rpm at 4° C. for 20 minutes) to clarify the lysate. An immobilized metal affinity chromatography column was prepared using a 20 mL Econo-Pac column support (Bio-Rad Laboratories, Hercules, Calif.) packed with 2.5-5.0 mL of TALON™ SuperFlow $Co^{2+}$affinity resin (BD Biosciences-Clontech, Palo Alto, Calif.), which was then equilibrated by rinsing with 5 column volumes of deionized, distilled water, followed by 5 column volumes of Column Binding Buffer. The clarified lysate was applied slowly to the equilibrated column by gravity flow (approximately 0.25-0.3 mL/minute). The column was then washed with 5 column volumes of Column Wash Buffer (N-(2-hydroxyethyl) piperazine-N'-(2-ethanesulfonic acid) (HEPES), pH 7.8; 500 mM sodium chloride; 10 mM imidazole; 0.1% (v/v) TRITON-X® 100, 4-octylphenol polyethoxylate; 10% (v/v) glycerol). His-iBoNT/E was eluted with 20-30 mL of Column Elution Buffer (25 mM N-(2-hydroxyethyl) piperazine-N'-(2-ethanesulfonic acid) (HEPES), pH 7.8; 500 mM sodium chloride; 500 mM imidazole; 0.1% (v/v) TRITON-X® 100, 4-octylphenol polyethoxylate; 10% (v/v) glycerol) and collected in approximately twelve 1 mL fractions. The amount of His-iBoNT/E (E213Q) peptide contained in each elution fraction was determined by a Bradford dye assay. In this procedure, 20 μL aliquots of each 1.0 mL fraction was combined with 200 μL of Bio-Rad Protein Reagent (Bio-Rad Laboratories, Hercules, Calif.), diluted 1 to 4 with deionized, distilled water, and then the intensity of the colorimetric signal was measured using a spectrophotometer. The five fractions with the strongest signal were considered the elution peak and pooled. Total protein yield was determined by estimating the total protein concentration of the pooled peak elution fractions using bovine gamma globulin as a standard (Bio-Rad Laboratories, Hercules, Calif.).

For purification of a BoNT/E using a FPLC desalting column, a HIPREP™ 26/10 size exclusion column (Amersham Biosciences, Piscataway, N.J.) was pre-equilibrated with 80 mL of 4° C. Column Buffer (50 mM sodium phosphate, pH 6.5). After the column was equilibrated, a His-iBoNT/E (E213Q) sample was applied to the size exclusion column with an isocratic mobile phase of 4° C. Column Buffer and at a flow rate of 10 mL/minute using a BioLogic DuoFlow chromatography system (Bio-Rad Laboratories, Hercules, Calif.). The desalted His-iBoNT/E (E213Q) sample was collected as a single fraction of approximately 7-12 mL.

For purification of a BoNT/E using a FPLC ion exchange column, a His-iBoNT/E (E213Q) sample that had been desalted following elution from an IMAC column was applied to a 1 mL UNO-S1™ cation exchange column (Bio-Rad Laboratories, Hercules, Calif.) using a BioLogic DuoFlow chromatography system (Bio-Rad Laboratories, Hercules, Calif.). The sample was applied to the column in 4° C. Column Buffer (50 mM sodium phosphate, pH 6.5) and eluted by linear gradient with 4° C. Elution Buffer (50 mM sodium phosphate, 1 M sodium chloride, pH 6.5) as follows: step 1, 5.0 mL of 5% Elution Buffer at a flow rate of 1 mL/minute; step 2, 20.0 mL of 5-30% Elution Buffer at a flow rate of 1 mL/minute; step 3, 2.0 mL of 50% Elution Buffer at a flow rate of 1.0 mL/minute; step 4, 4.0 mL of 100% Elution Buffer at a flow rate of 1.0 mL/minute; and step 5, 5.0 mL of 0% Elution Buffer at a flow rate of 1.0 mL/minute. Elution of peptides from the column was monitored at 280, 260, and 214 nm, and peaks absorbing above a minimum threshold (0.01 au) at 280 nm were collected. Most of the His-iBoNT/E eluted at a sodium chloride concentration of approximately 100 to 200 mM. Average total yields of His-iBoNT/E (E213Q) were approximately 5-12 mg/L as determined by a Bradford assay.

Expression of the His-iBoNT/E (E213Q) was analyzed by polyacrylamide gel electrophoresis. Samples purified using the procedure described above were added to 2×LDS Sample Buffer (Invitrogen, Inc, Carlsbad, Calif.) and peptides separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Gels were stained with SYPRO® Ruby (Bio-Rad Laboratories, Hercules, Calif.) and the separated peptides imaged using a Fluor-S MAX MultiImager (Bio-Rad Laboratories, Hercules, Calif.) for quantification of peptide expression levels. The size and amount of the His-iBoNT/E (E213Q) was determined by comparison to MagicMark™ protein molecular weight standards (Invitrogen, Inc, Carlsbad, Calif.). The gels revealed what appeared to be a full-length His-iBoNT/E (E213Q).

Expression of the His-iBoNT/E (E213Q) was also analyzed by Western blot analysis. Protein samples purified using the procedure described above were added to 2× LDS Sample Buffer (Invitrogen, Inc, Carlsbad, Calif.) and separated by MOPS polyacrylamide gel electrophoresis using NUPAGE® Novex 4-12% Bis-Tris precast polyacrylamide gels (Invitrogen, Inc, Carlsbad, Calif.) under denaturing, reducing conditions. Separated peptides were transferred from the gel onto polyvinylidene fluoride (PVDF) membranes (Invitrogen, Inc, Carlsbad, Calif.) by Western blotting using a TRANS-BLOT® SD semi-dry electrophoretic transfer cell apparatus (Bio-Rad Laboratories, Hercules, Calif.). PVDF membranes were blocked by incubating at room temperature for 2 hours in a solution containing 25 mM Tris-Buffered Saline (25 mM 2-amino-2-hydroxymethyl-1,3-propanediol hydrochloric acid (Tris-HCl)(pH 7.4), 137 mM sodium chloride, 2.7 mM potassium chloride), 0.1% TWEEN-20®, polyoxyethylene (20) sorbitan monolaureate, 2% bovine serum albumin, 5% nonfat dry milk. Blocked membranes were incubated at 4° C. for overnight in Tris-Buffered Saline TWEEN-20® (25 mM Tris-Buffered Saline, 0.1% TWEEN-20®, polyoxyethylene (20) sorbitan monolaureate) containing one of the following primary antibodies as a probe: a 1:50,000 dilution of rabbit polyclonal anti-BoNT/E antiserum (Metabiologics, Inc., Madison, Wis.); a 1:10,000 dilution of rabbit polyclonal anti-LC/E 3a antiserum (Allergan, Inc., generated under contract with Zymed Laboratories Inc., South San Francisco, Calif.); a 1:10,000 dilution of rabbit polyclonal anti-$H_c$/E 12 antiserum (Allergan, Inc., generated under contract with Zymed Laboratories Inc., South San Francisco, Calif.); or a 1:10,000 dilution of rabbit polyclonal anti-polyhistidine antiserum (Abcam Inc., Cambridge, Mass.). Primary antibody probed blots were washed three times for 15 minutes each time in Tris-Buffered Saline TWEEN-20®. Washed membranes were incubated at room temperature for 2 hours in Tris-Buffered Saline TWEEN-20® containing a 1:20,000 dilution of goat polyclonal anti-rabbit immunoglobulin G, heavy and light chains (IgG, H+L) antibody conjugated to horseradish peroxidase (HRP; Pierce Biotechnology, Inc., Rockford, Ill.) as a secondary antibody. Secondary antibody-probed blots were washed three times for 15 minutes each time in Tris-Buffered Saline TWEEN-20®. Signal detection of the labeled His-iBoNT/E (E213Q) was visualized using the ECL Plus™ Western Blot Detection System (Amersham Biosciences, Piscataway, N.J.) and imaged with a Typhoon 9410 Variable Mode Imager (Amersham Biosciences, Piscataway, N.J.) for quantification of His-iBoNT/E (E213Q) expression levels.

Example 7

Construction of pET28a/His-BoNT/E

Figure 2:
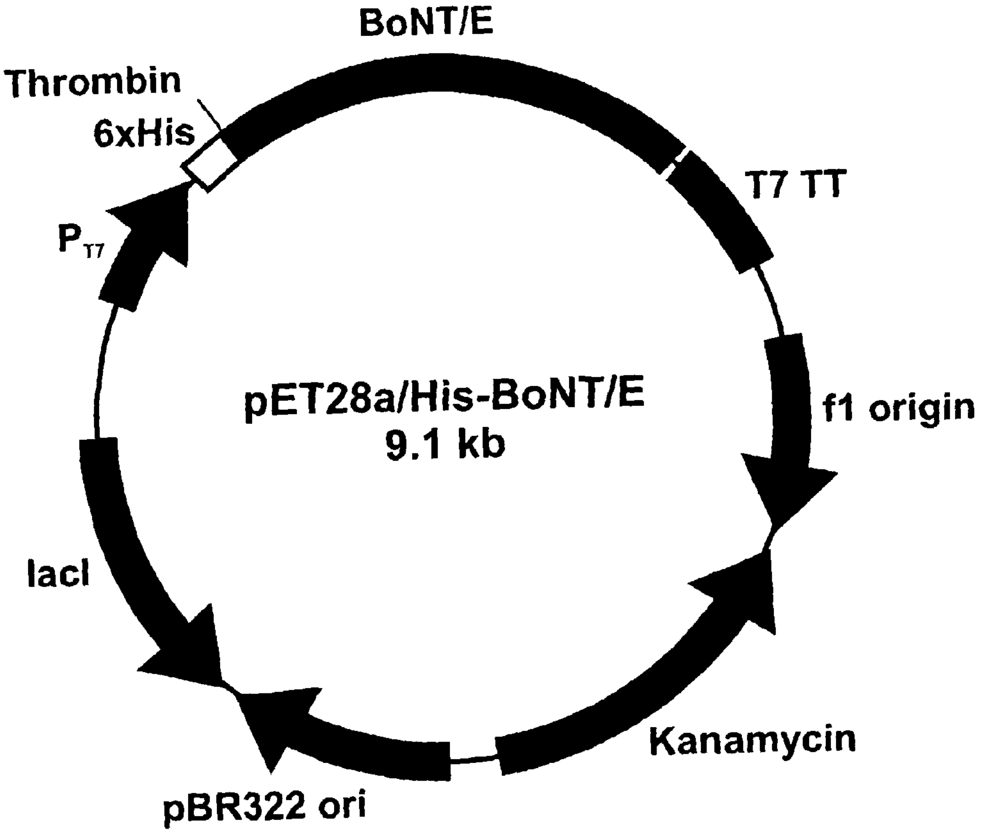
FIG. 2 shows a plasmid map of prokaryotic expression construct pET28a/His-BoNT/E comprising the modified open reading frame of SEQ ID NO: 122 encoding an active BoNT/E operably-linked to an amino-terminal polyhistidine binding peptide (SEQ ID NO: 123). A Thrombin protease cleavage site is operably-linked between the polyhistidine binding peptide and BoNT/E. Abbreviations are as follows: $P_{T7}$, a bacteriophage T7 promoter region; 6×His, a region encoding a polyhistidine binding peptide sequence; Thrombin, a region encoding a Thrombin cleavage site; BoNT/E, a modified open reading frame encoding an active BoNT/E; T7 TT, a bacteriophage T7 transcription termination region; f1 origin, a bacteriophage f1 origin of replication; Kanamycin, a region encoding an aminophosphotransferase peptide that confers Kanamycin resistance; pBR322 ori, a pBR322 origin of plasmid replication region; lacI, a region encoding a lactose I peptide.

A plasmid comprising a modified open reading frame encoding an active BoNT/E (FIG. 2), was prepared by in vitro site-directed mutagenesis of pET28a/His-iBoNT/E (E213Q). Correction of the inactivating E213Q mutation was accomplished in a single site-directed mutagenesis step using the procedure described in Example 4 and the following two oligonucleotides to yield pET28a/His-BoNT/E: Q213E Primer Pair, sense oligonucleotide, 5'-GCTGACTTTGATGCATGAACTGATCCATAGCTTGCACG GCCTG-3' (SEQ ID NO: 115) and antisense oligonucleotide, 5'-CAGGCCGTGCAAGCTATGGATCAGTT CATGCATCAAAGT CAGC-3' (SEQ ID NO: 116). The amino acid numbering corresponds to native sequence lacking an amino-terminal polyhistidine tag. The nucleotides that were changed to correct E213Q are shown in bold and underlined. This mutagenesis resulted in the modified open reading frame of SEQ ID NO: 122 encoding the active His-BoNT/E of SEQ ID NO: 123.

Activity was identified by proteolytic cleavage of a GFP-SNAP25 substrate using a GFP-SNAP25 Fluorescence Release Assay, see, e.g., Lance E. Steward et al., GFP-SNAP25 Fluorescence Release Assay for Botulinum Neurotoxin Protease Activity, U.S. Patent Publication No. 2005/0100973 (May 12, 2005). Candidate pET28a/His-BoNT/E expression constructs were transformed into chemically competent *E. coli* BL21 (DE3) cells (Invitrogen, Inc, Carlsbad, Calif.) using a heat-shock method, plated onto 1.5% Luria-Bertani agar plates (pH 7.0) containing 50 μg/mL of Kanamycin, and placed in a 37° C. incubator for overnight growth. Kanamycin-resistant colonies containing the pET28a/His-BoNT/E candidates were used to inoculate 1 mL cultures of ZYP-5052 autoinducing media containing 50 μg/mL of Kanamycin in Eppendorf Lid-Bac tubes fitted with membrane lids. The cultures were incubated in a thermomixer (1,400 rpm at 37° C.) located in a biosafety cabinet until turbid (approximately 7-8 hours). The temperature was then reduced to 22° C. and the cultures incubated for approximately 16 hours. The cells were collected by centrifugation (6,000×g at 4° C. for 30 minutes), decanted and frozen briefly at −80° C. to improve lysis. The cell pellets were defrosted on ice, each was resuspended in 350 μL of BugBuster® lysis solution (EMD Biosciences-Novagen, Madison, Wis.) containing 25 units/mL of benzonase nuclease (EMD Biosciences-Novagen, Madison, Wis.), 1 KU/mL rLysozyme (EMD Biosciences-Novagen, Madison, Wis.) and 2× Protease Inhibitor Cocktail III (EMD Biosciences-Novagen, Madison, Wis.) and the mixtures were incubated for 30 minutes at 22° C., 400 rpm in the thermomixer. The lysates were clarified by centrifugation (36,000×g at 4° C. for 15 minutes) and the supernatant solutions transferred to low-retention microcentrifuge tubes and placed on ice.

Figure 4:
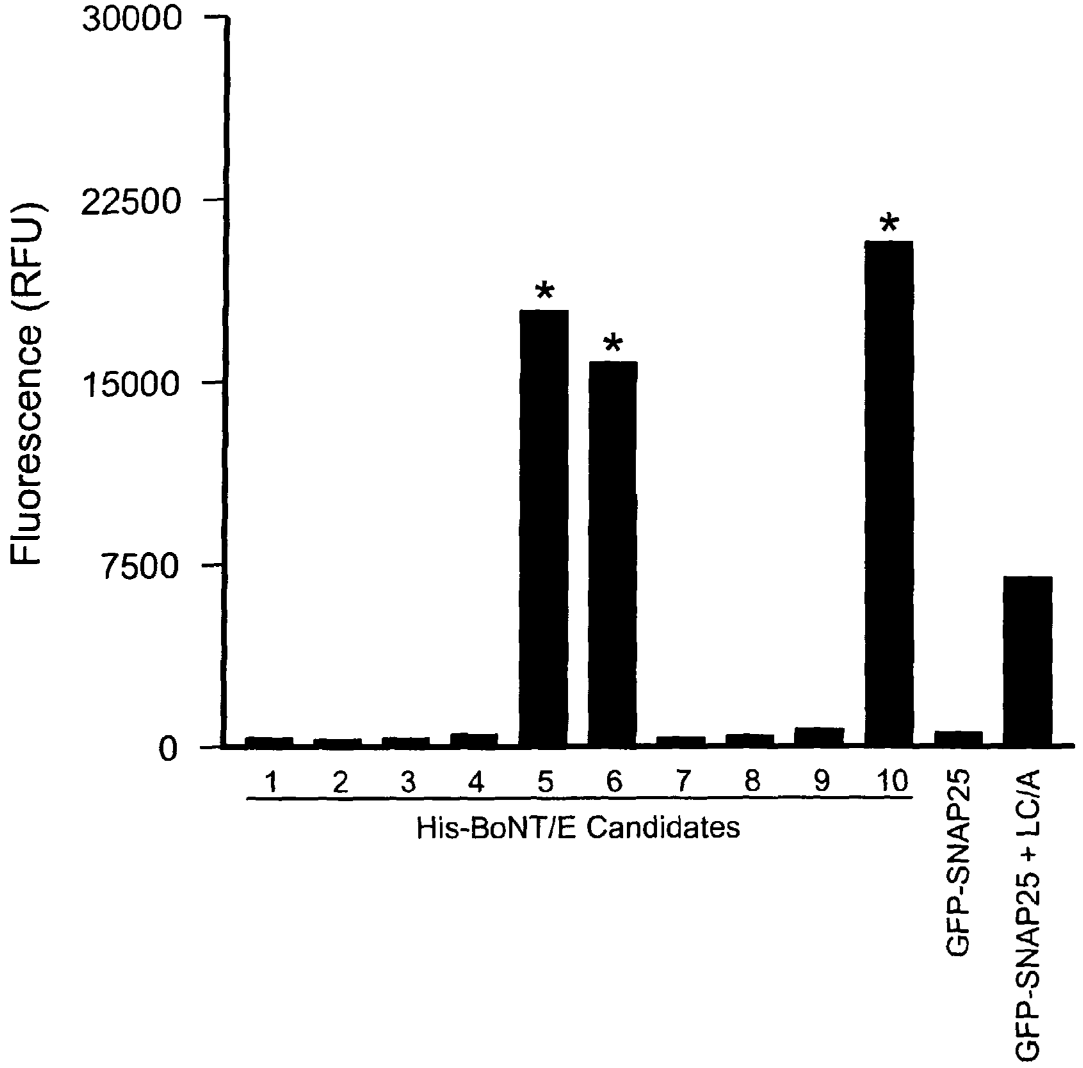
FIG. 4 shows the results of a GFP-SNAP25 activity assay used to identify constructs expressing active His-BoNT/E. His-BoNT/E candidates 5, 6 and 10 showed statistically significant BoNT/E enzymatic activity.

Activity of His-BoNT/E candidates was identified by proteolytic cleavage of a GFP-SNAP25 substrate. Each assay reaction contained 25 μL of 2× Toxin Reaction Buffer (100 mM N-(2-hydroxyethyl) piperazine-N'-(2-ethanesulfonic acid) (HEPES), pH 7.4; 20 μM zinc chloride; 20 mM dithiothreitol; 0.2% (v/v) TWEEN-20®, polyoxyethylene (20) sorbitan monolaureate), 10 μL of clarified lysate, and 15 μL of 50 μM GFP-$SNAP25_{(134-206)}$ substrate. The control reactions contained 10 μL of either water or 0.2 μg/mL of LC/A in lieu of lysate. The reactions were assembled in triplicate, incubated at 37° C. for 1 hour and then quenched with 20 μL of 8 M guanidine hydrochloride. The quenched reactions were transferred to filter-plate wells containing 75 μL of TALON™ SuperFlow $Co^{2+}$ affinity resin (BD Biosciences-Clontech, Palo Alto, Calif.) that had been conditioned by rinsing with 200 μL of deionized, distilled water and 200 μL of Assay Rinse Buffer (50 mM N-(2-hydroxyethyl) piperazine-N'-(2-ethanesulfonic acid) (HEPES), pH 7.4). Following 15 minutes incubation on the resin, the reaction solutions were eluted by vacuum filtration, collected in a black 96-well plate, passed over the resin beds twice more and collected after the final pass. Each resin bed was then rinsed with 210 μL of Assay Rinse Buffer which was eluted into the plate containing the reaction solutions. The fluorescence of the eluant reaction solutions was measured with a SpectraMax Gemini XS spectrophotometer (Molecular Devices, $\lambda_{Ex}$ 474 nm; $\lambda_{Em}$ 509 nm; 495 nm cutoff filter). The control reactions contained 10 μL of either water or 0.2 μg/mL of LC/A in lieu of lysate. Positive His-BoNT/E candidates showed significant protease activity (see FIG. 4).

TABLE 5

| Activities of Native and Recombinant BoNT/E expressed as ip $LD_{50}$ (ng/kg) | | | |
|---|---|---|---|
| BoNT/E | Single Chain | Dichain | Fold Activation |
| BTX-516 | 126 | 4.3 | 29 |
| BTX-541 | 3066 | 2.9 | 1057 |
| BTX-565 | 226 | 2.0 | 113 |
| His-BoNT/E | 7880 | 140 | 56 |
| BoNT/E-His | 1821 | 2.7 | 674 |

Example 8

Comparison of His-BoNT/E Amounts Expressed from Modified and Unmodified Open Reading Frames The amount of increased BoNT/E expressed from a modified open reading frame as compared to an unmodified open reading frame can be determined as follows. In separate reactions, a pET28a/His-BoNT/E expression construct comprising the modified open reading frame of SEQ ID NO: 4 and a pET28a/His-BoNT/E construct comprising the unmodified open reading frame of SEQ ID NO: 3 are introduced into chemically competent *E. coli* BL21 (DE3) cells (Invitrogen, Inc, Carlsbad, Calif.) using a heat-shock transformation protocol. The heat-shock reactions are plated onto 1.5% Luria-Bertani agar plates (pH 7.0) containing 50 μg/mL of Kanamycin and are placed in a 37° C. incubator for overnight growth. Kanamycin-resistant colonies of transformed *E. coli* containing pET28a/His-BoNT/E constructs from both expression construct are used to inoculate separate 15 mL tubes containing 3.0 mL Kanamycin-resistance selective PA-0.5 G media that are then placed in a 37° C. incubator, shaking at 250 rpm, for overnight growth. Approximately 600 μL of the resulting overnight starter culture from each construct is used to inoculate a 3.0 L baffled flask containing 600 mL Kanamycin-resistance, ZYP-5052 autoinducing media. The inoculated cultures are grown in a 37° C. incubator shaking at 250 rpm for approximately 5.5 hours until mid-log phase is reached ($OD_{600}$ of about 0.6-0.8). The flasks are then transferred to a 16° C. incubator shaking at 250 rpm for overnight expression. Cells are harvested by centrifugation (4,000 rpm at 4° C. for 20-30 minutes).

Figure 6A:
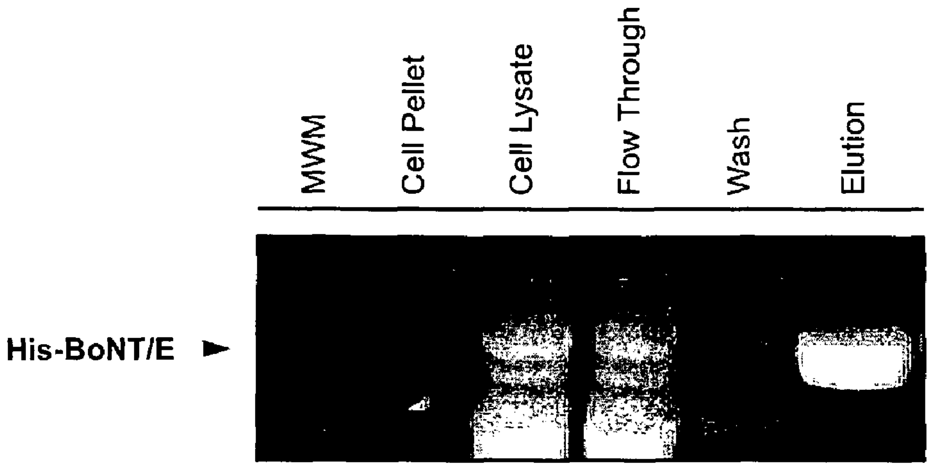
FIG. 6*a* shows an IMAC purification profile of His-BoNT/E expressed from the pET28a/His-BoNT/E expression construct comprising the modified open reading frame of SEQ ID NO: 122. Amounts of His-BoNT/E obtained averaged approximately 12 mg/L and represents a four-fold increase in protein amounts obtained from an unmodified open reading frame encoding the same active BoNT/E.

To analyze the His-BoNT/E expression levels obtained from both the modified and unmodified open reading frames, His-BoNT/E is purified using the IMAC procedure, as described in Example 6 (see FIG. 6*a*). Expression from each culture is evaluated by a Bradford dye assay, polyacrylamide gel electrophoresis and Western blot analysis (as described in Example 6) in order to determine whether the amounts of His-BoNT/E produced from the modified open reading frame of SEQ ID NO: 4 is greater when compared to the amount of His-BoNT/E expressed from the unmodified open reading frame of SEQ ID NO: 3. A four-fold increase in the amount of active His-iBoNT/E expressed from a modified open reading frame is anticipated. Average amounts of IMAC purified active His-iBoNT/E expressed from a modified open reading frame is expected to be approximately 9 mg/L, while IMAC purified active His-iBoNT/E expressed from a unmodified open reading frame in an otherwise identical nucleic acid molecule is expected to be approximately 3 mg/L.

Example 9

Construction of pET29a/iBoNT/E-His (E2130)

To construct pET29a/iBoNT/E-His (E213Q), pET29a/iBoNT/E (E213Q) construct was made by digesting a pET28a/His-iBoNT/E (E213Q) construct with HindIII and NdeI at 37° C. for 2.5 hours to excise the iBoNT/E (E213Q) insert. The resulting restriction fragment was purified by the QIAquick Gel Extraction Kit (QIAGEN, Inc., Valencia, Calif.), and the fragment containing the open reading frame comprising SEQ ID NO: 119 was subcloned into the pET29a vector (EMD Biosciences-Novagen, Madison, Wis.) that had been digested with restriction endonucleases HindIII and NdeI. The fragment and vector were ligated using T4 DNA ligase protocol to yield pET29a/BoNT/E (E213Q). An aliquot from this ligation mixture was transformed by a standard heat-shock protocol into competent TOP10 cells (Invitrogen, Inc, Carlsbad, Calif.), plated onto 1.5% Luria-Bertani agar plates (pH 7.0) containing 50 μg/mL of Kanamycin, and placed in a 37° C. incubator for overnight growth. Candidate expression constructs were selected as Kanamycin-resistant colonies. Resistant colonies were used to inoculate 2 mL of Luria-Bertani media containing 50 μg/mL of Kanamycin that were then grown in a 37° C. incubator, shaking at 250 rpm, for 5 hours. The bacteria cells were harvested by microcentrifugation and the plasmid DNA was isolated using QIAGEN miniprep kits (QIAGEN, Inc., Valencia, Calif.). Candidate expression constructs were screened by restriction digestion with NdeI and HindIII to determine the presence of the correct insert fragment. Cultures containing the desired expression construct were used to inoculate 1 L baffled flasks containing 200 mL of Luria-Bertani media containing 50 μg/mL of Kanamycin and placed in a 37° C. incubator, shaking at 250 rpm, for overnight growth. Purified plasmid DNA corresponding to an expression construct was isolated using the QIAGEN Maxi-prep method (QIAGEN, Inc., Valencia, Calif.) and sequenced to verify that the correct expression construct was made (service contract with Sequetech Corp., Mountain View, Calif.). This cloning strategy yielded a prokaryotic expression construct encoding an iBoNT/E (E213Q).

A polyhistidine affinity binding peptide was fused in frame to iBoNT/E (E213Q) using a site-directed mutagenesis protocol that eliminated a stop codon immediately following the iBoNT/E (E213Q) open reading frame. A 50 μL reaction was assembled with the pET29a/iBoNT/E (E213Q) expression construct as a template, reagents included with the QuickChange® II XL Site-Directed Mutagenesis kit (Stratagene, La Jolla, Calif.) and the following two oligonucleotide primers: CtermHis Primer Pair, sense oligonucleotide, 5'-CCGCCAGCTTGTCGACTTTTTCTTGCCAGCCGTGC-3' (SEQ ID NO: 120) and antisense oligonucleotide, 5'-GCACGGCTGGCAAGAAAAAGTCGACAAGCTGGCGG-3' (SEQ ID NO: 121). A polymerase chain reaction (PCR) mix contained 5 μL of 10× Buffer, 1 μL of deoxyribonucleotides (dNTPs), 1 μL of PfuUltra™ High Fidelity DNA polymerase (2.5 units/μL), 125 ng of each primer, 50 ng of template DNA, and nuclease-free water to a final volume of 50 μL. The thermocycler conditions were: one cycle of 95° C. for 120 seconds; 20 cycles of 95° C. for 60 seconds, 55° C. for 30 seconds, and 72° C. for 20 minutes; one cycle of 72° C. for 9 minutes; and 10° C. to hold. Following thermocycling, 1 μL of DpnI restriction enzyme was added to the reaction and incubated for 2 hour at 37° C. to digest the template DNA. The reaction was purified by QIAquick kit (QIAGEN, Inc., Valencia, Calif.) and analysis by agarose gel electrophoresis showed that the reaction produced full-length plasmid. The mutagenesis products were transformed into chemically competent *E. coli* TOP10 cells (Invitrogen, Inc, Carlsbad, Calif.) using a heat shock method, plated on 1.5% Luria-Bertani agar plates (pH 7.0) containing 50 μg/mL of Kanamycin, and placed in a 37° C. incubator for overnight growth. Candidate constructs were isolated as Kanamycin-resistant colonies and analyzed using an alkaline lysis plasmid mini-preparation procedure to isolate the expression construct and restriction endonuclease digests to determine the presence of the insert. Deletion of the stop codon and confirmation of fusion protein construction were determined by sequence analysis (service contract with Sequetech Corp., Mountain View, Calif.) of candidate plasmid constructs. This cloning strategy yielded a prokaryotic expression construct encoding a BoNT/E-His (E213Q) containing an carboxy-terminal thrombin cleavable polyhistidine affinity binding peptide.

Example 10

Construction of pET29a/BoNT/E-His

Figure 3:
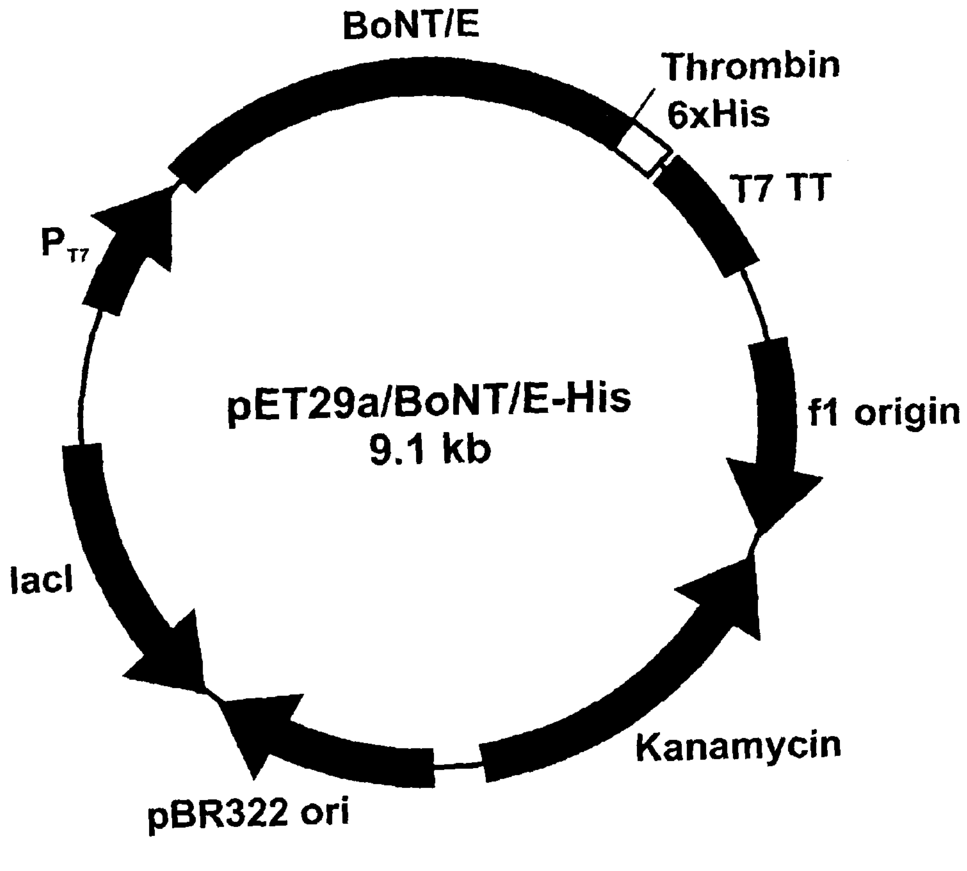
FIG. 3 shows a plasmid map of prokaryotic expression construct pET29a/BoNT/E-His comprising the modified open reading frame of SEQ ID NO: 124 encoding an active BoNT/E operably-linked to an carboxy-terminal polyhistidine binding peptide (SEQ ID NO: 125). A Thrombin protease cleavage site is operably-linked between the polyhistidine binding peptide and BoNT/E. Abbreviations are as follows: $P_{T7}$, a bacteriophage T7 promoter region; 6×His, a region encoding a polyhistidine binding peptide sequence; Thrombin, a region encoding a Thrombin cleavage site; BoNT/E, a modified open reading frame encoding an active BoNT/E; T7 TT, a bacteriophage T7 transcription termination region; f1 origin, a bacteriophage f1 origin of replication; Kanamycin, a region encoding an aminophosphotransferase peptide that confers Kanamycin resistance; pBR322 ori, a pBR322 origin of plasmid replication region; lacl, a region encoding a lactose I peptide.

A plasmid comprising a modified open reading frame encoding an active BoNT/E (FIG. 3), was prepared by in vitro site-directed mutagenesis of pET29a/iBoNT/E-His (E213Q). Correction of the inactivating E213Q mutation was accomplished in a single site-directed mutagenesis step using the procedure described in Example 4 and the following two oligonucleotides to yield pET29a/BoNT/E-His: 0213E Primer Pair, sense oligonucleotide, 5'-GCTGACTTTGATGCATGAACTGATCCATAGCTTGCACG GCCTG-3' (SEQ ID NO: 115) and antisense oligonucleotide, 5'-CAGGCCGTGCAAGCTATGGATCAGTT CATGCATCAAAGTCAGC-3' (SEQ ID NO: 116). The nucleotides that were changed to correct E213Q are shown in bold and underlined. This mutagenesis resulted in the modified open reading frame of SEQ ID NO: 123 encoding the active His-BoNT/E of SEQ ID NO: 125.

Activity of BoNT/-His candidates was identified by proteolytic cleavage of a GFP-SNAP25 substrate using a GFP-SNAP25 Fluorescence Release Assay, see, e.g., Lance E. Steward et al., GFP-SNAP25 Fluorescence Release Assay for Botulinum Neurotoxin Protease Activity, U.S. Patent Publication No. 2005/0100973 (May 12, 2005). Candidate pET29a/BoNT/E-His expression constructs were transformed into chemically competent *E. coli* BL21 (DE3) cells (Invitrogen, Inc, Carlsbad, Calif.) using a heat-shock method, plated onto 1.5% Luria-Bertani agar plates (pH 7.0) containing 50 μg/mL of Kanamycin, and placed in a 37° C. incubator for overnight growth. Kanamycin-resistant colonies containing the pET29a/BoNT/E-His candidates were used to inoculate 1 mL cultures of ZYP-5052 autoinducing media containing 50 μg/mL of Kanamycin in Eppendorf Lid-Bac tubes fitted with membrane lids. The cultures were incubated in a thermomixer (1,400 rpm at 37° C.) located in a biosafety cabinet until turbid (approximately 7-8 hours). The temperature was then reduced to 22° C. and the cultures incubated for approximately 16 hours. The cells were collected by centrifugation (6,000×g at 4° C. for 30 minutes), decanted and frozen briefly at −80° C. to improve lysis. The cell pellets were defrosted on ice, each was resuspended in 350 μL of Bug-Buster® lysis solution (EMD Biosciences-Novagen, Madison, Wis.) containing 25 units/mL of benzonase nuclease (EMD Biosciences-Novagen, Madison, Wis.), 1 KU/mL rLysozyme (EMD Biosciences-Novagen, Madison, Wis.) and 2× Protease Inhibitor Cocktail III (EMD Biosciences-Novagen, Madison, Wis.) and the mixtures were incubated for 30 minutes at 22° C., 400 rpm in the thermomixer. The lysates were clarified by centrifugation (36,000×g at 4° C. for 15 minutes) and the supernatant solutions transferred to low-retention microcentrifuge tubes and placed on ice.

Figure 5:
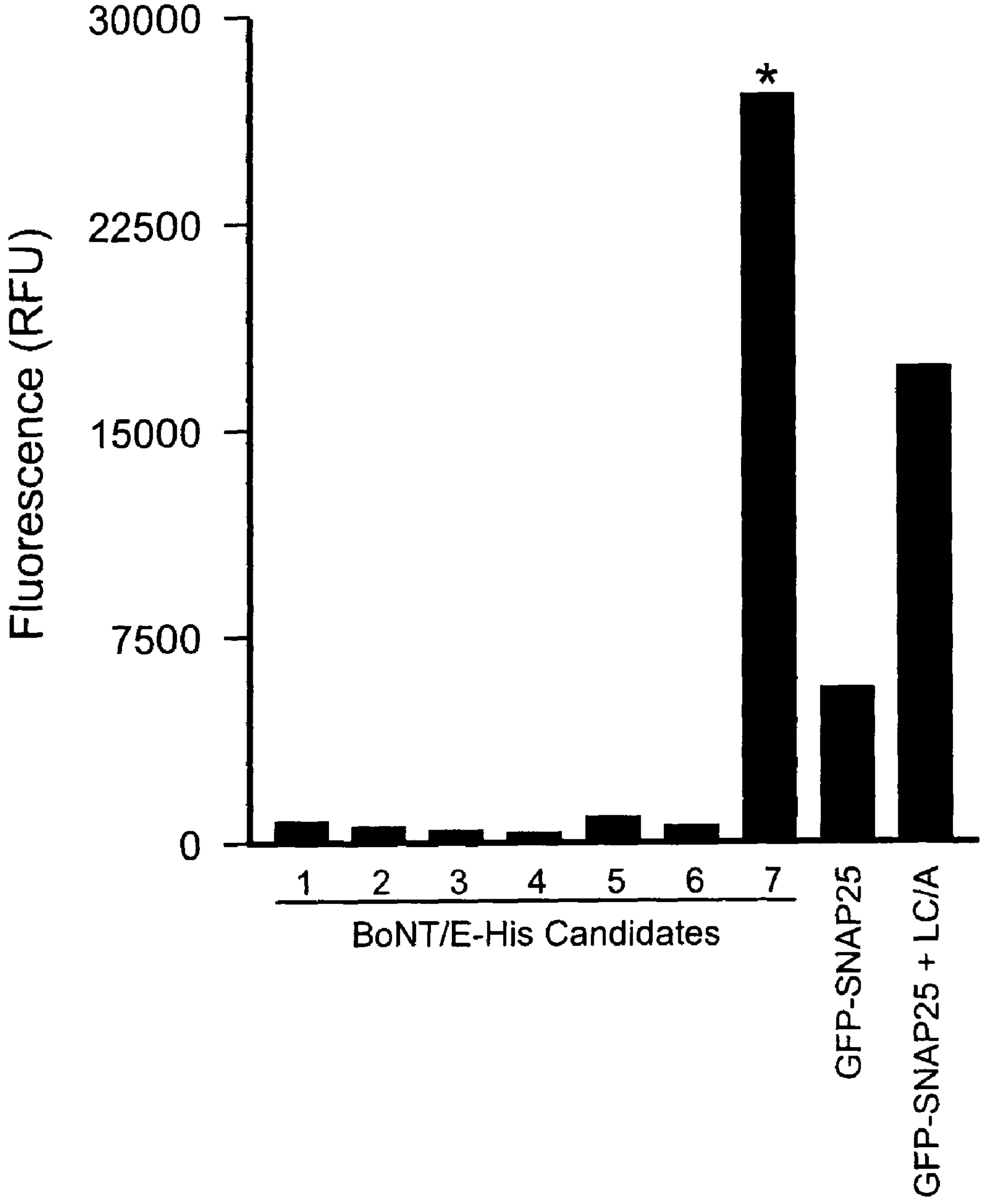
FIG. 5 shows the results of a GFP-SNAP25 activity assay used to identify constructs expressing active BoNT/E-His. BoNT/E-His candidate 7 showed statistically significant BoNT/E enzymatic activity.

Activity of BoNT/E-His candidates was identified by proteolytic cleavage of a GFP-SNAP25 substrate. Each assay reaction contained 25 μL of 2× Toxin Reaction Buffer (100 mM N-(2-hydroxyethyl) piperazine-N'-(2-ethanesulfonic acid) (HEPES), pH 7.4; 20 μM zinc chloride; 20 mM dithiothreitol; 0.2% (v/v) TWEEN-20®, polyoxyethylene (20) sorbitan monolaureate), 10 μL of clarified lysate, and 15 μL of 50 μM GFP-$SNAP25_{(134-206)}$ substrate. The control reactions contained 10 μL of either water or 0.2 μg/mL of LC/A in lieu of lysate. The reactions were assembled in triplicate, incubated at 37° C. for 1 hour and then quenched with 20 μL of 8 M guanidine hydrochloride. The quenched reactions were transferred to filter-plate wells containing 75 μL of TALON™ SuperFlow $Co^{2+}$ affinity resin (BD Biosciences-Clontech, Palo Alto, Calif.) that had been conditioned by rinsing with 200 μL of deionized, distilled water and 200 μL of Assay Rinse Buffer (50 mM N-(2-hydroxyethyl) piperazine-N'-(2-ethanesulfonic acid) (HEPES), pH 7.4). Following 15 minutes incubation on the resin, the reaction solutions were eluted by vacuum filtration, collected in a black 96-well plate, passed over the resin beds twice more and collected after the final pass. Each resin bed was then rinsed with 210 μL of Assay Rinse Buffer which was eluted into the plate containing the reaction solutions. The fluorescence of the eluant reaction solutions was measured with a SpectraMax Gemini XS spectrophotometer (Molecular Devices, $\lambda_{Ex}$ 474 nm; $\lambda_{Em}$ 509 nm; 495 nm cutoff filter). The control reactions contained 10 μL of either water or 0.2 μg/mL of LC/A in lieu of lysate. Positive BoNT/E-His candidates showed significant protease activity (see FIG. 5).

Example 11

Expression of pET29a/BoNT/E-His

The following example illustrates a procedure useful for expressing a BoNT/E from an expression construct disclosed in the present specification. An pET29a/BoNT/E-His expression construct was introduced into chemically competent *E. coli* BL21 (DE3) cells (Invitrogen, Inc, Carlsbad, Calif.) using a heat-shock transformation protocol. The heat-shock reaction was plated onto 1.5% Luria-Bertani agar plates (pH 7.0) containing 50 μg/mL of Kanamycin and placed in a 37° C. incubator for overnight growth. Kanamycin-resistant colonies of transformed *E. coli* containing pET29a/BoNT/E-His were used to inoculate baffled flask containing 3.0 mL of PA-0.5 G media containing 50 μg/mL of Kanamycin which was then placed in a 37° C. incubator, shaking at 250 rpm, for overnight growth. The resulting overnight starter culture was in turn used to inoculate a 3 L baffled flask containing ZYP-5052 autoinducing media containing 50 μg/mL of Kanamycin at a dilution of 1:1000. Culture volumes ranged from about 600 mL (20% flask volume) to about 750 mL (25% flask volume). These cultures were grown in a 37° C. incubator shaking at 250 rpm for approximately 5.5 hours until mid-log phase was reached ($OD_{600}$ of about 0.6-0.8). Cultures were then transferred to a 16° C. incubator shaking at 250 rpm for overnight expression. Cells were harvested by centrifugation (4,000 rpm at 4° C. for 20-30 minutes) and used immediately, or stored dry at −80° C. until needed.

Example 12

Purification and Quantification of BoNT/E-His

Figure 6B:
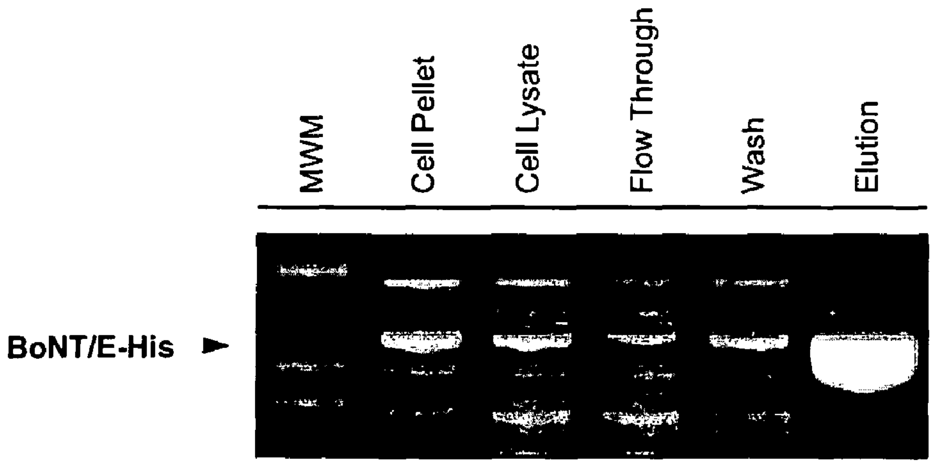
FIG. 6*b* shows an IMAC purification profile of BoNT/E-His expressed from the pET29a/BoNT/E-His expression construct comprising the modified open reading frame of SEQ ID NO: 124. Amounts of His-BoNT/E obtained averaged approximately 60 mg/L and represents a 20-fold increase in protein amounts obtained from an unmodified open reading frame encoding the same active BoNT/E.

The following example illustrates methods useful for purification and quantification of BoNT/E disclosed in the present specification. For immobilized metal affinity chromatography (IMAC) protein purification, *E. coli* BL21 (DE3) cell pellets used to express BoNT/E-His, as described in Example 11, were resuspended in Column Binding Buffer (25 mM N-(2-hydroxyethyl) piperazine-N'-(2-ethanesulfonic acid) (HEPES), pH 7.8; 500 mM sodium chloride; 10 mM imidazole; 2× Protease Inhibitor Cocktail Set III (EMD Biosciences-Calbiochem, San Diego Calif.); 5 units/mL of Benzonase (EMD Biosciences-Novagen, Madison, Wis.); 0.1% (v/v) TRITON-X® 100, 4-octylphenol polyethoxylate; 10% (v/v) glycerol), and then transferred to a cold Oakridge centrifuge tube. The cell suspension was sonicated on ice (10-12 pulses of 10 seconds at 40% amplitude with 60 seconds cooling intervals on a Branson Digital Sonifier) in order to lyse the cells and release the BoNT/E-His, and then centrifuged (16,000 rpm at 4° C. for 20 minutes) to clarify the lysate. An immobilized metal affinity chromatography column was prepared using a 20 mL Econo-Pac column support (Bio-Rad Laboratories, Hercules, Calif.) packed with 2.5-5.0 mL of TALON™ SuperFlow $Co^{2+}$ affinity resin (BD Biosciences-Clontech, Palo Alto, Calif.), which was then equilibrated by rinsing with 5 column volumes of deionized, distilled water, followed by 5 column volumes of Column Binding Buffer. The clarified lysate was applied slowly to the equilibrated column by gravity flow (approximately 0.25-0.3 mL/minute). The column was then washed with 5 column volumes of Column Wash Buffer (N-(2-hydroxyethyl) piperazine-N'-(2-ethanesulfonic acid) (HEPES), pH 7.8; 500 mM sodium chloride; 10 mM imidazole; 0.1% (v/v) TRITON-X® 100, 4-octylphenol polyethoxylate; 10% (v/v) glycerol). BoNT/E-His was eluted with 20-30 mL of Column Elution Buffer (25 mM N-(2-hydroxyethyl) piperazine-N'-(2-ethanesulfonic acid) (HEPES), pH 7.8; 500 mM sodium chloride; 500 mM imidazole; 0.1% (v/v) TRITON-X® 100, 4-octylphenol polyethoxylate; 10% (v/v) glycerol) and collected in approximately twelve 1 mL fractions. The amount of BoNT/E-His contained in each elution fraction was determined by a Bradford dye assay and the five fractions with the strongest signal were considered the elution peak and pooled (see FIG. 6*b*). Total protein yield was determined by estimating the total protein concentration of the pooled peak elution fractions using bovine gamma globulin as a standard (Bio-Rad Laboratories, Hercules, Calif.).

For purification of a BoNT/E using a FPLC desalting column, a HIPREP™ 26/10 size exclusion column (Amersham Biosciences, Piscataway, N.J.) was pre-equilibrated with 80 mL of 4° C. Column Buffer (50 mM sodium phosphate, pH 6.5). After the column was equilibrated, a BoNT/E-His sample was applied to the size exclusion column with an isocratic mobile phase of 4° C. Column Buffer and at a flow rate of 10 mL/minute using a BioLogic DuoFlow chromatography system (Bio-Rad Laboratories, Hercules, Calif.). The desalted BoNT/E-His sample was collected as a single fraction of approximately 7-12 mL.

For purification of a BoNT/E using a FPLC ion exchange column, a BoNT/E-His sample that had been desalted following elution from an IMAC column was applied to a 1 mL UNO-S1™ cation exchange column (Bio-Rad Laboratories, Hercules, Calif.) using a BioLogic DuoFlow chromatography system (Bio-Rad Laboratories, Hercules, Calif.). The sample was applied to the column in 4° C. Column Buffer (50 mM sodium phosphate, pH 6.5) and eluted by linear gradient with 4° C. Elution Buffer (50 mM sodium phosphate, 1 M sodium chloride, pH 6.5) as follows: step 1, 5.0 mL of 5% Elution Buffer at a flow rate of 1 mL/minute; step 2, 20.0 mL of 5-30% Elution Buffer at a flow rate of 1 mL/minute; step 3, 2.0 mL of 50% Elution Buffer at a flow rate of 1.0 mL/minute; step 4, 4.0 mL of 100% Elution Buffer at a flow rate of 1.0 mL/minute; and step 5, 5.0 mL of 0% Elution Buffer at a flow rate of 1.0 mL/minute. Elution of peptides from the column was monitored at 280, 260, and 214 nm, and peaks absorbing above a minimum threshold (0.01 au) at 280 nm were collected. Most of the BoNT/E-His eluted at a sodium chloride concentration of approximately 100 to 200 mM. Average total yields of BoNT/E-His were approximately 50-60 mg/L as determined by a Bradford assay.

Expression of BoNT/E-His was analyzed by polyacrylamide gel electrophoresis. Samples purified using the procedure described above were added to 2×LDS Sample Buffer (Invitrogen, Inc, Carlsbad, Calif.) and peptides separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Gels were stained with SYPRO® Ruby (Bio-Rad Laboratories, Hercules, Calif.) and the separated peptides imaged using a Fluor-S MAX MultiImager (Bio-Rad Laboratories, Hercules, Calif.) for quantification of peptide expression levels. The size and amount of the BoNT/E-His was determined by comparison to MagicMark™ protein molecular weight standards (Invitrogen, Inc, Carlsbad, Calif.). The gels revealed what appeared to be a full-length BoNT/E-His.

Expression of BoNT/E-His was also analyzed by Western blot analysis. Protein samples purified using the procedure described above were added to 2× LDS Sample Buffer (Invitrogen, Inc, Carlsbad, Calif.) and separated by MOPS polyacrylamide gel electrophoresis using NUPAGE® Novex 4-12% Bis-Tris precast polyacrylamide gels (Invitrogen, Inc, Carlsbad, Calif.) under denaturing, reducing conditions. Separated peptides were transferred from the gel onto polyvinylidene fluoride (PVDF) membranes (Invitrogen, Inc, Carlsbad, Calif.) by Western blotting using a TRANS-BLOT® SD semi-dry electrophoretic transfer cell apparatus (Bio-Rad Laboratories, Hercules, Calif.). PVDF membranes were blocked by incubating at room temperature for 2 hours in a solution containing 25 mM Tris-Buffered Saline (25 mM 2-amino-2-hydroxymethyl-1,3-propanediol hydrochloric acid (Tris-HCl)(pH 7.4), 137 mM sodium chloride, 2.7 mM potassium chloride), 0.1% TWEEN-20®, polyoxyethylene

(20) sorbitan monolaureate, 2% bovine serum albumin, 5% nonfat dry milk. Blocked membranes were incubated at 4° C. for overnight in Tris-Buffered Saline TWEEN-20® (25 mM Tris-Buffered Saline, 0.1% TWEEN-20®, polyoxyethylene (20) sorbitan monolaureate) containing one of the following primary antibodies as a probe: a 1:50,000 dilution of rabbit polyclonal anti-BoNT/E antiserum (Metabiologics, Inc., Madison, Wis.); a 1:10,000 dilution of rabbit polyclonal anti-LC/E 3*a* antiserum (Allergan, Inc., generated under contract with Zymed Laboratories Inc., South San Francisco, Calif.); a 1:10,000 dilution of rabbit polyclonal anti-$H_C$/E 12 antiserum (Allergan, Inc., generated under contract with Zymed Laboratories Inc., South San Francisco, Calif.); or a 1:10,000 dilution of rabbit polyclonal anti-polyhistidine antiserum (Abcam Inc., Cambridge, Mass.). Primary antibody probed blots were washed three times for 15 minutes each time in Tris-Buffered Saline TWEEN-20®. Washed membranes were incubated at room temperature for 2 hours in Tris-Buffered Saline TWEEN-20® containing a 1:20,000 dilution of goat polyclonal anti-rabbit immunoglobulin G, heavy and light chains (IgG, H+L) antibody conjugated to horseradish peroxidase (HRP; Pierce Biotechnology, Inc., Rockford, Ill.) as a secondary antibody. Secondary antibody-probed blots were washed three times for 15 minutes each time in Tris-Buffered Saline TWEEN-20®. Signal detection of the labeled BoNT/E-His was visualized using the ECL Plus™ Western Blot Detection System (Amersham Biosciences, Piscataway, N.J.) and imaged with a Typhoon 9410 Variable Mode Imager (Amersham Biosciences, Piscataway, N.J.) for quantification of peptide expression levels.

Example 13

Comparison of BoNT/E-His Amounts Expressed from Modified and Unmodified Open Reading Frames The amount of increased BoNT/E expressed from a modified open reading frame as compared to an unmodified open reading frame can be determined as follows. In separate reactions, a pET29a/BoNT/E-His expression construct comprising the modified open reading frame of SEQ ID NO: 4 and a pET29a/BoNT/E-His construct comprising the unmodified open reading frame of SEQ ID NO: 3 are introduced into chemically competent *E. coli* BL21 (DE3) cells (Invitrogen, Inc, Carlsbad, Calif.) using a heat-shock transformation protocol. The heat-shock reactions are plated onto 1.5% Luria-Bertani agar plates (pH 7.0) containing 50 μg/mL of Kanamycin and are placed in a 37° C. incubator for overnight growth. Kanamycin-resistant colonies of transformed *E. coli* containing pET29a/BoNT/E-His constructs from both expression construct are used to inoculate separate 15 mL tubes containing 3.0 mL Kanamycin-resistance selective PA-0.5 G media that are then placed in a 37° C. incubator, shaking at 250 rpm, for overnight growth. Approximately 600 μL of the resulting overnight starter culture from each construct are used to inoculate a 3.0 L baffled flask containing 600 mL Kanamycin-resistance, ZYP-5052 autoinducing media. The inoculated cultures are grown in a 37° C. incubator shaking at 250 rpm for approximately 5.5 hours until mid-log phase is reached ($OD_{600}$ of about 0.6-0.8). The flasks are then transferred to a 16° C. incubator shaking at 250 rpm for overnight expression. Cells are harvested by centrifugation (4,000 rpm at 4° C. for 20-30 minutes).

To analyze the BoNT/E-His expression amounts obtained from both the unmodified and modified open reading frames, BoNT/E-His is purified using the IMAC procedure (as described in Example 12). Expression from each culture is evaluated by a Bradford dye assay, polyacrylamide gel electrophoresis and Western blot analysis (as described in Example 12) in order to determine whether the amounts of His-BoNT/E produced from the modified open reading frame of SEQ ID NO: 4 is greater as compared to the amount of His-BoNT/E expressed from the unmodified open reading frame of SEQ ID NO: 3. An approximately 20-fold increase in the amount of active His-iBoNT/E expressed from a modified open reading frame is anticipated. Average amounts of IMAC purified active His-iBoNT/E expressed from a modified open reading frame is expected to be approximately 60 mg/L, while IMAC purified active BoNT/E-His expressed from a unmodified open reading frame in an otherwise identical nucleic acid molecule is expected to be approximately 3 mg/L.

Example 14

Construction and Expression of pRSET/BoNT/E-His

Figure 7:
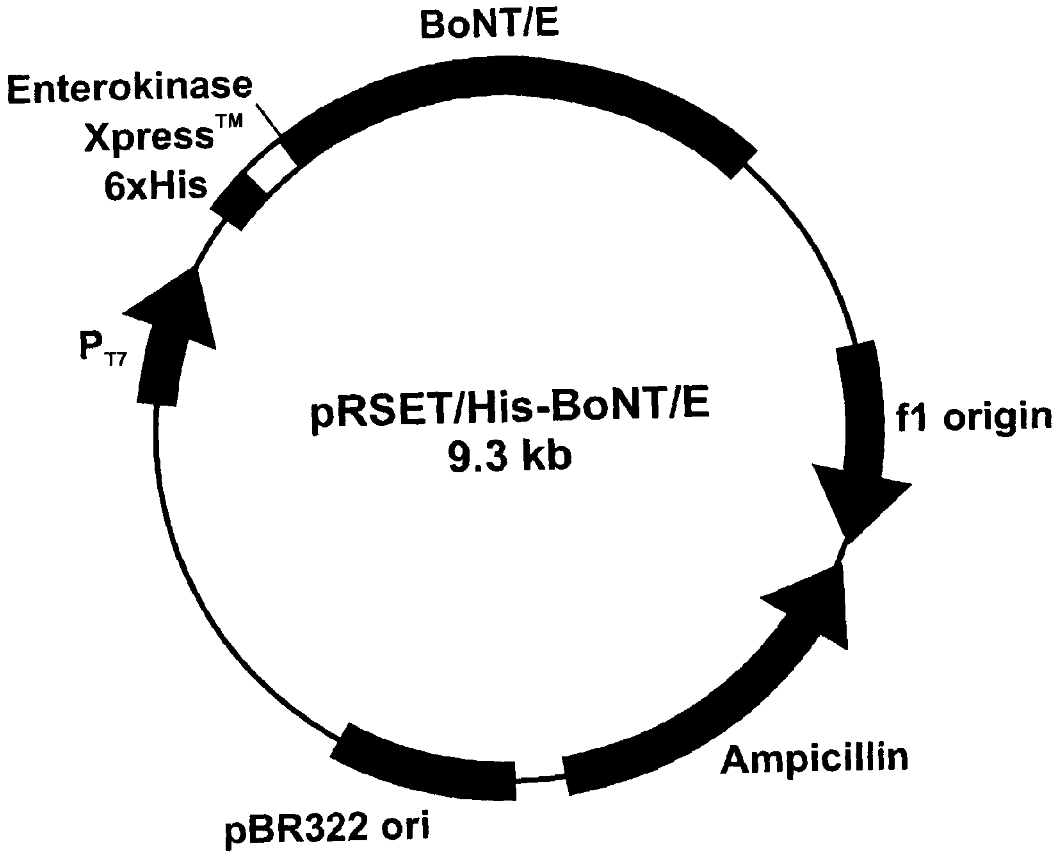
FIG. 7 shows a plasmid map of prokaryotic expression construct pRSETb/His-BoNT/E comprising the modified open reading frame encoding an active BoNT/E operably-linked to amino-terminal polyhistidine and Express™ binding peptides. An Enterokinase protease cleavage site is operably-linked between the polyhistidine and Express™ binding peptides and BoNT/E. Abbreviations are as follows: $P_{T7}$, a bacteriophage T7 promoter region; 6×His, a region encoding a polyhistidine binding peptide sequence; Express™, a region encoding an Express™ binding peptide sequence; Enterokinase, a region encoding a EnterokinaseMax™ cleavage site; BoNT/E, modified open reading frame of SEQ ID NO: 7 encoding an active BoNT/E; f1 origin, a bacteriophage f1 origin of replication; Ampicillin, a region encoding a β-lactamase peptide that confers Ampicillin resistance; pBR322 ori, a pBR322 origin of plasmid replication region.

Restriction endonuclease sites suitable for cloning an operably linked nucleic acid molecule into a pRSET vector (Invitrogen, Inc, Carlsbad, Calif.) are incorporated into the 5'- and 3' ends of modified open reading frame SEQ ID NO: 4. This nucleic acid molecule is synthesized and a pUCBHB1/BoNT/E construct obtained as described in Example 3. This construct is digested with restriction enzymes that 1) excise the insert containing the open reading frame of SEQ ID NO: 4 encoding an active BoNT/E; and 2) enable this insert to be operably-linked to a pRSET vector. This insert is subcloned using a T4 DNA ligase procedure into a pRSET vector that is digested with appropriate restriction endonucleases to yield pRSET/BoNT/E-His (FIG. 7). The ligation mixture is transformed into chemically competent *E. coli* DH5a cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the insert. This cloning strategy yields a prokaryotic expression construct encoding an active BoNT/E operably linked to carboxy-terminal polyhistidine binding peptide. A similar cloning strategy is used to make a pRSET construct containing the unmodified open reading frame of SEQ ID NO: 3 used as a control for expression levels, as well as, to produce pRSET expression constructs in which any one of the modified open reading frames of SEQ ID NO: 5 through SEQ ID NO: 34 is operably linked to a pRSET vector.

The amount of increased BoNT/E expression from a modified open reading frame is determined as follows. In separate reactions, a pRSET/BoNT/E-His expression construct comprising a modified open reading frame, such as, e.g., SEQ ID NO: 4 through SEQ ID NO: 34, and a pRSET/BoNT/E-His construct comprising an unmodified open reading frame, such as, e.g., SEQ ID NO: 3 are introduced into chemically competent bacterial cells suitable for expression of the pRET expression construct using a standard transformation protocol, such as, e.g., a heat-shock transformation protocol. The transformation reactions are plated onto 1.5% Luria-Bertani agar plates (pH 7.0) containing suitable antibiotics and placed in a 37° C. incubator for overnight growth. Antibiotic-resistant colonies of transformed cells containing pRSET/BoNT/E-His constructs from both nucleic acid molecules are used to inoculate separate 15 mL tubes containing 3.0 mL antibiotic-resistance selective PA-0.5 G media that are then placed in a 37° C. incubator, shaking at 250 rpm, for overnight growth. Approximately 600 μL of the resulting overnight starter culture from each construct is used to inoculate a 3.0 L baffled flask containing 600 mL of a suitable antibiotic-resistance growth media. The inoculated cultures are grown in a 37° C. incubator shaking at 250 rpm for approximately 5.5 hours until mid-log phase is reached ($OD_{600}$ of about 0.6-0.8). The cultures are then induced by adding IPTG to a final concentration of 0.5-1.0 mM, and the cultures are transferred to a 16° C. incubator shaking at 250 rpm for overnight expression. Cells are harvested by centrifugation (4,000 rpm at 4° C. for 20-30 minutes).

To analyze the BoNT/E-His expression levels obtained from both the native and modified nucleic acid molecules, BoNT/E-His is purified using the IMAC procedure (as described in Example 12). Expression from each culture is evaluated by a Bradford dye assay, polyacrylamide gel electrophoresis and Western blot analysis using either anti-BoNT/E or anti-His antibodies (as described in Example 12) in order to determine whether the amounts of BoNT/E-His produced from the modified open reading frame was greater relative to the amount of BoNT/E-His expressed from the unmodified open reading frame of SEQ ID NO: 3.

Example 15

Construction and Expression of pPICZ A/BoNT/E-myc-His

Figure 8:
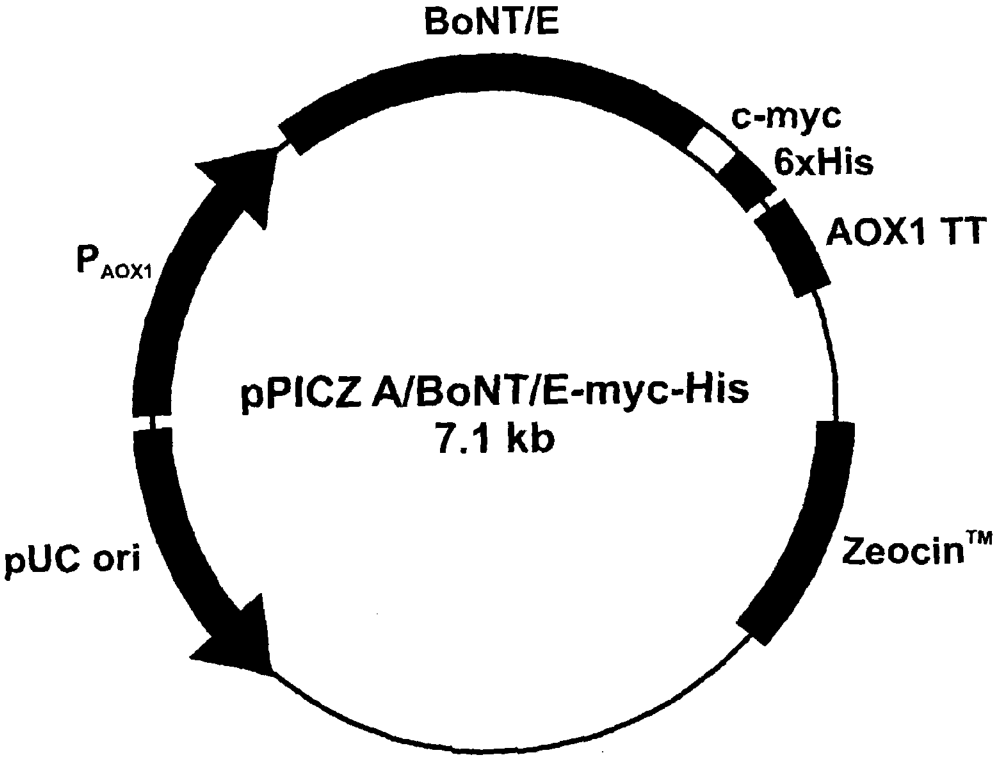
FIG. 8 shows a plasmid map of yeast expression construct pPICZ A/BoNT/E-myc-His comprising a modified open reading frame encoding an active BoNT/E operably-linked to carboxy-terminal c-myc and polyhistidine binding peptides. Abbreviations are as follows: $P_{AOX1}$, an aldehyde oxidase 1 promoter region; BoNT/E, modified open reading frame of SEQ ID NO: 37 encoding an active BoNT/E; c-myc, a region encoding a c-myc binding peptide sequence; 6×His, a region encoding a polyhistidine binding peptide sequence; AOX1 TT, an aldehyde oxidase 1 transcription termination region; Zeocin™, a region encoding a Zeocin™ resistance peptide; pUC ori, a pUC origin of plasmid replication region.

Restriction endonuclease sites suitable for cloning an operably linked nucleic acid molecule into a pPIC A vector (Invitrogen, Inc, Carlsbad, Calif.) are incorporated into the 5'- and 3' ends of modified open reading frame SEQ ID NO: 37. This nucleic acid molecule is synthesized and a pUCBHB1/BoNT/E construct is obtained as described in Example 3. This construct is digested with restriction enzymes that 1) excise the insert containing the open reading frame of SEQ ID NO: 37 encoding an active BoNT/E; and 2) enable this insert to be operably-linked to a pPIC A vector. This insert is subcloned using a T4 DNA ligase procedure into a pPIC A vector that is digested with appropriate restriction endonucleases to yield pPIC A/BoNT/E-myc-His (FIG. 8). The ligation mixture is transformed into chemically competent *E. coli* DH5a cells (Invitrogen, Inc, Carlsbad, Calif.) using a heat shock method, plated on 1.5% low salt Luria-Bertani agar plates (pH 7.5) containing 25 μg/mL of Zeocin™, and placed in a 37° C. incubator for overnight growth. Bacteria containing expression constructs are identified as Zeocin™ resistant colonies. Candidate constructs are isolated using an alkaline lysis plasmid mini-preparation procedure and analyzed by restriction endonuclease digest mapping to determine the presence and orientation of the insert. This cloning strategy yields a yeast expression construct encoding an active BoNT/E operably linked to carboxy-terminal c-myc and polyhistidine binding peptides. A similar cloning strategy is used to make a pPIC A expression construct containing the unmodified open reading frame of SEQ ID NO: 3 used as a control for expression levels, as well as, to produce pPIC A expression constructs in which any one of the modified open reading frames of SEQ ID NO: 35, SEQ ID NO: 36, SEQ ID NO: 38 through SEQ ID NO: 46 is operably linked to a pPIC A vector.

To construct a yeast cell line expressing an active BoNT/E, pPICZ A/BoNT/E-myc-His is digested with a suitable restriction endonuclease (i. e., SacI, PmeI or BstXI) and the resulting linearized expression construct is transformed into an appropriate *P. pastoris* $Mut^s$ strain KM71H using an electroporation method. The transformation mixture is plated on 1.5% YPDS agar plates (pH 7.5) containing 100 μg/mL of Zeocin™ and placed in a 28-30° C. incubator for 1-3 days of growth. Selection of transformants integrating the pPICZ A/BoNT/E-myc-His at the 5' AOX1 locus is determined by colony resistance to Zeocin™. A similar strategy is used to make a cell line containing a pPICZ A expression construct containing SEQ ID NO: 3 used as a control for expression levels. Cell lines integrating a pPICZ A/BoNT/E-myc-His construct is tested for BoNT/E-myc-His expression using a small-scale expression test. Isolated colonies from test cell lines that have integrated pPICZ A/BoNT/E-myc-His are used to inoculate 1.0 L baffled flasks containing 100 mL of MGYH media and grown at about 28-30° C. in a shaker incubator (250 rpm) until the culture reaches an $OD_{600}$=2-6 (approximately 16-18 hours). Cells are harvested by centrifugation (3,000×g at 22° C. for 5 minutes). To induce expression, the cell pellet is resuspended in 15 mL of MMH media and 100% methanol is added to a final concentration of 0.5%. Cultures are grown at about 28-30° C. in a shaker incubator (250 rpm) for six days. Additional 100% methanol is added to the culture every 24 hours to a final concentration of 0.5%. A 1.0 mL test aliquot is taken from the culture every 24 hours starting at time zero and ending at time 144 hours. Cells are harvested from the aliquots by microcentrifugation to pellet the cells and lysed using three freeze-thaw rounds consisting of −80° C. for 5 minutes, then 37° C. for 5 minutes. Lysis samples are added to 2×LDS Sample Buffer (Invitrogen, Inc, Carlsbad, Calif.) and expression from established cell lines is measured by Western blot analysis (as described in Example 12) using either anti-BoNT/E, anti-myc or anti-His antibodies in order to identify lines expressing increased amounts of BoNT/E-myc-His produced from SEQ ID NO: 37 relative to established cell lines expressing BoNT/E-myc-His from the SEQ ID NO: 3 control. The *P. pastoris* $Mut^s$ KM71H cell line showing the highest expression level of BoNT/E-myc-His relative to the SEQ ID NO: 3 control is selected for large-scale expression using commercial fermentation procedures. Procedures for large-scale expression are as outlined above except the culture volume is approximately 2.5 L MGYH media grown in a 5 L BioFlo 3000 fermentor and concentrations of all reagents will be proportionally increased for this volume. For greater details on all procedures described in this example, see EasySelect™ *Pichia* Expression Kit, version G, A Manual of Methods for Expression of Recombinant Proteins Using pPICZ and pPICZa in *Pichia pastoris,* 122701, 25-0172 (Invitrogen, Inc, Carlsbad, Calif.).

Example 16

Construction and Expression of pMET/BoNT/E-V5-His

Figure 9:
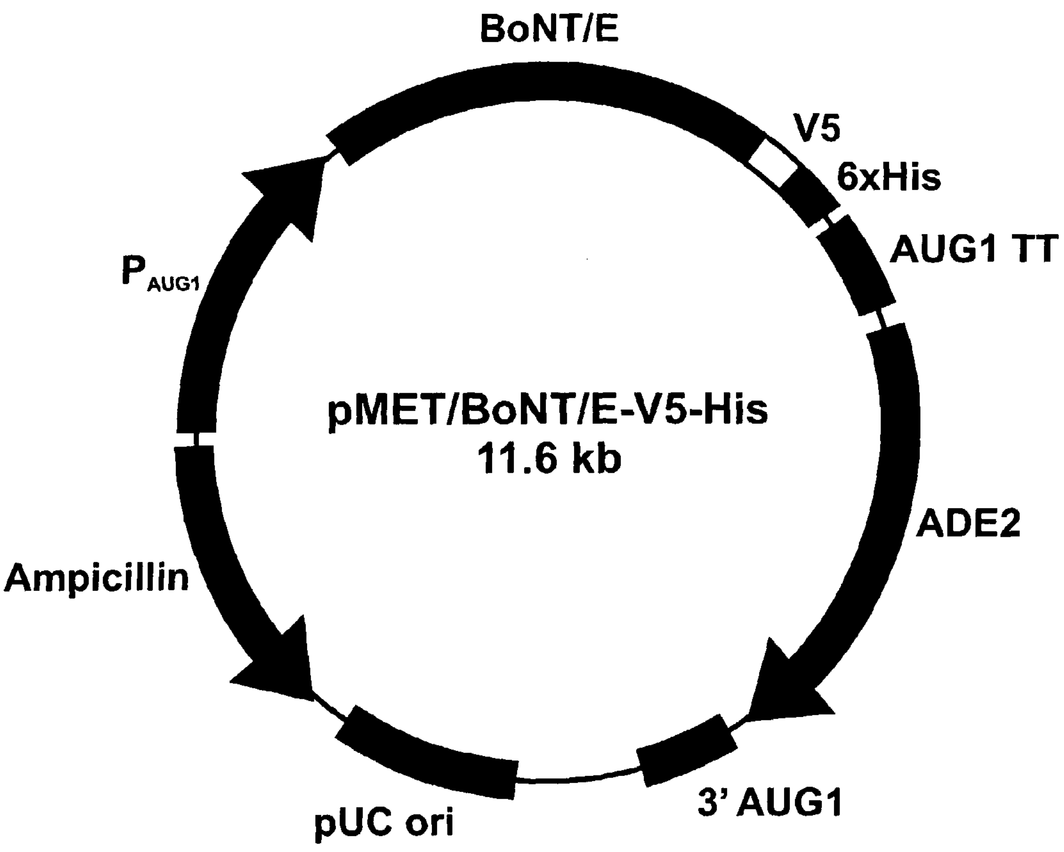
FIG. 9 shows a plasmid map of yeast expression construct pMET/BoNT/E-V5-His comprising a modified open reading frame encoding an active BoNT/E operably-linked to carboxy-terminal V5 and polyhistidine binding peptides. Abbreviations are as follows: $P_{AUG1}$, an alcohol oxidase promoter region; BoNT/E, modified open reading frame of SEQ ID NO: 37 encoding an active BoNT/E; V5, a region encoding a V5 binding peptide sequence; 6×His, a region encoding a polyhistidine binding peptide sequence; AUG1 TT, an alcohol oxidase transcription termination region; ADE2; ADE2 gene for auxotrophic selection; 3' AUG1; pUC ori, a pUC origin of plasmid replication region; Ampicillin, a region encoding a β-lactamase peptide that confers Ampicillin resistance.

Restriction endonuclease sites suitable for cloning an operably linked nucleic acid molecule into a pMET vector (Invitrogen, Inc, Carlsbad, Calif.) are incorporated into the 5'- and 3' ends of modified open reading frame SEQ ID NO: 37. This nucleic acid molecule is synthesized and a pUCBHB1/BoNT/E construct is obtained as described in Example 3. This construct is digested with restriction enzymes that 1) excise the insert containing the open reading frame of SEQ ID NO: 37 encoding an active BoNT/E; and 2) enable this insert to be operably-linked to a pMET vector. This insert is subcloned using a T4 DNA ligase procedure into a pMET vector that is digested with appropriate restriction endonucleases to yield pMET/BoNT/E-V5-His (FIG. 9). The ligation mixture is transformed into chemically competent *E. coli* DH5a cells (Invitrogen, Inc, Carlsbad, Calif.) using a heat shock method, plated on 1.5% low salt Luria-Bertani agar plates (pH 7.5) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the insert. This cloning strategy yields a yeast expression construct encoding an active BoNT/E operably linked to carboxy-terminal V5 and polyhistidine binding peptides. A similar cloning strategy is used to make a pMET expression construct containing the unmodified open reading frame of SEQ ID NO: 3 used as a control for expression levels, as well as, to produce pMET expression constructs in which any one of the modified open reading frames of SEQ ID NO: 35, SEQ ID NO: 36, SEQ ID NO: 38 through SEQ ID NO: 46 is operably linked to a pMET vector.

To construct a yeast cell line expressing an active BoNT/E, pMET/BoNT/E-V5-His is digested with a suitable restriction endonuclease (i.e., ApaI, AscI, FseI, PacI, KpnI or PstI) and the resulting linearized expression construct is transformed into an appropriate *P. methanolica* $Mut^S$ strain PMAD16 using an electroporation method. The transformation mixture is plated on 1.5% MD agar plates (pH 7.5) lacking adenine and grown in a 28-30° C. incubator for 3-4 days. Selection of transformants integrating the pMET/BoNT/E-V5-His is determined by colony growth on adenine-deficient media. A similar strategy is used to make a cell line containing a pMET expression construct containing SEQ ID NO: 3 used as a control for expression levels. $Ade^+$ cell lines integrating a pMET/BoNT/E-V5-His construct are tested for BoNT/E-myc-His expression using a small-scale expression test. Isolated $Ade^+$ colonies from test cell lines that have integrated pMET/BoNT/E-V5-His are used to inoculate 15 mL of BMDY media and cells are grown at about 28-30° C. in a shaker incubator (250 rpm) until the culture reaches an $OD_{600}$=2-10 (approximately 16-18 hours). Cells are harvested by centrifugation (1,500×g at 22° C. for 5 minutes). To induce expression, cell pellets are resuspended in 5 mL of BMMY media and cultures are grown at about 28-30° C. in a shaker incubator (250 rpm). After 24 hours, a 500 μL aliquot is removed, methanol is added to a final concentration of 0.5% and the cultures are grown at about 28-30° C. in a shaker incubator (250 rpm). A 500 μL aliquot is removed and additional methanol is added to a final concentration of 0.5% to the culture every 24 hours for 3-5 days. Harvested cells are centrifuged (1,500×g at 4° C. for 5 minutes), washed once in water and cell pellets stored at −80° C. until needed. To detect expression of the induced BoNT/E-V5-His, the cell pellets of each time point are lysed using an acid-washed glass bead method. Lysis samples are added to 2×LDS Sample Buffer (Invitrogen, Inc, Carlsbad, Calif.) and expression from established cell lines is measured by Western blot analysis (as described in Example 12) using either anti-BoNT/E, anti-V5 or anti-His antibodies in order to identify lines expressing increased amounts of BoNT/E-V5-His produced from SEQ ID NO: 37 relative to established cell lines expressing BoNT/E-V5-His from the SEQ ID NO: 3 control. The *P. methanolica* Muts PMAD16 cell line showing the highest expression level of BoNT/E-V5-His relative to the SEQ ID NO: 3 control is selected for large-scale expression using commercial fermentation procedures. Procedures for large-scale expression are as outlined above except the culture volume is approximately 2.5 L BMDY/BMMY media grown in a 5 L BioFlo 3000 fermentor and concentrations of all reagents will be proportionally increased for this volume. For greater details on all procedures described in this example, see *P. methanolica* Expression Kit, version C, A Manual of Methods for Expression of Recombinant Proteins in *Pichia methanolica,* 062101, 25-0288 (Invitrogen, Inc, Carlsbad, Calif.).

Example 17

Construction and Expression of pYES2/BoNT/E-V5-His

Figure 10:
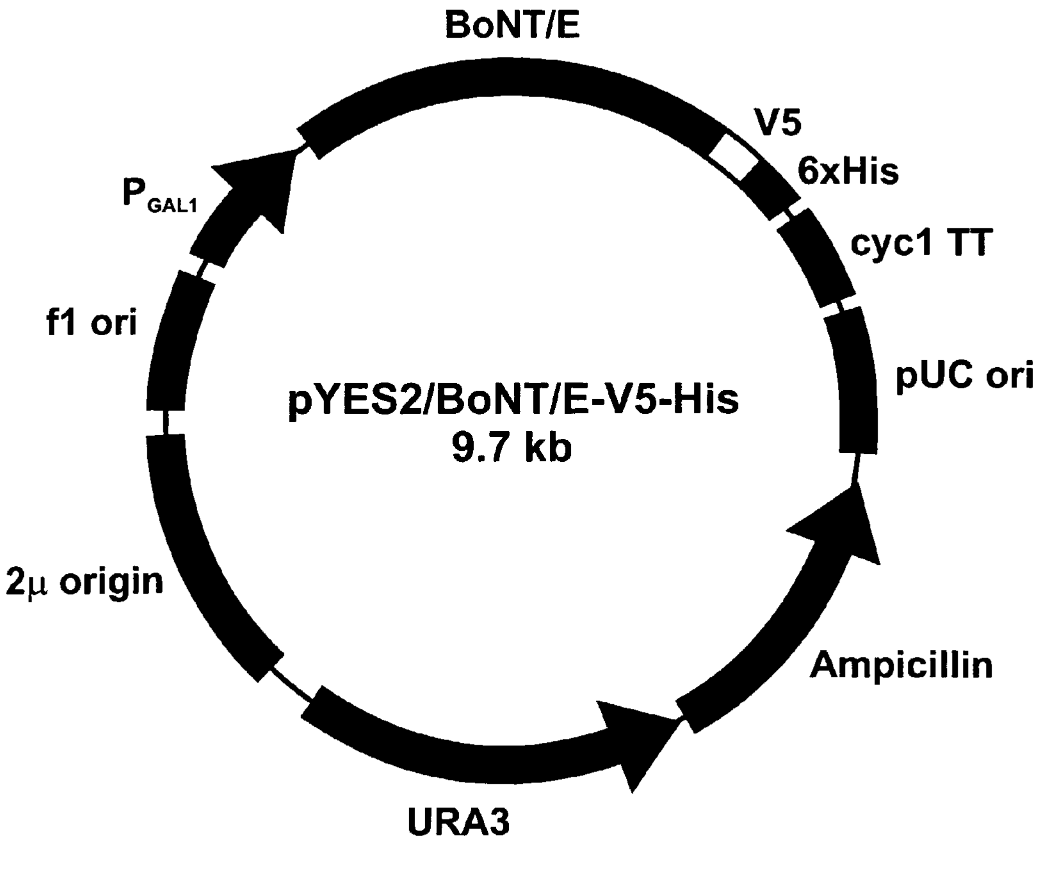
FIG. 10 shows a plasmid map of yeast expression construct pYES2.1/BoNT/E-V5-His comprising a modified open reading frame encoding an active BoNT/E operably-linked to carboxy-terminal V5 and polyhistidine binding peptides. Abbreviations are as follows: $P_{GAL1}$, an galactose-inducible promoter region; BoNT/E, modified open reading frame of SEQ ID NO: 40 encoding an active BoNT/E; V5, a region encoding a V5 binding peptide sequence; 6×His, a region encoding a polyhistidine binding peptide sequence; cyc1 TT, an alcohol oxidase transcription termination region; pUC ori, a pUC origin of plasmid replication region; Ampicillin, a region encoding a β-lactamase peptide that confers Ampicillin resistance; URA3; URA3 gene for auxotrophic selection; 2 μ origin of replication; a 2 μ origin of replication; f1 origin, a bacteriophage f1 origin of replication.

Restriction endonuclease sites suitable for cloning an operably linked nucleic acid molecule into a pYES2 vector (Invitrogen, Inc, Carlsbad, Calif.) are incorporated into the 5' and 3' ends of open reading frame SEQ ID NO: 40. This nucleic acid molecule is synthesized and a pUCBHB1/BoNT/E construct is obtained as described in Example 3. This construct is digested with restriction enzymes that 1) excise the insert containing the open reading frame of SEQ ID NO: 40 encoding an active BoNT/E; and 2) enable this insert to be operably-linked to a pYES2 vector. This insert is subcloned using a T4 DNA ligase procedure into a pYES2 vector that is digested with appropriate restriction endonucleases to yield pYES2/BoNT/E-V5-His (FIG. 10). The ligation mixture is transformed into chemically competent *E. coli* DH5α cells (Invitrogen, Inc, Carlsbad, Calif.) using a heat shock method, plated on 1.5% low salt Luria-Bertani agar plates (pH 7.5) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the insert. This cloning strategy yields a yeast expression construct encoding an active BoNT/E operably linked to carboxy-terminal V5 and polyhistidine binding peptides. A similar cloning strategy is used to make a pYES2 expression construct containing the unmodified open reading frame of SEQ ID NO: 3 used as a control for expression levels, as well as, to produce pYES2 expression constructs in which any one of the modified open reading frames of SEQ ID NO: 35 through SEQ ID NO: 39 and SEQ ID NO: 41 through SEQ ID NO: 46 is operably linked to a pYES2 vector.

To construct a yeast cell line expressing an active BoNT/E, pYES2/BoNT/E-V5-His is transformed into competent *S. cerevisiae* strain INVSc1 using a Lithium-based transformation method. The transformation mixture is plated on 2% SC minimal media agar plates (pH 7.5) containing 2% glucose, that either have 0.01% uracil or lack uracil and placed in a 28-30° C. incubator for 1-3 days of growth. Selection of transformants containing pYES2/BoNT/E-V5-His is determined by colony growth only on plates containing uracil. A similar strategy is used to make cells containing a pYES2 expression construct containing SEQ ID NO: 3 used as a control for expression levels. Cells containing a pYES2/BoNT/E-V5-His construct are tested for BoNT/E-V5-His expression using a small-scale expression test. Isolated colonies from test cells containing pYES2/BoNT/E-V5-His are used to inoculate 50 mL tubes containing 15 mL of SC media containing 2% glucose and 0.01% uracil and grown overnight at about 28-30° C. in a shaker incubator (250 rpm). The $OD_{600}$ of overnight cultures are determined and aliquoted to obtain a cell concentration of $OD_{600}$ of 0.4 in a 50 mL volume. These aliquots are centrifuged (1,500×g at 22° C. for 5 minutes) and the resulting cell pellet resuspended in SC media containing 20% galactose and 10% raffinose. Cells are grown at about 28-30° C. in a shaker incubator (250 rpm) and 5 mL aliquots are taken at 0 hours, 4 hours, 8 hours, 12 hours, 16 hours and 24 hours and $OD_{600}$ concentrations are determined for each sample. Harvested cells are centrifuged (1,500×g at 4° C. for 5 minutes), washed once in water and cell pellets stored at −80° C. until needed. To detect expression of the induced BoNT/E-V5-His, the cell pellets of each time point are lysed using an acid-washed glass bead method. Lysis samples are added to 2×LDS Sample Buffer (Invitrogen, Inc, Carlsbad, Calif.) and expression from each time point is measured by Western blot analysis (as described in Example 12) using either anti-BoNT/E, anti-V5 or anti-His antibodies to identify the optimal induction time necessary to obtain maximal BoNT/E-V5-His expression. The induction conditions resulting in the highest expression level of BoNT/E-V5-His encoded by the modified open reading frame as compared to the unmodified open reading frame of SEQ ID NO: 3 control are selected for large-scale expression using commercial fermentation procedures. Procedures for large-scale expression are as outlined above except the culture volume is approximately 2.5 L SC media grown in a 5 L BioFlo 3000 fermentor and concentrations of all reagents will be proportionally increased for this volume. For greater details on all procedures described in this example, see pYES2/CT, pYES3/CT, and pYC2/CT Yeast Expression Vectors with C-terminal Tags and Auxotrophic Selection Markers, version E, 25-0304, Jan. 27, 2003 (Invitrogen, Inc, Carlsbad, Calif.).

Example 18

Construction and Expression of pFastBacHT/His-BoNT/E

Figure 11:
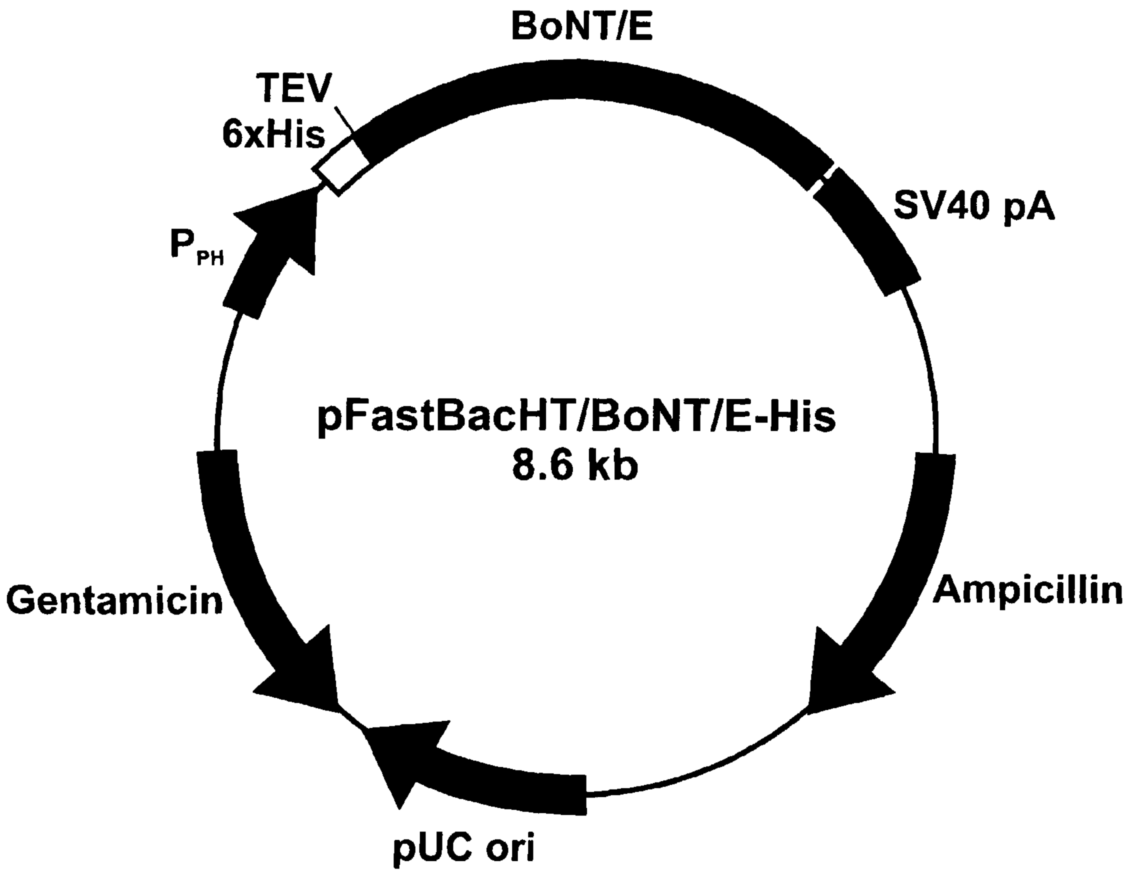
FIG. 11 shows a plasmid map of baculovirus transfer construct pFastBacHT/His-BoNT/E comprising a modified open reading frame encoding an active BoNT/E operably-linked to amino-terminal polyhistidine binding peptide. A tobacco etch virus (TEV) protease cleavage site is operably-linked between the polyhistidine binding peptide and BoNT/E. Abbreviations are as follows: $P_{PH}$, an polyhedrin promoter region; 6×His, a region encoding a polyhistidine binding peptide sequence; TEV, a region encoding a TEV protease cleavage sequence; BoNT/E, modified open reading frame of SEQ ID NO: 61 encoding an active BoNT/E; SV40 pA, a simian virus 40 polyadenylation site; Ampicillin, a region encoding a β-lactamase peptide that confers Ampicillin resistance; pUC ori, a pUC origin of plasmid replication region; Gentamicin, a region encoding an aminophosphotransferase peptide that confers Gentamicin resistance.

Restriction endonuclease sites suitable for cloning an operably linked nucleic acid molecule into a pFastBacHT vector (Invitrogen, Inc, Carlsbad, Calif.) are incorporated into the 5'- and 3' ends of modified open reading frame SEQ ID NO: 61. This nucleic acid molecule is synthesized and a pUCBHB1/BoNT/E construct is obtained as described in Example 3. This construct is digested with restriction enzymes that 1) excise the insert containing the open reading frame of SEQ ID NO: 61 encoding an active BoNT/E; and 2) enable this insert to be operably-linked to a pFastBacHT vector. This insert is subcloned using a T4 DNA ligase procedure into a pFastBacHT vector that is digested with appropriate restriction endonucleases to yield pFastBacHT/His-BoNT/E (FIG. 11). The ligation mixture is transformed into chemically competent *E. coli* DH5a cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the insert. This cloning strategy yields a baculovirus transfer construct encoding an active BoNT/E operably linked to an amino-terminal, TEV cleavable, polyhistidine affinity binding peptide. A similar cloning strategy is used to make a pFastBacHT construct containing the unmodified open reading frame of SEQ ID NO: 3 used as a control for expression levels, as well as, to produce pFastBacHT expression constructs in which any one of the modified open reading frames of SEQ ID NO: 56, SEQ ID NO: 57, SEQ ID NO: 58, SEQ ID NO: 59 or SEQ ID NO: 60 is operably linked to a pFastBacHT vector.

To make a bacmid construct expressing an active BoNT/E, pFastBacHT/His-BoNT/E constructs are transformed by a heat shock method into MAX Efficiency DH10Bac™ *E. coli* cells for transposition into a bacmid. The transformation mixture is plated on 1.5% Luria-Bertani agar plates (pH 7.0) containing 50 μg/mL of Kanamycin, 7 μg/mL of Gentamicin, 10 μg/mL of Tetracycline, 100 μg/mL of Bluo-gal and 40 μg/mL of IPTG and is grown for approximately 48 hours to isolate recombinant bacmid DNA. Candidate bacmid constructs are isolated as white colonies that are Kanamycin, Gentamicin and Tetracycline resistant. Candidate bacmid constructs are isolated using an alkaline lysis plasmid mini-preparation procedure and analyzed by restriction endonuclease digest mapping to determine the presence and orientation of the insert. A similar strategy is used to generate a recombinant baculoviral stock containing the unmodified open reading frame of SEQ ID NO: 3 construct. A P1 recombinant baculovirus stock is isolated by transfecting approximately $5\times10^5$ Sf9 cells plated in a 35 mm tissue culture dish containing 2 mL of complete Sf-900 II SFM media with 50 units/mL of penicillin and 50 μg/mL of streptomycin, with 1.0 mL of transfection solution. The transfection solution is prepared by adding 800 μL of unsupplemented Grace's media to 200 μL of unsupplemented Grace's media, containing 1.0 μg of a purified bacmid His-BoNT/E construct and 6 μL of Cellfectin® Reagent preincubated for 30 minutes to allow formation of DNA:lipid complexes. Cells are incubated with this trasfection solution for 5 hours in a 27° C. incubator, after which time this solution is replaced with 2.0 mL of complete Sf-900 II SFM media with 50 units/mL of penicillin and 50 μg/mL of streptomycin. Sf9 cells are grown for approximately 72 hours in a 27° C. incubator to allow for the release of virus into the medium. The virus is harvested by transferring the media from virally-infected insect cells to 15 mL snap-cap tubes and centrifuging tubes at 500×g for 5 minutes to remove debris. The clarified supernatant is transferred to fresh 15 mL snap-cap tubes and should contain approximately $1\times10^6$ to $10^7$ plaque forming units (pfu) of baculovirus. This P1 viral stock is then amplified to generate a P2 recombinant baculovirus stock. About $2\times10^6$ Sf9 cells are plated in a 35 mm culture dish containing 2 mL of Sf-900 II SFM media, supplemented with 50 units/mL of penicillin and 50 μg/mL of streptomycin, are inoculated with 400 μL of the P1 recombinant baculovirus stock (approximately $5\times10^6$ pfu/ml) and incubated for approximately 48 hours in a 27° C. incubator. The virus is harvested by transferring the media to 15 mL snap-cap tubes and centrifuging tubes at 500×g for 5 minutes to remove debris. The clarified supernatant is transferred to fresh 15 mL snap-cap tubes and should contain approximately $1\times10^7$ to $10^8$ pfu of baculovirus.

To express His-BoNT/E using a baculoviral expression system, about $2\times10^6$ Sf9 cells are plated in a 35 mm culture dish containing 2 mL of Sf-900 II SFM media, supplemented with 50 units/mL of penicillin and 50 μg/mL of streptomycin, are inoculated with approximately 4 μL of the P1 recombinant baculovirus stock (approximately $5\times10^7$ pfu/ml) and incubated for approximately 48 hours in a 27° C. incubator. Both media and cells are collected for BoNT/E-His expression. Media is harvested by transferring the media to 15 mL snap-cap tubes and centrifuging tubes at 500×g for 5 minutes to remove debris. Cells are harvested by rinsing cells once with 3.0 mL of 100 mM phosphate-buffered saline, pH 7.4 and lysing cells with a buffer containing 62.6 mM 2-amino-2-hydroxymethyl-1,3-propanediol hydrochloric acid (Tris-HCl), pH 6.8 and 2% sodium lauryl sulfate (SDS). Both media and cell samples are added to 2×LDS Sample Buffer (Invitrogen, Inc, Carlsbad, Calif.) and expression is measured by Western blot analysis (as described in Example 12) using either anti-BoNT/E or anti-His antibodies in order to identify P2 baculoviral stocks expressing increased amounts of His-BoNT/E produced from SEQ ID NO: 61 relative to stocks expressing His-BoNT/E from the SEQ ID NO: 3 control. For greater details on all procedures described in this example, see Bac-to-Bac® Baculovirus Expression System, version D, An Efficient Site-specific Transposition System to Generate Baculovirus for High-level Expression of Recombinant Proteins, 10359 (Invitrogen, Inc, Carlsbad, Calif.).

Example 19

Construction and Expression of pBACgus3/gp64-BoNT/E-His

Figure 12:
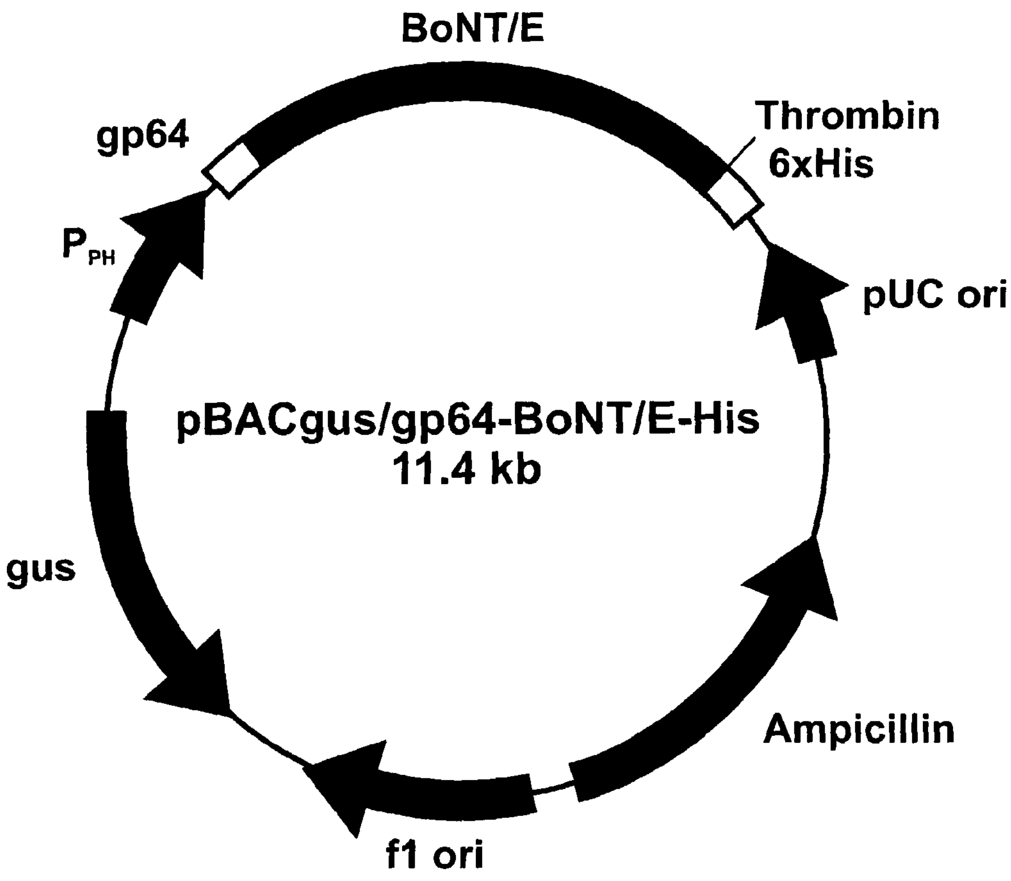
FIG. 12 shows a plasmid map of baculovirus transfer construct pBACgus3/BoNT/E-His comprising a modified open reading frame encoding an active BoNT/E operably-linked to carcoxy-terminal polyhistidine binding peptide. A thrombin protease cleavage site is operably-linked between the BoNT/E and the polyhistidine binding peptide. Abbreviations are as follows: $P_{PH}$, an polyhedrin promoter region; gp64, a region encoding a gp64 signal peptide; BoNT/E, modified open reading frame of SEQ ID NO: 61 encoding an active BoNT/E; Thrombin, a region encoding a Thrombin protease cleavage sequence; 6×His, a region encoding a polyhistidine binding peptide sequence; pUC ori, a pUC origin of plasmid replication region; Ampicillin, a region encoding a β-lactamase peptide that confers Ampicillin resistance; f1 origin, a bacteriophage f1 origin of replication; gus, a region encoding a β-glucuronidase peptide.

Restriction endonuclease sites suitable for cloning an operably linked nucleic acid molecule into a pBACgus3 vector (EMD Biosciences-Novagen, Madison, Wis.) are incorporated into the 5'- and 3' ends of modified open reading frame SEQ ID NO: 61. This nucleic acid molecule is synthesized and a pUCBHB1/BoNT/E construct is obtained as described in Example 3. This construct is digested with restriction enzymes that 1) excise the insert containing the open reading frame of SEQ ID NO: 61 encoding an active BoNT/E; and 2) enable this insert to be operably-linked to a pBACgus3 vector. This insert is subcloned using a T4 DNA ligase procedure into a pBACgus3 vector that is digested with appropriate restriction endonucleases to yield pBACgus3/BoNT/E-His (FIG. 12). The ligation mixture is transformed into chemically competent *E. coli* DH5a cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the insert. This cloning strategy yields a baculovirus transfer construct encoding an active BoNT/E operably linked to an amino-terminal gp64 signal peptide and a carboxy-terminal, thrombin cleavable, polyhistidine affinity binding peptide. A similar cloning strategy is used to make a pBACgus3 construct containing the unmodified open reading frame of SEQ ID NO: 3 used as a control for expression levels, as well as, to produce pBACgus3 expression constructs in which any one of the modified open reading frames of SEQ ID NO: 56, SEQ ID NO: 57, SEQ ID NO: 58, SEQ ID NO: 59 or SEQ ID NO: 60 is operably linked to a pBACgus3 vector.

To express BoNT/E-His using a baculoviral expression system, about $2.5\times10^6$ Sf9 cells are plated in four 60 mm culture dishes containing 2 mL of BACVECTOR® Insect media, a serum-free S19 insect cell growth media, (EMD Biosciences-Novagen, Madison, Wis.) and incubated for approximately 20 minutes in a 28° C. incubator. For each transfection, a 50 μL transfection solution is prepared in a 6 mL polystyrene tube by adding 25 μL of BACVECTOR® Insect media, a serum-free S19 insect cell growth media, containing 100 ng pBACgus3/gp64-BoNT/E-His and 500 ng TlowE transfer plasmid to 25 μL of diluted Insect GENEJUICE®, a cationic liposome based reagent,containing 5 μL Insect GENEJUICE®, a cationic liposome based reagent, (EMD Biosciences-Novagen, Madison, Wis.) and 20 μL nuclease-free water and this solution is incubated for approximately 15 minutes. After the 15 minute incubation, add 450 μL-BACVECTOR® media, a serum-free S19 insect cell growth media, to the transfection solution and mix gently. Using this stock transfection solution as the 1/10 dilution make additional transfection solutions of 1/50, 1/250 and 1/1250 dilutions. Add 100 μL of a transfection solution to the Sf9 cells from one of the four 60 mm culture dishes, twice washed with antibiotic-free, serum-free BACVECTOR® Insect media, a serum-free S19 insect cell growth media, and incubate at 22° C. After one hour, add 6 mL of 1% BacPlaque agarose BACVECTOR® Insect media, a serum-free S19 insect cell growth media, containing 5% bovine serum albumin. After the agarose is solidified, add 2 mL BACVECTOR® Insect media, a serum-free S19 insect cell growth media, containing 5% bovine serum albumin to the transfected cells and transfer the cells to a 28° C. incubator for 3-5 days until plaques are visible. After 3-5 days post-transfection, plaques in the monolayer will be stained for β-glucuronidase reporter gene activity to test for the presence of recombinant virus plaques containing pBACgus3/BoNT/E-His by incubating the washed monolayer with 2 mL of BACVECTOR® Insect media, a serum-free S19 insect cell growth media, containing 30 μL of 20 mg/mL X-Gluc Solution (EMD Biosciences-Novagen, Madison, Wis.) for approximately 2 hours in a 28° C. incubator.

After identifying candidate recombinant virus plaques, several candidate virus plaques are eluted and plaque purified. To elute a recombinant virus, transfer a plug containing a recombinant virus plaque with a sterile Pasteur pipet to 1 mL BACVECTOR® Insect media, a serum-free S19 insect cell growth media, (EMD Biosciences-Novagen, Madison, Wis.) in a sterile screw-cap vial. Incubate the vial for approximately 2 hours at 22° C. or for approximately 16 hours at 4° C. For each recombinant virus plaque, $2.5\times10^5$ Sf9 cells are plated in 35 mm culture dishes containing 2 mL of BACVECTOR® Insect media, a serum-free S19 insect cell growth media, (EMD Biosciences-Novagen, Madison, Wis.) and incubated for approximately 20 minutes in a 28° C. incubator. Remove the media and add 200 μL of eluted recombinant virus. After one hour, add 2 mL of 1% BacPlaque agarose-BACVECTOR® Insect media, a serum-free S19 insect cell growth media, containing 5% bovine serum albumin. After the agarose is solidified, add 1 mL BACVECTOR® Insect media, a serum-free S19 insect cell growth media, containing 5% bovine serum albumin to the transfected cells and transfer the cells to a 28° C. incubator for 3-5 days until plaques are visible. After 3-5 days post-transfection, plaques in the monolayer will be stained for β-glucuronidase reporter gene activity to test for the presence of recombinant virus plaques containing pBACgus3/BoNT/E-His by incubating the washed monolayer with 2 mL of BACVECTOR® Insect media, a serum-free S19 insect cell growth media, containing 30 μL of 20 mg/mL X-Gluc Solution (EMD Biosciences-Novagen, Madison, Wis.) for approximately 2 hours in a 28° C. incubator.

To prepare a seed stock of virus, elute a recombinant virus by transferring a plug containing a recombinant virus plaque with a sterile Pasteur pipet to 1 mL BACVECTOR® Insect media, a serum-free S19 insect cell growth media, (EMD Biosciences-Novagen, Madison, Wis.) in a sterile screw-cap vial. Incubate the vial for approximately 16 hours at 4° C. Approximately $5\times10^5$ Sf9 cells are plated in T-25 flask containing 5 mL of BACVECTOR® Insect media, a serum-free S19 insect cell growth media, (EMD Biosciences-Novagen, Madison, Wis.) and are incubated for approximately 20 minutes in a 28° C. incubator. Remove the media and add 300 μL of eluted recombinant virus. After one hour, add 5 mL BACVECTOR® Insect media, a serum-free S19 insect cell growth media, containing 5% bovine serum albumin to the transfected cells and transfer the cells to a 28° C. incubator for 3-5 days until the majority of cells become unattached and unhealthy. The virus is harvested by transferring the media to 15 mL snap-cap tubes and centrifuging tubes at 1000× g for 5 minutes to remove debris. The clarified supernatant is transferred to fresh 15 mL snap-cap tubes and are stored at 4° C.

To prepare a high titer stock of virus, approximately $2\times10^7$ Sf9 cells are plated in T-75 flask containing 10 mL of BACVECTOR® Insect media, a serum-free S19 insect cell growth media, (EMD Biosciences-Novagen, Madison, Wis.) and are incubated for approximately 20 minutes in a 28° C. incubator. Remove the media and add 500 μL of virus seed stock. After one hour, add 10 mL BACVECTOR® Insect media, a serum-free S19 insect cell growth media, containing 5% bovine serum albumin to the transfected cells and transfer the cells to a 28° C. incubator for 3-5 days until the majority of cells become unattached and unhealthy. The virus is harvested by transferring the media to 15 mL snap-cap tubes and centrifuging tubes at 1000× g for 5 minutes to remove debris. The clarified supernatant is transferred to fresh 15 mL snap-cap tubes and are stored at 4° C. High titer virus stocks should contain approximately $2\times10^8$ to $3\times10^9$ pfu of baculovirus.

To express gp64-BoNT/E-His using a baculoviral expression system, about $1.25\times10^8$ Sf9 cells are seeded in a 1 L flask containing 250 mL of BACVECTOR® Insect media, a serum-free S19 insect cell growth media, and are grown in an orbital shaker (150 rpm) to a cell density of approximately $5\times10^8$. The culture is inoculated with inoculated with approximately $2.5\times10^9$ of high titer stock recombinant baculovirus and incubated for approximately 48 hours in a 28° C. orbital shaker (150 rpm). Media is harvested by transferring the media to tubes and centrifuging tubes at 500× g for 5 minutes to remove debris. Media samples are added to 2× LDS Sample Buffer (Invitrogen, Inc, Carlsbad, Calif.) and expression is measured by Western blot analysis (as described in Example 12) using either anti-BoNT/E or anti-His antibodies in order to identify baculoviral stocks expressing increased amounts of His-BoNT/E produced from SEQ ID NO: 61 relative to stocks expressing gp64-BoNT/E-His from the SEQ ID NO: 3 control. For greater details on all procedures described in this example, see BACVECTOR® Transfection Kits, TB216, revision A 1203, a baculovirus expression vector and a cationic liposome based reagent, (EMD Biosciences-Novagen, Madison, Wis.).

Example 20

Construction and Expression of pMT/BiP-BoNT/E-V5-His

Figure 13:
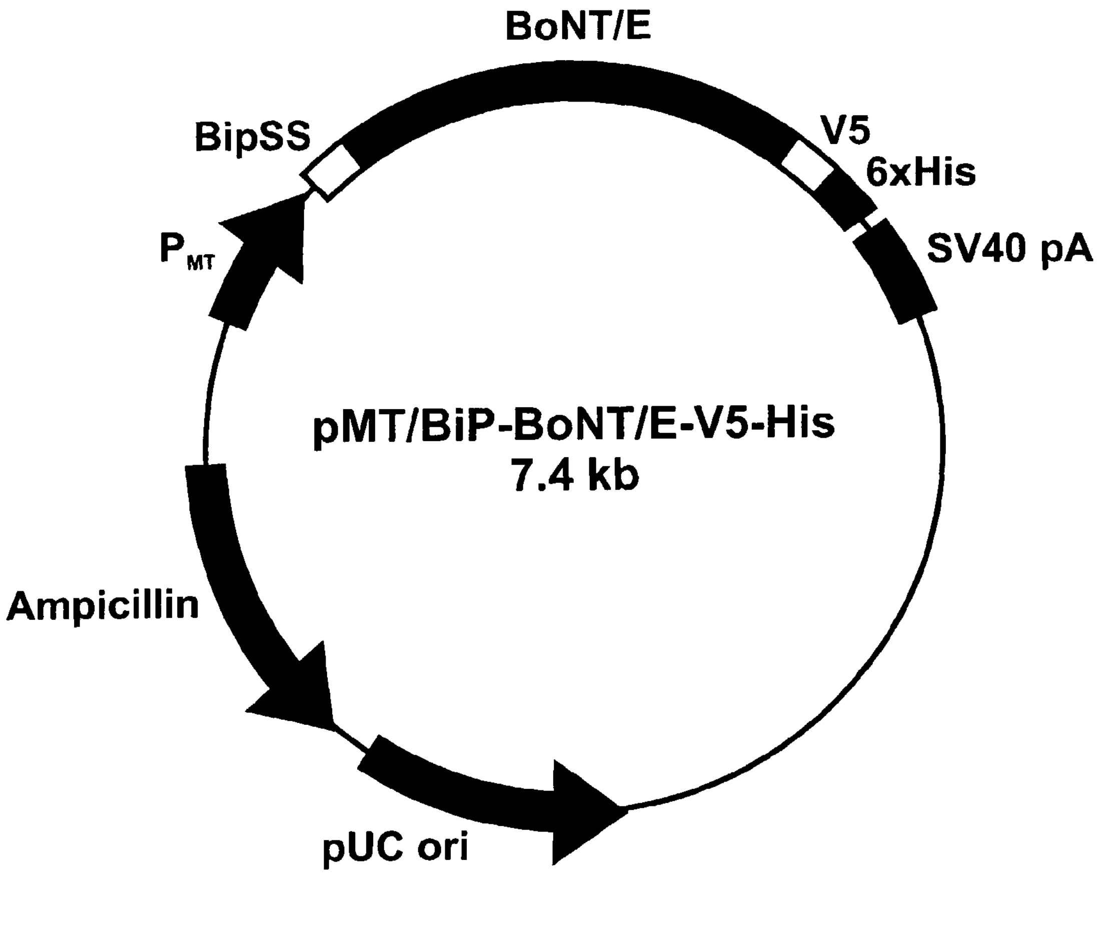
FIG. 13 shows a plasmid map of insect expression construct pMT/BiP-BoNT/E-V5-His comprising a modified open reading frame encoding an active BoNT/E operably-linked to carboxy-terminal V5 and polyhistidine binding peptides. Abbreviations are as follows: $P_{MT}$, an metallothionein promoter region; BipSS, a region encoding a BiP signal sequence; BoNT/E, modified open reading frame of SEQ ID NO: 58 encoding an active BoNT/E; V5, a region encoding a V5 binding peptide sequence; 6×His, a region encoding a polyhistidine binding peptide sequence; SV40 pA, a simian virus 40 polyadenylation site; pUC ori, a pUC origin of plasmid replication region; Ampicillin, a region encoding a β-lactamase peptide that confers Ampicillin resistance.

Restriction endonuclease sites suitable for cloning an operably linked nucleic acid molecule into a pMT vector (Invitrogen, Inc, Carlsbad, Calif.) are incorporated into the 5'- and 3' ends of modified open reading frame SEQ ID NO: 58. This nucleic acid molecule is synthesized and a pUCBHB1/BoNT/E construct obtained as described in Example 3. This construct is digested with restriction enzymes that 1) excise the insert containing the open reading frame of SEQ ID NO: 58 encoding an active BoNT/E; and 2) enable this insert to be operably-linked to a pMT vector. This insert is subcloned using a T4 DNA ligase procedure into a pMT vector that is digested with appropriate restriction endonucleases to yield pMT/BiP-BoNT/E-V5-His (FIG. 13). The ligation mixture is transformed into chemically competent *E. coli* DH5a cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the insert. This cloning strategy will yield an insect expression construct encoding an active BoNT/E operably linked to carboxy-terminal V5 and polyhistidine binding peptides. A similar cloning strategy is used to make a pMT construct containing the unmodified open reading frame of SEQ ID NO: 3 used as a control for expression levels, as well as, to produce pMT expression constructs in which any one of the modified open reading frames of SEQ ID NO: 56, SEQ ID NO: 57, SEQ ID NO: 59, SEQ ID NO: 60 or SEQ ID NO: 61 is operably linked to a pMT vector.

To transiently express active BoNT/E-V5-His in insect cells, about $3\times10^6$ S2 cells are plated in a 35 mm tissue culture dish containing 3 mL of Schneider's *Drosophila* media and are grown in a 28° C. incubator until cells reach a density of approximately $9\times10^6$ cells/ml (6-16 hours). A 600 μL transfection solution is prepared by adding 300 μL of 2×HEPES-Buffered Saline, pH 7.1 (50 mM N-(2-hydroxyethyl) piperazine-N'-(2-ethanesulfonic acid) (HEPES), pH 7.4; 1.5 mM sodium phosphate (monobasic); 280 mM sodium chloride) to 300 μL of 240 mM calcium chloride containing 19 μg of pMT/BiP-BoNT/E-V5-His and this solution is incubated for approximately 30 minutes. The transfection solution is added to S2 cells and the cells are incubated in a 28° C. incubator for approximately 16-24 hours. The transfection media is replaced with 3 mL of fresh Schneider's *Drosophila* media containing 500 μM copper sulfate to induce expression. Cells are incubated in a 28° C. incubator for an additional 48 hours. Media is harvested by transferring the media to 15 mL snap-cap tubes and centrifuging tubes at 500×g for 5 minutes to remove debris. Samples are added to 2×LDS Sample Buffer (Invitrogen, Inc, Carlsbad, Calif.) and expression is measured by Western blot analysis (as described in Example 12) using either anti-BoNT/E, anti-V5 or anti-His antibodies in order to identify pMT constructs expressing increased amounts of BiP-BoNT/E-V5-His produced from SEQ ID NO: 58 relative to constructs expressing BoNT/E-V5-His from the SEQ ID NO: 3 control.

To generate a stably-integrated insect cell line expressing active BoNT/E-V5-His, approximately $3\times10^6$ S2 cells are plated in a 35 mm tissue culture dish containing 3 mL of Schneider's *Drosophila* media and grown in a 28° C. incubator until cells reach a density of about $9\times10^6$ cells/ml (6-16 hours). A 600 μL transfection solution is prepared by adding 300 μL of 2×HEPES-Buffered Saline, pH 7.1 (50 mM N-(2-hydroxyethyl) piperazine-N'-(2-ethanesulfonic acid) (HEPES), pH 7.4; 1.5 mM sodium phosphate (monobasic); 280 mM sodium chloride) to 300 μL of 240 mM calcium chloride containing 19 μg of pMT/BiP-BoNT/E-V5-His and 1 μg of pCoHygro, and this solution is incubated for approximately 30 minutes. The transfection solution is added to S2 cells and incubate in a 28° C. incubator for approximately 16-24 hours. Transfection media is replaced with 3 mL of fresh Schneider's *Drosophila* media and the cells are incubated in a 28° C. incubator for approximately 48 hours. Media is replaced with 3 mL of fresh Schneider's *Drosophila* media containing approximately 500 μg/mL of hygromycin-B. Cells are incubated in a 28° C. incubator for approximately 3-4 weeks, and old media is replaced with fresh hygromycin-B selective media every 4 to 5 days. Once hygromycin-B-resistant colonies are established, resistant clones are replated to new 35 mm culture plates containing fresh Schneider's *Drosophila* media supplemented with approximately 500 μg/mL of hygromycin-B until these cells reach a density of about 6 to 20×10$^6$ cells/mL. To test for expression of BoNT/E-V5-His from S2 cell lines that have stably-integrated a pMT/BiP-BoNT/E-V5-His, approximately 3×10$^6$ S2 cells from each cell line are plated in a 35 mm tissue culture dish containing 3 mL of Schneider's *Drosophila* media and are grown in a 28° C. incubator until cells reach a density of about 9×10$^6$ cells/ml (6-16 hours). Transfection media is replaced with 3 mL of fresh Schneider's *Drosophila* media containing 500 μM copper sulfate to induce expression. Cells are incubated in a 28° C. incubator for an additional 48 hours. Media is harvested by transferring the media to 15 mL snap-cap tubes and centrifuging tubes at 500×g for 5 minutes to remove debris. Samples are added to 2×LDS Sample Buffer (Invitrogen, Inc, Carlsbad, Calif.) and expression is measured by Western blot analysis (as described in Example 12) using either anti-BoNT/E, anti-V5 or anti-His antibodies in order to identify S2 cell lines expressing increased amounts of BoNT/E-V5-His produced from SEQ ID NO: 58 relative to cell lines expressing BoNT/E-V5-His from the SEQ ID NO: 3 control. The established S2 cell line showing the highest expression level of BoNT/E-V5-His relative to the SEQ ID NO: 3 control is selected for large-scale expression using 3 L spinner flasks. Procedures for large-scale expression are as outlined above except the culture volume is approximately 800-1000 mL of Schneider's *Drosophila* media and concentrations of all reagents are proportionally increased for this volume. For greater details on all procedures described in this example, see *Drosophila* Expression System, version H, For the Stable Expression and Purification of Heterologous Proteins in Schneider 2 Cells, 25-0191 (Invitrogen, Inc, Carlsbad, Calif.).

Example 21

Construction and Expression of pQBI25/BoNT/E-GFP

Figure 14:
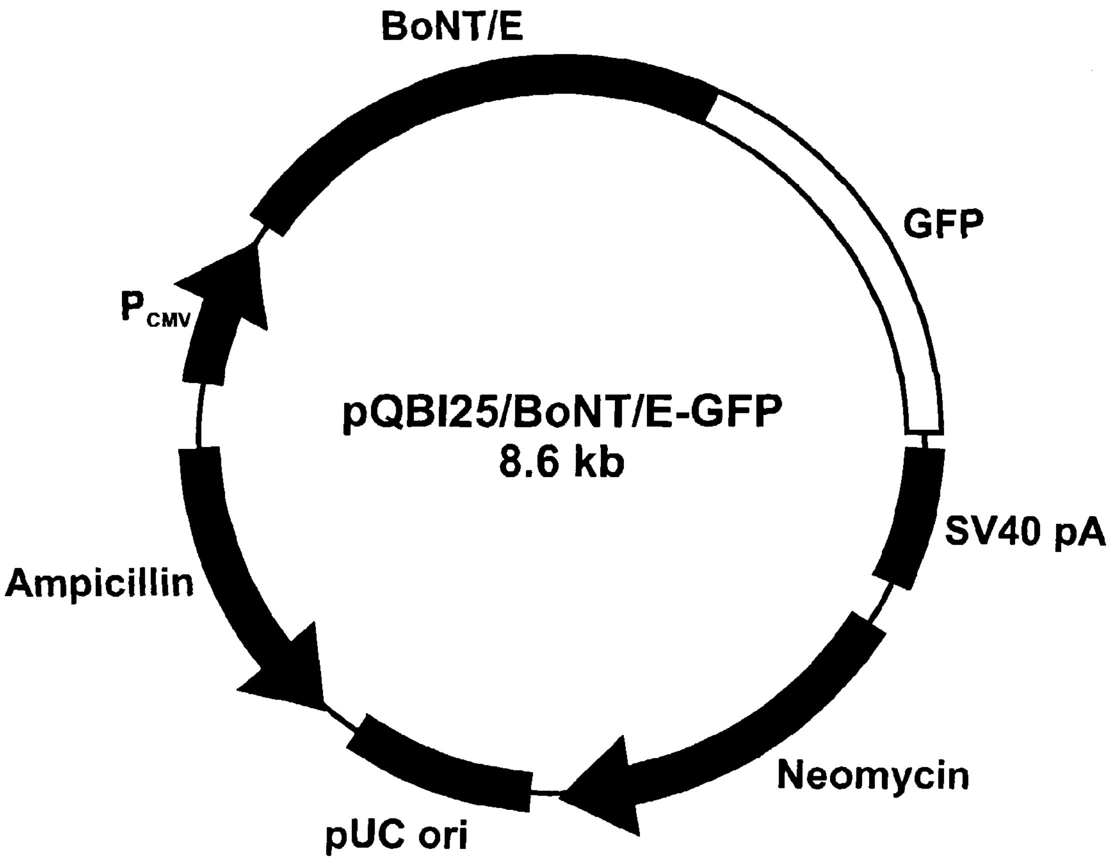
FIG. 14 shows a plasmid map of mammalian expression construct pQBI25/BoNT/E-GFP comprising a modified open reading frame encoding an active BoNT/E operably-linked to a carboxy-terminal GFP peptide. Abbreviations are as follows: $P_{CMV}$, an cytomegalovirus promoter region; BoNT/E, a modified open reading frame of SEQ ID NO: 97 encoding an active BoNT/E; GFP, a region encoding a Green Florescence Protein peptide; BGH pA, a bovine growth hormone polyadenylation site; Neomycin, a region encoding an aminophosphotransferase peptide that confers Neomycin resistance; pUC ori, a pUC origin of plasmid replication region; Ampicillin, a region encoding a β-lactamase peptide that confers Ampicillin resistance.

Restriction endonuclease sites suitable for cloning an operably linked nucleic acid molecule into a pQBI25 vector (Obiogene, Inc., Carlsbad, Calif.) are incorporated into the 5'- and 3' ends of modified open reading frame SEQ ID NO: 97. This nucleic acid molecule is synthesized and a pUCBHB1/BoNT/E construct is obtained as described in Example 3. This construct is digested with restriction enzymes that 1) excise the insert containing the open reading frame of SEQ ID NO: 97 encoding an active BoNT/E; and 2) enable this insert to be operably-linked to a pQBI25 vector. This insert is subcloned using a T4 DNA ligase procedure into a pQBI25 vector that is digested with appropriate restriction endonucleases to yield pQBI25/BoNT/E-GFP (FIG. 14). The ligation mixture is transformed into chemically competent *E. coli* DH5a cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the insert. This cloning strategy yields a mammalian expression construct encoding an active BoNT/E operably linked to carboxy-terminal GFP peptide. A similar cloning strategy is used to make a pQBI 25 construct containing the unmodified open reading frame of SEQ ID NO: 3 used as a control for expression levels, as well as, to produce pQBI25 expression constructs in which any one of the modified open reading frames of SEQ ID NO: 74 through SEQ ID NO: 96 is operably linked to a pQBI25 vector.

To transiently express an active BoNT/E-GFP in a cell line, about 1.5×10$^5$ SH-SY5Y cells are plated in a 35 mm tissue culture dish containing 3 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 1× MEM non-essential amino acids solution (MEM) (Invitrogen, Inc, Carlsbad, Calif.), and grown in a 37° C. incubator under 5% carbon dioxide until cells reach a density of about 5×10$^5$ cells/ml (6-16 hours). A 500 μL transfection solution is prepared by adding 250 pL of OPTI-MEM Reduced Serum Medium containing 15 μL of LIPOFECTAMINE 2000, a cationic liposome based reagent, (Invitrogen, Carlsbad, Calif.) incubated at room temperature for 5 minutes to 250 μL of OPTI-MEM Reduced Serum Medium containing 5 μg of a pQBI25/BoNT/E-GFP. This transfection was incubated at room temperature for approximately 20 minutes. The complete, supplemented DMEM media was replaced with 2 mL of OPTI-MEM Reduced Serum Medium and the 500 μL transfection solution was added to the SH-SY5Y cells and the cells incubated in a 37° C. incubator under 5% carbon dioxide for approximately 6 to 18 hours. Transfection media is replaced with 3 mL of fresh complete, supplemented DMEM and incubate cells in a 37° C. incubator under 5% carbon dioxide for 48 hours. Cells are harvest by rinsing cells once with 3.0 mL of 100 mM phosphate-buffered saline, pH 7.4 and lysing cells with a buffer containing 50 mM N-(2-hydroxyethyl) piperazine-N'-(2-ethanesulfonic acid) (HEPES), pH 6.8 150 mM sodium chloride, 1.5 mM magnesium chloride, 10% (v/v) glycerol, 1mM ethylene glycol bis(β-aminoethyl ether) N, N, N', N'-tetraacetic acid (EGTA), 2% (v/v) TRITON-X® 100 (4-octylphenol polyethoxylate) and 1× Complete protease inhibitor cocktail (Roche Applied Science, Indianapolis, Ind.). Cell samples are added to 2× LDS Sample Buffer (Invitrogen, Inc, Carlsbad, Calif.) and expression is measured by Western blot analysis (as described in Example 12) using either anti-BoNT/E or anti-GFP antibodies in order to identify pQBI 25 constructs expressing increased amounts of BoNT/E-GFP produced from SEQ ID NO: 97 relative to constructs expressing BoNT/E-GFP from the SEQ ID NO: 3 control.

Example 22

Construction and Expression of pcDNA™6/BoNT/E-V5-His

Figure 15:
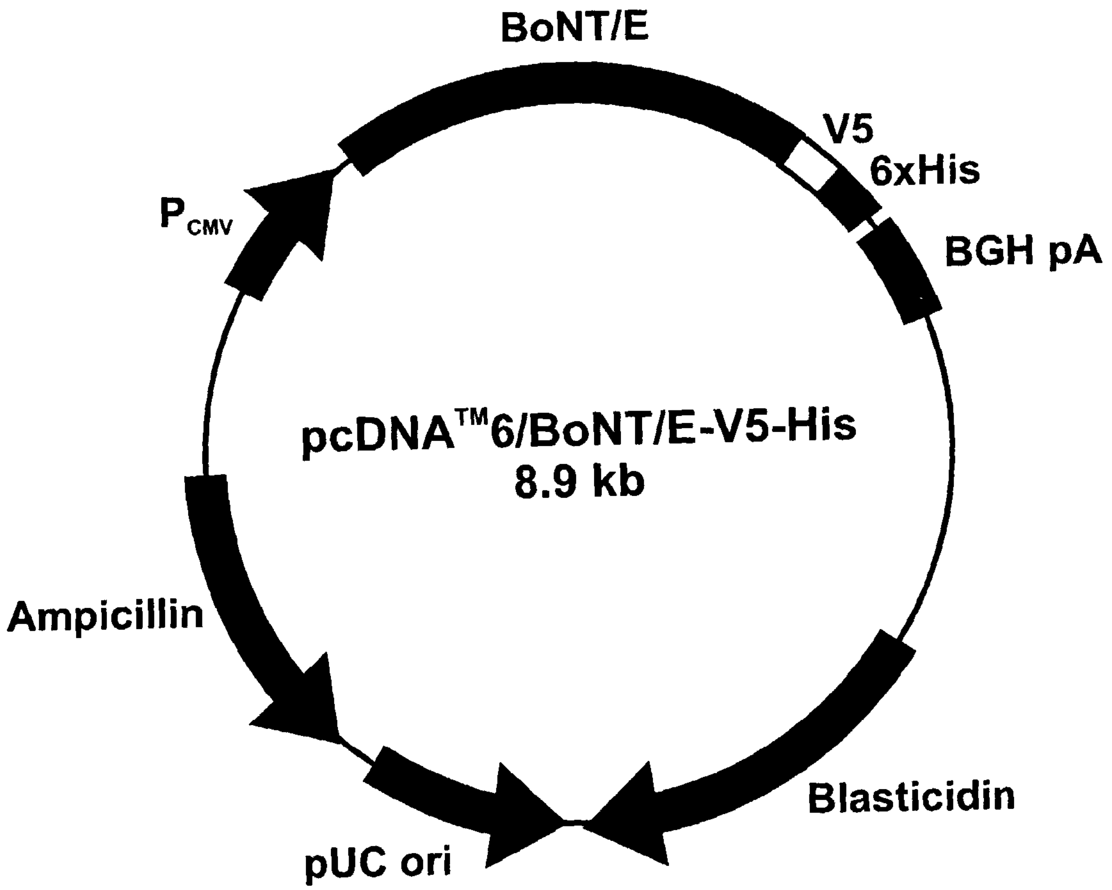
FIG. 15 shows a plasmid map of mammalian expression construct pcDNA T6/BoNT/E-V5-His comprising a modified open reading frame encoding an active BoNT/E operably-linked to carboxy-terminal V5 and polyhistidine binding peptides. Abbreviations are as follows: $P_{CMV}$, an cytomegalovirus promoter region; BoNT/E, a modified open reading frame of SEQ ID NO: 97 encoding an active BoNT/E; V5, a region encoding a V5 binding peptide sequence; 6×His, a region encoding a polyhistidine binding peptide sequence; BGH pA, a bovine growth hormone polyadenylation site; Blasticidin, a region encoding an blasticidin resistance peptide; pUC ori, a pUC origin of plasmid replication region; Ampicillin, a region encoding a β-lactamase peptide that confers Ampicillin resistance.

Restriction endonuclease sites suitable for cloning an operably linked nucleic acid molecule into a pcDNA™6 vector (Invitrogen, Inc, Carlsbad, Calif.) are incorporated into the 5'- and 3' ends of modified open reading frame SEQ ID NO: 97. This nucleic acid molecule is synthesized and a pUCBHB1/BoNT/E construct obtained as described in Example 3. This construct is digested with restriction enzymes that 1) excise the insert containing the open reading frame of SEQ ID NO: 97 encoding an active BoNT/E; and 2) enable this insert to be operably-linked to a pcDNA™6 vector. This insert is subcloned using a T4 DNA ligase procedure into a pcDNA™6 vector that is digested with appropriate restriction endonucleases to yield pcDNA™6/BoNT/E-V5-His (FIG. 15). The ligation mixture is transformed into chemically competent *E. coli* DH5a cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the insert. This cloning strategy yields a mammalian expression construct encoding an active BoNT/E operably linked to carboxy-terminal V5 and polyhistidine binding peptides. A similar cloning strategy is used to make a pcDNA™6 construct containing the unmodified open reading frame of SEQ ID NO: 3 used as a control for expression levels, as well as, to produce pcDNA™6 expression constructs in which any one of the modified open reading frames of SEQ ID NO: 74 through SEQ ID NO: 96 is operably linked to a pcDNA™6 vector.

To transiently express BoNT/E-V5-His in a cell line, about $1.5\times10^5$ SH-SY5Y cells are plated in a 35 mm tissue culture dish containing 3 mL of complete Dulbecco's Modified Eagle Media (DMEM), supplemented with 10% fetal bovine serum (FBS), 1×penicillin/streptomycin solution (Invitrogen, Inc, Carlsbad, Calif.) and 1×MEM non-essential amino acids solution (MEM) non-essential amino acids solution (Invitrogen, Inc, Carlsbad, Calif.), and grown in a 37 ° C. incubator under 5% carbon dioxide until cells reach a density of about $5\times10^5$ cells/ml (6-16 hours). A 500 μL transfection solution is prepared by adding 250 μL of OPTI-MEM Reduced Serum Medium containing 15 μL of LIPOFECTAMINE 2000, a cationic liposome based reagent, (Invitrogen, Carlsbad, Calif.) incubated at room temperature for 5 minutes to 250 μL of OPTI-MEM Reduced Serum Medium containing 5μg of a pcDNA™6/BoNT/E-V5-His. This transfection was incubated at room temperature for approximately 20 minutes. The complete, supplemented DMEM media was replaced with 2 mL of OPTI-MEM Reduced Serum Medium and the 500 μL transfection solution was added to the SH-SY5Y cells and the cells incubated in a 37 ° C. incubator under 5% carbon dioxide for approximately 6 to 18 hours. Transfection media is replaced with 3 mL of fresh complete, supplemented DMEM and cells are incubated in a 37 ° C. incubator under 5% carbon dioxide for 48 hours. Both media and cells are collected for expression analysis of the BoNT/E-V5-His peptide. Media is harvested by transferring the media to 15 mL snap-cap tubes and centrifuging tubes at 500×g for 5 minutes to remove debris. Cells are harvested by rinsing cells once with 3.0 mL of 100 mM phosphate-buffered saline, pH 7.4 and lysing cells with a buffer containing 62.6 mM 2-amino-2-hydroxymethyl -1,3-propanediol hydrochloric acid (Tris-HCl), pH 6.8 and 2% sodium lauryl sulfate (SDS). Both media and cell samples are added to 2×LDS Sample Buffer (Invitrogen, Inc, Carlsbad, Calif.) and expression is measured by Western blot analysis (as described in Example 12) using either anti-BoNT/E, anti-V5 or anti-His antibodies in order to identify pcDNA™6 constructs expressing increased amounts of BoNT/E-V5-His produced from SEQ ID NO: 97 relative to constructs expressing BoNT/E-V5-His from the SEQ ID NO: 3control.

To generate a stably-integrated cell line expressing BoNT/E-V5-His, approximately $1.5\times10^5$ SH-SY5Y cells are plated in a 35 mm tissue culture dish containing 3 mL of complete DMEM, supplemented with 10% FBS, 1× penicillin/streptomycin solution (Invitrogen, Inc, Carlsbad, Calif.) and 1× MEM non-essential amino acids solution (Invitrogen, Inc, Carlsbad, Calif.), and grown in a 37 ° C. incubator under 5% carbon dioxide until cells reach a density of about $5\times10^5$ cells/ml (6-16 hours). A 500 μL transfection solution is prepared by adding 250 μL of OPTI-MEM Reduced Serum Medium containing 15 μL of LIPOFECTAMINE 2000, a cationic liposome based reagent, (Invitrogen, Carlsbad, Calif.) incubated at room temperature for 5 minutes to 250 μL of OPTI-MEM Reduced Serum Medium containing 5 μg of a pcDNA™6/BoNT/E-V5-His. This transfection was incubated at room temperature for approximately 20 minutes. The complete, supplemented DMEM media was replaced with 2 mL of OPTI-MEM Reduced Serum Medium and the 500 μL transfection solution was added to the SH-SY5Y cells and the cells incubated in a 37 ° C. incubator under 5% carbon dioxide for approximately 6 to 18 hours. Transfection media is replaced with 3 mL of fresh complete, supplemented DMEM and cells are incubated in a 37 ° C. incubator under 5% carbon dioxide for approximately 48hours. Media is replaced with 3 mL of fresh complete DMEM, containing approximately 5μg/mL of blasticidin, 10% FBS, 1× penicillin/streptomycin solution (Invitrogen, Inc, Carlsbad, Calif.) and 1× MEM non-essential amino acids solution (Invitrogen, Inc, Carlsbad, Calif.). Cells are incubated in a 37 ° C. incubator under 5% carbon dioxide for approximately 3-4 weeks, with old media being replaced with fresh blasticidin selective, complete, supplemented DMEM every 4 to 5 days. Once blasticidin-resistant colonies are established, resistant clones are replated to new 35 mm culture plates containing fresh complete DMEM, supplemented with approximately 5 μg/mL of blasticidin, 10% FBS, 1× penicillin/streptomycin solution (Invitrogen, Inc, Carlsbad, Calif.) and 1× MEM non-essential amino acids solution (Invitrogen, Inc, Carlsbad, Calif.), until these cells reach a density of 6 to $20\times10^5$ cells/mL. To test for expression of BoNT/E-V5-His from SH-SY5Y cell lines that have stably-integrated a pcDNA™6/BoNT/E-V5-His, approximately $1.5\times10^5$ SH-SY5Y cells from each cell line are plated in a 35 mm tissue culture dish containing 3 mL of blasticidin selective, complete, supplemented DMEM and grown in a 37 ° C. incubator under 5% carbon dioxide until cells reach a density of about $5\times10^5$ cells/m1 (6-16 hours). Media is replaced with 3 mL of fresh blasticidin selective, complete, supplemented DMEM and cells are incubated in a 37 ° C. incubator under 5% carbon dioxide for 48 hours. Both media and cells are collected for expression analysis of BoNT/E-V5-His. Media is harvested by transferring the media to 15 mL snap-cap tubes and centrifuging tubes at 500× g for 5minutes to remove debris. Cells are harvest by rinsing cells once with 3.0 mL of 100 mM phosphate-buffered saline, pH 7.4 and lysing cells with a buffer containing 62.6 mM 2-amino -2-hydroxymethyl-1,3-propanediol hydrochloric acid (Tris-HCl), pH 6.8 and 2% sodium lauryl sulfate (SDS). Both media and cell samples are added to 2× LDS Sample Buffer (Invitrogen, Inc, Carlsbad, Calif.) and expression is measured by Western blot analysis (as described in Example 12) using either anti-BoNT/E, anti-V5 or anti-His antibodies in order to identify SH-SY5Y cell lines expressing increased amounts of BoNT/E-V5-His produced from SEQ ID NO: 97 relative to cell lines expressing BoNT/E-V 5-His from the SEQ ID NO: 3 control. The established SH-SY5Y cell line showing the highest expression level of BoNT/E-V5-His relative to the SEQ ID NO: 3 control is selected for large-scale expression using 3 L flasks. Procedures for large-scale expression are as outlined above except the starting volume is approximately 800-1000 mL of complete DMEM and concentrations of all reagents are proportionally increased for this volume. For greater details on all procedures described in this example, see pcDNA™6/V5-His A, B, and C, version C, 28-0183 (Invitrogen, Inc, Carlsbad, Calif.).

Example 23

Construction and Expression of pIVEX2.3d/BoNT/E-His

Figure 16:
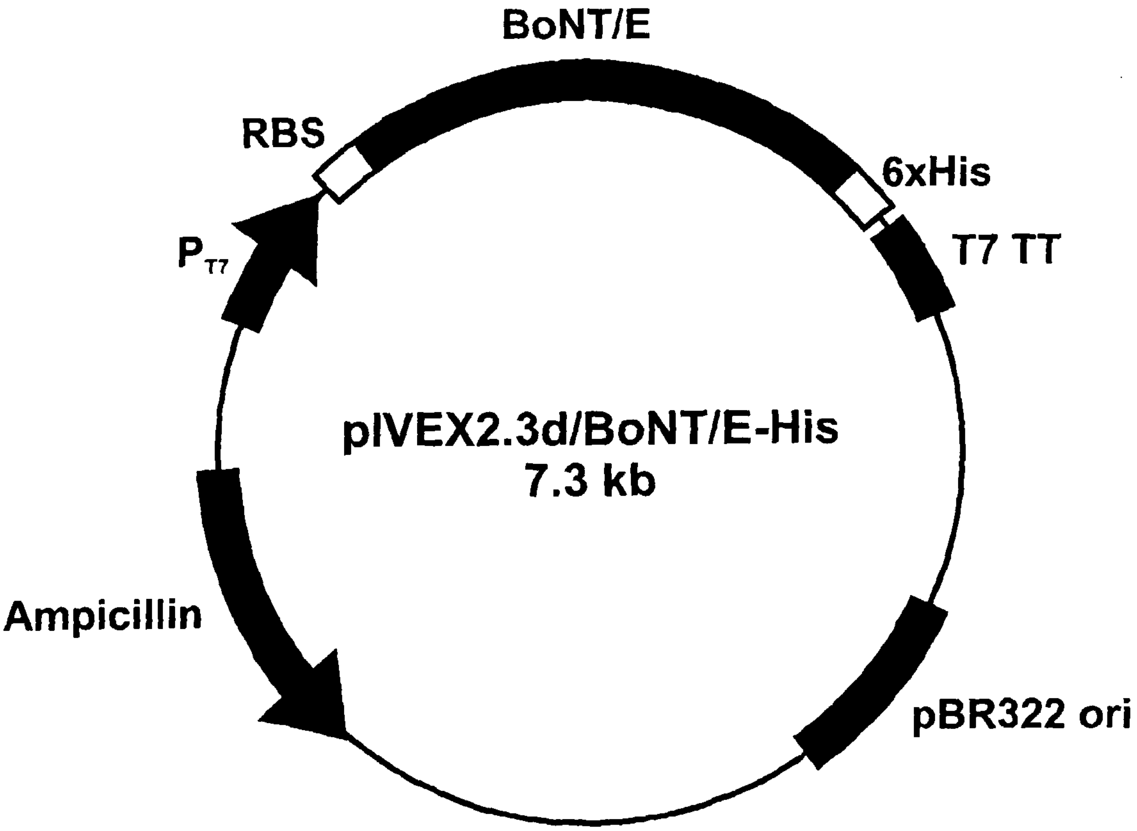
FIG. 16 shows a plasmid map of cell-free expression construct pIVEX2.3d/BoNT/E-His comprising a modified open reading frame encoding an active BoNT/E operably-linked to a carboxy-terminal polyhistidine binding peptide. Abbreviations are as follows: $P_{T7}$, a bacteriophage T7 promoter region; RBS, a ribosomal binding site region; BoNT/E, a modified open reading frame of SEQ ID NO: 4 encoding an active BoNT/E; 6×His, a region encoding a polyhistidine binding peptide sequence; T7 TT, a bacteriophage T7 transcription termination region; pUC ori, a pUC origin of plasmid replication region; Ampicillin, a region encoding a β-lactamase peptide that confers Ampicillin resistance.

Restriction endonuclease sites suitable for cloning an operably linked nucleic acid molecule into a pIVEX2.3d vector (Roche Applied Science, Indianapolis, Ind.) are incorporated into the 5'- and 3' ends of modified open reading frame SEQ ID NO: 4. This nucleic acid molecule is synthesized and a pUCBHB1/BoNT/E construct obtained as described in Example 3. This construct is digested with restriction enzymes that 1) excise the insert containing the open reading frame of SEQ ID NO: 4 encoding an active BoNT/E; and 2) enable this insert to be operably-linked to a pIVEX2.3d vector. This insert is subcloned using a T4 DNA ligase procedure into a pIVEX2.3d vector that is digested with appropriate restriction endonucleases to yield pIVEX2.3d/BoNT/E-His (FIG. 16). The ligation mixture is transformed into chemically competent *E. coli* DH5α cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the insert. This cloning strategy yields a prokaryotic expression construct encoding an active BoNT/E operably linked to a carboxy-terminal polyhistidine binding peptide. A similar cloning strategy is used to make a pIVEX2.3d construct containing the unmodified open reading frame of SEQ ID NO: 3 used as a control for expression levels, as well as, to produce pIVEX2.3d expression constructs in which any one of the modified open reading frames of SEQ ID NO: 5 through SEQ ID NO: 34 is operably linked to a pIVEX2.3d vector.

The RTS100 *E. coli* HY Kit (Roche Applied Science, Indianapolis, Ind.) is used to express an active BoNT/E using a cell-free expression system. A 50 μl reaction mixture consisting of 12 μl *E. coli* lysate, 10 μl reaction mix, 12 μl amino acids, 1 μl methionine, 5 μl reconstitution buffer and 0.5 μg of pIVEX2.3d/BoNT/E-His is incubated in a 30° C. thermomixer for 4-6 hours. A 5 μl sample from this reaction mixture is added to 2×LDS Sample Buffer (Invitrogen, Inc, Carlsbad, Calif.) and expression is measured by Western blot analysis (as described in Example 12) using either anti-BoNT/E or anti-His antibodies in order to identify pIVEX2.3d constructs expressing increased amounts of BoNT/E-His produced from SEQ ID NO: 4 relative to constructs expressing BoNT/E-His from SEQ ID NO: 3. Procedures for large-scale expression are as outlined above except the RTS 9000 *E. coli* HY Kit (Roche Applied Science, Indianapolis, Ind.) is used. For greater details on all procedures described in this example, see RTS100 *E. coli* HY Kit, In vitro protein synthesis system based on *E. coli* lysate, Instruction Manual, version 3, October 2003 (Roche Applied Science, Indianapolis, Ind.) and Rapid Translation System RTS 9000 *E. coli* HY Kit, In vitro protein synthesis system based on an enhanced *E. coli* lysate, Instruction Manual, version 3, November 2001 (Roche Applied Science, Indianapolis, Ind.).

Although aspects of the present invention have been described with reference to the disclosed embodiments, one skilled in the art will readily appreciate that the specific experiments disclosed are only illustrative of these aspects and in no way limit the present invention. Various modifications can be made without departing from the spirit of the present invention.

What is claimed:

1. A nucleic acid molecule comprising a modified open reading frame encoding an active BoNT/E wherein the modification comprises nucleotide changes that alter at least 500 synonymous codons to those preferred by an *Escherichia coli* cell as compared to an unmodified open reading frame encoding the same active BoNT/E;

wherein the active BoNT/E executes the overall cellular mechanism whereby the active BoNT/E enters a neuron and inhibit neurotransmitter release and encompasses the binding of the active BoNT/E to a low or high affinity receptor complex, the internalization of the active BoNT/E/receptor complex, the translocation of the active BoNT/E light chain into the cytoplasm and the enzymatic modification of the active BoNT/E substrate; and wherein the modified open reading frame comprises SEQ ID NO: 4.

2. The molecule according to claim 1, wherein the molecule is an expression construct.

3. An *Escherichia coli* cell comprising an expression construct, wherein the expression construct comprises the open reading frame of claim 1.

4. The cell according to claim 3, wherein the expression construct is transiently contained in the *Escherichia coli* cell.

5. The cell according to claim 3, wherein the expression construct is stably contained in the *Escherichia coli* cell.

* * * * *

UNITED STATES PATENT AND TRADEMARK OFFICE

CERTIFICATE OF CORRECTION

PATENT NO. : 7,825,233 B2
APPLICATION NO. : 11/568834
DATED : November 2, 2010
INVENTOR(S) : Lance E. Steward et al.

It is certified that error appears in the above-identified patent and that said Letters Patent is hereby corrected as shown below:

Title page, item (56), under "Other Publications", delete "Microbilogy" and insert -- Microbiology --, therefor.

Title page, item (56), under "Other Publications", delete "Yarowia" and insert -- Yarrowia --, therefor.

In column 1, line 12, delete "GeneBank" and insert -- GenBank --, therefor.

In column 3, line 20, delete "vescle" and insert -- vesicle --, therefor.

In column 3, line 20, delete "vescicle-" and insert -- vesicle --, therefor.

In column 3, line 21, delete "vescicle" and insert -- vesicle --, therefor.

In column 3, line 43, delete "vescle" and insert -- vesicle --, therefor.

In column 4, line 10, delete "lac1," and insert -- lacl, --, therefor.

In column 5, line 44, delete "carcoxy" and insert -- carboxy --, therefor.

In column 6, line 17, delete "pcDNA T6" and insert -- pcDNA™T6 --, therefor.

In column 9, line 23, after "the" delete "the".

In column 17, line 17, delete "hemagluttinin" and insert -- hemagglutinin --, therefor.

In column 18, line 27, delete "E43" and insert -- e43 --, therefor.

In column 18, line 33, delete "U.S. A." and insert -- U.S.A. --, therefor.

In column 19, line 12, delete "elctrophoresis." and insert -- electrophoresis. --, therefor.

In column 19, line 21, delete "Boiling," and insert -- Bolling, --, therefor.

Signed and Sealed this
Twenty-sixth Day of April, 2011

David J. Kappos

David J. Kappos
*Director of the United States Patent and Trademark Office*

In column 20, line 19, delete "BONT" and insert -- BoNT --, therefor.

In column 20, line 38, delete "HC($H_N$)" and insert -- HC ($H_N$) --, therefor.

In column 20, line 55, delete "Hc" and insert -- $H_C$ --, therefor.

In column 21, line 33, delete "11 (9)" and insert -- 11(9) --, therefor.

In column 22, line 33, delete "U.S. A." and insert -- U.S.A. --, therefor.

In column 22, line 60, delete "covalant" and insert -- covalent --, therefor.

In column 25, line 38, delete "diethyl-laminoethyl" and insert -- diethyl-aminoethyl --, therefor.

In column 25, line 41, delete "tranfection," and insert -- transfection, --, therefor.

In column 25, line 65-66, delete "lichenifonnis," and insert -- licheniformis, --, therefor.

In column 29, line 46, delete "G.gallus" and insert -- G. gallus --, therefor.

In column 30, line 4, delete "2cell" and insert -- 2 cell --, therefor.

In column 35, line 19, delete "lystae," and insert -- lysate, --, therefor.

In column 37, line 22, delete "100-told" and insert -- 100-fold --, therefor.

In column 45, line 45, delete "lactisand" and insert -- lactis and --, therefor.

In column 45, line 45-46, delete "Meningirulls;" and insert -- meningirulls; --, therefor.

In column 45, line 49, delete "cerevisiaeand" and insert -- cerevisiae and --, therefor.

In column 46, line 34, delete "16. 1-16. 62" and insert -- 16.1-16.62 --, therefor.

In column 46, line 62, delete "Calif.);-" and insert -- Calif.); --, therefor.

In column 47, line 10, delete "71 (1)" and insert -- 71(1) --, therefor.

In column 47, line 50, delete "U.S. A." and insert -- U.S.A. --, therefor.

In column 48, line 6, delete "Adenovirual" and insert -- Adenoviral --, therefor.

In column 49, line 15, delete "Clonetech," and insert -- Clontech, --, therefor.

In column 49, line 17, delete "Clonetech," and insert -- Clontech, --, therefor.

In column 58, line 56, delete "Meningirulls;" and insert -- meningirulls; --, therefor.

In column 59, line 46, delete "16. 1-16. 62" and insert -- 16.1-16.62 --, therefor.

In column 60, line 8, delete "inc.," and insert -- Inc., --, therefor.

In column 60, line 21, delete "(Ambion," and insert -- (Ambion, Inc., --, therefor.

In column 60, line 26, delete "inc.," and insert -- Inc., --, therefor.

In column 60, line 45, Delete "Calif,)" and insert -- Calif.) --, therefor.

In column 61, line 2, delete "Pharmigen," and insert -- Pharmingen, --, therefor.

In column 61, line 6, delete "Calif. A) and INSECTDIRECTTM" and insert -- Calif.) and INSECTDIRECT™ --, therefor.

In column 71, line 55-58, delete "BoNT/E from the modified open reading frame is at least ten-fold higher as compared to the expression level of the same active BoNT/E from the unmodified open reading frame." and insert the same on Col. 71, Line 54 as a continuation of the paragraph.

In column 80, line 35, delete "Hinlll" and insert -- Hindlll --, therefor.

In column 81, line 63, delete "HCI)," and insert -- HCl), --, therefor.

In column 81, line 66, delete "monolaureate" and insert -- monolaurate --, therefor.

In column 82, line 3, delete "monolaureate" and insert -- monolaurate --, therefor.

In column 82, line 47, delete "(i. e.," and insert -- (i.e., --, therefor.

In column 84, line 45, delete "L7731/" and insert -- L773I/ --, therefor.

In column 84, line 60, delete "F963UE" and insert -- F963L/E --, therefor.

In column 85, line 5, delete "E2130" and insert -- E213Q --, therefor.

In column 86, line 11, delete "$Co^{2+}$affinity" and insert -- $Co^{2+}$ affinity --, therefor.

In column 87, line 9, delete "2×LDS" and insert -- 2× LDS --, therefor.

In column 87, line 38, delete "HCI)" and insert -- HCl) --, therefor.

In column 87, line 40, delete "monolaureate" and insert -- monolaurate --, therefor.

In column 87, line 44, delete "monolaureate" and insert -- monolaurate --, therefor.

In column 88, line 66, delete "monolaureate" and insert -- monolaurate --, therefor.

In column 90, line 24, delete "(E2130)" and insert -- (E213Q) --, therefor.

In column 91, line 50, delete "0213E" and insert-- Q213E --, therefor.

In column 92, line 32, delete "monolaureate" and insert -- monolaurate --, therefor.

In column 94, line 38, delete “2×LDS” and insert -- 2× LDS --, therefor.

In column 94, line 66, delete “HCI)” and insert -- HCl) --, therefor.

In column 95, line 1, delete “monolaureate” and insert -- monolaurate --, therefor.

In column 2, line 5, delete “monolaureate” and insert -- monolaurate --, therefor.

In column 96, line 35, delete “DH5a” and insert -- DH5α --, therefor.

In column 97, line 45, delete “DH5a” and insert -- DH5α --, therefor.

In column 97, line 67, delete “(i. e.,” and insert -- (i.e., --, therefor.

In column 98, line 2, delete “$Mut^{s}$” and insert -- $Mut^{S}$ --, therefor.

In column 98, line 30, delete “2×LDS” and insert -- 2× LDS --, therefor.

In column 98, line 37, delete “$Mut^{s}$” and insert -- $Mut^{S}$ --, therefor.

In column 99, line 2, delete “DH5a” and insert -- DH5α --, therefor.

In column 99, line 54, delete “2×LDS” and insert -- 2× LDS --, therefor.

In column 99, line 62, delete “Muts” and insert -- $Mut^{S}$ --, therefor.

In column 101, line 9, delete “2×LDS” and insert -- 2× LDS --, therefor.

In column 101, line 49, delete “DH5a” and insert-- DH5α --, therefor.

In column 102, line 3, delete “Efficiency” and insert -- Efficiency® --, therefor.

In column 102, line 28, delete “trasfection” and insert -- transfection --, therefor.

In column 102, line 66, delete “2×LDS” and insert -- 2× LDS --, therefor.

In column 103, line 31, delete “DH5a” and insert -- DH5α --, therefor.

In column 103, line 62-63, delete “reagent,containing” and insert -- reagent, containing --, therefor.

In column 2, line 64, delete “DH5a” and insert -- DH5α --, therefor.

In column 106, line 21, delete “2×HEPES” and insert -- 2× HEPES --, therefor.

In column 106, line 35, delete “2×LDS” and insert -- 2× LDS --, therefor.

In column 106, line 49, delete “2×HEPES” and insert -- 2× HEPES --, therefor.

In column 107, line 14, delete “2×LDS” and insert -- 2× LDS --, therefor.

In column 107, line 41, delete “(Obiogene,” and insert -- (Qbiogene, --, therefor.

In column 107, line 53, delete "DH5a" and insert -- DH5α --, therefor.

In column 108, line 64, delete "DH5a" and insert -- DH5α --, therefor.

In column 109, line 19, delete "1×penicillin" and insert -- 1× penicillin --, therefor.

In column 109, line 20, delete "1×MEM" and insert -- 1× MEM --, therefor.

In column 109, line 46, delete "HCI)," and insert -- HCl), --, therefor.

In column 109, line 48, delete "2×LDS" and insert -- 2× LDS --, therefor.

In column 109, line 55, delete "3control." and insert -- 3 control. --, therefor.

In column 110, line 13, delete "48hours." and insert -- 48 hours. --, therefor.

In column 110, line 37, delete "cells/m1" and insert -- cells/ml --, therefor.

In column 110, line 45, delete "5minutes" and insert -- 5 minutes --, therefor.

In column 110, line 48, delete "amino -2" and insert -- amino-2 --, therefor.

In column 110, line 49, delete "HCI)," and insert -- HCl), --, therefor.

In column 2, line 4, delete "RTS100" and insert -- RTS 100 --, therefor.

In column 112, line 12, delete "2×LDS" and insert -- 2× LDS --, therefor.

In column 112, line 22, delete "RTS100" and insert -- RTS 100 --, therefor.

SEQUENCE LISTING

```
<160> NUMBER OF SEQ ID NOS: 140

<210> SEQ ID NO 1
<211> LENGTH: 1252
<212> TYPE: PRT
<213> ORGANISM: Clostridium botulinum
<220> FEATURE:
<221> NAME/KEY: DOMAIN
<222> LOCATION: (1)...(422)
<223> OTHER INFORMATION: Light Chain; enzymatic domain; therapeutic
      domain; catalytic domain (active)
<221> NAME/KEY: DOMAIN
<222> LOCATION: (423)...(1252)
<223> OTHER INFORMATION: Heavy chain
<221> NAME/KEY: DOMAIN
<222> LOCATION: (423)...(834)
<223> OTHER INFORMATION: amino terminal half of heavy chain;
      translocation domain
<221> NAME/KEY: DOMAIN
<222> LOCATION: (835)...(1252)
<223> OTHER INFORMATION: Carboxyl terminal half of heavy chain;
      targeting domain; binding domain; acceptor binding domain

<400> SEQUENCE: 1

Met Pro Lys Ile Asn Ser Phe Asn Tyr Asn Asp Pro Val Asn Asp Arg
 1              5                   10                  15

Thr Ile Leu Tyr Ile Lys Pro Gly Gly Cys Gln Glu Phe Tyr Lys Ser
            20                  25                  30
```

-continued

```
Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
```

-continued

```
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Leu Ile Asn Glu Val Lys Ile Asn Lys Leu Arg Glu
    770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880
```

-continued

```
Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
    930                 935                 940

Asp Asn Asn Ser Gly Trp Lys Val Ser Leu Asn His Asn Glu Ile Ile
945                 950                 955                 960

Trp Thr Leu Gln Asp Asn Ala Gly Ile Asn Gln Lys Leu Ala Phe Asn
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu Gly Asp Ser Lys Leu Tyr Ile Asn
        995                 1000                1005

Gly Asn Leu Ile Asp Gln Lys Ser Ile Leu Asn Leu Gly Asn Ile His
    1010                1015                1020

Val Ser Asp Asn Ile Leu Phe Lys Ile Val Asn Cys Ser Tyr Thr Arg
1025                1030                1035                1040

Tyr Ile Gly Ile Arg Tyr Phe Asn Ile Phe Asp Lys Glu Leu Asp Glu
                1045                1050                1055

Thr Glu Ile Gln Thr Leu Tyr Ser Asn Glu Pro Asn Thr Asn Ile Leu
            1060                1065                1070

Lys Asp Phe Trp Gly Asn Tyr Leu Leu Tyr Asp Lys Glu Tyr Tyr Leu
        1075                1080                1085

Leu Asn Val Leu Lys Pro Asn Asn Phe Ile Asp Arg Arg Lys Asp Ser
    1090                1095                1100

Thr Leu Ser Ile Asn Asn Ile Arg Ser Thr Ile Leu Leu Ala Asn Arg
1105                1110                1115                1120

Leu Tyr Ser Gly Ile Lys Val Lys Ile Gln Arg Val Asn Asn Ser Ser
                1125                1130                1135

Thr Asn Asp Asn Leu Val Arg Lys Asn Asp Gln Val Tyr Ile Asn Phe
            1140                1145                1150

Val Ala Ser Lys Thr His Leu Phe Pro Leu Tyr Ala Asp Thr Ala Thr
        1155                1160                1165

Thr Asn Lys Glu Lys Thr Ile Lys Ile Ser Ser Ser Gly Asn Arg Phe
    1170                1175                1180

Asn Gln Val Val Val Met Asn Ser Val Gly Asn Asn Cys Thr Met Asn
1185                1190                1195                1200

Phe Lys Asn Asn Asn Gly Asn Asn Ile Gly Leu Leu Gly Phe Lys Ala
                1205                1210                1215

Asp Thr Val Val Ala Ser Thr Trp Tyr Tyr Thr His Met Arg Asp His
            1220                1225                1230

Thr Asn Ser Asn Gly Cys Phe Trp Asn Phe Ile Ser Glu Glu His Gly
        1235                1240                1245

Trp Gln Glu Lys
    1250


<210> SEQ ID NO 2
<211> LENGTH: 1251
<212> TYPE: PRT
<213> ORGANISM: Clostridium botulinum
<220> FEATURE:
```

-continued

<221> NAME/KEY: DOMAIN
<222> LOCATION: (1)...(422)
<223> OTHER INFORMATION: Light Chain; enzymatic domain; therapeutic domain; catalytic domain (inactive)
<221> NAME/KEY: DOMAIN
<222> LOCATION: (423)...(1251)
<223> OTHER INFORMATION: Heavy chain
<221> NAME/KEY: DOMAIN
<222> LOCATION: (423)...(834)
<223> OTHER INFORMATION: Amino terminal half of heavy chain; translocation domain
<221> NAME/KEY: DOMAIN
<222> LOCATION: (835)...(1251)
<223> OTHER INFORMATION: Carboxyl terminal half of heavy chain; targeting domain; binding domain; acceptor binding domain

<400> SEQUENCE: 2

```
Met Pro Lys Ile Asn Ser Phe Asn Tyr Asn Asp Pro Val Asn Asp Arg
 1               5                  10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Arg Phe Gly Ser Ile Ala Ile Val Thr Phe Ser Pro Glu Tyr Ser Phe
            180                 185                 190

Arg Phe Asn Asp Asn Cys Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
```

-continued

```
                325                 330                 335

Phe Asp Leu Arg Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750
```

-continued

```
Ile Ala Met Asn Asn Ile Asp Arg Phe Leu Thr Glu Ser Ser Ile Ser
        755                 760                 765

Tyr Leu Met Lys Ile Ile Asn Glu Val Lys Ile Asn Lys Leu Arg Glu
    770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
    930                 935                 940

Asp Asn Asn Ser Gly Trp Lys Val Ser Leu Asn His Asn Glu Ile Ile
945                 950                 955                 960

Trp Thr Phe Glu Asp Asn Arg Gly Ile Asn Gln Lys Leu Ala Phe Asn
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu Gly Asp Ser Lys Leu Tyr Ile Asn
        995                 1000                1005

Gly Asn Leu Ile Asp Gln Lys Ser Ile Leu Asn Leu Gly Asn Ile His
    1010                1015                1020

Val Ser Asp Asn Ile Leu Phe Lys Ile Val Asn Cys Ser Tyr Thr Arg
1025                1030                1035                1040

Tyr Ile Gly Ile Arg Tyr Phe Asn Ile Phe Asp Lys Glu Leu Asp Glu
                1045                1050                1055

Thr Glu Ile Gln Thr Leu Tyr Ser Asn Glu Pro Asn Thr Asn Ile Leu
            1060                1065                1070

Lys Asp Phe Trp Gly Asn Tyr Leu Leu Tyr Asp Lys Glu Tyr Tyr Leu
        1075                1080                1085

Leu Asn Val Leu Lys Pro Asn Asn Phe Ile Asp Arg Arg Lys Asp Ser
    1090                1095                1100

Thr Leu Ser Ile Asn Asn Ile Arg Ser Thr Ile Leu Leu Ala Asn Arg
1105                1110                1115                1120

Leu Tyr Ser Gly Ile Lys Val Lys Ile Gln Arg Val Asn Asn Ser Ser
                1125                1130                1135

Thr Asn Asp Asn Leu Val Arg Lys Asn Asp Gln Val Tyr Ile Asn Phe
            1140                1145                1150

Val Ala Ser Lys Thr His Leu Phe Pro Leu Tyr Ala Asp Thr Ala Thr
        1155                1160                1165
```

-continued

```
Thr Asn Lys Glu Lys Thr Ile Lys Ile Ser Ser Ser Gly Asn Arg Phe
    1170                1175                1180

Asn Gln Val Val Val Met Asn Ser Val Gly Asn Cys Thr Met Asn Phe
1185                1190                1195                1200

Lys Asn Asn Asn Gly Asn Asn Ile Gly Leu Leu Gly Phe Lys Ala Asp
                1205                1210                1215

Thr Val Val Ala Ser Thr Trp Tyr Tyr Thr His Met Arg Asp His Thr
            1220                1225                1230

Asn Ser Asn Gly Cys Phe Trp Asn Phe Ile Ser Glu Glu His Gly Trp
        1235                1240                1245

Gln Glu Lys
    1250
```

```
<210> SEQ ID NO 3
<211> LENGTH: 3759
<212> TYPE: DNA
<213> ORGANISM: Clostridium botulinum
<220> FEATURE:
<221> NAME/KEY: mat_peptide
<222> LOCATION: (1)...(3756)
<223> OTHER INFORMATION: BoNT/E, unmodified

<400> SEQUENCE: 3

atgccaaaaa ttaatagttt taattataat gatcctgtta atgatagaac aattttatat     60

attaaaccag gcggttgtca agaattttat aaatcattta atattatgaa aaatatttgg    120

ataattccag agagaaatgt aattggtaca accccccaag attttcatcc gcctacttca    180

ttaaaaaatg gagatagtag ttattatgac cctaattatt tacaaagtga tgaagaaaag    240

gatagatttt taaaaatagt cacaaaaata tttaatagaa taaataataa tctttcagga    300

gggattttat tagaagaact gtcaaaagct aatccatatt tagggaatga taatactcca    360

gataatcaat tccatattgg tgatgcatca gcagttgaga ttaaattctc aaatggtagc    420

caagacatac tattacctaa tgttattata atgggagcag agcctgattt atttgaaact    480

aacagttcca atatttctct aagaaataat tatatgccaa gcaatcacgg ttttggatca    540

atagctatag taacattctc acctgaatat tcttttagat ttaatgataa tagtatgaat    600

gaatttattc aagatcctgc tcttacatta atgcatgaat taatacattc attacatgga    660

ctatatgggg ctaaagggat tactacaaag tatactataa cacaaaaaca aaatccccta    720

ataacaaata taagaggtac aaatattgaa gaattcttaa cttttggagg tactgattta    780

aacattatta ctagtgctca gtccaatgat atctatacta atcttctagc tgattataaa    840

aaaatagcgt ctaaacttag caaagtacaa gtatctaatc cactacttaa tccttataaa    900

gatgtttttg aagcaaagta tggattagat aaagatgcta gcggaattta ttcggtaaat    960

ataaacaaat ttaatgatat ttttaaaaaa ttatacagct ttacggaatt tgatttagca   1020

actaaatttc aagttaaatg taggcaaact tatattggac agtataaata cttcaaactt   1080

tcaaacttgt taaatgattc tatttataat atatcagaag gctataatat aaataattta   1140

aaggtaaatt ttagaggaca gaatgcaaat ttaaatccta gaattattac accaattaca   1200

ggtagaggac tagtaaaaaa aatcattaga ttttgtaaaa atattgtttc tgtaaaaggc   1260

ataaggaaat caatatgtat cgaaataaat aatggtgagt tattttttgt ggcttccgag   1320

aatagttata atgatgataa tataaatact cctaaagaaa ttgacgatac agtaacttca   1380

aataataatt atgaaaatga tttagatcag gttattttaa attttaatag tgaatcagca   1440

cctggacttt cagatgaaaa attaaattta actatccaaa atgatgctta tataccaaaa   1500
```

-continued

```
tatgattcta atggaacaag tgatatagaa caacatgatg ttaatgaact taatgtattt   1560
ttctatttag atgcacagaa agtgcccgaa ggtgaaaata atgtcaatct cacctcttca   1620
attgatacag cattattaga acaacctaaa atatatacat ttttttcatc agaatttatt   1680
aataatgtca ataaacctgt gcaagcagca ttatttgtaa gctggataca acaagtgtta   1740
gtagatttta ctactgaagc taaccaaaaa agtactgttg ataaaattgc agatatttct   1800
atagttgttc catatatagg tcttgcttta aatataggaa atgaagcaca aaaaggaaat   1860
tttaaagatg cacttgaatt attaggagca ggtattttat tagaatttga acccgagctt   1920
ttaattccta caattttagt attcacgata aaatcttttt taggttcatc tgataataaa   1980
aataaagtta ttaaagcaat aaataatgca ttgaaagaaa gagatgaaaa atggaaagaa   2040
gtatatagtt ttatagtatc gaattggatg actaaaatta atacacaatt taataaaaga   2100
aaagaacaaa tgtatcaagc tttacaaaat caagtaaatg caattaaaac aataatagaa   2160
tctaagtata atagttatac tttagaggaa aaaaatgagc ttacaaataa atatgatatt   2220
aagcaaatag aaaatgaact taatcaaaag gtttctatag caatgaataa tatagacagg   2280
ttcttaactg aaagttctat atcctattta atgaaattaa taaatgaagt aaaaattaat   2340
aaattaagag aatatgatga gaatgtcaaa acgtatttat tgaattatat tatacaacat   2400
ggatcaatct tgggagagag tcagcaagaa ctaaattcta tggtaactga taccctaaat   2460
aatagtattc cttttaagct ttcttcttat acagatgata aaattttaat ttcatatttt   2520
aataaattct ttaagagaat taaaagtagt tcagttttaa atatgagata taaaaatgat   2580
aaatacgtag atacttcagg atatgattca aatataaata ttaatggaga tgtatataaa   2640
tatccaacta ataaaaatca atttggaata tataatgata aacttagtga agttaatata   2700
tctcaaaatg attacattat atatgataat aaatataaaa attttagtat tagtttttgg   2760
gtaagaattc ctaactatga taataagata gtaaatgtta ataatgaata cactataata   2820
aattgtatga gagataataa ttcaggatgg aaagtatctc ttaatcataa tgaaataatt   2880
tggacattgc aagataatgc aggaattaat caaaaattag catttaacta tggtaacgca   2940
aatggtattt ctgattatat aaataagtgg atttttgtaa ctataactaa tgatagatta   3000
ggagattcta aactttatat taatggaaat ttaatagatc aaaaatcaat tttaaattta   3060
ggtaatattc atgttagtga caatatatta tttaaaatag ttaattgtag ttatacaaga   3120
tatattggta ttagatattt taatattttt gataaagaat tagatgaaac agaaattcaa   3180
actttatata gcaatgaacc taatacaaat attttgaagg atttttgggg aaattatttg   3240
ctttatgaca aagaatacta tttattaaat gtgttaaaac caaataactt tattgatagg   3300
agaaaagatt ctactttaag cattaataat ataagaagca ctattctttt agctaataga   3360
ttatatagtg gaataaaagt taaaatacaa agagttaata atagtagtac taacgataat   3420
cttgttagaa agaatgatca ggtatatatt aattttgtag ccagcaaaac tcacttattt   3480
ccattatatg ctgatacagc taccacaaat aaagagaaaa caataaaaat atcatcatct   3540
ggcaatagat ttaatcaagt agtagttatg aattcagtag gaaataattg tacaatgaat   3600
tttaaaaata ataatggaaa taatattggg ttgttaggtt tcaaggcaga tactgtagtt   3660
gctagtactt ggtattatac acatatgaga gatcatacaa acagcaatgg atgtttttgg   3720
aactttattt ctgaagaaca tggatggcaa gaaaaataa                          3759
```

<210> SEQ ID NO 4

-continued

<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, E. coli-modified 1

<400> SEQUENCE: 4
atgcctaaaa tcaattcgtt caactataat gacccggtta acgatcgcac gatcctgtat 60
atcaagccag gtggatgtca agaattttat aaatcattca acatcatgaa aaatatttgg 120
attatcccgg aacgcaacgt gatcggcacg acgcctcaag attttcaccc gccgacctcc 180
ctgaaaaatg gcgacagttc ctactatgac ccgaattatt tacaatcgga tgaagaaaaa 240
gatcgtttcc tcaagatcgt cacgaaaatt ttcaaccgca tcaataacaa tctgtccggt 300
ggcatcttac ttgaggaatt atctaaagct aatccgtatc tggggaacga taataccccg 360
gataatcagt tccacattgg cgatgcgagc gctgtggaaa ttaaattcag caacggcagt 420
caagatattc ttctcccaaa cgtgattatc atgggggctg aacctgatct tttcgaaact 480
aatagttcca atatttcact gcgcaataat tatatgccgt cgaaccatgg ctttggctca 540
atcgcaattg tgacgttctc acctgaatat agttttcgtt ttaacgacaa cagcatgaat 600
gaatttatcc aagacccggc gctgactttg atgcatgaac tgatccatag cttgcacggc 660
ctgtatggcg ctaaaggcat cactaccaaa tacacgatta cgcaaaaaca aaatccctta 720
atcaccaaca tccgcggcac caacattgaa gaatttctga ccttcggcgg aacggatctg 780
aacatcatta catctgccca aagcaacgac atctatacca atctgttagc agattataag 840
aaaatcgcca gcaaattatc taaagttcag gtcagcaatc cgctgttaaa cccgtataaa 900
gatgtgttcg aagcgaaata cggcttggac aaagacgcta gtggcatcta ttccgtcaat 960
attaataaat ttaacgatat tttcaaaaaa ttatattcct tcaccgaatt tgatttggcc 1020
accaaattcc aggtcaaatg tcgtcaaacc tatattggcc aatacaaata ttttaaactg 1080
agcaacctgc ttaatgattc catctacaat attagtgaag gttacaatat taataacctg 1140
aaagttaact ttcgtgggca aaatgcgaat ctgaaccccc gcatcattac acccatcacg 1200
ggccgtgggt tggtcaaaaa aattattcgc ttttgtaaga atatcgtgag cgtgaagggt 1260
attcgcaaaa gtatctgtat cgaaatcaat aatggcgaac tgtttttcgt cgcatctgaa 1320
aactcgtata acgatgacaa tatcaacaca ccgaaagaaa ttgatgacac tgtcacttct 1380
aacaacaatt acgaaaacga cctggaccag gtgatcctca atttcaatag cgaaagcgca 1440
cccggcctga gcgatgaaaa acttaatctc acgattcaga acgacgccta cattccaaaa 1500
tacgatagta atggtacatc tgatattgaa cagcatgatg tcaacgaatt aaatgttttc 1560
ttttacctcg atgcccagaa agtgccggaa ggtgagaaca acgtaaatct gacctcttcg 1620
attgatacgg cattattaga acagccgaaa atttatactt tcttttcgtc cgaatttatt 1680
aacaatgtta acaaaccggt tcaagcggcg ttattcgttt cctggattca gcaagttctt 1740
gtagatttta caaccgaggc taatcagaag agcacggtgg ataagatcgc cgacatcagc 1800
atcgtcgtgc cctacattgg tttggcatta aacattggta atgaggcgca aaaggggaac 1860
tttaaagacg ccctggaatt attaggagca ggtattctgc tggagttcga acctgagctg 1920
ctgattccga ctattttagt gttcaccatt aaatccttct taggctctag tgacaacaaa 1980
aataaagtga ttaaagcgat caataatgcc cttaaagaac gtgatgagaa atggaaagaa 2040
gtctactcct tcattgtctc aaattggatg acgaaaatca acacgcagtt taataaacgc 2100

-continued aaagaacaga tgtatcaggc gctgcaaaac caggttaatg cgatcaagac aattattgaa 2160
tctaagtaca actcgtacac cctggaggag aaaaatgaac tgactaataa gtacgatatt 2220
aaacaaatcg aaaacgaatt gaatcagaaa gtctccatcg ctatgaacaa tatcgatcgc 2280
tttctgaccg aaagctctat ttcctatttg atgaaactta tcaatgaagt caaaatcaac 2340
aaacttcgcg aatatgatga gaacgtaaaa acgtacctgc tcaattatat tattcaacat 2400
gggtcgattc tgggcgagtc tcaacaagaa ttgaactcga tggtgacgga tactttgaat 2460
aactcgattc cgtttaaatt atcgtcatac accgatgata aaattcttat ctcgtacttc 2520
aacaaattct ttaagcggat caaaagcagc agcgtcctta atatgcgcta taaaaacgat 2580
aagtacgtag atacgtctgg atacgacagt aacattaata ttaatgggga cgtctataaa 2640
tatccgacaa ataaaaacca attcgggatt tataatgata aactttcgga ggtgaacatc 2700
agccagaacg attatattat ttacgataat aaatacaaaa acttcagcat ttctttttgg 2760
gtgcgtatcc caaattacga caacaaaatt gtgaacgtga ataacgaata cacgatcatt 2820
aattgcatgc gcgataacaa ttctggttgg aaagttagcc tgaatcacaa tgagattatc 2880
tggactcttc aggacaatgc tggtatcaac caaaaaattag cgttcaacta cggtaatgcc 2940
aacggtattt ctgactacat caataagtgg atctttgtga ccatcaccaa tgaccgcctc 3000
ggcgatagca agctgtacat taacggtaac ctgatcgacc agaaatctat tctgaacctg 3060
ggtaacattc acgtaagtga caacatcctt tttaaaattg tcaattgctc gtatactcgt 3120
tatatcggca ttcgctattt caatattttc gacaaagaac tggatgagac ggaaatccag 3180
actctgtatt ctaacgaacc gaacaccaac atcctgaagg acttttgggg gaattatctt 3240
ctctacgata aagagtacta ccttcttaac gtgttgaagc cgaacaactt cattgatcgt 3300
cgtaaggata gcaccttgag cattaacaac attcgtagca ccattttact ggcaaaccgc 3360
ctgtacagcg gcattaaagt caaaattcag cgtgtcaata actccagtac gaatgacaat 3420
ctggtgcgga aaaatgacca agtctatatt aactttgtcg caagcaaaac tcacctcttt 3480
ccattatatg cggatacagc taccaccaat aaagaaaaaa ctattaaaat ctcctcttcc 3540
gggaaccgct ttaatcaggt ggtagttatg aactcggtcg gcaacaattg tactatgaat 3600
tttaaaaata ataacggcaa taacatcggc ctgctgggct tcaaagctga tacagttgtg 3660
gccagcacct ggtattacac ccacatgcgt gatcatacca atagtaatgg ctgcttttgg 3720
aattttattt ctgaagagca cggctggcaa gaaaaataa 3759

<210> SEQ ID NO 5
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, E. coli-modified 2

<400> SEQUENCE: 5
atgcccaaaa ttaattcctt taactataat gacccggtaa acgatcggac gattctatac 60
atcaaaccgg gtggctgtca ggaattctat aagtctttta atatcatgaa aaacatctgg 120
attatcccgg aacgaaatgt gattggcact acaccacaag attttcatcc cccaactagc 180
ctgaaaaatg gtgattctag ctattacgat ccgaattatt tacagagtga tgaagagaaa 240
gataggttcc tgaaaatcgt gacgaaaatt ttcaaccgga ttaataacaa tctgagtggc 300

-continued

```
ggtattctgt tagaagagtt aagtaaagcc aatccgtact taggtaatga taatacccca    360

gataatcagt tccatatcgg cgatgcttcg gcggtcgaga ttaaatttag taacggcagc    420

caggatattt tactccccaa cgtaattatc atgggggcag agcctgatct ctttgaaacc    480

aatagttcta acataagcct gcgcaacaat tatatgccct ccaaccacgg cttcggttca    540

attgcgattg ttacgttttc gcctgagtac tcttttaggt tcaacgacaa tagcatgaac    600

gaatttattc aggatccggc cctgaccttg atgcacgaac taatccacag tctccatgga    660

ctgtacggag cgaaaggaat taccacaaag tacaccataa cccagaaaca gaatccgctc    720

ataaccaata ttcgtggcac caacattgaa gagtttctta cgtttggtgg cacagatctt    780

aatattatca cctctgctca gagcaacgat atatatacga acttattggc ggactacaag    840

aaaatcgcat cgaaactttc aaaagttcag gtctccaacc cgctgctcaa tccgtataag    900

gatgtcttcg aagcgaaata tggccttgac aaagatgcgt cgggcatata cagcgtgaat    960

attaacaaat tcaacgatat ctttaaaaag ctgtactctt tcaccgagtt tgatctggcc   1020

acaaaatttc aagtgaaatg tcgccagacg tacattggtc agtacaaata ttttaaactg   1080

tcaaaccttc tgaatgactc catctataat atcagtgaag ggtataatat caataacctg   1140

aaggtaaatt ttcgtggcca aaacgcgaac ttgaacccgc gcatcattac tccgatcacg   1200

gggagaggcc tggtaaaaaa gattatccgc ttctgcaaaa acattgtaag cgtgaaaggt   1260

atccggaaaa gcatttgcat tgaaatcaat aacggggagt tatttttcgt ggcctcagaa   1320

aatagctata acgatgacaa tattaacacc ccaaaagaaa tcgatgacac agtcacgagc   1380

aataacaatt atgaaaatga tctggatcag gtcatcctga atttcaattc tgaaagcgcc   1440

ccaggtttat cagatgaaaa actgaatctg accatacaaa atgatgcgta tattccgaaa   1500

tacgactcaa atggaacctc ggacatcgaa cagcatgacg tgaatgaatt aaacgttttt   1560

ttctacctgg acgcacagaa agttccagaa ggtgaaaata acgtgaatct gactagctct   1620

attgatactg ccttattgga acagcctaaa atttatacat tttctcttc agaatttatc   1680

aacaatgtta acaaaccggt ccaggcggct ctgtttgtca gttggattca gcaagtactg   1740

gttgatttta ccacagaagc taatcaaaag tctactgttg acaaaatcgc ggacatctcg   1800

atagttgtac catacattgg cctcgccctg aatataggca atgaagcaca aaaggggaat   1860

ttcaaagatg cactcgaatt gctgggggcg ggattctgt tggagtttga accggagctt   1920

ctgattccga caatccttgt ttttacgatt aagagttttc tgggaagctc cgacaataaa   1980

aataaagtga ttaaagcgat caacaatgct ctgaaagaac gcgacgaaaa atggaaggaa   2040

gtctattcct tcattgtttc gaactggatg actaaaatta acacacaatt caacaagcgt   2100

aaagaacaaa tgtatcaagc attgcagaat caagttaatg ccatcaaaac cattatcgag   2160

tctaaatata acagttatac cctggaagag aaaaacgagc tgactaataa atatgacatc   2220

aaacagattg agaatgaatt gaaccaaaag gtgtcgattg caatgaacaa tattgaccgt   2280

ttcctgactg agagtagcat ctcttatctg atgaaactga ttaacgaggt taaaatcaac   2340

aagctgcgcg aatatgatga gaatgtcaag acttatctgc taaactacat cattcagcac   2400

ggaagtatac ttggagagag ccagcaagaa ctcaacagta tggttaccga taccctcaac   2460

aattcaattc ctttcaaatt aagctcgtac actgatgaca agattctgat aagctatttt   2520

aataagttct ttaaacgaat caagtcctct tcagttctta atatgcgtta caaaaacgac   2580

aaatacgtgg atacgtcagg ttacgacagc aatatcaaca ttaacgggga tgtttataaa   2640

taccccacga ataagaacca gtttggtata tataatgata agctgtccga agtaaatatc   2700
```

tctcagaacg attatattat atacgacaac aaatacaaaa atttctcgat cagtttctgg 2760
gtcagaattc cgaattatga taacaaaatc gtgaacgtga acaatgaata tacgattata 2820
aattgcatgc gtgacaacaa ttcaggctgg aaagtgtctt tgaatcataa tgaaattata 2880
tggacgttac aggataacgc tggcattaac cagaaattgg cctttaatta tggcaacgct 2940
aacggtatct cagactatat aaataaatgg attttcgtca ccatcaccaa tgatcgcctg 3000
ggtgattcga aactgtatat taacggcaac ttgatcgacc agaaatcgat tcttaactta 3060
ggcaacattc atgtctccga taatatccta tttaagatcg ttaattgctc ctatacccgt 3120
tatattggta tacgctactt caacattttt gacaaggaac tagatgagac cgaaattcag 3180
actctgtata gcaatgagcc taatacaaat atcctgaaag atttttgggg taactacctg 3240
ttgtacgata aagaatacta tctgttaaac gtgttgaaac ctaataactt tattgatcgt 3300
cgcaaagatt cgactctgtc catcaacaat attcgcagta cgatcctgct tgccaatcgt 3360
ctttacagcg gtattaaggt gaagatccag cgtgttaaca atagttccac aaacgacaac 3420
ctcgttcgta agaacgatca ggtctatatt aacttcgtgg catccaaaac acacctgttc 3480
ccgctgtatg cggacacagc cacgaccaac aaagaaaaga ccatcaaaat cagctcttca 3540
ggtaaccggt ttaaccaagt ggtagtgatg aactcagtgg gtaataactg taccatgaat 3600
tttaaaaaca ataacggtaa caatattggg ctgttaggct ttaaagctga taccgtagtg 3660
gcatccacct ggtattatac gcacatgcgc gatcatacga acagcaacgg atgtttttgg 3720
aattttattt ctgaagagca tggctggcaa gaaaaataa 3759

<210> SEQ ID NO 6
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, E. coli-modified 3

<400> SEQUENCE: 6
atgccgaaaa ttaatagctt taattataat gatccggtga atgatcgtac cattctgtat 60
attaaaccgg gcggctgtca ggaattttat aaaagcttta atattatgaa aaatatttgg 120
attattccgg aacgtaatgt gattggcacc accccgcagg attttcatcc gccgaccagc 180
ctgaaaaatg gcgatagcag ctattatgat ccgaattatc tgcagagcga tgaagaaaaa 240
gatcgttttc tgaaaattgt gaccaaaatt tttaatcgta ttaataataa tctgagcggc 300
ggcattctgc tggaagaact gagcaaagcg aatccgtatc tgggcaatga taataccccg 360
gataatcagt ttcatattgg cgatgcgagc gcggtggaaa ttaaatttag caatggcagc 420
caggatattc tgctgccgaa tgtgattatt atgggcgcgg aaccggatct gtttgaaacc 480
aatagcagca atattagcct gcgtaataat tatatgccga gcaatcatgg ctttggcagc 540
attgcgattg tgacctttag cccggaatat agctttcgtt ttaatgataa tagcatgaat 600
gaatttattc aggatccggc gctgaccctg atgcatgaac tgattcatag cctgcatggc 660
ctgtatggcg cgaaaggcat taccaccaaa tataccatta cccagaaaca gaatccgctg 720
attaccaata ttcgtggcac caatattgaa gaatttctga cctttggcgg caccgatctg 780
aatattatta ccagcgcgca gagcaatgat atttatacca atctgctggc ggattataaa 840
aaaattgcga gcaaactgag caaagtgcag gtgagcaatc cgctgctgaa tccgtataaa 900

-continued

```
gatgtgtttg aagcgaaata tggcctggat aaagatgcga gcggcattta tagcgtgaat    960
attaataaat ttaatgatat ttttaaaaaa ctgtatagct ttaccgaatt tgatctggcg   1020
accaaatttc aggtgaaatg tcgtcagacc tatattggcc agtataaata ttttaaactg   1080
agcaatctgc tgaatgatag catttataat attagcgaag gctataatat taataatctg   1140
aaagtgaatt ttcgtggcca gaatgcgaat ctgaatccgc gtattattac cccgattacc   1200
ggccgtggcc tggtgaaaaa aattattcgt ttttgtaaaa atattgtgag cgtgaaaggc   1260
attcgtaaaa gcatttgtat tgaaattaat aatggcgaac tgttttttgt ggcgagcgaa   1320
aatagctata atgatgataa tattaatacc ccgaaagaaa ttgatgatac cgtgaccagc   1380
aataataatt atgaaaatga tctggatcag gtgattctga attttaatag cgaaagcgcg   1440
ccgggcctga gcgatgaaaa actgaatctg accattcaga atgatgcgta tattccgaaa   1500
tatgatagca atggcaccag cgatattgaa cagcatgatg tgaatgaact gaatgtgttt   1560
ttttatctgg atgcgcagaa agtgccggaa ggcgaaaata atgtgaatct gaccagcagc   1620
attgataccg cgctgctgga acagccgaaa atttatacct tttttagcag cgaatttatt   1680
aataatgtga ataaaccggt gcaggcggcg ctgtttgtga gctggattca gcaggtgctg   1740
gtggatttta ccaccgaagc gaatcagaaa agcaccgtgg ataaaattgc ggatattagc   1800
attgtggtgc cgtatattgg cctggcgctg aatattggca atgaagcgca gaaaggcaat   1860
tttaaagatg cgctggaact gctgggcgcg ggcattctgc tggaatttga accggaactg   1920
ctgattccga ccattctggt gtttaccatt aaaagctttc tgggcagcag cgataataaa   1980
aataaagtga ttaaagcgat taataatgcg ctgaaagaac gtgatgaaaa atggaaagaa   2040
gtgtatagct ttattgtgag caattggatg accaaaatta atacccagtt taataaacgt   2100
aaagaacaga tgtatcaggc gctgcagaat caggtgaatg cgattaaaac cattattgaa   2160
agcaaatata atagctatac cctggaagaa aaaaatgaac tgaccaataa atatgatatt   2220
aaacagattg aaaatgaact gaatcagaaa gtgagcattg cgatgaataa tattgatcgt   2280
tttctgaccg aaagcagcat tagctatctg atgaaactga ttaatgaagt gaaaattaat   2340
aaactgcgtg aatatgatga aaatgtgaaa acctatctgc tgaattatat tattcagcat   2400
ggcagcattc tgggcgaaag ccagcaggaa ctgaatagca tggtgaccga taccctgaat   2460
aatagcattc cgtttaaact gagcagctat accgatgata aaattctgat tagctatttt   2520
aataaatttt ttaaacgtat taaaagcagc agcgtgctga atatgcgtta taaaaatgat   2580
aaatatgtgg ataccagcgg ctatgatagc aatattaata ttaatggcga tgtgtataaa   2640
tatccgacca ataaaaatca gtttggcatt tataatgata aactgagcga agtgaatatt   2700
agccagaatg attatattat ttatgataat aaatataaaa attttagcat tagcttttgg   2760
gtgcgtattc cgaattatga taataaaatt gtgaatgtga ataatgaata taccattatt   2820
aattgtatgc gtgataataa tagcggctgg aaagtgagcc tgaatcataa tgaaattatt   2880
tggaccctgc aggataatgc gggcattaat cagaaactgg cgtttaatta tggcaatgcg   2940
aatggcatta gcgattatat taataaatgg attttttgtga ccattaccaa tgatcgtctg   3000
ggcgatagca aactgtatat taatggcaat ctgattgatc agaaaagcat tctgaatctg   3060
ggcaatattc atgtgagcga taatattctg tttaaaattg tgaattgtag ctatacccgt   3120
tatattggca ttcgttattt taatattttt gataaagaac tggatgaaac cgaaattcag   3180
accctgtata gcaatgaacc gaataccaat attctgaaag atttttgggg caattatctg   3240
ctgtatgata aagaatatta tctgctgaat gtgctgaaac cgaataattt tattgatcgt   3300
```

-continued

```
cgtaaagata gcaccctgag cattaataat attcgtagca ccattctgct ggcgaatcgt   3360
ctgtatagcg gcattaaagt gaaaattcag cgtgtgaata atagcagcac caatgataat   3420
ctggtgcgta aaaatgatca ggtgtatatt aattttgtgg cgagcaaaac ccatctgttt   3480
ccgctgtatg cggataccgc gaccaccaat aaagaaaaaa ccattaaaat tagcagcagc   3540
ggcaatcgtt ttaatcaggt ggtggtgatg aatagcgtgg gcaataattg taccatgaat   3600
tttaaaaata ataatggcaa taatattggc ctgctgggct ttaaagcgga taccgtggtg   3660
gcgagcacct ggtattatac ccatatgcgt gatcatacca atagcaatgg ctgtttttgg   3720
aattttatta gcgaagaaca tggctggcag gaaaaataa                         3759
```

<210> SEQ ID NO 7
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, E. coli-modified 4

<400> SEQUENCE: 7

```
atgccaaaaa ttaattcgtt caattataat gatccagtta acgatcgcac aatcctctac     60
atcaaacctg gtggctgcca ggaattctac aaatcattca acattatgaa gaatatttgg    120
atcattcccg aacgtaacgt cattgggacc actccgcagg acttccatcc gccaacgtct    180
ctgaaaaacg gggacagctc ttattacgat cctaactatc tgcagtcgga tgaagagaaa    240
gatcgtttcc tgaaaattgt aactaaaatt ttcaaccgca ttaacaataa cttgtcaggt    300
gggattctgt tagaagagct gagcaaagcg aacccctatc tcggtaacga taatacaccg    360
gacaaccagt ttcatattgg agacgcgtcg gcagtggaaa ttaaattcag caatggttct    420
caggatattt tactgcctaa tgtgattatc atgggggcgg agccggatct gtttgaaacc    480
aatagctcca atattagttt acgtaacaat tacatgccga gcaaccacgg tttcggaagc    540
attgccatcg ttacctttag tcccgaatat agttttcgtt ttaatgataa tagtatgaat    600
gaatttattc aagaccctgc cctgacactt atgcacgagc ttatccactc actgcacggc    660
ctgtatggag ccaagggcat taccactaag tatactatta cgcaaaaaca gaatccgctg    720
attacaaata tccgtggcac taatattgaa gagttcttga ccttcggcgg taccgatctc    780
aatattatca catctgcaca gtcaaatgac atctacacaa acctgctcgc agactataaa    840
aagattgcgt cgaaactgtc taaagtccaa gtctctaacc cactgttgaa cccctacaaa    900
gatgtgttcg aagcaaagta cgggttggat aaggatgcat caggtattta tagtgtcaat    960
attaacaagt ttaatgacat cttcaaaaag ttgtatagct ttacggaatt tgacctggcg   1020
accaaatttc aggtgaaatg ccggcaaacc tacattggtc agtacaaata ttttaaactg   1080
agcaacttgc tgaatgattc gatttataat atttccgaag ggtacaatat caacaatctt   1140
aaagtgaact ttcgcggtca gaatgcgaat ctgaatccgc gtatcattac accgattact   1200
ggccgcggcc tcgtgaaaaa gatcattcgc ttctgcaaaa atatcgtgag cgttaaaggc   1260
atccgtaaat ccatttgtat cgagattaat aacggcgaat tgtttttcgt tgcttccgag   1320
aacagttaca acgacgataa tatcaacacg ccgaaagaga tcgacgatac tgttaccagt   1380
aacaataact acgaaaatga tcttgatcag gtaattctta atttcaactc ggaatctgcc   1440
ccaggactta gcgacgaaaa actgaacctg acgatccaga acgatgccta tatcccgaaa   1500
```

-continued

```
tatgattcaa acggtacatc agatatcgag cagcatgacg ttaacgaatt gaatgtgttt   1560
ttctatctgg acgctcagaa agtgcctgaa ggcgagaaca atgtgaatct gacatcctct   1620
attgatacgg cgttacttga acaaccgaaa atctatacct ttttcagttc tgaatttatt   1680
aacaatgtta ataaaccggt gcaggcagcg ctgttcgtct catggattca gcaagtgctt   1740
gtagatttta ctaccgaggc taatcaaaaa tctacggtgg acaaaatcgc ggacatcagc   1800
attgtggtcc cttacatcgg tctggccctg aacattggga atgaagcaca gaaaggtaac   1860
ttcaaggatg ccttggaact cctgggcgca gggatcttac ttgaatttga accggaactg   1920
cttattccga cgatcctggt gtttaccatt aagagttttc tgggcagttc agacaataaa   1980
aacaaagtga tcaaagcgat taataacgcg cttaaagaac gtgatgaaaa atggaaagaa   2040
gtatattcgt ttattgtatc gaattggatg accaaaatca atacgcagtt taacaaacgt   2100
aaagagcaga tgtaccaggc gctgcaaaac caggtcaacg ctattaagac catcattgag   2160
agtaaatata atagctatac gctcgaagag aaaaacgaat taacgaacaa gtatgatatt   2220
aagcaaatcg aaaacgagtt aaatcaaaaa gtttctatcg ctatgaacaa tatcgaccgt   2280
ttcctgaccg aatcaagcat tagctactta atgaagctga ttaatgaagt gaagattaat   2340
aaactgcggg aatacgatga gaatgtaaaa acatatttac tgaactacat tatccagcac   2400
ggaagcatcc tgggcgaatc tcaacaggag ctgaacagta tggtgaccga tactttaaac   2460
aattctatcc cctttaaact gagcagttac acggatgaca aaatcctgat ttcatatttc   2520
aataaatttt tcaaacgcat taaatcttcc agtgtattga acatgcgcta taaaaatgac   2580
aagtatgtcg atacttctgg ttatgatagc aacatcaaca ttaacggcga tgtttacaaa   2640
tacccaacca ataaaaacca atttggcatt tataacgata agctgtccga ggttaacatc   2700
tcacagaacg attatattat ctatgacaac aaatacaaga acttttcaat ttccttttgg   2760
gtccgcatcc cgaactacga caataaaatc gtcaacgtta ataacgaata tacaattatc   2820
aattgtatgc gtgataataa ctccggttgg aaggtcagcc tgaatcataa cgaaattatc   2880
tggacgttac aggataacgc tggaatcaac cagaagctgg cctttaatta tggtaatgcg   2940
aacggaatta gcgattatat taacaagtgg atcttcgtga caattactaa tgatcgtctg   3000
ggtgactcca agctgtacat caatggaaat ttaattgatc agaaatccat tttaaacctg   3060
ggtaacattc atgtatccga caatattttg tttaaaattg taaactgttc ctatacccgg   3120
tatatcggca ttcgttactt caacattttt gataaagaat tagatgagac ggaaattcaa   3180
accctctatt cgaacgagcc gaatactaat attctgaaag atttttgggg caactatttg   3240
ctttatgaca aagaatacta tttactgaac gtcctgaaac caaataactt cattgatcgt   3300
cgcaaggact ccaccctgag tattaacaat atccgttcga ccattctgtt ggccaatcgc   3360
ctgtactcgg gtattaaagt taaaattcaa cgggttaaca atagcagtac aaatgataac   3420
ctcgttcgca aaaatgatca agtttatatt aatttcgtcg ccagcaaaac ccatctgttt   3480
ccgctgtatg ctgataccgc cactacgaat aaggaaaaaa cgattaagat ttcgtcttcg   3540
ggcaatcgtt ttaaccaggt ggttgtgatg aattcagttg gtaacaattg taccatgaac   3600
tttaaaaata acaatggcaa taacattggc ctgctcggtt ttaaagcaga caccgtagtt   3660
gctagcacgt ggtattacac ccacatgcgt gatcatacca actctaatgg gtgcttttgg   3720
aattttatta gcgaagagca tggctggcag gaaaaataa                          3759
```

<210> SEQ ID NO 8
<211> LENGTH: 3759

-continued

<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, B. fragilis-modified 1

<400> SEQUENCE: 8
atgcccaaga taaattcgtt taattataat gaccctgtga atgatcgaac tatcctgtat 60
atcaaacctg gcggatgtca agaattttac aaatctttca atataatgaa aaacatttgg 120
ataatccccg agcggaatgt gataggaaca acgccccagg attttcatcc gccaacgtct 180
ttgaagaatg gtgactcgag ttattacgat ccgaactatc tgcagtccga cgaagagaaa 240
gatcgttttc ttaagattgt aacaaaaatt tttaacagaa taaataacaa tttgtcagga 300
ggcatccttc tggaagagct gtcgaaagcc aacccttatt tgggaaatga taatactcca 360
gataatcagt ttcatatagg cgatgccagc gcggttgaga tcaaattttc caatggttct 420
caagatattt tgttacccaa cgtgataatt atgggcgccg aacctgacct gtttgaaacc 480
aattcctcta atatatcttt acgtaacaat tatatgccca gtaaccatgg attcggctct 540
atcgctattg ttacgttcag cccggagtat tcatttagat tcaacgataa ttcgatgaat 600
gagttcattc aagatccagc acttacactt atgcacgaac ttatccactc gctgcatgga 660
ctttatggtg cgaaaggcat aacgactaag tatacaatca ctcaaaaaca gaatccgctg 720
attactaaca ttcgtggtac aaatatcgaa gagtttttaa ccttcggagg tacggatcta 780
aatataatta caagcgcgca gagtaacgat atctatacaa atttgctggc tgattataaa 840
aagatagctt ctaaattgag caaagtccag gtgagcaacc ctttgctgaa tccgtacaaa 900
gatgttttcg aagcaaaata tggactcgat aaggatgcct caggaatcta ttctgtcaat 960
ataaataagt ttaacgacat cttcaaaaag ctgtattcct tcactgagtt cgatctcgcc 1020
accaagttcc aggtaaagtg ccgccaaaca tatatcggtc agtataagta cttcaagtta 1080
tcgaacctct tgaacgactc aatttataat attagcgaag gatacaatat aaacaatctt 1140
aaagtaaact tccgcggcca aaacgccaat ttaaacccgc gtattataac ccctattacc 1200
gggcgggggt tagtaaagaa aataatccgt ttctgtaaga atatcgtctc ggttaaaggc 1260
attagaaaat cgatctgtat cgaaatcaac aatggtgaat tgttctttgt agcatcagaa 1320
aactcatata atgatgacaa tatcaacacc cctaaagaga ttgacgatac tgttacatct 1380
aataacaatt acgaaaacga tcttgaccaa gttattctta acttcaattc tgaaagcgcc 1440
ccgggtttga gtgatgagaa attgaatctg actattcaga atgatgccta tatcccaaaa 1500
tatgactcca acggtacctc tgacatcgaa caacatgacg ttaacgaact aaacgtcttt 1560
ttctaccttg acgctcagaa agtaccggaa ggagaaaaca atgtgaactt aacgtcttca 1620
atagacactg cattgctgga gcagcctaag atttatacat ttttctcgag tgaattcata 1680
aataacgtga ataaaccggt tcaagcagcc ttattcgtga gttggataca gcaagtgctg 1740
gttgatttca caaccgaagc caatcaaaaa tcgacagtag acaaaattgc tgatatcagt 1800
atagtagttc cctacatcgg cctagctttg aatataggta atgaagccca gaaaggcaat 1860
ttcaaagatg cactggaact tctcggcgca ggtatcctgt tggagttcga acctgaattg 1920
cttatcccga ccattctcgt atttacaatt aaaagctttc tgggatcatc ggacaataaa 1980
aataaagtga ttaaggccat taataacgca ttaaaggagc gcgacgaaaa gtggaaagaa 2040
gtctacagtt ttattgtctc aaattggatg accaaaatta acacgcagtt taacaaacgc 2100

-continued

```
aaagagcaga tgtaccaagc tttacagaat caggtgaatg caataaagac catcattgaa   2160
agtaagtaca acagttatac gttggaagag aaaaatgaat tgactaataa atacgatatc   2220
aaacagattg aaaacgagct gaaccaaaaa gtatctattg caatgaataa catcgatagg   2280
tttctaactg aaagtagcat cagctatctc atgaaactga tcaatgaagt aaaaatcaat   2340
aagctgcgtg agtatgatga aaatgtgaag acgtacttgt taaattacat tatacaacat   2400
ggttcgattc tgggagaaag ccaacaggaa ttgaatagta tggtaactga cacgctgaac   2460
aattccatcc cgtttaaact ctcgagctac acagacgata agatcctcat ttcatatttt   2520
aacaagttct ttaaaaggat taaaagttcg agtgtactaa acatgcggta taaaaatgat   2580
aagtatgtgg acacatccgg ttacgattcc aacattaaca tcaatggaga cgtgtataag   2640
tatccgacta ataagaatca atttgggatc tataatgata aattatccga ggtcaacatt   2700
agtcagaatg actacattat ctatgataat aaatacaaga acttttctat aagcttttgg   2760
gttcgcatcc ctaattacga caacaaaatt gtcaatgtaa ataacgaata caccataatc   2820
aattgcatgc gagataacaa ttccgggtgg aaagtatctt taaaccataa tgaaattatc   2880
tggaccctgc aagataacgc tggaataaat caaaagcttg ctttcaatta tggaaatgct   2940
aacggaatct cagactatat aaacaaatgg atctttgtga caataacgaa cgatcggttg   3000
ggggactcta agctgtatat taacggaaat ctgattgatc agaagagtat cttgaacctg   3060
ggtaatattc acgtatctga taacatattg ttcaaaatag taaattgttc gtatacgcgt   3120
tatataggaa tccgatattt taatatcttt gacaaggaac tggacgagac tgaaatacaa   3180
acattatatt caaacgagcc caatacaaac attttaaaag atttctgggg aaattatctc   3240
ttgtatgaca aggaatatta cctgctcaat gtgctgaaac cgaataactt tatcgacaga   3300
cggaaagata gtaccctttc gatcaataac attcgttcta ccattttgct tgctaatcgc   3360
ctgtattccg gtattaaagt aaaaattcag cgtgtgaata actcatctac taacgataat   3420
ctggtgcgta agaatgatca agtctatatc aactttgtcg cgagcaaaac tcacctattt   3480
cccctttatg cagatactgc gaccacgaat aaagagaaaa ccataaaaat ttccagttca   3540
ggtaacagat tcaatcaagt tgtagtgatg aactctgttg gtaataactg cacaatgaat   3600
ttcaaaaata acaatggtaa taacattgga ttgttgggat ttaaagccga taccgtagta   3660
gcttccacct ggtattatac ccacatgcgt gatcatacta attccaatgg gtgtttttgg   3720
aattttatta gcgaagaaca tgggtggcag gaaaagtaa                          3759
```

<210> SEQ ID NO 9
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, B. fragilis-modified 2

<400> SEQUENCE: 9

```
atgccgaaaa ttaattcttt taattataat gatccggtaa atgatcgtac cattctgtat     60
attaaaccgg gaggatgtca ggaattttat aaatctttta atattatgaa aaatatttgg    120
attattccgg aacgtaatgt aattggaacc accccgcagg attttcatcc gccgacctct    180
ctgaaaaatg gagattcttc ttattatgat ccgaattatc tgcagtctga tgaagaaaaa    240
gatcgttttc tgaaaattgt aaccaaaatt tttaatcgta ttaataataa tctgtctgga    300
ggaattctgc tggaagaact gtctaaagcc aatccgtatc tgggaaatga taataccccg    360
```

-continued

```
gataatcagt ttcatattgg agatgcctct gccgtagaaa ttaaattttc taatggatct    420
caggatattc tgctgccgaa tgtaattatt atgggagccg aaccggatct gtttgaaacc    480
aattcttcta atatttctct gcgtaataat tatatgccgt ctaatcatgg atttggatct    540
attgccattg taacctttc tccggaatat tcttttcgtt ttaatgataa ttctatgaat    600
gaatttattc aggatccggc cctgaccctg atgcatgaac tgattcattc tctgcatgga    660
ctgtatggag ccaaaggaat taccaccaaa tataccatta cccagaaaca gaatccgctg    720
attaccaata ttcgtggaac caatattgaa gaatttctga cctttggagg aaccgatctg    780
aatattatta cctctgccca gtctaatgat atttatacca atctgctggc cgattataaa    840
aaaattgcct ctaaactgtc taaagtacag gtatctaatc cgctgctgaa tccgtataaa    900
gatgtatttg aagccaaata tggactggat aaagatgcct ctggaattta ttctgtaaat    960
attaataaat ttaatgatat ttttaaaaaa ctgtattctt ttaccgaatt tgatctggcc   1020
accaaatttc aggtaaaatg tcgtcagacc tatattggac agtataaata ttttaaactg   1080
tctaatctgc tgaatgattc tatttataat atttctgaag gatataatat taataatctg   1140
aaagtaaatt ttcgtggaca gaatgccaat ctgaatccgc gtattattac cccgattacc   1200
ggacgtggac tggtaaaaaa aattattcgt ttttgtaaaa atattgtatc tgtaaaagga   1260
attcgtaaat ctatttgtat tgaaattaat aatggagaac tgttttttgt agcctctgaa   1320
aattcttata atgatgataa tattaatacc ccgaaagaaa ttgatgatac cgtaacctct   1380
aataataatt atgaaaatga tctggatcag gtaattctga attttaattc tgaatctgcc   1440
ccgggactgt ctgatgaaaa actgaatctg accattcaga atgatgccta tattccgaaa   1500
tatgattcta atggaacctc tgatattgaa cagcatgatg taaatgaact gaatgtattt   1560
ttttatctgg atgcccagaa agtaccggaa ggagaaaata atgtaaatct gacctcttct   1620
attgataccg ccctgctgga acagccgaaa atttatacct ttttttcttc tgaatttatt   1680
aataatgtaa ataaaccggt acaggccgcc ctgtttgtat cttggattca gcaggtactg   1740
gtagatttta ccaccgaagc caatcagaaa tctaccgtag ataaaattgc cgatatttct   1800
attgtagtac cgtatattgg actggccctg aatattggaa atgaagccca gaaaggaaat   1860
tttaaagatg ccctggaact gctgggagcc ggaattctgc tggaatttga accggaactg   1920
ctgattccga ccattctggt atttaccatt aaatcttttc tgggatcttc tgataataaa   1980
aataaagtaa ttaaagccat taataatgcc ctgaaagaac gtgatgaaaa atggaaagaa   2040
gtatattctt ttattgtatc taattggatg accaaaatta atacccagtt taataaacgt   2100
aaagaacaga tgtatcaggc cctgcagaat caggtaaatg ccattaaaac cattattgaa   2160
tctaaatata attcttatac cctggaagaa aaaaatgaac tgaccaataa atatgatatt   2220
aaacagattg aaaatgaact gaatcagaaa gtatctattg ccatgaataa tattgatcgt   2280
tttctgaccg aatcttctat ttcttatctg atgaaactga ttaatgaagt aaaaattaat   2340
aaactgcgtg aatatgatga aaatgtaaaa acctatctgc tgaattatat tattcagcat   2400
ggatctattc tgggagaatc tcagcaggaa ctgaattcta tggtaaccga taccctgaat   2460
aattctattc cgtttaaact gtcttcttat accgatgata aaattctgat ttcttatttt   2520
aataaatttt ttaaacgtat taaatcttct tctgtactga atatgcgtta taaaaatgat   2580
aaatatgtag atacctctgg atatgattct aatattaata ttaatggaga tgtatataaa   2640
tatccgacca ataaaaatca gtttggaatt tataatgata aactgtctga agtaaatatt   2700
```

-continued

```
tctcagaatg attatattat ttatgataat aaatataaaa atttttctat ttctttttgg   2760

gtacgtattc cgaattatga taataaaatt gtaaatgtaa ataatgaata taccattatt   2820

aattgtatgc gtgataataa ttctggatgg aaagtatctc tgaatcataa tgaaattatt   2880

tggaccctgc aggataatgc cggaattaat cagaaactgg cctttaatta tggaaatgcc   2940

aatggaattt ctgattatat taataaatgg atttttgtaa ccattaccaa tgatcgtctg   3000

ggagattcta aactgtatat taatggaaat ctgattgatc agaaatctat tctgaatctg   3060

ggaaatattc atgtatctga taatattctg tttaaaattg taaattgttc ttatacccgt   3120

tatattggaa ttcgttattt taatattttt gataaagaac tggatgaaac cgaaattcag   3180

accctgtatt ctaatgaacc gaataccaat attctgaaag atttttgggg aaattatctg   3240

ctgtatgata aagaatatta tctgctgaat gtactgaaac cgaataattt tattgatcgt   3300

cgtaaagatt ctaccctgtc tattaataat attcgttcta ccattctgct ggccaatcgt   3360

ctgtattctg gaattaaagt aaaaattcag cgtgtaaata attcttctac caatgataat   3420

ctggtacgta aaaatgatca ggtatatatt aattttgtag cctctaaaac ccatctgttt   3480

ccgctgtatg ccgataccgc caccaccaat aaagaaaaaa ccattaaaat ttcttcttct   3540

ggaaatcgtt ttaatcaggt agtagtaatg aattctgtag gaaataattg taccatgaat   3600

tttaaaaata ataatggaaa taatattgga ctgctgggat ttaaagccga taccgtagta   3660

gcctctacct ggtattatac ccatatgcgt gatcatacca attctaatgg atgtttttgg   3720

aattttattt ctgaagaaca tggatggcag gaaaaataa                          3759
```

<210> SEQ ID NO 10
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, B. fragilis-modified 3

<400> SEQUENCE: 10

```
atgcctaaga ttaacagttt caattacaat gacccggtga acgatagaac cattctgtac     60

ataaagccgg gaggctgtca agaattttat aagtcattta atattatgaa aaacatttgg    120

atcataccgg aaagaaatgt aattggaaca actccgcaag attttcaccc ccctacgtcc    180

ctgaaaaatg gagacagttc ttattacgat cctaactatc ttcagtcgga cgaagagaaa    240

gaccgttttt tgaaaatagt aacgaaaatc ttcaaccgca tcaataacaa tttgtccggt    300

ggaatcctcc ttgaagagtt gtcaaaagca aacccgtatc ttggaaacga taatactccc    360

gataaccagt tccatatagg agacgcctcg gccgtagaga taaagttttc taacggaagt    420

caggatatct tattgcccaa tgtaatcata atgggcgcag agcctgatct gtttgaaact    480

aacagttcca acatttctct gcgcaataac tatatgccgt ccaaccatgg tttcggcagc    540

attgcaatcg ttactttctc ccctgaatat agttttcgtt ttaacgataa cagtatgaat    600

gagttcatcc aagaccctgc cctgacactt atgcatgagc ttatacactc gcttcacgga    660

ttatatggcg caaagggaat taccacaaag tataccataa cccaaaagca gaatcccctg    720

attactaaca tacgtggtac taacatagaa gagtttttga cgttcggagg tacagacttg    780

aatataatca cgtcagccca gtccaacgat atctacacga atctgttggc agattacaaa    840

aagatcgcta gtaaactgtc caaggtacag gtctctaacc cgttactgaa tccttacaaa    900

gatgttttg aggctaaata tggacttgac aaagatgctt ctggtatcta ttctgttaat     960
```

-continued

```
atcaacaaat ttaacgatat ttttaagaaa ctttatagtt ttacggagtt tgaccttgcc   1020
acaaaattcc aagttaaatg tcgtcagact tatattggtc aatacaaata tttcaaatta   1080
tcaaacttac tgaatgatag catctataat atctcggagg gatataatat taataacttg   1140
aaagttaatt tccgtggaca aaatgccaat ttgaatccgc ggattataac accgattacc   1200
ggacgtggtc tcgtaaaaaa gatcattcgt ttttgcaaaa acatcgttag cgtaaagggt   1260
attcgtaaat caatttgtat cgaaattaat aacggagagt tgtttttcgt tgccagcgaa   1320
aatagctata atgacgataa tataaatacc cccaaagaaa tcgatgacac agtgacctcg   1380
aataacaatt atgaaaacga tctggatcaa gtcatactga attttaacag tgagtctgct   1440
ccgggactgt cagacgagaa actgaacttg actatccaaa atgatgcata cattccgaag   1500
tatgacagca acggtacttc tgatatagaa cagcacgatg taaatgaact caatgtgttc   1560
ttttacctgg atgcccaaaa agtgcctgag ggagaaaaca atgtaaacct cacttcctcg   1620
attgacacag cactgttaga acagccgaaa atatatacct tttctcttc ggagtttata   1680
aataacgtaa ataagcctgt acaagctgcc ctgttcgtgt cctggatcca acaggtctta   1740
gtggacttca ctacggaagc caaccaaaag tcgacagtgg acaagattgc cgatatctct   1800
attgtggtcc cttacatagg tctggcactg aatataggta atgaagcaca aaaaggaaac   1860
tttaaagacg ccctggaact gttgggcgcc ggcattcttc tcgaatttga accggaattg   1920
ctcatcccga caatactggt atttacgatt aaatcgtttc tgggtagttc agataataaa   1980
aacaaggtca ttaaagctat caataacgct ctgaaagagc gggatgaaaa gtggaaagag   2040
gtctacagct ttatcgtatc taactggatg acgaaaataa atacgcaatt caataaacgt   2100
aaagaacaga tgtaccaagc tttgcagaac caggtaaatg ccatcaagac aatcatagaa   2160
tcaaagtaca atagttatac cttggaagag aaaaatgaat tgactaacaa atatgatatc   2220
aaacagatag aaaatgaatt aaatcagaaa gtttcgatcg caatgaacaa tatagatcgg   2280
tttctgaccg aaagctccat tagctatctg atgaaactta taaacgaagt aaaaattaac   2340
aaacttcgcg aatatgacga aaatgtcaag acttacctct taaattacat tatccaacat   2400
ggttccatcc tcggagaaag ccagcaagaa ctgaattcca tggtgacaga tactctgaat   2460
aactcgattc ccttcaaatt gagcagttat acggacgata aaattctgat ttcttatttc   2520
aataaatttt tcaaacggat aaaatcgtct agcgttctca atatgcgtta taaaaacgat   2580
aagtatgttg acaccagtgg ttatgattct aatattaata ttaacggaga tgtatataaa   2640
tatccgacaa ataaaaatca gttcggaatc tataatgata aacttagtga agttaatatt   2700
tcgcaaaacg actatatcat ttatgataat aaatataaaa acttttcaat tagtttctgg   2760
gtgcgtattc cgaattatga taacaagatt gtcaatgtaa ataacgaata taccatcata   2820
aactgcatgc gcgacaataa ctctggatgg aaggtgtctt tgaatcataa tgaaattata   2880
tggactttac aggacaatgc aggaattaac cagaaactgg ctttcaacta tggaaatgct   2940
aatggcatca gtgattacat taataaatgg atattcgtga ctattacaaa cgatcgtttg   3000
ggagattcta aactgtatat caatggaaat ttgatcgatc aaaagtccat attgaatctg   3060
ggtaacatcc atgtgtccga caacatctta tttaagatcg tgaattgcag ttacacccgt   3120
tacattggca tcagatattt caacattttc gacaaagaac tggatgaaac agaaattcag   3180
accctctatt ctaatgaacc caatacaaat atattgaagg atttctgggg caattatctg   3240
ttatacgata aggagtatta cttacttaac gttttgaagc ccaacaattt tatcgaccgc   3300
```

-continued

```
cgtaaagatt ctaccttgag catcaataac attcgctcaa ctatcttgct tgccaatcgg   3360
ctgtactcag gcataaaagt gaaaatccaa agagtaaata acagttcgac caatgataac   3420
ttggtccgta agaatgacca ggtgtatatc aacttcgtag ctagcaagac gcatcttttc   3480
ccgttatatg ccgataccgc tacgactaat aaagaaaaga caatcaagat ttcttcatcg   3540
ggaaacagat ttaatcaggt tgtggtaatg aacagcgtgg gaaataactg taccatgaat   3600
tttaagaata ataatggaaa taatattggt ttactgggtt ttaaggccga cacagtagtc   3660
gcctcgacct ggtattatac acacatgcgt gaccatacca attcaaatgg ttgtttttgg   3720
aatttcattt cagaagagca tggctggcag gagaaataa                          3759
```

<210> SEQ ID NO 11
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, B. licheniformis-modified 1

<400> SEQUENCE: 11

```
atgccgaaaa ttaacagctt taattataac gatccggtga atgatcgcac cattctttat     60
attaaaccgg gcggatgtca ggaattctat aaatctttca acataatgaa aaatatctgg    120
attatccctg aacggaacgt aattgggaca acgccgcagg atttccaccc tccgacatcg    180
ctaaaaaacg gagactcgtc atattacgat ccaaattatc tccagtcaga cgaggaaaag    240
gatcgcttcc ttaagattgt cactaagatt tttaacagga taaataacaa tctttcaggc    300
ggaattctgc tagaggaact ctcgaaggcg aatccgtacc tcggaaatga taatacgccg    360
gataaccagt tccacatcgg cgacgcctct gctgtggaga tcaaatttag caatggctcg    420
caagatatct tgctgccaaa cgtcatcatt atgggagcgg aacctgactt gtttgaaacg    480
aactcctcta atatctcact gcgcaacaat tacatgccta gcaaccacgg gtttggatcg    540
atcgcgatcg taacgttttc tcccgagtac agctttcgtt ttaatgacaa ctcaatgaac    600
gagttcattc aagatccggc cctgacgtta atgcacgaac tcatccactc tttgcatgga    660
ctgtatggcg ccaaaggaat caccacaaaa tatacgatta cacagaaaca gaaccccctg    720
attacgaaca tcagaggtac caatatcgag gaatttctga catttggcgg tacggacttg    780
aacattataa cgtcagcaca aagcaatgac atttatacca atttattggc tgattacaag    840
aaaatcgcat caaaactctc aaaagtccag gtttcaaatc ctttattgaa tccgtacaaa    900
gatgtgttcg aagctaaata cggactagat aaggatgcca gcggcatata ttcggtaaac    960
atcaacaaat tcaacgacat cttcaaaaag ttgtatagct ttactgaatt tgacttggca   1020
accaaatttc aggtcaaatg tagacaaact tacattgggc agtacaaata tttcaaattg   1080
tctaatctcc ttaacgatag tatctataac atcagcgaag gatataatat taacaatctg   1140
aaagttaatt ttagaggcca aaacgccaac ctcaatccgc gaatcattac cccgatcaca   1200
gggcgcggac tggttaagaa aatcattcgt ttttgcaaaa acattgtgag cgtgaagggc   1260
attagaaaat caatctgcat cgaaattaat aacggcgagc tttttttcgt cgctagcgaa   1320
aattcataca atgatgacaa tattaacacc cctaaggaga ttgatgacac ggtcacctcg   1380
aacaataact atgaaaacga cttagaccag gttattctga attttaattc ggaatccgcg   1440
ccgggcctgt cagacgaaaa actcaacctg accattcaga atgatgcgta catccccaag   1500
tacgactcta atggcacatc ggatattgaa caacatgatg tgaatgaact taatgtgttt   1560
```

-continued

```
ttctatctgg atgcccagaa agtcccggaa ggtgagaaca atgtaaatct tacaagctca   1620
atcgataccg cacttctgga gcagccaaaa atctatacgt ttttcagctc ggaattcata   1680
aataacgtca ataaaccggt gcaagctgcc cttttcgtca gctggattca acaggttctc   1740
gttgatttta cgacagaagc caaccagaaa tctactgttg acaaaatagc ggacatttca   1800
attgtagttc cctacatcgg actggcattg aacataggca atgaggcaca aaaaggcaac   1860
tttaaagatg ctttggaact tctgggtgcg gggatactcc tggaatttga acctgaactc   1920
ctgatcccga cgatcctggt gtttacaatt aagtcttttt taggatcctc agataataaa   1980
aataaggtga taaaagcgat caataacgca cttaaagagc gcgacgaaaa atggaaagaa   2040
gtctacagct ttattgtttc taactggatg acaaaaatca acacgcagtt taacaaaaga   2100
aaggaacaga tgtaccaagc tttacagaac caagtcaatg cgatcaaaac catcattgag   2160
agtaaatata actcctatac tctggaagag aagaacgaac tcacaaataa gtatgatatc   2220
aagcaaattg agaacgaact taaccagaaa gtctcgatcg caatgaataa cattgatcgc   2280
tttcttacgg agtcaagcat cagctatctt atgaagctga tcaacgaggt aaagattaat   2340
aagctgcgcg aatacgatga aaatgtgaaa acatatttac ttaattatat cattcagcat   2400
ggttctattt taggcgaaag ccaacaggag ttaaactcca tggtaacaga cactttaaac   2460
aatagcattc catttaaatt atcatcgtac acagacgata aaattcttat ttcgtacttt   2520
aacaaatttt tcaagagaat caaatcctca agtgttctta atatgcgcta taagaacgat   2580
aaatatgttg atacaagcgg atatgattcc aatatcaata ttaatggtga tgtctataaa   2640
tatcctacaa acaaaaatca atttgggata tacaacgaca aactcagcga agttaacatc   2700
tcccagaatg actacatcat ttacgacaat aaatataaga acttttctat ttcgttttgg   2760
gtcagaatcc cgaactacga taataagatc gtgaatgtta acaatgaata tacgatcatt   2820
aactgcatgc gggataacaa ttccgggtgg aaagtttcct tgaatcataa tgagatcatt   2880
tggacgttgc aggataacgc cggaattaac cagaaacttg cgtttaacta tggcaacgcc   2940
aacggcattt ccgactacat caataagtgg atcttcgtca cgatcacaaa tgatcggctc   3000
ggagactcca agctttatat taacggaaat cttattgatc aaaagagtat cttgaacctg   3060
ggtaatatcc atgtctcaga taacatcctg tttaaaattg tcaattgttc gtacactagg   3120
tatatcggga ttaggtattt caacatcttt gacaaagaat tagacgaaac agaaatccaa   3180
acgctgtaca gcaatgaacc taacacaaac atcctcaaag atttctgggg caattatctc   3240
ttgtatgaca aagaatatta cttactgaac gtcttgaaac cgaataactt tatcgaccgt   3300
aggaaagact ctacgttgag tataaacaat atccggtcaa caatcctttt agcgaatagg   3360
ctgtatagcg gcataaaagt caagatccaa cgggtgaata acagttcgac gaacgacaac   3420
ttggtgcgaa aaaacgatca agtatacatc aatttcgtcg cgagcaaaac gcatttattc   3480
ccgctttatg ccgacacagc aaccacgaat aaagaaaaaa cgatcaagat atctagctcc   3540
ggtaatcggt tcaatcaagt tgtggtaatg aatagcgttg gaaataactg caccatgaac   3600
tttaagaaca ataacggcaa taacattggg cttcttggct ttaaagctga tactgtcgtc   3660
gcatccacat ggtattatac gcatatgcgt gatcatacga atagcaatgg ctgcttttgg   3720
aactttattt ccgaagaaca tgggtggcaa gaaaaataa                           3759
```

<210> SEQ ID NO 12
<211> LENGTH: 3759
<212> TYPE: DNA

-continued

<213> ORGANISM: Artificial Sequence
<220> FEATURE:
<221> NAME/KEY: mat_peptide
<222> LOCATION: (1)...(3756)
<223> OTHER INFORMATION: BoNT/E, B. licheniformis-modified 2

<400> SEQUENCE: 12

```
atgccgaaaa tcaacagctt taactataac gatccggtca acgatcgcac gatcctgtat     60
atcaaaccgg gcggctgcca ggaattttat aaaagcttta acatcatgaa aaacatctgg    120
atcatcccgg aacgcaacgt catcggcacg acgccgcagg attttcatcc gccgacgagc    180
ctgaaaaacg gcgatagcag ctattatgat ccgaactatc tgcagagcga tgaagaaaaa    240
gatcgctttc tgaaaatcgt cacgaaaatc tttaaccgca tcaacaacaa cctgagcggc    300
ggcatcctgc tggaagaact gagcaaagcg aacccgtatc tgggcaacga taacacgccg    360
gataaccagt ttcatatcgg cgatgcgagc gcggtcgaaa tcaaatttag caacggcagc    420
caggatatcc tgctgccgaa cgtcatcatc atgggcgcgg aaccggatct gtttgaaacg    480
aacagcagca acatcagcct gcgcaacaac tatatgccga gcaaccatgg ctttggcagc    540
atcgcgatcg tcacgtttag cccggaatat agctttcgct ttaacgataa cagcatgaac    600
gaatttatcc aggatccggc gctgacgctg atgcatgaac tgatccatag cctgcatggc    660
ctgtatggcg cgaaaggcat cacgacgaaa tatacgatca cgcagaaaca gaacccgctg    720
atcacgaaca tccgcggcac gaacatcgaa gaatttctga cgtttggcgg cacggatctg    780
aacatcatca cgagcgcgca gagcaacgat atctatacga acctgctggc ggattataaa    840
aaaatcgcga gcaaactgag caaagtccag gtcagcaacc cgctgctgaa cccgtataaa    900
gatgtctttg aagcgaaata tggcctggat aaagatgcga gcggcatcta tagcgtcaac    960
atcaacaaat ttaacgatat ctttaaaaaa ctgtatagct ttacggaatt tgatctggcg   1020
acgaaatttc aggtcaaatg ccgccagacg tatatcggcc agtataaata ttttaaactg   1080
agcaacctgc tgaacgatag catctataac atcagcgaag gctataacat caacaacctg   1140
aaagtcaact ttcgcggcca gaacgcgaac ctgaacccgc gcatcatcac gccgatcacg   1200
ggccgcggcc tggtcaaaaa aatcatccgc ttttgcaaaa acatcgtcag cgtcaaaggc   1260
atccgcaaaa gcatctgcat cgaaatcaac aacggcgaac tgttttttgt cgcgagcgaa   1320
aacagctata acgatgataa catcaacacg ccgaaagaaa tcgatgatac ggtcacgagc   1380
aacaacaact atgaaaacga tctggatcag gtcatcctga actttaacag cgaaagcgcg   1440
ccgggcctga gcgatgaaaa actgaacctg acgatccaga acgatgcgta tatcccgaaa   1500
tatgatagca acggcacgag cgatatcgaa cagcatgatg tcaacgaact gaacgtcttt   1560
ttttatctgg atgcgcagaa agtcccggaa ggcgaaaaca acgtcaacct gacgagcagc   1620
atcgatacgg cgctgctgga acagccgaaa atctatacgt tttttagcag cgaatttatc   1680
aacaacgtca acaaaccggt ccaggcggcg ctgtttgtca gctggatcca gcaggtcctg   1740
gtcgatttta cgacggaagc gaaccagaaa agcacggtcg ataaaatcgc ggatatcagc   1800
atcgtcgtcc cgtatatcgg cctggcgctg aacatcggca acgaagcgca gaaaggcaac   1860
tttaaagatg cgctggaact gctgggcgcg ggcatcctgc tggaatttga accggaactg   1920
ctgatcccga cgatcctggt ctttacgatc aaaagctttc tgggcagcag cgataacaaa   1980
aacaaagtca tcaaagcgat caacaacgcg ctgaaagaac gcgatgaaaa atggaaagaa   2040
gtctatagct ttatcgtcag caactggatg acgaaaatca acacgcagtt taacaaacgc   2100
aaagaacaga tgtatcaggc gctgcagaac caggtcaacg cgatcaaaac gatcatcgaa   2160
```

-continued

```
agcaaatata acagctatac gctggaagaa aaaaacgaac tgacgaacaa atatgatatc   2220
aaacagatcg aaaacgaact gaaccagaaa gtcagcatcg cgatgaacaa catcgatcgc   2280
tttctgacgg aaagcagcat cagctatctg atgaaactga tcaacgaagt caaaatcaac   2340
aaactgcgcg aatatgatga aaacgtcaaa acgtatctgc tgaactatat catccagcat   2400
ggcagcatcc tgggcgaaag ccagcaggaa ctgaacagca tggtcacgga tacgctgaac   2460
aacagcatcc cgtttaaact gagcagctat acggatgata aaatcctgat cagctatttt   2520
aacaaatttt ttaaacgcat caaaagcagc agcgtcctga acatgcgcta taaaaacgat   2580
aaatatgtcg atacgagcgg ctatgatagc aacatcaaca tcaacggcga tgtctataaa   2640
tatccgacga acaaaaacca gtttggcatc tataacgata aactgagcga agtcaacatc   2700
agccagaacg attatatcat ctatgataac aaatataaaa actttagcat cagcttttgg   2760
gtccgcatcc cgaactatga taacaaaatc gtcaacgtca acaacgaata tacgatcatc   2820
aactgcatgc gcgataacaa cagcggctgg aaagtcagcc tgaaccataa cgaaatcatc   2880
tggacgctgc aggataacgc gggcatcaac cagaaactgg cgtttaacta tggcaacgcg   2940
aacggcatca gcgattatat caacaaatgg atctttgtca cgatcacgaa cgatcgcctg   3000
ggcgatagca aactgtatat caacggcaac ctgatcgatc agaaaagcat cctgaacctg   3060
ggcaacatcc atgtcagcga taacatcctg tttaaaatcg tcaactgcag ctatacgcgc   3120
tatatcggca tccgctattt taacatcttt gataaagaac tggatgaaac ggaaatccag   3180
acgctgtata gcaacgaacc gaacacgaac atcctgaaag atttttgggg caactatctg   3240
ctgtatgata aagaatatta tctgctgaac gtcctgaaac cgaacaactt tatcgatcgc   3300
cgcaaagata gcacgctgag catcaacaac atccgcagca cgatcctgct ggcgaaccgc   3360
ctgtatagcg gcatcaaagt caaaatccag cgcgtcaaca acagcagcac gaacgataac   3420
ctggtccgca aaaacgatca ggtctatatc aactttgtcg cgagcaaaac gcatctgttt   3480
ccgctgtatg cggatacggc gacgacgaac aaagaaaaaa cgatcaaaat cagcagcagc   3540
ggcaaccgct ttaaccaggt cgtcgtcatg aacagcgtcg gcaacaactg cacgatgaac   3600
tttaaaaaca acaacggcaa caacatcggc ctgctgggct ttaaagcgga tacggtcgtc   3660
gcgagcacgt ggtattatac gcatatgcgc gatcatacga acagcaacgg ctgcttttgg   3720
aactttatca gcgaagaaca tggctggcag gaaaaataa                          3759
```

<210> SEQ ID NO 13
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, B. licheniformis-modified 3

<400> SEQUENCE: 13

```
atgccgaaaa tcaactcctt caactacaac gaccctgtca atgatcgcac gattctctat     60
attaaacctg gcgggtgcca ggagttctat aaatcattta acatcatgaa aaatatctgg    120
atcattccgg aaagaaacgt aatcggtaca accccgcaag acttccatcc gcctacgtca    180
ttaaaaaatg gcgattcatc gtattacgat ccgaactact tgcagagcga tgaggaaaaa    240
gacagatttc ttaagatcgt gacgaaaatc ttcaatcgga ttaacaataa cctgagcggc    300
ggaattcttt tagaagagtt atcaaaggct aacccgtact tgggaaacga taatacgccg    360
```

-continued

```
gataatcagt tccatatcgg agatgccagc gctgtcgaaa tcaagttctc caatggctct    420
caggacatct tgctgccgaa cgttattatc atgggcgctg agccggattt gtttgaaacg    480
aatagctcga atatcagctt gcgcaataac tacatgccgt caaaccatgg atttggaagc    540
atcgcgatcg ttacattttc cccggagtat tcatttagat ttaacgacaa tagcatgaac    600
gaatttattc aggatccggc cctgacgttg atgcacgaat tgattcactc gctccacgga    660
ctgtatggcg cgaaagggat cacgacaaag tatacaatta cacagaagca gaatccgctt    720
atcacgaaca ttcgtgggac aaatatcgaa gagttcttaa cgtttggcgg aacagacttg    780
aacatcatta cgtcggcaca aagcaacgac atttatacga accttctggc tgattataag    840
aaaatcgcat cgaagctcag caaagtccag gtctccaatc cgctgttaaa tccttacaaa    900
gatgtttttg aagcaaaata tggtctggat aaagatgcgt caggaatcta ttctgtcaac    960
atcaataaat ttaatgacat tttcaaaaag ctctatagct ttaccgaatt tgaccttgcg   1020
accaaatttc aggtcaaatg ccgccaaaca tatatcggcc aatataaata cttcaaactg   1080
tccaacctgc ttaacgactc gatctacaat atcagcgagg gatacaatat taataacctg   1140
aaagtcaact ttcgggggca aaacgcaaac ctcaacccga ggatcattac gccgattacc   1200
ggccgcggct tggttaaaaa gatcattcgg ttttgtaaaa atatcgtgtc tgttaaaggg   1260
atccggaaat ccatttgtat tgagatcaac aatggtgaat tgtttttcgt ggcgagcgaa   1320
aacagctaca acgatgacaa catcaatacg cctaaggaaa ttgacgatac ggtcacgtct   1380
aataacaatt acgaaaatga tcttgaccag gtcattttaa actttaactc cgaaagcgcc   1440
cctggactga gcgacgaaaa gctcaatttg acgattcaaa atgatgccta tatcccgaaa   1500
tacgatagca atgggacatc agacattgaa cagcatgatg tcaatgaact taatgtcttc   1560
ttttatctgg atgcgcaaaa agtcccggag ggcgagaaca atgtcaacct gacctccagc   1620
atcgatacag cccttctcga gcaaccgaaa atctatacat tcttttcttc ggaattcatc   1680
aacaatgtaa acaaaccggt gcaagctgcc ctctttgttt cttggattca gcaagtgctc   1740
gttgacttta cgacagaagc caatcagaaa tcaacagttg acaaaatcgc agacatttcc   1800
atcgtggttc cttatattgg cctcgcactg aatatcggca acgaagccca aaaaggcaac   1860
tttaaagatg cgctggagct gcttggcgcg ggtatcctgc ttgaatttga acctgaactc   1920
ttaatcccga cgatccttgt ctttacaatc aaaagctttc tcggatcgtc tgataataaa   1980
aataaagtaa tcaaagcgat caataacgct cttaaagaaa gagacgaaaa atggaaagag   2040
gtgtactcat ttattgtcag caattggatg acgaaaatta acacacagtt taacaagcgc   2100
aaagaacaga tgtaccaggc tctccagaac caggttaatg cgatcaaaac cattatcgaa   2160
tcaaaataca attcttatac gctggaagag aagaacgagc tgacgaataa gtacgatatt   2220
aaacagatcg aaaacgaact gaaccagaaa gtgtcgatcg ccatgaataa catcgatagg   2280
tttcttacag aaagctcgat ctcatacttg atgaaactga tcaatgaggt gaagattaat   2340
aaattgcgcg agtacgatga aaacgtcaag acctatctgt taaattatat tatccaacat   2400
ggaagcatcc ttggcgaaag ccaacaggaa ctgaattcta tggtgacaga tacgttaaat   2460
aactcaattc cgtttaaatt gagctcgtac acggacgata agattcttat cagctatttc   2520
aataagttct ttaagaggat taaatcgagc tccgttttga atatgagata caaaaacgat   2580
aagtatgtgg atacgagcgg ctatgattca aacatcaata tcaatggtga tgtgtacaaa   2640
tacccgacga ataagaacca atttgggatt tataacgaca agctttcgga agttaatatt   2700
tcccaaaacg actatattat ctacgataac aaatataaaa atttagcat ctcattctgg   2760
```

-continued

```
gtccggatcc cgaattacga caacaaaatt gtaaacgtca acaatgaata taccattatc   2820

aactgcatga gggataataa cagcggctgg aaggtatccc tgaaccacaa tgagattatc   2880

tggacgctgc aagacaacgc aggaattaac caaaaactgg cgtttaatta cggcaatgcc   2940

aatggcattt ctgattatat caacaaatgg atcttcgtaa cgattacaaa cgatcgcctt   3000

ggagattcaa agctctatat taatggtaac ctgatcgacc agaagtccat tcttaatctt   3060

gggaatattc atgtttctga caacatcctc tttaagattg tgaattgttc gtatacgcgg   3120

tatatcggca tccgttactt taatattttc gacaaagaat tagatgaaac cgaaattcaa   3180

acactttatt cgaatgaacc taatacgaac attcttaagg acttctgggg taattatttg   3240

ttatatgata aggagtatta ccttctgaat gtgctgaaac cgaacaattt catcgaccgt   3300

cgcaaagact ccaccctgtc aatcaataac atccgcagca cgattttact tgcgaacagg   3360

ttatatagcg ggatcaaagt caaaatccaa agagtaaata actcttccac aaatgacaat   3420

ttagttagaa aaaatgacca ggtttatatc aactttgtag catcaaagac ccatttgttt   3480

ccgttatatg ccgatacagc tacgaccaat aaggaaaaaa cgatcaaaat ttcatctagc   3540

ggaaaccgct ttaatcaagt cgttgtgatg aacagcgtcg gcaataactg cacaatgaac   3600

ttcaaaaata acaatggaaa caacatcgga ttgctcggtt ttaaagcaga taccgtagtc   3660

gcatctacgt ggtattatac acatatgcgt gatcatacga actcaaacgg gtgcttctgg   3720

aactttatct cggaagaaca cggatggcag gaaaaataa                          3759
```

```
<210> SEQ ID NO 14
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, B. subtilis-modified 1

<400> SEQUENCE: 14
```

```
atgcccaaga taaattcgtt taactacaac gatcctgtga atgatcgtac gattctttat     60

ataaaaccgg gaggctgtca ggagttttat aaatcgttca acattatgaa aaatatttgg    120

attatcccgg agcgcaatgt gataggaaca acgcctcaag actttcatcc acctacctca    180

ctgaaaaacg gtgattcgag ttattacgat cccaattatt tacagagtga tgaggaaaaa    240

gacagatttc ttaaaattgt tactaaaatt tttaaccgta tcaataacaa tctgtcagga    300

gggatcttac tggaagagct tagtaaagcg aacccgtatc ttgggaatga taatactcct    360

gacaatcagt tccatattgg agacgcttca gcagtcgaga taaaattttc taatgggagc    420

caagacattc tgcttccgaa cgttattatc atgggtgcag aacccgatct gtttgaaacc    480

aatagcagta atatctctct gagaaataac tatatgccgt ccaaccacgg ctttgggagc    540

attgcaattg ttacgttttc tcctgaatat tcttttcgct tcaatgacaa tagcatgaac    600

gaatttatcc aggacccggc gttaacgtta atgcacgaac tcatccatag ccttcatggc    660

ctctatggag caaagggaat tacaacgaaa tatactatca ctcaaaagca aaacccattg    720

ataactaaca tcagaggcac aaacattgaa gagttcctga cattcggcgg aaccgattta    780

aatatcatta caagtgctca gagtaatgat atttatacga acctgctcgc tgattataaa    840

aagattgcat ctaagctgtc taaagtccag gtgtctaatc ctctactcaa cccgtacaaa    900

gatgtgtttg aagctaagta tggactagac aaagatgcct ccggtatcta tagcgtcaac    960
```

-continued

```
attaacaaat ttaatgatat cttcaaaaag ttatattctt ttacagagtt tgacttagcg   1020
acaaaatttc aggttaagtg caggcagacc tacattggcc agtataaata ctttaagctt   1080
tcaaacctgc ttaacgattc gatttacaac atcagcgagg gctataatat taacaattta   1140
aaagtaaatt tccgaggtca aaacgcgaac cttaatccgc gcattataac accgattaca   1200
ggacggggcc tggtgaaaaa gatcattaga ttttgtaaga acattgtatc cgtgaaagga   1260
atccggaaaa gtatatgtat cgaaatcaac aatggtgagt tatttttcgt agcgtctgaa   1320
aattcttaca acgatgacaa catcaacaca ccaaaagaaa ttgacgatac agtcacttca   1380
aataacaatt atgaaaatga tttagatcaa gtcattctga acttcaattc ggaaagcgcg   1440
ccaggacttt cagacgaaaa attaaatctg acgatccaaa atgatgcgta tattccgaag   1500
tatgattcta acggcacatc agacatcgaa caacatgatg ttaatgaact gaatgtcttt   1560
ttctatctgg acgctcaaaa ggtcccagag ggcgaaaata acgttaatct tacgtcgtca   1620
atagacacag cacttttgga gcaaccgaag atttatactt tcttttcgag cgaatttatt   1680
aataacgtga ataaaccggt acaagctgcc ctatttgtaa gctggatcca acaggttttg   1740
gtggatttta caacggaggc caaccagaag agcacagttg acaaaatcgc tgatatatct   1800
atcgttgtac catatatcgg acttgcgttg aacatcggca acgaagcaca gaaagggaac   1860
ttcaaggatg ccctagagct cctgggagca gggattttgt tagaattcga acctgagttg   1920
cttataccta caattttagt ttttactata aaatcttttt tgggctccag cgacaataaa   1980
aataaggtca tcaaagcaat caacaatgct ctcaaggagc gggatgaaaa atggaaggaa   2040
gtctacagct tcattgtttc taattggatg acaaagatta atacccaatt caataaacga   2100
aaagaacaaa tgtaccaagc gcttcagaat caggtaaatg ccatcaagac tattatcgag   2160
agcaaataca actcctatac acttgaagag aaaaatgaac tgacaaataa atatgatatt   2220
aaacaaattg agaatgaatt gaaccagaag gttagcattg cgatgaataa cattgacaga   2280
tttctcacag aaagctcaat ctcatattta atgaaattga ttaacgaggt aaaaattaat   2340
aaattgcgcg aatatgatga aaatgtcaaa acgtacctcc tgaactatat cattcaacat   2400
ggaagcatct tgggagaatc acaacaggaa ttgaattcaa tggtaaccga tacgttaaat   2460
aactccatcc cgtttaaact gtcatcctac acagatgaca aaatcttgat cagttatttt   2520
aacaagttct ttaagcgaat caagtcctct agcgttttaa atatgcgcta caagaacgat   2580
aaatatgttg acacgtcagg gtacgattca aatattaata ttaacgggga tgtatacaaa   2640
tatcctacta acaaaaacca attcggcata tataacgata agttatcgga agtcaatatt   2700
tcacaaaatg attatattat atatgataat aaatataaaa acttttctat cagtttctgg   2760
gtgagaattc caaactatga taacaaaatc gtgaacgtta ataacgaata cacgattatc   2820
aattgcatga gagataataa cagcggctgg aaagtgtcac tgaatcacaa tgaaatcatt   2880
tggacgttgc aagacaatgc aggtattaac caaaagctcg cttttaatta tggtaacgcc   2940
aatggtatta gcgactacat taataaatgg attttcgtga caatcaccaa tgaccgcctg   3000
ggagactcca aactgtatat caatggcaac cttatagacc agaaatcgat actcaatctt   3060
ggtaacattc atgtgtccga taacattctg tttaaaattg tgaattgctc atatacccgg   3120
tacatcggca ttaggtattt taatattttt gataaagaat tggatgaaac agaaatccaa   3180
acactgtact caaatgaacc gaatacgaat attttgaaag atttttgggg caactattta   3240
ctttatgata aagaatatta cttgttaaat gtattaaaac cgaataactt cattgaccgt   3300
aggaaagata gcacacttag cataaataac attcgttcta caatactttt agccaatcgg   3360
```

-continued

```
ctatactccg gcattaaagt gaaaattcag cgcgtcaata actccagtac aaacgataac   3420
cttgttcgta aaaatgatca ggtctacatc aattttgtcg cgtctaaaac gcacctcttt   3480
cctctttatg cagatacagc caccacaaat aaagaaaaga cgattaaaat ctcatcttca   3540
ggcaacagat ttaatcaggt tgtcgttatg aactcagtag gtaataactg tacgatgaat   3600
tttaaaaaca ataacggcaa caatatcggg cttctgggat ttaaagccga taccgtggtc   3660
gcttcgacgt ggtactatac tcacatgcgt gaccatacca attccaatgg ttgcttttgg   3720
aattttattt ctgaggaaca tggatggcag gaaaaataa                         3759
```

<210> SEQ ID NO 15
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, B. subtilis-modified 2

<400> SEQUENCE: 15

```
atgccgaaaa ttaatagctt taattataat gatccggtta atgatagaac aattctgtat     60
attaaaccgg gcggctgtca agaattttat aaaagcttta atattatgaa aaatatttgg    120
attattccgg aaagaaatgt tattggcaca acaccgcaag attttcatcc gccgacaagc    180
ctgaaaaatg gcgatagcag ctattatgat ccgaattatc tgcaaagcga tgaagaaaaa    240
gatagatttc tgaaaattgt tacaaaaatt tttaatagaa ttaataataa tctgagcggc    300
ggcattctgc tggaagaact gagcaaagca aatccgtatc tgggcaatga taatacaccg    360
gataatcaat ttcatattgg cgatgcaagc gcagttgaaa ttaaatttag caatggcagc    420
caagatattc tgctgccgaa tgttattatt atgggcgcag aaccggatct gtttgaaaca    480
aatagcagca atattagcct gagaaataat tatatgccga gcaatcatgg ctttggcagc    540
attgcaattg ttacatttag cccggaatat agctttagat ttaatgataa tagcatgaat    600
gaatttattc aagatccggc actgacactg atgcatgaac tgattcatag cctgcatggc    660
ctgtatggcg caaaaggcat tacaacaaaa tatacaatta cacaaaaaca aaatccgctg    720
attacaaata ttagaggcac aaatattgaa gaatttctga catttggcgg cacagatctg    780
aatattatta caagcgcaca aagcaatgat atttatacaa atctgctggc agattataaa    840
aaaattgcaa gcaaactgag caaagttcaa gttagcaatc cgctgctgaa tccgtataaa    900
gatgtttttg aagcaaaata tggcctggat aaagatgcaa gcggcattta tagcgttaat    960
attaataaat ttaatgatat ttttaaaaaa ctgtatagct ttacagaatt tgatctggca   1020
acaaaatttc aagttaaatg tagacaaaca tatattggcc aatataaata ttttaaactg   1080
agcaatctgc tgaatgatag catttataat attagcgaag gctataatat taataatctg   1140
aaagttaatt ttagaggcca aaatgcaaat ctgaatccga gaattattac accgattaca   1200
ggcagaggcc tggttaaaaa aattattaga ttttgtaaaa atattgttag cgttaaaggc   1260
attagaaaaa gcatttgtat tgaaattaat aatggcgaac tgttttttgt tgcaagcgaa   1320
aatagctata atgatgataa tattaataca ccgaaagaaa ttgatgatac agttacaagc   1380
aataataatt atgaaaatga tctggatcaa gttattctga attttaatag cgaaagcgca   1440
ccgggcctga gcgatgaaaa actgaatctg acaattcaaa atgatgcata tattccgaaa   1500
tatgatagca atggcacaag cgatattgaa caacatgatg ttaatgaact gaatgttttt   1560
```

-continued ttttatctgg atgcacaaaa agttccggaa ggcgaaaata atgttaatct gacaagcagc 1620
attgatacag cactgctgga acaaccgaaa atttatacat tttttagcag cgaatttatt 1680
aataatgtta ataaaccggt tcaagcagca ctgtttgtta gctggattca acaagttctg 1740
gttgatttta caacagaagc aaatcaaaaa agcacagttg ataaaattgc agatattagc 1800
attgttgttc cgtatattgg cctggcactg aatattggca atgaagcaca aaaaggcaat 1860
tttaaagatg cactggaact gctgggcgca ggcattctgc tggaatttga accggaactg 1920
ctgattccga caattctggt ttttacaatt aaaagctttc tgggcagcag cgataataaa 1980
aataaagtta ttaaagcaat taataatgca ctgaaagaaa gagatgaaaa atggaaagaa 2040
gtttatagct ttattgttag caattggatg acaaaaatta atacacaatt taataaaaga 2100
aaagaacaaa tgtatcaagc actgcaaaat caagttaatg caattaaaac aattattgaa 2160
agcaaatata atagctatac actggaagaa aaaaatgaac tgacaaataa atatgatatt 2220
aaacaaattg aaaatgaact gaatcaaaaa gttagcattg caatgaataa tattgataga 2280
tttctgacag aaagcagcat tagctatctg atgaaactga ttaatgaagt taaaattaat 2340
aaactgagag aatatgatga aaatgttaaa acatatctgc tgaattatat tattcaacat 2400
ggcagcattc tgggcgaaag ccaacaagaa ctgaatagca tggttacaga tacactgaat 2460
aatagcattc cgtttaaact gagcagctat acagatgata aaattctgat tagctatttt 2520
aataaatttt ttaaaagaat taaaagcagc agcgttctga atatgagata taaaaatgat 2580
aaatatgttg atacaagcgg ctatgatagc aatattaata ttaatggcga tgtttataaa 2640
tatccgacaa ataaaaatca atttggcatt tataatgata aactgagcga agttaatatt 2700
agccaaaatg attatattat ttatgataat aaatataaaa attttagcat tagcttttgg 2760
gttagaattc cgaattatga taataaaatt gttaatgtta ataatgaata tacaattatt 2820
aattgtatga gagataataa tagcggctgg aaagttagcc tgaatcataa tgaaattatt 2880
tggacactgc aagataatgc aggcattaat caaaaactgg catttaatta tggcaatgca 2940
aatggcatta gcgattatat taataaatgg attttttgtta caattacaaa tgatagactg 3000
ggcgatagca aactgtatat taatggcaat ctgattgatc aaaaaagcat tctgaatctg 3060
ggcaatattc atgttagcga taatattctg tttaaaattg ttaattgtag ctatacaaga 3120
tatattggca ttagatattt taatattttt gataaagaac tggatgaaac agaaattcaa 3180
acactgtata gcaatgaacc gaatacaaat attctgaaag atttttgggg caattatctg 3240
ctgtatgata aagaatatta tctgctgaat gttctgaaac cgaataattt tattgataga 3300
agaaaagata gcacactgag cattaataat attagaagca caattctgct ggcaaataga 3360
ctgtatagcg gcattaaagt taaaattcaa agagttaata atagcagcac aaatgataat 3420
ctggttagaa aaaatgatca agtttatatt aattttgttg caagcaaaac acatctgttt 3480
ccgctgtatg cagatacagc aacaacaaat aaagaaaaaa caattaaaat tagcagcagc 3540
ggcaatagat ttaatcaagt tgttgttatg aatagcgttg gcaataattg tacaatgaat 3600
tttaaaaata ataatggcaa taatattggc ctgctgggct ttaaagcaga tacagttgtt 3660
gcaagcacat ggtattatac acatatgaga gatcatacaa atagcaatgg ctgtttttgg 3720
aattttatta gcgaagaaca tggctggcaa gaaaaataa 3759

<210> SEQ ID NO 16
<211> LENGTH: 3759
<212> TYPE: DNA
<213> ORGANISM: Artificial Sequence -continued
<220> FEATURE:
<221> NAME/KEY: mat_peptide
<222> LOCATION: (1)...(3756)
<223> OTHER INFORMATION: BoNT/E, B. subtilis-modified 3

<400> SEQUENCE: 16
atgccgaaga tcaattcatt taactataac gatccggtca atgatcgtac aattctgtat 60
attaaaccag gcgggtgtca agagttctat aaatcgttta atattatgaa aaatatctgg 120
atcattcctg aacgcaatgt tattggtaca acgcctcaag actttcatcc tccgacttct 180
cttaaaaacg gggactctag ctactatgac ccgaactact tgcaatcgga cgaggaaaaa 240
gaccggtttt tgaagattgt caccaaaatt ttcaatcgca ttaacaataa cctgtccggc 300
ggtatcttac tggaagagct ttcaaaagcc aatccttacc tgggaaatga taatacaccg 360
gataatcaat ttcatattgg agatgccagt gctgtcgaaa tcaaatttag caatgggagc 420
caagatattc tgttaccgaa tgttatcatt atgggagctg agccggatct gtttgaaacc 480
aattcttcga atattagcct tcggaataac tatatgccga gcaatcacgg atttggctcc 540
attgcaattg tcacgttcag cccggaatac tctttcagat ttaacgataa ttccatgaat 600
gagtttatcc aagatccggc gctcacactg atgcacgaac tgattcattc gttgcacggc 660
ctgtatggag caaagggaat cacgacaaaa tacactatta cacaaaaaca gaatcctctt 720
attacgaata ttcgaggaac taacattgaa gagttcttaa cctttggagg cacagactta 780
aatattatca catcagctca gagtaacgac atctacacga atctgcttgc tgactataag 840
aaaatcgcct ctaaattatc aaaagttcaa gtatctaatc cgttactgaa cccgtacaaa 900
gacgtgtttg aagccaaata tgggctggac aaagatgctt ctggaattta ttctgtaaac 960
atcaataagt tcaacgacat ttttaagaaa ttatactcct tcaccgagtt cgatttggcg 1020
acgaaatttc aggtcaaatg caggcaaacg tacattggac aatataagta cttcaaattg 1080
tctaatcttc tgaacgacag tatctataac atttcagaag ggtataatat taacaattta 1140
aaggttaatt tccgcggaca aaacgctaat cttaatccaa gaatcattac gccgatcaca 1200
ggtaggggtc ttgtgaaaaa gattatccgc ttttgtaaaa atatcgtatc tgtgaaaggt 1260
atccgtaaat caatttgtat cgaaattaat aacggagaac tgttctttgt agcctcagaa 1320
aattcatata acgacgataa catcaacact ccgaaggaga tcgatgacac cgtcacatct 1380
aataacaatt atgaaaacga tctcgatcag gttattttaa attttaacag tgaatccgct 1440
ccaggattga gcgacgaaaa gctcaacctt acgattcaga acgatgccta catcccgaaa 1500
tatgattcga acggtacgag tgatattgaa cagcatgatg ttaacgagct caatgtcttt 1560
ttctatcttg atgcacagaa agtacctgaa ggcgagaaca atgtgaatct cacatccagc 1620
attgacacag cgctgctcga acaaccgaag atttacacgt tctttagttc agagtttatt 1680
aataacgtga ataaacctgt gcaggctgca ctttttgtat cttggatcca acaggttctc 1740
gtggacttca caactgaagc aaaccaaaaa agtaccgtcg acaaaattgc tgatatttca 1800
atcgtcgtac catatattgg gctggcgtta aatattggta acgaagcaca gaaaggcaat 1860
tttaaagacg cgcttgaact gcttggtgca ggcatcctcc ttgaattcga accggaatta 1920
cttatcccaa caatcctggt ttttactatt aaatcatttc tgggtagctc ggataacaag 1980
aacaaagtga tcaaagcgat taataacgcg cttaaggaac gagatgagaa gtggaaagaa 2040
gtgtatagct ttattgttag caattggatg acaaaaatta atacacagtt caataagcgg 2100
aaagaacaaa tgtaccaagc cctgcaaaat caggttaacg caatcaaaac gattatcgag 2160

-continued

```
tcgaagtaca actcttacac actggaagag aaaaatgagc tgacaaacaa atacgacatt   2220

aaacaaattg agaatgaact taatcagaaa gtgtccattg cgatgaataa cattgatagg   2280

tttctgaccg aaagcagtat ttcctatctg atgaaattga ttaacgaagt taaaatcaac   2340

aaactcagag aatacgatga aaacgtgaag acatatcttt tgaattatat tatccaacac   2400

ggcagtattc tgggggaaag ccagcaagaa ttgaacagca tggtaacaga cacgttaaat   2460

aactccattc cttttaaact tagctcctat acagatgaca aaattttaat tagctacttt   2520

aacaagtttt tcaaaagaat taaatcgagc tctgtgctta atatgcgata caaaaatgat   2580

aagtatgtgg acacttctgg ctacgactcc aacattaaca tcaatggcga tgtctataaa   2640

tatccaacaa ataaaaatca gtttggcatt tataacgata aactgtcaga agtcaatatc   2700

tctcagaacg attatatcat ttatgataac aaatataaaa acttctcaat ctcattttgg   2760

gtaagaattc cgaactatga taataaaatc gttaacgtta acaatgaata tacaatcatt   2820

aattgtatga gagataataa ctcaggatgg aaggtaagcc ttaatcataa tgagatcatt   2880

tggacattgc aagataatgc tggcattaac caaaagctgg catttaatta tggtaatgcc   2940

aacggaatta gcgattacat taataaatgg atttttgtca ctattaccaa tgatcgtttg   3000

ggcgactcca agctttatat taacggcaac ttgattgatc agaaatctat tctgaatttg   3060

ggcaatatcc atgtatcaga taacatctta tttaaaattg tgaattgcag ctacactcgc   3120

tatatcggga ttcggtattt taatattttc gataaggaat tagatgagac ggaaattcag   3180

accctgtatt caaacgagcc taataccaac attctgaagg atttttgggg caattattta   3240

ttgtatgata aagaatatta cttgcttaac gtcctcaagc ctaacaattt tatcgatcgc   3300

agaaaggatt ctacattaag catcaacaat attcgctcaa caattttgtt agcaaaccgt   3360

ctttattctg gtattaaggt taaaattcag agagttaaca atagttcaac taacgataac   3420

ttagttcgga aaaatgacca ggtgtatatc aattttgttg ccagcaaaac acatttgttc   3480

ccattatatg cggatactgc gacgacaaat aaagaaaaaa caatcaagat ctcctcgtca   3540

ggaaaccgtt ttaatcaggt cgttgtgatg aattcagtcg gcaataactg caccatgaat   3600

tttaaaaaca ataacggaaa taacattgga ctcttaggct ttaaagcgga cacggtcgta   3660

gcatcgacgt ggtattatac gcatatgcgt gatcacacga attcaaatgg ctgcttttgg   3720

aattttattt ctgaagagca tgggtggcaa gaaaaataa                          3759
```

```
<210> SEQ ID NO 17
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, C. difficile-modified 1

<400> SEQUENCE: 17
```

```
atgcctaaaa ttaattcttt taattataat gatcctgtta acgatagaac aatattatat     60

attaaaccgg gtgggtgtca ggagttttat aaatctttta atataatgaa gaatatatgg    120

ataattcctg aaagaaatgt tataggaacg acacctcaag attttcaccc acctacgagt    180

cttaaaaatg gggactctag ttattacgat ccaaattatc tacagtcaga tgaagagaag    240

gacagatttt taaaaattgt tactaaaatt tttaatcgta ttaataacaa tttatcagga    300

ggtattttac ttgaagagct atctaaagca aacccatatc tggggaatga taatacacca    360

gataatcaat ttcatattgg agacgctagt gccgtagaaa ttaaatttag caatggttct    420
```

-continued

```
caggatatct tgctgccaaa tgtaattatc atgggagctg aaccagattt atttgagacc    480
aattcttcca atataagcct tagaaacaat tatatgcctt ctaatcacgg ttttggatca    540
attgcaattg ttacattttc gccagaatat tcttttagat ttaatgacaa ctctatgaac    600
gaatttatac aagatcctgc tttaacacta atgcacgagt taatacactc tcttcatgga    660
ttgtatggtg caaaaggtat tactacaaag tatactatta cacaaaaaca gaatcctcta    720
ataacaaaca tacgtggtac aaatatagaa gagtttctaa catttggagg tacagatctt    780
aatataatta cttcagctca atcaaacgat atatatacga atttgttagc tgattacaaa    840
aagattgcta gcaaattaag caaagtacaa gtctcaaatc cattacttaa tccatataaa    900
gatgtatttg aagctaaata tggtttagat aaggatgcat caggtatata ttcagtgaac    960
ataaacaaat ttaatgatat atttaaaaag ctctattcat tcactgaatt tgacttagca   1020
acaaaatttc aagtaaaatg tagacaaact tatattggac agtataagta ttttaagctt   1080
tctaacttac taaatgattc tatttataat atatctgaag gatataacat taataacctt   1140
aaagttaatt ttagaggcca aaatgctaac ttgaatccta gaattataac tccaataact   1200
ggaagaggat tagtaaaaaa gattataaga ttttgtaaaa atattgtatc agttaaagga   1260
attagaaaat caatttgcat cgaaatcaat aacggagaac tatttttcgt agcatccgaa   1320
aactcataca atgatgacaa cataaataca cctaaagaaa tagatgacac tgtaacaagt   1380
aataacaatt atgaaaatga tctagatcaa gtaatactaa attttaattc tgaatcagct   1440
ccaggtttat cagatgaaaa attaaatcta acaatacaga atgacgctta tatcccaaaa   1500
tatgattcaa atggtactag tgatatagag caacatgatg taaatgaatt aaatgtgttt   1560
ttctatttag atgctcagaa ggtacctgaa ggagaaaaca atgttaatct gactagctca   1620
attgataccg cattactcga acaacctaaa atttatacat tttcagttc agaatttata    1680
aataacgtta ataaacctgt acaagcagcg ttatttgtat cgtggattca acaggtatta   1740
gtcgatttta ctacagaagc aaatcaaaaa tcaactgtag ataaaatagc cgatataagt   1800
attgtggtac catatatagg attagcacta aacataggca atgaagctca aaaagggaat   1860
tttaaagatg cattagagct gttaggcgct ggaattttat tggagtttga gccagaatta   1920
cttataccta ctatcttagt tttcacaata aaaagtttct taggaagttc tgacaataaa   1980
aataaagtta tcaaagcaat aaacaatgct ttaaaagaaa gagacgaaaa atggaaggaa   2040
gtttatagtt ttatagtatc caattggatg actaaaatta atacacaatt taataagcgc   2100
aaggaacaaa tgtaccaagc acttcaaaat caagtgaatg ctattaaaac tataattgag   2160
tctaaatata atagttatac attggaagag aaaaatgaat taacaaataa gtatgatatt   2220
aaacaaatag aaaatgaatt aaatcaaaaa gttagtattg ctatgaataa catagataga   2280
ttccttactg aatctagtat atcatattta atgaaattaa taaatgaagt aaagattaat   2340
aaattaagag aatatgacga aaatgtaaaa acttatttat tgaattatat aatccaacat   2400
ggttctattt tgggtgaaag tcaacaagaa ttaaattcta tggtaactga tactttaaat   2460
aacagtatac catttaaatt aagttcttat acagatgaca aaattttaat ttcttatttt   2520
aataaatttt tcaaaagaat aaaatctagc tcagttctta atatgaggta taaaaatgat   2580
aagtatgttg atacctctgg atacgattca aatattaata ttaacggtga tgtgtataaa   2640
tatccaacaa ataaaaatca attcggtata tataatgata aattaagtga agttaatata   2700
agtcaaaatg attatatcat atacgataat aaatataaaa attttagtat atctttttgg   2760
```

-continued

```
gtgagaatac ccaattatga taacaaaata gttaatgtaa ataacgagta tactattata   2820

aactgtatgc gagataataa ctctggatgg aaagtttctt tgaatcataa tgaaataatc   2880

tggactttac aagataatgc aggaattaat caaaaattag cctttaatta tggtaatgca   2940

aatggaatta gtgattacat taataaatgg atatttgtta cgataactaa cgataggtta   3000

ggtgatagta aactttacat aaatggaaat ttaattgatc aaaagtcaat tttaaatctt   3060

ggtaatatac atgttagtga taatatatta tttaaaatag taaattgttc atatactaga   3120

tatataggaa taagatattt taatatattt gataaagaac ttgatgaaac agaaattcaa   3180

acactttact caaatgaacc taatactaat attttaaaag atttttgggg aaattattta   3240

ttgtacgata aagaatacta tcttttaaat gtactaaaac caaataattt tatagataga   3300

cgaaaagata gtactttatc aataaataat ataagaagta caatattatt ggcaaatcgt   3360

ttatacagtg gaataaaggt aaagatacaa cgtgttaata attcatctac taatgataat   3420

ttagttcgga aaaatgatca agtatatata aattttgtag catctaaaac tcatttattc   3480

cctttatatg ctgatactgc aactaccaat aaagaaaaaa ctataaagat aagttctagt   3540

ggtaatagat ttaatcaagt agttgtcatg aattctgttg gcaataattg tactatgaat   3600

ttcaaaaata ataatggtaa taatattggt ttattaggat ttaaggctga tacagttgtt   3660

gcaagtactt ggtattatac acatatgaga gatcatacta atagtaatgg ttgcttttgg   3720

aattttatat cagaagaaca tggatggcaa gaaaaataa                          3759
```

<210> SEQ ID NO 18
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, C. difficile-modified 2

<400> SEQUENCE: 18

```
atgccaaaaa taaattcttt taattataat gatccagtaa atgatagaac tatattatat     60

ataaaaccag gaggatgtca agaattttat aaatctttta atataatgaa aaatatatgg    120

ataataccag aaagaaatgt aataggaact actccacaag attttcatcc accaacttct    180

ttaaaaaatg gagattcttc ttattatgat ccaaattatt tacaatctga tgaagaaaaa    240

gatagatttt taaaaatagt aactaaaata tttaatagaa taaataataa tttatctgga    300

ggaatattat tagaagaatt atctaaagca aatccatatt taggaaatga taatactcca    360

gataatcaat ttcatatagg agatgcatct gcagtagaaa taaaattttc taatggatct    420

caagatatat tattaccaaa tgtaataata atgggagcag aaccagattt atttgaaact    480

aattcttcta atatatcttt aagaaataat tatatgccat ctaatcatgg atttggatct    540

atagcaatag taacttttc tccagaatat tcttttagat ttaatgataa ttctatgaat    600

gaatttatac aagatccagc attaacttta atgcatgaat taatacattc tttacatgga    660

ttatatggag caaaaggaat aactactaaa tatactataa ctcaaaaaca aaatccatta    720

ataactaata taagaggaac taatatagaa gaatttttaa cttttggagg aactgattta    780

aatataataa cttctgcaca atctaatgat atatatacta atttattagc agattataaa    840

aaaatagcat ctaaattatc taaagtacaa gtatctaatc cattattaaa tccatataaa    900

gatgtatttg aagcaaaata tggattagat aaagatgcat ctggaatata ttctgtaaat    960

ataaataaat ttaatgatat atttaaaaaa ttatattctt ttactgaatt tgatttagca   1020
```

-continued

```
actaaatttc aagtaaaatg tagacaaact tatataggac aatataaata ttttaaatta   1080
tctaatttat taaatgattc tatatataat atatctgaag gatataatat aaataattta   1140
aaagtaaatt ttagaggaca aaatgcaaat ttaaatccaa gaataataac tccaataact   1200
ggaagaggat tagtaaaaaa aataataaga ttttgtaaaa atatagtatc tgtaaaagga   1260
ataagaaaat ctatatgtat agaaataaat aatggagaat tattttttgt agcatctgaa   1320
aattcttata atgatgataa tataaatact ccaaaagaaa tagatgatac tgtaacttct   1380
aataataatt atgaaaatga tttagatcaa gtaatattaa attttaattc tgaatctgca   1440
ccaggattat ctgatgaaaa attaaattta actatacaaa atgatgcata tataccaaaa   1500
tatgattcta atggaacttc tgatatagaa caacatgatg taaatgaatt aaatgtattt   1560
ttttatttag atgcacaaaa agtaccagaa ggagaaaata atgtaaattt aacttcttct   1620
atagatactg cattattaga acaaccaaaa atatatactt ttttttcttc tgaatttata   1680
aataatgtaa ataaaccagt acaagcagca ttatttgtat cttggataca acaagtatta   1740
gtagatttta ctactgaagc aaatcaaaaa tctactgtag ataaaatagc agatatatct   1800
atagtagtac catatatagg attagcatta aatataggaa atgaagcaca aaaaggaaat   1860
tttaaagatg cattagaatt attaggagca ggaatattat tagaatttga accagaatta   1920
ttaataccaa ctatattagt atttactata aaatcttttt taggatcttc tgataataaa   1980
aataaagtaa taaaagcaat aaataatgca ttaaaagaaa gagatgaaaa atggaaagaa   2040
gtatattctt ttatagtatc taattggatg actaaaataa atactcaatt taataaaaga   2100
aaagaacaaa tgtatcaagc attacaaaat caagtaaatg caataaaaac tataatagaa   2160
tctaaatata attcttatac tttagaagaa aaaaatgaat taactaataa atatgatata   2220
aaacaaatag aaaatgaatt aaatcaaaaa gtatctatag caatgaataa tatagataga   2280
tttttaactg aatcttctat atcttattta atgaaattaa taaatgaagt aaaaataaat   2340
aaattaagag aatatgatga aaatgtaaaa acttatttat taaattatat aatacaacat   2400
ggatctatat taggagaatc tcaacaagaa ttaaattcta tggtaactga tactttaaat   2460
aattctatac catttaaatt atcttcttat actgatgata aaatattaat atcttatttt   2520
aataaatttt ttaaaagaat aaaatcttct tctgtattaa atatgagata taaaaatgat   2580
aaatatgtag atacttctgg atatgattct aatataaata taaatggaga tgtatataaa   2640
tatccaacta ataaaaatca atttggaata tataatgata aattatctga agtaaatata   2700
tctcaaaatg attatataat atatgataat aaatataaaa atttttctat atctttttgg   2760
gtaagaatac caaattatga taataaaata gtaaatgtaa ataatgaata tactataaat   2820
aattgtatga gagataataa ttctggatgg aaagtatctt taaatcataa tgaaataata   2880
tggactttac aagataatgc aggaataaat caaaaattag catttaatta tggaaatgca   2940
aatggaatat ctgattatat aaataaatgg atatttgtaa ctataactaa tgatagatta   3000
ggagattcta aattatatat aaatggaaat ttaatagatc aaaaatctat attaaattta   3060
ggaaatatac atgtatctga taatatatta tttaaaatag taaattgttc ttatactaga   3120
tatataggaa taagatattt taatatattt gataaagaat tagatgaaac tgaaatacaa   3180
actttatatt ctaatgaacc aaatactaat atattaaaag atttttgggg aaattattta   3240
ttatatgata aagaatatta tttattaaat gtattaaaac caaataattt tatagataga   3300
agaaaagatt ctactttatc tataaataat ataagatcta ctatattatt agcaaataga   3360
```

-continued

```
ttatattctg gaataaaagt aaaaatacaa agagtaaata attcttctac taatgataat   3420

ttagtaagaa aaaatgatca agtatatata aattttgtag catctaaaac tcatttattt   3480

ccattatatg cagatactgc aactactaat aaagaaaaaa ctataaaaat atcttcttct   3540

ggaaatagat ttaatcaagt agtagtaatg aattctgtag gaaataattg tactatgaat   3600

tttaaaaata ataatggaaa taatatagga ttattaggat ttaaagcaga tactgtagta   3660

gcatctactt ggtattatac tcatatgaga gatcatacta attctaatgg atgtttttgg   3720

aattttatat ctgaagaaca tggatggcaa gaaaaataa                           3759
```

<210> SEQ ID NO 19
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, C. difficile-modified 3

<400> SEQUENCE: 19

```
atgcctaaaa ttaattcttt taattataat gatccagtaa atgatagaac aatactatat     60

attaaacctg gtggatgtca agaattttat aaatcattta atattatgaa aaatatatgg    120

ataattcctg aaagaaatgt tataggaact acaccacaag attttcatcc tccaactagt    180

cttaaaaatg gtgattcttc atattatgat ccaaattatc tacaatctga tgaagaaaaa    240

gatagatttt taaaaattgt aactaaaata tttaatagaa taaataataa tttatctggt    300

ggaattttac tagaagaatt atcaaaagct aatccatatt taggaaatga taatactcct    360

gataatcaat ttcatattgg agatgcaagt gctgtagaaa taaaattttc taatggtagt    420

caagatatat tattgccaaa tgtaattata atgggtgcag aaccagattt atttgaaaca    480

aatagttcaa atattagttt aagaaataat tatatgccat ctaatcatgg atttggttct    540

atagctattg taacttttag tccagaatat agttttagat ttaatgataa ttctatgaat    600

gaatttatac aagatcctgc tttaacatta atgcacgaat taatacattc tctacatggt    660

ttatatggtg ctaaaggaat aactacaaaa tatactatta ctcaaaaaca aaatcctcta    720

attacaaata ttagaggaac taatatagaa gaatttttaa cttttggtgg aactgatcta    780

aatattataa cttcagcaca atctaatgat atatatacta atttacttgc tgattataaa    840

aaaattgctt ctaaactttc taaagttcaa gtttcaaatc cattactaaa tccatataaa    900

gatgtatttg aagctaaata tggacttgat aaagatgcaa gtggaattta ttcagttaat    960

attaataaat ttaatgatat ttttaaaaaa ttatattcat ttacagaatt tgatttagca   1020

actaaatttc aagttaaatg tagacaaaca tatattggtc aatataaata ttttaaatta   1080

agtaatcttt taaatgattc tatatataat atatcagaag gttataatat aaataatctt   1140

aaagtaaatt ttagaggtca aaatgcaaat ttgaatcctc gtataattac tcctataaca   1200

ggtagaggat tagttaaaaa aataattaga ttttgtaaaa atatagtaag tgtaaaaggt   1260

attagaaaaa gtatatgtat tgaaattaat aatggagaat tattttttgt agcatctgaa   1320

aattcatata atgatgataa tataaatact cctaaagaaa tagatgatac tgtaacttca   1380

aataataatt atgaaaatga tttagatcaa gttatattaa attttaatag tgaatctgct   1440

cctggacttt ctgatgaaaa attaaattta actattcaaa atgatgcata tattccaaaa   1500

tatgattcaa atggtacttc tgatatagaa caacacgatg taaatgaatt aaatgtattt   1560

ttttatttag atgcacaaaa agtaccagaa ggagaaaata atgttaattt aacttcttca   1620
```

-continued

```
atagatactg cattgttaga acaaccaaaa atatatacat ttttttcatc tgaatttata   1680
aataatgtta ataaacctgt acaagctgca ctatttgtta gttggattca acaagtttta   1740
gtagatttta caactgaagc aaatcaaaaa tcaactgtag ataaaatagc agatatttct   1800
atagtagttc cttatattgg tttggcattg aatattggaa atgaagcaca aaaaggaaat   1860
tttaaagatg cattggaatt actaggagct ggaatacttt tagaatttga acctgaattg   1920
cttataccaa ctattttagt atttacaata aaatcttttc ttggatcaag tgataataaa   1980
aataaagtaa taaaagcaat aaataatgca ttaaaagaaa gagatgaaaa atggaaagaa   2040
gtttatagtt ttatagtttc taattggatg actaaaataa atactcaatt taataaaaga   2100
aaagaacaaa tgtatcaagc tttacaaaat caagtaaatg ctataaaaac aataattgaa   2160
tcaaaatata attcttatac tttagaagaa aaaaatgaat taacaaataa atatgatata   2220
aaacaaatag aaaatgaatt aaatcaaaaa gtaagtatag ctatgaataa tatagataga   2280
tttttaactg aatcttcaat ttcttatctt atgaaactta taaatgaagt aaaaattaat   2340
aaattgagag aatatgatga aaatgtaaaa acttatttac ttaattatat tatacaacat   2400
ggatctatat taggtgaatc tcaacaagaa ttaaattcaa tggttactga tacattaaat   2460
aattcaattc cttttaaatt atcttcatat actgatgata aaatacttat atcttatttt   2520
aataaatttt ttaaacgtat taaatcttca tctgttttaa atatgagata taaaaatgat   2580
aaatatgttg atacaagtgg atatgatagt aatataaata taaatggaga tgtatataaa   2640
tatccaacaa ataaaaatca atttggaatt tataatgata aattatcaga agttaatata   2700
tctcaaaatg attatattat atatgataat aaatataaaa atttttcaat aagtttttgg   2760
gtaagaattc caaattatga taataaaata gtaaatgtaa ataatgaata tacaataatt   2820
aattgtatgc gtgataataa tagtggttgg aaagttagtc ttaatcacaa tgaaataatt   2880
tggactcttc aagataatgc aggaattaat caaaaaattag catttaatta tggtaatgct   2940
aatggaatat ctgattatat taataaatgg atatttgtta caataactaa tgatagatta   3000
ggagatagta aattatatat taatggaaat ttaatagatc aaaaaagtat tttaaatttg   3060
ggaaatatac atgtaagtga taatatatta tttaaaatag ttaattgttc ttatactaga   3120
tatataggaa ttagatattt taatatattt gataaagaac tagatgaaac agaaattcaa   3180
actttatatt ctaatgaacc aaatactaat atattaaaag atttttgggg taattatcta   3240
ttatatgata aagaatatta tcttttgaat gtattgaaac ctaataattt tatagatcgt   3300
agaaaagata gtacattatc tataaataat ataagatcta ctatactatt agctaataga   3360
ttatatagtg gaataaaagt taaaatacaa agagtaaata attcttcaac taatgataat   3420
ttagttagaa aaaatgatca agtttatatt aattttgtag caagtaaaac acatttattt   3480
ccattatatg ctgatacagc aacaactaat aaagaaaaaa ctataaaaat aagttcttca   3540
ggtaatagat ttaatcaagt agttgtaatg aattctgtag gtaataattg tacaatgaat   3600
tttaaaaata ataatggaaa taatatagga ttattaggat ttaaagcaga tactgtagta   3660
gcttcaacat ggtattatac acatatgaga gatcacacaa atagtaatgg atgtttttgg   3720
aattttatat ctgaagaaca tggttggcaa gaaaaataa                          3759
```

<210> SEQ ID NO 20
<211> LENGTH: 3759
<212> TYPE: DNA
<213> ORGANISM: Artificial Sequence
<220> FEATURE:

-continued

<221> NAME/KEY: mat_peptide
<222> LOCATION: (1)...(3756)
<223> OTHER INFORMATION: BoNT/E, C. perfringens-modified 1

<400> SEQUENCE: 20
atgccaaaaa ttaattcttt taactataat gatccagtta atgataggac tatcttatat 60
ataaaacctg gaggttgcca agaattttat aaaagtttta acataatgaa aaatatttgg 120
ataattcctg aaagaaatgt tataggaaca acccctcaag attttcatcc tccaacaagt 180
cttaagaatg gagattcaag ctattacgac ccaaattatt tacaaagtga tgaagagaag 240
gatagatttt taaagatagt tactaaaata tttaacagaa ttaataacaa tttaagcggc 300
ggaattcttt tagaggaatt atctaaagca aatccatatt taggtaatga taatactcct 360
gataatcaat ttcacattgg tgatgctagc gctgtagaga taaaattttc taatggaagt 420
caagatatac ttctaccaaa cgtaattata atgggtgctg aaccagattt attcgaaaca 480
aattcatcta atatatcatt aagaaataac tatatgccat ccaatcacgg attcggaagt 540
atagctatag ttacattttc acctgaatat tcatttagat ttaatgataa cagtatgaat 600
gaatttatac aagatcctgc tttaacatta atgcatgagt taatacattc attacatgga 660
ttatatggag caaaaggaat tactaccaaa tatacaataa cacaaaagca aaaccccttta 720 ataacaaata taagaggaac taatattgaa gagtttttaa cttttggagg tacagattta 780
aatattataa catctgcaca atctaacgat atatatacta atcttttagc tgattataaa 840
aagattgcat caaaactgag caaagttcaa gttagtaatc cacttttaaa tccatataag 900
gatgtgtttg aagctaaata tgggttagat aaagatgcat caggaattta cagcgttaat 960
ataaataagt ttaatgatat attcaaaaag ttatatagtt tcacagaatt tgatttagca 1020
acaaaatttc aagtaaaatg tagacagact tatattggac aatataaata ttttaaatta 1080
agtaatttac ttaatgatag tatctacaat atatcagaag gatataacat taataacttg 1140
aaagtgaatt ttagaggcca aaatgctaat ttaaatccaa gaataattac tcctattact 1200
ggaagaggtt tagtaaaaaa gattataaga ttttgtaaaa atatagtgtc agttaaagga 1260
ataagaaaga gtatttgtat agaaataaat aacggagaac tattctttgt tgcctcagaa 1320
aatagttaca atgatgacaa tattaacact ccaaaagaga tagatgacac agtaacaagc 1380
aataacaatt atgaaaacga tttagaccaa gttatactta attttaattc tgaatcagct 1440
cctgggctat ctgatgagaa acttaattta actatacaaa acgatgcata tataccaaaa 1500
tacgatagta atggtacatc agatatcgaa caacatgatg taaatgaatt aaatgtattt 1560
ttctaccttg atgcccaaaa agttcctgag ggagaaaata acgttaattt aacttcttcc 1620
atagatacag cattactaga acaacctaag atatacactt ttttcagttc tgagtttata 1680
aataacgtta ataaacctgt acaagctgca ctttttgtat cttggattca acaggtttta 1740
gtagatttta ctacagaagc aaaccaaaaa agtactgtag ataaaattgc tgatatatca 1800
attgtagttc catatattgg gcttgcttta aatatcggaa atgaagcaca aaaaggaaat 1860
tttaaagatg ctttagaatt actaggagct ggaatattac ttgagtttga accagagtta 1920
cttataccaa caatattagt atttactatt aagagttttt taggttcttc agataataaa 1980
aataaagtta taaaagctat taataacgct cttaaagaaa gagatgaaaa gtggaaagaa 2040
gtttatagtt ttatagtatc aaattggatg acaaagataa atactcaatt taataagaga 2100
aaagagcaaa tgtatcaggc tctacaaaac caagtaaatg ctataaaaac gataatcgaa 2160
tctaagtata acagttatac attagaggaa aagaatgaac taactaataa atatgatata 2220

-continued aagcaaatag aaaacgaatt aaatcaaaag gtttcaatag caatgaataa cattgataga 2280
tttttaactg aatcaagcat atcatattta atgaagttaa taaatgaagt taaaattaat 2340
aaattaaggg aatatgatga aaatgtaaag acttaccttt taaattacat aattcaacat 2400
ggttcaattt taggtgaatc acaacaggaa ttaaattcta tggtcacaga cactttgaat 2460
aactctatac catttaagtt atcaagttat actgatgaca agatattaat aagttatttt 2520
aataaatttt tcaaaagaat aaaatcttca tctgttctta atatgagata taagaatgat 2580
aaatatgtag atacatctgg ttatgatagt aatattaata taaatggtga tgtatataaa 2640
tatcccacta ataaaaacca gtttggaatt tataatgata aattatcaga agtgaacata 2700
tctcaaaatg attacataat ttatgataat aaatataaaa attttagtat tagtttctgg 2760
gttagaatac ctaattatga caataaaata gtaaatgtaa ataacgaata tacaataatt 2820
aattgtatga gagataataa ctctgggtgg aaagtttcat taaatcataa tgaaataatt 2880
tggacattac aagataatgc tggaataaat caaaaactag cctttaatta tggaaatgct 2940
aatggcatat ctgattatat aaataagtgg atatttgtta ctattactaa tgatagatta 3000
ggagattcaa agttatatat aaatggaaat ttaatagatc aaaaaagtat tttaaattta 3060
ggtaatatac atgtttccga taatatactt tttaagatag ttaattgttc ttacacaaga 3120
tatataggta taagatattt caatatattt gataaagaac tagatgagac tgaaattcag 3180
actttatatt ccaatgaacc aaatactaat atattaaaag atttttgggg taattatctt 3240
ttatatgata aagaatatta tttattgaat gttttgaaac caaataattt tatagacagg 3300
agaaaagatt caactttatc aataaataat attagaagta ctatactttt agcaaataga 3360
ttatatagtg gaataaaagt aaagatacaa agagttaata attcaagcac taatgataat 3420
cttgttagaa aaaatgacca agtatatatt aattttgtag cttcgaaaac ccatttattt 3480
cctttatatg ctgatacagc gacaactaat aaagaaaaga caataaaaat ttctagttct 3540
ggtaatagat ttaatcaagt tgtagttatg aattcagtag gaaataattg tactatgaat 3600
ttcaaaaata ataatggaaa taatatcgga ttacttgggt ttaaagcaga taccgttgtt 3660
gcaagtactt ggtattatac acatatgcgt gatcacacta attcaaatgg atgcttttgg 3720
aatttcattt ctgaggaaca tggatggcaa gaaaaataa 3759

<210> SEQ ID NO 21
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, C. perfringens-modified 2

<400> SEQUENCE: 21
atgccaaaaa taaattcatt taattataat gatccagtta atgatagaac tatattatat 60
ataaaaccag gaggatgtca agaattttat aaatcattta atataatgaa aaatatatgg 120
ataataccag aaagaaatgt tataggaact actccacaag attttcatcc accaacttca 180
ttaaaaaatg gagattcatc atattatgat ccaaattatt tacaatcaga tgaagaaaaa 240
gatagatttt taaaaatagt tactaaaata tttaatagaa taaataataa tttatcagga 300
ggaatattat tagaagaatt atcaaaagct aatccatatt taggaaatga taatactcca 360
gataatcaat ttcatatagg agatgcttca gctgttgaaa taaaattttc aaatggatca 420

-continued

```
caagatatat tattaccaaa tgttataata atgggagctg aaccagattt atttgaaact     480
aattcatcaa atatatcatt aagaaataat tatatgccat caaatcatgg atttggatca     540
atagctatag ttactttttc accagaatat tcatttagat ttaatgataa ttcaatgaat     600
gaatttatac aagatccagc tttaacttta atgcatgaat taatacattc attacatgga     660
ttatatggag ctaaaggaat aactactaaa tatactataa ctcaaaaaca aaatccatta     720
ataactaata taagaggaac taatatagaa gaatttttaa cttttggagg aactgattta     780
aatataataa cttcagctca atcaaatgat atatatacta atttattagc tgattataaa     840
aaaatagctt caaaattatc aaaagttcaa gtttcaaatc cattattaaa tccatataaa     900
gatgtttttg aagctaaata tggattagat aaagatgctt caggaatata ttcagttaat     960
ataaataaat ttaatgatat atttaaaaaa ttatattcat ttactgaatt tgatttagct    1020
actaaatttc aagttaaatg tagacaaact tatataggac aatataaata ttttaaatta    1080
tcaaatttat taaatgattc aatatataat atatcagaag gatataatat aaataattta    1140
aaagttaatt ttagaggaca aaatgctaat ttaaatccaa gaataataac tccaataact    1200
ggaagaggat tagttaaaaa aataataaga ttttgtaaaa atatagtttc agttaaagga    1260
ataagaaaat caatatgtat agaaataaat aatggagaat tattttttgt tgcttcagaa    1320
aattcatata atgatgataa tataaatact ccaaaagaaa tagatgatac tgttacttca    1380
aataataatt atgaaaatga tttagatcaa gttatattaa attttaattc agaatcagct    1440
ccaggattat cagatgaaaa attaaattta actatacaaa atgatgctta tataccaaaa    1500
tatgattcaa atggaacttc agatatagaa caacatgatg ttaatgaatt aaatgttttt    1560
ttttatttag atgctcaaaa agttccagaa ggagaaaata atgttaattt aacttcatca    1620
atagatactg ctttattaga acaaccaaaa atatatactt tttttcatc agaatttata    1680
aataatgtta ataaaccagt tcaagctgct ttatttgttt catggataca acaagtttta    1740
gttgatttta ctactgaagc taatcaaaaa tcaactgttg ataaaatagc tgatatatca    1800
atagttgttc catatatagg attagcttta aatataggaa atgaagctca aaaaggaaat    1860
tttaaagatg ctttagaatt attaggagct ggaatattat tagaatttga accagaatta    1920
ttaataccaa ctatattagt ttttactata aaatcatttt taggatcatc agataataaa    1980
aataaagtta taaaagctat aaataatgct ttaaaagaaa gagatgaaaa atggaaagaa    2040
gtttattcat ttatagtttc aaattggatg actaaaataa atactcaatt taataaaaga    2100
aaagaacaaa tgtatcaagc tttacaaaat caagttaatg ctataaaaac tataatagaa    2160
tcaaaatata attcatatac tttagaagaa aaaaatgaat taactaataa atatgatata    2220
aaacaaatag aaaatgaatt aaatcaaaaa gtttcaatag ctatgaataa tatagataga    2280
tttttaactg aatcatcaat atcatattta atgaaattaa taaatgaagt taaaataaat    2340
aaattaagag aatatgatga aaatgttaaa acttatttat taaattatat aatacaacat    2400
ggatcaatat taggagaatc acaacaagaa ttaaattcaa tggttactga tactttaaat    2460
aattcaatac catttaaatt atcatcatat actgatgata aaatattaat atcatatttt    2520
aataaatttt ttaaaagaat aaaatcatca tcagttttaa atatgagata taaaaatgat    2580
aaatatgttg atacttcagg atatgattca aatataaata taaatggaga tgtttataaa    2640
tatccaacta ataaaaatca atttggaata tataatgata aattatcaga agttaatata    2700
tcacaaaatg attatataat atatgataat aaatataaaa atttttcaat atcattttgg    2760
gttagaatac caaattatga taataaaata gttaatgtta ataatgaata tactataata    2820
```

-continued

```
aattgtatga gagataataa ttcaggatgg aaagtttcat taaatcataa tgaaataata   2880

tggactttac aagataatgc tggaataaat caaaaattag cttttaatta tggaaatgct   2940

aatggaatat cagattatat aaataaatgg atatttgtta ctataactaa tgatagatta   3000

ggagattcaa aattatatat aaatggaaat ttaatagatc aaaaatcaat attaaattta   3060

ggaaatatac atgtttcaga taatatatta tttaaaatag ttaattgttc atatactaga   3120

tatataggaa taagatattt taatatattt gataaagaat tagatgaaac tgaaatacaa   3180

actttatatt caaatgaacc aaatactaat atattaaaag atttttgggg aaattattta   3240

ttatatgata aagaatatta tttattaaat gttttaaaac caaataattt tatagataga   3300

agaaaagatt caactttatc aataaataat ataagatcaa ctatattatt agctaataga   3360

ttatattcag gaataaaagt taaaatacaa agagttaata attcatcaac taatgataat   3420

ttagttagaa aaaatgatca agtttatata aattttgttg cttcaaaaac tcatttattt   3480

ccattatatg ctgatactgc tactactaat aaagaaaaaa ctataaaaat atcatcatca   3540

ggaaatagat ttaatcaagt tgttgttatg aattcagttg gaaataattg tactatgaat   3600

tttaaaaata ataatggaaa taatatagga ttattaggat ttaaagctga tactgttgtt   3660

gcttcaactt ggtattatac tcatatgaga gatcatacta attcaaatgg atgtttttgg   3720

aattttatat cagaagaaca tggatggcaa gaaaaataa                          3759
```

```
<210> SEQ ID NO 22
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, C. perfringens-modified 3

<400> SEQUENCE: 22
```

```
atgcctaaaa taaattcatt taattataat gatcctgtta atgatagaac aatactatat     60

ataaaaccag gaggttgtca agaattttat aagagtttta atattatgaa aaatatatgg    120

ataattccag aaagaaatgt aataggaact acacctcaag attttcatcc acctacatca    180

ttaaaaaatg gagattcaag ttattatgat cctaattatt tacaaagtga tgaagaaaaa    240

gatagatttc taaaaattgt tactaaaatt tttaatagaa taaataataa tttaagtggt    300

ggaattttac tagaagaatt atcaaaagct aatccatatt taggaaatga taatactcca    360

gataatcaat ttcatatagg agatgctagc gctgtagaaa ttaaattttc aaatggatca    420

caagatatat tacttcctaa tgtaataatt atgggtgctg aacctgattt atttgaaact    480

aattcatcta atatttcttt aaggaataat tatatgccaa gcaatcatgg ttttggatca    540

atagctatag taacattttc accagaatat tcttttagat ttaatgataa ttcaatgaat    600

gaatttatac aagatccagc tttaactctt atgcatgaat taattcattc attacatgga    660

ctttatggtg ctaaaggaat aacaactaaa tatacaataa cacaaaaaca aaatccactt    720

attacaaata ttagaggtac aaatatagaa gaattttaa cttttggagg tactgattta    780

aatataatta caagtgctca atcaaatgat atatatacaa atttacttgc tgattataaa    840

aagatagcat caaagcttag taaagttcaa gtttcaaatc cattactaaa tccatataaa    900

gatgtatttg aagcaaaata tggtttagat aaagatgcaa gcggaatata tagcgtaaat    960

attaataagt ttaatgatat ttttaaaaag ttatatagtt ttactgaatt tgatcttgct   1020
```

-continued

```
actaaatttc aagttaaatg taggcaaact tatataggac aatataagta ttttaaactt   1080
agtaatttac ttaatgattc aatatataat atatcagaag gttataatat aaataattta   1140
aaagttaatt ttagaggaca aaatgcaaat ttaaatccaa gaataattac tccaataaca   1200
ggaagaggtt tagttaaaaa gataattaga ttttgtaaaa atatagtatc tgtaaaagga   1260
ataagaaaat ctatatgtat agaaataaat aatggagaac tttttttgt tgcttctgaa   1320
aatagttata atgatgataa tataaataca cctaaagaaa tagatgatac tgtaacttca   1380
aataataatt atgaaaatga tttagatcaa gtaattttaa attttaatag tgaatcagct   1440
cctggattaa gcgatgaaaa attaaattta acaatacaaa atgatgcata tataccaaaa   1500
tatgatagta atggaacttc agatatagaa caacatgatg ttaatgaatt aaatgttttt   1560
ttttatttag atgctcaaaa agtacctgaa ggagaaaata atgttaatct tactagttct   1620
atagatactg cactattaga acaaccaaaa atatatactt ttttttcatc tgaatttatt   1680
aataatgtta ataaaccagt tcaagcagct ttatttgttt cttggataca acaagtttta   1740
gttgatttta caactgaagc aaatcaaaag agtactgttg ataagattgc tgatataagt   1800
attgtagttc cttatatagg tttagcttta aatataggaa atgaagctca aaaaggaaat   1860
tttaaagatg ctttagaatt acttggagct ggaatattac ttgaatttga accagaatta   1920
cttataccta caattctagt ttttactatt aagagttttt taggatcaag cgataataag   1980
aataaagtta taaaggcaat taataatgct ttaaaagaaa gagatgaaaa atggaaggaa   2040
gtatattcat ttattgtttc aaattggatg actaaaataa atactcaatt taataaaaga   2100
aaggaacaaa tgtatcaagc tttacaaaat caagttaatg caataaaaac tataattgaa   2160
agcaagtata attcatatac acttgaagaa aaaaatgaat taactaataa atatgatata   2220
aagcaaatag aaaatgaatt aaatcaaaag gtaagtatag caatgaataa tatagataga   2280
tttttaactg aaagttcaat atcttattta atgaagttaa taaatgaagt aaaaataaat   2340
aaattaagag aatatgatga aaatgttaaa acatatcttt taaattatat tatacaacat   2400
ggaagtattt taggtgaatc acaacaagaa ttaaatagta tggttacaga tactttaaat   2460
aatagtattc cttttaaatt aagttcttat actgatgata aaatattaat atcatatttt   2520
aataaatttt ttaaaagaat aaaatcatct tcagtattaa atatgagata taagaatgat   2580
aaatatgttg atacaagtgg ttatgattct aatataaata taaatggtga tgtttataaa   2640
tatcctacaa ataaaaatca atttggaatt tataatgata agttatctga agttaatatt   2700
tctcaaaatg attatattat atatgataat aagtataaaa atttttcaat aagtttttgg   2760
gttagaatac caaattatga taataaaatt gtaaatgtta ataatgaata tactataatt   2820
aattgtatga gagataataa tagcggatgg aaggtttctc taaatcataa tgaaattata   2880
tggacattac aagataatgc tggaataaat caaaaattag catttaatta tggaaatgca   2940
aatggaatat ctgattatat aaataagtgg atatttgtta ctataacaaa tgatagacta   3000
ggtgattcta agttatatat aaatggaaat ttaatagatc aaaaatctat attaaattta   3060
ggaaatatac atgtatcaga taatatatta tttaaaatag ttaattgtag ttatactagg   3120
tatataggaa ttagatattt taatattttt gataaggaat tagatgaaac tgaaatacaa   3180
actctttatt caaatgaacc aaatacaaat attctaaagg atttttgggg aaattatctt   3240
ttatatgata aagaatatta tttacttaat gttttaaaac caaataattt tattgataga   3300
agaaaggatt ctacattatc aattaataat ataagatcaa ctattttact tgcaaataga   3360
ttatatagtg gaataaaagt aaaaatacaa agagtaaata attctagtac taatgataat   3420
```

-continued ttagtaagaa agaatgatca agtatatata aattttgttg catctaaaac acatttattt 3480
cctctttatg ctgatactgc tactacaaat aaagaaaaaa ctataaagat ttcatctagt 3540
ggaaatagat ttaatcaagt agttgtaatg aattctgtag gaaataattg tacaatgaat 3600
tttaaaaata ataatggaaa taatattgga ttattaggat ttaaagctga tactgttgtt 3660
gcttcaactt ggtattatac acatatgaga gatcatacta atagtaatgg ttgtttttgg 3720
aattttatat ctgaagaaca tggatggcaa gaaaaataa 3759

<210> SEQ ID NO 23
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, C. crescentus-modified 1

<400> SEQUENCE: 23
atgccgaaga tcaactcctt caactataac gacccggtca atgaccgcac catcctctac 60
atcaagccgg gcgggtgcca ggagttctac aagagcttca acatcatgaa gaacatctgg 120
atcattccag aacgcaacgt tatcggcacg accccccagg acttccatcc tccgacctcg 180
ctcaagaacg gcgactccag ttattacgac ccgaactatc tgcagagcga cgaggaaaag 240
gaccgcttcc tgaagatcgt gacgaagatc ttcaatcgta tcaacaataa cctcagcggc 300
gggatcctcc tggaggaact gagcaaggcg aacccgtatc tgggaaatga taacacgccg 360
gacaaccagt tccacatcgg cgacgcctcg gccgtcgaga tcaaattctc gaacggttcg 420
caggacatcc tgcttccgaa cgtgatcatt atgggcgcgg agccggacct gttcgagacc 480
aactcctcga acatatcgct gcgcaacaat tacatgccgt cgaaccacgg cttcgggtcc 540
atcgcgatcg tcaccttcag cccggagtat tcgttccgat ttaacgacaa cagcatgaac 600
gagttcatcc aggacccggc cctgacgctg atgcacgaac tcatccattc cctgcacggc 660
ttgtacggcg cgaagggcat caccacaaag tacacgatca cgcaaaagca gaacccgctc 720
atcaccaaca tccggggtac caacatcgaa gagtttctga ccttcggcgg gaccgatctg 780
aacatcatta cgtcggcgca gtcgaacgat atctacacca acctgcttgc ggactataag 840
aaaatcgcct cgaagctgag caaggtccag gtgagcaacc ccctgctaaa tccctataag 900
gacgtcttcg aggccaagta cggcctggat aaagacgcct ctggcatcta ctcggtcaac 960
atcaacaagt tcaacgatat tttcaagaaa ctgtattcct ttaccgagtt cgacctggcg 1020
accaagttcc aggtcaagtg tcgccagacc tatatcggcc agtataagta cttcaagctg 1080
agcaacctgc tcaatgactc gatctacaac atcagcgagg ggtataacat caacaatctg 1140
aaggtcaact tccgcggcca gaacgcgaac cttaaccccc gcatcattac gccgatcacc 1200
ggccggggcc tggtcaagaa aatcatacgc ttctgcaaga atatcgtgtc cgtcaagggc 1260
atccgcaaga gcatctgcat cgagatcaac aatggcgagc tgttctttgt cgccagcgag 1320
aactcgtata acgatgacaa catcaacacc cccaaggaga tcgatgacac ggtgacctcg 1380
aacaataact acgaaaatga cctggaccaa gtcatcttga acttcaactc ggagtcggcg 1440
cccggcctgt ccgacgagaa gctgaatctg acgatccaga acgacgccta catccccaag 1500
tacgacagca acggtacgtc ggatatcgag cagcacgacg tcaacgagct gaatgtgttc 1560
ttttacctgg atgcccagaa ggttcccgag ggcgagaaca atgtgaacct gacgtcgagc 1620

-continued

```
atcgacaccg ccctcctgga gcagccgaag atctatacgt tctttagtag cgagttcatc   1680

aacaatgtga acaagccggt ccaagccgcg ctcttcgtct cttggatcca gcaagtgctg   1740

gtcgacttca ccacggaagc gaaccagaag tcgacggtgg acaagatcgc cgacatcagc   1800

atcgtcgtgc cgtatatcgg cctggcgctg aacatcggca acgaggctca gaagggcaac   1860

ttcaaggacg cgctggagct gctcggcgcc ggcatcctgc tagagttcga gcctgagctg   1920

ttgatcccca ccatccttgt gttcaccatt aagagcttcc tcggctcgag cgacaataag   1980

aataaggtca ttaaggccat caacaatgcc ctgaaggagc gcgacgaaaa gtggaaagaa   2040

gtttactcct tcatcgtgtc gaactggatg accaagatca acactcagtt caacaagcgc   2100

aaggaacaga tgtaccaagc cttgcagaat caggtcaatg cgatcaagac catcattgaa   2160

tcgaagtata actcatacac gctcgaggaa aagaacgaac tgaccaacaa gtatgatatc   2220

aagcagatcg agaatgagct gaaccagaag gtctccatcg ctatgaacaa tatcgaccgc   2280

ttccttactg agagctcgat ctcgtacctg atgaagttga tcaatgaagt gaagatcaac   2340

aagctgcggg agtatgatga aaacgtcaag acctacttgc tgaactacat catccagcac   2400

ggttccatcc tgggcgagag ccagcaagag ctgaactcca tggtaaccga caccctgaac   2460

aatagcatcc ccttcaagct gtcgagctac accgatgaca agatcctgat cagctatttc   2520

aataagttct ttaagcgcat caagagctcc tcggtgctga acatgcggta caagaacgat   2580

aagtatgtcg atacctcggg ctatgactcc aacatcaaca tcaatggcga cgtgtataag   2640

taccccacga acaagaacca gttcgggatc tataacgaca agctgagcga ggtgaacatc   2700

tcccagaacg actacatcat ctacgacaac aagtacaaga acttcagcat cagcttctgg   2760

gttcgcatcc cgaactatga caacaagatc gtgaatgtga ataacgagta taccatcatc   2820

aactgcatgc gcgacaacaa tagtggctgg aaggtctcac tgaaccacaa cgagatcatc   2880

tggacactgc aggacaacgc cggcatcaac cagaagctgg ccttcaacta tggcaacgcc   2940

aacggaatct cggactatat caacaagtgg atcttcgtga ccatcacgaa cgaccgcctc   3000

ggcgacagca agctgtacat caacggcaac ctcatcgacc agaagtcgat cctgaacctg   3060

ggcaacatcc acgtctcgga caacatcctg ttcaagatcg tgaattgctc gtacacccgg   3120

tatatcggca tccggtattt caacatcttc gacaaagaac tggacgagac cgagatccag   3180

acgctgtaca gcaacgaacc gaacacgaac atcttgaagg atttctgggg aaactacctg   3240

ctctatgaca aggagtacta tctcctgaac gtcctgaagc caaacaattt catcgatcgc   3300

cggaaggatt cgaccctcag catcaacaat atccgctcca ccatcctgct tgccaaccgt   3360

ctgtactcag gcatcaaggt caagatccag cgtgtgaaca actcgtccac caacgacaac   3420

ctggtgcgaa agaacgacca ggtctacatc aacttcgtgg catcgaagac gcacctgttc   3480

cccctctacg ccgacaccgc caccacgaac aaggagaaga ccatcaagat ctcgtctagc   3540

ggcaacaggt tcaaccaggt cgtggtcatg aactcggtcg gcaacaactg caccatgaac   3600

ttcaagaaca acaacggcaa caacatcggt ctgctgggtt tcaaggccga caccgtcgtc   3660

gcctcgacct ggtactatac ccatatgcgc gaccacacca actcgaacgg ctgcttctgg   3720

aactttatct cggaggaaca tgggtggcag gagaagtaa                          3759
```

<210> SEQ ID NO 24
<211> LENGTH: 3759
<212> TYPE: DNA
<213> ORGANISM: Artificial Sequence
<220> FEATURE:
<221> NAME/KEY: mat_peptide -continued
<222> LOCATION: (1)...(3756)
<223> OTHER INFORMATION: BoNT/E, C. crescentus-modified 2

<400> SEQUENCE: 24
atgccgaaga tcaactcgtt caactacaac gacccggtca acgaccgcac catcctgtac 60
atcaagccgg gcggctgcca ggagttctac aagtcgttca acatcatgaa gaacatctgg 120
atcatcccgg agcgcaacgt catcggcacc accccgcagg acttccaccc gccgacctcg 180
ctgaagaacg gcgactcgtc gtactacgac ccgaactacc tgcagtcgga cgaggagaag 240
gaccgcttcc tgaagatcgt caccaagatc ttcaaccgca tcaacaacaa cctgtcgggc 300
ggcatcctgc tggaggagct gtcgaaggcc aacccgtacc tgggcaacga caacaccccg 360
gacaaccagt tccacatcgg cgacgcctcg gccgtcgaga tcaagttctc gaacggctcg 420
caggacatcc tgctgccgaa cgtcatcatc atgggcgccg agccggacct gttcgagacc 480
aactcgtcga acatctcgct gcgcaacaac tacatgccgt cgaaccacgg cttcggctcg 540
atcgccatcg tcaccttctc gccggagtac tcgttccgct tcaacgacaa ctcgatgaac 600
gagttcatcc aggacccggc cctgaccctg atgcacgagc tgatccactc gctgcacggc 660
ctgtacggcg ccaagggcat caccaccaag tacaccatca cccagaagca gaacccgctg 720
atcaccaaca tccgcggcac caacatcgag gagttcctga ccttcggcgg caccgacctg 780
aacatcatca cctcggccca gtcgaacgac atctacacca acctgctggc cgactacaag 840
aagatcgcct cgaagctgtc gaaggtccag gtctcgaacc cgctgctgaa cccgtacaag 900
gacgtcttcg aggccaagta cggcctggac aaggacgcct cgggcatcta ctcggtcaac 960
atcaacaagt tcaacgacat cttcaagaag ctgtactcgt tcaccgagtt cgacctggcc 1020
accaagttcc aggtcaagtg ccgccagacc tacatcggcc agtacaagta cttcaagctg 1080
tcgaacctgc tgaacgactc gatctacaac atctcggagg gctacaacat caacaacctg 1140
aaggtcaact tccgcggcca gaacgccaac ctgaacccgc gcatcatcac cccgatcacc 1200
ggccgcggcc tggtcaagaa gatcatccgc ttctgcaaga acatcgtctc ggtcaagggc 1260
atccgcaagt cgatctgcat cgagatcaac aacggcgagc tgttcttcgt cgcctcggag 1320
aactcgtaca acgacgacaa catcaacacc ccgaaggaga tcgacgacac cgtcacctcg 1380
aacaacaact acgagaacga cctggaccag gtcatcctga acttcaactc ggagtcggcc 1440
ccgggcctgt cggacgagaa gctgaacctg accatccaga acgacgccta catcccgaag 1500
tacgactcga acggcacctc ggacatcgag cagcacgacg tcaacgagct gaacgtcttc 1560
ttctacctgg acgcccagaa ggtcccggag ggcgagaaca acgtcaacct gacctcgtcg 1620
atcgacaccg ccctgctgga gcagccgaag atctacacct tcttctcgtc ggagttcatc 1680
aacaacgtca acaagccggt ccaggccgcc ctgttcgtct cgtggatcca gcaggtcctg 1740
gtcgacttca ccaccgaggc caaccagaag tcgaccgtcg acaagatcgc cgacatctcg 1800
atcgtcgtcc cgtacatcgg cctggccctg aacatcggca acgaggccca gaagggcaac 1860
ttcaaggacg ccctggagct gctgggcgcc ggcatcctgc tggagttcga gccggagctg 1920
ctgatcccga ccatcctggt cttcaccatc aagtcgttcc tgggctcgtc ggacaacaag 1980
aacaaggtca tcaaggccat caacaacgcc ctgaaggagc gcgacgagaa gtggaaggag 2040
gtctactcgt tcatcgtctc gaactggatg accaagatca acacccagtt caacaagcgc 2100
aaggagcaga tgtaccaggc cctgcagaac caggtcaacg ccatcaagac catcatcgag 2160
tcgaagtaca actcgtacac cctggaggag aagaacgagc tgaccaacaa gtacgacatc 2220

-continued

```
aagcagatcg agaacgagct gaaccagaag gtctcgatcg ccatgaacaa catcgaccgc   2280

ttcctgaccg agtcgtcgat ctcgtacctg atgaagctga tcaacgaggt caagatcaac   2340

aagctgcgcg agtacgacga gaacgtcaag acctacctgc tgaactacat catccagcac   2400

ggctcgatcc tgggcgagtc gcagcaggag ctgaactcga tggtcaccga caccctgaac   2460

aactcgatcc cgttcaagct gtcgtcgtac accgacgaca agatcctgat ctcgtacttc   2520

aacaagttct tcaagcgcat caagtcgtcg tcggtcctga acatgcgcta caagaacgac   2580

aagtacgtcg acacctcggg ctacgactcg aacatcaaca tcaacggcga cgtctacaag   2640

tacccgacca acaagaacca gttcggcatc tacaacgaca agctgtcgga ggtcaacatc   2700

tcgcagaacg actacatcat ctacgacaac aagtacaaga acttctcgat ctcgttctgg   2760

gtccgcatcc cgaactacga caacaagatc gtcaacgtca acaacgagta caccatcatc   2820

aactgcatgc gcgacaacaa ctcgggctgg aaggtctcgc tgaaccacaa cgagatcatc   2880

tggaccctgc aggacaacgc cggcatcaac cagaagctgg ccttcaacta cggcaacgcc   2940

aacggcatct cggactacat caacaagtgg atcttcgtca ccatcaccaa cgaccgcctg   3000

ggcgactcga agctgtacat caacggcaac ctgatcgacc agaagtcgat cctgaacctg   3060

ggcaacatcc acgtctcgga caacatcctg ttcaagatcg tcaactgctc gtacacccgc   3120

tacatcggca tccgctactt caacatcttc gacaaggagc tggacgagac cgagatccag   3180

accctgtact cgaacgagcc gaacaccaac atcctgaagg acttctgggg caactacctg   3240

ctgtacgaca aggagtacta cctgctgaac gtcctgaagc cgaacaactt catcgaccgc   3300

cgcaaggact cgaccctgtc gatcaacaac atccgctcga ccatcctgct ggccaaccgc   3360

ctgtactcgg gcatcaaggt caagatccag cgcgtcaaca actcgtcgac caacgacaac   3420

ctggtccgca agaacgacca ggtctacatc aacttcgtcg cctcgaagac ccacctgttc   3480

ccgctgtacg ccgacaccgc caccaccaac aaggagaaga ccatcaagat ctcgtcgtcg   3540

ggcaaccgct tcaaccaggt cgtcgtcatg aactcggtcg gcaacaactg caccatgaac   3600

ttcaagaaca acaacggcaa caacatcggc ctgctgggct tcaaggccga caccgtcgtc   3660

gcctcgacct ggtactacac ccacatgcgc gaccacacca actcgaacgg ctgcttctgg   3720

aacttcatct cggaggagca cggctggcag gagaagtaa                          3759
```

<210> SEQ ID NO 25
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, C. crescentus-modified 3

<400> SEQUENCE: 25

```
atgccgaaga tcaacagctt caactacaac gaccccgtca acgaccggac catcctgtat     60

atcaagccgg gcgggtgcca ggagttctac aagtccttca acatcatgaa gaacatctgg    120

atcatccccg aacggaacgt gatcgggacc acgccgcagg acttccaccc cccgacctcg    180

ctcaagaacg gcgacagctc gtactatgac ccgaactacc tccagagcga cgaagagaag    240

gaccgcttcc tgaagatcgt cacgaagatc ttcaaccgta tcaacaacaa cctcagcggg    300

ggcatcctgc tcgaggaact gtcgaaggcc aacccgtatc tggggaacga caacacgccc    360

gacaaccagt tccatatcgg cgacgcctcc gccgtcgaga tcaagttcag caacggcagc    420

caggacatcc tgctccccaa cgtcatcatc atgggcgccg aaccggacct gttcgagacc    480
```

-continued

```
aactcgtcca acatcagcct gcgcaacaac tacatgccgt ccaaccacgg cttcggctcg    540
atcgccatcg tgaccttcag cccggagtac tcgttccgct tcaacgacaa ctcgatgaac    600
gagttcatcc aggaccccgc gctgacgctg atgcacgagc tgatccacag cctgcacggc    660
ctgtatggcg ccaaggggat cacgaccaag tacaccatca cccagaagca gaaccccctg    720
atcaccaaca tccggggcac caacatcgag gaattcctca ccttcggcgg gaccgacctg    780
aacatcatca cctcggcgca gagcaacgac atctacacca acctgctcgc ggactataag    840
aagatcgcgt cgaagctgag caaggtgcag gtgagcaacc cgctgctcaa cccgtacaag    900
gacgtgttcg aggcgaagta cggcctggac aaggacgcct cgggcatcta ctcggtgaac    960
atcaacaagt tcaacgacat cttcaagaag ctgtactcgt tcaccgagtt cgacctggcc   1020
accaagttcc aggtgaagtg ccggcagacc tacatcggcc agtacaagta cttcaagctg   1080
tccaacctgc tcaacgacag catctataac atcagcgagg gctacaacat caacaacctg   1140
aaggtcaact tccgcggcca gaacgccaac ctgaacccgc gcatcatcac gcccatcacc   1200
ggccgcggcc tcgtgaagaa gatcatccgt ttctgcaaga acatcgtctc ggtgaagggc   1260
atccgcaagt cgatctgcat cgaaatcaac aacggcgagc tgttcttcgt cgcgtcggag   1320
aactcgtata acgacgacaa catcaacacg ccgaaggaga tcgacgacac ggtgacgagc   1380
aacaacaact acgagaacga cctggaccag gtcatcctga acttcaactc cgaatccgcc   1440
ccgggcctgt ccgacgagaa gctgaacctg accatccaga acgacgcgta tatcccgaag   1500
tacgactcga acggcaccag cgacatcgaa cagcacgacg tcaacgagct caacgtcttc   1560
ttctacctgg acgcccagaa ggtcccggag ggcgagaaca acgtcaacct gacctcgtcc   1620
atcgacaccg ccctgctcga gcagcccaag atctatacct tcttcagctc ggagttcatc   1680
aacaacgtga acaagccggt ccaggccgcg ctgttcgtgt cgtggatcca gcaggtgctg   1740
gtggacttca cgaccgaagc gaaccagaag tcgaccgtcg acaagatcgc cgacatcagc   1800
atcgtcgtgc cgtatatcgg cctggccctg aacatcggca acgaggccca gaagggcaac   1860
ttcaaggacg cgctggaact gctcggcgcc ggcatcctgc tcgagttcga gcccgagctg   1920
ctcatcccca cgatcctggt cttcaccatc aagtccttcc tgggctcgag cgacaacaag   1980
aacaaggtca tcaaggccat caacaacgcc ctgaaggagc gcgacgagaa gtggaaggaa   2040
gtctactcct tcatcgtctc gaactggatg accaagatca acacccagtt caacaagcgc   2100
aaggaacaga tgtaccaggc cctgcagaac caggtcaacg cgatcaagac gatcatcgag   2160
tcgaagtaca actcgtatac gctggaggaa aagaacgagc tgacgaacaa gtatgacatc   2220
aagcagatcg agaacgagct gaaccagaag gtctccatcg ccatgaacaa catcgaccgg   2280
ttcctgacgg agtcgagcat ctcgtatctc atgaagctga tcaacgaggt caagatcaac   2340
aagctgcgcg agtacgacga gaacgtcaag acctacctgc tcaactacat catccagcac   2400
ggctcgatcc tgggcgagag ccagcaggag ctgaactcga tggtgacgga caccctgaac   2460
aactcgatcc cgttcaagct gagctcgtat accgacgaca agatcctgat cagctacttc   2520
aacaagttct tcaagcgcat caagtcgagc tcggtgctga acatgcgcta taagaacgac   2580
aagtatgtcg acacgagcgg ctatgactcc aacatcaaca tcaacggcga cgtgtataag   2640
tacccgacca acaagaacca gttcggcatc tataacgaca agctgtccga agtcaacatc   2700
agccagaacg actatatcat ctatgacaac aagtacaaga acttctcgat cagcttctgg   2760
gtccgcatcc cgaactatga caacaagatc gtgaacgtca acaacgagta taccatcatc   2820
```

-continued aactgcatgc gcgacaacaa cagcggctgg aaggtctcgc tgaaccataa cgaaatcatc 2880
tggaccctgc aggacaacgc cggcatcaac cagaagctgg ccttcaacta cggcaacgcc 2940
aacggcatct cggactatat caacaagtgg atcttcgtga ccatcacgaa cgaccgtctg 3000
ggcgactcga agctgtatat caacggcaac ctgatcgacc agaagtcgat cctgaacctg 3060
ggcaacatcc atgtgtcgga caacatcctg ttcaagatcg tcaactgctc gtacacgcgc 3120
tatatcggca tccgctattt caacatcttc gacaaggaac tggacgaaac cgagatccag 3180
acgctgtatt cgaacgagcc gaacaccaac atcctgaagg acttctgggg caactatctg 3240
ctctatgaca aggagtacta tctgctgaac gtgctgaagc cgaacaactt catcgaccgc 3300
cggaaggact cgaccctgtc gatcaacaac atccggagca ccatcctgct ggcgaaccgc 3360
ctgtactccg gcatcaaggt caagatccag cgcgtgaaca actcgagcac caacgacaac 3420
ctggtccgca agaacgacca ggtctacatc aacttcgtcg ccagcaagac gcatctgttc 3480
cccctgtacg ccgacaccgc caccacgaac aaggagaaga ccatcaagat ctcctcgtcc 3540
ggcaaccgct tcaaccaggt ggtcgtgatg aactcggtcg ggaacaactg caccatgaac 3600
ttcaagaaca acaacggcaa caacatcggc ctgctgggct tcaaggcgga caccgtcgtc 3660
gcgtcgacct ggtactacac ccacatgcgc gaccacacca actcgaacgg ctgcttctgg 3720
aacttcatct cggaagagca cggctggcag gagaagtaa 3759

<210> SEQ ID NO 26
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, L. lactis-modified 1

<400> SEQUENCE: 26
atgccaaaaa tcaatagctt caattataat gatccggtta atgatagaac aatcttatat 60
attaaaccag gaggttgtca ggaattttat aaatctttta atattatgaa gaatatttgg 120
attatacctg aaagaaatgt tattggtaca actccacagg attttcatcc accgacttca 180
ttaaaaaatg gcgattcttc atattacgat cctaattatc ttcaatcgga tgaagagaaa 240
gacagatttc ttaagattgt tactaaaatt tttaatcgaa tcaataacaa tctttcaggt 300
ggaatattat tggaagagtt atcgaaagct aacccctacc ttggtaacga caatacccca 360
gataaccaat ttcacattgg tgatgcctcc gcggtcgaaa ttaaattttc aaatggctct 420
caagacattt tacttcctaa cgttattatc atgggagctg aacctgatct gtttgaaaca 480
aacagtagca acatcagtct gcgtaataac tatatgccaa gtaatcatgg ttttggctcg 540
atcgctattg ttacatttag tcctgaatat tcattccgct ttaatgacaa tagtatgaat 600
gagtttattc aagatcctgc tttgacttta atgcatgaac taatacacag cctacatggt 660
ctttatggtg ccaaaggcat tactacgaag tatacaataa cacaaaaaca aaatccccta 720
atcacaaata tacggggaac taacattgaa gagttcctca ctttcggcgg tacagatctt 780
aatattataa catcagcgca aagtaacgat atatacacga atcttttagc agactacaaa 840
aagattgcat ctaagcttag taaagtccaa gtatcaaatc cattgttaaa cccttataaa 900
gatgtttttg aggctaaata tggtttggat aaagacgcga gtggtattta ttcagttaat 960
attaataaat tcaatgacat ttttaaaaag ctatatagtt ttactgaatt tgatcttgct 1020
acaaaattcc aagtaaaatg tagacaaacc tatatcgggc aatacaaata ttttaaactt 1080

-continued

```
agtaatcttt taaatgattc gatttataat atttcagaag ggtataatat aaataaccta   1140
aaggttaact ttagaggtca gaatgcgaat cttaatcctc gtataattac tcctattact   1200
gggcgtggtt tagttaaaaa gattatccgt ttttgtaaaa atatagtttc cgtcaaaggt   1260
attaggaaat caatttgtat tgaaattaat aacggagaat tgttctttgt agcatcagaa   1320
aacagttata atgacgataa cattaataca ccaaaagaaa tagatgacac cgttacttca   1380
aataacaatt atgaaaatga cctagatcaa gtaattttga attttaattc agaatctgct   1440
ccaggactct ctgatgaaaa attaaattta acaattcaaa acgatgcata tattccaaaa   1500
tacgatagta acggaacatc agatattgaa caacatgatg taaatgaact taatgttttt   1560
ttctatctag atgctcaaaa agtgccagaa ggagaaaata acgtcaatct cacaagctct   1620
attgatactg cattgttaga acaaccaaaa atttatacgt tcttttcttc agaatttata   1680
aacaatgtga ataaacctgt acaagcagcc ttgtttgtat catggattca acaggtttta   1740
gttgatttta caaccgaagc aaatcaaaaa agcactgtag ataaaatcgc tgatatttct   1800
attgtggttc cttatattgg actggcttta aatattggta acgaagctca aaaaggtaac   1860
tttaaagatg ccctcgaact gttaggtgca ggaatattat tggaatttga gccagagtta   1920
ttgatcccca caattttagt gtttacaatt aaatcattct taggatcttc agataataaa   1980
aataaagtca ttaaagcaat taataacgca cttaaggaac gtgacgaaaa atggaaagaa   2040
gtatactctt ttattgtttc gaattggatg acgaagataa atacacaatt taataaaaga   2100
aaagaacaaa tgtatcaagc cctacaaaat caagtcaacg caattaaaac cattatagag   2160
agtaaataca acagttacac tttggaagag aaaaatgaat tgactaataa atacgatatt   2220
aaacaaatcg aaaatgaatt gaatcaaaaa gtttcaattg ctatgaataa catagatcga   2280
ttcttgacgg aatcttcaat ttcttattta atgaaactta taaatgaagt aaaaattaac   2340
aaattacgtg agtatgatga aaatgttaag acatatttac ttaattatat cattcaacac   2400
gggagtatct taggagaatc tcaacaggaa ctcaattcaa tggttacaga tacgctcaat   2460
aactcaattc ctttcaaatt aagttcatat actgatgaca aaattctgat ttcctatttc   2520
aataagtttt tcaagagaat caaatctagc tctgttttga atatgcgata caaaaacgat   2580
aaatatgttg acacaagcgg gtatgattct aacatcaata ttaatggaga tgtctacaaa   2640
tatccaacta ataaaaacca atttggaatt tacaatgata aactttctga agtaaatatc   2700
agtcaaaatg attatattat ctatgataat aaatacaaaa attttagtat ttcattttgg   2760
gttcgtattc ctaattatga caataaaatt gtaaatgtta ataacgagta tactattatc   2820
aattgtatgc gagataacaa tagcggatgg aaagtgtccc ttaatcataa tgaaattatc   2880
tggactttgc aagacaacgc tgggatcaat caaaaattgg ctttcaatta tgggaatgca   2940
aatggaattt cagattacat caataaatgg atttttgtaa ctattacaaa tgatcgtttg   3000
ggtgattcta aattatatat taacggtaat ttaatagacc aaaaatcaat cttaaatctc   3060
ggaaatattc acgtatcaga taatattctt tttaaaatag ttaactgctc ttatacgcga   3120
tatattggta ttcgttattt taatattttt gataaggaat tggatgaaac cgaaattcaa   3180
actttatatt ctaatgagcc aaatactaat attcttaagg acttttgggg taattactta   3240
ttgtatgata aagaatatta ccttttaaat gttttaaaac cgaacaattt tatagataga   3300
cgcaaggaca gtactctttc cattaataac attagaagca ctattttgtt agccaatcgc   3360
ctttatagtg gcattaaagt caaaatacaa agggttaata acagttcaac caatgataat   3420
```

-continued

```
ttagttcgga aaaatgacca agtgtatatc aattttgttg ctagtaagac gcatcttttt   3480

ccactatatg ctgacacagc aactacaaat aaagaaaaga ccattaaaat ttcttcatct   3540

ggaaatcgtt tcaatcaggt ggtcgttatg aattctgttg gtaataattg tacaatgaat   3600

tttaaaaata ataatggtaa taatatcggc ttgttaggat ttaaggcaga taccgtcgtg   3660

gctagcacat ggtattatac acatatgcgt gatcatacaa attctaatgg atgcttttgg   3720

aattttatct cagaagaaca tggatggcag gaaaaataa                          3759
```

<210> SEQ ID NO 27
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, L. lactis-modified 2

<400> SEQUENCE: 27

```
atgccaaaaa ttaattcatt taattataat gatccagtta atgatcgtac aattttatat     60

attaaaccag gtggttgtca agaattttat aaatcattta atattatgaa aaatatttgg    120

attattccag aacgtaatgt tattggtaca acaccacaag attttcatcc accaacatca    180

ttaaaaaatg gtgattcatc atattatgat ccaaattatt tacaatcaga tgaagaaaaa    240

gatcgttttt taaaaattgt tacaaaaatt tttaatcgta ttaataataa tttatcaggt    300

ggtattttat tagaagaatt atcaaaagct aatccatatt taggtaatga taatacacca    360

gataatcaat ttcatattgg tgatgcttca gctgttgaaa ttaaattttc aaatggttca    420

caagatattt tattaccaaa tgttattatt atgggtgctg aaccagattt atttgaaaca    480

aattcatcaa atatttcatt acgtaataat tatatgccat caaatcatgg ttttggttca    540

attgctattg ttacattttc accagaatat tcatttcgtt ttaatgataa ttcaatgaat    600

gaatttattc aagatccagc tttaacatta atgcatgaat taattcattc attacatggt    660

ttatatggtg ctaaaggtat tacaacaaaa tatacaatta cacaaaaaca aaatccatta    720

attacaaata ttcgtggtac aaatattgaa gaatttttaa catttggtgg tacagattta    780

aatattatta catcagctca atcaaatgat atttatacaa atttattagc tgattataaa    840

aaaattgctt caaaattatc aaaagttcaa gtttcaaatc cattattaaa tccatataaa    900

gatgtttttg aagctaaata tggtttagat aaagatgctt caggtattta ttcagttaat    960

attaataaat ttaatgatat ttttaaaaaa ttatattcat ttacagaatt tgatttagct   1020

acaaaatttc aagttaaatg tcgtcaaaca tatattggtc aatataaata ttttaaatta   1080

tcaaatttat taaatgattc aatttataat atttcagaag gttataatat taataattta   1140

aaagttaatt ttcgtggtca aaatgctaat ttaaatccac gtattattac accaattaca   1200

ggtcgtggtt tagttaaaaa aattattcgt ttttgtaaaa atattgtttc agttaaaggt   1260

attcgtaaat caatttgtat tgaaattaat aatggtgaat tattttttgt tgcttcagaa   1320

aattcatata atgatgataa tattaataca ccaaaagaaa ttgatgatac agttacatca   1380

aataataatt atgaaaatga tttagatcaa gttattttaa attttaattc agaatcagct   1440

ccaggtttat cagatgaaaa attaaattta acaattcaaa atgatgctta tattccaaaa   1500

tatgattcaa atggtacatc agatattgaa caacatgatg ttaatgaatt aaatgttttt   1560

ttttatttag atgctcaaaa agttccagaa ggtgaaaata atgttaattt aacatcatca   1620

attgatacag ctttattaga acaaccaaaa atttatacat ttttttcatc agaatttatt   1680
```

-continued

```
aataatgtta ataaaccagt tcaagctgct ttatttgttt catggattca acaagtttta   1740
gttgatttta caacagaagc taatcaaaaa tcaacagttg ataaaattgc tgatatttca   1800
attgttgttc catatattgg tttagcttta aatattggta atgaagctca aaaaggtaat   1860
tttaaagatg ctttagaatt attaggtgct ggtattttat tagaatttga accagaatta   1920
ttaattccaa caattttagt ttttacaatt aaatcatttt taggttcatc agataataaa   1980
aataaagtta ttaaagctat taataatgct ttaaaagaac gtgatgaaaa atggaaagaa   2040
gtttattcat ttattgtttc aaattggatg acaaaaatta atacacaatt taataaacgt   2100
aaagaacaaa tgtatcaagc tttacaaaat caagttaatg ctattaaaac aattattgaa   2160
tcaaaatata attcatatac attagaagaa aaaaatgaat taacaaataa atatgatatt   2220
aaacaaattg aaaatgaatt aaatcaaaaa gtttcaattg ctatgaataa tattgatcgt   2280
tttttaacag aatcatcaat ttcatattta atgaaattaa ttaatgaagt taaaattaat   2340
aaattacgtg aatatgatga aaatgttaaa acatatttat taaattatat tattcaacat   2400
ggttcaattt taggtgaatc acaacaagaa ttaaattcaa tggttacaga tacattaaat   2460
aattcaattc catttaaatt atcatcatat acagatgata aaattttaat ttcatatttt   2520
aataaatttt ttaaacgtat taaatcatca tcagttttaa atatgcgtta taaaaatgat   2580
aaatatgttg atacatcagg ttatgattca aatattaata ttaatggtga tgtttataaa   2640
tatccaacaa ataaaaatca atttggtatt tataatgata aattatcaga agttaatatt   2700
tcacaaaatg attatattat ttatgataat aaatataaaa atttttcaat ttcattttgg   2760
gttcgtattc caaattatga taataaaatt gttaatgtta ataatgaata tacaattatt   2820
aattgtatgc gtgataataa ttcaggttgg aaagtttcat taaatcataa tgaaattatt   2880
tggacattac aagataatgc tggtattaat caaaaattag cttttaatta tggtaatgct   2940
aatggtattt cagattatat taataaatgg atttttgtta caattacaaa tgatcgttta   3000
ggtgattcaa aattatatat taatggtaat ttaattgatc aaaaatcaat tttaaattta   3060
ggtaatattc atgtttcaga taatatttta tttaaaattg ttaattgttc atatacacgt   3120
tatattggta ttcgttattt taatattttt gataaagaat tagatgaaac agaaattcaa   3180
acattatatt caaatgaacc aaatacaaat attttaaaag atttttgggg taattattta   3240
ttatatgata aagaatatta tttattaaat gttttaaaac caaataattt tattgatcgt   3300
cgtaaagatt caacattatc aattaataat attcgttcaa caattttatt agctaatcgt   3360
ttatattcag gtattaaagt taaaattcaa cgtgttaata attcatcaac aaatgataat   3420
ttagttcgta aaaatgatca agtttatatt aattttgttg cttcaaaaac acatttattt   3480
ccattatatg ctgatacagc tacaacaaat aaagaaaaaa caattaaaat ttcatcatca   3540
ggtaatcgtt ttaatcaagt tgttgttatg aattcagttg gtaataattg tacaatgaat   3600
tttaaaaata ataatggtaa taatattggt ttattaggtt ttaaagctga tacagttgtt   3660
gcttcaacat ggtattatac acatatgcgt gatcatacaa attcaaatgg ttgtttttgg   3720
aattttattt cagaagaaca tggttggcaa gaaaaataa                          3759
```

```
<210> SEQ ID NO 28
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
```

-continued

<223> OTHER INFORMATION: BoNT/E, L. lactis-modified 3

<400> SEQUENCE: 28

```
atgccaaaaa ttaattcatt taattacaat gaccctgtca atgatcgtac aattctttat     60
attaaaccag gaggttgtca agaattttac aaatctttta atatcatgaa aaatatttgg    120
attatccctg aacgaaatgt tattggtact acaccacaag attttcatcc acctacatca    180
ttaaaaaatg gagatagttc atactatgat ccaaattatc ttcaatctga tgaagaaaaa    240
gatcgatttt taaaaatcgt tactaaaatt tttaatcgta ttaataataa tttatcaggt    300
ggaatcttac tagaagaatt atctaaagca aatccttatt taggtaatga taatacccca    360
gataatcaat ttcacattgg tgacgcaagc gctgttgaaa ttaaattttc taatggttct    420
caagatattt tacttccaaa tgtgattatc atgggagccg aaccagattt atttgaaact    480
aattcaagta atatttcttt acgtaataat tacatgccaa gcaatcatgg atttggaagc    540
attgctattg ttactttttc tccagaatac tcttttcgct ttaatgataa tagtatgaat    600
gaatttattc aagacccagc cctaactcta atgcatgaat taatccatag tttacatggt    660
ttatatggag ctaaaggtat tacaaccaaa tatacaatta cacaaaaaca aaatcctctt    720
atcacaaata ttcgtggaac aaatattgaa gaatttttaa cctttggtgg aaccgattta    780
aatattatca ctagtgctca atcaaatgac atttatacaa atcttttagc cgattataaa    840
aaaattgctt caaaattgag taaagtccaa gtgtcaaatc ctttattgaa tccatataaa    900
gatgtatttg aagccaaata cggattagat aaagatgctt caggtattta cagtgtgaat    960
attaataaat ttaatgatat ttttaaaaaa ctttattcat ttactgaatt tgatctagct   1020
actaaatttc aagtgaaatg tcgtcaaact tatattggtc aatataaata ttttaaactt   1080
agtaatttac ttaatgattc tatttataat attagtgaag gttacaatat taataattta   1140
aaagtgaatt ttagaggtca aaatgctaat ttaaatccta gaattatcac accaattaca   1200
ggtcgaggtt tggtcaaaaa aattatccgt ttttgtaaaa atattgtaag tgttaaaggt   1260
attcgtaaat caatttgtat tgaaattaat aatggtgaac ttttttttgt agcttcagaa   1320
aattcatata atgatgacaa tattaatact cctaaagaaa ttgatgacac agtaacatca   1380
aataataatt atgaaaatga cttagatcaa gttattctta attttaattc tgaaagtgca   1440
cctggtttgt cagatgaaaa attgaatttg actattcaaa atgatgctta cattccaaaa   1500
tatgattcta atggaacatc agatattgaa caacatgatg taaatgaact aaatgttttt   1560
ttttatttag atgcacaaaa agttccagaa ggagaaaata atgttaattt aacttctagt   1620
attgatactg ctttgctaga acaaccaaaa atctacacat ttttttcatc tgaatttatt   1680
aataatgtga ataaaccagt acaagcagcc ttatttgtct catggatcca acaagttttg   1740
gtagacttta caactgaagc taatcaaaaa tctacagttg acaaaattgc tgatatttct   1800
atcgttgtac catacattgg tttggctcta aatattggaa atgaagcaca aaaaggaaat   1860
tttaaagatg cattagaatt attgggtgca ggtatcttac ttgaatttga acctgaatta   1920
cttattccta ctatcttagt ttttactatc aaatcatttc ttggttcttc agataataaa   1980
aataaagtca ttaaagccat taataatgca ttaaaagaaa gagatgaaaa atggaaagaa   2040
gtttatagtt ttattgtttc aaattggatg acaaaaatta atacacaatt taataaacgc   2100
aaagaacaaa tgtaccaagc tttgcaaaat caagttaatg caatcaaaac aattatcgaa   2160
agtaaataca attcttatac ccttgaagaa aaaaatgaat taacaaataa atatgatatt   2220
aaacaaattg aaaatgaatt gaatcaaaaa gtaagcattg caatgaataa tattgataga   2280
```

-continued

```
tttttaactg aaagttctat ttcatatctt atgaaattga ttaatgaagt aaaaattaat   2340

aaattgcgtg aatatgatga aaatgtgaaa acatatcttt taaattatat cattcaacac   2400

ggaagcattt taggtgaatc tcaacaagaa ttaaattcaa tggtcactga tacactaaat   2460

aattcaattc cttttaaatt aagctcatat actgatgaca aaattttgat ctcatatttt   2520

aataaatttt ttaaacgaat taaatctagt tcagttttga atatgagata taaaaatgac   2580

aaatatgtcg acaccagcgg ttacgactct aatattaata ttaatggtga tgtgtacaaa   2640

tatccaacaa ataaaaatca atttggtatt tataatgata aattgagtga agtcaatatc   2700

tcacaaaatg attatatcat ttatgataat aaatataaaa atttttcaat tagtttttgg   2760

gtacgtattc caaattatga caataaaatt gttaatgtca ataatgaata tacaattatc   2820

aattgtatgc gagataataa ttcaggttgg aaagtttcac ttaatcacaa tgaaattatc   2880

tggaccottc aagacaatgc tggaattaat caaaaattag catttaatta tggaaatgct   2940

aatggtattt cagattatat taataaatgg attttttgtta caattaccaa tgatagattg   3000

ggtgattcta aattatatat taatggtaat cttattgacc aaaaaagcat tcttaatttg   3060

ggaaatattc atgtttcaga caatatttta tttaaaattg ttaattgttc ttatacacgt   3120

tatattggta ttagatattt taatattttt gataaagaat tagatgaaac agaaattcaa   3180

acattatatt caaatgaacc taatacaaat attttaaaag acttttgggg taattatcta   3240

ttatatgata aagaatacta tttgcttaat gttttaaaac caaataattt tattgatcgt   3300

agaaaagata gtaccttgtc aattaataat atccgtagta ctattttgct tgctaatcgt   3360

ttatactctg gtattaaagt taaaattcaa cgcgttaata attcaagtac aaatgacaat   3420

ttagtacgta aaaatgacca agtttatatc aattttgtag caagtaaaac tcatttattt   3480

ccactttatg ctgatactgc tacaactaat aaagaaaaaa caattaaaat ttcatctagc   3540

ggtaatagat ttaatcaagt tgtagttatg aattcagtcg gtaataattg tacaatgaat   3600

tttaaaaata ataatggtaa taatattggt cttcttggat ttaaagctga tacagttgtt   3660

gcatcaactt ggtattatac acatatgcgt gatcatacta atagcaatgg atgtttttgg   3720

aattttattt cagaagaaca cggatggcaa gaaaaataa                          3759
```

<210> SEQ ID NO 29
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, M. extorquens-modified 1

<400> SEQUENCE: 29

```
atgccgaaga tcaactcctt caactacaac gacccggtga acgaccgcac catcctgtac     60

atcaagccgg gcgggtgcca ggagttctac aagtcgttca atatcatgaa gaacatctgg    120

atcattccgg agcgcaacgt gatcggtacg accccacagg acttccaccc cccgacctcc    180

ctcaagaacg gcgacagctc ctactatgac ccgaactacc tgcagtcgga cgaggaaaag    240

gaccggttcc tgaagatagt caccaagatc tttaaccgga tcaacaataa cctctctggc    300

gggatcctgc tcgaggaact gagcaaggcc aacccgtacc tcggcaacga caacaccccg    360

gataatcagt tccacatcgg cgatgcctcg gccgtggaga tcaagttctc gaacgggtcc    420

caggatatcc tgttgccgaa cgtcatcatt atgggtgcgg agcccgacct gttcgagact    480
```

-continued

```
aactcatcga acatctcgct ccgcaacaat tacatgccga gtaaccatgg cttcggcagc    540
atcgccatcg tgaccttcag ccccgagtac agcttccgat tcaacgacaa ctcgatgaac    600
gaattcatcc aggatccggc cctcacgctc atgcatgagc tgatccacag cctgcacggc    660
ctctacggcg ctaaggggat caccacgaag tacacaatca cccagaagca gaacccgctg    720
atcaccaaca tccggggaac caacatcgag gaattcctca ccttcggcgg aaccgacctg    780
aatatcatta ccagcgccca gtcgaacgac atctacacga acctcctggc ggactacaag    840
aaaatcgcca gcaagctgtc gaaggtccag gtcagcaacc cgctcctgaa cccgtacaag    900
gacgtcttcg aggcgaaata cggcctcgac aaggacgcgt caggcatcta cagcgtgaac    960
atcaacaagt ttaacgacat cttcaagaaa ctctacagct tcaccgagtt cgacctggct   1020
accaagttcc aagttaagtg ccgccagacc tacattggcc agtacaagta cttcaagctc   1080
tccaatcttc tcaacgactc catctacaac atcagcgagg gctataacat caacaatctg   1140
aaggtcaact tccggggcca gaacgcgaac ctgaacccgc gcatcattac gccgatcacc   1200
ggccgcggcc tcgtgaagaa aatcattcgc ttctgcaaga atatcgtgtc cgtgaagggc   1260
atccgcaagt cgatctgcat cgagatcaac aatggcgagc tgtttttcgt cgcctcggag   1320
aactcgtaca acgacgataa catcaatacc ccgaaggaga tcgacgatac cgtcacctcg   1380
aacaataact acgagaacga tctggatcag gtcatcctga acttcaactc ggagagcgca   1440
ccgggcctgt cggatgagaa gctgaacctt acgatccaga acgacgccta catccccaag   1500
tacgacagca acggcacctc ggacatcgag cagcacgatg tgaacgaact gaacgtgttc   1560
ttttacctcg acgcccagaa ggtgcccgag ggggagaaca atgtcaacct cacctcctct   1620
atcgacaccg cgctactgga gcaaccgaag atctatacgt tcttctcgtc cgagttcatc   1680
aacaatgtca acaagcccgt ccaggcggcc ctgttcgtct cctggatcca gcaagttctc   1740
gtggacttca ccacggaggc gaatcagaag tcgacggtcg acaagatcgc cgatatctcg   1800
atcgtggtcc cctacatcgg tctcgcgctc aacatcggca acgaggccca aaagggcaac   1860
ttcaaggatg ccctcgaact gctcggcgcc gggatcctgc tcgagttcga gccggaactg   1920
ctcatcccca ccatcctcgt cttcaccatc aagtcgttcc tcggcagctc ggataataag   1980
aacaaggtga tcaaggcgat caacaatgcg ctcaaggaac gcgacgagaa gtggaaggag   2040
gtctacagct tcatcgtgtc gaactggatg acgaagatca acacccagtt caacaagcgg   2100
aaggagcaga tgtaccaggc cttgcagaac caggtgaacg ccatcaagac gatcatcgag   2160
tccaaatata actcgtacac ccttgaggaa aagaacgagc tcaccaacaa gtatgatatc   2220
aagcagatcg agaacgaact caaccagaag gtgagcatcg ccatgaacaa tatcgaccgg   2280
ttcctgaccg agagctcgat ctcgtacctc atgaagctca tcaacgaagt gaagatcaac   2340
aagctccgcg agtatgatga gaacgtcaag acctatctcc tgaactatat catccagcat   2400
ggctcgatcc tcggcgagtc gcagcaggaa ctgaacagca tggtcaccga cacactcaac   2460
aattccatcc cgttcaagct ctcgtcctat accgacgata agatcctgat cagctatttc   2520
aacaagttct tcaagcggat caagtcgtcc tcggtcctca acatgcgcta taagaacgac   2580
aagtacgtcg acacgtccgg ctacgacagc aatatcaaca tcaacggcga tgtctacaag   2640
taccctacga acaagaacca gttcggcatc tataacgata aactgtccga ggtgaacatc   2700
tcgcagaacg actatatcat ctatgacaac aagtacaaaa acttcagcat ctccttctgg   2760
gtccgcatcc ccaactacga caacaagatc gtgaacgtga acaatgagta taccatcatc   2820
aactgcatgc gcgacaacaa ttccggctgg aaggtcagcc tcaaccacaa cgagatcatc   2880
```

-continued

```
tggaccctcc aggacaacgc cggcatcaac cagaagctcg ccttcaacta cggcaacgcc   2940

aacggcatct cggactacat caacaagtgg atcttcgtga cgatcaccaa cgatcgcctc   3000

ggtgactcga agctctacat caacgggaat ctcatcgacc agaagagcat cctgaacctg   3060

ggcaacatcc acgtgtcgga caacatcctg ttcaagatcg tgaactgctc ctacacccgt   3120

tacatcggca tccgctactt caacatcttc gataaggagc tcgatgagac ggagatccag   3180

acgctctact ccaacgaacc caacacgaac atcctgaagg acttctgggg caactacctg   3240

ctctacgaca aggagtacta tctgttgaac gtcctgaagc ccaacaactt catcgaccgt   3300

cggaaggact ccacgttgtc gatcaacaac atccgctcga ccatcctgct cgcgaaccgc   3360

ctttactcgg gtatcaaggt gaagatccag cgcgtgaaca actcgtccac caacgacaac   3420

ctggtacgca agaacgacca ggtgtacatc aacttcgttg cctccaagac gcatctgttc   3480

cccctctacg cggacaccgc caccacgaac aaggagaaga cgatcaagat ctcgagctcg   3540

ggcaacaggt tcaaccaggt cgtggtcatg aactccgtcg gcaacaactg caccatgaac   3600

ttcaagaaca acaacggcaa caacatcggc ctgctgggct tcaaggcgga caccgtcgtc   3660

gcgtccacgt ggtactacac gcacatgcgc gaccacacca acagcaacgg ctgcttctgg   3720

aacttcatct cggaggagca cggctggcag gagaagtaa                          3759
```

<210> SEQ ID NO 30
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, M. extorquens-modified 2

<400> SEQUENCE: 30

```
atgccgaaga tcaactcgtt caactacaac gacccggtca acgaccgcac catcctctac     60

atcaagccgg gcggctgcca ggagttctac aagtcgttca acatcatgaa gaacatctgg    120

atcatcccgg agcgcaacgt catcggcacc accccgcagg acttccaccc gccgacctcg    180

ctcaagaacg gcgactcgtc gtactacgac ccgaactacc tccagtcgga cgaggagaag    240

gaccgcttcc tcaagatcgt caccaagatc ttcaaccgca tcaacaacaa cctctcgggc    300

ggcatcctcc tcgaggagct ctcgaaggcc aacccgtacc tcggcaacga caacaccccg    360

gacaaccagt tccacatcgg cgacgcctcg gccgtcgaga tcaagttctc gaacggctcg    420

caggacatcc tcctcccgaa cgtcatcatc atgggcgccg agccggacct cttcgagacc    480

aactcgtcga acatctcgct ccgcaacaac tacatgccgt cgaaccacgg cttcggctcg    540

atcgccatcg tcaccttctc gccggagtac tcgttccgct tcaacgacaa ctcgatgaac    600

gagttcatcc aggacccggc cctcaccctc atgcacgagc tcatccactc gctccacggc    660

ctctacggcg ccaagggcat caccaccaag tacaccatca cccagaagca gaacccgctc    720

atcaccaaca tccgcggcac caacatcgag gagttcctca ccttcggcgg caccgacctc    780

aacatcatca cctcggccca gtcgaacgac atctacacca acctcctcgc cgactacaag    840

aagatcgcct cgaagctctc gaaggtccag gtctcgaacc cgctcctcaa cccgtacaag    900

gacgtcttcg aggccaagta cggcctcgac aaggacgcct cgggcatcta ctcggtcaac    960

atcaacaagt tcaacgacat cttcaagaag ctctactcgt tcaccgagtt cgacctcgcc   1020

accaagttcc aggtcaagtg ccgccagacc tacatcggcc agtacaagta cttcaagctc   1080
```

-continued

```
tcgaacctcc tcaacgactc gatctacaac atctcggagg gctacaacat caacaacctc   1140
aaggtcaact tccgcggcca gaacgccaac ctcaacccgc gcatcatcac cccgatcacc   1200
ggccgcggcc tcgtcaagaa gatcatccgc ttctgcaaga acatcgtctc ggtcaagggc   1260
atccgcaagt cgatctgcat cgagatcaac aacggcgagc tcttcttcgt cgcctcggag   1320
aactcgtaca acgacgacaa catcaacacc ccgaaggaga tcgacgacac cgtcacctcg   1380
aacaacaact acgagaacga cctcgaccag gtcatcctca acttcaactc ggagtcggcc   1440
ccgggcctct cggacgagaa gctcaacctc accatccaga acgacgccta catcccgaag   1500
tacgactcga acggcacctc ggacatcgag cagcacgacg tcaacgagct caacgtcttc   1560
ttctacctcg acgcccagaa ggtcccggag ggcgagaaca acgtcaacct cacctcgtcg   1620
atcgacaccg ccctcctcga gcagccgaag atctacacct tcttctcgtc ggagttcatc   1680
aacaacgtca acaagccggt ccaggccgcc ctcttcgtct cgtggatcca gcaggtcctc   1740
gtcgacttca ccaccgaggc caaccagaag tcgaccgtcg acaagatcgc cgacatctcg   1800
atcgtcgtcc cgtacatcgg cctcgccctc aacatcggca acgaggccca gaagggcaac   1860
ttcaaggacg ccctcgagct cctcggcgcc ggcatcctcc tcgagttcga gccggagctc   1920
ctcatcccga ccatcctcgt cttcaccatc aagtcgttcc tcggctcgtc ggacaacaag   1980
aacaaggtca tcaaggccat caacaacgcc ctcaaggagc gcgacgagaa gtggaaggag   2040
gtctactcgt tcatcgtctc gaactggatg accaagatca acacccagtt caacaagcgc   2100
aaggagcaga tgtaccaggc cctccagaac caggtcaacg ccatcaagac catcatcgag   2160
tcgaagtaca actcgtacac cctcgaggag aagaacgagc tcaccaacaa gtacgacatc   2220
aagcagatcg agaacgagct caaccagaag gtctcgatcg ccatgaacaa catcgaccgc   2280
ttcctcaccg agtcgtcgat ctcgtacctc atgaagctca tcaacgaggt caagatcaac   2340
aagctccgcg agtacgacga gaacgtcaag acctacctcc tcaactacat catccagcac   2400
ggctcgatcc tcggcgagtc gcagcaggag ctcaactcga tggtcaccga caccctcaac   2460
aactcgatcc cgttcaagct ctcgtcgtac accgacgaca agatcctcat ctcgtacttc   2520
aacaagttct tcaagcgcat caagtcgtcg tcggtcctca acatgcgcta caagaacgac   2580
aagtacgtcg acacctcggg ctacgactcg aacatcaaca tcaacggcga cgtctacaag   2640
tacccgacca acaagaacca gttcggcatc tacaacgaca agctctcgga ggtcaacatc   2700
tcgcagaacg actacatcat ctacgacaac aagtacaaga acttctcgat ctcgttctgg   2760
gtccgcatcc cgaactacga caacaagatc gtcaacgtca acaacgagta caccatcatc   2820
aactgcatgc gcgacaacaa ctcgggctgg aaggtctcgc tcaaccacaa cgagatcatc   2880
tggaccctcc aggacaacgc cggcatcaac cagaagctcg ccttcaacta cggcaacgcc   2940
aacggcatct cggactacat caacaagtgg atcttcgtca ccatcaccaa cgaccgcctc   3000
ggcgactcga agctctacat caacggcaac ctcatcgacc agaagtcgat cctcaacctc   3060
ggcaacatcc acgtctcgga caacatcctc ttcaagatcg tcaactgctc gtacacccgc   3120
tacatcggca tccgctactt caacatcttc gacaaggagc tcgacgagac cgagatccag   3180
accctctact cgaacgagcc gaacaccaac atcctcaagg acttctgggg caactacctc   3240
ctctacgaca aggagtacta cctcctcaac gtcctcaagc cgaacaactt catcgaccgc   3300
cgcaaggact cgaccctctc gatcaacaac atccgctcga ccatcctcct cgccaaccgc   3360
ctctactcgg gcatcaaggt caagatccag cgcgtcaaca actcgtcgac caacgacaac   3420
ctcgtccgca agaacgacca ggtctacatc aacttcgtcg cctcgaagac ccacctcttc   3480
```

-continued

```
ccgctctacg ccgacaccgc caccaccaac aaggagaaga ccatcaagat ctcgtcgtcg   3540
ggcaaccgct tcaaccaggt cgtcgtcatg aactcggtcg gcaacaactg caccatgaac   3600
ttcaagaaca acaacggcaa caacatcggc ctcctcggct tcaaggccga caccgtcgtc   3660
gcctcgacct ggtactacac ccacatgcgc gaccacacca actcgaacgg ctgcttctgg   3720
aacttcatct cggaggagca cggctggcag gagaagtaa                         3759
```

<210> SEQ ID NO 31
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, M. extorquens-modified 3

<400> SEQUENCE: 31

```
atgcccaaga tcaactcctt caactacaac gacccggtca acgatcggac gatcctctac     60
atcaagccgg gcggctgcca ggagttctac aagtcgttca acatcatgaa gaacatctgg    120
atcatccccg agcgcaacgt catcggcacc acgccccagg acttccatcc cccgacgtcc    180
ctcaagaacg gcgactcgag ctactacgac ccgaactacc tccagtccga cgaggagaag    240
gatcgcttcc tcaagatcgt gacgaagatc ttcaaccgca tcaacaacaa cctgagcggc    300
ggcatcctgc tcgaggagct gtcgaaggcc aacccctacc tgggcaacga caacacgccg    360
gacaaccagt tccacatcgg cgacgccagc gccgtcgaga tcaagttctc gaacggctcc    420
caggacatcc tcctgccgaa cgtgatcatc atgggcgccg agccggacct gttcgagacg    480
aactcctcga acatctccct ccgcaacaac tacatgccgt ccaaccacgg cttcggctcg    540
atcgcgatcg tgaccttcag cccggagtac tccttccgct tcaacgataa ctccatgaac    600
gagttcatcc aggacccggc gctcacgctc atgcatgagc tcatccacag cctccatggc    660
ctctacggcg cgaagggcat cacgaccaag tacaccatca cccagaagca gaaccccctg    720
atcaccaaca tccgcggcac caacatcgag gagttcctga cgttcggcgg cacggatctc    780
aacatcatca cgtcggcgca gagcaacgac atctacacca acctgctcgc cgactacaag    840
aagatcgcct cgaagctctc gaaggtccag gtctcgaacc cgctcctgaa cccctacaag    900
gacgtgttcg aggcgaagta cggcctcgat aaggatgcgt ccggcatcta ctccgtcaac    960
atcaacaagt tcaacgacat cttcaagaag ctctacagct tcaccgagtt cgacctcgcc   1020
acgaagttcc aggtgaagtg ccgccagacc tacatcggcc agtacaagta cttcaagctc   1080
tcgaacctgc tcaacgactc gatctacaac atctcggagg gctacaacat caacaacctg   1140
aaggtcaact tccgcggcca gaacgccaac ctgaacccgc gcatcatcac cccgatcacc   1200
ggccggggcc tcgtgaagaa gatcatccgc ttctgcaaga acatcgtcag cgtgaagggc   1260
atccgcaaga gcatctgcat cgagatcaac aacggcgagc tgttcttcgt ggcctcggag   1320
aactcctaca acgatgacaa catcaacacg ccgaaggaga tcgacgatac cgtcacctcc   1380
aacaacaact acgagaacga cctggatcag gtcatcctga acttcaacag cgagagcgcc   1440
ccgggcctca gcgatgagaa gctcaacctc accatccaga acgatgcgta catccccaag   1500
tacgattcga acggcaccag cgatatcgag cagcacgacg tgaacgagct caacgtcttc   1560
ttctacctgg acgcgcagaa ggtcccggag ggcgagaaca acgtcaacct cacctcgtcc   1620
atcgacacgg ccctcctgga gcagcccaag atctacacct tcttctcgag cgagttcatc   1680
```

-continued

```
aacaacgtga acaagccggt ccaggccgcg ctgttcgtgt cctggatcca gcaggtcctg   1740

gtggacttca ccacggaggc gaaccagaag tccaccgtcg acaagatcgc cgatatcagc   1800

atcgtcgtgc cctacatcgg cctggccctc aacatcggca acgaggcgca gaagggcaac   1860

ttcaaggacg cgctggagct gctcggcgcc ggcatcctcc tggagttcga gccggagctg   1920

ctcatcccga ccatcctcgt cttcaccatc aagtcgttcc tcggctcgtc cgacaacaag   1980

aacaaggtca tcaaggccat caacaacgcc ctgaaggagc gggatgagaa gtggaaggag   2040

gtctactcgt tcatcgtgtc gaactggatg accaagatca acacccagtt caacaagcgg   2100

aaggagcaga tgtaccaggc cctgcagaac caggtgaacg ccatcaagac catcatcgag   2160

tcgaagtaca actcctacac cctcgaggag aagaacgagc tgacgaacaa gtacgacatc   2220

aagcagatcg agaacgagct caaccagaag gtgtcgatcg ccatgaacaa catcgatcgc   2280

ttcctcaccg agagctcgat ctcgtacctg atgaagctca tcaacgaggt caagatcaac   2340

aagctgcgcg agtacgacga gaacgtgaag acgtacctcc tgaactacat catccagcat   2400

ggctcgatcc tgggcgagtc gcagcaggag ctcaactcga tggtcaccga caccctcaac   2460

aactccatcc ccttcaagct gtcgagctac accgacgata agatcctcat ctcgtacttc   2520

aacaagttct tcaagcgcat caagagctcg tccgtcctca acatgcgcta caagaacgac   2580

aagtacgtcg acacctccgg ctacgactcg aacatcaaca tcaacggcga cgtgtacaag   2640

tacccgacga acaagaacca gttcggcatc tacaacgaca agctgtcgga ggtgaacatc   2700

agccagaacg actacatcat ctacgataac aagtacaaga acttctcgat ctcgttctgg   2760

gtccggatcc cgaactacga caacaagatc gtcaacgtca acaacgagta cacgatcatc   2820

aactgcatgc gcgacaacaa ctccggctgg aaggtgagcc tgaaccacaa cgagatcatc   2880

tggaccctcc aggacaacgc gggcatcaac cagaagctgg ccttcaacta cggcaacgcc   2940

aacggcatca gcgattacat caacaagtgg atcttcgtca cgatcaccaa cgaccgcctg   3000

ggcgactcga agctgtacat caacggcaac ctcatcgatc agaagtcgat cctcaacctc   3060

ggcaacatcc acgtgtcgga caacatcctc ttcaagatcg tgaactgcag ctacacgcgg   3120

tacatcggca tccggtactt caacatcttc gacaaggagc tggacgagac cgagatccag   3180

acgctgtact cgaacgagcc caacaccaac atcctcaagg atttctgggg caactacctc   3240

ctgtacgaca aggagtacta cctgctcaac gtgctgaagc cgaacaactt catcgaccgc   3300

cggaaggact ccaccctctc gatcaacaac atccgctcga ccatcctgct cgccaaccgc   3360

ctctacagcg gcatcaaggt gaagatccag cgcgtcaaca acagctccac caacgacaac   3420

ctcgtccgca agaacgacca ggtctacatc aacttcgtcg cctccaagac ccacctgttc   3480

ccgctctacg cggacaccgc cacgaccaac aaggagaaga ccatcaagat ctcgagctcg   3540

ggcaaccgct tcaaccaggt ggtcgtgatg aactcggtcg gcaacaactg caccatgaac   3600

ttcaagaaca acaacggcaa caacatcggc ctcctcggct tcaaggccga caccgtggtg   3660

gcgtcgacct ggtactacac ccacatgcgc gaccacacca actcgaacgg ctgcttctgg   3720

aacttcatca gcgaggagca cggctggcag gagaagtaa                          3759
```

<210> SEQ ID NO 32
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, S. typhimurium-modified 1

-continued

<400> SEQUENCE: 32

```
atgccgaaaa ttaacagctt taattataat gacccggtaa acgatcgcac cattctctat     60
attaaaccag gcggatgcca ggagttttac aaatctttta acatcatgaa aaatatctgg    120
ataattcctg aaagaaatgt gatcggtacc actccccaag attttcatcc gcctacctca    180
ctaaaaaacg gagatagcag ttattacgat ccgaattact tacagagcga cgaggaaaaa    240
gaccgttttt tgaaaatagt caccaaaatt ttcaatcgca taaataacaa tctgagcggc    300
ggtatccttc tggaggaatt gtccaaggcc aatccgtact taggtaacga taacacgccc    360
gataatcagt ttcatattgg cgatgcctcc gcagtagaga ttaagttcag caatggaagc    420
caagacatcc tgctcccgaa tgtgattatc atgggcgcag agccagatct gtttgagaca    480
aacagcagta acatttctct acgtaacaat tacatgccta gtaaccacgg ctttggttcg    540
attgcgattg tgacgttctc accggagtat tcatttcgtt tcaatgataa ttcaatgaac    600
gagtttattc aggatcccgc gctgaccctg atgcatgaac ttattcattc tctgcatggc    660
ctgtacgggg cgaaaggcat taccacaaaa tacaccatta cgcagaaaca aaatcctttg    720
atcaccaaca ttcgtggcac gaatatagaa gagttcctga cgttcggtgg gaccgacctg    780
aatattatca ccagcgcgca atcgaatgat atctatacga atctactggc cgattataaa    840
aagatcgcgt ctaaattaag caaagtgcag gttagcaacc cgctcctgaa cccatataaa    900
gatgtcttcg aagcaaaata tggtttagat aaagatgcct cgggcattta ttcagtcaac    960
attaacaaat tcaacgacat cttcaagaaa ctgtactcgt ttaccgaatt tgatctggcg   1020
actaagttcc aggtgaaatg ccgtcaaacg tatatcgggc aatacaaata ttttaagctg   1080
tccaatctac tgaacgactc catatacaat attagcgaag gatataatat taacaatctg   1140
aaggttaatt tccgcggcca gaatgcaaat ctgaacccgc gtattatcac cccgattacg   1200
ggccgggggc tcgtcaagaa aatcattcgc ttctgcaaga acattgtttc agtcaagggc   1260
atccgcaaaa gcatttgcat tgaaattaat aacggcgagc tgttctttgt tgcgagcgaa   1320
aactcgtata atgacgataa tatcaacacg cccaaagaga tcgatgacac ggttaccagt   1380
aataacaatt atgaaaacga tttagaccaa gtgatcctga actttaatag cgaaagcgct   1440
ccgggcctga gcgacgaaaa actgaacctt actatccaga acgatgcgta tatcccgaag   1500
tatgactcta acggcacgtc cgatatcgaa cagcacgatg taaacgaact gaacgtcttt   1560
ttctacttag atgcccaaaa agtgccggaa ggtgaaaaca atgttaatct tacttcttcg   1620
atcgatacgg cgctgttgga gcaaccgaag atttacacat tcttttcttc ggagtttatc   1680
aacaatgtga acaaaccagt acaggccgcg ctgtttgtgt cctggattca acaggtatta   1740
gttgatttta ccacggaagc gaaccagaag agcaccgtcg ataaaatcgc cgatatatcg   1800
atcgtcgtgc cgtatattgg cctggcgctg aatattggca acgaagccca gaaaggcaat   1860
ttcaaagacg cattagaact gcttggtgcc ggtatcttgc tggaattcga accggaactc   1920
ttaattccta cgatcctggt ttttactatt aaatcgtttc tgggctccag cgataataaa   1980
aacaaagtta tcaaagccat taataacgcc ttgaaagagc gcgacgaaaa atggaaagaa   2040
gtgtactcct tcattgtgtc gaactggatg accaaaatca acacgcagtt taacaaacgt   2100
aaagaacaga tgtatcaggc tttacagaat caggtcaacg caattaaaac aatcattgag   2160
tcgaaataca attcctatac ccttgaggaa aaaaacgagc tgaccaacaa atatgatatt   2220
aaacagatcg aaaatgagct gaaccagaag gtctcgatcg cgatgaacaa tatcgatcgt   2280
```

-continued tttttgaccg aaagtagcat atcatacctg atgaaactga ttaatgaagt aaaaataaac 2340
aaacttcgag agtacgatga aaatgttaag acgtatttac tgaattatat tatccagcat 2400
ggcagcatcc tgggggaatc tcagcaagag ctgaactcga tggttaccga tactctgaac 2460
aatagcatac cattcaaact gtccagttac accgacgata aaatactgat ctcatatttt 2520
aacaaatttt tcaagcggat taagtcgagc tccgtgctga atatgcgtta caaaaatgac 2580
aaatatgtcg acacttccgg ttacgacagc aatatcaaca ttaacggaga tgtatacaaa 2640
tacccgacga acaagaatca gtttggcatt tacaatgata agcttagcga agtgaatatt 2700
tctcagaatg attatattat ctatgacaac aagtataaaa atttttctat tagtttttgg 2760
gttcgtattc cgaactacga taataagatt gttaacgtca ataacgaata tacaatcatt 2820
aactgtatgc gggacaacaa ttcaggatgg aaagtgagct taaaccacaa tgagatcatt 2880
tggacgttgc aggataatgc cggcatcaat cagaaactag cttttaatta tggtaacgcg 2940
aacggcatct ccgactatat taataaatgg attttcgtga ccatcaccaa cgatcgcctt 3000
ggtgatagca agctgtatat taacggcaac ctcattgacc agaaatcgat cttgaacctt 3060
gggaacattc acgtgagcga taacatcctc tttaaaattg tcaattgctc ttatacacgc 3120
tacatcggca ttcgctattt taatattttt gacaaagagt tagatgaaac agaaatccag 3180
accctctatt cgaacgagcc gaacacgaac atactgaaag atttttgggg caattatctg 3240
ttgtacgaca aagaatacta tctgctcaat gtgctgaaac ccaataactt tattgaccgt 3300
aggaaggatt ctaccctgtc cattaacaat atccgcagca cgatccttct cgctaaccgc 3360
ctgtactcag gcataaaggt aaaaatccag cgagtgaaca atagtagcac gaacgacaac 3420
ttggtccgca aaaatgacca agtgtatatc aatttcgttg cgagtaaaac tcatctgttt 3480
cctctgtatg cggacacggc gacgaccaac aaggagaaaa ccattaaaat ctcctcaagt 3540
gggaatcgct tcaaccaagt ggtcgtaatg aacagtgtgg gtaacaattg taccatgaac 3600
tttaaaaata acaatggaaa taacatcggg ttgctgggtt ttaaagcgga taccgtcgta 3660
gcttccacct ggtattatac gcacatgcgg gaccatacta acagtaacgg ctgtttctgg 3720
aacttcattt ccgaagaaca cgggtggcag gaaaaataa 3759

<210> SEQ ID NO 33
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, S. typhimurium-modified 2

<400> SEQUENCE: 33
atgccgaaaa ttaacagctt taactataac gatccggtga acgatcgcac cattctgtat 60
attaaaccgg gcggctgcca ggaattttat aaaagcttta acattatgaa aaacatttgg 120
attattccgg aacgcaacgt gattggcacc accccgcagg attttcatcc gccgaccagc 180
ctgaaaaacg gcgatagcag ctattatgat ccgaactatc tgcagagcga tgaagaaaaa 240
gatcgctttc tgaaaattgt gaccaaaatt tttaaccgca ttaacaacaa cctgagcggc 300
ggcattctgc tggaagaact gagcaaagcg aacccgtatc tgggcaacga taacaccccg 360
gataaccagt ttcatattgg cgatgcgagc gcggtggaaa ttaaatttag caacggcagc 420
caggatattc tgctgccgaa cgtgattatt atgggcgcgg aaccggatct gtttgaaacc 480
aacagcagca acattagcct gcgcaacaac tatatgccga gcaaccatgg ctttggcagc 540

-continued

```
attgcgattg tgacctttag cccggaatat agctttcgct ttaacgataa cagcatgaac    600
gaatttattc aggatccggc gctgaccctg atgcatgaac tgattcatag cctgcatggc    660
ctgtatggcg cgaaaggcat taccaccaaa tataccatta cccagaaaca gaacccgctg    720
attaccaaca ttcgcggcac caacattgaa gaatttctga cctttggcgg caccgatctg    780
aacattatta ccagcgcgca gagcaacgat atttatacca acctgctggc ggattataaa    840
aaaattgcga gcaaactgag caaagtgcag gtgagcaacc cgctgctgaa cccgtataaa    900
gatgtgtttg aagcgaaata tggcctggat aaagatgcga gcggcattta tagcgtgaac    960
attaacaaat ttaacgatat ttttaaaaaa ctgtatagct ttaccgaatt tgatctggcg   1020
accaaatttc aggtgaaatg ccgccagacc tatattggcc agtataaata ttttaaactg   1080
agcaacctgc tgaacgatag catttataac attagcgaag gctataacat taacaacctg   1140
aaagtgaact ttcgcggcca gaacgcgaac ctgaacccgc gcattattac cccgattacc   1200
ggccgcggcc tggtgaaaaa aattattcgc ttttgcaaaa acattgtgag cgtgaaaggc   1260
attcgcaaaa gcatttgcat tgaaattaac aacggcgaac tgttttttgt ggcgagcgaa   1320
aacagctata acgatgataa cattaacacc ccgaaagaaa ttgatgatac cgtgaccagc   1380
aacaacaact atgaaaacga tctggatcag gtgattctga actttaacag cgaaagcgcg   1440
ccgggcctga gcgatgaaaa actgaacctg accattcaga acgatgcgta tattccgaaa   1500
tatgatagca acggcaccag cgatattgaa cagcatgatg tgaacgaact gaacgtgttt   1560
ttttatctgg atgcgcagaa agtgccggaa ggcgaaaaca acgtgaacct gaccagcagc   1620
attgataccg cgctgctgga acagccgaaa atttatacct tttttagcag cgaatttatt   1680
aacaacgtga acaaaccggt gcaggcggcg ctgtttgtga gctggattca gcaggtgctg   1740
gtggatttta ccaccgaagc gaaccagaaa agcaccgtgg ataaaattgc ggatattagc   1800
attgtggtgc cgtatattgg cctggcgctg aacattggca acgaagcgca gaaaggcaac   1860
tttaaagatg cgctggaact gctgggcgcg ggcattctgc tggaatttga accggaactg   1920
ctgattccga ccattctggt gtttaccatt aaaagctttc tgggcagcag cgataacaaa   1980
aacaaagtga ttaaagcgat taacaacgcg ctgaaagaac gcgatgaaaa atggaaagaa   2040
gtgtatagct ttattgtgag caactggatg accaaaatta acacccagtt taacaaacgc   2100
aaagaacaga tgtatcaggc gctgcagaac caggtgaacg cgattaaaac cattattgaa   2160
agcaaatata acagctatac cctggaagaa aaaaacgaac tgaccaacaa atatgatatt   2220
aaacagattg aaaacgaact gaaccagaaa gtgagcattg cgatgaacaa cattgatcgc   2280
tttctgaccg aaagcagcat tagctatctg atgaaactga ttaacgaagt gaaaattaac   2340
aaactgcgcg aatatgatga aaacgtgaaa acctatctgc tgaactatat tattcagcat   2400
ggcagcattc tgggcgaaag ccagcaggaa ctgaacagca tggtgaccga taccctgaac   2460
aacagcattc cgtttaaact gagcagctat accgatgata aaattctgat tagctatttt   2520
aacaaatttt ttaaacgcat taaaagcagc agcgtgctga acatgcgcta taaaaacgat   2580
aaatatgtgg ataccagcgg ctatgatagc aacattaaca ttaacggcga tgtgtataaa   2640
tatccgacca acaaaaacca gtttggcatt tataacgata aactgagcga agtgaacatt   2700
agccagaacg attatattat ttatgataac aaatataaaa actttagcat tagcttttgg   2760
gtgcgcattc cgaactatga taacaaaatt gtgaacgtga acaacgaata taccattatt   2820
aactgcatgc gcgataacaa cagcggctgg aaagtgagcc tgaaccataa cgaaattatt   2880
```

-continued tggaccctgc aggataacgc gggcattaac cagaaactgg cgtttaacta tggcaacgcg 2940
aacggcatta gcgattatat taacaaatgg atttttgtga ccattaccaa cgatcgcctg 3000
ggcgatagca aactgtatat taacggcaac ctgattgatc agaaaagcat tctgaacctg 3060
ggcaacattc atgtgagcga taacattctg tttaaaattg tgaactgcag ctatacccgc 3120
tatattggca ttcgctattt taacattttt gataaagaac tggatgaaac cgaaattcag 3180
accctgtata gcaacgaacc gaacaccaac attctgaaag atttttgggg caactatctg 3240
ctgtatgata aagaatatta tctgctgaac gtgctgaaac cgaacaactt tattgatcgc 3300
cgcaaagata gcaccctgag cattaacaac attcgcagca ccattctgct ggcgaaccgc 3360
ctgtatagcg gcattaaagt gaaaattcag cgcgtgaaca acagcagcac caacgataac 3420
ctggtgcgca aaaacgatca ggtgtatatt aactttgtgg cgagcaaaac ccatctgttt 3480
ccgctgtatg cggataccgc gaccaccaac aaagaaaaaa ccattaaaat tagcagcagc 3540
ggcaaccgct ttaaccaggt ggtggtgatg aacagcgtgg gcaacaactg caccatgaac 3600
tttaaaaaca acaacggcaa caacattggc ctgctgggct ttaaagcgga taccgtggtg 3660
gcgagcacct ggtattatac ccatatgcgc gatcatacca acagcaacgg ctgcttttgg 3720
aactttatta gcgaagaaca tggctggcag gaaaaataa 3759

<210> SEQ ID NO 34
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, S. typhimurium-modified 3

<400> SEQUENCE: 34
atgccaaaaa ttaattcctt caattataat gacccggtaa acgatcgcac gattttgtac 60
atcaaaccgg gcggttgcca ggaattttat aaaagcttta atattatgaa gaatatctgg 120
attatccctg agcgtaacgt cattggcacg acccctcagg acttccatcc acctacctcg 180
ctgaaaaatg gcgactcctc atattacgac ccgaactacc tgcagagcga tgaagagaaa 240
gatcgctttc ttaaaattgt gacgaagatc tttaaccgta ttaataacaa tctgagcggt 300
ggcattctgc tcgaagagct gagcaaagcg aacccctacc tgggcaatga caacacccct 360
gataaccagt ttcacattgg tgacgcgtct gcggttgaaa tcaaatttag taatggctcc 420
caggatatct tgcttcctaa tgttattatc atgggcgcag agccggattt atttgaaacc 480
aacagttcaa acatttcgct gcggaataac tacatgccgt cgaaccacgg gttcggcagc 540
attgcgattg tgaccttttc tccggaatat tccttccgtt tcaacgacaa ctcaatgaat 600
gaatttatcc aggatccggc gctgaccctt atgcacgaac tgattcatag tctgcatggc 660
ctctatggcg cgaaaggcat taccacgaaa tataccatta cgcagaagca gaatccgctc 720
attaccaata ttcgcggcac gaatatcgaa gagtttctga cgtttggggg taccgacttg 780
aatatcatta cgagcgcgca aagcaacgat atttatacca acctgttggc ggattataaa 840
aagattgcta gcaagctgtc aaaggtacag gtatctaacc ccttactgaa cccgtacaaa 900
gatgtgtttg aagcaaagta tggccttgat aaggatgcat cgggcattta cagcgtgaat 960
attaacaaat ttaacgacat tttcaaaaag ctgtatagct tcaccgagtt tgatttagcc 1020
acgaaattcc aggttaaatg ccgccagacc tacattggtc agtataaata ctttaaactg 1080
agcaatctct tgaatgattc aatctataat atctcggaag gctataacat caacaatctg 1140

-continued aaagtcaact ttcgtggtca aaatgctaat ctcaatccgc gcatcattac ccccatcacc 1200
ggccgcggcc tggtgaaaaa gattatccgc ttttgtaaaa acatcgtgtc ggtaaaaggc 1260
atccgcaaat caatctgcat cgagatcaac aatggcgagc tgtttttcgt cgctagcgag 1320
aactcctaca atgatgacaa cattaatacc ccgaaagaga ttgatgacac cgtcacgagc 1380
aataacaatt acgaaaatga cctggaccag gtcattctga acttcaatag tgaatcagca 1440
cccgggctgt cggatgaaaa acttaacctg accattcaga acgatgcgta tattccaaag 1500
tatgacagta acggcaccag cgacattgaa cagcatgatg tcaatgaact caatgtgttc 1560
ttttacctgg atgcacagaa agtgccggaa ggggaaaaca atgtcaacct gacctccagt 1620
attgacaccg cgctgcttga acagcccaaa atctatacct tttctcatc ggaattcatc 1680
aacaatgtaa ataagccagt acaagcggcc ctgtttgttt cctggatcca acaggtgctt 1740
gtagacttca cgaccgaagc gaaccagaaa agcaccgtcg ataagatcgc cgatatttcg 1800
atcgtcgtgc catacatcgg cctggcgttg aacatcggca atgaggctca aaagggcaac 1860
tttaaggatg ctctggaatt actgggcgcc ggtattctgc tcgaatttga gccggagtta 1920
ttgatcccga ccatcttagt gtttacgatt aaatcgttct tgggcagttc cgataataaa 1980
aataaggtca tcaaagccat taataacgcg ctgaaagaac gcgatgagaa atggaaagag 2040
gtgtactctt ttatcgttag caactggatg accaaaatca atacccagtt caataaacgc 2100
aaagaacaga tgtatcaggc cctgcaaaat caggtcaacg ccatcaaaac cattatcgaa 2160
agcaaatata atagctacac gctggaagag aaaaatgagc tgaccaataa atacgatatc 2220
aagcaaattg agaatgagtt aaaccagaaa gtaagcattg ccatgaacaa tattgaccgt 2280
tttctgaccg agagtagcat ttcctatctc atgaaactta tcaacgaggt caaaattaac 2340
aaactgcgcg aatatgatga aaatgtgaag acgtacctgt taaactatat tatccagcat 2400
ggctctattc tgggggaaag ccaacaggaa ttaaactcga tggttaccga caccctgaat 2460
aacagcattc ctttcaaact gtcttcatat accgatgaca agattctgat ctcctatttt 2520
aataaatttt tcaagcgtat caaaagttcc agcgtgctga atatgcggta taaaaatgat 2580
aaatacgtgg acaccagcgg ttatgactcg aatattaata ttaacggtga tgtttataag 2640
tacccgacga acaaaaatca gtttggcatt tataacgata agctcagtga agttaacatc 2700
tcacagaatg attacatcat ttatgataat aaatataaaa acttttctat ttccttctgg 2760
gttcgtattc cgaactacga taataaaatt gtaaacgtta acaatgaata taccattatc 2820
aattgtatgc gtgataataa ctcgggctgg aaagtgtccc ttaaccacaa cgaaatcatt 2880
tggacgctgc aggacaacgc gggcattaac caaaaattag cctttaacta tgggaacgcc 2940
aacgggattt ctgattatat caacaaatgg atctttgtca cgattacgaa cgaccgcttg 3000
ggtgactcca aattatacat taacggtaat ctgattgacc aaaaaagcat cttgaacttg 3060
ggcaacattc acgtttctga taatatcctg tttaaaatcg tcaattgttc atatacccgt 3120
tatattggca ttcgttattt caacattttc gataaagaac tggacgagac ggagattcaa 3180
acgctgtata gcaacgaacc gaacacgaac atccttaaag atttttgggg taactacttg 3240
ttatatgata aagagtacta tctgcttaac gtgctgaagc cgaacaattt catcgatcgg 3300
cgcaaagata gtacgctgag catcaacaat attcgttcca ccattctgtt agccaatcgc 3360
ctctacagcg gcattaaagt caagattcag cgcgtgaata actcgtccac caacgataac 3420
ctggttcgca aaaatgacca agtgtatatt aacttcgtgg cgagcaaaac ccatctgttt 3480

-continued ccgctgtacg cggataccgc caccacgaac aaagaaaaaa ccattaaaat ttcgtcttcg 3540
ggcaaccggt tcaatcaggt cgttgtgatg aacagtgttg ggaataactg caccatgaat 3600
tttaaaaaca ataacggtaa taacattggg ctgctgggtt ttaaagcgga taccgtggta 3660
gcatctacct ggtactatac gcatatgcgc gaccacacca attctaacgg ctgcttttgg 3720
aatttcatct ccgaagaaca tggctggcaa gaaaagtaa 3759

<210> SEQ ID NO 35
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, P. pastoris-modified 1

<400> SEQUENCE: 35
atgccaaaaa ttaactcctt caattacaat gatcctgtaa acgatagaac tattttgtat 60
attaaaccag gcggttgtca agagttttac aaatcattta atatcatgaa aaacatttgg 120
ataatcccag agcgcaatgt gataggtacg actccacaag atttccaccc gcccactagc 180
ttaaaaaacg gagactcttc atattacgat cctaactacc tgcaaagtga cgaagagaag 240
gatagattcc tgaaaattgt tacaaagatt ttcaacagga taaacaataa cttgagtggc 300
ggtatccttt tggaggaact ttctaaagca aatccttatc tgggcaacga caacacccca 360
gacaaccaat tccacatcgg tgacgcctcc gctgtagaaa ttaaattctc taatggatct 420
caggatatct tgctaccaaa tgtgatcatt atgggagcag agccagacct gttcgaaaca 480
aactcttcca atatatccct tagaaataac tacatgcctt ctaatcatgg atttgggagc 540
atcgcaatcg tgaccttttc tcccgagtat tcttttaggt tcaatgacaa ctcaatgaac 600
gaatttatcc aggaccctgc tctaacattg atgcacgaat tgattcattc tttacatggt 660
ttatatggag caaagggaat cacaactaaa tacacaatta ctcagaagca aaatcctttg 720
atcacaaata ttagaggtac aaacatcgaa gagtttttga cgtttggggg tacagattta 780
aatatcatta catccgcaca atctaacgat atttacacaa acctattggc ggactataaa 840
aagattgctt ctaaactgtc gaaggtacaa gttagtaatc ccttgttaaa cccttacaag 900
gacgttttcg aggctaaata cggtttggac aaagatgctt caggcatcta tagcgttaat 960
attaataaat tcaacgatat ctttaagaaa ttgtattcct tcactgaatt tgatttggcc 1020
acgaagtttc aagttaaatg tcgacagacg tatattggcc aatacaaata ttttaagctc 1080
agcaacctct tgaacgactc aatatataat atttccgagg gttataacat taacaatctg 1140
aaggttaact tcagaggaca aaatgctaac ctaaacccaa gaataattac cccaatcact 1200
ggtcgtggtt tggttaaaaa gattatccgt ttttgcaaaa atattgtgtc tgttaagggt 1260
attcgaaagt cgatctgtat tgaaatcaac aatggtgaat tgtttttcgt agcctccgaa 1320
aactcctaca acgatgacaa cattaacact ccgaaggaga ttgatgacac tgtcacgtct 1380
aacaataact acgagaatga cttagaccaa gttatactaa atttcaactc tgagagcgcc 1440
cctgggttat ctgatgaaaa attgaacctt actattcaaa acgacgctta tattcctaaa 1500
tatgattcta atggaacgtc tgatatcgaa caacatgacg tcaatgaatt gaacgtcttt 1560
ttctatctag acgcacaaaa ggtcccagag ggagagaata acgtcaattt aacaagttcg 1620
attgataccg ctttgctaga acagccaaag atctacacct tttctctag tgaattcata 1680 aacaatgtta acaagccagt tcaagccgct ttatttgtgt cgtggattca gcaagtcctt 1740

-continued

```
gttgatttca ctaccgaagc caatcagaag tcaaccgttg ataagatagc cgatatttct   1800
attgtcgtac cttacattgg gttggctctg aatattggaa acgaagcaca aaaaggtaac   1860
tttaaagacg cattagaact cctgggtgct ggaatcttgc tggagttcga gccagagctg   1920
ttgattccca caatcttggt gttcacaatt aagtcctttc taggatcttc agataataaa   1980
aacaaagtga tcaaggcaat taataacgct ttgaaagaaa gggacgaaaa atggaaggaa   2040
gtttacagct ttatcgtcag taactggatg accaagatta acacccaatt caataagaga   2100
aaggaacaga tgtaccaggc tttgcaaaat caggtgaacg ctataaagac tattatcgag   2160
tctaaataca actcttacac actggaggaa aagaatgagc tgactaacaa atatgacatt   2220
aaacaaattg aaaacgaact caatcagaag gttagtatcg ctatgaataa catagataga   2280
ttcttgaccg agtctagtat ttcttactta atgaaattga taaatgaggt taagataaac   2340
aaattaagag aatacgatga aaacgttaag acttacttac ttaattacat tatacaacac   2400
ggttctatac ttggtgagtc tcaacaggag ctgaattcta tggttactga cacccttaac   2460
aattcaatac cctttaagct tagttcctat actgatgaca agatactaat tagttacttc   2520
aataagtttt tcaagagaat taaatcatcc tcagttctta acatgcgata caaaaaacgat   2580
aaatatgttg atactagtgg ttacgattcc aacataaaca tcaatgggga tgtttataag   2640
tatccgacta acaagaacca gtttggaatt tataatgata agctatcaga ggttaatatc   2700
tcacaaaatg attatattat ctacgacaat aagtataaga atttcagtat ttcattctgg   2760
gtccgcatcc ctaactacga caacaagatt gttaacgtaa acaatgagta cactattata   2820
aactgtatga gagataacaa ttccggttgg aaggtctcgc tgaatcacaa cgaaattata   2880
tggacgcttc aggataatgc tggtatcaac caaaagttag catttaatta tggtaatgcc   2940
aacggaattt cagattacat taataagtgg atctttgtta ctattaccaa tgatagactt   3000
ggcgatagta aattgtatat taacggaaac ctaattgatc aaaaaagcat tctgaatctc   3060
ggtaatatcc atgtctccga caatattttg ttcaagattg ttaactgctc atatactagg   3120
tacatcggta ttcggtattt taatatattt gataaggaac ttgacgaaac agaaatccag   3180
accctttata gtaacgagcc taatacgaac attttaaaag acttttgggg gaactacttg   3240
ctgtacgata aggagtacta tctcttgaac gtcctaaagc caaacaattt tatcgacaga   3300
cgtaaagact ctactttgtc aataaacaat atacggagta ccatcctcct tgctaaccgt   3360
ttgtactcag gaattaaagt gaaaattcaa agggtaaata actcgtccac aaacgataat   3420
ctcgttcgta agaatgatca ggtctacatt aactttgtcg cgtccaaaac tcatttgttc   3480
ccccttatg ctgataccgc cacaactaat aaagaaaaga ctatcaaaat tagctcatcg   3540
ggtaatagat ttaatcaagt cgtagtgatg aattcggtgg gcaataactg taccatgaat   3600
tttaagaaca ataacggcaa caatatcggt ttacttggat ttaaggccga tactgtagtg   3660
gcctccactt ggtactacac ccatatgaga gatcatacta attccaacgg atgcttctgg   3720
aactttatca gcgaagaaca cggttggcag gaaaagtaa                          3759
```

<210> SEQ ID NO 36
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, P. pastoris-modified 2

-continued

<400> SEQUENCE: 36

```
atgccaaaga tcaactcgtt caactataac gaccctgtta atgatcgtac catcctatat      60
attaagcctg gtgggtgtca ggaattttat aagtcattca atattatgaa gaatatttgg     120
attataccgg agagaaatgt cattgggacc actccccaag actttcatcc tcccactagt     180
ctaaaaaatg gtgactcatc ctactatgac cctaattacc tccaatccga tgaagagaag     240
gatagatttc tgaagattgt caccaaaatc tttaacagaa ttaataacaa tttgtctggt     300
ggcattctgt tggaagagct gagtaaagcc aacccgtacc tcggtaatga caatacgcca     360
gataaccaat ttcacatagg tgacgcatca gcggtagaga ttaaatttag caacggttca     420
caggatatcc tgttgcctaa tgttataatt atgggagctg aaccagatct tttcgaaact     480
aactcatcca atatctcctt aaggaacaat tatatgccat cgaatcacgg atttggctcg     540
attgctattg ttacattcag cccagagtac tcattcaggt tcaacgacaa ctccatgaac     600
gaatttatcc aagatccagc attgacgctg atgcatgaac ttattcatag cttgcacggc     660
ctttacggag ccaagggtat tacaactaaa tataccatta ctcaaaagca gaaccctttg     720
attactaaca tccgtggaac taacatagag gaattcctaa ccttcggtgg aacggacctt     780
aatataatca cctccgctca atcaaacgat atttatacaa atttgctagc agattataag     840
aaaattgcct ccaaattgag caaagtacaa gtctcaaacc ctttgcttaa cccatataaa     900
gacgttttcg aggctaagta cggtctagat aaagacgcca gcggtattta ttcggttaat     960
attaataagt ttaatgatat atttaaaaag ttatacagct ttacagagtt tgatctggca    1020
accaaattcc aggtgaagtg tagacaaacc tacatcggtc agtataagta cttcaaactg    1080
tcaaacctct tgaacgactc aatctataat atttctgaag gatataacat aaataacttg    1140
aaagttaact tccgaggaca gaacgctaat ttgaatccta gaattatcac acctatcacc    1200
ggccggggac tggtgaaaaa gattatcaga ttttgcaaga acatcgtttc cgttaaagga    1260
ataagaaaaa gtatttgcat cgaaatcaat aacggcgaac tcttctttgt tgcttctgaa    1320
aactcataca acgacgataa tatcaatacg cccaaagaga ttgacgatac tgttaccagt    1380
aataacaatt acgagaatga cctggatcaa gtcatcctaa attttaacag tgagtctgct    1440
ccagggttgt cagacgaaaa gcttaacttg acgatacaga atgatgctta tattcctaaa    1500
tacgattcca atggtacttc tgatattgaa caacatgacg ttaacgaatt gaacgttttc    1560
ttttatttgg acgcccaaaa ggttcccgaa ggagaaaaca atgtgaactt gacatcctct    1620
attgatacag ccccttttgga acaaccaaaa atttacacat tttctcgtc tgaattcatc    1680
aataacgtca acaaacctgt gcaagcggct ttatttgtgt cttggataca gcaagttctg    1740
gtagatttca caactgaggc taaccaaaag agtactgttg ataagatagc tgatatctcc    1800
atcgttgtcc cctacattgg tctagctttg aacattggta acgaagctca gaaaggtaac    1860
tttaaggatg ctttagaatt acttggtgca ggaattctct tggagttcga gccagaacta    1920
cttattccga cgatcttagt gttcacaatt aagagtttcc ttgggtcatc tgataataaa    1980
aacaaggtta ttaaggccat taacaatgct ttaaaggaaa gagatgaaaa atggaaggag    2040
gtttactctt ttatcgtgtc aaattggatg actaaaatta atactcagtt taataagcgg    2100
aaggaacaaa tgtaccaggc attacaaaac caagtcaatg ccattaaaac tataatcgag    2160
tccaagtaca attcttatac acttgaggaa aaaaacgaac ttaccaataa atacgatatt    2220
aaacaaatcg agaacgagtt gaatcaaaaa gtctctatag caatgaataa cattgacagg    2280
ttcttgactg aatcttccat ctcttatctg atgaaattga ttaacgaagt caaaattaac    2340
```

-continued aagttgcgtg agtacgatga gaatgttaag acatatcttt tgaattatat aattcaacat 2400
ggtagcattt taggtgaatc tcagcaagag ttaaactcca tggtaactga cacgttgaat 2460
aacagcatac cttttaaatt gagttcttat actgacgata agatcctgat ttcgtatttc 2520
aataagttct ttaaacgcat caagtctagt tctgtcctta atatgaggta caagaacgac 2580
aaatacgtcg atacttctgg atatgattct aatattaaca ttaatggcga tgtctataag 2640
tacccaacca ataagaatca atttggtatc tacaatgaca aactttccga agttaatata 2700
tctcaaaatg actacattat atacgacaac aagtataaaa actttagtat aagtttttgg 2760
gttagaatcc ccaactatga caacaagatt gtcaacgtaa ataacgagta cactattatc 2820
aactgtatga gagataataa ctctggctgg aaggtttcgc tcaaccataa cgaaattata 2880
tggacactgc aggataatgc aggaattaac cagaagcttg ccttcaatta cggtaacgcc 2940
aacggaatct ccgattacat caacaagtgg atttttgtga ctattaccaa tgatagactg 3000
ggggactcga aactctatat taacggtaac cttatagacc agaagtctat cctaaatttg 3060
ggtaacatcc atgtttcaga taatattcta tttaagatcg ttaactgtag ttacactaga 3120
tatattggta tcagatattt taacatattt gacaaggaat tggatgaaac tgagattcaa 3180
accttgtaca gcaacgaacc aaacactaac atactcaagg atttttgggg aaactactta 3240
ctatatgata aggagtacta tttattgaac gtcttaaagc caaacaattt tattgataga 3300
aggaaggact ctactttatc cattaataac attcgatcta ccattctgtt agccaaccgc 3360
ttgtactccg gtatcaaggt gaaaatccaa agagtaaaca attctagtac aaacgacaat 3420
ttggttcgta aaaatgatca agtatacatc aacttcgtgg catcaaagac tcacttattc 3480
ccactatacg ctgatactgc aaccacaaac aaggagaaaa ccataaaaat tagttcaagt 3540
gggaatcgtt ttaaccaggt ggtagttatg aattctgtcg gaaataactg tacaatgaat 3600
ttcaagaata acaatggtaa taacatcgga ctgttgggct tcaaagctga tacagtggta 3660
gcttctactt ggtactacac tcacatgcga gaccacacga attccaatgg ttgcttctgg 3720
aattttattt cagaggaaca tggatggcag gagaaataa 3759

<210> SEQ ID NO 37
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, P. pastoris-modified 3

<400> SEQUENCE: 37
atgccaaaga tcaatagttt caactacaac gatccggtta atgacagaac tattctgtac 60
attaagcctg gtggctgtca ggagttctat aaaagcttta acattatgaa gaatatttgg 120
attatacccg agcgaaatgt gattggaaca actccacaag atttccatcc gccaacatcc 180
ttgaaaaatg gtgattcttc ctactatgat ccaaactacc tgcaatcaga cgaagagaag 240
gaccggtttc taaagatcgt taccaagata tttaatagaa tcaataacaa tctttcaggc 300
ggtatcttgt tagaggaact gtctaaagcc aatccctact tgggtaatga caacacacca 360
gacaatcagt tccatatcgg tgatgcttcc gctgttgaaa ttaagttctc caacgggtcc 420
caagatattc ttctgcccaa tgtgattatc atgggagctg aaccagacct tttgaaact 480 aactcgtcta acatatctct acgtaacaat tacatgccaa gtaatcatgg ttttggaagt 540

-continued

```
atcgcaatcg ttacttttag tcctgagtat agttttagat ttaatgataa ctctatgaac    600
gagtttatcc aagacccagc tttgacgttg atgcacgaat taattcactc tttacacgga    660
ttgtatggcg ctaaaggaat cacaactaaa tacacaatta ctcaaaaaca gaaccctttg    720
ataacgaata tacgtggcac taacattgag gaatttttaa catttggtgg aactgatctt    780
aatatcatta cctctgccca atccaacgac atatacacta atttgctcgc agattacaag    840
aaaatcgcct ctaagctttc taaagtgcag gtatcaaatc ctttgctaaa cccttataag    900
gatgtatttg aggctaagta tggtttggac aaagacgcca gcggtattta ttccgtgaat    960
ataaacaagt ttaatgatat tttcaaaaag ttatactcct tcacagagtt cgatctagca   1020
acaaagtttc aggtcaagtg tagacaaact tatatcggac agtataagta cttcaaacta   1080
tcaaacttac ttaatgattc catatataac atttcagagg gttacaacat taacaatctt   1140
aaggtaaact tcagaggaca aaatgcaaac ttaaacccta gaattatcac tcctattacc   1200
ggcagagggc tggttaagaa aatcattcgc ttctgcaaaa acattgtatc ggttaagggt   1260
attaggaaaa gtatttgcat cgaaatcaac aatggtgaat tgttctttgt ggcttctgag   1320
aactcataca acgatgacaa cattaatact cctaaggaaa tcgatgacac tgtcacctcc   1380
aataacaatt atgagaatga cctcgatcaa gtgatattaa actttaattc agaaagcgct   1440
ccaggattat cagacgagaa gttaaatctt actatacaga acgatgctta catacccaaa   1500
tacgacagta acggtacttc agacattgag caacatgatg ttaatgaact gaacgtcttt   1560
ttctatttag acgcccaaaa ggttcctgag ggtgaaaata acgtcaattt gacgagctca   1620
atcgatactg ctttactgga acaaccaaag atttacacct tttctcttc cgaattcatt    1680
aataacgtca ataaacccgt tcaagcagct ctattcgttt catggattca acaggttttg   1740
gtcgatttca ctacagaggc caatcaaaaa tcaactgtcg ataagatagc cgacatttcg   1800
attgtggtac catacattgg tttggcctta aacatcggta atgaggctca aaagggaaac   1860
ttcaaagatg cacttgaact tttgggtgcg ggaattcttt tagaatttga gcctgagctg   1920
ttgattccaa ccattcttgt attcactatt aaatcgtttc tgggatctag cgataataaa   1980
aacaaggtca tcaaggcaat taataacgca ttaaaagaaa gagatgaaaa gtggaaagag   2040
gtttacagct ttatcgtgtc gaattggatg acaaaaatca acacacagtt caacaagaga   2100
aaagaacaaa tgtatcaagc cctacaaaat caagtcaatg ccattaaaac aattatcgaa   2160
tcgaagtaca actcttacac tctagaggaa aaaaacgaac tgaccaacaa atatgacatt   2220
aagcagatcg aaaatgaatt gaaccaaaaa gtctctatcg caatgaataa cattgataga   2280
tttctgactg aatcttcgat atcttacctt atgaaactta taaacgaggt taagattaat   2340
aaactaagag aatatgatga aaatgtcaag acatatttgc tgaactacat aattcaacac   2400
ggttcaatcc tcggggaatc tcagcaagaa ctaaactcta tggtcacgga taccctcaac   2460
aatagtatac cctttaagtt gtccagctac accgacgata agattctaat aagctatttt   2520
aataagttct ttaagagaat caagtcctca tctgttttga acatgaggta caagaacgat   2580
aaatacgtag acacttcggg atacgactca aacattaata tcaacggcga tgtttataag   2640
taccctacaa ataagaacca gttcggtatc tataatgata agttgtcaga agtgaatatc   2700
tctcagaacg actatattat ctacgataac aagtataaaa attttagtat cagtttctgg   2760
gtgcgaatac caaactacga taacaagata gtcaacgtca acaatgagta caccattatc   2820
aactgtatga gagacaacaa ttcaggatgg aaggtgagtt tgaatcacaa cgagattatc   2880
tggacgctgc aggataacgc aggtatcaat caaaaactcg cttttaacta cggtaatgct   2940
```

-continued

```
aacggtattt ccgattatat taataaatgg atatttgtta cgattactaa cgataggcta   3000

ggagattcta aattgtacat taatggtaac ttgatcgacc aaaaatccat tctgaacttg   3060

ggaaacattc atgtttccga taatatcttg ttcaagattg ttaactgttc ctataccaga   3120

tatattggta taaggtactt caacattttc gacaaagaat tggacgagac tgaaatacag   3180

accctttatt ccaacgaacc gaacaccaac atattgaagg atttttgggg taattatttg   3240

ctgtatgata aggagtatta ccttttgaat gttttgaaac ctaacaattt tattgaccga   3300

cggaaggatt ctactttgtc tattaacaat attagaagca ctattttact ggcgaaccgt   3360

ttgtattctg gaattaaagt caagattcag agggtgaata actcttccac aaatgataat   3420

cttgtacgca agaacgacca agtttacatc aacttcgttg ccagtaaaac acatttgttc   3480

ccactctacg ctgatactgc tacgacaaat aaagaaaaaa ccatcaaaat ttctagttct   3540

ggtaaccgtt ttaatcaagt tgtagttatg aactcagttg gcaataactg tactatgaat   3600

ttcaaaaata acaatggaaa taacattggg ctcctcgggt ttaaggctga caccgttgtt   3660

gctagtacgt ggtattacac ccacatgcgt gaccatacca actctaatgg ctgcttttgg   3720

aattttatca gtgaagagca tgggtggcag gagaagtaa                          3759
```

```
<210> SEQ ID NO 38
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, S. cerevisiae-modified 1

<400> SEQUENCE: 38
```

```
atgccaaaaa ttaattcatt taactacaat gaccctgtaa atgacagaac aatcttgtac     60

attaaacctg gtgggtgtca agagttttac aaaagtttca acatcatgaa gaatatttgg    120

attataccgg aaaggaatgt tataggtact acaccacaag attttcatcc acctacttcc    180

ctaaaaaacg gggattcatc gtattacgac cctaactatt tacaaagcga cgaggaaaag    240

gataggttcc ttaagatcgt tacaaaaatc tttaatagaa tcaacaataa cttgagcgga    300

ggtatcttgt tagaagagct tagtaaagca aatccatact taggtaacga taatactcca    360

gataaccaat ttcatattgg tgatgcatcc gctgttgaaa ttaagttctc taatggttca    420

caagatatac tcttaccaaa tgttattatc atgggcgctg aaccagatct attcgaaacc    480

aactcctcta acatctcact gagaaataac tacatgccgt cgaatcacgg ctttggttct    540

attgcgatcg tgacgttttc acccgaatac tcgttcagat ttaacgataa tagcatgaat    600

gaatttattc aagatcctgc tttaacttta atgcacgagt taatacatag tttgcatggc    660

ttgtacggag ctaaaggcat taccacaaag tatactataa ctcaaaagca aaatccgttg    720

attaccaata taagaggtac caatatagag gaattcttaa catttggtgg aactgatttg    780

aatattataa cttcagccca gtctaacgat atttatacta atttactggc tgattacaaa    840

aagatcgctt ctaaattgag taaggtgcaa gtctctaacc cactattgaa cccctacaaa    900

gacgtttttg aggccaaata cggattggac aaggatgcaa gtggcatcta ctctgttaat    960

attaacaagt tcaatgatat ttttaagaaa ctatactcct ttacagaatt tgatttggca   1020

acaaaatttc aagtaaaatg tagacaaacg tatatcggtc aatataaata cttcaaatta   1080

tctaacttac taaacgattc tatctacaat atcagcgaag gatataatat aaacaattta   1140
```

-continued

```
aaagtaaatt tccgaggaca gaatgcaaac ttaaacccaa gaatcataac tcccattacg   1200
ggtagaggtc tagtcaaaaa gatcattcga ttctgtaaga atattgtgag cgttaaaggt   1260
atacggaaga gtatctgcat agaaattaat aacggcgaat tatttttcgt tgcttctgag   1320
aattcataca acgacgataa cattaatact ccaaaagaaa ttgatgacac agtcacaagc   1380
aacaataact atgaaaatga cttagaccaa gtaatcctaa atttcaattc ggaatcagct   1440
ccaggtttat ccgatgaaaa actgaaccta acaatacaga atgatgcgta cataccaaaa   1500
tacgattcta atggcacatc agacattgag cagcatgacg tcaatgagct aaatgtattt   1560
ttctatttgg atgctcaaaa ggtcccagaa ggtgaaaata acgttaacct aaccagttca   1620
atagacaccg cgcttttaga acaacctaaa atctatactt tctttagttc tgagtttatc   1680
aataacgtca ataagcctgt ccaagccgca ctgtttgtta gttggatcca acaggtgttg   1740
gttgatttta ccacggaagc aaaccagaag tcgacagttg acaaaattgc cgatatatca   1800
atagtagttc cctatattgg attagctctc aatataggaa atgaagctca aaagggtaat   1860
tttaaagacg ctttggaact tttgggcgct ggtatattac ttgaatttga accagagttg   1920
ctgattccga ctatcctggt ctttaccata aaatcttttt taggatctag tgataacaaa   1980
aataaagtaa ttaaggcaat taataacgca ctaaaagaaa gggatgaaaa atggaaggaa   2040
gtgtattcat tcatcgtgtc caattggatg actaaaataa atacccaatt caacaagcgc   2100
aaggaacaaa tgtatcaggc cttgcagaac caagtgaatg cgataaaaac aattatcgag   2160
tctaaatata attcgtacac tttggaggaa aaaaatgaac tgactaataa atacgatatc   2220
aagcagattg aaaatgaatt aaaccaaaaa gtgagtatag ccatgaataa catcgatagg   2280
tttttgaccg aatcttccat ttcctatttg atgaaattga ttaatgaggt taaaattaat   2340
aaattgagag aatatgatga gaacgttaaa acgtatctat taaactacat tatacaacat   2400
ggctccatct tgggtgaatc tcaacaggag ctgaatagca tggtcacaga tacactgaac   2460
aattcaatac ccttcaagtt gtcgtcatac acggacgata agatccttat ttcctacttc   2520
aacaagtttt tcaagagaat caaaagtagc tcagtcttaa atatgcgcta taaaaatgat   2580
aagtatgtag acacttctgg atatgactct aatattaaca tcaatggtga cgtgtataag   2640
taccctacga acaagaacca gttcggcatt tataacgaca agttaagcga agttaatata   2700
agtcaaaatg actatattat atacgacaac aaatataaaa atttttcgat atctttctgg   2760
gttaggattc ctaactatga taataagatc gtgaatgtaa ataacgaata tacaattata   2820
aactgtatgc gtgataacaa ttcgggttgg aaggtgagtc taaaccataa cgaaattata   2880
tggacactcc aggataacgc agggattaat caaaaattgg catttaatta cgggaatgcc   2940
aacggcattt ctgattatat taataagtgg attttcgtaa caattactaa cgatagactg   3000
ggtgattcaa aattatatat taatgggaat ctcattgacc aaaaaagtat tttgaatctt   3060
ggtaatatcc acgtaagcga caatatcctt tttaagatag ttaattgctc ttataccaga   3120
tatattggta ttcgttactt caacattttt gataaggagt tggacgagac cgaaattcaa   3180
acgctctact caaatgaacc taatacgaac attctgaagg atttttgggg taattatttg   3240
ctttatgata aagaatacta tttgttaaac gttctcaaac caaacaattt catagataga   3300
aggaaagact ccactctatc tataaataac attcgttcta ccattttgct tgccaatcgt   3360
ctttattcag gaattaaagt taaaattcaa agggttaata actcctctac aaatgataac   3420
cttgtcagaa agaatgatca ggtttatatt aattttgtgg catcaaaaac tcaccttttc   3480
cctttatatg ccgatactgc tactaccaat aaagagaaga cgataaagat ttcctcaagc   3540
```

-continued

```
gggaacagat ttaaccaagt cgttgtaatg aattccgttg gtaataactg tactatgaat   3600

tttaagaaca ataacggaaa taacatcggt ctattagggt tcaaagcgga tacagtagtc   3660

gcttctacct ggtattatac tcatatgcgt gatcacacaa attccaatgg atgcttttgg   3720

aattttatat ccgaagaaca tggttggcag gaaaaataa                          3759
```

<210> SEQ ID NO 39
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, S. cerevisiae-modified 2

<400> SEQUENCE: 39

```
atgccaaaaa ttaattcttt taattataat gatccagtta atgatagaac tattttgtat     60

attaaaccag gtggttgtca agaattttat aaatctttta atattatgaa aaatatttgg    120

attattccag aaagaaatgt tattggtact actccacaag attttcatcc accaacttct    180

ttgaaaaatg gtgattcttc ttattatgat ccaaattatt tgcaatctga tgaagaaaaa    240

gatagatttt tgaaaattgt tactaaaatt tttaatagaa ttaataataa tttgtctggt    300

ggtattttgt tggaagaatt gtctaaagct aatccatatt tgggtaatga taatactcca    360

gataatcaat ttcatattgg tgatgcttct gctgttgaaa ttaaattttc taatggttct    420

caagatattt tgttgccaaa tgttattatt atgggtgctg aaccagattt gtttgaaact    480

aattcttcta atatttcttt gagaaataat tatatgccat ctaatcatgg ttttggttct    540

attgctattg ttactttttc tccagaatat tcttttagat ttaatgataa ttctatgaat    600

gaatttattc aagatccagc tttgactttg atgcatgaat tgattcattc tttgcatggt    660

ttgtatggtg ctaaaggtat tactactaaa tatactatta ctcaaaaaca aaatccattg    720

attactaata ttagaggtac taatattgaa gaatttttga cttttggtgg tactgatttg    780

aatattatta cttctgctca atctaatgat atttatacta atttgttggc tgattataaa    840

aaaattgctt ctaaattgtc taaagttcaa gtttctaatc cattgttgaa tccatataaa    900

gatgtttttg aagctaaata tggtttggat aaagatgctt ctggtattta ttctgttaat    960

attaataaat ttaatgatat ttttaaaaaa ttgtattctt ttactgaatt tgatttggct   1020

actaaatttc aagttaaatg tagacaaact tatattggtc aatataaata ttttaaattg   1080

tctaatttgt tgaatgattc tatttataat atttctgaag gttataatat taataatttg   1140

aaagttaatt ttagaggtca aaatgctaat ttgaatccaa gaattattac tccaattact   1200

ggtagaggtt tggttaaaaa aattattaga ttttgtaaaa atattgtttc tgttaaaggt   1260

attagaaaat ctatttgtat tgaaattaat aatggtgaat tgttttttgt tgcttctgaa   1320

aattcttata atgatgataa tattaatact ccaaaagaaa ttgatgatac tgttacttct   1380

aataataatt atgaaaatga tttggatcaa gttattttga attttaattc tgaatctgct   1440

ccaggtttgt ctgatgaaaa attgaatttg actattcaaa atgatgctta tattccaaaa   1500

tatgattcta atggtacttc tgatattgaa caacatgatg ttaatgaatt gaatgttttt   1560

ttttatttgg atgctcaaaa agttccagaa ggtgaaaata atgttaattt gacttcttct   1620

attgatactg ctttgttgga acaaccaaaa atttatactt ttttttcttc tgaatttatt   1680

aataatgtta ataaaccagt tcaagctgct ttgtttgttt cttggattca acaagttttg   1740
```

-continued

```
gttgatttta ctactgaagc taatcaaaaa tctactgttg ataaaattgc tgatatttct   1800
attgttgttc catatattgg tttggctttg aatattggta atgaagctca aaaaggtaat   1860
tttaaagatg ctttggaatt gttgggtgct ggtattttgt tggaatttga accagaattg   1920
ttgattccaa ctattttggt ttttactatt aaatcttttt tgggttcttc tgataataaa   1980
aataaagtta ttaaagctat taataatgct ttgaaagaaa gagatgaaaa atggaaagaa   2040
gtttattctt ttattgtttc taattggatg actaaaatta atactcaatt taataaaaga   2100
aaagaacaaa tgtatcaagc tttgcaaaat caagttaatg ctattaaaac tattattgaa   2160
tctaaatata attcttatac tttggaagaa aaaaatgaat tgactaataa atatgatatt   2220
aaacaaattg aaaatgaatt gaatcaaaaa gtttctattg ctatgaataa tattgataga   2280
tttttgactg aatcttctat ttcttatttg atgaaattga ttaatgaagt taaaattaat   2340
aaattgagag aatatgatga aaatgttaaa acttatttgt tgaattatat tattcaacat   2400
ggttctattt tgggtgaatc tcaacaagaa ttgaattcta tggttactga tactttgaat   2460
aattctattc catttaaatt gtcttcttat actgatgata aaattttgat ttcttatttt   2520
aataaatttt ttaaaagaat taaatcttct tctgttttga atatgagata taaaaatgat   2580
aaatatgttg atacttctgg ttatgattct aatattaata ttaatggtga tgtttataaa   2640
tatccaacta ataaaaatca atttggtatt tataatgata aattgtctga agttaatatt   2700
tctcaaaatg attatattat ttatgataat aaatataaaa atttttctat ttctttttgg   2760
gttagaattc caaattatga taataaaatt gttaatgtta ataatgaata tactattatt   2820
aattgtatga gagataataa ttctggttgg aaagtttctt tgaatcataa tgaaattatt   2880
tggactttgc aagataatgc tggtattaat caaaaattgg cttttaatta tggtaatgct   2940
aatggtattt ctgattatat taataaatgg atttttgtta ctattactaa tgatagattg   3000
ggtgattcta aattgtatat taatggtaat ttgattgatc aaaaatctat tttgaatttg   3060
ggtaatattc atgtttctga taatattttg tttaaaattg ttaattgttc ttatactaga   3120
tatattggta ttagatattt taatattttt gataaagaat tggatgaaac tgaaattcaa   3180
actttgtatt ctaatgaacc aaatactaat attttgaaag atttttgggg taattatttg   3240
ttgtatgata aagaatatta tttgttgaat gttttgaaac caaataattt tattgataga   3300
agaaaagatt ctactttgtc tattaataat attagatcta ctattttgtt ggctaataga   3360
ttgtattctg gtattaaagt taaaattcaa agagttaata attcttctac taatgataat   3420
ttggttagaa aaaatgatca agtttatatt aattttgttg cttctaaaac tcatttgttt   3480
ccattgtatg ctgatactgc tactactaat aaagaaaaaa ctattaaaat ttcttcttct   3540
ggtaatagat ttaatcaagt tgttgttatg aattctgttg gtaataattg tactatgaat   3600
tttaaaaata ataatggtaa taatattggt ttgttgggtt ttaaagctga tactgttgtt   3660
gcttctactt ggtattatac tcatatgaga gatcatacta attctaatgg ttgtttttgg   3720
aattttattt ctgaagaaca tggttggcaa gaaaaataa                         3759
```

<210> SEQ ID NO 40
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, S. cerevisiae-modified 3

<400> SEQUENCE: 40

-continued

```
atgccaaaga taaattcatt taactataat gatcccgtga atgatcgtac aatactttat     60
attaaaccag gaggttgcca agagttttac aagtctttca atataatgaa gaatatctgg    120
ataatcccag aaagaaatgt gattggaact acacctcagg attttcatcc acccacatca    180
cttaagaatg gtgattcttc atattacgat ccaaattatt tgcaaagcga cgaagagaag    240
gacaggttct taaaaatagt cactaaaata tttaatagaa ttaataacaa tttgagcggt    300
ggaatattac tagaagagtt gtccaaggct aatccatatt tgggtaacga taatacccca    360
gataatcaat ttcacattgg cgatgcttcc gctgtggaaa tcaagttctc gaacggttct    420
caagatatac tattgcctaa tgtgatcatt atgggtgctg agccagattt gttcgaaact    480
aatagttcta atatcagtct aaggaataac tatatgccat caaatcatgg tttcggttct    540
atcgcaattg taaccttctc ccctgaatat tcatttagat ttaacgataa ttcaatgaat    600
gaatttattc aggaccccgc cttgacactg atgcatgagt tgattcattc tttgcacggt    660
ctgtacggtg caaaaggtat cactaccaag tatacaataa cgcaaaaaca aaatccttta    720
attaccaaca ttagaggtac caacatcgaa gagttcttga cctttggcgg aacggattta    780
aacatcatta cgagcgcaca atcgaatgat atttacacaa atctacttgc tgattacaag    840
aaaatcgctt cgaagttgag caaagttcaa gtttctaacc cattgctgaa tccatataag    900
gatgtattcg aggccaaata tggtttagac aaagacgcat ccggtatcta ttcagtcaac    960
attaacaagt ttaacgatat ttttaagaaa ttgtattcct tcacggagtt tgaccttgct   1020
acaaagtttc aagtcaagtg cagacagaca tatataggcc aatataaata cttcaaattg   1080
tctaacctat taaatgactc tatttacaat atttctgaag gctacaacat aaacaatttg   1140
aaagttaatt tcagaggtca aaacgcaaat ttaaatccca ggatcataac gccaatcacg   1200
ggacgtggtc tggttaaaaa gattatcaga ttttgtaaaa atattgtttc tgttaaaggt   1260
ataagaaaat caatctgtat tgaaataaac aatggtgaac tgtttttcgt cgctagtgaa   1320
aactcttata atgacgataa tataaacacg cctaaagaaa ttgacgatac tgtaacttcg   1380
aacaataact atgaaaacga tctagatcaa gtgatcctaa acttcaactc ggaaagtgct   1440
cctggattgt ccgacgaaaa gttaaacctt acaattcaga acgatgccta tatccctaaa   1500
tatgactcaa acggaacttc agacatagaa caacatgatg taaacgaact taatgtattt   1560
ttctaccttg acgcacaaaa ggttccagag ggcgaaaata acgtgaactt aacctcatcg   1620
attgataccg cattgcttga acaaccaaaa atctacacat tcttttcttc cgagtttatt   1680
aacaatgtta acaagccagt ccaagctgcc ctattcgttt cttggattca gcaagtgcta   1740
gttgatttca ctacagaggc taatcaaaaa tctaccgtag ataagatcgc cgatatttca   1800
attgtagtcc catatatagg acttgcccta aacattggta acgaagcaca aaaaggtaat   1860
tttaaggacg ccctagagtt actgggtgca ggtattttgt tagaattcga accagaatta   1920
ttgattccaa ctatattggt ctttacgata aagagttttc ttggaagcag tgataacaag   1980
aataaagtta tcaaagctat aaataacgcc ttaaaggaaa gggatgaaaa atggaaagaa   2040
gtgtacagtt tcattgtgag caattggatg actaagatta atactcaatt taataagaga   2100
aaagaacaga tgtaccaagc attacagaat caggtaaatg ctattaagac tataattgaa   2160
tccaaataca atagttatac cctggaggaa aaaaatgagc ttactaacaa atatgatatc   2220
aaacagattg aaaatgaatt aaaccaaaaa gtttccatcg caatgaataa catagataga   2280
ttcttaaccg aatcgtctat ctcctaccta atgaaactta taaatgaagt taagataaac   2340
```

-continued

```
aaattacgtg aatatgacga aaacgtcaaa acctacttgc tgaactatat aatccaacac   2400
ggttcaatct tgggagaaag ccaacaggag ttgaattcta tggtaaccga cactttgaac   2460
aatagtattc cttttaaatt atcctcttac actgacgata agattttaat ctcttatttt   2520
aacaagtttt tcaagagaat taaatcgtct tcggttttaa atatgagata caaaaaatgat   2580
aaatatgtcg atacgagtgg ctatgattcc aatatcaata taaacggtga tgtatacaaa   2640
tacccaacta ataaaaatca gttcggtatt tataatgaca aactgtctga agtaaatatt   2700
tcacagaacg attacataat ctatgataat aagtataaga acttttccat atcattttgg   2760
gtaaggattc ctaattatga caacaaaata gtgaatgtaa ataacgagta cacaatcata   2820
aattgcatga gagataataa ctccggctgg aaagtcagtt tgaaccataa cgaaatcata   2880
tggacattgc aggataacgc tggcattaat caaaagttgg cctttaacta tggtaatgct   2940
aatggaatct cagactacat taataagtgg atatttgtta caattactaa tgatagactg   3000
ggcgattcta aattgtacat aaacggtaat ttgattgatc aaaaaagcat tttgaactta   3060
ggtaacattc acgtttcaga taatatatta tttaaaattg ttaattgtag ctacacacgt   3120
tacatcggta taaggtactt caatattttc gacaaagaat tagacgaaac tgagatccaa   3180
acactatact ctaacgagcc caatacaaat attctaaagg atttttgggg taattactta   3240
ttgtatgaca aggaatacta tttattgaat gttttaaaac ctaacaattt tattgataga   3300
aggaaagact ctacactttc cattaataac attagaagta ctatcttact ggctaacaga   3360
ctatatagtg gaattaaagt taagattcag agagtcaata actccagtac caatgataat   3420
ttagtgagaa aaaatgacca agtttatatt aacttcgttg catcaaagac tcatttgttc   3480
cctttgtatg ctgatacggc tacaaccaat aaggaaaaga ctattaaaat tagtagctct   3540
ggcaatcgtt ttaatcaagt tgtcgtgatg aattcagttg gaaataactg tacaatgaac   3600
tttaaaaata acaatggcaa taacattggt ttgttgggtt ttaaagctga tactgtcgtt   3660
gcttctactt ggtattatac acatatgaga gaccacacta attcaaatgg ttgtttttgg   3720
aattttatta gcgaggaaca tggttggcaa gaaaaataa                          3759
```

<210> SEQ ID NO 41
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, S. pombe-modified 1

<400> SEQUENCE: 41

```
atgcccaaga taaactcgtt taattataac gacccggtta atgaccgtac catactttat     60
atcaaaccag gaggttgtca agaattttat aaaagtttta atattatgaa aaatatatgg    120
ataattccag aacgcaacgt tataggtacc acgcctcaag actttcatcc ccctacgtcg    180
ttaaagaacg gtgattcatc ctattacgat ccaaattatc tccaatctga tgaagagaag    240
gatcgattcc taaaaattgt tactaaaatt tttaatcgta ttaacaataa cctatctgga    300
ggtattcttt tagaggaatt gtctaaagca aacccttatt taggaaacga caacacgcct    360
gacaaccagt ttcacatagg cgatgcctcc gcagtggaga taaaatttag caatggatct    420
caagacatct tacttccgaa tgtaataatt atgggagccg agccagattt atttgaaact    480
aattcaagta atatctcttt aagaaataac tatatgccat ccaatcatgg ctttggttcg    540
atagcaatag ttacttttag ccctgaatac tcattcagat ttaacgacaa ttcaatgaac    600
```

-continued

```
gaatttattc aggacccagc gttgacttta atgcacgaac ttattcactc ccttcatggc    660
ctctatggag caaaggggat tacaactaaa tatacaatca cacaaaagca gaacccctta    720
attactaaca tcaggggtac taatattgaa gagttcctta ctttcggcgg taccgatcta    780
aatattataa ctagtgctca aagcaacgat atctatacta atcttctcgc cgattataaa    840
aagatcgcat ctaaattatc caaagtacaa gttagtaatc ctcttttgaa tccttacaag    900
gacgtatttg aggctaaata tggctcgat aaagatgcta gtggaattta ttccgttaat    960
ataaacaaat ttaatgatat ttttaagaaa ctatactctt tcactgaatt tgatttagcc   1020
acaaaatttc aagtcaagtg ccgtcaaact tatatcggtc aatacaagta ttttaaactc   1080
tctaatttac tcaatgattc gatttataat atttctgaag gttacaatat taataacctg   1140
aaagttaatt ttaggggtca aaatgctaat cttaaccctc gcatcataac tcctataact   1200
ggacgagggt tggtcaagaa aataattcgt ttttgtaaaa atatcgtttc cgttaaagga   1260
attcgtaaat ctatttgtat agaaattaac aatggagaat tatttttcgt ggctagcgag   1320
aattcttata atgacgataa tattaacaca cctaaggaaa tcgacgatac tgtcacttct   1380
aataacaatt atgagaacga ccttgatcaa gtgatactaa attttaactc agaatctgca   1440
cctggattga gtgatgagaa gttaaatctt actatacaaa acgatgctta tatcccgaaa   1500
tatgatagca atggaacctc tgatattgag cagcatgatg tgaacgaatt gaatgtgttt   1560
ttctatttag acgctcaaaa agtacctgaa ggtgagaata acgtaaactt aacctcttcg   1620
attgataccg ctttgcttga acaacctaaa atttatacat tttcagttc agaattcatt   1680
aacaatgtta ataagcctgt tcaagcagct cttttcgtat catggattca acaggtcctt   1740
gtggatttta ccactgaggc taaccaaaaa tcaacagtag ataagattgc tgacattagc   1800
atagtcgtac catacatcgg ccttgcgctt aatattggta atgaggcaca gaaaggaaat   1860
ttcaaggatg cccttgaatt attgggcgct gggattctgt tagagtttga acccgaactg   1920
cttattccaa ccattcttgt cttcaccatc aaatcttttc taggttcttc agataataag   1980
aacaaagtta ttaaagctat aaataacgca ttaaaagaac gtgatgaaaa atggaaggag   2040
gtgtatagtt tcattgtttc aaattggatg acaaagatta atactcaatt taataaaaga   2100
aaagaacaga tgtaccaagc tcttcaaaat caagttaatg ctattaagac aataattgaa   2160
tctaaatata actcatatac actggaggaa aagaatgaat tgactaataa atatgatatt   2220
aaacaaatcg aaaacgaatt aaatcaaaaa gttagtattg ctatgaataa catagatcgc   2280
tttttgactg aatctagtat ttcctattta atgaagttaa ttaatgaggt taagatcaac   2340
aaattacgag agtatgatga aaatgtcaag acgtacttgc ttaattatat tatccaacat   2400
gggtccatcc ttggtgagtc tcagcaagaa ttgaactcaa tggttactga tacattaaat   2460
aactctatcc ctttcaaact tagctcatat actgacgata aaattctgat ttcttatttt   2520
aataaatttt tcaaacgtat taaaagttcg tcagttctta atatgcgata caagaatgat   2580
aaatacgtcg acacatcggg ctatgattca aatattaaca ttaatggtga cgtgtataaa   2640
tatccaacta ataaaaacca atttggtata tacaatgata agttgtctga ggtcaatatt   2700
tctcagaatg attacatcat ttacgacaac aaatacaaaa atttttccat ctctttttgg   2760
gttcgtatcc caaactacga taacaaaata gtcaatgtta ataacgaata tacaataatt   2820
aactgtatgc gagataataa ctcaggttgg aaggtatccc taaatcataa cgaaattatc   2880
tggactttgc aggacaacgc tggaattaat caaaagctcg cttttaatta tggtaatgcg   2940
```

-continued

```
aatggtataa gtgattacat taataaatgg atctttgtaa ccattacaaa tgacagatta   3000

ggcgattcta agctttatat caatggaaat ctaattgatc agaaaagtat tttgaatctt   3060

ggtaatattc atgtcagcga taacattttg ttcaagattg ttaattgctc ctacactagg   3120

tatattggaa tacgttactt taacatcttt gataaagagt tggatgaaac tgaaatacaa   3180

acgttatata gcaatgaacc taatacgaat attttgaaag acttttgggg caactacctg   3240

ttgtatgata aagaatatta cttgctaaat gttttgaagc ccaacaattt tattgataga   3300

cggaaagatt ctaccttgtc gattaataac attcggtcta ctattctctt agccaataga   3360

ttgtacagtg gaattaaagt taaaattcaa agagttaata actcctctac taatgataat   3420

ttagttcgca agaatgatca agtatatatt aattttgttg ctagcaagac ccacttgttc   3480

cccctgtacg cagacacggc gacgacaaac aaagaaaaga ccatcaaaat ttcatcttca   3540

ggcaatagat ttaatcaggt tgtagttatg aactcagtag gtaataactg cacaatgaat   3600

tttaagaata ataatggtaa taatattgga ttattgggtt ttaaggctga tacagttgtt   3660

gcctctactt ggtattatac ccatatgcgt gatcatacaa atagtaatgg ttgtttttgg   3720

aatttcattt ctgaagaaca tggttggcaa gaaaagtaa                          3759
```

<210> SEQ ID NO 42
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, S. pombe-modified 2

<400> SEQUENCE: 42

```
atgcctaaaa ttaattcttt taattataat gatcctgtta atgatcgtac tattttatat     60

attaaacctg gtggttgtca agaattttat aaatctttta atattatgaa aaatatttgg    120

attattcctg aacgtaatgt tattggtact actcctcaag attttcatcc tcctacttct    180

ttaaaaaatg gtgattcttc ttattatgat cctaattatt tacaatctga tgaagaaaaa    240

gatcgttttt taaaaattgt tactaaaatt tttaatcgta ttaataataa tttatctggt    300

ggtattttat tagaagaatt atctaaagct aatccttatt taggtaatga taatactcct    360

gataatcaat ttcatattgg tgatgcttct gctgttgaaa ttaaattttc taatggttct    420

caagatattt tattacctaa tgttattatt atgggtgctg aacctgattt atttgaaact    480

aattcttcta atatttcttt acgtaataat tatatgcctt ctaatcatgg ttttggttct    540

attgctattg ttactttttc tcctgaatat tcttttcgtt ttaatgataa ttctatgaat    600

gaatttattc aagatcctgc tttaacttta atgcatgaat taattcattc tttacatggt    660

ttatatggtg ctaaaggtat tactactaaa tatactatta ctcaaaaaca aaatccttta    720

attactaata ttcgtggtac taatattgaa gaatttttaa cttttggtgg tactgattta    780

aatattatta cttctgctca atctaatgat atttatacta atttattagc tgattataaa    840

aaaattgctt ctaaattatc taaagttcaa gtttctaatc ctttattaaa tccttataaa    900

gatgtttttg aagctaaata tggtttagat aaagatgctt ctggtattta ttctgttaat    960

attaataaat ttaatgatat ttttaaaaaa ttatattctt ttactgaatt tgatttagct   1020

actaaatttc aagttaaatg tcgtcaaact tatattggtc aatataaata ttttaaatta   1080

tctaatttat taaatgattc tatttataat atttctgaag gttataatat taataattta   1140

aaagttaatt ttcgtggtca aaatgctaat ttaaatcctc gtattattac tcctattact   1200
```

-continued

```
ggtcgtggtt tagttaaaaa aattattcgt ttttgtaaaa atattgtttc tgttaaaggt   1260
attcgtaaat ctatttgtat tgaaattaat aatggtgaat tattttttgt tgcttctgaa   1320
aattcttata atgatgataa tattaatact cctaaagaaa ttgatgatac tgttacttct   1380
aataataatt atgaaaatga tttagatcaa gttattttaa attttaattc tgaatctgct   1440
cctggtttat ctgatgaaaa attaaattta actattcaaa atgatgctta tattcctaaa   1500
tatgattcta atggtacttc tgatattgaa caacatgatg ttaatgaatt aaatgttttt   1560
ttttatttag atgctcaaaa agttcctgaa ggtgaaaata atgttaattt aacttcttct   1620
attgatactg ctttattaga acaacctaaa atttatactt ttttttcttc tgaatttatt   1680
aataatgtta ataaacctgt tcaagctgct ttatttgttt cttggattca acaagtttta   1740
gttgatttta ctactgaagc taatcaaaaa tctactgttg ataaaattgc tgatatttct   1800
attgttgttc cttatattgg tttagcttta aatattggta atgaagctca aaaaggtaat   1860
tttaaagatg ctttagaatt attaggtgct ggtattttat tagaatttga acctgaatta   1920
ttaattccta ctattttagt ttttactatt aaatcttttt taggttcttc tgataataaa   1980
aataaagtta ttaaagctat taataatgct ttaaaagaac gtgatgaaaa atggaaagaa   2040
gtttattctt ttattgtttc taattggatg actaaaatta atactcaatt taataaacgt   2100
aaagaacaaa tgtatcaagc tttacaaaat caagttaatg ctattaaaac tattattgaa   2160
tctaaatata attcttatac tttagaagaa aaaaatgaat taactaataa atatgatatt   2220
aaacaaattg aaaatgaatt aaatcaaaaa gtttctattg ctatgaataa tattgatcgt   2280
tttttaactg aatcttctat ttcttattta atgaaattaa ttaatgaagt taaaattaat   2340
aaattacgtg aatatgatga aaatgttaaa acttatttat taaattatat tattcaacat   2400
ggttctattt taggtgaatc tcaacaagaa ttaaattcta tggttactga tactttaaat   2460
aattctattc cttttaaatt atcttcttat actgatgata aaattttaat ttcttatttt   2520
aataaatttt ttaaacgtat taaatcttct tctgttttaa atatgcgtta taaaaatgat   2580
aaatatgttg atacttctgg ttatgattct aatattaata ttaatggtga tgtttataaa   2640
tatcctacta ataaaaatca atttggtatt tataatgata aattatctga agttaatatt   2700
tctcaaaatg attatattat ttatgataat aaatataaaa atttttctat ttctttttgg   2760
gttcgtattc ctaattatga taataaaatt gttaatgtta ataatgaata tactattatt   2820
aattgtatgc gtgataataa ttctggttgg aaagtttctt taaatcataa tgaaattatt   2880
tggactttac aagataatgc tggtattaat caaaaattag cttttaatta tggtaatgct   2940
aatggtattt ctgattatat taataaatgg atttttgtta ctattactaa tgatcgttta   3000
ggtgattcta aattatatat taatggtaat ttaattgatc aaaaatctat tttaaattta   3060
ggtaatattc atgtttctga taatatttta tttaaaattg ttaattgttc ttatactcgt   3120
tatattggta ttcgttattt taatattttt gataaagaat tagatgaaac tgaaattcaa   3180
actttatatt ctaatgaacc taatactaat attttaaaag atttttgggg taattattta   3240
ttatatgata aagaatatta tttattaaat gttttaaaac ctaataattt tattgatcgt   3300
cgtaaagatt ctactttatc tattaataat attcgttcta ctattttatt agctaatcgt   3360
ttatattctg gtattaaagt taaaattcaa cgtgttaata attcttctac taatgataat   3420
ttagttcgta aaaatgatca agtttatatt aattttgttg cttctaaaac tcatttattt   3480
cctttatatg ctgatactgc tactactaat aaagaaaaaa ctattaaaat ttcttcttct   3540
```

-continued ggtaatcgtt ttaatcaagt tgttgttatg aattctgttg gtaataattg tactatgaat 3600
tttaaaaata ataatggtaa taatattggt ttattaggtt ttaaagctga tactgttgtt 3660
gcttctactt ggtattatac tcatatgcgt gatcatacta attctaatgg ttgtttttgg 3720
aattttattt ctgaagaaca tggttggcaa gaaaaataa 3759

<210> SEQ ID NO 43
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, S. pombe-modified 3

<400> SEQUENCE: 43
atgcctaaaa tcaactcatt taactacaat gatccagtga acgatagaac tatcttatat 60
ataaaaccag gtggatgtca agaattttat aagtcgttca atataatgaa gaatatatgg 120
attatccctg aacgtaatgt tattggaacc acaccacaag actttcaccc tccaacttct 180
ttaaaaaatg gcgattcctc atactatgat cctaattatt tgcaatccga tgaagagaaa 240
gaccgcttcc taaaaatagt tactaaaatt tttaatagaa ttaacaataa cttaagtgga 300
ggtattcttt tggaggaatt gagtaaagct aacccttatc ttggaaatga taatacaccc 360
gataatcagt ttcatatcgg tgatgctagt gcagtggaaa ttaagttctc taacggatct 420
caagatatct tgcttcccaa tgttataatt atgggagctg agccagactt atttgaaacc 480
aactcctcta atataagctt acgtaataac tatatgcctt ccaaccatgg tttcggtagc 540
atcgctattg ttacattttc acccgaatat agttttcgtt ttaatgataa tagtatgaat 600
gaatttatcc aagatccagc cttgacttta atgcatgagt taattcattc attacatggt 660
ttatacggtg caaagggcat tactacaaag tacactatta cccaaaaaca aaatcccttg 720
attactaata ttagaggtac taatattgag gaatttttaa catttggtgg cactgatttg 780
aacatcatta cttcagctca atcaaatgat atttatacta atttgttagc agactataaa 840
aagattgctt ctaaattaag taaagtacaa gtttccaatc ctcttttaaa tccttataaa 900
gatgtctttg aagctaagta tggtttggat aaagatgcct ctggaattta ctctgttaat 960
ataaacaagt ttaatgatat ttttaagaaa ttatattcgt tcactgaatt cgatctagca 1020
actaaatttc aagttaaatg taggcaaact tatattggtc aatataaata ttttaagtta 1080
tctaatttat tgaatgactc aatatataac atatctgagg gttataacat aaataacttg 1140
aaagtcaact ttcgtggaca aaacgcaaat ctaaatccta gaataattac tccaattact 1200
ggtcgtggac ttgtgaagaa aattatccga ttttgcaaga acattgtaag cgttaagggt 1260
atccgtaagt cgatatgcat tgagataaat aacggtgagc ttttttttcgt cgcctctgaa 1320 aacagttata acgatgacaa tataaataca cctaaagaga tagatgacac tgtgactagc 1380
aacaataact acgaaaacga cttagatcag gttattttaa actttaattc ggaatctgct 1440
ccaggattat ctgatgaaaa acttaatctt actatacaga acgatgccta cattcctaag 1500
tatgactcga atggtacctc cgacatcgag cagcacgatg ttaatgaatt aaatgttttt 1560
ttctatcttg atgcacaaaa agttcccgaa ggagaaaata acgtcaattt gactagctct 1620
attgacactg ctttgctaga gcaacctaag atttatacct ttttcagttc agaatttatt 1680
aataacgtta ataaacctgt acaagccgca ttatttgttt cttggattca gcaagtgttg 1740
gtagacttta ctaccgaagc aaaccaaaaa tctacagttg acaagatcgc agatatttca 1800

-continued

```
attgttgtac catatattgg tttagctttg aatattggaa atgaagctca aaaaggaaat   1860
tttaaagacg cccttgagtt attgggcgca ggtattttat tggaatttga gcctgaatta   1920
cttatcccta ctattttagt ttttacaata aaaagcttcc ttggatcttc agataataag   1980
aataaagtca ttaaagccat caataacgct ttaaaggaaa gagacgaaaa atggaaagaa   2040
gtctactcat ttatagtgag taattggatg actaagatta acactcaatt caataaacgc   2100
aaagaacaaa tgtatcaagc tttacagaat caggtaaatg ctattaagac tatcattgag   2160
tccaaatata attcttatac acttgaagag aaaaatgaat tgactaataa gtacgacatc   2220
aaacaaatcg aaaacgagtt gaatcaaaag gtttccattg ctatgaataa cattgatcgt   2280
ttccttacag aatcctctat ctcatacttg atgaaattaa tcaatgaggt aaaaatcaat   2340
aagcttcgtg aatatgatga aaacgtcaaa acttatcttc taaattatat tatccagcat   2400
ggttcaattt taggtgagtc ccaacaggag cttaatagca tggtcaccga cactcttaac   2460
aatagcattc cttttaagtt atcatcttat accgacgata aaattttaat ttcatatttc   2520
aacaagtttt tcaaaaggat taaatcaagt tctgttttga atatgagata taaaaatgat   2580
aaatacgttg atacaagtgg ttatgattct aatattaaca ttaatggcga tgtttataaa   2640
tatcctacca ataaaaatca atttggcatt tataatgata aactttccga agtaaatatt   2700
tctcaaaatg attacattat ctacgataat aagtataaaa atttcagtat ttccttttgg   2760
gtaaggattc caaattacga taataaaatt gttaacgtaa acaatgagta taccataatt   2820
aattgtatgc gtgacaacaa tagtggttgg aaagtttcgc taaatcacaa tgaaataatt   2880
tggactttac aagataatgc tggaataaat caaaagttag cttttaacta cggtaatgct   2940
aatggtatat ctgattacat caacaaatgg atttttgtga caattacaaa tgatcgattg   3000
ggcgattcaa aattatacat taacggtaac ctaattgatc agaagagcat tttaaacctt   3060
ggtaacattc atgtcagtga taatatacta tttaaaatag taaattgctc ttatacacgt   3120
tatattggaa ttcgttactt caatatattc gataaagaat tagatgaaac agaaatccag   3180
actttatatt ctaacgaacc caacaccaat atcttgaagg atttttgggg aaattacctt   3240
ttatatgata aggaatacta tcttttaaat gtgcttaagc ctaataactt cattgataga   3300
cgaaaggact ctacacttag tattaataac attcgatcaa ccattctttt agctaatcga   3360
ctatattctg gtatcaaagt taagattcaa cgcgttaata actcttcgac taacgataat   3420
ttggtaagaa aaaatgatca agtctatatt aattttgttg cttcgaagac tcatcttttt   3480
cctttatacg ctgacactgc tacaaccaat aaagaaaaaa ctatcaagat atctagctct   3540
ggtaatcgct ttaatcaggt agttgtcatg aattctgttg gtaataactg tactatgaat   3600
tttaaaaaca ataacggaaa taacataggt ttgttaggct ttaaggctga tactgttgtt   3660
gcttccacat ggtactacac ccacatgcgt gaccatacta attctaatgg ctgtttttgg   3720
aactttatat cagaagagca tggctggcaa gaaaaataa                          3759
```

<210> SEQ ID NO 44
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, Y. lipolytica-modified 1

<400> SEQUENCE: 44

-continued

```
atgcccaaga tcaacagttt taactacaac gatcctgtta acgaccgaac tattctctac     60
atcaaacccg gtggctgtca ggagttttac aagtctttca atattatgaa gaacatctgg    120
atcattcccg agagaaacgt gattgggacc acaccgcagg atttccaccc ccctacctca    180
ctgaagaacg gagactctag ctactatgac cccaactacc ttcagagcga cgaggaaaag    240
gatcggtttc tcaagatcgt gaccaagatc tttaaccgta ttaacaataa cttgtcaggt    300
gggattctcc tagaggaatt gagcaaggct aacccttatc ttggtaatga caacactccc    360
gacaaccagt ttcacatcgg agacgcttct gccgttgaga ttaagttttc taacggctcc    420
caggatattc tccttcctaa cgtcatcatt atgggcgccg agcctgatct gtttgagact    480
aattcttcga acatttcact ccgtaacaat tacatgccct ccaaccacgg cttcgggtca    540
atagccatcg taacctttc accagagtac tctttccgat tcaacgacaa ctccatgaac    600
gagttcatcc aggatccagc cctgaccctc atgcatgagc tgatccattc acttcacggt    660
ctgtacggtg cgaaaggcat cactaccaag tacacaatca cccagaaaca aaatcctctc    720
attaccaata ttcgaggaac caacattgag gaattcctta cattcggtgg caccgatttg    780
aatattatca ccagtgccca gtcgaacgac atctacacga acctgctcgc tgactacaag    840
aaaatcgctt ccaagctttc gaaagttcag gtgagcaacc ctctactgaa tccctacaag    900
gacgtctttg aagccaagta tggcttggac aaggatgcat ctggcattta cagcgttaat    960
atcaataagt tcaacgatat tttcaagaaa ctttactctt ttactgagtt tgatttggcc   1020
accaagtttc aggtcaagtg tcgacagacg tacatcggac aatataagta cttcaaactc   1080
tcgaacctcc ttaacgatag tatttacaac atttccgaag gctacaacat caataacctc   1140
aaggtgaact tcagaggtca gaacgcgaac ctcaaccccc ggatcattac ccctattaca   1200
ggccggggcc ttgtcaagaa aattatacga ttttgcaaga acatcgtcag cgtgaaaggc   1260
attcgtaagt ccatctgcat agagattaac aatggcgagt tattctttgt cgcctccgag   1320
aactcgtaca atgacgataa catcaacact cccaaggaaa tcgatgacac agtgacatct   1380
aacaataact acgaaaacga cctggatcag gttatcctga acttcaattc cgagtctgct   1440
cccggtctgt ctgatgagaa gctcaacctt actattcaga atgatgccta catcccaaag   1500
tacgactcga acggaacctc ggacatcgaa cagcacgacg tgaacgagct gaatgtcttt   1560
ttctacctcg acgcgcagaa ggtcccggag ggagaaaaca atgtgaacct tacgtccagc   1620
atcgatactg cacttttgga gcaacccaag atctatactt ttttctctag cgagttcatt   1680
aacaatgtta acaaacccgt ccaagctgcc ctgtttgtgt cctggattca gcaagtactc   1740
gtcgacttta ccactgaggc aaaccaaaaa tcgaccgtgg acaagatcgc tgacatttcc   1800
attgtggtcc cttatattgg actggctctc aacattggaa acgaagcgca gaagggaaac   1860
tttaaggacg ctttggagct gctcggagca ggaatcctcc tggaatttga accagagcta   1920
ctgattccta caatcctcgt attcaccatc aaaagtttct taggctcctc tgacaacaaa   1980
aacaaggtga tcaaggctat caacaatgca ctgaaagagc gggatgagaa gtggaaggaa   2040
gtttactcgt tcattgtgtc caactggatg acaaagatta acacacaatt taacaagcgc   2100
aaggagcaga tgtaccaagc tctgcagaat caggtgaacg cgatcaagac cattatcgag   2160
tcaaagtata actcttatac cctggaggaa aaaaacgagc tcaccaacaa gtacgacatc   2220
aagcagattg agaacgagct gaaccagaag gtctccattg ccatgaacaa tattgaccga   2280
ttcttgaccg agtcttcgat ctcctacctc atgaagctga tcaacgaggt caaaattaac   2340
aagctgcggg aatatgacga aaacgttaag acttacttgc tgaactacat tatccagcat   2400
```

```
ggttccatcc tgggcgagtc ccagcaagag ctgaactcca tggtgaccga cactcttaat   2460

aactctattc ctttcaagct gtcttcctac acagacgata agatcctgat ctcgtacttc   2520

aacaaatttt tcaagagaat taagtcctct agtgtcttga atatgcgcta caagaacgac   2580

aagtacgtcg acactagcgg ctacgattct aacattaaca ttaacggaga cgtgtacaag   2640

taccccacta ataagaacca gttcggcatc tacaatgaca agctctctga agtgaacatc   2700

tcgcaaaacg actacatcat ttacgacaac aagtacaaga atttttctat cagcttctgg   2760

gttcgcatcc cgaactacga taataagatc gtgaatgtca acaatgagta tacgatcata   2820

aactgtatgc gagacaacaa ttccggatgg aaggtgtcac tcaaccacaa cgagatcatt   2880

tggaccttgc aggacaacgc cggtattaac cagaagctag ccttcaacta tgggaacgcc   2940

aacggaattt ccgattacat taacaagtgg atattcgtta ccatcacgaa cgatagactg   3000

ggcgactcaa aactgtacat caacggaaac ctaatcgatc agaagtccat tctcaacctg   3060

ggtaatattc atgtctctga caacatcctt ttcaagatcg tcaactgctc ttatacgaga   3120

tacatcggta tccgatactt taatattttc gataaggagc tggatgagac cgagattcag   3180

actctctact cgaacgagcc caacaccaat atcctgaagg acttctgggg caactatctg   3240

ctttatgata aggagtacta tctgctcaac gttctcaaac caaacaattt cattgaccgt   3300

cgaaaggaca gcacactgag catcaacaat attcgatcga ccatcctgtt ggcaaacagg   3360

ctgtactcgg gaatcaaggt taagattcag cgagtgaaca actccagtac gaacgacaac   3420

cttgtgcgaa agaacgacca ggtttacatt aacttcgtgg cttctaagac ccacctattc   3480

ccgctgtacg ccgacaccgc tacgactaac aaggagaaaa cgatcaagat ttcttcgagt   3540

ggaaaccgat tcaaccaggt cgttgtaatg aactctgtgg gaaacaactg tacgatgaac   3600

tttaagaaca acaacggcaa caacattggt ctgctgggtt ttaaggccga cacagtggtc   3660

gccagtactt ggtactacac tcatatgcga gaccacacta actcgaacgg atgcttctgg   3720

aacttcattt cggaggaaca tggttggcag gagaagtaa                          3759
```

<210> SEQ ID NO 45
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, Y. lipolytica-modified 2

<400> SEQUENCE: 45

```
atgcccaaga tcaactcttt caactacaac gaccccgtga acgaccgaac catcctgtac     60

atcaagcccg gcggctgtca ggagttctac aagtctttca acatcatgaa gaacatctgg    120

atcatccccg agcgaaacgt gatcggcacc accccccagg acttccaccc ccccacctct    180

ctgaagaacg gcgactcttc ttactacgac cccaactacc tgcagtctga cgaggagaag    240

gaccgattcc tgaagatcgt gaccaagatc ttcaaccgaa tcaacaacaa cctgtctggc    300

ggcatcctgc tggaggagct gtctaaggcc aacccctacc tgggcaacga caacaccccc    360

gacaaccagt tccacatcgg cgacgcctct gccgtggaga tcaagttctc taacggctct    420

caggacatcc tgctgcccaa cgtgatcatc atgggcgccg agcccgacct gttcgagacc    480

aactcttcta acatctctct gcgaaacaac tacatgccct ctaaccacgg cttcggctct    540

atcgccatcg tgaccttctc tcccgagtac tctttccgat tcaacgacaa ctctatgaac    600
```

-continued

```
gagttcatcc aggaccccgc cctgaccctg atgcacgagc tgatccactc tctgcacggc    660
ctgtacggcg ccaagggcat caccaccaag tacaccatca cccagaagca gaaccccctg    720
atcaccaaca tccgaggcac caacatcgag gagttcctga ccttcggcgg caccgacctg    780
aacatcatca cctctgccca gtctaacgac atctacacca acctgctggc cgactacaag    840
aagatcgcct ctaagctgtc taaggtgcag gtgtctaacc ccctgctgaa cccctacaag    900
gacgtgttcg aggccaagta cggcctggac aaggacgcct ctggcatcta ctctgtgaac    960
atcaacaagt tcaacgacat cttcaagaag ctgtactctt tcaccgagtt cgacctggcc   1020
accaagttcc aggtgaagtg tcgacagacc tacatcggcc agtacaagta cttcaagctg   1080
tctaacctgc tgaacgactc tatctacaac atctctgagg gctacaacat caacaacctg   1140
aaggtgaact tccgaggcca gaacgccaac ctgaaccccc gaatcatcac ccccatcacc   1200
ggccgaggcc tggtgaagaa gatcatccga ttctgtaaga acatcgtgtc tgtgaagggc   1260
atccgaaagt ctatctgtat cgagatcaac aacggcgagc tgttcttcgt ggcctctgag   1320
aactcttaca acgacgacaa catcaacacc cccaaggaga tcgacgacac cgtgacctct   1380
aacaacaact acgagaacga cctggaccag gtgatcctga acttcaactc tgagtctgcc   1440
cccggcctgt ctgacgagaa gctgaacctg accatccaga acgacgccta catccccaag   1500
tacgactcta acggcacctc tgacatcgag cagcacgacg tgaacgagct gaacgtgttc   1560
ttctacctgg acgcccagaa ggtgcccgag ggcgagaaca acgtgaacct gacctcttct   1620
atcgacaccg ccctgctgga gcagcccaag atctacacct tcttctcttc tgagttcatc   1680
aacaacgtga acaagcccgt gcaggccgcc ctgttcgtgt cttggatcca gcaggtgctg   1740
gtggacttca ccaccgaggc caaccagaag tctaccgtgg acaagatcgc cgacatctct   1800
atcgtggtgc cctacatcgg cctggccctg aacatcggca acgaggccca gaagggcaac   1860
ttcaaggacg ccctggagct gctgggcgcc ggcatcctgc tggagttcga gcccgagctg   1920
ctgatcccca ccatcctggt gttcaccatc aagtctttcc tgggctcttc tgacaacaag   1980
aacaaggtga tcaaggccat caacaacgcc ctgaaggagc gagacgagaa gtggaaggag   2040
gtgtactctt tcatcgtgtc taactggatg accaagatca acacccagtt caacaagcga   2100
aaggagcaga tgtaccaggc cctgcagaac caggtgaacg ccatcaagac catcatcgag   2160
tctaagtaca actcttacac cctggaggag aagaacgagc tgaccaacaa gtacgacatc   2220
aagcagatcg agaacgagct gaaccagaag gtgtctatcg ccatgaacaa catcgaccga   2280
ttcctgaccg agtcttctat ctcttacctg atgaagctga tcaacgaggt gaagatcaac   2340
aagctgcgag agtacgacga gaacgtgaag acctacctgc tgaactacat catccagcac   2400
ggctctatcc tgggcgagtc tcagcaggag ctgaactcta tggtgaccga caccctgaac   2460
aactctatcc ccttcaagct gtcttcttac accgacgaca agatcctgat ctcttacttc   2520
aacaagttct tcaagcgaat caagtcttct tctgtgctga acatgcgata caagaacgac   2580
aagtacgtgg acacctctgg ctacgactct aacatcaaca tcaacggcga cgtgtacaag   2640
taccccacca acaagaacca gttcggcatc tacaacgaca agctgtctga ggtgaacatc   2700
tctcagaacg actacatcat ctacgacaac aagtacaaga acttctctat ctctttctgg   2760
gtgcgaatcc ccaactacga caacaagatc gtgaacgtga acaacgagta caccatcatc   2820
aactgtatgc gagacaacaa ctctggctgg aaggtgtctc tgaaccacaa cgagatcatc   2880
tggaccctgc aggacaacgc cggcatcaac cagaagctgg ccttcaacta cggcaacgcc   2940
aacggcatct ctgactacat caacaagtgg atcttcgtga ccatcaccaa cgaccgactg   3000
```

-continued

```
ggcgactcta agctgtacat caacggcaac ctgatcgacc agaagtctat cctgaacctg   3060

ggcaacatcc acgtgtctga caacatcctg ttcaagatcg tgaactgttc ttacacccga   3120

tacatcggca tccgatactt caacatcttc gacaaggagc tggacgagac cgagatccag   3180

accctgtact ctaacgagcc caacaccaac atcctgaagg acttctgggg caactacctg   3240

ctgtacgaca aggagtacta cctgctgaac gtgctgaagc ccaacaactt catcgaccga   3300

cgaaaggact ctaccctgtc tatcaacaac atccgatcta ccatcctgct ggccaaccga   3360

ctgtactctg gcatcaaggt gaagatccag cgagtgaaca actcttctac caacgacaac   3420

ctggtgcgaa agaacgacca ggtgtacatc aacttcgtgg cctctaagac ccacctgttc   3480

cccctgtacg ccgacaccgc caccaccaac aaggagaaga ccatcaagat ctcttcttct   3540

ggcaaccgat tcaaccaggt ggtggtgatg aactctgtgg gcaacaactg taccatgaac   3600

ttcaagaaca acaacggcaa caacatcggc ctgctgggct tcaaggccga caccgtggtg   3660

gcctctacct ggtactacac ccacatgcga gaccacacca actctaacgg ctgtttctgg   3720

aacttcatct ctgaggagca cggctggcag gagaagtaa                          3759
```

<210> SEQ ID NO 46
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, Y. lipolytica-modified 3

<400> SEQUENCE: 46

```
atgcctaaga ttaactcttt caactacaac gatcccgtta acgaccgcac tatcctgtac     60

atcaagccag gtggatgcca ggagttctac aagtcgttta acatcatgaa gaacatctgg    120

atcattcccg agcgaaacgt gattggcact acgcctcagg acttccaccc acctacgtcc    180

ctcaagaacg gcgattcttc gtactacgac cctaactacc tgcagagcga tgaggaaaag    240

gaccgctttc tcaagatcgt tactaagatc tttaaccgca tcaacaacaa cctgtcgggc    300

ggaatccttc tggaggaact gagcaaggca aacccttacc tcggaaacga caacaccccc    360

gacaaccagt tccacatcgg agacgcatcc gctgtcgaaa ttaagttttc aaacggatcg    420

caggacattc tgcttcccaa cgtgatcatt atgggtgccg aacccgactt gtttgagact    480

aactcttcca acatctccct gagaaacaac tacatgccct ctaaccacgg attcggatct    540

atcgccattg tgacgttctc gcctgagtac tcgttccgat ttaacgacaa ctctatgaac    600

gagtttatcc aggaccccgc attgactctg atgcatgagc ttattcattc cctgcatggc    660

ctttacggcg caaagggtat tacgactaag tacactatta ctcagaagca gaaccccctg    720

atcaccaaca tccggggcac taacatcgag gaattcctga ccttcggagg caccgacctc    780

aacattatca catccgccca gtctaacgac atctacacaa acctcctggc tgattacaag    840

aagatcgctt ctaagctgtc taaggttcag gtgtctaacc ccctgttgaa cccctacaag    900

gacgtgttcg aggccaagta cggcttggat aaggacgcca gcggtattta ctccgtcaac    960

atcaacaagt ttaacgatat ttttaagaag ctctactctt tcacagagtt cgacctcgcc   1020

actaagtttc aggtgaagtg ccgtcagacc tacattggtc agtacaagta cttcaagctg   1080

tctaacctgc ttaacgactc tatctacaac atttctgagg gctacaacat taacaacctc   1140

aaggttaact tccgtggcca gaacgcaaac cttaacccac gaatcattac ccctatcacg   1200
```

-continued

```
ggacgaggcc tggtgaagaa gatcattcgg ttttgtaaga acatcgtctc tgtgaagggt   1260
attcggaagt caatctgcat tgagatcaac aacggtgaac ttttctttgt ggcctctgaa   1320
aactcttaca acgacgataa cattaacacc ccgaaggaga ttgacgatac tgtcacatcc   1380
aacaacaact acgagaacga cctggatcag gtcatcttga acttcaactc tgaatccgcc   1440
ccgggcctct ctgatgagaa gcttaacctg accatccaga acgatgccta cattcctaag   1500
tacgattcta acggcacctc agatattgag cagcacgatg tcaacgaact caacgtcttc   1560
ttttacctcg acgctcagaa ggtgcctgaa ggtgagaaca acgtcaacct tacgtcgagc   1620
atcgataccg cccttctcga gcagcccaag atttacacct tttctcctc ggagttcatc   1680
aacaacgtga acaagcccgt gcaggccgct ctgttcgtgt cttggattca gcaggttctg   1740
gtcgacttta caaccgaggc caaccagaag tcaaccgtgg acaagatcgc cgatatctct   1800
atcgtcgttc cttacatcgg actggctctt aacattggca acgaggctca gaagggaaac   1860
ttcaaggatg ctttggaact cctgggtgcc ggaatcctgc tcgagtttga gcctgagttg   1920
ctcatcccca ccatcctggt ttttacaatc aagagcttcc ttggcagctc tgataacaag   1980
aacaaggtta tcaaggccat taacaacgct cttaaggaac gggacgagaa gtggaaggag   2040
gtgtactctt ttattgtttc gaactggatg acaaagatta acacccagtt taacaagaga   2100
aaggagcaga tgtaccaggc actgcagaac caggttaacg ccatcaagac gatcattgag   2160
agcaagtaca actcttacac cctcgaggaa aagaacgagc tgaccaacaa gtacgacatt   2220
aagcagatcg aaaacgagct caaccagaag gtctccattg ctatgaacaa cattgaccga   2280
ttcctgactg aatcttcgat cagctacctt atgaagctca tcaacgaggt caagatcaac   2340
aagctgcgag agtacgacga gaacgtcaag acatacctcc tgaactacat cattcagcat   2400
ggctcaattc tgggagagtc gcagcaggaa ctcaactcca tggtcacaga cacactcaac   2460
aacagcatcc cattcaagct gtcgtcctac acggacgata agatcctgat ttcctacttc   2520
aacaagttct ttaagagaat caagtcgtcc tctgtgttga acatgcggta caagaacgac   2580
aagtacgtgg atacctcagg ctacgattct aacatcaaca ttaacggtga cgtttacaag   2640
taccccacta acaagaacca gttcggtatc tacaacgaca agctgtcgga agtgaacatc   2700
tcgcagaacg attacatcat ttacgacaac aagtacaaga acttctcaat tagcttctgg   2760
gtgcgaatcc cgaactacga caacaagatt gtgaacgtca acaacgaata cactattatc   2820
aactgtatgc gagataacaa ctctggatgg aaggtgtcac tgaaccataa cgagattatc   2880
tggaccctgc aggacaacgc cggtattaac cagaagctgg ccttcaacta cggcaacgct   2940
aacggtatct ccgattacat taacaagtgg atttttgtga cgatcaccaa cgaccgactc   3000
ggcgattcta agctgtacat taacggcaac ctgattgacc agaagtcgat tctgaacctg   3060
ggcaacattc acgtttccga caacatcttg tttaagatcg tcaactgttc ctacaccaga   3120
tacatcggaa tccgatactt caacattttc gacaaggagc tggacgagac tgagattcag   3180
acgctgtact ccaacgagcc aaacacaaac attctgaagg acttctgggg aaactacctg   3240
ctttacgaca aggagtacta cctcctgaac gtcctcaagc cgaacaactt tatcgaccga   3300
agaaaggact ccaccctttc gatcaacaac atccgatcta ccattttgct ggccaaccgt   3360
ctctacagcg gcattaaggt gaagattcag cgagtgaaca actcctctac taacgataac   3420
ttggtgcgaa agaacgacca ggtgtacatt aactttgtcg cctccaagac acacttgttt   3480
cccctgtacg ctgatactgc taccactaac aaggagaaga ccattaagat ctcatcgtcc   3540
ggcaaccgat ttaaccaggt tgtggtcatg aactctgtcg gaaacaactg taccatgaac   3600
```

ttcaagaaca acaacggaaa caacatcggc ctcctcggat tcaaggccga caccgttgtg 3660
gccagcacct ggtactacac tcatatgcgt gaccacacca actctaacgg ttgcttctgg 3720
aacttcattt ccgaggagca cggttggcag gagaagtaa 3759

<210> SEQ ID NO 47
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, D. discoideum-modified 1

<400> SEQUENCE: 47
atgccaaaaa ttaattcttt taactataat gatcctgtta atgatagaac aatattatat 60
attaaaccag gtggctgtca agaattttat aaatcattca atattatgaa aaatatatgg 120
attataccag aaagaaatgt tatcggtaca acgccacaag atttccatcc tccaacctca 180
ttaaagaatg gtgattcaag ttattacgat ccaaattatt tacaatcaga tgaggaaaaa 240
gatagatttt tgaaaattgt tacaaagatt tttaatagaa ttaataacaa tttaagtggt 300
ggcatattgc ttgaagagtt atctaaagcc aatccatatt taggtaatga taatacacca 360
gacaatcaat ttcatattgg tgatgcatca gctgtagaaa ttaaattctc taatggtagc 420
caagatatct tattgccaaa tgttataatt atgggtgcag aacccgattt atttgaaaca 480
aattcttcaa atatatcatt aagaaataac tacatgccta gtaatcatgg atttggttct 540
attgctattg tgacatttag tccagagtat tcttttcgtt ttaatgataa ttcaatgaat 600
gaattcattc aggatccagc acttacttta atgcatgaat tgattcatag cttacatggt 660
ttatatggag ctaaaggtat cactacaaaa tatacaatta cccaaaaaca aaatccatta 720
atcacaaata ttagaggaac taatattgaa gagtttctaa cctttggtgg aacagatcta 780
aatataatta cttctgctca atcaaatgat atttatacaa atctattagc tgattataaa 840
aagatcgcat ctaaattatc aaaagtacaa gtttcaaatc cattacttaa tccatataag 900
gatgtattcg aagcaaaata tggtttagat aaagatgctt caggtattta ttcagttaat 960
attaataaat ttaatgatat ttttaagaaa ttatactctt tcaccgaatt tgatctagca 1020
acaaaatttc aagttaaatg tagacaaact tatattggac aatataaata ttttaaattg 1080
tcaaatttat tgaatgattc aatatataat attagtgaag gttataatat taataactta 1140
aaggtcaatt ttagaggtca aaatgccaat ttaaatccaa gaataattac tccaattaca 1200
ggcagaggac tagtaaaaaa gattatacgt ttctgtaaaa atattgtctc tgttaaaggt 1260
ataagaaaat caatttgtat tgaaattaac aatggagaat tatttttcgt tgcttcagaa 1320
aattcatata atgatgacaa tatcaatact cctaaagaaa ttgatgacac agtaacttca 1380
aataacaatt atgaaaatga tcttgatcaa gtgattctta attttaattc ggaatctgca 1440
ccaggattat cagatgaaaa attaaatctt acaattcaaa atgatgccta tattccaaaa 1500
tatgatagta atggtacaag tgatatagaa caacatgatg ttaatgaatt aaatgttttc 1560
ttttacttag atgcacagaa agtcccagaa ggtgaaaata acgttaattt gacatcaagt 1620
atcgatacag cattattgga acaaccaaaa atatatacat tttctcctc agaattcatt 1680 aataacgtaa ataaaccagt tcaagcagct ttatttgttt catggatcca acaagtactc 1740
gttgatttta caaccgaggc taatcaaaaa tcaactgttg ataaaatagc agacattagt 1800

-continued atagttgtac catacattgg tttagcttta aatattggta atgaagccca aaagggtaat 1860
tttaaagatg cattagagtt gttaggtgca ggtattttac ttgagtttga acctgaactt 1920
ttaattccaa ctattctcgt tttcacaata aaaagttttt taggttcaag tgataataaa 1980
aataaagtta ttaaagccat aaataacgca ttaaaagaaa gagatgaaaa gtggaaagaa 2040
gtttattcat ttattgtatc aaattggatg actaaaatta acacacaatt caataaacgt 2100
aaagaacaaa tgtatcaagc attgcaaaat caagtaaatg ctattaaaac catcattgaa 2160
tcaaaatata attcttatac acttgaagag aaaaatgaat tgacaaataa atacgatatt 2220
aaacaaattg aaaatgaatt aaatcaaaaa gtttcaattg ctatgaataa catcgataga 2280
ttcttaactg aatcgagtat ttcatattta atgaagttaa ttaatgaagt taagattaat 2340
aaacttagag aatatgatga aaatgtaaaa acttatttat tgaattatat aatccaacat 2400
ggtagtatct taggtgaaag tcaacaagaa ttaaattcaa tggttactga tacattaaat 2460
aactcaattc catttaaatt atctagttat actgatgaca aaattcttat atcatacttc 2520
aataaatttt tcaaacgtat caaatcaagc tcagtattaa atatgagata taagaatgat 2580
aaatatgttg atacatccgg ttacgattca aatattaata ttaatggtga tgtatataaa 2640
tatccaacaa ataaaaatca atttggtatt tataatgata agttatccga ggtcaatatt 2700
agtcaaaatg attatattat atatgataat aaatataaaa atttttctat ttccttctgg 2760
gtaagaatcc caaattatga taataaaata gttaacgtaa ataacgaata taccattata 2820
aattgtatga gagataataa ctcaggttgg aaagtgtcat taaatcataa tgaaataatt 2880
tggactttac aagataatgc tgggattaat caaaaaattag catttaatta tggtaatgca 2940
aatggtatca gtgattacat taataaatgg atatttgtta ctattacaaa tgatagatta 3000
ggtgatagta aactatatat taatggtaat ttaattgacc aaaaaagtat tctcaattta 3060
ggtaatattc atgtttcaga taatatttta tttaagattg taaattgctc atataccaga 3120
tatattggta tcagatattt caatatattt gataaagaat tagatgaaac agaaatacaa 3180
acattatatt ctaatgaacc aaatactaat attttaaaag atttttgggg taattatttg 3240
ttatatgata aagaatatta ccttttaaat gttttaaaac caaataactt cattgataga 3300
cgtaaagatt caacattatc aattaataac atacgttcaa ctatattatt ggcgaatagg 3360
ttatatagtg gaattaaagt taagattcaa cgtgttaata attcaagtac aaatgataat 3420
ctcgtacgta aaaatgatca agtttatatt aattttgtcg caagtaaaac acatttattt 3480
ccattatatg cagatactgc aaccactaat aaagagaaaa ccatcaaaat atcttcatca 3540
ggtaatcgat tcaatcaagt tgtagttatg aattcagttg gaaataattg tacaatgaat 3600
tttaagaata ataatggtaa taatatcggt ctcttaggtt ttaaagcaga tactgtagtt 3660
gcttcaactt ggtattatac tcacatgaga gatcacacta attcaaatgg ttgtttttgg 3720
aattttatat cagaagaaca tggttggcaa gaaaaataa 3759

<210> SEQ ID NO 48
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, D. discoideum-modified 2

<400> SEQUENCE: 48
atgccaaaaa ttaattcatt taattataat gatccagtta atgatagaac aattttatat 60

-continued attaaaccag gtggttgtca agaattttat aaatcattta atattatgaa aaatatttgg 120
attattccag aaagaaatgt tattggtaca acaccacaag attttcatcc accaacatca 180
ttaaaaaatg gtgattcatc atattatgat ccaaattatt tacaatcaga tgaagaaaaa 240
gatagatttt taaaaattgt tacaaaaatt tttaatagaa ttaataataa tttatcaggt 300
ggtattttat tagaagaatt atcaaaagca aatccatatt taggtaatga taatacacca 360
gataatcaat ttcatattgg tgatgcatca gcagttgaaa ttaaattttc aaatggttca 420
caagatattt tattaccaaa tgttattatt atgggtgcag aaccagattt atttgaaaca 480
aattcatcaa atatttcatt aagaaataat tatatgccat caaatcatgg ttttggttca 540
attgcaattg ttacattttc accagaatat tcatttagat ttaatgataa ttcaatgaat 600
gaatttattc aagatccagc attaacatta atgcatgaat taattcattc attacatggt 660
ttatatggtg caaaaggtat tacaacaaaa tatacaatta cacaaaaaca aaatccatta 720
attacaaata ttagaggtac aaatattgaa gaatttttaa catttggtgg tacagattta 780
aatattatta catcagcaca atcaaatgat atttatacaa atttattagc agattataaa 840
aaaattgcat caaaattatc aaaagttcaa gtttcaaatc cattattaaa tccatataaa 900
gatgtttttg aagcaaaata tggtttagat aaagatgcat caggtattta ttcagttaat 960
attaataaat ttaatgatat ttttaaaaaa ttatattcat ttacagaatt tgatttagca 1020
acaaaatttc aagttaaatg tagacaaaca tatattggtc aatataaata ttttaaatta 1080
tcaaatttat taaatgattc aatttataat atttcagaag gttataatat taataattta 1140
aaagttaatt ttagaggtca aaatgcaaat ttaaatccaa gaattattac accaattaca 1200
ggtagaggtt tagttaaaaa aattattaga ttttgtaaaa atattgtttc agttaaaggt 1260
attagaaaat caatttgtat tgaaattaat aatggtgaat tattttttgt tgcatcagaa 1320
aattcatata atgatgataa tattaataca ccaaaagaaa ttgatgatac agttacatca 1380
aataataatt atgaaaatga tttagatcaa gttattttaa attttaattc agaatcagca 1440
ccaggtttat cagatgaaaa attaaattta acaattcaaa atgatgcata tattccaaaa 1500
tatgattcaa atggtacatc agatattgaa caacatgatg ttaatgaatt aaatgttttt 1560
ttttatttag atgcacaaaa agttccagaa ggtgaaaata atgttaattt aacatcatca 1620
attgatacag cattattaga acaaccaaaa atttatacat ttttttcatc agaatttatt 1680
aataatgtta ataaaccagt tcaagcagca ttatttgttt catggattca acaagtttta 1740
gttgatttta caacagaagc aaatcaaaaa tcaacagttg ataaaattgc agatatttca 1800
attgttgttc catatattgg tttagcatta aatattggta atgaagcaca aaaaggtaat 1860
tttaaagatg cattagaatt attaggtgca ggtattttat tagaatttga accagaatta 1920
ttaattccaa caattttagt ttttacaatt aaatcatttt taggttcatc agataataaa 1980
aataaagtta ttaaagcaat taataatgca ttaaaagaaa gagatgaaaa atggaaagaa 2040
gtttattcat ttattgtttc aaattggatg acaaaaatta atacacaatt taataaaaga 2100
aaagaacaaa tgtatcaagc attacaaaat caagttaatg caattaaaac aattattgaa 2160
tcaaaatata attcatatac attagaagaa aaaaatgaat taacaaataa atatgatatt 2220
aaacaaattg aaaatgaatt aaatcaaaaa gtttcaattg caatgaataa tattgataga 2280
tttttaacag aatcatcaat ttcatattta atgaaattaa ttaatgaagt taaaattaat 2340
aaattaagag aatatgatga aaatgttaaa acatatttat taaattatat tattcaacat 2400

-continued

```
ggttcaattt taggtgaatc acaacaagaa ttaaattcaa tggttacaga tacattaaat   2460

aattcaattc catttaaatt atcatcatat acagatgata aaattttaat ttcatatttt   2520

aataaatttt ttaaaagaat taaatcatca tcagttttaa atatgagata taaaaatgat   2580

aaatatgttg atacatcagg ttatgattca aatattaata ttaatggtga tgtttataaa   2640

tatccaacaa ataaaaatca atttggtatt tataatgata aattatcaga agttaatatt   2700

tcacaaaatg attatattat ttatgataat aaatataaaa atttttcaat ttcattttgg   2760

gttagaattc caaattatga taataaaatt gttaatgtta ataatgaata tacaattatt   2820

aattgtatga gagataataa ttcaggttgg aaagtttcat taaatcataa tgaaattatt   2880

tggacattac aagataatgc aggtattaat caaaaattag catttaatta tggtaatgca   2940

aatggtattt cagattatat taataaatgg atttttgtta caattacaaa tgatagatta   3000

ggtgattcaa aattatatat taatggtaat ttaattgatc aaaaatcaat tttaaattta   3060

ggtaatattc atgtttcaga taatatttta tttaaaattg ttaattgttc atatacaaga   3120

tatattggta ttagatattt taatattttt gataaagaat tagatgaaac agaaattcaa   3180

acattatatt caaatgaacc aaatacaaat attttaaaag atttttgggg taattattta   3240

ttatatgata aagaatatta tttattaaat gttttaaaac caaataattt tattgataga   3300

agaaaagatt caacattatc aattaataat attagatcaa caattttatt agcaaataga   3360

ttatattcag gtattaaagt taaaattcaa agagttaata attcatcaac aaatgataat   3420

ttagttagaa aaaatgatca agtttatatt aattttgttg catcaaaaac acatttattt   3480

ccattatatg cagatacagc aacaacaaat aaagaaaaaa caattaaaat ttcatcatca   3540

ggtaatagat ttaatcaagt tgttgttatg aattcagttg gtaataattg tacaatgaat   3600

tttaaaaata ataatggtaa taatattggt ttattaggtt ttaaagcaga tacagttgtt   3660

gcatcaacat ggtattatac acatatgaga gatcatacaa attcaaatgg ttgtttttgg   3720

aattttattt cagaagaaca tggttggcaa gaaaaataa                           3759
```

<210> SEQ ID NO 49
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, D. discoideum-modified 3

<400> SEQUENCE: 49

```
atgcctaaaa ttaattcatt caattataat gatccagtta atgatagaac aattttatat     60

attaaaccag gaggttgtca agaattttat aaaagtttta atattatgaa aaatatatgg    120

attataccag aaagaaatgt tattggtact acaccacaag atttccatcc acctacttca    180

cttaaaaatg gtgattcatc ttattatgat ccaaattatt tgcaatcaga tgaagaaaaa    240

gatagatttt taaaaattgt tacaaaaatt ttcaatcgta ttaataataa tttatcaggt    300

ggaatattat tggaagaatt atcaaaagca aatccatatt taggtaatga taatacacca    360

gataatcaat ttcatattgg tgatgcatca gcagtagaaa ttaaattcag taatggttct    420

caagatatat tacttccaaa tgttataatt atgggtgcag aaccagattt gttcgaaaca    480

aattcatcta atatatcatt aagaaataat tatatgccat caaatcatgg ttttggtagt    540

attgctattg ttacattctc accagaatat tcttttagat tcaatgataa ttcaatgaat    600

gaatttattc aagatccagc tttgacttta atgcatgaat taattcattc attacatggt    660
```

-continued

```
ttatatggtg ctaaaggaat tactacaaaa tatactatta cccaaaaaca aaatccactt    720
attacaaata ttcgtggtac caatattgaa gaatttttaa cttttggagg tactgattta    780
aatattataa catcagcaca atctaatgat atttatacta atttattggc agattataaa    840
aaaattgcat caaaattgag taaagtacaa gtttcaaatc cattacttaa tccatataaa    900
gatgtttttg aagcaaaata tggtttagat aaagatgcat caggaattta tagtgtaaat    960
attaataaat ttaatgatat ttttaaaaaa ttgtatagtt ttaccgaatt tgatcttgct   1020
actaaatttc aagttaaatg tagacaaact tatattggtc aatataaata ttttaaactt   1080
tcaaatttat tgaatgattc aatttataat atttctgaag gatataatat taataattta   1140
aaagttaatt ttagaggtca aaatgcaaat ttgaatcctc gtattataac tcctattact   1200
ggtcgtggtt tagtaaaaaa aataattaga ttttgtaaaa atattgtttc agtaaaaggt   1260
ataagaaaat caatttgtat agaaataaat aatggtgaat tatttttcgt tgcaagtgaa   1320
aattcttata atgatgataa tattaataca ccaaaagaaa ttgatgatac tgtaactagt   1380
aataataatt atgaaaatga tttagatcaa gttattttaa attttaatag tgaatcagca   1440
ccaggtttat cagatgaaaa acttaattta acaattcaaa atgatgctta tataccaaaa   1500
tatgattcta atggtacatc agatattgaa caacatgatg ttaatgaatt aaatgttttc   1560
ttttatttag atgcacaaaa agtaccagaa ggtgaaaata atgttaattt gacatcaagt   1620
attgatacag cacttttgga acaaccaaaa atttatactt ttttctcaag tgaatttata   1680
aataatgtta ataaaccagt tcaagctgca ttattcgttt catggataca acaagtatta   1740
gttgatttta caactgaagc taatcaaaaa tcaaccgttg ataaaattgc tgatatttca   1800
attgttgtac catatattgg attagcattg aatataggta atgaagcaca aaaaggtaat   1860
tttaaagatg cattagaatt attgggtgca ggtattttac ttgaattcga accagaatta   1920
ttgattccaa ctattttagt atttaccatt aaaagtttct taggttcatc tgataataaa   1980
aataaagtta ttaaagcaat taataatgct ttaaaagaac gtgatgaaaa atggaaagaa   2040
gtttattctt tcattgtttc aaattggatg actaaaatta atactcaatt taataaaaga   2100
aaagaacaaa tgtatcaagc tttacaaaat caagtaaatg caattaaaac aataattgaa   2160
tcaaaatata attcatatac attagaagaa aaaaatgaat taacaaataa atatgatatt   2220
aaacaaattg aaaatgaatt aaatcaaaaa gtatcaattg caatgaataa tattgataga   2280
ttcttaaccg aaagttcaat atcatattta atgaaattaa taaatgaagt taaaataaat   2340
aaattaagag aatatgatga aaatgttaaa acttatttac ttaattatat tatacaacat   2400
ggttctattt taggtgaatc acaacaagaa ttaaattcaa tggttactga tactttaaat   2460
aatagtattc catttaaatt atcatcttat acagatgata aaattttaat ttcatatttc   2520
aataaattct ttaaaagaat taaatcaagt tcagtattaa atatgcgtta taaaaatgat   2580
aaatatgtag atacctcagg ttatgattca aatattaata ttaatggtga tgtatataaa   2640
tatccaacaa ataaaaatca atttggtatt tataatgata aattaagtga agttaatata   2700
tcacaaaatg attatattat atatgataat aaatataaaa atttttcaat ttcattttgg   2760
gttagaattc caaattatga taataaaatt gttaatgtta ataatgaata tacaattata   2820
aattgtatga gagataataa ttctggttgg aaagtttcat taaatcataa tgaaattata   2880
tggactttac aagataatgc aggtataaat caaaaattag cttttaatta tggtaatgct   2940
aatggtattt cagattatat aaataaatgg atttttgtta caattacaaa tgatagatta   3000
```

-continued

```
ggagatagta aattatatat taatggtaat ttaattgatc aaaaaagtat attaaattta   3060
ggtaatattc atgtatcaga taatatatta tttaaaattg ttaattgtag ttatactaga   3120
tatattggta ttagatattt taatattttt gataaagaat tagatgaaac agaaattcaa   3180
acattatata gtaatgaacc aaataccaat attttaaaag atttctgggg taattatctt   3240
ttatatgata aagaatatta tttacttaat gtattaaaac caaataattt cattgataga   3300
cgtaaagatt ctacattatc aataaataat attagatcaa caattttatt agcaaatcgt   3360
ttatatagtg gtattaaagt taaaattcaa agagtaaata attcatctac caatgataat   3420
ttagttagaa aaaatgatca agtatatatt aattttgttg cttcaaaaac tcatttattt   3480
cctttatatg cagatacagc tacaaccaat aaagaaaaaa caattaaaat ttcttcaagt   3540
ggtaatagat ttaatcaagt tgttgttatg aattcagttg gtaataattg tacaatgaat   3600
tttaaaaata ataatggtaa taatattgga ttattaggtt tcaaagcaga tacagttgtt   3660
gcatcaacat ggtattatac acatatgaga gatcatacaa attcaaatgg atgtttttgg   3720
aattttattt cagaagaaca tggttggcaa gaaaaataa                          3759
```

<210> SEQ ID NO 50
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, Z. mays-modified 1

<400> SEQUENCE: 50

```
atgccgaaga taaactcatt taactacaac gatcccgtga atgacaggac catcctgtac     60
atcaagccgg gtggctgtca ggaattctac aaatctttca acatcatgaa aaacatatgg    120
atcattccag aacggaatgt gatcggtact accccccagg actttcatcc tcccacaagc    180
cttaagaatg gtgacagctc atattacgat ccgaactacc tgcaatccga tgaggaaaag    240
gaccggtttc ttaagatcgt gacgaaaatt ttcaaccgta tcaacaataa cctttctgga    300
ggcatcctac tggaggaact ttctaaggcg aacccatacc tcggcaacga caatacccct    360
gataaccagt tccacatagg tgatgcatcg gcggttgaaa ttaagtttag caatgggagc    420
caggacatcc ttctgccaaa cgtcattata atgggggccg agccagacct ctttgagact    480
aactcaagca atatttcgtt gcgcaataac tacatgccct caaaccacgg ctttgggtcc    540
atagcaatag tgactttcag ccccgaatac tccttcagat tcaacgataa ctcaatgaac    600
gaattcattc aggacccggc gctcacgctg atgcacgagc tcatccattc cctccatgga    660
ctctacggcg cgaaaggcat cactaccaag tacacaatta cacagaagca aaacccgctc    720
atcacaaaca tccgtgggac taatattgag gaatttctga cgttcggcgg taccgatctc    780
aacattatca cgtctgcgca gtctaatgat atctacacta acctgttagc agactacaaa    840
aagattgcct ccaagttgtc aaaagtgcag gtatccaacc ctctcttaaa cccttataag    900
gatgtcttcg aggccaagta tgggttggat aaagatgcct ctggtattta ttccgttaac    960
ataaacaagt tcaatgatat tttcaagaaa ctttattctt tcacagagtt cgacttagct   1020
accaagtttc aggtgaagtg tcggcagact tatattggcc aatacaaata cttcaaactt   1080
agcaacctcc tgaacgactc aatttacaac atttccgagg gctacaacat aaataacctc   1140
aaggtgaatt ttcgcgggca gaatgccaac ttgaacccca ggatcataac tcctatcacc   1200
gggagggggc tagtcaaaaa gatcattcgc ttctgcaaga acattgtatc cgtcaagggg   1260
```

-continued atccgaaaga gcatctgcat agagatcaat aacggcgagt tatttttcgt ggcgtccgag 1320
aattcctata acgatgacaa catcaatacc ccgaaggaga tagacgatac ggttacgagc 1380
aataacaatt atgagaatga tttggaccag gtgatattga acttcaactc agaatccgct 1440
cctggactca gcgatgagaa gctcaatctg accatccaaa acgatgctta catcccaaag 1500
tacgacagta acggaacatc ggatatcgag cagcacgatg tcaacgagct taatgttttt 1560
ttctacctcg acgcccagaa agtcccagag ggagagaaca atgtgaatct gactagcagt 1620
atcgacaccg ctctgctcga acagccgaag atttacacct tttctcgtc tgagttcatt 1680
aacaatgtca acaagccggt acaagctgcc cttttcgtgt catggattca gcaagtgctg 1740
gtggacttca ccacggaggc aaaccaaaag tcaactgttg acaagatcgc agacatatcc 1800
atcgttgtcc cttatatcgg tcttgccctg aacatcggca acgaggctca gaagggaaac 1860
ttcaaggacg cgctagagct gcttggagcc ggcatactgc tcgaattcga acccgagcta 1920
ctcatcccga ccatcctcgt gtttaccatt aagtcattcc tcggcagctc cgacaacaaa 1980
aacaaagtca tcaaagctat caacaatgcg ttgaaggagc gcgacgagaa gtggaaggaa 2040
gtgtacagct tcatcgtttc gaattggatg acgaaaatca atacccagtt caacaagaga 2100
aaggaacaaa tgtaccaggc cctgcagaat caagtaaacg cgattaagac gatcattgaa 2160
tctaaataca actcttacac gttggaggaa aaaaacgagc taactaataa atacgacatc 2220
aagcaaattg aaaatgagtt gaaccaaaag gtttctatcg ctatgaacaa tatcgatcgg 2280
tttctgacgg agtcgtccat tagctatctt atgaagctca taaacgaggt caagataaat 2340
aaactgaggg agtatgacga gaatgtaaag acatatctgc ttaattacat cattcagcac 2400
ggctcaatct tgggggagag tcagcaagag ctgaattcga tggtcaccga caccctaaac 2460
aatagcattc ccttcaaact ttctagctac acagatgaca agatactgat ctcatatttc 2520
aacaagttct ttaaaagaat caaaagctcc tctgtcttga acatgcggta caagaatgac 2580
aagtacgtcg acacttcggg gtacgacagt aacattaaca tcaacggtga cgtttataag 2640
tatcctacaa acaagaacca gtttgggatt tacaacgaca agctctcgga agtgaatata 2700
tcgcaaaatg attacataat ctacgataac aagtataaaa acttttccat tagcttttgg 2760
gtgcgtatcc caaactacga taataagata gtgaacgtca acaatgagta cacaattata 2820
aactgcatga gggacaacaa ttctggatgg aaggtaagtc taaatcacaa cgagattatc 2880
tggaccctgc aggacaatgc gggcatcaac cagaaattgg ccttcaacta cggaaacgca 2940
aacggcatta gcgactacat taataagtgg attttcgtca ccattacaaa tgatagactg 3000
ggcgatagta agctgtatat caatggcaac ctgattgatc aaaagtccat tttgaatctc 3060
ggtaacattc atgtttctga caacatcttg ttcaagatcg ttaattgctc atacacgcgc 3120
tacatcggaa taagatactt taatatcttt gacaaggagc tcgatgagac agaaatccaa 3180
actctctatt cgaacgaacc aaatacaaat atcttgaagg atttctgggg caactactta 3240
ctttacgaca aggagtacta tctgctaaac gtgttaaagc caaacaattt catcgaccgt 3300
aggaaggaca gcactctctc tatcaacaat atcaggagta caatccttct cgccaacagg 3360
ctctactccg gcattaaggt gaagatccag cgcgttaata actcgagtac caacgataat 3420
ctcgtccgca agaacgacca agtctatatc aacttcgtgg ccagcaaaac ccatcttttc 3480
ccgctgtacg cagacaccgc cacaacgaat aaggagaaga cgataaagat ttcctcaagt 3540
ggtaatcgat tcaaccaggt tgtggtcatg aatagcgtcg gaaacaattg cactatgaat 3600

-continued

```
tttaagaata acaatggcaa caacatcggt cttctgggct tcaaagctga taccgtggtt   3660

gctagtactt ggtattatac gcacatgcgc gaccatacca actcgaacgg ctgtttctgg   3720

aactttatct ccgaggaaca cggttggcag gagaagtaa                          3759


<210> SEQ ID NO 51
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, Z. mays-modified 2

<400> SEQUENCE: 51

atgccgaaga tcaacagctt caactacaac gacccggtga acgacaggac catcctgtac     60

atcaagccgg gcggctgcca ggagttctac aagagcttca acatcatgaa gaacatctgg    120

atcatcccgg agaggaacgt gatcggcacc accccgcagg acttccaccc gccgaccagc    180

ctgaagaacg gcgacagcag ctactacgac ccgaactacc tgcagagcga cgaggagaag    240

gacaggttcc tgaagatcgt gaccaagatc ttcaacagga tcaacaacaa cctgagcggc    300

ggcatcctgc tggaggagct gagcaaggcc aacccgtacc tgggcaacga caacaccccg    360

gacaaccagt tccacatcgg cgacgccagc gccgtggaga tcaagttcag caacggcagc    420

caggacatcc tgctgccgaa cgtgatcatc atgggcgccg agccggacct gttcgagacc    480

aacagcagca acatcagcct gaggaacaac tacatgccga gcaaccacgg cttcggcagc    540

atcgccatcg tgaccttcag cccggagtac agcttcaggt tcaacgacaa cagcatgaac    600

gagttcatcc aggacccggc cctgaccctg atgcacgagc tgatccacag cctgcacggc    660

ctgtacggcg ccaagggcat caccaccaag tacaccatca cccagaagca gaacccgctg    720

atcaccaaca tcaggggcac caacatcgag gagttcctga ccttcggcgg caccgacctg    780

aacatcatca ccagcgccca gagcaacgac atctacacca acctgctggc cgactacaag    840

aagatcgcca gcaagctgag caaggtgcag gtgagcaacc cgctgctgaa cccgtacaag    900

gacgtgttcg aggccaagta cggcctggac aaggacgcca gcggcatcta cagcgtgaac    960

atcaacaagt tcaacgacat cttcaagaag ctgtacagct tcaccgagtt cgacctggcc   1020

accaagttcc aggtgaagtg caggcagacc tacatcggcc agtacaagta cttcaagctg   1080

agcaacctgc tgaacgacag catctacaac atcagcgagg gctacaacat caacaacctg   1140

aaggtgaact tcaggggcca gaacgccaac ctgaacccga ggatcatcac cccgatcacc   1200

ggcaggggcc tggtgaagaa gatcatcagg ttctgcaaga acatcgtgag cgtgaagggc   1260

atcaggaaga gcatctgcat cgagatcaac aacggcgagc tgttcttcgt ggccagcgag   1320

aacagctaca acgacgacaa catcaacacc ccgaaggaga tcgacgacac cgtgaccagc   1380

aacaacaact acgagaacga cctggaccag gtgatcctga acttcaacag cgagagcgcc   1440

ccgggcctga gcgacgagaa gctgaacctg accatccaga acgacgccta catcccgaag   1500

tacgacagca acggcaccag cgacatcgag cagcacgacg tgaacgagct gaacgtgttc   1560

ttctacctgg acgcccagaa ggtgccggag ggcgagaaca acgtgaacct gaccagcagc   1620

atcgacaccg ccctgctgga gcagccgaag atctacacct tcttcagcag cgagttcatc   1680

aacaacgtga acaagccggt gcaggccgcc ctgttcgtga gctggatcca gcaggtgctg   1740

gtggacttca ccaccgaggc caaccagaag agcaccgtgg acaagatcgc cgacatcagc   1800

atcgtggtgc cgtacatcgg cctggccctg aacatcggca acgaggccca gaagggcaac   1860
```

-continued

```
ttcaaggacg ccctggagct gctgggcgcc ggcatcctgc tggagttcga gccggagctg   1920

ctgatcccga ccatcctggt gttcaccatc aagagcttcc tgggcagcag cgacaacaag   1980

aacaaggtga tcaaggccat caacaacgcc ctgaaggaga gggacgagaa gtggaaggag   2040

gtgtacagct tcatcgtgag caactggatg accaagatca acacccagtt caacaagagg   2100

aaggagcaga tgtaccaggc cctgcagaac caggtgaacg ccatcaagac catcatcgag   2160

agcaagtaca acagctacac cctggaggag aagaacgagc tgaccaacaa gtacgacatc   2220

aagcagatcg agaacgagct gaaccagaag gtgagcatcg ccatgaacaa catcgacagg   2280

ttcctgaccg agagcagcat cagctacctg atgaagctga tcaacgaggt gaagatcaac   2340

aagctgaggg agtacgacga gaacgtgaag acctacctgc tgaactacat catccagcac   2400

ggcagcatcc tgggcgagag ccagcaggag ctgaacagca tggtgaccga caccctgaac   2460

aacagcatcc cgttcaagct gagcagctac accgacgaca agatcctgat cagctacttc   2520

aacaagttct tcaagaggat caagagcagc agcgtgctga acatgaggta caagaacgac   2580

aagtacgtgg acaccagcgg ctacgacagc aacatcaaca tcaacggcga cgtgtacaag   2640

tacccgacca acaagaacca gttcggcatc tacaacgaca agctgagcga ggtgaacatc   2700

agccagaacg actacatcat ctacgacaac aagtacaaga acttcagcat cagcttctgg   2760

gtgaggatcc cgaactacga caacaagatc gtgaacgtga acaacgagta caccatcatc   2820

aactgcatga gggacaacaa cagcggctgg aaggtgagcc tgaaccacaa cgagatcatc   2880

tggaccctgc aggacaacgc cggcatcaac cagaagctgg ccttcaacta cggcaacgcc   2940

aacggcatca gcgactacat caacaagtgg atcttcgtga ccatcaccaa cgacaggctg   3000

ggcgacagca agctgtacat caacggcaac ctgatcgacc agaagagcat cctgaacctg   3060

ggcaacatcc acgtgagcga caacatcctg ttcaagatcg tgaactgcag ctacaccagg   3120

tacatcggca tcaggtactt caacatcttc gacaaggagc tggacgagac cgagatccag   3180

accctgtaca gcaacgagcc gaacaccaac atcctgaagg acttctgggg caactacctg   3240

ctgtacgaca aggagtacta cctgctgaac gtgctgaagc cgaacaactt catcgacagg   3300

aggaaggaca gcaccctgag catcaacaac atcaggagca ccatcctgct ggccaacagg   3360

ctgtacagcg gcatcaaggt gaagatccag agggtgaaca acagcagcac caacgacaac   3420

ctggtgagga agaacgacca ggtgtacatc aacttcgtgg ccagcaagac ccacctgttc   3480

ccgctgtacg ccgacaccgc caccaccaac aaggagaaga ccatcaagat cagcagcagc   3540

ggcaacaggt tcaaccaggt ggtggtgatg aacagcgtgg gcaacaactg caccatgaac   3600

ttcaagaaca acaacggcaa caacatcggc ctgctgggct tcaaggccga caccgtggtg   3660

gccagcacct ggtactacac ccacatgagg gaccacacca acagcaacgg ctgcttctgg   3720

aacttcatca gcgaggagca cggctggcag gagaagtaa                          3759
```

<210> SEQ ID NO 52
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, Z. mays-modified 3

<400> SEQUENCE: 52

```
atgccaaaga ttaattcatt taattacaac gatccggtca acgacaggac catcctctac     60
```

-continued

```
atcaagcccg gcggatgcca ggaattctac aagtcattca acatcatgaa gaatatttgg    120

ataattcccg agcgaaacgt aattggaact accccgcagg actttcaccc gccaacgtcg    180

ttaaaaaacg gcgactcaag ttactatgat cccaactacc tccaaagtga tgaggaaaaa    240

gacagattct taaaaatcgt tacgaaaata ttcaaccgca taaacaataa cctgtctggg    300

ggaatcctct tggaagagct atctaaggca aacccttatc tgggcaacga taataccca     360

gacaaccaat tccatatcgg cgacgcgtct gcagtcgaga ttaaattctc caacggaagc    420

caggatatcc tgctccccaa tgttattatc atgggcgccg aaccagacct ctttgagact    480

aatagttcta atatatccct tcggaacaat tatatgccat cgaaccacgg tttcggctct    540

attgctattg ttacgttcag tccggagtat tccttccggt ttaatgataa tagtatgaat    600

gagttcattc aggacccagc acttacactt atgcatgaat taatccattc tctgcacggg    660

ctttatggcg caaagggaat taccacgaag tacactatca cccaaaagca aaatccactg    720

atcacgaata tcagaggaac caacattgaa gagttcctca cttttggcgg tacggacctg    780

aacattatca catcggccca gtcaaacgac atttatacca acctcctggc cgactacaaa    840

aagatcgctt ccaagctcag caaagtccag gtttctaatc ccttacttaa tccgtataag    900

gacgtgtttg aggccaagta tggtctggac aaagatgcaa gtgggatata ctctgtgaac    960

atcaacaagt ttaacgacat ttttaaaaag ctctactcct tcacagagtt tgacctcgct   1020

accaagttcc aggtgaagtg tcgtcagacg tacattgggc aatacaagta ctttaagctc   1080

agcaacctac tgaacgactc aatctacaat atatctgaag gctataatat taacaatctg   1140

aaggtcaact ttcgcgggca gaatgccaac ctcaatcctc gtattataac cctatcaca    1200

ggccgcggct tggtgaaaaa gatcattagg ttttgtaaaa acatcgtttc ggttaagggt   1260

ataaggaagt ccatatgcat cgagataaat aacggagagc tattctttgt ggcttcagaa   1320

aactcgtaca acgacgataa tatcaacacc ccgaaggaga tcgatgacac ggtgacttct   1380

aacaataact acgaaaatga cctcgatcaa gtcatcctca acttcaattc cgagagcgcc   1440

ccgggtctta gcgacgagaa gctaaacctc accatacaga atgacgccta tattcccaag   1500

tatgacagta acgggactag cgacatagag cagcatgacg tcaacgagct aaatgtattc   1560

ttttatctag acgcgcagaa ggtgcctgaa ggcgaaaaca atgtcaacct tacctcgtct   1620

atcgacactg ccctcctgga gcaaccgaag atctacacat tcttttcatc cgagttcatc   1680

aataacgtca acaagcccgt ccaggccgct ctgttcgtct cctggattca gcaagtcctg   1740

gttgatttca ctacggaggc gaatcagaaa tcaaccgttg acaagatcgc cgacatttct   1800

attgtcgtgc catacatcgg cctagcgctc aatattggaa acgaggcaca aaaaggcaac   1860

ttcaaggacg ctcttgagct gcttggtgcg ggtatccttc tcgaattcga gcccgagctt   1920

ctgataccaa ctatcctggt ctttaccatt aagagctttc tcggttcatc cgataataaa   1980

aacaaggtta tcaaggctat taacaatgcg ttgaaggagc gcgacgaaaa atggaaggag   2040

gtgtactcct tcatcgtttc aaactggatg actaagatca atactcagtt caacaaaaga   2100

aaggaacaaa tgtatcaggc cctccaaaac caagtcaacg ctataaagac catcatagag   2160

tcgaagtaca atagctacac tctggaggaa aaaaacgagc ttacgaacaa gtacgacatc   2220

aaacagattg agaacgaact caatcagaag gtctcgatcg ccatgaacaa tatcgacagg   2280

tttcttacag aatcctcgat ttcctatctc atgaagctca tcaatgaagt taagatcaac   2340

aagctgcggg agtacgatga gaatgtgaag acatacctgt tgaactacat catacagcat   2400

ggctcgatct tgggcgaatc gcagcaagaa ctgaacagta tggtgaccga taccctaaat   2460
```

-continued aactcaatac cttttaagtt gagttcttat acggatgaca agatcctcat aagttatttc 2520
aacaagttct ttaagcgtat taagtcttca agcgtactca acatgcgata caaaaatgat 2580
aagtacgtgg acacatctgg ttacgatagc aatatcaaca taaacggcga tgtgtacaaa 2640
taccctacaa ataagaacca gttcggcatt tataatgata agctttccga ggtgaacatt 2700
tcacaaaatg attacatcat ttacgataac aagtacaaga acttctccat cagcttctgg 2760
gtcaggatcc cgaactacga taataagatt gtgaacgtaa acaatgagta caccatcatt 2820
aactgcatgc gggataacaa tagcggctgg aaggtgtcat tgaatcacaa cgagataatt 2880
tggaccctcc aagataacgc cggcatcaat cagaagctgg cgttcaatta tggaaacgct 2940
aatggcatct cagactacat caacaaatgg atattcgtta caatcactaa cgatcgcctg 3000
ggggatagca agctttatat taacgggaac ttgattgatc agaagtccat tttgaacctg 3060
ggcaacatcc acgtcagcga caacatcctg ttcaagatcg tgaactgtag ctacacccgc 3120
tacatcggta tccgttactt caatattttc gataaggagc tcgacgagac ggagatccag 3180
actctgtact cgaacgagcc gaacacaaac atcttaaaag acttctgggg gaactacttg 3240
ctttatgata aagagtatta cctgttgaac gtgttgaagc ctaataactt cattgaccgc 3300
aggaaggact cgacattatc cattaacaat attaggagca ccatcctgtt ggcgaataga 3360
ctctactccg ggatcaaggt gaagatccag cgggtaaaca attccagcac caacgacaac 3420
ttggtcagaa agaacgacca ggtgtacatc aacttcgtgg cgagcaaaac acatttgttc 3480
cctctgtacg ccgataccgc aacaacgaac aaggagaaga caatcaaaat aagctccagc 3540
ggcaacaggt tcaaccaagt cgtggtaatg aattccgtgg gaaacaattg cacgatgaat 3600
ttcaagaaca ataacgggaa caatataggg cttcttggtt ttaaagcgga tacggttgtt 3660
gcttctacct ggtactatac tcacatgcgc gaccacacta acagcaacgg ttgcttttgg 3720
aatttcatca gcgaggaaca cggatggcag gagaaataa 3759

<210> SEQ ID NO 53
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, A. thaliana-modified 1

<400> SEQUENCE: 53
atgcccaaaa tcaactcttt taattataac gatcctgtta acgatcgcac gattttatac 60
atcaagccag gaggttgtca agagttctat aaaagtttta atattatgaa aaatatatgg 120
attataccgg agcgtaacgt tatcggaacg actcctcagg acttccatcc accgacaagt 180
ctgaaaaatg gtgattccag ttactatgat cccaattatc tacaatctga cgaggaaaaa 240
gaccgttttc taaagatcgt caccaaaatt tttaacagga tcaataacaa tttaagcggc 300
gggatcctgc tcgaggaatt atcgaaagct aacccttatc tgggcaacga taatactccg 360
gataatcaat ttcatatcgg agatgcatca gccgtcgaga tcaaattctc gaatggttct 420
caagatatac tcttgccaaa cgttatcata atgggcgcag agccagactt atttgagaca 480
aattcctcga atatttccct ccgcaacaat tatatgccat cgaaccatgg ttttggttcg 540
atagctattg tgacattctc cccagaatat tcattcagat ttaacgataa ctcgatgaac 600
gagtttatac aagaccctgc tcttacactt atgcatgaac tcattcacag cctgcatgga 660

-continued

```
ctttatggtg ctaaggggat tactacaaag tacacgatta ctcaaaaaca gaatcctttg    720
ataacaaata ttcggggtac aaacatcgaa gagttcttaa cattcggagg cactgatcta    780
aacataatca catcagcgca aagtaatgat atctatacta acctccttgc agattacaaa    840
aagatagctt ctaaactatc aaaggtgcaa gtgtcgaacc cattgctgaa tccttacaaa    900
gacgttttcg aagctaaata tggattggat aaagatgcta gcggaatata cagtgtgaac    960
attaataagt tcaatgacat ctttaagaaa ctatatagtt tcacggagtt tgacctagcg   1020
acaaagttcc aagtgaaatg ccgtcagacc tacataggtc agtacaagta cttcaagctg   1080
tctaacctgt taaatgactc tatttacaac atctctgaag gatacaatat taataactta   1140
aaggttaatt ttcggggaca gaacgctaac cttaacccaa ggattataac cccaataacg   1200
ggaaggggtc tcgttaaaaa gatcattaga ttctgcaaaa acattgtgtc ggttaaaggt   1260
attaggaaga gcatttgtat agagattaat aacggagaac tgtttttcgt tgcttcagag   1320
aattcttata atgatgacaa tatcaatact cccaaggaaa tcgatgacac tgtcacaagc   1380
aataacaatt acgagaatga tctggaccaa gttattttga actttaacag cgaatccgct   1440
ccgggtttgt ccgatgaaaa gctaaattta actattcaaa acgacgcata catccctaaa   1500
tatgatagta acggcactag cgatatcgag caacatgatg ttaacgagct caatgttttt   1560
ttctatcttg atgctcaaaa ggtccctgaa ggagagaaca atgtaaattt aactagctcc   1620
atcgacacgg cgcttctaga gcagccaaag atatatactt tctttagcag tgagttcatc   1680
aacaatgtga acaaaccagt tcaagctgca ctttttgttt catggattca gcaagtccta   1740
gtggacttta ccacagaagc taaccaaaag agtactgtag acaagattgc cgacatatcg   1800
atcgttgtcc catacatagg tctcgctttg aatattggaa atgaagcgca gaaaggcaac   1860
ttcaaggatg cacttgagct cctaggggca ggaatcctgt tggaatttga acctgagtta   1920
ctgattccga caatattagt gttcactatc aagagttttc tcggaagctc tgataataag   1980
aacaaagtga tcaaagcgat caacaatgct ctcaaggaaa gagatgagaa atggaaagag   2040
gtttattcat ttatcgtctc aaactggatg accaaaatta atacacaatt taacaagcgt   2100
aaggagcaaa tgtatcaggc cctccaaaat caagtaaatg caatcaagac catcattgaa   2160
agcaagtata actcgtacac ccttgaagag aagaacgagc tgacgaacaa atatgatatt   2220
aagcaaattg aaaatgaatt aaaccagaag gtttccattg caatgaacaa tatcgaccgg   2280
ttcctaaccg agtcatccat ttcttatcta atgaaactca taaacgaagt gaaaatcaac   2340
aagttgcgag aatatgacga aaacgtaaaa acttaccttc taaactatat cattcagcat   2400
ggttccatac ttggagaatc ccagcaagaa ttgaactcaa tggttacaga cactctgaac   2460
aattcaatac cttttaagtt gagttcatac actgatgaca agatattaat tagctatttt   2520
aataaatttt tcaaaagaat caagtcttca tctgtactaa atatgagata taaaaatgat   2580
aaatacgtcg acacctcggg ctatgatagt aacattaata ttaacggtga tgtatacaag   2640
tatcctacca acaagaatca gttcggaatt tataatgata agctctctga ggttaatatc   2700
tcccagaatg actacattat ctacgataac aaatacaaga acttctccat aagcttctgg   2760
gttagaatac ctaattacga taacaagatc gtcaatgtga ataacgagta cactattatc   2820
aattgtatga gagataataa ctccggttgg aaagtgtctt taaaccacaa tgaaataatt   2880
tggacgctac aggataatgc aggaatcaac cagaagctgg catttaacta cgggaacgcc   2940
aatggcatta gtgattacat taataagtgg atatttgtta cgattacaaa cgatcgtctg   3000
ggggatagta aactttatat aaacggtaat ttgattgatc aaaagtctat tttgaatttg   3060
```

-continued

```
ggtaacattc acgtctcaga taacattctg ttcaaaatcg tcaattgttc atacactcga   3120

tatatcggta tcagatactt caacatcttt gataaagagc tcgatgaaac cgagatccag   3180

acattatatt ccaatgaacc gaacaccaat attctcaagg atttttgggg aaactacttg   3240

ctttatgaca aggaatacta tttgctaaat gttcttaaac ctaataactt catcgatcga   3300

aggaaggatt caacattatc catcaataac attagaagca caattctact tgctaatcga   3360

ttatatagtg ggataaaggt aaaaattcag agggttaaca attcgagcac caatgataat   3420

ttagttagga aaaatgatca ggtgtacatt aactttgtgg cctcgaagac ccacctgttc   3480

cccctctatg cggatactgc tactacaaac aaagagaaaa ctataaaaat aagttcgtct   3540

gggaatagat tcaatcaagt cgtggtaatg aattcggtag ggaataactg cacaatgaac   3600

tttaaaaaca ataacggaaa taatattggg ttgcttggtt tcaaggctga tacggttgtt   3660

gccagcactt ggtactatac gcacatgaga gatcatacta atagtaatgg ttgtttctgg   3720

aattttatat cggaagaaca tggatggcaa gaaaagtaa                          3759


<210> SEQ ID NO 54
<211> LENGTH: 3759
<212> TYPE: DNA
<213> ORGANISM: Artificial Sequence
<220> FEATURE:
<221> NAME/KEY: CDS
<222> LOCATION: (1)...(3759)
<223> OTHER INFORMATION: BoNT/E, A. thaliana-modified 2

<400> SEQUENCE: 54

atg cct aag att aat agt ttt aat tat aat gat cct gtt aat gat aga       48
Met Pro Lys Ile Asn Ser Phe Asn Tyr Asn Asp Pro Val Asn Asp Arg
1               5                   10                  15

act att tta tat att aag cct gga gga tgt caa gaa ttt tat aag agt       96
Thr Ile Leu Tyr Ile Lys Pro Gly Gly Cys Gln Glu Phe Tyr Lys Ser
            20                  25                  30

ttt aat att atg aag aat att tgg att att cct gaa aga aat gtt att      144
Phe Asn Ile Met Lys Asn Ile Trp Ile Ile Pro Glu Arg Asn Val Ile
        35                  40                  45

gga act act cct caa gat ttt cat cct cct act agt tta aag aat gga      192
Gly Thr Thr Pro Gln Asp Phe His Pro Pro Thr Ser Leu Lys Asn Gly
    50                  55                  60

gat agt agt tat tat gat cct aat tat tta caa agt gat gaa gaa aag      240
Asp Ser Ser Tyr Tyr Asp Pro Asn Tyr Leu Gln Ser Asp Glu Glu Lys
65                  70                  75                  80

gat aga ttt tta aag att gtt act aag att ttt aat aga att aat aat      288
Asp Arg Phe Leu Lys Ile Val Thr Lys Ile Phe Asn Arg Ile Asn Asn
                85                  90                  95

aat tta agt gga gga att tta tta gaa gaa tta agt aag gct aat cct      336
Asn Leu Ser Gly Gly Ile Leu Leu Glu Glu Leu Ser Lys Ala Asn Pro
            100                 105                 110

tat tta gga aat gat aat act cct gat aat caa ttt cat att gga gat      384
Tyr Leu Gly Asn Asp Asn Thr Pro Asp Asn Gln Phe His Ile Gly Asp
        115                 120                 125

gct agt gct gtt gaa att aag ttt agt aat gga agt caa gat att tta      432
Ala Ser Ala Val Glu Ile Lys Phe Ser Asn Gly Ser Gln Asp Ile Leu
    130                 135                 140

tta cct aat gtt att att atg gga gct gaa cct gat tta ttt gaa act      480
Leu Pro Asn Val Ile Ile Met Gly Ala Glu Pro Asp Leu Phe Glu Thr
145                 150                 155                 160

aat agt agt aat att agt tta aga aat aat tat atg cct agt aat cat      528
Asn Ser Ser Asn Ile Ser Leu Arg Asn Asn Tyr Met Pro Ser Asn His
```

-continued

```
                165                 170                 175

gga ttt gga agt att gct att gtt act ttt agt cct gaa tat agt ttt      576
Gly Phe Gly Ser Ile Ala Ile Val Thr Phe Ser Pro Glu Tyr Ser Phe
            180                 185                 190

aga ttt aat gat aat agt atg aat gaa ttt att caa gat cct gct tta      624
Arg Phe Asn Asp Asn Ser Met Asn Glu Phe Ile Gln Asp Pro Ala Leu
        195                 200                 205

act tta atg cat gaa tta att cat agt tta cat gga tta tat gga gct      672
Thr Leu Met His Glu Leu Ile His Ser Leu His Gly Leu Tyr Gly Ala
    210                 215                 220

aag gga att act act aag tat act att act caa aag caa aat cct tta      720
Lys Gly Ile Thr Thr Lys Tyr Thr Ile Thr Gln Lys Gln Asn Pro Leu
225                 230                 235                 240

att act aat att aga gga act aat att gaa gaa ttt tta act ttt gga      768
Ile Thr Asn Ile Arg Gly Thr Asn Ile Glu Glu Phe Leu Thr Phe Gly
                245                 250                 255

gga act gat tta aat att att act agt gct caa agt aat gat att tat      816
Gly Thr Asp Leu Asn Ile Ile Thr Ser Ala Gln Ser Asn Asp Ile Tyr
            260                 265                 270

act aat tta tta gct gat tat aag aag att gct agt aag tta agt aag      864
Thr Asn Leu Leu Ala Asp Tyr Lys Lys Ile Ala Ser Lys Leu Ser Lys
        275                 280                 285

gtt caa gtt agt aat cct tta tta aat cct tat aag gat gtt ttt gaa      912
Val Gln Val Ser Asn Pro Leu Leu Asn Pro Tyr Lys Asp Val Phe Glu
    290                 295                 300

gct aag tat gga tta gat aag gat gct agt gga att tat agt gtt aat      960
Ala Lys Tyr Gly Leu Asp Lys Asp Ala Ser Gly Ile Tyr Ser Val Asn
305                 310                 315                 320

att aat aag ttt aat gat att ttt aag aag tta tat agt ttt act gaa     1008
Ile Asn Lys Phe Asn Asp Ile Phe Lys Lys Leu Tyr Ser Phe Thr Glu
                325                 330                 335

ttt gat tta gct act aag ttt caa gtt aag tgt aga caa act tat att     1056
Phe Asp Leu Ala Thr Lys Phe Gln Val Lys Cys Arg Gln Thr Tyr Ile
            340                 345                 350

gga caa tat aag tat ttt aag tta agt aat tta tta aat gat agt att     1104
Gly Gln Tyr Lys Tyr Phe Lys Leu Ser Asn Leu Leu Asn Asp Ser Ile
        355                 360                 365

tat aat att agt gaa gga tat aat att aat aat tta aag gtt aat ttt     1152
Tyr Asn Ile Ser Glu Gly Tyr Asn Ile Asn Asn Leu Lys Val Asn Phe
    370                 375                 380

aga gga caa aat gct aat tta aat cct aga att att act cct att act     1200
Arg Gly Gln Asn Ala Asn Leu Asn Pro Arg Ile Ile Thr Pro Ile Thr
385                 390                 395                 400

gga aga gga tta gtt aag aag att att aga ttt tgt aag aat att gtt     1248
Gly Arg Gly Leu Val Lys Lys Ile Ile Arg Phe Cys Lys Asn Ile Val
                405                 410                 415

agt gtt aag gga att aga aag agt att tgt att gaa att aat aat gga     1296
Ser Val Lys Gly Ile Arg Lys Ser Ile Cys Ile Glu Ile Asn Asn Gly
            420                 425                 430

gaa tta ttt ttt gtt gct agt gaa aat agt tat aat gat gat aat att     1344
Glu Leu Phe Phe Val Ala Ser Glu Asn Ser Tyr Asn Asp Asp Asn Ile
        435                 440                 445

aat act cct aag gaa att gat gat act gtt act agt aat aat aat tat     1392
Asn Thr Pro Lys Glu Ile Asp Asp Thr Val Thr Ser Asn Asn Asn Tyr
    450                 455                 460

gaa aat gat tta gat caa gtt att tta aat ttt aat agt gaa agt gct     1440
Glu Asn Asp Leu Asp Gln Val Ile Leu Asn Phe Asn Ser Glu Ser Ala
465                 470                 475                 480

cct gga tta agt gat gaa aag tta aat tta act att caa aat gat gct     1488
```

-continued

```
Pro Gly Leu Ser Asp Glu Lys Leu Asn Leu Thr Ile Gln Asn Asp Ala
                485                 490                 495

tat att cct aag tat gat agt aat gga act agt gat att gaa caa cat      1536
Tyr Ile Pro Lys Tyr Asp Ser Asn Gly Thr Ser Asp Ile Glu Gln His
            500                 505                 510

gat gtt aat gaa tta aat gtt ttt ttt tat tta gat gct caa aag gtt      1584
Asp Val Asn Glu Leu Asn Val Phe Phe Tyr Leu Asp Ala Gln Lys Val
        515                 520                 525

cct gaa gga gaa aat aat gtt aat tta act agt agt att gat act gct      1632
Pro Glu Gly Glu Asn Asn Val Asn Leu Thr Ser Ser Ile Asp Thr Ala
    530                 535                 540

tta tta gaa caa cct aag att tat act ttt ttt agt agt gaa ttt att      1680
Leu Leu Glu Gln Pro Lys Ile Tyr Thr Phe Phe Ser Ser Glu Phe Ile
545                 550                 555                 560

aat aat gtt aat aag cct gtt caa gct gct tta ttt gtt agt tgg att      1728
Asn Asn Val Asn Lys Pro Val Gln Ala Ala Leu Phe Val Ser Trp Ile
                565                 570                 575

caa caa gtt tta gtt gat ttt act act gaa gct aat caa aag agt act      1776
Gln Gln Val Leu Val Asp Phe Thr Thr Glu Ala Asn Gln Lys Ser Thr
            580                 585                 590

gtt gat aag att gct gat att agt att gtt gtt cct tat att gga tta      1824
Val Asp Lys Ile Ala Asp Ile Ser Ile Val Val Pro Tyr Ile Gly Leu
        595                 600                 605

gct tta aat att gga aat gaa gct caa aag gga aat ttt aag gat gct      1872
Ala Leu Asn Ile Gly Asn Glu Ala Gln Lys Gly Asn Phe Lys Asp Ala
    610                 615                 620

tta gaa tta tta gga gct gga att tta tta gaa ttt gaa cct gaa tta      1920
Leu Glu Leu Leu Gly Ala Gly Ile Leu Leu Glu Phe Glu Pro Glu Leu
625                 630                 635                 640

tta att cct act att tta gtt ttt act att aag agt ttt tta gga agt      1968
Leu Ile Pro Thr Ile Leu Val Phe Thr Ile Lys Ser Phe Leu Gly Ser
                645                 650                 655

agt gat aat aag aat aag gtt att aag gct att aat aat gct tta aag      2016
Ser Asp Asn Lys Asn Lys Val Ile Lys Ala Ile Asn Asn Ala Leu Lys
            660                 665                 670

gaa aga gat gaa aag tgg aag gaa gtt tat agt ttt att gtt agt aat      2064
Glu Arg Asp Glu Lys Trp Lys Glu Val Tyr Ser Phe Ile Val Ser Asn
        675                 680                 685

tgg atg act aag att aat act caa ttt aat aag aga aag gaa caa atg      2112
Trp Met Thr Lys Ile Asn Thr Gln Phe Asn Lys Arg Lys Glu Gln Met
    690                 695                 700

tat caa gct tta caa aat caa gtt aat gct att aag act att att gaa      2160
Tyr Gln Ala Leu Gln Asn Gln Val Asn Ala Ile Lys Thr Ile Ile Glu
705                 710                 715                 720

agt aag tat aat agt tat act tta gaa gaa aag aat gaa tta act aat      2208
Ser Lys Tyr Asn Ser Tyr Thr Leu Glu Glu Lys Asn Glu Leu Thr Asn
                725                 730                 735

aag tat gat att aag caa att gaa aat gaa tta aat caa aag gtt agt      2256
Lys Tyr Asp Ile Lys Gln Ile Glu Asn Glu Leu Asn Gln Lys Val Ser
            740                 745                 750

att gct atg aat aat att gat aga ttt tta act gaa agt agt att agt      2304
Ile Ala Met Asn Asn Ile Asp Arg Phe Leu Thr Glu Ser Ser Ile Ser
        755                 760                 765

tat tta atg aag tta att aat gaa gtt aag att aat aag tta aga gaa      2352
Tyr Leu Met Lys Leu Ile Asn Glu Val Lys Ile Asn Lys Leu Arg Glu
    770                 775                 780

tat gat gaa aat gtt aag act tat tta tta aat tat att att caa cat      2400
Tyr Asp Glu Asn Val Lys Thr Tyr Leu Leu Asn Tyr Ile Ile Gln His
785                 790                 795                 800
```

-continued

```
gga agt att tta gga gaa agt caa caa gaa tta aat agt atg gtt act     2448
Gly Ser Ile Leu Gly Glu Ser Gln Gln Glu Leu Asn Ser Met Val Thr
                805                 810                 815

gat act tta aat aat agt att cct ttt aag tta agt agt tat act gat     2496
Asp Thr Leu Asn Asn Ser Ile Pro Phe Lys Leu Ser Ser Tyr Thr Asp
            820                 825                 830

gat aag att tta att agt tat ttt aat aag ttt ttt aag aga att aag     2544
Asp Lys Ile Leu Ile Ser Tyr Phe Asn Lys Phe Phe Lys Arg Ile Lys
        835                 840                 845

agt agt agt gtt tta aat atg aga tat aag aat gat aag tat gtt gat     2592
Ser Ser Ser Val Leu Asn Met Arg Tyr Lys Asn Asp Lys Tyr Val Asp
    850                 855                 860

act agt gga tat gat agt aat att aat att aat gga gat gtt tat aag     2640
Thr Ser Gly Tyr Asp Ser Asn Ile Asn Ile Asn Gly Asp Val Tyr Lys
865                 870                 875                 880

tat cct act aat aag aat caa ttt gga att tat aat gat aag tta agt     2688
Tyr Pro Thr Asn Lys Asn Gln Phe Gly Ile Tyr Asn Asp Lys Leu Ser
                885                 890                 895

gaa gtt aat att agt caa aat gat tat att att tat gat aat aag tat     2736
Glu Val Asn Ile Ser Gln Asn Asp Tyr Ile Ile Tyr Asp Asn Lys Tyr
            900                 905                 910

aag aat ttt agt att agt ttt tgg gtt aga att cct aat tat gat aat     2784
Lys Asn Phe Ser Ile Ser Phe Trp Val Arg Ile Pro Asn Tyr Asp Asn
        915                 920                 925

aag att gtt aat gtt aat aat gaa tat act att att aat tgt atg aga     2832
Lys Ile Val Asn Val Asn Asn Glu Tyr Thr Ile Ile Asn Cys Met Arg
    930                 935                 940

gat aat aat agt gga tgg aag gtt agt tta aat cat aat gaa att att     2880
Asp Asn Asn Ser Gly Trp Lys Val Ser Leu Asn His Asn Glu Ile Ile
945                 950                 955                 960

tgg act tta caa gat aat gct gga att aat caa aag tta gct ttt aat     2928
Trp Thr Leu Gln Asp Asn Ala Gly Ile Asn Gln Lys Leu Ala Phe Asn
                965                 970                 975

tat gga aat gct aat gga att agt gat tat att aat aag tgg att ttt     2976
Tyr Gly Asn Ala Asn Gly Ile Ser Asp Tyr Ile Asn Lys Trp Ile Phe
            980                 985                 990

gtt act att act aat gat aga tta gga gat agt aag tta tat att aat     3024
Val Thr Ile Thr Asn Asp Arg Leu Gly Asp Ser Lys Leu Tyr Ile Asn
        995                 1000                1005

gga aat tta att gat caa aag agt att tta aat tta gga aat att cat     3072
Gly Asn Leu Ile Asp Gln Lys Ser Ile Leu Asn Leu Gly Asn Ile His
    1010                1015                1020

gtt agt gat aat att tta ttt aag att gtt aat tgt agt tat act aga     3120
Val Ser Asp Asn Ile Leu Phe Lys Ile Val Asn Cys Ser Tyr Thr Arg
1025                1030                1035                1040

tat att gga att aga tat ttt aat att ttt gat aag gaa tta gat gaa     3168
Tyr Ile Gly Ile Arg Tyr Phe Asn Ile Phe Asp Lys Glu Leu Asp Glu
                1045                1050                1055

act gaa att caa act tta tat agt aat gaa cct aat act aat att tta     3216
Thr Glu Ile Gln Thr Leu Tyr Ser Asn Glu Pro Asn Thr Asn Ile Leu
            1060                1065                1070

aag gat ttt tgg gga aat tat tta tta tat gat aag gaa tat tat tta     3264
Lys Asp Phe Trp Gly Asn Tyr Leu Leu Tyr Asp Lys Glu Tyr Tyr Leu
        1075                1080                1085

tta aat gtt tta aag cct aat aat ttt att gat aga aga aag gat agt     3312
Leu Asn Val Leu Lys Pro Asn Asn Phe Ile Asp Arg Arg Lys Asp Ser
    1090                1095                1100

act tta agt att aat aat att aga agt act att tta tta gct aat aga     3360
Thr Leu Ser Ile Asn Asn Ile Arg Ser Thr Ile Leu Leu Ala Asn Arg
1105                1110                1115                1120
```

-continued

```
tta tat agt gga att aag gtt aag att caa aga gtt aat aat agt agt     3408
Leu Tyr Ser Gly Ile Lys Val Lys Ile Gln Arg Val Asn Asn Ser Ser
                1125                1130                1135

act aat gat aat tta gtt aga aag aat gat caa gtt tat att aat ttt     3456
Thr Asn Asp Asn Leu Val Arg Lys Asn Asp Gln Val Tyr Ile Asn Phe
            1140                1145                1150

gtt gct agt aag act cat tta ttt cct tta tat gct gat act gct act     3504
Val Ala Ser Lys Thr His Leu Phe Pro Leu Tyr Ala Asp Thr Ala Thr
        1155                1160                1165

act aat aag gaa aag act att aag att agt agt agt gga aat aga ttt     3552
Thr Asn Lys Glu Lys Thr Ile Lys Ile Ser Ser Ser Gly Asn Arg Phe
    1170                1175                1180

aat caa gtt gtt gtt atg aat agt gtt gga aat aat tgt act atg aat     3600
Asn Gln Val Val Val Met Asn Ser Val Gly Asn Asn Cys Thr Met Asn
1185                1190                1195                1200

ttt aag aat aat aat gga aat aat att gga tta tta gga ttt aag gct     3648
Phe Lys Asn Asn Asn Gly Asn Asn Ile Gly Leu Leu Gly Phe Lys Ala
                1205                1210                1215

gat act gtt gtt gct agt act tgg tat tat act cat atg aga gat cat     3696
Asp Thr Val Val Ala Ser Thr Trp Tyr Tyr Thr His Met Arg Asp His
            1220                1225                1230

act aat agt aat gga tgt ttt tgg aat ttt att agt gaa gaa cat gga     3744
Thr Asn Ser Asn Gly Cys Phe Trp Asn Phe Ile Ser Glu Glu His Gly
        1235                1240                1245

tgg caa gaa aag taa                                                 3759
Trp Gln Glu Lys  *
    1250
```

<210> SEQ ID NO 55
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, A. thaliana-modified 3

<400> SEQUENCE: 55

```
atgccgaaga tcaacagttt taattataac gatcctgtga acgaccgtac aattttatac     60

ataaagccgg gcggttgcca ggaattctac aagagtttca acattatgaa aaacatttgg    120

ataattccgg aaagaaatgt gattggtact acacctcagg actttcaccc accgactagt    180

ttaaaaaacg ggatagtag ttactatgat cctaattact tacaaagtga tgaggaaaag    240

gacaggttct taaagattgt tacaaagata ttcaaccgta tcaataacaa tttaagtgga    300

gggatattat tagaggaatt aagtaaagcg aatccatatt taggcaatga taatactcca    360

gacaaccagt ttcatatcgg agacgctagt gctgttgaga ttaaatttag taacggtagt    420

caagacatat tattaccaaa cgttattata atgggagctg aacctgattt attcgagacc    480

aacagtagta acataagttt acgaaataac tatatgccta gtaatcatgg tttcggaagt    540

attgccattg tcacctttag tcctgagtat agttttaggt ttaatgataa tagtatgaat    600

gaattcatcc aggacccagc tttaacatta atgcatgagt taatccatag tttacacgga    660

ttatacggag cgaaaggtat cactacaaag tatactatta cacagaaaca aaacccatta    720

attaccaaca tcagagggac aaacattgag gaatttttaa cgttcggagg cacggattta    780

aatattatca ccagtgctca gagtaatgac atttatacca atttattagc ggattataag    840

aaaattgcca gtaaattaag taaagttcaa gtgagtaacc cattattaaa cccttacaaa    900
```

-continued

```
gacgtgttcg aggcgaagta cggattagac aaggatgcta gtgggatata cagtgttaat    960
attaacaaat tcaacgatat tttcaagaaa ttatatagtt ttactgagtt cgatttagct   1020
actaagtttc aggttaagtg tagacagacc tacataggtc agtataagta ttttaagtta   1080
agtaacttat taaatgatag tatttataac atcagtgagg gttataatat taacaattta   1140
aaggtaaatt tccggggaca gaacgctaat ttaaacccaa gaattatcac tcctatcact   1200
gggagaggat tagtcaagaa aattatcaga ttttgcaaaa acattgtaag tgttaaggga   1260
attcgaaaga gtatttgtat cgaaattaat aacggtgaat tatttttcgt cgcaagtgag   1320
aacagttata acgatgacaa tattaacacg ccgaaggaga tagacgatac cgttacaagt   1380
aataacaatt atgaaaacga cttagatcag gtgatattaa acttcaatag tgagagtgct   1440
ccaggattaa gtgatgagaa attaaattta acgatccaga atgacgccta cattccaaaa   1500
tatgatagta atgggacgag tgatatcgaa caacatgatg ttaatgaatt aaacgttttt   1560
ttctatttag atgcacaaaa agtgcctgaa ggagaaaata acgtcaattt aactagtagt   1620
atagatacag cattattaga gcagcctaaa atatacactt tctttagtag tgagttcatt   1680
aacaatgtta ataaacctgt acaagcagct ttatttgtga gttggatcca acaggtttta   1740
gttgatttca ctacggaagc gaatcaaaaa agtaccgtgg ataaaatagc tgatattagt   1800
atagtagtgc cttacattgg gttagcctta aatattggta acgaagcaca aaagggaaac   1860
ttcaaagatg ctttagagtt attaggagct ggtatattat tagaattcga gcctgaatta   1920
ttaataccta ccatattagt ttttactata aaaagttttt tagggagtag tgataacaaa   1980
aataaagtga ttaaggcaat aaataacgca ttaaaggaac gtgatgaaaa atggaaagag   2040
gtgtatagtt ttatcgtcag taactggatg acgaagatta atacacaatt taacaagagg   2100
aaagagcaaa tgtatcaagc cttacagaat caggtcaatg ctattaagac tattatcgaa   2160
agtaaataca acagttacac attagaggaa aaaaacgagt taacaaacaa gtacgatatc   2220
aaacaaattg aaaatgaatt aaatcaaaaa gtcagtatcg caatgaataa catagatcga   2280
ttcttaactg agagtagtat cagttattta atgaaattaa ttaatgaggt aaagattaat   2340
aaattacggg agtacgacga aaatgtcaaa acctacttat taaattacat tatacagcat   2400
ggtagtattt taggcgagag tcaacaggaa ttaaacagta tggtaacaga cacgttaaac   2460
aatagtatcc catttaaatt aagtagttat acagacgata agatcttaat aagttatttt   2520
aataaatttt tcaaacgaat taaaagtagt agtgttttaa acatgcggta caagaatgac   2580
aagtatgtcg atacaagtgg ttacgatagt aatatcaata tcaacggaga tgtatataag   2640
tacccaacta ataaaaatca attcggcata tataatgaca aattaagtga agtgaacatt   2700
agtcaaaatg actacataat ttatgataat aaatataaga atttcagtat cagtttttgg   2760
gtaagaattc ctaactacga taacaagatc gtgaatgtaa acaatgaata caccattata   2820
aattgtatga gagataataa cagtggttgg aaggttagtt taaatcacaa cgaaatcata   2880
tggacattac aagacaatgc tggtatcaat caaaaaattag ctttcaacta tggtaatgct   2940
aatggaatta gtgattacat aaacaagtgg atttttgtta caattacgaa cgataggtta   3000
ggtgatagta aattatacat taacgggaac ttaatcgatc aaaagagtat cttaaattta   3060
ggaaatatac acgttagtga taacatttta tttaagatcg tcaactgtag ttacacgaga   3120
tacatcggta tcagatattt taacatcttt gataaggagt tagatgaaac agagatccaa   3180
actttatata gtaatgagcc taacacaaat atcttaaagg atttttgggg caattattta   3240
ttatacgata aggagtacta tttattaaat gtgttaaagc ctaacaattt catcgatcgt   3300
```

-continued

```
agaaaagata gtacgttaag tattaacaat atccgtagta ccatcttatt agcaaatagg   3360

ttatatagtg gaatcaaagt caagatacaa agagttaaca atagtagtac caacgataac   3420

ttagttagaa agaacgacca agtgtacatc aacttcgttg ccagtaagac tcacttattc   3480

ccgttatacg cggatactgc aacaactaat aaagaaaaga caatcaagat cagtagtagt   3540

ggaaataggt tcaaccaggt tgtggttatg aacagtgttg gtaataactg tactatgaac   3600

ttcaagaaca ataacggcaa taacataggc ttattaggtt ttaaggcaga caccgttgtc   3660

gctagtactt ggtattatac tcatatgagg gaccatacta atagtaatgg atgcttttgg   3720

aactttatca gtgaggaaca tggttggcaa gaaaagtaa                          3759
```

```
<210> SEQ ID NO 56
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, D. melanogaster-modified 1

<400> SEQUENCE: 56
```

```
atgcctaaga tcaattcttt taactacaac gacccagtga acgaccgcac cattctatac     60

attaaaccgg gcggttgtca ggaattttac aagtcgttta acatcatgaa gaacatctgg    120

atcattccgg aacgaaatgt gatcggcact acaccacaag acttccatcc cccaacgtca    180

cttaagaatg gcgattcttc ctattacgac cccaattatc tgcagtcgga cgaagagaag    240

gatcggttcc ttaagattgt gaccaagatt tttaatagga tcaataacaa tctgagcggc    300

ggaattctac tggaagagct gagcaaggcc aacccctacc tcggtaacga caatactccg    360

gacaatcaat tccatattgg agacgcgtcg gccgtggaaa ttaaattttc caatggttcc    420

caggacatcc tgttgcccaa cgtgatcatt atgggcgcag agcccgatct gtttgaaacc    480

aattcgagca acatatcgct acggaacaat tacatgccga gcaaccatgg atttggttca    540

atcgccatcg ttaccttcag ccctgagtac agctttcgct tcaacgacaa tagcatgaac    600

gagttcatcc aggatccggc cctcactctg atgcatgagc tgattcattc gctgcacggt    660

ctctacggag ccaagggcat aacaacgaag tataccatca cacagaagca gaacccgctt    720

atcacaaata tccgtggaac taacatcgag gaattcctca cattcggcgg aaccgatctg    780

aatatcatta cgagcgccca gagtaatgat atctacacta acctgcttgc agactataag    840

aaaattgcct cgaagcttag caaggtgcaa gtgtcaaatc ctttgttaaa cccatacaaa    900

gatgtttttg aggccaagta cggactggac aaggatgcaa gcggaatcta ctccgtcaac    960

ataaacaaat tcaacgatat tttcaagaaa ttatactcct ttaccgagtt tgatctggcc   1020

acaaaattcc aggtgaagtg cagacagaca tatattgggc aatacaaata tttcaagctg   1080

agcaatctat tgaatgactc gatatacaat atcagcgagg gctacaatat aaataacttg   1140

aaggtgaact tccggggcca gaatgctaat ctgaacccga ggatcattac gccaatcacc   1200

ggccgcggtt tagtaaagaa aattatacgc ttctgcaaaa atatcgtgtc ggttaagggg   1260

ataaggaaat cgatctgcat cgagattaat aacggtgagt tgttctttgt cgcgtccgaa   1320

aattcctaca acgacgataa cattaacacg cccaaggaaa tcgacgatac tgtcaccagt   1380

aataacaatt atgagaatga tctggatcag gtcatcctga actttaacag cgaatcagca   1440

ccagggctta gcgatgaaaa actcaatcta accattcaaa atgacgctta cattcctaag   1500
```

-continued

```
tacgattcga atggcacaag tgacatcgag caacacgatg taaacgagct caacgttttc   1560
ttttatttag atgcgcagaa agttcccgag ggtgagaaca atgtgaactt gacgtcctct   1620
atcgataccg ctctcttgga gcaaccaaag atctacacgt tctttagctc ggagtttatc   1680
aataacgtaa acaagccggt tcaagccgcg ctgtttgtga gctggatcca gcaagtgctt   1740
gtcgacttca ccacggaggc taaccagaag agcaccgtgg ataaaatcgc cgacatcagc   1800
attgttgtgc cctacatagg actggccttg aacatcggca acgaggcgca aaagggaaat   1860
ttcaaagacg cgctggagct cttgggagct ggaatcttgc tcgagttcga accagaactg   1920
ctaattccga ccatcctggt cttcacgatt aagtcttttt tgggcagtag cgataacaag   1980
aacaaggtta ttaaggcaat caataacgcc ctcaaggaga gagatgagaa atggaaggag   2040
gtctacagct tcattgtctc taactggatg actaaaataa atacacagtt caacaagcga   2100
aaggagcaga tgtaccaggc attgcagaac caggtcaatg ccatcaagac cataattgag   2160
tcgaagtaca actcctacac cctggaagag aagaatgaac tgacaaacaa gtatgacatc   2220
aagcagatcg agaatgaact gaaccagaag gtaagtatag ccatgaacaa tatcgatcgt   2280
ttcctgacgg agagtagcat tagttatctt atgaagctga ttaatgaagt gaaaatcaat   2340
aagttgcgtg agtacgacga gaacgtcaaa acctacctcc tgaattatat tatccagcat   2400
ggcagtattc tcggtgagtc gcagcaagag ctgaactcga tggtgaccga cacactgaat   2460
aactccatcc cattcaaact gagttcctat acggatgaca agatccttat ttcctacttt   2520
aacaagttct ttaagcgaat caagtccagc tcggtcttga atatgcgcta caagaatgac   2580
aagtacgttg acacttcagg ctacgactcc aatatcaaca taaacggaga cgtgtataag   2640
tatccgacca acaagaacca attcggcata tacaacgata agctaagtga agtaaatatc   2700
tcacagaacg attatattat atacgataat aaatataaga atttctcaat aagtttctgg   2760
gttcgaattc ccaactacga taataagatc gtgaatgtga acaatgaata taccataatt   2820
aattgtatgc gcgacaacaa ttccggttgg aaggtgtctt tgaaccacaa tgaaatcatt   2880
tggaccctgc aggacaacgc cgggatcaac cagaaactgg ctttcaacta tggcaacgcc   2940
aatggcatct cggattacat caacaagtgg attttcgtca cgataacgaa cgaccggctg   3000
ggtgattcca aactgtacat taatggcaac ttgatcgatc agaagagtat actgaacctg   3060
ggcaacattc acgtgtccga caacattttg ttcaagatcg tgaattgctc ctacacgagg   3120
tatattggca tacgatactt caacatcttc gacaaagaac tggatgagac cgagatacag   3180
acgctgtact ctaacgagcc caacacgaac attctcaagg acttctgggg aaattacctg   3240
ctctatgata aggagtacta tctgttgaat gtgctaaagc ccaacaattt catagatcgt   3300
cgcaaggatt ccaccctgtc catcaacaat atacgcagta ccattctctt agccaatcgc   3360
ctctattccg gcataaaagt caaaatccag cgtgtgaaca attctagcac caatgataac   3420
ctagtacgga aaaatgatca ggtgtacatc aactttgtag cttccaaaac acacctgttt   3480
cccctgtatg cggatactgc aactacgaat aaggagaaaa cgataaagat ttcctcgtca   3540
ggaaaccgct tcaaccaagt ggttgtcatg aatagcgtgg gcaataactg cacaatgaac   3600
ttcaagaaca ataacggcaa caatataggc ttgcttggtt tcaaggcgga tacagtcgtg   3660
gcttcgactt ggtattatac ccacatgaga gaccacacta actcaaacgg atgcttttgg   3720
aactttatct cggaggagca cggatggcag gagaagtaa                          3759
```

<210> SEQ ID NO 57
<211> LENGTH: 3759

-continued

<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, D. melanogaster-modified 2

<400> SEQUENCE: 57
atgccaaaga taaactcttt caactacaat gacccagtga acgataggac aattttgtat 60
atcaagccgg gaggttgtca ggaattttat aagtccttca atattatgaa gaacatttgg 120
attatacccg aacgaaacgt catcggcacg accccacaag acttccaccc acccacgagt 180
ctcaagaacg gtgactccag ctactatgat cctaattact tacagtccga tgaggaaaag 240
gataggttcc tcaagatagt gacaaaaatt ttcaaccgaa tcaacaataa ccttagcggc 300
ggaatcctgt tggaggaact gtccaaggct aatccctact taggcaacga taacacacca 360
gacaatcagt tccacatagg cgacgctagc gccgtggaaa tcaagttttc caacggctcg 420
caggatatct tgctgccgaa cgtgatcata atgggtgctg agccggacct gttcgagaca 480
aactcgtcta atattagtct tcgcaataac tacatgccct cgaaccatgg attcggcagc 540
atcgccatag ttaccttctc gcctgagtac agttttcgtt tcaatgataa ttcgatgaat 600
gagttcatac aagatcccgc actgactttg atgcatgagc tcatccatag cttacatggc 660
ttgtatggtg ccaagggtat cacaaccaag tacaccatca cccagaaaca aaatccactc 720
atcacaaata tccgcggaac aaatatcgag gaattcttga ccttcggagg cacagatctt 780
aacataatca catcagcgca gagtaacgat atttatacta atctgcttgc ggattataag 840
aaaatcgcga gtaagctgtc aaaagtccag gtgagtaatc cgctgctcaa cccgtataag 900
gatgtttttg aagctaagta tggcctggac aaggacgcca gcgggatcta ctcagtgaac 960
attaacaagt ttaacgacat ttttaagaaa ctgtacagtt tcaccgagtt tgacctggcc 1020
accaagttcc aagttaaatg ccggcagacc tacataggac aatacaaata cttcaagttg 1080
agtaatctgt taaatgattc gatatataac atctccgagg gctacaatat caacaatctc 1140
aaggttaact ttcgcggaca gaatgccaac ctgaaccccc gcatcattac acccattaca 1200
ggcaggggcc tggtcaaaaa gatcatacga ttctgcaaaa acatcgtcag cgtgaagggc 1260
ataagaaaga gcatctgcat cgaaatcaac aatggtgagc tatttttcgt ggccagcgag 1320
aatagctaca acgatgacaa tattaacacc ccgaaagaga tagacgatac cgtcaccagc 1380
aataacaatt acgagaatga tctggaccag gtcattttga atttcaactc tgagtcagcc 1440
cctggcctgt cggatgagaa gctcaatctc acgatacaga acgacgcata tatcccgaag 1500
tacgactcca atggcacttc cgacatcgaa cagcatgatg tgaacgaact taacgtcttt 1560
ttctacctag acgcccagaa ggtccccgag gggagaata acgtcaatct cacgagcagt 1620
atagatacgg ctctgttgga gcagccgaag atctacacct tttcagcag tgagttcatc 1680 aataacgtta ataagccggt tcaggcggcc ctgttcgtgt cgtggatcca gcaagtgctt 1740
gtggatttca cgaccgaagc gaatcaaaag tcgactgtgg acaagattgc agacatctcg 1800
attgtggtcc catatatcgg actggcacta aatatcggga acgaagccca gaaaggtaat 1860
tttaaggatg cattggagct actgggagca ggaatactac tggagttcga accggaactg 1920
ttgattccca ccatactcgt gttcaccatc aaatcctttc tgggttccag cgacaataag 1980
aacaaggtga taaaagcgat taacaatgcc ttgaaggagc gcgacgaaaa gtggaaggag 2040
gtctatagtt ttatagtgtc aaattggatg accaagatca acacccaatt taacaagcgg 2100

-continued

```
aaggagcaga tgtaccaggc actgcagaac caagtgaacg ctatcaaaac catcattgag   2160

tccaagtaca attcgtacac tttggaagag aaaaatgagc tgacgaacaa atacgatatc   2220

aagcaaatcg agaatgagct gaaccagaaa gtgagtattg cgatgaataa catcgaccgt   2280

ttcctcacgg aaagctccat ctcgtacctg atgaagctta ttaatgaggt gaagattaac   2340

aagctgcgcg agtacgacga gaacgtaaag acgtacttgc tgaactatat tatccaacac   2400

ggttcaatcc tgggagagtc ccagcaagag ctgaatagca tggtgactga tacactcaac   2460

aatagtatcc cattcaagct ctcatcctac accgatgaca aaattctaat cagctatttc   2520

aataaattct ttaaacggat taaaagctca tcggtcctca atatgcgcta caaaaacgac   2580

aagtatgtag atacctccgg atatgatagc aacatcaaca taaatggcga cgtgtataag   2640

taccccacca acaagaatca gtttggaatt tataacgaca agctgtccga ggtcaacatc   2700

agccagaatg attacattat ctatgacaac aagtacaaga acttctctat ttcgttctgg   2760

gtacgcattc ctaattacga taataagatc gtaaacgtga acaatgaata tacgatcatt   2820

aattgtatgc gtgataacaa ttccgggtgg aaggtctcgc tgaaccacaa tgaaattatc   2880

tggacgctgc aggacaacgc tggtattaac cagaagctgg ccttcaatta cggaaacgcc   2940

aatggcatta gcgattacat taacaaatgg atttttgtga caatcaccaa tgatcgacta   3000

ggcgattcta aattgtacat taatggcaat cttattgatc agaagtctat cttgaacctc   3060

ggcaatatcc acgtctccga caacatactt ttcaaaatag tgaactgctc ctacaccaga   3120

tacattggca tccgttactt taatatcttc gataaggagc tggacgagac tgagattcag   3180

accctgtatt ccaacgagcc aaacacaaac atactaaaag acttctgggg caattatttg   3240

ctgtacgaca aggaatacta tcttctgaac gtgttgaagc ccaacaattt tatagatcgg   3300

aggaaggatt cgactctgtc aattaacaat attagatcga cgatcctcct ggcgaaccgc   3360

ttgtattctg gtatcaaagt taaaatccag cgtgttaaca attcctcgac taacgacaac   3420

ttagtacgga agaacgacca agtgtatatt aatttcgtgg cctccaagac ccacctattt   3480

cccctgtacg ctgatacggc cacgactaac aaggagaaga cgataaagat ttcgtctagc   3540

ggtaatcgct ttaaccaggt tgtagtgatg aatagcgtag gaaacaattg cactatgaac   3600

tttaaaaaca ataacggaaa caacatcgga ctgctgggct tcaaggccga tactgttgtt   3660

gcctcgacgt ggtactacac gcacatgcga gatcatacga acagcaacgg ctgcttttgg   3720

aacttcattt ccgaagagca cggctggcag gagaagtaa                          3759
```

<210> SEQ ID NO 58
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, D. melanogaster-modified 3

<400> SEQUENCE: 58

```
atgcctaaga tcaatagctt caactacaat gaccctgtca acgacagaac aatcttgtac     60

atcaagcccg ggggctgcca ggaattttac aaaagcttca atattatgaa aaacatctgg    120

ataatcccag agcggaacgt tatcggcacc acgccacagg actttcatcc gccaacttcc    180

ctgaagaacg gagattcgtc atattacgac ccgaactatt tgcagtccga cgaagagaag    240

gatagatttc taaagatcgt tactaagata tttaaccgaa ttaacaataa cctaagcggc    300

ggaatcctgc ttgaggaact gagtaaggct aacccgtacc taggcaacga taataccccc    360
```

-continued

```
gacaaccagt tccatatcgg cgatgcgagc gccgttgaaa taaagttttc taacggttct    420
caggacatac ttttgccaaa tgtgattata atgggcgcgg agcccgacct ctttgaaacg    480
aattccagca acattagctt gcgaaacaat tatatgcctt ccaaccacgg cttcggttcc    540
atcgcaattg tgaccttttc gccagagtat tcgtttcgct tcaacgacaa ctcgatgaat    600
gagttcatcc aggaccccgc tctgacgctg atgcacgaac tgattcatag cctccacggt    660
ctttacgggg ccaaggggat caccacaaaa tacaccataa cacagaagca gaacccgctg    720
attacgaaca ttaggggtac caacatagaa gagttcctca ccttcggagg gaccgatctt    780
aatatcatta ctagcgcaca gagcaatgat atttatacca acttgctggc cgactacaaa    840
aagatcgcct ccaagctgag caaagtgcag gtaagcaatc cgctgctaaa cccctataaa    900
gacgtcttcg aggccaaata cggactggat aaggacgcta gtggcatata ctcggtcaat    960
attaataaat tcaacgatat cttcaagaaa ctgtattctt tcacggagtt tgatctggct   1020
acgaaatttc aggtgaagtg ccgacagaca tatatcggtc aatacaagta cttcaaactg   1080
agcaacctct tgaatgacag tatctataat atctccgagg gatacaacat taataacctg   1140
aaggttaatt tcaggggcca aaacgcaaat ctgaacccac gcataatcac gcccattaca   1200
ggacggggtc tagtcaaaaa gataatccgc ttctgcaaga atatcgtgag tgtgaaaggc   1260
attaggaagt ccatctgcat tgagataaac aatggcgagt tgtttttcgt ggcttccgag   1320
aacagttata atgatgacaa catcaataca ccgaaagaga tcgatgacac cgtgacctcc   1380
aataacaatt acgaaaatga cctggaccag gtcatcctga atttcaactc cgagagcgcc   1440
ccaggtctct ccgatgaaaa gctgaatcta acaatacaga acgatgccta catccccaag   1500
tacgatagca atggcacctc cgatattgag caacatgatg ttaatgagct caatgtattc   1560
ttttatctcg atgcgcagaa agtgccggaa ggcgagaata acgtcaacct aacctcgtct   1620
attgacaccg cactgttaga acaaccaaag atctatactt ttttcagcag tgagttcatt   1680
aataacgtga acaagccggt ccaagccgca ttgttcgtga gctggataca gcaagtgctc   1740
gtggacttta ccacggaggc aaaccagaag tccaccgtcg ataagatcgc tgatatatcc   1800
attgtggtac catacatcgg cttggccctg aatattggaa atgaggccca gaagggaaac   1860
tttaaggacg cgcttgagct gctcggcgcc ggcatcctgt tggagttcga gccggaactg   1920
ttgatcccca ccatcctcgt gttcacgatt aagtccttcc tgggatcgtc agacaacaag   1980
aataaagtaa tcaaggccat taataacgcc ttaaaggagc gcgatgagaa atggaaggaa   2040
gtttactcgt tcatagtttc gaactggatg acgaaaatta atacgcaatt taacaaacga   2100
aaggaacaaa tgtaccaagc cctccagaat caggtcaatg cgatcaagac tataatcgaa   2160
agcaagtata actcgtacac cctggaggaa aaaaacgagt tgacaaacaa gtacgatatt   2220
aaacagatcg agaatgagtt gaaccagaag gtctcaattg cgatgaacaa tatagacaga   2280
ttcttaaccg aaagctccat cagttacctt atgaagttga ttaacgaagt gaagattaat   2340
aagctgcgtg aatacgatga gaacgtgaaa acttacctgc ttaattatat catacaacac   2400
ggaagtattc tgggcgagag ccagcaagag ctgaatagta tggtgacgga taccctgaac   2460
aattcaatac cttttaagct ttcttcctat accgatgaca agatcctcat cagttacttt   2520
aacaagttct ttaagaggat taagtcttcc tcagtgctga atatgcgcta taagaacgat   2580
aaatacgtgg atacttccgg atacgactca aatatcaaca tcaacggaga cgtgtataaa   2640
tatcccacga ataagaatca gttcggtatt tacaatgata aactgtcgga ggtaaacatt   2700
```

-continued

```
agccaaaacg actatatcat atatgacaat aaatataaga acttctcaat ttcgttttgg   2760

gtacgcatac cgaactacga taataagata gttaatgtca acaatgagta cacaatcatt   2820

aactgcatgc gcgataataa ctccggatgg aaagtatcgc tgaatcacaa cgagatcata   2880

tggacacttc aagataacgc tggcatcaac cagaagttgg cctttaacta cggcaacgcc   2940

aacggcatta gtgattacat taacaagtgg atcttcgtga cgatcactaa cgatcgcctg   3000

ggtgactcga agctgtacat taatggcaac ctaatcgacc agaagtcgat tctgaatctg   3060

ggaaacatcc acgttagcga caacatcctg ttcaagattg tcaattgtag ctacactcgc   3120

tacataggta tccgttattt taatattttc gataaggagc ttgacgagac agaaatccag   3180

accctctaca gtaacgaacc caacacgaat atactaaagg atttctgggg caattacttg   3240

ctgtacgata aggagtacta tctcctgaac gttttgaagc ccaataactt catcgatcgg   3300

cgtaaggaca gcactttaag tatcaacaat atccggagca ccatcctctt ggcaaatcgt   3360

ctgtactcgg gtatcaaggt taaaattcag cgggtgaaca attcttcgac caatgataat   3420

ttagtgcgta agaacgacca ggtgtatatc aacttcgtgg cgtcgaagac gcacctcttt   3480

cccctgtacg ccgatacggc tacaactaac aaggagaaga ccattaaaat ctcctcgtca   3540

ggtaatcgct tcaatcaggt cgtggtcatg aactcggtcg gcaacaattg taccatgaac   3600

ttcaagaaca ataacggcaa caatattgga ttgctgggct ttaaggccga cacggtggtg   3660

gcgtcaacat ggtactatac acacatgcga gatcatacta actctaacgg atgcttctgg   3720

aacttcattt ccgaggagca tggatggcag gagaagtaa                          3759
```

<210> SEQ ID NO 59
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, S. frugiperda-modified 1

<400> SEQUENCE: 59

```
atgcctaaaa tcaactcgtt caactacaac gaccccgtga atgatcgaac gatcctgtac     60

atcaagcccg ggggctgcca ggaattctac aaatctttta acatcatgaa gaacatctgg    120

atcattccag agcggaatgt catcggtacc acaccgcaag acttccaccc gcccacctct    180

ctaaagaacg gtgacagttc gtactatgat ccaaactact tgcagtccga cgaagagaaa    240

gaccgctttc tcaagatcgt gacgaaaatt tttaacagga tcaataacaa tctgtcgggt    300

ggaatacttt tggaggaact ctccaaagcc aacccctacc tgggaaacga caacacacca    360

gacaaccagt ttcatatcgg cgacgctagc gccgtagaga ttaagttctc caacggatcg    420

caggacatct tgctgccaaa cgtgatcatt atgggtgcgg agcccgacct gttcgaaaca    480

aactcctcta acatctcatt acgtaataac tatatgccaa gtaatcacgg cttcggttct    540

atcgctatcg tgactttcag tccagagtat tcatttcgct tcaatgacaa ttccatgaac    600

gagttcatcc aggatcccgc cttaactctg atgcacgagc ttattcattc tctgcatggc    660

ctgtacggtg ccaagggtat caccactaag tacaccatta cacagaagca aaacccccta    720

attaccaata tccggggaac caacatagaa gagtttctga cttttggagg taccgacttg    780

aatatcatta catcagccca gtctaacgat atctatacca atctgttggc tgactacaag    840

aaaatcgcat ccaaactctc aaaggtgcag gtaagtaacc ccctgctcaa cccttacaag    900

gatgtgttcg aggcaaagta cggcctcgat aaggacgcca gtggtattta ttccgtcaac    960
```

-continued

```
attaacaagt tcaacgacat cttcaaaaag ctttattctt ttactgagtt tgacttagct   1020
acaaagttcc aagtgaagtg caggcagacg tacattggtc agtacaagta cttcaagctg   1080
agtaacctgc ttaatgactc aatttataac atctcggagg gatacaacat caacaatctc   1140
aaagtcaact tccgtggcca gaatgcaaac ttaaacccgc gtatcataac tcctatcact   1200
ggcagaggac ttgtgaagaa aatcattagg ttctgtaaaa acattgtaag cgttaagggg   1260
atccgtaagt cgatttgtat tgaaatcaac aatggagaat tattctttgt ggcatccgag   1320
aattcataca acgacgataa cataaatacg cctaaggaga ttgacgatac tgtcacttcg   1380
aataacaatt atgagaacga cttggatcag gtgattctaa atttcaattc tgaatcggct   1440
cctggcttga gcgacgaaaa gctgaatctg acaatacaga atgatgccta catcccgaaa   1500
tacgattcaa acggcacttc tgacatagaa caacacgacg taaacgagct caacgtcttc   1560
ttttacttgg atgcacaaaa agtccctgag ggtgaaaaca atgttaacct tactagctca   1620
atcgatacag ctttgctgga gcaaccaaag atctacacct tcttttcttc agagttcatc   1680
aataacgtca acaagcctgt tcaagcggcc ttgttcgtga gctggattca gcaagtcctc   1740
gtcgatttca ccacagaggc taatcaaaag tccaccgtgg ataaaatcgc ggacatttcc   1800
atcgttgtgc cctatatcgg actggctttg aacataggca acgaagctca aaaaggaaac   1860
tttaaggacg ccctagaact tctgggtgca ggaatcctcc tggaattcga accagagctg   1920
ttgatcccca ctattctggt gttcactatc aagagttttc tgggctcttc ggataacaaa   1980
aataaagtta ttaaagctat caacaatgcg ctcaaggagc gtgatgaaaa gtggaaagag   2040
gtctattctt tcattgtgtc aaattggatg actaagatta acacgcaatt taacaagaga   2100
aaggagcaga tgtaccaggc attgcagaac caggttaacg ctattaagac catcatagag   2160
agcaagtata actcatacac attggaagag aagaatgagt tgacgaataa atatgacatc   2220
aaacaaatcg aaaacgagct aaaccagaag gtcagcatcg cgatgaacaa tatcgaccgt   2280
ttcctaacgg agtccagcat ctcttacttg atgaagctca tcaacgaggt aaagataaac   2340
aagttacgcg agtacgatga aaacgtgaaa acgtacttgc tcaactacat catacagcat   2400
ggttctattc tgggtgagag ccaacaggaa ttgaactcca tggtcaccga cacccttaac   2460
aattccattc cgttcaagct tagctcttat acggacgata aaatcctcat tagctacttc   2520
aacaagttct ttaagagaat caagagctcc agtgtgctaa acatgaggta caagaacgat   2580
aagtacgtcg acacctccgg atatgattcc aatatcaata tcaatggcga cgtttacaag   2640
taccctacca acaagaacca attcggtatc tacaacgaca agctttccga ggtaaatatc   2700
agtcaaaacg actacattat ctacgacaac aaatacaaga acttctcgat ctccttctgg   2760
gtgcgcatcc ctaactacga caacaagatc gtaaacgtta ataacgagta caccataatc   2820
aactgcatga gagacaataa ctccggctgg aaggtctcgt tgaatcacaa tgaaatcatt   2880
tggactttgc aggataatgc tggcatcaac cagaaactcg ccttcaacta cggtaacgct   2940
aacggcatta gcgactacat caataagtgg atcttcgtta ccattaccaa cgatcgcctc   3000
ggagattcaa agctctatat caacggtaac ctcatcgacc aaaagagcat tctaaacctc   3060
ggaaacatcc acgtatccga caacatcctg ttcaagatag ttaactgctc atacactagg   3120
tacattggca tcaggtactt caacatcttc gacaaggaac tcgacgaaac ggaaatacaa   3180
actctgtata gtaacgaacc caacaccaac atcctcaagg acttctgggg caactacctt   3240
ctctacgaca aagagtacta tctcctgaat gtccttaaac cgaacaattt catcgaccgc   3300
```

-continued

```
cgtaaggatt ccacactgtc catcaacaat attagatcaa caatcctgtt agcgaaccgt   3360

ctgtacagcg gtattaaggt taagatacag cgcgtgaata actcatctac gaacgataac   3420

cttgtccgaa agaacgacca ggtgtacatc aatttcgtag cctccaagac ccacctgttc   3480

cctctctacg ccgacactgc tacaaccaac aaggagaaaa ccatcaaaat atcgagtagc   3540

ggtaacaggt tcaatcaggt ggtcgttatg aactctgtcg gaaacaactg tactatgaac   3600

ttcaagaaca acaacgggaa caacattggt ctgctgggat tcaaggcgga tacagtcgtg   3660

gctagcacat ggtactacac ccacatgcgc gaccatacca actccaacgg ttgcttctgg   3720

aacttcattt ctgaagagca cggctggcag gagaaataa                          3759
```

```
<210> SEQ ID NO 60
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, S. frugiperda-modified 2

<400> SEQUENCE: 60
```

```
atgcccaaga tcaactcctt caactacaac gaccccgtga acgaccgtac catcctgtac     60

atcaagcccg gtggttgcca ggagttctac aagtccttca acatcatgaa gaacatctgg    120

atcatccccg agcgtaacgt gatcggtacc accccccagg acttccaccc ccccacctcc    180

ctgaagaacg gtgactcctc ctactacgac cccaactacc tgcagtccga cgaggagaag    240

gaccgtttcc tgaagatcgt gaccaagatc ttcaaccgta tcaacaacaa cctgtccggt    300

ggtatcctgc tggaggagct gtccaaggct aacccctacc tgggtaacga caacaccccc    360

gacaaccagt tccacatcgg tgacgcttcc gctgtggaga tcaagttctc caacggttcc    420

caggacatcc tgctgcccaa cgtgatcatc atgggtgctg agcccgacct gttcgagacc    480

aactcctcca acatctccct gcgtaacaac tacatgccct ccaaccacgg tttcggttcc    540

atcgctatcg tgaccttctc ccccgagtac tccttccgtt tcaacgacaa ctccatgaac    600

gagttcatcc aggaccccgc tctgaccctg atgcacgagc tgatccactc cctgcacggt    660

ctgtacggtg ctaagggtat caccaccaag tacaccatca cccagaagca gaacccccctg    720

atcaccaaca tccgtggtac caacatcgag gagttcctga ccttcggtgg taccgacctg    780

aacatcatca cctccgctca gtccaacgac atctacacca acctgctggc tgactacaag    840

aagatcgctt ccaagctgtc caaggtgcag gtgtccaacc ccctgctgaa cccctacaag    900

gacgtgttcg aggctaagta cggtctggac aaggacgctt ccggtatcta ctccgtgaac    960

atcaacaagt tcaacgacat cttcaagaag ctgtactcct tcaccgagtt cgacctggct   1020

accaagttcc aggtgaagtg ccgtcagacc tacatcggtc agtacaagta cttcaagctg   1080

tccaacctgc tgaacgactc catctacaac atctccgagg gttacaacat caacaacctg   1140

aaggtgaact tccgtggtca gaacgctaac ctgaaccccc gtatcatcac ccccatcacc   1200

ggtcgtggtc tggtgaagaa gatcatccgt ttctgcaaga acatcgtgtc cgtgaagggt   1260

atccgtaagt ccatctgcat cgagatcaac aacggtgagc tgttcttcgt ggcttccgag   1320

aactcctaca acgacgacaa catcaacacc cccaaggaga tcgacgacac cgtgacctcc   1380

aacaacaact acgagaacga cctggaccag gtgatcctga acttcaactc cgagtccgct   1440

cccggtctgt ccgacgagaa gctgaacctg accatccaga acgacgctta catccccaag   1500

tacgactcca acggtacctc cgacatcgag cagcacgacg tgaacgagct gaacgtgttc   1560
```

-continued

```
ttctacctgg acgctcagaa ggtgcccgag ggtgagaaca acgtgaacct gacctcctcc   1620
atcgacaccg ctctgctgga gcagcccaag atctacacct tcttctcctc cgagttcatc   1680
aacaacgtga acaagcccgt gcaggctgct ctgttcgtgt cctggatcca gcaggtgctg   1740
gtggacttca ccaccgaggc taaccagaag tccaccgtgg acaagatcgc tgacatctcc   1800
atcgtggtgc cctacatcgg tctggctctg aacatcggta acgaggctca gaagggtaac   1860
ttcaaggacg ctctggagct gctgggtgct ggtatcctgc tggagttcga gcccgagctg   1920
ctgatcccca ccatcctggt gttcaccatc aagtccttcc tgggttcctc cgacaacaag   1980
aacaaggtga tcaaggctat caacaacgct ctgaaggagc gtgacgagaa gtggaaggag   2040
gtgtactcct tcatcgtgtc caactggatg accaagatca acacccagtt caacaagcgt   2100
aaggagcaga tgtaccaggc tctgcagaac caggtgaacg ctatcaagac catcatcgag   2160
tccaagtaca actcctacac cctggaggag aagaacgagc tgaccaacaa gtacgacatc   2220
aagcagatcg agaacgagct gaaccagaag gtgtccatcg ctatgaacaa catcgaccgt   2280
ttcctgaccg agtcctccat ctcctacctg atgaagctga tcaacgaggt gaagatcaac   2340
aagctgcgtg agtacgacga gaacgtgaag acctacctgc tgaactacat catccagcac   2400
ggttccatcc tgggtgagtc ccagcaggag ctgaactcca tggtgaccga caccctgaac   2460
aactccatcc ccttcaagct gtcctcctac accgacgaca agatcctgat ctcctacttc   2520
aacaagttct tcaagcgtat caagtcctcc tccgtgctga acatgcgtta caagaacgac   2580
aagtacgtgg acacctccgg ttacgactcc aacatcaaca tcaacggtga cgtgtacaag   2640
taccccacca acaagaacca gttcggtatc tacaacgaca agctgtccga ggtgaacatc   2700
tcccagaacg actacatcat ctacgacaac aagtacaaga acttctccat ctccttctgg   2760
gtgcgtatcc ccaactacga caacaagatc gtgaacgtga acaacgagta caccatcatc   2820
aactgcatgc gtgacaacaa ctccggttgg aaggtgtccc tgaaccacaa cgagatcatc   2880
tggaccctgc aggacaacgc tggtatcaac cagaagctgg ctttcaacta cggtaacgct   2940
aacggtatct ccgactacat caacaagtgg atcttcgtga ccatcaccaa cgaccgtctg   3000
ggtgactcca agctgtacat caacggtaac ctgatcgacc agaagtccat cctgaacctg   3060
ggtaacatcc acgtgtccga caacatcctg ttcaagatcg tgaactgctc ctacacccgt   3120
tacatcggta tccgttactt caacatcttc gacaaggagc tggacgagac cgagatccag   3180
accctgtact ccaacgagcc caacaccaac atcctgaagg acttctgggg taactacctg   3240
ctgtacgaca aggagtacta cctgctgaac gtgctgaagc ccaacaactt catcgaccgt   3300
cgtaaggact ccaccctgtc catcaacaac atccgttcca ccatcctgct ggctaaccgt   3360
ctgtactccg gtatcaaggt gaagatccag cgtgtgaaca actcctccac caacgacaac   3420
ctggtgcgta agaacgacca ggtgtacatc aacttcgtgg cttccaagac ccacctgttc   3480
cccctgtacg ctgacaccgc taccaccaac aaggagaaga ccatcaagat ctcctcctcc   3540
ggtaaccgtt tcaaccaggt ggtggtgatg aactccgtgg gtaacaactg caccatgaac   3600
ttcaagaaca acaacggtaa caacatcggt ctgctgggtt tcaaggctga caccgtggtg   3660
gcttccacct ggtactacac ccacatgcgt gaccacacca actccaacgg ttgcttctgg   3720
aacttcatct ccgaggagca cggttggcag gagaagtaa                          3759
```

<210> SEQ ID NO 61
<211> LENGTH: 3759
<212> TYPE: DNA

-continued

<213> ORGANISM: Artificial Sequence
<220> FEATURE:
<221> NAME/KEY: mat_peptide
<222> LOCATION: (1)...(3756)
<223> OTHER INFORMATION: BoNT/E, S. frugiperda-modified 3

<400> SEQUENCE: 61
atgccgaaga tcaattcctt caactacaac gaccccgtca atgatcgcac catcctatac 60
atcaagcctg gcggatgtca ggagttttac aaatcattca acatcatgaa gaacatttgg 120
attatcccag agcgtaacgt aattggtact acccctcagg atttccaccc cccaacctca 180
ttgaaaaacg gcgactcttc gtattacgac cccaactacc tacaatccga cgaagagaag 240
gaccgtttct tgaagatcgt caccaagatt ttcaacagaa ttaacaataa cttgtctgga 300
ggtatactac ttgaggaatt atcgaaggcc aatccgtatt tgggtaacga caacactccc 360
gacaaccaat tccacatcgg agacgcgtca gcagtggaaa tcaagttctc taacggctcc 420
caagacatcc ttctgccgaa cgtgataatc atgggagccg aacctgacct gttcgagacc 480
aactcgtcta atatcagtct ccgtaataac tacatgcctt caaaccacgg ctttggaagc 540
atcgccattg tcaccttctc acctgaatat tcattccgct ttaacgacaa cagcatgaat 600
gagttcattc aggaccccgc tttgaccttg atgcacgagc tcatccatag tttgcatggt 660
ctgtacggtg caaagggaat aacgacaaaa tatacaatca cccagaagca gaaccctctg 720
atcactaaca tcaggggaac taatattgaa gagttcctaa ccttcggcgg taccgacctg 780
aacattatca ccagcgctca aagcaacgat atttatacga atctgctcgc tgattacaag 840
aaaatcgctt cgaagttgag taaggtccaa gtttcaaatc cgctgcttaa cccttacaaa 900
gatgttttcg aggccaagta cgggttggac aaggacgcta gtggcatcta ctccgtgaac 960
attaacaagt tcaatgatat cttcaagaaa ctttactcat ttaccgagtt cgatctggcg 1020
acaaaattcc aggtcaaatg tagacagact tatattggcc aatacaaata ctttaaactt 1080
tcgaatctac tgaatgatag tatctacaac atttctgagg gttacaatat aaataacctg 1140
aaagttaact ttcgcggtca gaacgcaaac ctgaacccac gtatcattac tcctataact 1200
ggcagaggtt tggtgaaaaa gattatccga ttctgcaaaa atatcgtctc ggtcaaaggc 1260
atccgcaagt ctatctgcat cgagatcaac aatggagaac tgttctttgt cgcgtctgaa 1320
aacagctaca acgatgacaa cataaacaca ccaaaggaaa ttgacgatac agtaacgtct 1380
aacaataact acgagaatga ccttgatcag gtgatcctga acttcaattc tgagtccgcg 1440
ccaggcctct cggacgagaa gttgaatctg acgattcaga acgacgccta catcccgaag 1500
tatgactcga acggcacatc cgacatcgag caacacgatg tgaacgagct gaacgttttc 1560
ttttacctgg acgcacagaa ggtgcccgag ggtgaaaata acgtgaactt aacatccagc 1620
attgataccg ccctgttgga gcaacctaag atctacactt ttttctctag cgaatttatt 1680
aacaatgtaa ataaacccgt ccaagctgca ctattcgtct catggatcca acaggtgtta 1740
gtcgatttca caaccgaggc caatcagaag tccactgttg ataaaatcgc tgacatctcc 1800
atcgtcgttc cctacatcgg tctcgctctg aacattggca acgaagccca gaagggaaat 1860
ttcaaggatg ccctggaact gttaggggcc ggcatcttac tcgagtttga acccgaactg 1920
ttaattccaa caattctcgt ctttaccatt aaatccttcc tcggtagttc agacaacaaa 1980
aacaaagtaa taaaggctat taacaatgca ttgaaggaac gtgatgagaa atggaaggag 2040
gtatattcct tcattgtgtc taactggatg accaagatca atactcagtt caacaaaagg 2100
aaagaacaga tgtatcaggc gttgcagaac caggtgaacg ccatcaagac aattatcgaa 2160

-continued

```
agcaaatata actcctacac actggaggaa aaaaacgaac ttactaacaa gtacgacatt   2220

aagcaaatcg agaacgagct caaccaaaag gtctccatcg ctatgaacaa tatcgatcgt   2280

ttcctgactg agtcctctat ttcctacctt atgaagctca tcaacgaggt aaagatcaat   2340

aagctgcgcg aatacgatga gaacgtcaag acgtatttgc ttaactatat catacagcac   2400

ggtagcatcc tcggtgagag tcaacaggaa ctcaacagca tggtaaccga cactttgaac   2460

aattccatcc cattcaaact ctccagctac actgatgaca agatcctcat cagctacttc   2520

aacaagttct ttaaaagaat taagtcctct tcggtgctca atatgcggta caagaacgac   2580

aagtacgtag acacatcagg atacgacagt aacataaaca ttaatggcga cgtttacaag   2640

taccccacaa acaaaaacca gttcggtatc tataacgaca agctctccga agtgaatatc   2700

tctcagaatg attacataat ctacgacaac aagtacaaga acttcagcat ttctttctgg   2760

gtcaggattc ctaactatga caacaagatc gtgaacgtta acaatgaata cactataatc   2820

aactgcatgc gtgacaataa ctcaggctgg aaggtcagcc taaaccataa cgaaatcatt   2880

tggaccttgc aggacaacgc tggcatcaac caaaagcttg cgttcaacta cggaaatgct   2940

aatgggataa gcgactacat taacaagtgg atcttcgtga ctataaccaa cgatcgcttg   3000

ggagatagca agctgtacat caacggaaac ctaatagatc aaaagtccat ccttaacctg   3060

ggtaacatcc acgtgtcaga caacattctt ttcaagattg ttaactgcag ttataccagg   3120

tacatcggaa tccgctactt caacattttc gacaaggagc tggatgagac cgagatccaa   3180

acattgtact ctaacgagcc aaacactaac atcctgaagg atttctgggg taactatctg   3240

ctctacgata aagagtatta cctcctgaac gtactgaagc cgaacaattt catcgaccga   3300

aggaaggact cgacactctc tatcaacaat atacgcagca cgatcctctt ggctaacagg   3360

ctgtactccg gtatcaaggt gaagatccag agagttaaca atagttccac taacgacaat   3420

ctcgtgcgta agaatgacca ggtttacatc aatttcgtcg cttcaaaaac ccatttattc   3480

ccccttttacg cagacacggc gactacgaat aaggagaaga cgattaagat ctcgtcttcc   3540

ggaaacaggt ttaatcaggt tgtggtcatg aactcggtgg gcaacaattg tacgatgaac   3600

tttaagaaca ataacggtaa caacatcggt ctcctcggct tcaaggccga cacggtggtg   3660

gcttccacct ggtactacac ccacatgcgg gaccatacca acagtaacgg ttgcttttgg   3720

aacttcatct cagaagagca cggatggcaa gagaaataa                          3759
```

<210> SEQ ID NO 62
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, D. rerio-modified 1

<400> SEQUENCE: 62

```
atgccaaaga tcaactcgtt taactacaat gacccagtta acgatcgcac tatcctttat     60

atcaagcccg gtggatgcca ggagttttac aaatccttca atatcatgaa gaatatttgg    120

atcattcctg agcgtaacgt cattggaact acaccgcagg atttccaccc tcccacgtct    180

ctgaaaaatg gcgattcaag ttactatgat ccaaactatc tgcagtctga tgaggaaaaa    240

gataggtttc ttaaaatcgt gaccaagatc ttcaacagaa tcaacaataa cctcagtggt    300

ggcattctgc tagaagagct tagcaaagct aatccctact tggggaacga caatacgccg    360
```

-continued

```
gataaccaat ttcatatagg cgacgcctct gcagtggaga ttaaattctc aaatggtagc    420

caggatatat tgctgcctaa cgttattata atgggcgcgg agccggacct atttgagacg    480

aactcgtcca atatttccct ccggaacaat tatatgccga gtaaccacgg gtttggcagt    540

atagctattg tgacatttag tccagaatat tcatttaggt ttaacgacaa ctctatgaac    600

gaattcatcc aagatccagc attgactttg atgcatgagc tgattcattc attgcacggc    660

ctgtatggtg ccaaaggcat taccactaaa tacactatca cccagaagca gaacccgctg    720

attacaaaca tcaggggcac caacatagaa gagttcctga cattcggagg taccgacctt    780

aacattatca cttcagcaca gagtaacgac atctacacca acctgcttgc cgactataaa    840

aagatcgcct caaaactttc caaagttcag gtcagtaacc cactgctaaa tccatataag    900

gatgtgttcg aagccaagta tggattggac aaggacgcca gtggaatcta ctctgtaaat    960

attaataaat tcaacgacat atttaagaaa ctgtattctt tcaccgagtt cgacctggct   1020

actaagtttc aggtcaaatg tagacagaca tacatcggcc aatacaagta cttcaagctg   1080

tcaaacctgc ttaacgatag tatttacaac attagcgagg ggtataatat caacaatcta   1140

aaggtgaact tccgtgggca gaacgccaac ctcaacccac gcataatcac gcccatcact   1200

ggtagagggc tcgtcaaaaa gatcattaga ttttgtaaaa acatcgtctc tgttaagggt   1260

atccgcaaaa gcatatgcat cgagatcaat aacggcgagc tcttctttgt ggccagcgag   1320

aactcctata acgacgataa tataaacaca cctaaggaaa ttgatgacac agtcacctcc   1380

aacaataact atgaaaacga cctggatcag gtcattctca acttcaattc ggaaagtgcg   1440

cctggactca gcgacgagaa gctaaacctg actatccaga acgatgcata cattcccaag   1500

tatgattcaa acggtacatc cgatatcgag cagcatgatg tgaatgaact gaatgtgttc   1560

ttttatctgg atgcgcaaaa ggtgccagag ggtgagaata acgtgaacct gacttctagc   1620

atcgatacgg ctctcctgga gcagccaaaa atctacacat tttctcatc ggagtttatt   1680

aacaatgtca ataagcctgt gcaggcagcg ctgttcgtct catggatcca acaggtactc   1740

gtggacttta ccacggaagc taatcagaaa tctactgttg acaagattgc agacatctca   1800

atcgtggttc cttatatcgg attggcactg aacattggta acgaggcaca aaaaggcaac   1860

ttcaaggacg ctttggagtt actcggagct ggcatcctgt tagagtttga acccgagctc   1920

ttgatcccca caatactggt gttcaccata aagtcattcc ttggcagctc agacaacaag   1980

aacaaggtaa taaaagccat taacaatgcg ctgaaggagc gagacgagaa gtggaaagaa   2040

gtctattcct ttatagtcag caattggatg accaaaatca acacccaatt caacaaacgg   2100

aaagaacaga tgtaccaggc cttacagaat caagttaacg ctattaaaac catcatagag   2160

agcaaatata actcgtatac cctcgaggaa aaaaatgaac tgactaataa atacgatatt   2220

aaacagatcg aaaatgagct caaccagaaa gtgtctatcg ctatgaataa catcgaccgc   2280

tttctcactg agtcttccat ctcatatctg atgaagctca ttaatgaagt taaaatcaat   2340

aagcttagag agtacgacga gaacgtgaag acctacttgc tgaactacat cattcaacac   2400

ggcagcatcc tgggagagtc ccagcaagaa ctaaactcta tggtaaccga cacgctgaat   2460

aacagcatac ccttcaaact atcctcttac acagatgaca aaatcctgat cagctacttc   2520

aataagttct ttaagcgaat taaatcctca agtgtgctga acatgcggta caaaaacgac   2580

aagtacgtgg acacatctgg gtacgacagc aatatcaata ttaatggaga tgtttataag   2640

taccccacaa acaagaacca attcggaatc tacaatgata agctttctga ggtgaatatc   2700

tctcagaacg actatatcat atatgataac aaatacaaaa actttctat cagcttctgg   2760
```

-continued

```
gtgcgtatcc ctaactacga caataagatc gttaacgtga acaatgagta cacgatcatt   2820
aactgcatga gagacaataa cagtggttgg aaggtttcct tgaatcataa tgaaatcatt   2880
tggacgctgc aggataatgc agggataaat cagaagcttg cttttaatta cggaaacgct   2940
aatggaattt ccgactatat aaacaagtgg atcttcgtaa ctatcacaaa cgaccgatta   3000
ggagatagta aactgtacat caacgggaat ctcattgatc agaaaagcat cctcaacctg   3060
ggaaatattc acgtctcgga caatatcctt tttaagatcg tgaattgtag ctacacaaga   3120
tacattggaa ttagatattt taacatcttt gataaggaat tggacgagac cgaaatccag   3180
actctttaca gcaatgagcc taacaccaat attttgaagg atttttgggg aaattacctg   3240
ttatacgaca aggagtacta tttactgaac gtgctgaaac ctaacaattt tattgatcga   3300
cgtaaggatt ccactctcag cattaacaat atccgcagca ccattctgct tgctaacagg   3360
ctctattcgg gaataaaagt caagatccag agggtgaaca attctagtac taatgacaac   3420
ctggtgcgca agaatgatca ggtgtacatt aacttcgtgg cttctaagac ccacttattc   3480
cctctgtacg ccgacactgc aacaaccaac aaagagaaga caattaaaat cagctccagt   3540
ggcaacaggt ttaatcaggt agtcgttatg aattccgtcg ggaacaattg tacgatgaac   3600
ttcaaaaaca acaacggtaa caacattgga ctgctgggat tcaaagccga cacagttgtg   3660
gcctctacat ggtattacac acatatgcgg gatcacacaa acagcaacgg ttgcttctgg   3720
aacttcatct ccgaggaaca cggctggcag gagaagtaa                           3759
```

<210> SEQ ID NO 63
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, D. rerio-modified 2

<400> SEQUENCE: 63

```
atgcctaaga tcaacagctt caactacaac gaccctgtga acgacagaac aatcctgtac     60
atcaagcctg gaggatgtca ggagttctac aagagcttca acatcatgaa gaacatctgg    120
atcatccctg agagaaacgt gatcggaaca acacctcagg acttccaccc tcctacaagc    180
ctgaagaacg gagacagcag ctactacgac cctaactacc tgcagagcga cgaggagaag    240
gacagattcc tgaagatcgt gacaaagatc ttcaacagaa tcaacaacaa cctgagcgga    300
ggaatcctgc tggaggagct gagcaaggct aacccttacc tgggaaacga caacacacct    360
gacaaccagt tccacatcgg agacgctagc gctgtggaga tcaagttcag caacggaagc    420
caggacatcc tgctgcctaa cgtgatcatc atgggagctg agcctgacct gttcgagaca    480
aacagcagca acatcagcct gagaaacaac tacatgccta gcaaccacgg attcggaagc    540
atcgctatcg tgacattcag ccctgagtac agcttcagat tcaacgacaa cagcatgaac    600
gagttcatcc aggaccctgc tctgacactg atgcacgagc tgatccacag cctgcacgga    660
ctgtacggag ctaagggaat cacaacaaag tacacaatca cacagaagca gaaccctctg    720
atcacaaaca tcagaggaac aaacatcgag gagttcctga cattcggagg aacagacctg    780
aacatcatca caagcgctca gagcaacgac atctacacaa acctgctggc tgactacaag    840
aagatcgcta gcaagctgag caaggtgcag gtgagcaacc ctctgctgaa cccttacaag    900
gacgtgttcg aggctaagta cggactggac aaggacgcta gcggaatcta cagcgtgaac    960
```

-continued

```
atcaacaagt tcaacgacat cttcaagaag ctgtacagct tcacagagtt cgacctggct   1020
acaaagttcc aggtgaagtg tagacagaca tacatcggac agtacaagta cttcaagctg   1080
agcaacctgc tgaacgacag catctacaac atcagcgagg gatacaacat caacaacctg   1140
aaggtgaact tcagaggaca gaacgctaac ctgaacccta gaatcatcac acctatcaca   1200
ggaagaggac tggtgaagaa gatcatcaga ttctgtaaga acatcgtgag cgtgaaggga   1260
atcagaaaga gcatctgtat cgagatcaac aacggagagc tgttcttcgt ggctagcgag   1320
aacagctaca acgacgacaa catcaacaca cctaaggaga tcgacgacac agtgacaagc   1380
aacaacaact acgagaacga cctggaccag gtgatcctga acttcaacag cgagagcgct   1440
cctggactga gcgacgagaa gctgaacctg acaatccaga acgacgctta catccctaag   1500
tacgacagca acggaacaag cgacatcgag cagcacgacg tgaacgagct gaacgtgttc   1560
ttctacctgg acgctcagaa ggtgcctgag ggagagaaca acgtgaacct gacaagcagc   1620
atcgacacag ctctgctgga gcagcctaag atctacacat tcttcagcag cgagttcatc   1680
aacaacgtga acaagcctgt gcaggctgct ctgttcgtga gctggatcca gcaggtgctg   1740
gtggacttca caacagaggc taaccagaag agcacagtgg acaagatcgc tgacatcagc   1800
atcgtggtgc cttacatcgg actggctctg aacatcggaa acgaggctca gaagggaaac   1860
ttcaaggacg ctctggagct gctgggagct ggaatcctgc tggagttcga gcctgagctg   1920
ctgatcccta caatcctggt gttcacaatc aagagcttcc tgggaagcag cgacaacaag   1980
aacaaggtga tcaaggctat caacaacgct ctgaaggaga gagacgagaa gtggaaggag   2040
gtgtacagct tcatcgtgag caactggatg acaaagatca acacacagtt caacaagaga   2100
aaggagcaga tgtaccaggc tctgcagaac caggtgaacg ctatcaagac aatcatcgag   2160
agcaagtaca acagctacac actggaggag aagaacgagc tgacaaacaa gtacgacatc   2220
aagcagatcg agaacgagct gaaccagaag gtgagcatcg ctatgaacaa catcgacaga   2280
ttcctgacag agagcagcat cagctacctg atgaagctga tcaacgaggt gaagatcaac   2340
aagctgagag agtacgacga gaacgtgaag acatacctgc tgaactacat catccagcac   2400
ggaagcatcc tgggagagag ccagcaggag ctgaacagca tggtgacaga cacactgaac   2460
aacagcatcc ctttcaagct gagcagctac acagacgaca agatcctgat cagctacttc   2520
aacaagttct tcaagagaat caagagcagc agcgtgctga acatgagata caagaacgac   2580
aagtacgtgg acacaagcgg atacgacagc aacatcaaca tcaacggaga cgtgtacaag   2640
taccctacaa acaagaacca gttcggaatc tacaacgaca agctgagcga ggtgaacatc   2700
agccagaacg actacatcat ctacgacaac aagtacaaga acttcagcat cagcttctgg   2760
gtgagaatcc ctaactacga caacaagatc gtgaacgtga acaacgagta cacaatcatc   2820
aactgtatga gagacaacaa cagcggatgg aaggtgagcc tgaaccacaa cgagatcatc   2880
tggacactgc aggacaacgc tggaatcaac cagaagctgg ctttcaacta cggaaacgct   2940
aacggaatca gcgactacat caacaagtgg atcttcgtga caatcacaaa cgacagactg   3000
ggagacagca agctgtacat caacggaaac ctgatcgacc agaagagcat cctgaacctg   3060
ggaaacatcc acgtgagcga caacatcctg ttcaagatcg tgaactgtag ctacacaaga   3120
tacatcggaa tcagatactt caacatcttc gacaaggagc tggacgagac agagatccag   3180
acactgtaca gcaacgagcc taacacaaac atcctgaagg acttctgggg aaactacctg   3240
ctgtacgaca aggagtacta cctgctgaac gtgctgaagc ctaacaactt catcgacaga   3300
agaaaggaca gcacactgag catcaacaac atcagaagca caatcctgct ggctaacaga   3360
```

-continued

```
ctgtacagcg gaatcaaggt gaagatccag agagtgaaca acagcagcac aaacgacaac   3420

ctggtgagaa agaacgacca ggtgtacatc aacttcgtgg ctagcaagac acacctgttc   3480

cctctgtacg ctgacacagc tacaacaaac aaggagaaga caatcaagat cagcagcagc   3540

ggaaacagat tcaaccaggt ggtggtgatg aacagcgtgg gaaacaactg tacaatgaac   3600

ttcaagaaca acaacggaaa caacatcgga ctgctgggat tcaaggctga cacagtggtg   3660

gctagcacat ggtactacac acacatgaga gaccacacaa acagcaacgg atgtttctgg   3720

aacttcatca gcgaggagca cggatggcag gagaagtaa                          3759
```

<210> SEQ ID NO 64
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, D. rerio-modified 3

<400> SEQUENCE: 64

```
atgcccaaga tcaattcctt taactacaac gaccctgtca atgaccggac aattttgtac     60

atcaagcctg gagggtgcca ggagttctat aagagcttca acattatgaa aaatatttgg    120

atcattcctg aaagaaacgt catcggcacc acaccgcagg atttccaccc tcccactagc    180

ctgaagaacg gcgattctag ctattacgac cctaattacc ttcagtcaga cgaggaaaag    240

gatcgttttc ttaagatcgt gacaaagatc tttaaccgaa tcaacaataa cttgtcaggc    300

ggtatccttc tggaggaact gtctaaggcg aacccatatc tgggcaacga taacactcca    360

gataaccagt ttcatatcgg cgatgctagc gctgtggaaa ttaaattcag taacggctcc    420

caggacattc tcctgcctaa tgtgatcatt atgggtgctg agcctgacct cttcgagacc    480

aatagctcaa acatttctct gagaaacaat tacatgccat caaatcacgg gttcggaagt    540

attgctatcg tcacgttcag cccggagtat tcatttcgat ttaacgacaa tagtatgaac    600

gagttcatcc aggaccctgc tttgacactc atgcatgagc ttatccactc tcttcacgga    660

ttgtacgggg caaaaggtat cactacaaag tacaccatca cgcagaagca gaatccactg    720

atcaccaaca tcagaggcac gaatattgaa gagttcctta cctttggagg gacagacctg    780

aacatcatta cttctgccca gagcaacgac atctatacta acctgttggc agattacaag    840

aaaatcgcaa gtaagctgag taaagtgcag gtctcaaacc ccctgctcaa cccatataag    900

gacgtcttcg aggccaaata tggactggat aaggacgcat caggaatcta cagcgtgaat    960

atcaacaaat ttaacgatat tttcaagaaa ctgtattcct ttacagagtt tgaccttgct   1020

accaagttcc aggtgaagtg caggcagacg tacatcggtc agtacaagta cttcaaattg   1080

agcaatctgt tgaatgactc aatctataat attagcgagg gctataacat caataacctg   1140

aaagtcaatt ttcgtggtca gaacgccaat ctcaacccca ggattatcac accaatcact   1200

ggccggggac tcgtgaagaa aatcattcgc ttctgtaaga acatcgtgtc tgtgaaggga   1260

atccgtaaat ccatttgcat cgagatcaat aacggcgaac tgttctttgt ggctagtgag   1320

aattcctaca acgacgataa catcaacacg ccgaaagaaa tcgacgatac tgttacatcc   1380

aacaataact atgagaatga tctggaccag gttattctta acttcaactc tgagtcagca   1440

ccaggactga gcgatgagaa actcaacctt acaatccaga acgatgcata cattcccaaa   1500

tacgactcta acggaacctc cgacattgaa cagcacgacg tgaatgaact gaatgtgttc   1560
```

-continued

```
ttttacctgg atgctcagaa ggtgccagaa ggagagaaca atgtgaacct gacgagctcc   1620

atcgacacag ccctcctgga gcagcccaag atctacacat tctttagcag tgagttcatc   1680

aataacgtta acaagccggt ccaggccgct ctctttgtgt cttggatcca gcaggtcctg   1740

gttgacttta ctacagaagc aaatcagaag tccactgttg ataaaatcgc ggacatcagc   1800

atcgttgtcc cttacatcgg actggccctg aatatcggaa acgaggctca gaaggggaac   1860

tttaaagacg cgctggagct gttgggcgct ggtatcctgc tcgagtttga gcccgagctg   1920

ttgatcccta ctattcttgt gtttacgatc aaatcctttc tgggtagctc agataataag   1980

aataaagtta tcaaggctat taacaatgcc ctcaaagaaa gagacgagaa gtggaaggag   2040

gtttattctt tcatcgtgag taattggatg accaagatta acacacagtt taataaacga   2100

aaggagcaga tgtaccaggc cctccagaac caggtcaacg ccatcaagac cattatcgag   2160

agcaagtaca actcttatac actggaagag aaaaacgagc tgacaaacaa gtatgatatt   2220

aaacagatcg agaatgagct gaaccagaag gtttctatcg cgatgaacaa tatcgacaga   2280

tttctgacgg aaagctctat ctcctacctg atgaaactga tcaatgaagt taaaatcaat   2340

aagctgaggg agtatgacga aaacgtcaaa acctacctcc tgaattatat tatccagcat   2400

ggaagcattt tgggagaatc acagcaggaa ctgaactcca tggtgaccga cactttgaac   2460

aatagcatcc cattcaagct cagcagttac acagatgaca agattctgat tagttatttc   2520

aacaagtttt tcaagagaat taagtcctct agcgtgctga acatgagata caagaatgat   2580

aaatacgttg acacatctgg ctacgatagt aacatcaaca ttaacgggga cgtctacaaa   2640

taccccacca ataaaaacca gttcggcatc tacaacgata aactgtcaga ggtgaacatc   2700

agtcagaacg attatatcat ttacgataat aaatataaaa atttctccat cagtttctgg   2760

gtcagaatcc ctaattacga taataagatt gtgaatgtga ataacgaata taccattatc   2820

aactgcatga gggacaataa ctctggctgg aaagtgagcc tcaaccataa cgagatcatt   2880

tggactctgc aggataacgc cggaatcaat cagaagctcg ccttcaatta cgggaatgca   2940

aatgggatta gcgattacat caacaaatgg atttttgtta caatcaccaa cgaccggctt   3000

ggtgactcta agctgtatat caatggtaac ctgattgatc agaaatccat cctgaacctt   3060

gggaatatcc acgtgtcaga taacattctg tttaagatcg tgaattgttc ttacaccagg   3120

tacatcggta tcaggtattt caatattttc gataaagagc tggatgagac cgaaattcag   3180

accctgtatt caaacgagcc aaacactaac attctgaaag acttttgggg caactacttg   3240

ctgtacgaca aggaatacta tctgttgaac gtcctcaagc cgaataactt catcgatcgc   3300

cgtaaagata gcaccctgtc cattaacaat atccgctcca caatcctgct tgcgaatcga   3360

ctgtactctg gtattaaagt gaaaatccag cgggtgaaca atagctccac caacgacaac   3420

ctggtccgca agaacgatca ggtgtatatc aactttgtgg catctaaaac ccaccttttc   3480

cccctgtatg ccgacacagc tacgactaac aaagaaaaaa cgatcaagat cagctcaagt   3540

ggtaatcgct tcaatcaggt ggttgtgatg aacagtgtgg gaaacaattg tactatgaac   3600

ttcaaaaaca ataacggcaa caacatcgga ctcctcggtt tcaaagcaga cactgtggtg   3660

gccagcactt ggtattatac tcatatgcgc gaccatacca acagcaacgg atgtttttgg   3720

aactttatca gcgaggaaca cggatggcag gagaaataa                          3759
```

<210> SEQ ID NO 65
<211> LENGTH: 3759
<212> TYPE: DNA
<213> ORGANISM: Artificial Sequence

```
<220> FEATURE:
<221> NAME/KEY: mat_peptide
<222> LOCATION: (1)...(3756)
<223> OTHER INFORMATION: BoNT/E, X. laevis-modified 1

<400> SEQUENCE: 65

atgccaaaaa ttaactcttt caattataac gacccagtga acgatcggac tatcttgtac     60

atcaaacctg ggggatgtca ggagttttat aaatccttca acattatgaa gaatatatgg    120

attatccctg aaaggaatgt aataggtact acaccccagg actttcaccc accgacctcc    180

ctaaagaatg gagattctag ctattacgat cctaactacc tacagagtga cgaagagaaa    240

gataggtttc tgaagattgt cacaaagatc ttcaacagga taaataacaa tctaagcggg    300

ggcattcttt tggaggaact gagcaaggcc aatccctatc tgggaaacga caatactccc    360

gataaccagt ttcatatagg agacgctagc gctgtggaga tcaagttctc aaatggatcc    420

caagatattc tcttaccaaa cgttattatc atgggtgccg agccggatct cttcgaaact    480

aacagctcaa acatatctct gaggaacaat tatatgccat ctaaccacgg gtttggaagt    540

attgctatcg tgaccttttc acctgaatat agttttagat ttaatgacaa ttctatgaat    600

gagttcatcc aagaccccgc actaactctc atgcacgagt taattcactc attacatggc    660

ctgtatggag caaaggggat aaccacgaag tacaccatca cccagaaaca gaacccactc    720

atcactaaca tccgaggaac caatattgaa gagttcctga ccttcggagg gaccgatctg    780

aacatcatta ccagtgctca atctaacgat atttatacaa atctgctagc tgattacaaa    840

aagatagcca gtaagttaag caaggtgcag gttagtaacc cactacttaa tccgtacaaa    900

gacgtgttcg aggctaaata cggtttagat aaagacgcat ccggtattta ctcggttaac    960

atcaataagt tcaatgatat tttcaagaaa ctttatagct tcacagagtt tgacttggct   1020

accaaatttc aggtgaaatg ccgacagacg tatatcggac agtataagta cttcaaattg   1080

tccaacttgc tcaatgactc catttacaac attagtgaag gctataatat caacaatttg   1140

aaagttaact ttaggggcca aaatgccaac ctgaacccta gaataatcac acctattaca   1200

ggccgcggcc ttgttaagaa aatcattaga ttttgtaaaa atattgtatc tgttaaggga   1260

atccgcaaat ccatttgcat tgaaattaat aacggagaac tcttctttgt cgcttctgag   1320

aactcctata acgatgacaa catcaacacg ccaaaagaga tagacgatac agtcacgtct   1380

aataacaatt acgagaatga cttggaccaa gtaatcttga attttaatag tgaatcggca   1440

cctggtttgt ctgatgagaa acttaatctg acaatacaga acgatgcata cataccaaaa   1500

tacgactcca atgggactag tgacattgag cagcacgatg tgaacgaact taacgttttt   1560

ttctatctag acgcgcagaa ggtccccgaa ggtgaaaata acgtgaatct cacatcatct   1620

atagatacag cacttttaga acagccaaaa atctacacat tttctcatc ggaatttatc    1680

aataacgtga ataagcctgt gcaagccgca ctctttgtct cttggataca acaggtgtta   1740

gttgatttca ctacagaagc taatcaaaaa agtacagtgg acaagatagc cgacatttcg   1800

attgtagttc cctatatcgg actggcactc aatatcggta atgaggctca gaaaggaaat   1860

ttcaaggacg ccctggagct tttgggggcc ggcattttgc tcgaatttga accagagctg   1920

ctaattccta ctattctggt cttcacaatt aagtcctttc taggcagttc agataacaag   1980

aataaagtga ttaaggcaat taataacgcc cttaaagaaa gagatgagaa atggaaggag   2040

gtgtacagct tcatcgtctc aaactggatg actaagatca acactcaatt taataagcga   2100

aaagagcaaa tgtatcaggc tcttcaaaat caagtgaacg ccatcaagac tatcattgaa   2160
```

-continued

```
tctaaatata attcatacac actggaggaa aagaacgaat taaccaataa atacgacatc   2220

aaacaaatcg agaatgaact caaccagaag gtaagcatcg caatgaacaa tattgatcgt   2280

tttcttactg agtcttccat ttcatattta atgaaactga tcaacgaagt gaagatcaat   2340

aagctccggg aatacgatga aaacgtcaaa acttatctgt tgaactacat aattcagcac   2400

ggctcaatcc ttggagaatc tcagcaagag ttaaatagca tggttactga cacacttaat   2460

aacagcatac ccttcaaatt gagttcctac acagacgata agattcttat ttcctatttt   2520

aataaatttt tcaagcgtat aaagtcatcc tcagtactga acatgcgcta caaaaatgat   2580

aagtacgtag acacatctgg ttatgattct aatataaata tcaatggaga tgtctacaag   2640

tacccaacta acaaaaatca gtttggcatt tataatgaca aactttcgga ggtaaacatt   2700

tcccaaaacg actacataat ttacgataat aaatataaga acttttccat tagcttttgg   2760

gtcagaatac ccaactacga taataaaatc gttaatgtca acaatgaata taccattata   2820

aattgtatgc gtgataataa ctccggttgg aaggtttcac tcaatcacaa tgaaattatc   2880

tggacattgc aggataacgc tggaattaac cagaaactgg cctttaacta cggaaacgca   2940

aacggtatta gcgattatat caataaatgg atattcgtga ctataaccaa tgatcggctt   3000

ggcgacagca agctgtatat aaatgggaac cttatcgatc agaagtctat ccttaatctg   3060

gggaatatcc atgtgagcga caacatcctg ttcaagatag tgaactgcag ctacacacgg   3120

tatataggca tcaggtattt taacattttc gataaagaat tagatgaaac cgagattcag   3180

acactgtact caaatgaacc aaacaccaat atattgaaag atttttgggg gaactatctg   3240

ctatacgaca aagagtatta cctgctcaat gtgctgaaac ctaataactt tatcgacaga   3300

aggaaggata gtactcttag cattaacaat attagaagta ccatcctgct cgcaaacaga   3360

ttgtatagtg gtattaaagt caaaatacag cgcgtaaata actcttcaac taacgataat   3420

ctggtgcgaa aaaatgatca agtatatatc aattttgtag cgagcaagac acatctgttc   3480

cctttgtacg ctgataccgc gacaaccaat aaagagaaga cgataaagat ttctagttct   3540

ggcaaccgtt ttaaccaggt ggttgtgatg aattctgttg ggaacaattg tactatgaac   3600

tttaagaata acaatggaaa caatattggt ctgctggggt ttaaggcaga tacggttgtt   3660

gcttccactt ggtattatac ccatatgaga gaccatacaa acagcaacgg ctgcttctgg   3720

aatttcatta gtgaggaaca tggatggcag gagaagtaa                          3759
```

<210> SEQ ID NO 66
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, X. laevis-modified 2

<400> SEQUENCE: 66

```
atgccaaaaa ttaattcttt taattataat gatccagtga atgatagaac aattctgtat     60

attaaaccag gaggatgtca ggaattttat aaatctttta atattatgaa aaatatttgg    120

attattccag aaagaaatgt gattggaaca acaccacagg attttcatcc accaacatct    180

ctgaaaaatg gagattcttc ttattatgat ccaaattatc tgcagtctga tgaagaaaaa    240

gatagatttc tgaaaattgt gacaaaaatt tttaatagaa ttaataataa tctgtctgga    300

ggaattctgc tggaagaact gtctaaagct aatccatatc tgggaaatga taatacacca    360

gataatcagt ttcatattgg agatgcttct gctgtggaaa ttaaattttc taatggatct    420
```

-continued

```
caggatattc tgctgccaaa tgtgattatt atgggagctg aaccagatct gtttgaaaca    480
aattcttcta atatttctct gagaaataat tatatgccat ctaatcatgg atttggatct    540
attgctattg tgacattttc tccagaatat tcttttagat ttaatgataa ttctatgaat    600
gaatttattc aggatccagc tctgacactg atgcatgaac tgattcattc tctgcatgga    660
ctgtatggag ctaaaggaat tacaacaaaa tatacaatta cacagaaaca gaatccactg    720
attacaaata ttagaggaac aaatattgaa gaatttctga catttggagg aacagatctg    780
aatattatta catctgctca gtctaatgat atttatacaa atctgctggc tgattataaa    840
aaaattgctt ctaaactgtc taaagtgcag gtgtctaatc cactgctgaa tccatataaa    900
gatgtgtttg aagctaaata tggactggat aaagatgctt ctggaattta ttctgtgaat    960
attaataaat ttaatgatat ttttaaaaaa ctgtattctt ttacagaatt tgatctggct   1020
acaaaatttc aggtgaaatg tagacagaca tatattggac agtataaata ttttaaactg   1080
tctaatctgc tgaatgattc tatttataat atttctgaag gatataatat taataatctg   1140
aaagtgaatt ttagaggaca gaatgctaat ctgaatccaa gaattattac accaattaca   1200
ggaagaggac tggtgaaaaa aattattaga ttttgtaaaa atattgtgtc tgtgaaagga   1260
attagaaaat ctatttgtat tgaaattaat aatggagaac tgttttttgt ggcttctgaa   1320
aattcttata atgatgataa tattaataca ccaaaagaaa ttgatgatac agtgacatct   1380
aataataatt atgaaaatga tctggatcag gtgattctga attttaattc tgaatctgct   1440
ccaggactgt ctgatgaaaa actgaatctg acaattcaga atgatgctta tattccaaaa   1500
tatgattcta atggaacatc tgatattgaa cagcatgatg tgaatgaact gaatgtgttt   1560
ttttatctgg atgctcagaa agtgccagaa ggagaaaata atgtgaatct gacatcttct   1620
attgatacag ctctgctgga acagccaaaa atttatacat ttttttcttc tgaatttatt   1680
aataatgtga ataaaccagt gcaggctgct ctgtttgtgt cttggattca gcaggtgctg   1740
gtggatttta caacagaagc taatcagaaa tctacagtgg ataaaattgc tgatatttct   1800
attgtggtgc catatattgg actggctctg aatattggaa atgaagctca gaaaggaaat   1860
tttaaagatg ctctggaact gctgggagct ggaattctgc tggaatttga accagaactg   1920
ctgattccaa caattctggt gtttacaatt aaatcttttc tgggatcttc tgataataaa   1980
aataaagtga ttaaagctat taataatgct ctgaaagaaa gagatgaaaa atggaaagaa   2040
gtgtattctt ttattgtgtc taattggatg acaaaaatta atacacagtt taataaaaga   2100
aaagaacaga tgtatcaggc tctgcagaat caggtgaatg ctattaaaac aattattgaa   2160
tctaaatata attcttatac actggaagaa aaaaatgaac tgacaaataa atatgatatt   2220
aaacagattg aaaatgaact gaatcagaaa gtgtctattg ctatgaataa tattgataga   2280
tttctgacag aatcttctat ttcttatctg atgaaactga ttaatgaagt gaaaattaat   2340
aaactgagag aatatgatga aaatgtgaaa acatatctgc tgaattatat tattcagcat   2400
ggatctattc tgggagaatc tcagcaggaa ctgaattcta tggtgacaga tacactgaat   2460
aattctattc catttaaact gtcttcttat acagatgata aaattctgat ttcttatttt   2520
aataaatttt ttaaaagaat taaatcttct tctgtgctga atatgagata taaaaatgat   2580
aaatatgtgg atacatctgg atatgattct aatattaata ttaatggaga tgtgtataaa   2640
tatccaacaa ataaaaatca gtttggaatt tataatgata aactgtctga agtgaatatt   2700
tctcagaatg attatattat ttatgataat aaatataaaa atttttctat ttctttttgg   2760
```

-continued

```
gtgagaattc caaattatga taataaaatt gtgaatgtga ataatgaata tacaattatt   2820

aattgtatga gagataataa ttctggatgg aaagtgtctc tgaatcataa tgaaattatt   2880

tggacactgc aggataatgc tggaattaat cagaaactgg cttttaatta tggaaatgct   2940

aatggaattt ctgattatat taataaatgg atttttgtga caattacaaa tgatagactg   3000

ggagattcta aactgtatat taatggaaat ctgattgatc agaaatctat tctgaatctg   3060

ggaaatattc atgtgtctga taatattctg tttaaaattg tgaattgttc ttatacaaga   3120

tatattggaa ttagatattt taatattttt gataaagaac tggatgaaac agaaattcag   3180

acactgtatt ctaatgaacc aaatacaaat attctgaaag atttttgggg aaattatctg   3240

ctgtatgata aagaatatta tctgctgaat gtgctgaaac caaataattt tattgataga   3300

agaaaagatt ctacactgtc tattaataat attagatcta caattctgct ggctaataga   3360

ctgtattctg gaattaaagt gaaaattcag agagtgaata attcttctac aaatgataat   3420

ctggtgagaa aaaatgatca ggtgtatatt aattttgtgg cttctaaaac acatctgttt   3480

ccactgtatg ctgatacagc tacaacaaat aaagaaaaaa caattaaaat ttcttcttct   3540

ggaaatagat ttaatcaggt ggtggtgatg aattctgtgg gaaataattg tacaatgaat   3600

tttaaaaata ataatggaaa taatattgga ctgctgggat ttaaagctga tacagtggtg   3660

gcttctacat ggtattatac acatatgaga gatcatacaa attctaatgg atgtttttgg   3720

aattttattt ctgaagaaca tggatggcag gaaaaataa                          3759
```

<210> SEQ ID NO 67
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, X. laevis-modified 3

<400> SEQUENCE: 67

```
atgcctaaaa tcaatagttt taactacaat gatcctgtta atgaccgcac aatcctgtac     60

atcaaacccg ggggatgtca agaattttac aaaagtttca atattatgaa gaatatctgg    120

atcattcccg aaagaaatgt gattggtaca acccctcagg actttcaccc acccacctct    180

ctgaaaaatg gcgactcttc atactatgac cctaactacc ttcaaagtga tgaggaaaag    240

gatcgattct tgaaaatcgt tacaaaaatt tttaacagga taaataacaa tctgagcggt    300

gggatccttc tagaggaact tagtaaggcc aacccctacc tgggcaacga caacacacca    360

gataatcagt tccacattgg agatgcttca gcagtggaga tcaagttctc taatggctct    420

caggatatac tgcttccaaa cgttattata atgggagccg agcctgattt atttgagacc    480

aattctagta acattagctt gagaaataac tatatgccaa gcaaccatgg atttggctct    540

atcgccatcg tgacattctc cccagaatac tcattcaggt ttaatgataa ctctatgaat    600

gagttcattc aagaccctgc tctgactctg atgcacgaac taatacactc tctgcacggg    660

ttgtacggag ctaagggaat taccactaaa tatactataa cacaaaaaca gaatccattg    720

attaccaaca tccgcggtac caatatagag gaatttttaa ctttcggcgg taccgatctg    780

aacataatca caagcgctca atccaatgac atctacacaa atcttttggc tgattacaaa    840

aagattgcaa gtaaattatc aaaggtgcag gtctccaatc cactgcttaa cccttataag    900

gatgtctttg aggctaaata tggcctggac aaagacgctt ccggtatcta ttccgtgaat    960

ataaacaagt ttaacgatat atttaaaaag ctatactctt tcaccgagtt tgatctggcc   1020
```

-continued

```
actaagttcc aggtgaaatg caggcaaaca tatattgggc agtataaata tttcaagttg   1080
tctaatcttc tgaatgatag tatttataac atctcagaag ggtataacat caataaccta   1140
aaagtgaatt ttcgcggaca gaatgccaac ctcaacccac gaatcattac tcctatcaca   1200
ggccgggggc ttgttaagaa aattatcagg ttttgtaaga atatcgtcag tgtaaaagga   1260
attagaaaaa gtatatgcat tgaaatcaac aatggtgaac tcttctttgt ggctagtgaa   1320
aatagctaca acgacgataa tataaatact ccaaaagaga tagatgacac tgtgacatca   1380
aataacaatt atgagaacga tttggaccag gttatcctca actttaattc tgaatcagca   1440
ccaggacttt ctgacgagaa gctcaacctg actattcaaa atgatgcata cattccaaag   1500
tatgattcaa acggcacaag cgacatcgaa cagcatgacg taaatgagtt aaatgtgttc   1560
ttttatcttg atgcccagaa ggtgccagaa ggagaaaaca atgtaaattt gacatcttcc   1620
attgatacag ccttgttaga gcagcctaag atttatacat tctttagttc tgaatttatt   1680
aataacgtga acaagccagt gcaggccgct ttgtttgtat cttggatcca acaggtgctt   1740
gttgacttta ctacagaagc aaatcagaaa agcacagtcg ataagatcgc tgatatttcc   1800
attgtagttc catacattgg actggctcta aatatcggca acgaagcaca gaaggggaac   1860
ttcaaagacg ccttggagct attaggggct ggtatactgc tcgaattcga acccgagctg   1920
cttatcccca ctatcttagt gtttaccatt aagagtttcc tgggtagctc agacaataag   1980
aacaaagtta taaaggctat taataacgcc ttgaaagaga gagatgaaaa gtggaaggag   2040
gtatattcct ttattgtgtc taattggatg actaaaataa atacccagtt taataaacgc   2100
aaggagcaaa tgtaccaggc tctgcaaaat caggttaacg caataaaaac aattatagaa   2160
tcaaaatata actcttacac cctggaagag aaaaacgagc ttactaataa atacgacatt   2220
aaacagattg agaatgagct gaaccaaaaa gtgagcattg ctatgaataa cattgatcgg   2280
ttcctgaccg aaagcagtat cagctacctt atgaaactca tcaatgaagt aaaaatcaat   2340
aagctccgtg aatacgatga gaacgtcaaa acctatttac taaattacat aattcaacat   2400
ggatcaattt taggagaatc tcagcaagag ttaaattcca tggtcactga caccctcaat   2460
aactctattc ctttcaaatt aagctcttat actgacgata agatcctgat atcatacttc   2520
aacaagtttt tcaaacgaat taagagctcc tctgtgctaa atatgcgtta taaaaacgac   2580
aagtatgttg acacatctgg atacgatagt aatatcaata taaatggaga tgtttacaaa   2640
tatccaacaa ataagaacca gttcggtatc tataacgaca aattgagcga agtcaacatt   2700
agtcaaaacg attacattat atacgacaac aagtacaaga acttctccat tagcttttgg   2760
gtcagaatac ccaactacga taacaaaatt gtcaacgtta acaatgaata caccatcatt   2820
aactgtatga gagataataa cagcggctgg aaagtgtccc tcaaccacaa cgagatcatt   2880
tggacacttc aggataacgc aggaatcaat cagaagctgg catttaacta tggcaatgct   2940
aacggcattt ctgattatat caacaaatgg atctttgtga ctataacaaa cgatagattg   3000
ggcgacagta agctttatat aaatggaaat ctgatagatc aaaagtctat cctcaacttg   3060
gggaatatcc atgtatccga caatattctc tttaagattg tgaactgctc ttatactaga   3120
tacattggta tccgatactt caacattttt gataaggagc ttgacgaaac agagatacag   3180
accctatact ccaacgaacc aaatacaaat attctgaagg atttctgggg aaactatctg   3240
ttgtacgaca aggagtatta cctactgaac gtcctgaagc ctaataactt tattgaccgt   3300
cggaaggatt caacactttc aatcaataac atcagatcaa ctatactcct tgcaaatcgg   3360
```

-continued

```
ctgtatagcg ggatcaaagt taaaatccag cgtgtgaata actcatccac aaacgacaat   3420

ctcgttagga agaacgatca ggtgtatatt aattttgttg catctaagac tcatctgttc   3480

cccctctatg cagacaccgc aactaccaat aaggaaaaaa caattaaaat aagttccagc   3540

gggaacaggt ttaaccaagt agttgtcatg aactccgtag gtaataactg tacaatgaat   3600

ttcaagaata acaatggaaa taacataggt ctcttgggat tcaaagccga tactgtcgta   3660

gcttccacct ggtattatac acatatgagg gatcacacaa attctaatgg gtgcttttgg   3720

aattttatta gcgaggaaca tggctggcag gagaaataa                         3759
```

<210> SEQ ID NO 68
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, X. tropicalis-modified 1

<400> SEQUENCE: 68

```
atgccaaaga tcaatagttt caattacaac gatcctgtta atgatcgtac aatactgtac     60

attaagcctg gggctgcca ggagttctat aaatcgttta atataatgaa aaacatatgg    120

attatccctg agaggaatgt gattggaact acgccacagg atttccaccc acctacgtct    180

ttgaagaacg gtgatagtag ctattacgat cctaattacc ttcagtctga tgaggaaaaa    240

gatagattcc tgaagatagt cacaaaaatc ttcaacagaa ttaataacaa tctctctggg    300

ggaatattgc tagaagagct tagcaaagca aatccatacc tggggaatga taatacacca    360

gataatcaat tccatatcgg agatgctagc gcagtagaaa ttaagttcag caacggttct    420

caggatattt tgttaccgaa tgtaatcata atgggggcag agccagatct ctttgaaacc    480

aattccagta atatctcact taggaacaat tatatgccca gcaaccatgg attcggatcc    540

atcgccattg tcacattttc acccgaatat agttttagat ttaatgataa ttcgatgaac    600

gagttcatcc aagatccagc actgacttta atgcacgagc tcattcattc attacatggt    660

ctctatggcg ccaaggggat taccacaaag tataccatca cccagaaaca gaaccccttg    720

attaccaaca tccgagggac taatattgag gaattcctga cgtttggtgg aacggactta    780

aacattataa cgtctgccca gagtaacgac atttacacta accttttggc tgactataaa    840

aagattgcgt caaagctctc aaaggtacag gtatcaaacc ctcttctaaa tccatacaaa    900

gatgtttttg aagctaagta tggcttggac aaggacgctt ccggaatcta ctcagtgaat    960

ataaacaaat ttaatgatat cttcaagaaa ctatactcat ttacagaatt cgatctggca   1020

actaagttcc aagtcaaatg tcgtcagaca tatatcggtc agtataaata ctttaaactt   1080

tctaacctct taaacgactc catctacaac atatctgagg gctacaacat aaacaatctt   1140

aaggttaatt tccgcggcca aaatgccaat ttgaacccca gaatcattac accaatcaca   1200

ggccgtggac tggtgaaaaa gattatccga ttctgcaaga acattgtgtc cgttaagggc   1260

ataaggaaaa gcatctgtat tgagataaac aatggcgagc tatttttcgt tgcttctgag   1320

aactcgtaca atgacgataa tatcaacacc cccaaagaga tagacgatac agtaaccagt   1380

aataacaatt acgaaaatga tcttgatcag gtcattttaa attttaacag cgaaagtgca   1440

ccgggcctat ctgacgagaa gctgaattta accatccaaa acgatgccta cattcctaaa   1500

tatgattcca acggaactag tgatattgag cagcacgacg ttaacgaact gaatgtcttt   1560

ttctatcttg atgcccagaa ggtacctgaa ggagagaata acgttaatct aactagctcc   1620
```

-continued

```
attgacactg ccctgttgga acagcccaag atttacacat tcttttcctc tgaattcatt   1680
aacaatgtga ataagcccgt ccaggctgcc ctatttgttt cctggataca gcaagtcctg   1740
gtagacttta ctacggaggc aaaccagaag agcaccgtcg acaagatagc tgatatcagc   1800
atagtggtcc cttatatcgg cctggccctc aatatcggga acgaagccca gaaagggaac   1860
tttaaggacg cgcttgagct gcttggagct gggatcttgc tggaattcga accagagttg   1920
ctcattccga caatcctggt tttactattt aagagtttcc tcggatcatc cgacaataag   1980
aataaggtga taaaagcaat aaacaatgct cttaaggaac gcgatgagaa gtggaaagag   2040
gtgtattctt ttatagtgag caactggatg actaaaataa acacccagtt taacaaacgg   2100
aaagagcaaa tgtatcaggc tctgcaaaac caggtgaatg cgatcaaaac cattatcgaa   2160
agtaaataca attcgtatac attagaagag aaaaacgaac ttacaaataa atacgacatt   2220
aaacagatcg aaaatgaact gaaccagaag gtgagcattg caatgaataa cattgaccgc   2280
ttccttactg aaagctccat atcctatctg atgaagctga tcaatgaggt aaagatcaac   2340
aaactgagag aatacgacga gaacgttaaa acatatctac ttaactacat tatacaacat   2400
ggcagcatcc tgggtgaaag tcaacaggag ttgaacagta tggtcacaga cacacttaat   2460
aactctatcc cctttaaact ctcatcttat accgacgata agatactaat tagttatttc   2520
aataaatttt tcaaaagaat caagtcttcc agcgtgctca acatgaggta taaaaatgat   2580
aaatacgttg atacaagcgg atacgatagc aacattaaca tcaatgggga tgtttacaag   2640
tatccaacaa ataaaaacca gtttggtata tataatgaca agttgagcga agtgaatatt   2700
tcccaaaatg actatataat ctacgataat aaatataaaa acttttctat atcgttttgg   2760
gtgagaatcc caaattacga taataagatc gtgaacgtga ataacgaata tactataatt   2820
aactgtatga gggataataa ctccggatgg aaagtgagtt taaaccacaa tgaaattatc   2880
tggacactcc aggataatgc cggaattaac caaaaattgg catttaatta cggaaacgct   2940
aatggtatct ctgactatat taataaatgg atctttgtga ccattactaa cgaccggctg   3000
ggagactcta aattgtacat taacgggaat ctgattgatc aaaaatccat ccttaacctc   3060
ggcaatattc acgtgtcaga taatatcctg tttaagatcg taaattgcag ttacactcgg   3120
tacattggta ttcgctattt taatattttt gacaaagagt tggacgaaac cgaaatccag   3180
accctgtata gcaacgagcc aaacactaat attctgaagg acttctgggg caactacctg   3240
ctctatgaca aggagtacta tttgctgaac gtcttaaagc ctaataactt catcgatcga   3300
agaaaagatt caacactgtc tataaacaat attcggtcta ccatcctact tgcaaacagg   3360
ctgtattccg ggattaaagt taagattcag cgagtaaata actcatctac caacgataac   3420
ctggtaagga agaatgatca ggtttatatt aattttgtgg cttcaaagac tcacctcttc   3480
cctctgtacg ctgacaccgc cacaactaac aaagagaaga ccattaagat atcatcttcc   3540
gggaaccgtt tcaatcaagt ggttgtgatg aatagcgttg gtaacaattg cactatgaat   3600
tttaagaata acaatggaaa caacattggt ctgcttggat ttaaggcaga cactgtcgtg   3660
gcaagtacgt ggtactacac acatatgcgc gaccacacaa actccaacgg ctgtttctgg   3720
aactttattt ctgaggaaca tggttggcaa gagaagtaa                         3759
```

<210> SEQ ID NO 69
<211> LENGTH: 3759
<212> TYPE: DNA
<213> ORGANISM: Artificial Sequence
<220> FEATURE:

-continued

<221> NAME/KEY: mat_peptide
<222> LOCATION: (1)...(3756)
<223> OTHER INFORMATION: BoNT/E, X. tropicalis-modified 2

<400> SEQUENCE: 69
atgccaaaga ttaattcttt taattacaat gatccagtga atgatagaac aattctgtac 60
attaagccag gaggatgtca ggaattttac aagtctttta atattatgaa gaatatttgg 120
attattccag aaagaaatgt gattggaaca acaccacagg attttcatcc accaacatct 180
ctgaagaatg gagattcttc ttactacgat ccaaattacc tgcagtctga tgaagaaaag 240
gatagatttc tgaagattgt gacaaagatt tttaatagaa ttaataataa tctgtctgga 300
ggaattctgc tggaagaact gtctaaggca aatccatacc tgggaaatga taatacacca 360
gataatcagt ttcatattgg agatgcatct gcagtggaaa ttaagttttc taatggatct 420
caggatattc tgctgccaaa tgtgattatt atgggagcag aaccagatct gtttgaaaca 480
aattcttcta atatttctct gagaaataat tacatgccat ctaatcatgg atttggatct 540
attgcaattg tgacattttc tccagaatac tcttttagat ttaatgataa ttctatgaat 600
gaatttattc aggatccagc actgacactg atgcatgaac tgattcattc tctgcatgga 660
ctgtacggag caaagggaat tacaacaaag tacacaatta cacagaagca gaatccactg 720
attacaaata ttagaggaac aaatattgaa gaatttctga catttggagg aacagatctg 780
aatattatta catctgcaca gtctaatgat atttacacaa atctgctggc agattacaag 840
aagattgcat ctaagctgtc taaggtgcag gtgtctaatc cactgctgaa tccatacaag 900
gatgtgtttg aagcaaagta cggactggat aaggatgcat ctggaattta ctctgtgaat 960
attaataagt ttaatgatat ttttaagaag ctgtactctt ttacagaatt tgatctggca 1020
acaaagtttc aggtgaagtg tagacagaca tacattggac agtacaagta ctttaagctg 1080
tctaatctgc tgaatgattc tatttacaat atttctgaag gatacaatat taataatctg 1140
aaggtgaatt ttagaggaca gaatgcaaat ctgaatccaa gaattattac accaattaca 1200
ggaagaggac tggtgaagaa gattattaga ttttgtaaga atattgtgtc tgtgaaggga 1260
attagaaagt ctatttgtat tgaaattaat aatggagaac tgttttttgt ggcatctgaa 1320
aattcttaca atgatgataa tattaataca ccaaaggaaa ttgatgatac agtgacatct 1380
aataataatt acgaaaatga tctggatcag gtgattctga attttaattc tgaatctgca 1440
ccaggactgt ctgatgaaaa gctgaatctg acaattcaga atgatgcata cattccaaag 1500
tacgattcta atggaacatc tgatattgaa cagcatgatg tgaatgaact gaatgtgttt 1560
ttttacctgg atgcacagaa ggtgccagaa ggagaaaata atgtgaatct gacatcttct 1620
attgatacag cactgctgga acagccaaag atttacacat ttttttcttc tgaatttatt 1680
aataatgtga ataagccagt gcaggcagca ctgtttgtgt cttggattca gcaggtgctg 1740
gtggatttta caacagaagc aaatcagaag tctacagtgg ataagattgc agatatttct 1800
attgtggtgc catacattgg actggcactg aatattggaa atgaagcaca gaagggaaat 1860
tttaaggatg cactggaact gctgggagca ggaattctgc tggaatttga accagaactg 1920
ctgattccaa caattctggt gtttacaatt aagtcttttc tgggatcttc tgataataag 1980
aataaggtga ttaaggcaat taataatgca ctgaaggaaa gagatgaaaa gtggaaggaa 2040
gtgtactctt ttattgtgtc taattggatg acaaagatta atacacagtt taataagaga 2100
aaggaacaga tgtaccaggc actgcagaat caggtgaatg caattaagac aattattgaa 2160
tctaagtaca attcttacac actggaagaa aagaatgaac tgacaaataa gtacgatatt 2220

-continued

```
aagcagattg aaaatgaact gaatcagaag gtgtctattg caatgaataa tattgataga   2280

tttctgacag aatcttctat ttcttacctg atgaagctga ttaatgaagt gaagattaat   2340

aagctgagag aatacgatga aaatgtgaag acatacctgc tgaattacat tattcagcat   2400

ggatctattc tgggagaatc tcagcaggaa ctgaattcta tggtgacaga tacactgaat   2460

aattctattc catttaagct gtcttcttac acagatgata agattctgat ttcttacttt   2520

aataagtttt ttaagagaat taagtcttct tctgtgctga atatgagata caagaatgat   2580

aagtacgtgg atacatctgg atacgattct aatattaata ttaatggaga tgtgtacaag   2640

tacccaacaa ataagaatca gtttggaatt tacaatgata agctgtctga agtgaatatt   2700

tctcagaatg attacattat ttacgataat aagtacaaga atttttctat ttctttttgg   2760

gtgagaattc caaattacga taataagatt gtgaatgtga ataatgaata cacaattatt   2820

aattgtatga gagataataa ttctggatgg aaggtgtctc tgaatcataa tgaaattatt   2880

tggacactgc aggataatgc aggaattaat cagaagctgg catttaatta cggaaatgca   2940

aatggaattt ctgattacat taataagtgg atttttgtga caattacaaa tgatagactg   3000

ggagattcta agctgtacat taatggaaat ctgattgatc agaagtctat tctgaatctg   3060

ggaaatattc atgtgtctga taatattctg tttaagattg tgaattgttc ttacacaaga   3120

tacattggaa ttagatactt taatattttt gataaggaac tggatgaaac agaaattcag   3180

acactgtact ctaatgaacc aaatacaaat attctgaagg atttttgggg aaattacctg   3240

ctgtacgata aggaatacta cctgctgaat gtgctgaagc caaataattt tattgataga   3300

agaaaggatt ctacactgtc tattaataat attagatcta caattctgct ggcaaataga   3360

ctgtactctg gaattaaggt gaagattcag agagtgaata attcttctac aaatgataat   3420

ctggtgagaa agaatgatca ggtgtacatt aattttgtgg catctaagac acatctgttt   3480

ccactgtacg cagatacagc aacaacaaat aaggaaaaga caattaagat ttcttcttct   3540

ggaaatagat ttaatcaggt ggtggtgatg aattctgtgg gaaataattg tacaatgaat   3600

tttaagaata ataatggaaa taatattgga ctgctgggat ttaaggcaga tacagtggtg   3660

gcatctacat ggtactacac acatatgaga gatcatacaa attctaatgg atgtttttgg   3720

aattttattt ctgaagaaca tggatggcag gaaaagtaa                         3759
```

```
<210> SEQ ID NO 70
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, X. tropicalis-modified 3

<400> SEQUENCE: 70
```

```
atgcccaaga ttaatagctt caactacaac gatccagtga atgacagaac aatactgtat     60

attaagcctg gcggatgtca ggagttctat aagtccttca acattatgaa aaacatctgg    120

attatccccg aacggaatgt catagggact acaccccagg acttccaccc tccaactagt    180

ctcaaaaatg gggattcttc ctactatgat ccaaactatc ttcagtccga cgaggaaaag    240

gatcgttttc tgaaaatcgt taccaagata tttaacagaa taaacaataa cctgtctggc    300

ggaattttgc tggaggaatt gagtaaagct aacccatacc ttggaaatga caatacccca    360

gacaaccaat ttcatattgg agatgcttct gccgtcgaaa tcaagttttc taacggttca    420
```

-continued

```
caagatatcc tactgcctaa tgttataatt atgggagctg aacctgattt attcgaaaca    480
aacagttcta acatatccct caggaataac tatatgccca gtaaccacgg cttcgggtca    540
attgccatcg tcacattttc cccagaatat agttttcggt ttaacgacaa ctccatgaat    600
gaattcattc aggacccagc attgacactt atgcacgaac tgattcattc actgcatggc    660
ctttacggag caaagggaat cactaccaaa tatactatta cccagaaaca gaacccactc    720
attacaaata tcagaggcac caacattgaa gagtttctaa ctttcggagg gactgatctc    780
aatattatca caagcgctca gtccaacgac atctacacaa acttactggc tgattacaaa    840
aagatagctt caaaactgag caaagtgcag gtgtccaacc cacttctgaa tccttataaa    900
gatgttttcg aagcaaagta cggcctggat aaagatgctt cagggatata ttctgtaaac    960
attaataagt tcaacgacat cttcaaaaag ctttattctt tcacagaatt tgatttagca   1020
accaagtttc aagtcaagtg ccgtcaaacc tatattgggc agtacaagta ttttaaactt   1080
tctaatttgc ttaatgacag catatataat atttcagaag gttataacat aaacaattta   1140
aaagtgaatt tccgcggaca gaatgccaat ctgaatccta ggattatcac cccaataacc   1200
ggaagggggc tggttaagaa aattatccgt ttttgcaaga acattgtaag cgtcaaaggt   1260
atccggaaat ctatttgcat cgagattaat aacggggagt tgttctttgt tgcatctgag   1320
aatagttata atgacgataa tatcaacact cccaaggaga ttgatgacac tgttacttct   1380
aacaataact atgagaatga tttggaccaa gtcatactta attttaattc cgaatcagcc   1440
cccggcctct ccgatgagaa gctgaattta acaatacaga atgatgcata catcccaaag   1500
tatgacagca atggtacatc tgatatcgaa cagcacgatg ttaacgaact gaatgtattc   1560
ttttacctgg acgcacagaa agtgcccgag ggagagaata acgtgaacct gacaagcagt   1620
attgatacag ccccttttgga gcagccaaaa atatatactt ttttcagctc tgagttcatc   1680
aataacgtaa ataagcctgt gcaagctgca ctatttgtga gctggattca gcaagtctta   1740
gtggatttta caaccgaagc taaccagaaa tctacagttg acaaaatagc agatatttct   1800
attgtagttc catatattgg cttggcattg aacatcggaa acgaagcaca aaagggcaac   1860
ttcaaggatg ccctcgagct gttgggagct ggtattttgc tagaatttga accagagctc   1920
ctgatcccta caatcctggt atttacaatt aaaagctttt taggtagttc tgacaacaag   1980
aacaaagtaa tcaaggctat caataacgct cttaaagaaa gagatgagaa gtggaaagaa   2040
gtgtattcat ttatcgtgag caattggatg actaagatta atacccaatt taataagcga   2100
aaggagcaga tgtaccaggc cctgcagaac caggtaaatg ccataaagac aattatcgag   2160
tctaaataca actcctacac ccttgaggaa aaaaacgagc tcacaaataa gtacgatata   2220
aagcagatag agaatgagct taaccaaaaa gtgtccattg ccatgaacaa tatagatcgc   2280
ttcctgactg agagttccat cagttacttg atgaaactaa tcaatgaagt caaaatcaat   2340
aaactgagag aatatgacga gaacgtcaaa acttacctac tgaattacat aattcagcat   2400
gggtctattt tgggtgagag tcaacaggaa ctgaattcta tggttactga cacactaaac   2460
aatagcattc ctttcaaact ctcaagttat acagatgaca agattctgat ttcttacttt   2520
aataaatttt tcaagcgcat taaatcctct agcgtcctta acatgagata taaaaacgat   2580
aagtacgtgg acacaagtgg ctacgattcc aatattaaca ttaatgggga cgtgtacaaa   2640
taccccacca ataagaatca gtttggaatt tataatgata aacttagcga agtgaatata   2700
tcacaaaatg attacatcat ttacgacaac aaatataaaa atttttccat ctcattctgg   2760
gttaggattc ctaactacga taataagatt gtgaacgtca acaatgagta tacaatcatt   2820
```

-continued aactgcatga gagacaataa ctccgggtgg aaggtttcct tgaaccataa tgagatcata 2880
tggaccctcc aggataatgc tggaataaac caaaagctgg cattcaacta tgggaacgca 2940
aatggtatct cagattacat caacaagtgg atattcgtta ctattactaa tgatcgactg 3000
ggtgattcta agctttacat aaacggcaat ctgatcgacc aaaagtctat tctgaatctg 3060
gggaatattc acgtctcaga caatatactc tttaagatcg taaactgttc ttataccaga 3120
tacatcggca tccgatactt taatattttc gacaaggaac tggacgagac cgaaattcag 3180
actctatata gcaacgagcc taacacaaat atcttaaagg acttttgggg aaactatctc 3240
ctttacgata aagaatacta tctacttaat gtgttgaaac caaacaattt cattgatagg 3300
cggaaggata gcacattgag cataaacaat atccgctcaa caatattact agcaaaccga 3360
ttatattctg gaattaaggt taagatccag agggtgaata actccagtac aaacgataac 3420
ctcgtacgta agaacgacca ggtgtatatc aacttcgtgg cctctaaaac acatctgttt 3480
ccactttacg cagacactgc cacaactaat aaggagaaga caatcaaaat cagtagctca 3540
ggtaacaggt ttaaccaggt agtggttatg aacagcgtgg gaaacaattg taccatgaac 3600
ttcaaaaaca ataacggcaa taatataggc ctcctcggtt ttaaagccga caccgttgtg 3660
gcaagtacat ggtactacac ccacatgcgc gatcacacta attctaatgg ttgtttttgg 3720
aatttcatca gcgaagagca tggatggcaa gaaaaataa 3759

<210> SEQ ID NO 71
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, G. gallus-modified 1

<400> SEQUENCE: 71
atgcccaaga tcaatagttt taactacaac gacccagtga acgaccgcac aatactgtac 60
ataaagccag gtggctgtca ggaattttat aaatcattca acatcatgaa aaatatctgg 120
atcattcccg aaagaaatgt catcggaaca actccacaag acttccatcc acccacttca 180
ctcaaaaacg gagatagctc atactatgat cctaactatc tgcagtcaga cgaggaaaag 240
gaccggtttc tgaaaatcgt aactaagatt ttcaatcgga tcaacaataa cttatcgggc 300
ggaatcctgt tggaggaatt gtcaaaggca aacccgtacc taggaaacga caacacacca 360
gacaaccaat tccacattgg ggacgcctct gcggtcgaga ttaaatttag caacggctcc 420
caggatatcc tgttacctaa tgttatcatt atgggggccg aacccgatct gtttgagaca 480
aacagctcaa acatatctct gagaaacaat tacatgccaa gcaatcacgg ctttgggtct 540
atcgcaatcg tgacatttag ccccgaatat agtttcaggt tcaacgacaa ttctatgaac 600
gaattcattc aagatcccgc ccttacctta atgcatgagc taatccacag tcttcacggc 660
ctgtatgggg ctaagggaat aacgacaaag tacacaatca cccagaaaca gaatccgctg 720
atcacgaaca tccgcggaac aaatattgaa gagttcctta ccttcggagg gacagacctg 780
aacattataa cgagcgcaca gtctaacgac atttacacta acttactggc tgattataaa 840
aagattgctt caaagctgag taaggtccag gtcagtaatc ccctcctgaa cccctataag 900
gacgtgtttg aggccaagta tggcttggat aaagacgcct ccggaatcta cagtgtcaac 960
atcaataaat ttaacgatat ctttaagaaa ctgtactctt tcactgagtt cgatctggca 1020

-continued

```
acaaaattcc aggtcaagtg tagacaaacc tatattggcc agtataaata ctttaaacta   1080
agtaacctcc tgaacgactc tatctacaac attagcgagg gatacaatat taataacctg   1140
aaagtgaatt ttcgaggaca gaatgctaac cttaacccga ggataatcac cccaatcact   1200
ggacggggcc tggttaagaa aatcataagg ttctgcaaga acattgttag tgttaaagga   1260
attcgtaagt cgatctgcat tgaaattaac aatggtgagc tcttctttgt ggcatctgaa   1320
aactcctaca acgatgacaa cattaacaca cctaaagaaa tcgatgacac tgtgactagc   1380
aataacaatt acgagaacga ccttgaccag gtcattctca acttcaactc cgagtctgcc   1440
cccgggctgt ccgatgaaaa gctgaacctg acgatacaaa atgacgctta catcccaaaa   1500
tacgatagta acgggacaag cgacattgag cagcatgatg tgaatgagct caatgttttt   1560
ttctatctgg acgcccagaa ggtgccagag ggggaaaaca atgtcaacct cacttccagc   1620
atagataccg cgctgcttga acagccaaag atctacacct tttctccag tgagttcatc   1680
aataacgtaa ataaacctgt ccaggccgca ttgttcgtgt cgtggattca acaggtcctc   1740
gtagatttca ccacggaggc aaaccagaag tcaacagtgg ataagattgc agacatctct   1800
atcgtagtgc cctacatcgg gctggccttg aacatcggca atgaggcaca gaagggcaac   1860
tttaaggacg ctctggagct tctgggtgcg ggaattctgt tagaatttga accggagctc   1920
ctaatcccta caatcctggt attcacaatc aaatcctttt tgggttccag tgacaataag   1980
aataaagtga taaaggctat taacaatgcc ctgaaagaac gcgatgagaa gtggaaggag   2040
gtttactcat ttatcgtttc taactggatg accaaaataa acacccaatt taataaaaga   2100
aaagagcaga tgtatcaggc gctgcaaaat caggtgaacg ctattaaaac aattatagaa   2160
tccaagtaca attcttacac tctggaagag aaaaatgagc ttactaataa gtacgatata   2220
aagcagatcg agaacgagtt gaatcagaag gttagcattg cgatgaataa cattgacagg   2280
ttcctcacgg agagctcgat tagctatctg atgaagctta ttaacgaggt taaaattaac   2340
aagcttagag aatacgatga aaacgtgaag acatatttgt taaattacat catacaacat   2400
ggttccattc taggggaatc acagcaagaa ctgaattcta tggtcacgga cacgttaaac   2460
aattcgattc ctttcaagct gagctcctac accgatgaca agattcttat ctcctacttt   2520
aataaatttt tcaagcggat caaaagttcc agcgttctga acatgcgcta taaaaatgat   2580
aaatacgttg atacctcagg ctacgattct aatatcaata tcaatggcga cgtgtacaaa   2640
tatccgacta ataaaaacca gtttggtatt tataatgata agctgagcga ggttaatatc   2700
tcacagaacg attacatcat atatgataac aagtacaaga acttttcaat ctccttttgg   2760
gtgcgtatcc ctaattacga caataagata gtgaatgtga acaatgagta taccatcatt   2820
aactgcatgc gagacaacaa ttcaggctgg aaagtgtccc tgaatcacaa cgagattatc   2880
tggacacttc aagataacgc agggatcaat cagaaactgg ctttcaacta tgggaatgcc   2940
aatggtattt ccgattatat aaacaagtgg atattcgtaa ccattacgaa cgatagactc   3000
ggtgactcga aactttacat aaatggtaac ttgatagatc agaagagcat actcaacttg   3060
ggaaacatcc atgtgtccga taacatactg tttaagatcg tgaattgcag ctacactagg   3120
tatattggta ttaggtattt caatatcttc gacaaggagc tggacgaaac cgaaatccag   3180
acgctctata gcaacgaacc caacaccaac atcctcaaag atttctgggg aaattacctc   3240
ttgtatgata aggagtacta tctccttaat gtgctcaagc ctaacaattt catcgaccga   3300
cggaaagaca gtactttgag cattaacaat attagaagca ccatattgct cgctaatagg   3360
ctatactccg gaatcaaagt caagatccag cgcgtgaaca attctagcac caatgacaac   3420
```

-continued ctggtgcgga agaacgatca ggtttacatc aacttcgtag catccaagac tcacctgttc 3480
cctttatacg ctgatactgc tacaaccaac aaagagaaaa ccattaagat cagcagttct 3540
ggcaaccgct tcaaccaagt ggtagtgatg aacagcgtcg ggaataactg caccatgaac 3600
ttcaagaaca ataacggcaa taacatcggg ctgttgggct ttaaagccga caccgtggtg 3660
gcctcgactt ggtattacac acatatgcgt gatcacacaa actctaatgg ctgtttttgg 3720
aactttatta gcgaagagca cggctggcag gaaaagtaa 3759

<210> SEQ ID NO 72
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, G. gallus-modified 2

<400> SEQUENCE: 72
atgcccaaga tcaacagctt caactacaac gatcccgtga acgatagaac catcctgtac 60
atcaagcccg gcggctgcca ggagttctac aagagcttca acatcatgaa gaacatctgg 120
atcatccccg agagaaacgt gatcggcacc accccccagg atttccaccc ccccaccagc 180
ctgaagaacg gcgatagcag ctactacgat cccaactacc tgcagagcga tgaggagaag 240
gatagattcc tgaagatcgt gaccaagatc ttcaacagaa tcaacaacaa cctgagcggc 300
ggcatcctgc tggaggagct gagcaaggcc aacccctacc tgggcaacga taacaccccc 360
gataaccagt tccacatcgg cgatgccagc gccgtggaga tcaagttcag caacggcagc 420
caggatatcc tgctgcccaa cgtgatcatc atgggcgccg agcccgatct gttcgagacc 480
aacagcagca acatcagcct gagaaacaac tacatgccca gcaaccacgg cttcggcagc 540
atcgccatcg tgaccttcag ccccgagtac agcttcagat tcaacgataa cagcatgaac 600
gagttcatcc aggatcccgc cctgaccctg atgcacgagc tgatccacag cctgcacggc 660
ctgtacggcg ccaagggcat caccaccaag tacaccatca cccagaagca gaaccccctg 720
atcaccaaca tcagaggcac caacatcgag gagttcctga ccttcggcgg caccgatctg 780
aacatcatca ccagcgccca gagcaacgat atctacacca acctgctggc cgattacaag 840
aagatcgcca gcaagctgag caaggtgcag gtgagcaacc ccctgctgaa cccctacaag 900
gatgtgttcg aggccaagta cggcctggat aaggatgcca gcggcatcta cagcgtgaac 960
atcaacaagt tcaacgatat cttcaagaag ctgtacagct tcaccgagtt cgatctggcc 1020
accaagttcc aggtgaagtg cagacagacc tacatcggcc agtacaagta cttcaagctg 1080
agcaacctgc tgaacgatag catctacaac atcagcgagg gctacaacat caacaacctg 1140
aaggtgaact tcagaggcca gaacgccaac ctgaacccca gaatcatcac ccccatcacc 1200
ggcagaggcc tggtgaagaa gatcatcaga ttctgcaaga acatcgtgag cgtgaagggc 1260
atcagaaaga gcatctgcat cgagatcaac aacggcgagc tgttcttcgt ggccagcgag 1320
aacagctaca acgatgataa catcaacacc cccaaggaga tcgatgatac cgtgaccagc 1380
aacaacaact acgagaacga tctggatcag gtgatcctga acttcaacag cgagagcgcc 1440
cccggcctga gcgatgagaa gctgaacctg accatccaga acgatgccta catccccaag 1500
tacgatagca acggcaccag cgatatcgag cagcacgatg tgaacgagct gaacgtgttc 1560
ttctacctgg atgcccagaa ggtgcccgag ggcgagaaca acgtgaacct gaccagcagc 1620

-continued

```
atcgataccg ccctgctgga gcagcccaag atctacacct tcttcagcag cgagttcatc   1680

aacaacgtga acaagcccgt gcaggccgcc ctgttcgtga gctggatcca gcaggtgctg   1740

gtggatttca ccaccgaggc caaccagaag agcaccgtgg ataagatcgc cgatatcagc   1800

atcgtggtgc cctacatcgg cctggccctg aacatcggca acgaggccca gaagggcaac   1860

ttcaaggatg ccctggagct gctgggcgcc ggcatcctgc tggagttcga gcccgagctg   1920

ctgatcccca ccatcctggt gttcaccatc aagagcttcc tgggcagcag cgataacaag   1980

aacaaggtga tcaaggccat caacaacgcc ctgaaggaga gagatgagaa gtggaaggag   2040

gtgtacagct tcatcgtgag caactggatg accaagatca acacccagtt caacaagaga   2100

aaggagcaga tgtaccaggc cctgcagaac caggtgaacg ccatcaagac catcatcgag   2160

agcaagtaca acagctacac cctggaggag aagaacgagc tgaccaacaa gtacgatatc   2220

aagcagatcg agaacgagct gaaccagaag gtgagcatcg ccatgaacaa catcgataga   2280

ttcctgaccg agagcagcat cagctacctg atgaagctga tcaacgaggt gaagatcaac   2340

aagctgagag agtacgatga gaacgtgaag acctacctgc tgaactacat catccagcac   2400

ggcagcatcc tgggcgagag ccagcaggag ctgaacagca tggtgaccga taccctgaac   2460

aacagcatcc ccttcaagct gagcagctac accgatgata agatcctgat cagctacttc   2520

aacaagttct tcaagagaat caagagcagc agcgtgctga acatgagata caagaacgat   2580

aagtacgtgg ataccagcgg ctacgatagc aacatcaaca tcaacggcga tgtgtacaag   2640

taccccacca acaagaacca gttcggcatc tacaacgata agctgagcga ggtgaacatc   2700

agccagaacg attacatcat ctacgataac aagtacaaga acttcagcat cagcttctgg   2760

gtgagaatcc ccaactacga taacaagatc gtgaacgtga acaacgagta caccatcatc   2820

aactgcatga gagataacaa cagcggctgg aaggtgagcc tgaaccacaa cgagatcatc   2880

tggaccctgc aggataacgc cggcatcaac cagaagctgg ccttcaacta cggcaacgcc   2940

aacggcatca gcgattacat caacaagtgg atcttcgtga ccatcaccaa cgatagactg   3000

ggcgatagca agctgtacat caacggcaac ctgatcgatc agaagagcat cctgaacctg   3060

ggcaacatcc acgtgagcga taacatcctg ttcaagatcg tgaactgcag ctacaccaga   3120

tacatcggca tcagatactt caacatcttc gataaggagc tggatgagac cgagatccag   3180

accctgtaca gcaacgagcc caacaccaac atcctgaagg atttctgggg caactacctg   3240

ctgtacgata aggagtacta cctgctgaac gtgctgaagc ccaacaactt catcgataga   3300

agaaaggata gcaccctgag catcaacaac atcagaagca ccatcctgct ggccaacaga   3360

ctgtacagcg gcatcaaggt gaagatccag agagtgaaca acagcagcac caacgataac   3420

ctggtgagaa agaacgatca ggtgtacatc aacttcgtgg ccagcaagac ccacctgttc   3480

cccctgtacg ccgataccgc caccaccaac aaggagaaga ccatcaagat cagcagcagc   3540

ggcaacagat tcaaccaggt ggtggtgatg aacagcgtgg gcaacaactg caccatgaac   3600

ttcaagaaca acaacggcaa caacatcggc ctgctgggct tcaaggccga taccgtggtg   3660

gccagcacct ggtactacac ccacatgaga gatcacacca acagcaacgg ctgcttctgg   3720

aacttcatca gcgaggagca cggctggcag gagaagtaa                          3759
```

<210> SEQ ID NO 73
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, G. gallus-modified 3

<400> SEQUENCE: 73

```
atgccgaaga taaattcatt taattataac gacccagtta acgaccggac catactttac     60
atcaagccag gggctgccca agagttttac aaaagcttta acatcatgaa gaatatttgg    120
attataccgg aacgcaatgt gattggaact acgcctcagg atttccaccc tccaacaagt    180
ctgaagaacg gtgatagttc ctactatgat cccaactacc ttcagtctga cgaagagaag    240
gataggttcc ttaagattgt gacgaaaatt ttcaatcgta tcaataacaa tctcagcggc    300
ggtattctgt tggaggaact tagcaaagcc aatccgtacc tcggtaacga taacactccg    360
gataaccagt tccatatcgg tgacgcgtct gcagtcgaga tcaaattttc aaatggctct    420
caggacatac tgctcccaaa cgtgatcatt atgggcgcag agcctgacct gtttgaaacc    480
aattctagca acatatccct ccgcaataac tacatgccct ccaaccacgg atttggaagt    540
atcgctattg tgactttcag ccctgagtat agctttcgat ttaacgacaa cagcatgaat    600
gaatttattc aggaccccgc tctgacactg atgcatgagc tgatacatag ccttcacgga    660
ctgtatgggg ctaaggggat tacgacaaaa tataccatca cgcagaaaca gaaccccctg    720
atcaccaaca tcagaggcac taatatcgag gaattcctta cattcggcgg aaccgacctg    780
aatataatta catccgctca aagcaacgat atctatacaa acctgcttgc agattacaaa    840
aagatcgcat caaaactgag caaagtccag gttagtaacc ccctgctcaa tccatacaaa    900
gacgttttcg aggccaaata tggtctggac aaggatgcca gcgggattta cagtgtgaac    960
attaataaat ttaacgacat tttcaagaaa ctgtacagct tcacggagtt tgacctggct   1020
actaagtttc aagttaagtg cagacagacg tacatcgggc aatacaagta cttcaaactc   1080
agcaacctgc tcaacgacag tatctacaac attagtgagg gatacaatat caataacttg   1140
aaggtgaact tcaggggtca gaatgccaac ctgaacccaa gaattatcac tcctattacg   1200
gggcgcggat tggttaagaa aatcattagg ttctgcaaga acatcgtcag cgtgaaaggc   1260
attaggaagt ctatctgtat cgagataaac aatggagaac tgtttttcgt ggcttccgaa   1320
aatagctaca acgacgataa cattaatacc cctaaagaga tcgacgatac agtgacatca   1380
aataacaatt acgagaacga tctggaccaa gttatcttga actttaactc cgaatctgca   1440
ccaggtctga gcgacgaaaa gctgaatctg acgattcaga atgacgcgta cattcccaag   1500
tatgattcca atggaacctc agacatcgag cagcacgatg tgaacgaact gaacgtgttc   1560
ttttacctgg atgctcagaa agtgcctgaa ggagaaaata acgtgaacct gacttcttcc   1620
atagacaccg ccttgctgga gcagcccaaa atctatacct tcttttctag tgaattcatc   1680
aataacgtga acaagcccgt ccaggcggct ctctttgtgt cctggatcca gcaagtgctg   1740
gtggatttta caaccgaagc taaccagaaa tcaactgtcg ataagattgc tgatatctca   1800
atagtggttc cttacattgg cctggccctg aatataggga acgaggctca gaagggcaac   1860
tttaaagacg cactggagct gttgggagcc gggatccttc tggaatttga gccagagctg   1920
ctcataccca ccattctggt gttcacaata aaatcatttc tgggatccag cgataataaa   1980
aacaaagtca tcaaagcgat taacaatgcc ctcaaggagc gcgacgagaa gtggaaggag   2040
gtgtactcct tcattgtgag caattggatg actaagatca acactcagtt caataagcga   2100
aaagaacaaa tgtatcaggc cctgcaaaac caagtgaacg caatcaagac aataatcgag   2160
tcaaaatata attcctacac actggaggaa aagaacgagt tgaccaacaa gtacgatatt   2220
```

-continued

```
aagcaaattg agaacgagct caaccagaag gtgagtattg ccatgaacaa tattgaccgc   2280

tttttgaccg agtcctctat cagctacctg atgaagctta ttaacgaagt gaagattaac   2340

aaactcaggg aatatgacga gaacgtgaag acttatctct tgaattatat aatccaacac   2400

gggtctatcc ttggagaaag tcagcaagaa cttaatagca tggttaccga cactctgaat   2460

aacagcattc cattcaaact gagctcctat accgacgata aaatcctcat ctcatatttc   2520

aacaaattct ttaaacggat caagagcagt tctgtcctga atatgcgtta caagaatgat   2580

aaatacgtgg acacgagcgg ctacgatagc aacatcaaca tcaatggaga cgtgtacaag   2640

tatccgacga acaaaaatca gttcggcatt tataatgata agctgagcga ggtgaatatc   2700

tctcagaacg attacattat ctacgataat aaatacaaga atttctctat atccttctgg   2760

gtgagaattc ccaattatga taacaaaatc gttaacgtga ataacgagta cactataatc   2820

aactgtatga gggataacaa ttccggttgg aaagtttctc ttaaccacaa cgagatcata   2880

tggacactgc aggataatgc aggcatcaac cagaagttgg cattcaacta cggcaatgca   2940

aatgggatta gcgactacat caacaagtgg attttcgtca ccatcaccaa tgatcgtctt   3000

ggcgactcaa aactgtatat taacggcaac ttgatcgacc agaaaagcat tctgaacctg   3060

ggaaacatcc acgtctcaga caatatcttg ttcaaaatcg tcaactgctc ttatactcgg   3120

tatatcggca tcagatattt taatattttt gataaggaac tcgatgaaac agagattcag   3180

acactgtata gcaacgaacc taacactaat atactcaagg acttttgggg gaactacctt   3240

ctgtatgata aagaatacta tttgctgaat gtgctgaagc caaacaattt catcgatcgg   3300

cgcaaggact caaccctgtc tatcaataac attagatcca ccatcctcct ggctaaccgg   3360

ttgtattcag ggattaaggt caagatacag agagtgaaca atagttccac aaatgataac   3420

ctggtgcgga agaacgacca ggtgtacata aacttcgttg cctccaagac tcatctgttc   3480

cccctctacg cagacaccgc cactacaaat aaggaaaaaa caatcaagat cagctccagc   3540

ggcaataggt tcaaccaggt tgtcgtgatg aacagtgttg gtaataactg cacaatgaac   3600

tttaagaata acaatgggaa caatatagga ctgctgggct ttaaggcgga taccgtcgtg   3660

gcctctacct ggtactacac acatatgcga gatcacacaa atagtaatgg ttgtttctgg   3720

aattttataa gcgaggaaca tgggtggcag gagaaataa                          3759
```

```
<210> SEQ ID NO 74
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, M. musculus-modified 1

<400> SEQUENCE: 74
```

```
atgcccaaaa taaacagctt taactataat gaccctgtga acgatagaac aattctgtac     60

atcaagccag gggatgcca ggagttttat aagagcttca atattatgaa aaatatttgg    120

atcattcctg aacgcaacgt catcgggacc acaccacaag atttccatcc tccgacatct    180

ctgaagaatg gcgactcatc ctattacgac ccaaactacc tgcaatccga cgaagagaaa    240

gacagattcc tgaaaattgt gaccaagatc tttaatcgaa taaacaataa cctgtctggt    300

ggcatcctcc tggaggaact gtcaaaggcc aatccttacc tggggaatga caatacaccc    360

gataaccagt tccacattgg cgatgcctcc gccgtcgaaa taaagtttag caacggaagc    420

caagacattt tgcttccaaa cgttattatc atgggcgcag agccagatct gttcgagact    480
```

-continued

```
aattcaagta acatcagtct gcgaaacaat tacatgcctt ccaaccacgg gtttggcagt    540
atcgctattg tgacgttttc tcccgagtac tcttttcgtt ttaatgacaa cagcatgaac    600
gagttcatcc aggatcccgc cctcactttg atgcacgagc ttattcacag tctacatgga    660
ctttatggcg ctaagggtat tacgaccaaa tacacgatca cacaaaaaca gaacccactc    720
atcactaata tcagagggac aaatatcgaa gagttcttaa cgttcggcgg aacggatctt    780
aacatcatta cctccgcaca gtccaatgac atttatacta acctgctagc agactacaaa    840
aagatcgcaa gcaagctgag caaagttcag gtctctaatc cattgctgaa tccctacaaa    900
gatgtgtttg aggctaagta tggtctagat aaggatgctt ccggtatcta ttctgtaaat    960
attaacaaat ttaacgacat cttcaaaaag ctttacagct tcactgagtt tgacctcgcc   1020
acaaagttcc aggtaaagtg taggcagaca tacataggcc agtacaagta ctttaaactg   1080
tccaacctat tgaatgattc gatatataac atttccgaag gatataacat aaataacctc   1140
aaggtaaatt tccgcggcca gaacgccaat ctgaatcccc gcattatcac acccataact   1200
ggcaggggac tcgtcaaaaa gatcattagg ttctgtaaga atattgtgtc ggtgaaaggc   1260
attcgaaaaa gtatctgcat tgagattaac aatggagaac tcttctttgt tgcctcagaa   1320
aactcctaca atgacgataa catcaataca cccaaagaaa tcgatgacac cgttacttcc   1380
aacaataact atgagaacga cctggaccag gtgatcctta atttcaactc tgagagcgcc   1440
ccaggattgt ccgatgagaa gcttaatctg accattcaga acgacgccta cattcctaag   1500
tatgattcca atggcacaag tgatatcgaa cagcatgacg tgaacgagtt aaacgtgttc   1560
ttttacttag atgcacaaaa agtccctgaa ggagagaaca atgtgaactt aacctctagc   1620
attgacaccg ccctcttgga acagcccaaa atatacactt tcttttcttc agagtttata   1680
aacaatgtaa acaagcccgt gcaggctgcg ctgttcgtgt cttggatcca gcaagtgctg   1740
gtggatttca caaccgaagc caaccagaag tcaaccgtgg acaagatagc cgacatctcc   1800
attgtcgtgc cttatatcgg cctcgctctg aacatcggaa acgaggcgca gaagggtaac   1860
ttcaaggacg ccctcgagct cctgggcgcg ggtatcctgc tcgagttcga gccggaattg   1920
ctaatcccta ccatccttgt gttcaccatc aaaagtttcc tggggtcctc tgacaacaag   1980
aacaaagtta taaaggctat caacaatgct ttgaaagaac gcgatgagaa gtggaaggaa   2040
gtgtacagct ttatcgtgtc caactggatg acaaagatta atacccagtt taacaagcgg   2100
aaagagcaga tgtatcaagc actgcagaat caggtcaacg ctattaagac cataattgag   2160
agcaagtaca atagttatac tctggaggaa aagaacgaac tgaccaacaa atacgatatc   2220
aagcagatcg aaaacgagtt aaaccagaag gtgagcattg caatgaataa catcgatagg   2280
tttctcacag agtcttcaat ctcttacttg atgaagttga ttaatgaggt gaagattaac   2340
aaactgagag agtacgatga gaacgttaaa acttacctac tgaattacat aattcagcac   2400
gggtctatcc tgggcgaatc ccaacaggag cttaacagta tggtgactga tactctgaat   2460
aactcgatac catttaagct gagttcatat actgatgaca agatcttgat ctcatacttt   2520
aacaagttct ttaaacggat caagtcgagc tcagtgctga acatgaggta taagaacgac   2580
aagtacgtcg ataccagcgg ctatgatagc aacatcaaca tcaacgggga cgtgtacaag   2640
taccccacta ataaaaacca gttcggaatc tataacgata agctaagcga ggtaaacatt   2700
agccagaatg actacatcat ttacgacaac aagtacaaaa acttcagtat atcgttctgg   2760
gttcggatac cgaattacga caataagatt gttaacgtaa ataacgagta tacaatcatt   2820
```

```
aactgtatgc gggataataa ctcagggtgg aaagtatcac tgaaccacaa cgagatcata   2880

tggaccttgc aggacaacgc aggaatcaat caaaagcttg cctttaatta cgggaatgcg   2940

aatgggattt ctgattacat caataaatgg atctttgtga ctattacaaa cgataggctc   3000

ggtgactcca aactgtatat aaatggaaat ctgatagacc agaagagcat cctcaatctg   3060

ggtaacatcc atgtctcaga taatatcctc ttcaagattg ttaattgttc ttatacccgg   3120

tatatcggga tccggtattt taatattttc gacaaggaac tggacgaaac agaaatccag   3180

accctctatt ctaacgaacc taacaccaat attttgaagg atttttgggg taattatcta   3240

ctctacgaca aggagtatta cctgctcaat gtgcttaaac caaacaattt cattgaccgt   3300

agaaaggact ccacactctc cattaacaat atcagaagta ctatcttact ggctaacaga   3360

ctgtatagcg ggatcaaggt caaaatccaa agggtcaaca atagcagtac aaatgacaac   3420

cttgtgcgaa agaacgatca agtctacatc aacttcgtcg ccagcaagac ccatcttttc   3480

cctctgtacg ccgacactgc taccacgaat aaggagaaga cgatcaaaat aagttctagt   3540

ggcaaccgct ttaaccaggt cgttgtgatg aattctgtcg ggaataactg cacaatgaat   3600

ttcaaaaaca ataacggaaa caatatcggc ttactcggat tcaaagcaga caccgtggtt   3660

gcttcaacgt ggtattacac ccatatgcgt gaccacacca actccaatgg ctgcttctgg   3720

aacttcatca gcgaagagca cggttggcag gaaaaatga                          3759
```

<210> SEQ ID NO 75
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, M. musculus-modified 2

<400> SEQUENCE: 75

```
atgcccaaaa tcaattcttt taactacaac gaccctgtga acgacagaac tattctttat     60

atcaagccag gagggtgtca ggagttctat aaatcattca atataatgaa gaacatctgg    120

atcattcccg agagaaacgt gataggcacc acacctcaag actttcaccc ccctacatct    180

ctgaagaacg gcgacagttc ctattacgac ccaaactatc tgcaatctga cgaagagaag    240

gaccgattct taaagatcgt gactaagatc ttcaatcgta tcaacaataa cttgtcagga    300

gggatcctgt tggaggaact gagcaaggct aatccttacc tcggtaatga caataccccc    360

gacaaccagt ttcatatcgg cgacgcctca gctgtggaga ttaagttttc aaatggctct    420

caggatatcc tcctgcctaa tgtgatcatt atgggcgccg agcctgatct atttgagaca    480

aattcctcta acattagcct caggaacaat tatatgcctt ccaaccatgg atttgggagc    540

atcgccatag ttactttcag cccagagtat agttttcgtt ttaacgataa ctctatgaac    600

gaatttatcc aggacccCgc actgactctc atgcacgagc tcattcacag cctgcacggg    660

ctctacggcg caaaagggat tacaaccaag tacaccatta cccagaagca aaatcccctg    720

attaccaaca tccgaggaac aaacattgag gaatttctta ctttcggggg tacagacctt    780

aatatcatta cttccgctca gagtaatgac atatacacta atctccttgc cgactataag    840

aaaatcgcat ccaagctgag caaggtgcag gtttctaacc ccctcctgaa tccgtacaag    900

gacgtcttcg aggcgaaata tggcctggac aaggacgcct ccggcattta cagtgtcaat    960

atcaacaagt ttaacgatat ctttaagaaa ctctactcgt ttacggagtt tgacctggcc   1020

accaaattcc aggtgaagtg caggcaaacg tacatcgggc agtacaagta tttcaaactg   1080
```

-continued agtaatctac tcaacgactc catctacaac atttcagagg gctataacat caacaattta 1140
aaggtgaatt tcagaggcca gaacgcaaac ctgaacccca gaatcataac acccattacc 1200
ggacgaggac tagtgaaaaa gatcattaga ttctgtaaaa atattgtttc cgtaaaaggt 1260
atcaggaagt cgatctgcat agagatcaat aacggtgaac tgttctttgt ggcttcagag 1320
aatagctaca acgatgacaa cataaacacg ccaaaagaga ttgacgatac cgtgacatct 1380
aacaataact acgaaaacga cctggaccag gttatcttga acttcaactc tgagtctgct 1440
cctggtctga gcgatgaaaa acttaacctt acaattcaga atgacgccta tatacctaag 1500
tacgattcta atggtacttc tgacatcgag caacacgacg taaacgagct taacgttttc 1560
ttttacctgg atgcacagaa ggtcccggaa ggagagaata acgtgaattt gacgtcaagc 1620
atagataccg cgcttttaga gcagccaaag atctatactt tctttagttc agaatttatc 1680
aacaatgtga acaagcccgt gcaggccgca cttttcgtgt cttggattca gcaagtcctt 1740
gtcgatttta cgaccgaggc caaccagaag agcacagttg ataaaattgc agacatttca 1800
atagtagtcc catacattgg tcttgctctg aacataggga atgaagcgca aaagggcaat 1860
ttcaaggacg ctttggagct cctgggggct ggcattctcc tagagtttga gcccgaatta 1920
ttgatcccaa ctattctcgt gttcaccatc aaatccttct tgggatccag cgataataaa 1980
aacaaggtta tcaaagcaat caacaatgct ctgaaggaaa gagatgaaaa gtggaaagag 2040
gtctactcct tcatcgtatc aaactggatg actaagatca acacccagtt taataagcgt 2100
aaggaacaaa tgtaccaggc cttacagaat caggtgaacg ccattaaaac aataatcgag 2160
tcgaaatata atagttatac actagaggaa aaaaatgaac tgacaaacaa atacgatatc 2220
aaacagatcg aaaatgagct caatcaaaag gttagtattg ccatgaacaa tatcgatagg 2280
ttcctgacgg aatcaagcat ctcctatttg atgaagttga ttaacgaagt aaaaatcaat 2340
aagctgcgcg agtatgacga gaacgtgaaa acatacctcc tgaattatat catacagcac 2400
ggaagtatcc tgggcgagag tcagcaagaa ctgaattcaa tggttaccga taccctaaac 2460
aattcaatcc ctttcaagct gagttcctat accgacgata agatattgat atcttacttc 2520
aacaagtttt tcaagcggat aaaatctagc tctgtcctaa acatgcggta caaaaacgat 2580
aagtatgtgg acacctcggg ctatgatagc aatataaata ttaacgggga cgtgtataaa 2640
tacccaacca acaagaacca gtttggcatt tacaacgata aactgagtga ggttaatatc 2700
tctcagaatg attacattat ctacgataac aagtacaaaa atttcagcat ctccttctgg 2760
gtgaggatcc ctaattacga taacaagatc gtgaacgtca ataacgagta taccatcatt 2820
aattgtatgc gagacaataa ctctggctgg aaagtcagcc ttaatcataa cgagataatc 2880
tggactctgc aggataacgc tggaatcaac cagaagctgg cctttaatta cgggaacgcc 2940
aacggtatta gcgattacat caacaaatgg atcttcgtga ctattacgaa tgataggctc 3000
ggtgattcca agctctacat taatggcaac ctgattgatc agaaaagcat cctgaatctt 3060
ggaaacattc acgtttccga taatatactc tttaaaattg taaattgcag ctatacacgg 3120
tatattggaa tcaggtactt caacatcttc gataaggagc tcgacgaaac agaaatccag 3180
accttatata gtaacgagcc gaatacaaac attttaaagg acttctgggg taactacctc 3240
ctgtacgaca aggaatacta tctgttgaac gtactgaagc caaataactt cattgatcgc 3300
cggaaggaca gtactctgtc cattaacaat atcagatcca ctatcctgct agctaaccgc 3360
ttgtactctg ggataaaagt gaagatccag cgggtgaata actcaagcac aaatgacaac 3420

-continued

```
ctggtgcgga agaatgacca ggtctatatt aatttcgtcg cttccaagac ccatctcttc   3480

ccactgtatg cggacaccgc cacaactaac aaggaaaaaa caatcaaaat cagtagctcc   3540

ggcaaccgct tcaaccaggt ggtcgtgatg aacagcgtcg gaaataactg tactatgaat   3600

tttaagaaca ataacggaaa caatattggg ctgttgggct tcaaggccga caccgtggtc   3660

gcatccacgt ggtactacac ccatatgcgc gatcatacca actcgaatgg gtgcttttgg   3720

aacttcatca gcgaagagca cggatggcaa gaaaagtga                          3759
```

<210> SEQ ID NO 76
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, M. musculus-modified 3

<400> SEQUENCE: 76

```
atgcctaaga ttaattcctt caactataac gaccctgtga atgaccggac tattctttat     60

atcaaacctg gcggatgtca ggagttctac aaaagcttta atattatgaa aaatatctgg    120

atcattccag aacgtaacgt gatcgggacc acacctcagg atttccatcc ccctactagc    180

ctgaagaacg gggacagttc ttattacgat cctaattatc tgcagtccga cgaagagaag    240

gacaggttcc tcaaaattgt gacaaaaatc ttcaatagga tcaacaataa cctgagcggt    300

ggcatcctgc tcgaggaact gagcaaggca aatccctatc tgggcaacga caataccccc    360

gataaccagt ttcacatcgg cgacgcctca gccgtggaga tcaagttttc caacggaagc    420

caggatatcc tgttgcctaa cgtgattatc atgggcgccg aacctgatct gttcgagacc    480

aattccagca atatctcact cagaaataac tacatgccct ctaaccacgg atttggctcc    540

atcgcaattg tgactttcag ccccgaatac agctttcggt ttaacgataa ctcaatgaac    600

gagtttatcc aggatccagc tctgaccctt atgcatgaac tcatccatag cctgcacgga    660

ctgtacggcg ccaaggggat caccactaag tacaccatca cccagaaaca gaacccactg    720

attactaata tcagggggac caatatcgaa gagttcctca ccttcggggg caccgacctc    780

aacatcatta cttctgctca gagcaacgac atttatacca atctcctggc cgactataag    840

aaaatcgcta gtaagctcag taaggtgcag gtgtcaaacc cccttctgaa tccatacaaa    900

gatgtgtttg aggcaaagta cggcctggac aaggacgcct ccggaatcta ctctgtcaac    960

atcaataagt tcaacgacat tttcaagaaa ctgtactcct tcactgagtt cgatttggcc   1020

acaaagttcc aggtgaagtg cagacagact tatatcggac agtataaata ctttaaactc   1080

agtaatcttc tgaacgattc catctataac atctccgaag gctacaacat taacaatctg   1140

aaggtgaatt tccgcgggca gaatgccaac ctgaatccac gcatcattac acctatcaca   1200

gggaggggac ttgtgaagaa aatcattcga ttttgtaaga atatcgtcag cgtgaaggga   1260

attcggaaga gcatttgcat tgagatcaac aatggtgaac tgttctttgt ggctagcgag   1320

aattcttaca acgacgataa cattaacaca ccaaaagaga ttgacgatac agttacaagc   1380

aacaataact atgagaacga tctggaccag gtcatcctta actttaattc agagtctgct   1440

cccggtctga gcgacgaaaa actgaatctg acaatccaga acgatgccta tattcccaag   1500

tacgattcaa acggcacttc tgacatcgag cagcatgatg tgaatgaact caatgtgttc   1560

ttttacctgg acgcccagaa ggtcccagag ggcgagaaca atgtgaacct gaccagcagt   1620

atcgatacag ctctgctcga gcagcccaaa atttatacat tcttttcttc cgaatttatt   1680
```

-continued aacaatgtga acaaaccagt gcaggccgct ctttttgttt cttggatcca gcaggtgctg 1740
gttgacttta ccactgaggc caaccagaaa agtaccgtcg acaaaattgc tgacatttca 1800
attgttgtcc catacatcgg actcgctctg aacatcggaa acgaggcaca gaaaggaaac 1860
ttcaaggacg ccttggaact tttgggggct ggcattctgt tggagttcga acctgagctt 1920
ctgattccta ctatcctcgt gttcaccatt aaatcctttt tgggttccag tgacaataaa 1980
aacaaggtca tcaaggcaat caataacgcc ctgaaggaac gcgatgaaaa gtggaaggaa 2040
gtctatagct ttattgtgtc caattggatg actaaaatca acactcagtt caacaagaga 2100
aaggagcaga tgtatcaggc cctccagaac caggttaacg ccattaagac catcattgaa 2160
tcaaagtata attcctatac cttggaggaa aaaaacgagt tgactaataa gtacgacatc 2220
aagcagatcg agaacgaact gaaccagaag gtgtcaatcg ccatgaataa cattgacaga 2280
ttcttgactg agagctctat ttcatatctg atgaagctga tcaacgaagt gaagatcaac 2340
aagctgcgcg agtatgacga gaatgttaaa acatatttgc tgaactacat cattcagcac 2400
gggagcatcc ttggggagtc tcagcaggag ctgaattcta tggtgaccga taccctgaac 2460
aatagcattc cattcaagct gtcctcttac acagacgata aaatcctgat ctcctacttc 2520
aacaaattct ttaaacggat taagagttct agtgttctga atatgcggta caagaatgac 2580
aagtacgtcg ataccagcgg atacgattct aacatcaata tcaatggaga cgtctacaaa 2640
tatcctacca ataagaatca gttcggcatc tacaatgata agctgagcga agtcaacatc 2700
agccagaacg actacatcat ttacgataat aagtacaaga actttagcat cagcttctgg 2760
gttaggatcc ctaactacga caacaaaatc gtgaatgtta acaatgaata caccatcatt 2820
aactgtatga gggacaacaa ttccggttgg aaggtgtccc tgaaccataa tgagatcatt 2880
tggacactgc aggacaacgc aggtatcaat cagaagctgg cttttaacta tggcaacgca 2940
aacggcatct cagactatat taacaaatgg atcttcgtga ccatcacaaa cgatcgactg 3000
ggggatagca aactgtacat caacgggaac ttgatcgacc agaagagcat cctcaacctc 3060
ggtaacatcc acgtgagtga caacatcctg ttcaagattg tgaattgttc ttacacccgg 3120
tacatcggaa tccgttattt caacatcttt gataaggagc tggacgagac cgaaatccag 3180
acactctact ctaatgagcc caataccaac atcctgaagg atttctgggg gaattacctg 3240
ctttacgata aggaatatta cctgctcaat gtcttgaagc ctaataactt tatcgatcgc 3300
agaaaagatt caaccttgag tatcaacaat attagaagta ccatccttct ggccaacaga 3360
ctctattccg gcatcaaggt taaaatccag agggtcaata acagttccac caatgataac 3420
ctcgtccgaa aaaacgacca ggtgtatatt aattttgtgg ctagtaaaac ccacctgttc 3480 ccccttttatg cagatactgc aaccacaaac aaggagaaaa caatcaagat ctccagttca 3540
ggaaatcgat tcaatcaggt tgtggtcatg aattcagtgg gcaacaattg caccatgaac 3600
ttcaagaaca ataacggcaa caatatcggt ctcctggggt ttaaagccga cacagtggtg 3660
gcctctacct ggtactacac tcatatgcgt gaccacacaa atagcaatgg ttgcttctgg 3720
aactttatct ctgaagagca cggttggcag gagaagtga 3759

<210> SEQ ID NO 77
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)

-continued

<223> OTHER INFORMATION: BoNT/E, R. norvegicus-modified 1

<400> SEQUENCE: 77

```
atgcccaaaa ttaactcctt caactacaac gatcctgtta acgacaggac aattctttat     60
atcaaaccgg gcggttgcca ggaattctac aagtctttca acatcatgaa aaatatctgg    120
atcattcccg agcggaacgt gattggtact acacctcaag attttcatcc cccaacctcc    180
ctcaagaacg gcgatagctc ctactatgat ccaaactatt tgcagagcga cgaggaaaag    240
gatagatttc tcaagattgt cactaagatt ttcaacagga tcaacaataa cctgtcaggt    300
gggatcctcc ttgaggaact cagcaaagcc aacccatact tgggaaacga caacacccct    360
gataaccagt ttcacattgg cgacgcctct gcagtagaga ttaagttctc caacggcagc    420
caggacatcc tactgcccaa tgtcatcatt atgggagccg aacccgacct gttcgaaaca    480
aatagttcta atatctcact gcgtaacaat tatatgccat ccaatcacgg gtttggcagc    540
atcgcaatcg tgacctttag tcccgaatac agctttcgct ttaacgacaa cagtatgaat    600
gaattcattc aggaccctgc tttgacacta atgcatgaac tgattcatag tctgcacggc    660
ctgtatggag cgaaaggtat cactacgaaa tacacaatta ctcagaaaca gaatccttta    720
attaccaaca tcaggggcac caacatcgag gaattcctga catttggcgg aacagatctg    780
aacattatca catcggctca gtccaatgat atctacacta acctcctggc cgactacaag    840
aaaattgcca gcaaattgag caaagtgcaa gtgtctaatc cgttgctgaa cccgtacaag    900
gatgtgttcg aggctaagta tgggttagat aaggacgcgt caggaatcta ttcagtcaac    960
attaataaat ttaacgatat cttcaagaaa ctctactctt ttaccgagtt tgatctggcc   1020
acgaagtttc aagtgaaatg ccggcaaacc tatatcggac aatacaaata ctttaaacta   1080
tcgaacttgc tgaacgatag catctacaat atatctgaag gctacaatat caacaatctg   1140
aaggtcaact tccgtggcca gaacgctaat cttaacccaa ggattataac cccaatcaca   1200
gggcgagggc tggttaagaa aattatccgg ttctgcaaga atatagtgtc agtgaaggga   1260
attcgcaagt ctatctgcat cgaaatcaat aacggtgaac tgtttttcgt cgctagcgaa   1320
aactcataca acgatgacaa cataaacact ccgaaggaaa ttgacgatac cgtgaccagc   1380
aacaataact atgagaacga cctcgatcaa gtgatcctga acttcaattc agagtccgcc   1440
cctggactgt ctgacgaaaa gttgaacctg acaattcaga atgacgcgta tatccctaaa   1500
tatgactcga acggcactag cgacatcgag cagcatgacg tgaacgagct caacgtcttt   1560
ttctatcttg acgctcagaa ggtacctgag ggggagaata acgtcaatct tacttcctca   1620
attgacacag ccctgctcga gcagccaaag atttatacct tttcagcag tgagttcata   1680
aacaatgtaa ataagcccgt gcaggcagct ctgtttgttt cttggatcca gcaagtactc   1740
gtggatttca ccacggaggc caaccagaag tctacggttg ataaaatcgc ggacatatcc   1800
attgtggtcc cctacatcgg tctggccttg aacatcggca atgaggcaca gaagggaaac   1860
ttcaaggacg cacttgagtt gctgggggca ggtattctgt tggaattcga gcccgagctc   1920
ctgatcccaa ctattctcgt gttcactatc aagtctttcc tcgggtcaag tgataataag   1980
aacaaggtga tcaaagccat caataacgca ctcaaggaga gagacgaaaa gtggaaggag   2040
gtgtactcct ttatagttag taactggatg accaagatca atacacaatt taataaaaga   2100
aaagagcaga tgtatcaggc actgcagaat caggttaacg ccatcaagac catcattgag   2160
agcaagtaca attcttacac cctcgaggaa aagaacgaac taactaataa gtatgacatt   2220
aagcagattg agaacgagct caaccagaag gtgtccatcg ctatgaataa catcgacaga   2280
```

-continued tttttaactg agagcagtat tagctacctc atgaagctga ttaatgaagt taagatcaac 2340
aagcttcggg agtatgatga gaatgttaag acctacctgc ttaactacat cattcaacac 2400
ggcagtattc taggagaaag ccagcaagaa cttaattcga tggtcacaga tacactcaac 2460
aatagcattc ctttcaaact atctagctac acggatgaca agatcctgat ctcttacttt 2520
aataaattct ttaagaggat caagagttct agcgtgctga acatgcgcta caaaaacgac 2580
aagtacgtcg acacctccgg gtatgactca aatataaaca tcaatggcga cgtatacaag 2640
tatccaacca ataaaaatca gttcggtatc tacaatgaca agctgagtga ggtgaacatt 2700
tctcagaacg actacattat ctatgacaac aaatataaaa atttctctat ctcattttgg 2760
gtgcgaatcc ccaactacga caataagatc gtcaacgtca acaatgagta tacgataatc 2820
aactgtatgc gggataacaa tagcggctgg aaagtctccc tgaatcacaa cgagatcatt 2880
tggaccctgc aggacaacgc tggtatcaac cagaaactgg ccttcaacta cggcaacgct 2940
aacggtatct ccgactacat taacaaatgg atcttcgtta ccataaccaa tgacagactt 3000
ggggactcca agctatacat caatggaaat ttgatcgacc aaaagtccat cctgaacctg 3060
gggaacattc acgtctccga caacatactg tttaagattg tgaattgtag ttacacacga 3120
tacataggaa tcagatactt caatatattt gataaggaat tagacgaaac cgaaattcag 3180
actctttact ctaacgagcc caataccaat atcctgaaag atttctgggg caactacctt 3240
ctgtatgaca aagagtatta cctgctcaac gtgttaaagc ctaacaattt catcgatcgc 3300
cgtaaggatt ccaccctcag cataaataac atccgctcca caatcttgct cgccaaccga 3360
ctctattccg ggatcaaagt gaagatacag cgcgtgaaca attccagcac taacgataac 3420
ctggtccgca agaacgatca ggtctacatc aatttcgtgg cctccaaaac ccatctgttc 3480
cctctgtatg ccgataccgc taccacgaac aaggagaaga caatcaaaat ctcttcgagc 3540
ggaaaccggt tcaaccaggt ggttgtgatg aattccgtgg gcaataactg tactatgaat 3600
ttcaaaaaca ataacgggaa taacatcggc ctgttgggct ttaaggctga cacggtcgta 3660
gcctccactt ggtattacac tcacatgagg gatcacacca acagtaacgg atgcttctgg 3720
aacttcatct cagaggagca cggttggcag gagaagtga 3759

<210> SEQ ID NO 78
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, R. norvegicus-modified 2

<400> SEQUENCE: 78
atgcctaaga tcaacagctt caactacaac gaccctgtga acgaccgcac catcctgtac 60
atcaagcctg gcggctgcca ggagttctac aagagcttca acatcatgaa gaacatctgg 120
atcatccctg agcgcaacgt gatcggcacc acccctcagg acttccaccc tcctaccagc 180
ctgaagaacg gcgacagcag ctactacgac cctaactacc tgcagagcga cgaggagaag 240
gaccgcttcc tgaagatcgt gaccaagatc ttcaaccgca tcaacaacaa cctgagcggc 300
ggcatcctgc tggaggagct gagcaaggcc aacccttacc tgggcaacga caacacccct 360
gacaaccagt tccacatcgg cgacgccagc gccgtggaga tcaagttcag caacggcagc 420
caggacatcc tgctgcctaa cgtgatcatc atgggcgccg agcctgacct gttcgagacc 480

-continued

```
aacagcagca acatcagcct gcgcaacaac tacatgccta gcaaccacgg cttcggcagc    540
atcgccatcg tgaccttcag ccctgagtac agcttccgct tcaacgacaa cagcatgaac    600
gagttcatcc aggaccctgc cctgaccctg atgcacgagc tgatccacag cctgcacggc    660
ctgtacggcg ccaagggcat caccaccaag tacaccatca cccagaagca gaaccctctg    720
atcaccaaca tccgcggcac caacatcgag gagttcctga ccttcggcgg caccgacctg    780
aacatcatca ccagcgccca gagcaacgac atctacacca acctgctggc cgactacaag    840
aagatcgcca gcaagctgag caaggtgcag gtgagcaacc ctctgctgaa cccttacaag    900
gacgtgttcg aggccaagta cggcctggac aaggacgcca gcggcatcta cagcgtgaac    960
atcaacaagt tcaacgacat cttcaagaag ctgtacagct tcaccgagtt cgacctggcc   1020
accaagttcc aggtgaagtg ccgccagacc tacatcggcc agtacaagta cttcaagctg   1080
agcaacctgc tgaacgacag catctacaac atcagcgagg gctacaacat caacaacctg   1140
aaggtgaact tccgcggcca gaacgccaac ctgaaccctc gcatcatcac ccctatcacc   1200
ggccgcggcc tggtgaagaa gatcatccgc ttctgcaaga acatcgtgag cgtgaagggc   1260
atccgcaaga gcatctgcat cgagatcaac aacggcgagc tgttcttcgt ggccagcgag   1320
aacagctaca acgacgacaa catcaacacc cctaaggaga tcgacgacac cgtgaccagc   1380
aacaacaact acgagaacga cctggaccag gtgatcctga acttcaacag cgagagcgcc   1440
cctggcctga gcgacgagaa gctgaacctg accatccaga acgacgccta catccctaag   1500
tacgacagca acggcaccag cgacatcgag cagcacgacg tgaacgagct gaacgtgttc   1560
ttctacctgg acgcccagaa ggtgcctgag ggcgagaaca acgtgaacct gaccagcagc   1620
atcgacaccg ccctgctgga gcagcctaag atctacacct tcttcagcag cgagttcatc   1680
aacaacgtga acaagcctgt gcaggccgcc ctgttcgtga gctggatcca gcaggtgctg   1740
gtggacttca ccaccgaggc caaccagaag agcaccgtgg acaagatcgc cgacatcagc   1800
atcgtggtgc cttacatcgg cctggccctg aacatcggca acgaggccca gaagggcaac   1860
ttcaaggacg ccctggagct gctgggcgcc ggcatcctgc tggagttcga gcctgagctg   1920
ctgatcccta ccatcctggt gttcaccatc aagagcttcc tgggcagcag cgacaacaag   1980
aacaaggtga tcaaggccat caacaacgcc ctgaaggagc gcgacgagaa gtggaaggag   2040
gtgtacagct tcatcgtgag caactggatg accaagatca acacccagtt caacaagcgc   2100
aaggagcaga tgtaccaggc cctgcagaac caggtgaacg ccatcaagac catcatcgag   2160
agcaagtaca acagctacac cctggaggag aagaacgagc tgaccaacaa gtacgacatc   2220
aagcagatcg agaacgagct gaaccagaag gtgagcatcg ccatgaacaa catcgaccgc   2280
ttcctgaccg agagcagcat cagctacctg atgaagctga tcaacgaggt gaagatcaac   2340
aagctgcgcg agtacgacga gaacgtgaag acctacctgc tgaactacat catccagcac   2400
ggcagcatcc tgggcgagag ccagcaggag ctgaacagca tggtgaccga caccctgaac   2460
aacagcatcc ctttcaagct gagcagctac accgacgaca agatcctgat cagctacttc   2520
aacaagttct tcaagcgcat caagagcagc agcgtgctga acatgcgcta caagaacgac   2580
aagtacgtgg acaccagcgg ctacgacagc aacatcaaca tcaacggcga cgtgtacaag   2640
taccctacca acaagaacca gttcggcatc tacaacgaca agctgagcga ggtgaacatc   2700
agccagaacg actacatcat ctacgacaac aagtacaaga acttcagcat cagcttctgg   2760
gtgcgcatcc ctaactacga caacaagatc gtgaacgtga acaacgagta caccatcatc   2820
aactgcatgc gcgacaacaa cagcggctgg aaggtgagcc tgaaccacaa cgagatcatc   2880
```

-continued tggaccctgc aggacaacgc cggcatcaac cagaagctgg ccttcaacta cggcaacgcc 2940
aacggcatca gcgactacat caacaagtgg atcttcgtga ccatcaccaa cgaccgcctg 3000
ggcgacagca agctgtacat caacggcaac ctgatcgacc agaagagcat cctgaacctg 3060
ggcaacatcc acgtgagcga caacatcctg ttcaagatcg tgaactgcag ctacacccgc 3120
tacatcggca tccgctactt caacatcttc gacaaggagc tggacgagac cgagatccag 3180
accctgtaca gcaacgagcc taacaccaac atcctgaagg acttctgggg caactacctg 3240
ctgtacgaca aggagtacta cctgctgaac gtgctgaagc ctaacaactt catcgaccgc 3300
cgcaaggaca gcaccctgag catcaacaac atccgcagca ccatcctgct ggccaaccgc 3360
ctgtacagcg gcatcaaggt gaagatccag cgcgtgaaca acagcagcac caacgacaac 3420
ctggtgcgca agaacgacca ggtgtacatc aacttcgtgg ccagcaagac ccacctgttc 3480
cctctgtacg ccgacaccgc caccaccaac aaggagaaga ccatcaagat cagcagcagc 3540
ggcaaccgct tcaaccaggt ggtggtgatg aacagcgtgg gcaacaactg caccatgaac 3600
ttcaagaaca acaacggcaa caacatcggc ctgctgggct tcaaggccga caccgtggtg 3660
gccagcacct ggtactacac ccacatgcgc gaccacacca acagcaacgg ctgcttctgg 3720
aacttcatca gcgaggagca cggctggcag gagaagtga 3759

<210> SEQ ID NO 79
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, R. norvegicus-modified 3

<400> SEQUENCE: 79
atgcccaaaa tcaattcttt caactataac gacccagtaa acgatcgcac catcttgtat 60
atcaagcctg gggctgtca ggaattttat aagtctttca atattatgaa aaacatatgg 120
atcattccgg agcgaaacgt gatcggaacg acaccacagg actttcatcc cccaaccagc 180
ctgaaaaatg gagatagttc ttattacgac ccgaactacc tccagtcgga tgaagagaag 240
gacagattct tgaagatcgt cacaaagatt ttcaaccgta tcaataacaa tttgagcggt 300
ggaatcttat tggaagagct gagtaaggct aacccctacc tggggaacga taatacccct 360
gataaccaat tccacatcgg agacgccagt gccgtagaga tcaaattcag caacgggtcc 420
caagacattt tgctgcctaa cgttatcatt atgggggccg agcctgatct tttcgagaca 480
aatagctcta acatcagcct gcgaaacaat tacatgccct ccaatcacgg attcggaagc 540
attgctattg tgacattttc acctgaatac agcttccgct ttaatgacaa cagtatgaac 600
gagtttattc aggatcctgc tctgacttta atgcatgagt tgatccactc actacacgga 660
ctttatggcg ctaaggggat cactaccaag tatactatca cccagaagca gaacccgctc 720
attaccaata tccggggcac taatatcgag gaattcctga ctttcggagg tacggacctt 780
aacattataa cctcggcaca gtctaacgac atctacacaa acctactggc agattacaag 840
aaaatcgcta gtaaactcag caaggtgcaa gtctccaacc cccttctcaa cccctacaaa 900
gacgtgtttg aggccaagta tggtctggat aaggatgcga gtggcatcta ttcagtgaac 960
atcaacaagt tcaatgacat ttttaaaaag ctttatagct tcactgaatt cgatctggct 1020
accaaatttc aggttaagtg taggcaaact tacattggcc agtataagta ctttaaactg 1080

-continued

```
tctaacctgt taaacgacag catctacaac ataagtgagg gctacaacat caataacctg   1140
aaggtgaatt ttcgcggtca aaatgctaat ttgaatccca gaataattac accaattact   1200
ggcagggggc ttgtgaagaa aattatccgc ttctgcaaga acattgtgtc tgtcaagggc   1260
atccggaagt cgatctgtat cgaaatcaat aacggagagc tcttctttgt tgcatccgag   1320
aacagctaca acgacgataa cataaacacc ccaaaagaga tagacgatac cgtgacctca   1380
aacaataact acgagaacga tctggatcaa gtgattctaa attttaattc tgagtctgca   1440
cccggcttgt ccgacgagaa gcttaatctc accattcaga acgacgccta tatcccaaaa   1500
tacgatagca atggaacaag tgatatcgag cagcatgacg tgaatgaact aaacgtcttc   1560
ttttacctgg acgcgcagaa ggtgccagag ggtgaaaaca atgtgaacct cacttcctca   1620
attgacacgg ccctgcttga acagcccaaa atctatacct tcttttcttc cgagttcatt   1680
aacaatgtca ataagcctgt tcaagctgcc ctgtttgtct catggattca gcaagtactc   1740
gtcgacttta cgaccgaggc aaaccagaag tctacggttg acaagatcgc cgacattagc   1800
atcgtggttc cttatatagg tctggcattg aatattggga atgaggccca gaagggcaac   1860
ttcaaggacg ccctggagct tctcggcgcg ggcatcctgc tcgaatttga accagagctg   1920
ctcataccta ccattcttgt cttcactatt aagagcttcc tgggctcaag tgacaacaag   1980
aacaaggtta tcaaggctat taacaatgca ctgaaggaaa gagatgaaaa gtggaaggaa   2040
gtctattcct ttatcgtgtc gaactggatg accaagatta acacacagtt caataaaaga   2100
aaggagcaga tgtaccaggc cctgcagaat caggtcaacg ccataaaaac tatcatagag   2160
tctaaataca attcatatac ccttgaggaa aaaaatgaac tcacaaacaa atacgatatc   2220
aaacaaatag aaaatgaact gaatcagaaa gtgagcatcg ccatgaacaa tatcgatcgg   2280
tttctcaccg agtccagcat ctcctatctc atgaaactga tcaacgaggt gaagattaac   2340
aaactgcggg aatacgacga gaatgtcaag acatacctgt tgaactacat cattcagcac   2400
ggaagcatcc taggtgagtc tcagcaagag ctgaacagca tggtgactga cacactgaac   2460
aattctatcc cgttcaaatt gagttcttac accgacgata agattctgat ctcttacttc   2520
aacaagtttt tcaagcggat caagtcatcg agcgtcctga acatgaggta caaaaacgac   2580
aaatacgtcg ataccagcgg gtacgattca aacatcaaca tcaacgggga tgtctacaaa   2640
tatcctacta ataagaacca gtttggaatt tacaacgata agctttccga agtgaatatc   2700
tcccaaaacg actacatcat ttacgacaac aagtacaaaa atttttccat ctccttctgg   2760
gtgaggatcc ctaactacga taacaagatt gtcaatgtaa acaatgaata taccatcatt   2820
aactgcatgc gggacaacaa tagtggctgg aaggtgtccc tgaaccataa cgagattatc   2880
tggaccttgc aggacaacgc cggtatcaac cagaagctgg ctttcaacta tggtaatgca   2940
aatggcatct cagactacat caacaaatgg atctttgtga ccattacaaa tgaccgcctg   3000
ggcgactcca aattatatat caatgggaac ctcatcgacc agaagtccat cctgaaccta   3060
ggaaatatcc atgtttccga caacatcctc ttcaagatag tgaactgctc ttacactcgc   3120
tatatcggaa tccgctattt taacatcttc gacaaagagc tggatgagac cgagatccag   3180
acactgtaca gcaatgagcc aaacacaaac atcctgaagg atttttgggg taattacctc   3240
ctgtatgata aagaatacta tctgttgaat gtactgaagc ccaataactt cattgaccga   3300
aggaaggact ccacgctgag cattaacaat attagaagta cgattctcct agccaaccgt   3360
ttatattccg gcataaaggt caagatccag cgtgttaaca attcctctac caacgataac   3420
ctcgtaagga agaatgacca ggtgtacata aacttcgttg cttccaaaac tcacctcttc   3480
```

-continued

```
cccctgtatg ctgatactgc gaccacgaac aaagagaaga ctatcaagat aagtagctcc   3540

ggcaacagat tcaaccaggt ggtcgtgatg aattctgtgg gtaataactg cacaatgaat   3600

tttaaaaata acaatgggaa caatatcggg ctcctcgggt tcaaggccga caccgtggtg   3660

gccagcacat ggtactacac acacatgcga gaccacacca attccaacgg ctgcttctgg   3720

aacttcattt cagaggaaca cggctggcag gaaaaatga                          3759


<210> SEQ ID NO 80
<211> LENGTH: 3759
<212> TYPE: DNA
<213> ORGANISM: Artificial Sequence
<220> FEATURE:
<221> NAME/KEY: CDS
<222> LOCATION: (1)...(3759)
<223> OTHER INFORMATION: BoNT/E, C. griseus-modified 1

<400> SEQUENCE: 80

atg cca aaa att aac agt ttt aat tac aat gat ccc gtg aac gac cgc       48
Met Pro Lys Ile Asn Ser Phe Asn Tyr Asn Asp Pro Val Asn Asp Arg
1               5                   10                  15

aca atc ctt tac att aaa ccc ggt gga tgt cag gag ttc tac aaa agc       96
Thr Ile Leu Tyr Ile Lys Pro Gly Gly Cys Gln Glu Phe Tyr Lys Ser
            20                  25                  30

ttt aac atc atg aag aac atc tgg ata atc cca gaa cgt aac gtg att      144
Phe Asn Ile Met Lys Asn Ile Trp Ile Ile Pro Glu Arg Asn Val Ile
        35                  40                  45

gga aca acc cct cag gac ttc cat cca ccg aca agt tta aaa aat ggc      192
Gly Thr Thr Pro Gln Asp Phe His Pro Pro Thr Ser Leu Lys Asn Gly
    50                  55                  60

gac agc tct tat tac gac ccc aac tac ctt cag agt gat gaa gag aag      240
Asp Ser Ser Tyr Tyr Asp Pro Asn Tyr Leu Gln Ser Asp Glu Glu Lys
65                  70                  75                  80

gac cga ttc ctg aag atc gtc aca aaa atc ttt aac agg atc aac aat      288
Asp Arg Phe Leu Lys Ile Val Thr Lys Ile Phe Asn Arg Ile Asn Asn
                85                  90                  95

aac ctg agt ggc gga atc ctg ttg gag gaa cta agt aaa gca aat cct      336
Asn Leu Ser Gly Gly Ile Leu Leu Glu Glu Leu Ser Lys Ala Asn Pro
            100                 105                 110

tac ctc ggg aac gac aac aca ccc gac aac cag ttc cac atc ggc gat      384
Tyr Leu Gly Asn Asp Asn Thr Pro Asp Asn Gln Phe His Ile Gly Asp
        115                 120                 125

gcc agc gct gtc gaa atc aaa ttt agc aac ggg agc cag gac atc ctg      432
Ala Ser Ala Val Glu Ile Lys Phe Ser Asn Gly Ser Gln Asp Ile Leu
    130                 135                 140

ttg cct aac gtc atc att atg ggt gct gag cca gac ctt ttc gaa acc      480
Leu Pro Asn Val Ile Ile Met Gly Ala Glu Pro Asp Leu Phe Glu Thr
145                 150                 155                 160

aac tcc agc aac atc agc ctc agg aac aat tac atg ccg agc aat cac      528
Asn Ser Ser Asn Ile Ser Leu Arg Asn Asn Tyr Met Pro Ser Asn His
                165                 170                 175

ggc ttt ggc tct att gcc atc gtg acg ttt tcg ccc gag tac agc ttc      576
Gly Phe Gly Ser Ile Ala Ile Val Thr Phe Ser Pro Glu Tyr Ser Phe
            180                 185                 190

aga ttt aat gac aac agc atg aac gaa ttc att caa gat cca gct ctc      624
Arg Phe Asn Asp Asn Ser Met Asn Glu Phe Ile Gln Asp Pro Ala Leu
        195                 200                 205

aca ctc atg cat gaa ctc att cac agc ctg cac ggg ctc tac ggc gct      672
Thr Leu Met His Glu Leu Ile His Ser Leu His Gly Leu Tyr Gly Ala
    210                 215                 220
```

-continued

```
aag ggc ata act acc aag tat act atc act cag aag caa aac cca ctg      720
Lys Gly Ile Thr Thr Lys Tyr Thr Ile Thr Gln Lys Gln Asn Pro Leu
225                 230                 235                 240

atc aca aat atc cgg ggc acc aac atc gag gaa ttc ctc aca ttc gga      768
Ile Thr Asn Ile Arg Gly Thr Asn Ile Glu Glu Phe Leu Thr Phe Gly
                245                 250                 255

ggg act gac tta aat atc att acg agt gct caa tcc aac gat atc tac      816
Gly Thr Asp Leu Asn Ile Ile Thr Ser Ala Gln Ser Asn Asp Ile Tyr
            260                 265                 270

act aat ctt ctg gcc gat tat aag aaa att gca tcg aag ctc agt aag      864
Thr Asn Leu Leu Ala Asp Tyr Lys Lys Ile Ala Ser Lys Leu Ser Lys
        275                 280                 285

gtg caa gtg tca aat cct ctc ctg aat cca tat aaa gac gtg ttc gag      912
Val Gln Val Ser Asn Pro Leu Leu Asn Pro Tyr Lys Asp Val Phe Glu
    290                 295                 300

gcg aaa tat ggc ctg gat aag gat gcc agt ggt atc tac tcg gtg aat      960
Ala Lys Tyr Gly Leu Asp Lys Asp Ala Ser Gly Ile Tyr Ser Val Asn
305                 310                 315                 320

atc aac aag ttt aat gat atc ttt aag aaa cta tac tct ttc acc gag     1008
Ile Asn Lys Phe Asn Asp Ile Phe Lys Lys Leu Tyr Ser Phe Thr Glu
                325                 330                 335

ttt gat ctt gca act aag ttt cag gtc aag tgt cgg cag act tac atc     1056
Phe Asp Leu Ala Thr Lys Phe Gln Val Lys Cys Arg Gln Thr Tyr Ile
            340                 345                 350

ggg cag tat aag tac ttt aag ctg tca aat ctg ttg aac gac tcc atc     1104
Gly Gln Tyr Lys Tyr Phe Lys Leu Ser Asn Leu Leu Asn Asp Ser Ile
        355                 360                 365

tat aat atc tca gaa ggc tac aac ata aac aat ctg aaa gta aac ttc     1152
Tyr Asn Ile Ser Glu Gly Tyr Asn Ile Asn Asn Leu Lys Val Asn Phe
    370                 375                 380

cgc ggc cag aac gcc aac cta aac ccc cgg atc att acg ccg ata acc     1200
Arg Gly Gln Asn Ala Asn Leu Asn Pro Arg Ile Ile Thr Pro Ile Thr
385                 390                 395                 400

ggc aga ggg tta gtg aaa aag atc att cga ttc tgc aaa aat atc gtg     1248
Gly Arg Gly Leu Val Lys Lys Ile Ile Arg Phe Cys Lys Asn Ile Val
                405                 410                 415

tct gtt aaa gga atc agg aag tcc atc tgt atc gag att aac aat ggc     1296
Ser Val Lys Gly Ile Arg Lys Ser Ile Cys Ile Glu Ile Asn Asn Gly
            420                 425                 430

gaa tta ttc ttt gta gcc agc gag aat tct tac aac gat gac aac atc     1344
Glu Leu Phe Phe Val Ala Ser Glu Asn Ser Tyr Asn Asp Asp Asn Ile
        435                 440                 445

aat aca cct aag gag att gac gat aca gtt acc agc aac aat aac tat     1392
Asn Thr Pro Lys Glu Ile Asp Asp Thr Val Thr Ser Asn Asn Asn Tyr
    450                 455                 460

gag aat gat ttg gac cag gtg att cta aat ttt aac agt gaa tcc gcc     1440
Glu Asn Asp Leu Asp Gln Val Ile Leu Asn Phe Asn Ser Glu Ser Ala
465                 470                 475                 480

ccc ggt cta tct gat gag aag ttg aat ctg acc atc cag aat gat gct     1488
Pro Gly Leu Ser Asp Glu Lys Leu Asn Leu Thr Ile Gln Asn Asp Ala
                485                 490                 495

tat atc cca aag tac gat tca aac ggg act tcg gat att gag cag cat     1536
Tyr Ile Pro Lys Tyr Asp Ser Asn Gly Thr Ser Asp Ile Glu Gln His
            500                 505                 510

gac gtc aat gaa ctg aat gtg ttc ttt tat ctg gac gct cag aaa gtc     1584
Asp Val Asn Glu Leu Asn Val Phe Phe Tyr Leu Asp Ala Gln Lys Val
        515                 520                 525

ccc gag ggt gag aac aat gtt aat ctg aca tcc tct ata gac acc gca     1632
Pro Glu Gly Glu Asn Asn Val Asn Leu Thr Ser Ser Ile Asp Thr Ala
    530                 535                 540
```

-continued

```
ttg ctc gaa cag cct aaa atc tac acc ttt ttc tcc agt gaa ttt atc      1680
Leu Leu Glu Gln Pro Lys Ile Tyr Thr Phe Phe Ser Ser Glu Phe Ile
545                 550                 555                 560

aac aat gtg aac aaa cct gta cag gcc gca ctg ttc gtt tct tgg att      1728
Asn Asn Val Asn Lys Pro Val Gln Ala Ala Leu Phe Val Ser Trp Ile
                565                 570                 575

cag caa gtt ttg gtt gac ttt acc act gag gcc aat caa aag agt act      1776
Gln Gln Val Leu Val Asp Phe Thr Thr Glu Ala Asn Gln Lys Ser Thr
            580                 585                 590

gtg gac aaa atc gcc gac atc tcg att gtg gtc cca tac ata gga ttg      1824
Val Asp Lys Ile Ala Asp Ile Ser Ile Val Val Pro Tyr Ile Gly Leu
        595                 600                 605

gca ctg aac atc gga aac gag gct cag aag ggt aat ttc aag gac gcc      1872
Ala Leu Asn Ile Gly Asn Glu Ala Gln Lys Gly Asn Phe Lys Asp Ala
    610                 615                 620

ctc gag ctg ttg gga gca ggc ata ctg ctt gag ttc gaa ccc gag ctg      1920
Leu Glu Leu Leu Gly Ala Gly Ile Leu Leu Glu Phe Glu Pro Glu Leu
625                 630                 635                 640

tta att cct acc att ctg gtt ttc act atc aaa tcc ttt ctc gga tct      1968
Leu Ile Pro Thr Ile Leu Val Phe Thr Ile Lys Ser Phe Leu Gly Ser
                645                 650                 655

tcc gac aat aag aat aag gtc atc aag gct ata aac aat gcc ctt aag      2016
Ser Asp Asn Lys Asn Lys Val Ile Lys Ala Ile Asn Asn Ala Leu Lys
            660                 665                 670

gag cgc gat gag aag tgg aaa gag gta tac tct ttt att gtg agt aac      2064
Glu Arg Asp Glu Lys Trp Lys Glu Val Tyr Ser Phe Ile Val Ser Asn
        675                 680                 685

tgg atg aca aaa att aat acc cag ttt aat aag aga aag gaa cag atg      2112
Trp Met Thr Lys Ile Asn Thr Gln Phe Asn Lys Arg Lys Glu Gln Met
    690                 695                 700

tac caa gct ctc cag aat cag gtc aac gct ata aaa acc ata att gag      2160
Tyr Gln Ala Leu Gln Asn Gln Val Asn Ala Ile Lys Thr Ile Ile Glu
705                 710                 715                 720

tcc aaa tac aat agt tat act ctg gaa gag aag aac gag cta aca aat      2208
Ser Lys Tyr Asn Ser Tyr Thr Leu Glu Glu Lys Asn Glu Leu Thr Asn
                725                 730                 735

aaa tat gat atc aag cag att gag aat gaa ctc aat cag aag gtc tca      2256
Lys Tyr Asp Ile Lys Gln Ile Glu Asn Glu Leu Asn Gln Lys Val Ser
            740                 745                 750

att gcc atg aac aat att gat agg ttc cta aca gaa tca tct atc tct      2304
Ile Ala Met Asn Asn Ile Asp Arg Phe Leu Thr Glu Ser Ser Ile Ser
        755                 760                 765

tac ctc atg aag ctg ata aat gag gtc aag att aac aaa ttg cgg gag      2352
Tyr Leu Met Lys Leu Ile Asn Glu Val Lys Ile Asn Lys Leu Arg Glu
    770                 775                 780

tac gac gaa aat gtt aaa acc tac ctt ttg aat tac ata att cag cac      2400
Tyr Asp Glu Asn Val Lys Thr Tyr Leu Leu Asn Tyr Ile Ile Gln His
785                 790                 795                 800

gga agc atc ctg ggc gaa tca cag caa gaa ctc aat tcc atg gtt acg      2448
Gly Ser Ile Leu Gly Glu Ser Gln Gln Glu Leu Asn Ser Met Val Thr
                805                 810                 815

gat aca ctg aac aat tcc atc cca ttc aag tta tct tcc tat act gac      2496
Asp Thr Leu Asn Asn Ser Ile Pro Phe Lys Leu Ser Ser Tyr Thr Asp
            820                 825                 830

gat aag ata ttg att tct tac ttc aat aaa ttc ttt aag aga atc aag      2544
Asp Lys Ile Leu Ile Ser Tyr Phe Asn Lys Phe Phe Lys Arg Ile Lys
        835                 840                 845

agc tcc tct gtg cta aat atg cgt tac aag aac gat aaa tat gtg gac      2592
Ser Ser Ser Val Leu Asn Met Arg Tyr Lys Asn Asp Lys Tyr Val Asp
```

-continued

```
    850                 855                 860

act tca ggg tac gat tca aac att aac atc aat ggt gat gtg tat aag     2640
Thr Ser Gly Tyr Asp Ser Asn Ile Asn Ile Asn Gly Asp Val Tyr Lys
865                 870                 875                 880

tat ccc acc aac aaa aac caa ttc ggg ata tac aat gac aag ctg agt     2688
Tyr Pro Thr Asn Lys Asn Gln Phe Gly Ile Tyr Asn Asp Lys Leu Ser
                885                 890                 895

gag gtg aac atc tct cag aac gac tat att atc tac gac aat aaa tac     2736
Glu Val Asn Ile Ser Gln Asn Asp Tyr Ile Ile Tyr Asp Asn Lys Tyr
            900                 905                 910

aag aac ttc agc att tct ttc tgg gtg cgc att cct aat tat gac aac     2784
Lys Asn Phe Ser Ile Ser Phe Trp Val Arg Ile Pro Asn Tyr Asp Asn
        915                 920                 925

aag atc gtg aat gtg aat aac gag tac aca atc att aac tgt atg cgc     2832
Lys Ile Val Asn Val Asn Asn Glu Tyr Thr Ile Ile Asn Cys Met Arg
    930                 935                 940

gac aat aac tcc ggc tgg aag gta agt ctc aac cac aac gag att atc     2880
Asp Asn Asn Ser Gly Trp Lys Val Ser Leu Asn His Asn Glu Ile Ile
945                 950                 955                 960

tgg acc ctt cag gat aat gcg gga att aac cag aaa ctg gcc ttc aat     2928
Trp Thr Leu Gln Asp Asn Ala Gly Ile Asn Gln Lys Leu Ala Phe Asn
                965                 970                 975

tat ggc aat gcg aac gga atc tct gat tac atc aac aag tgg atc ttt     2976
Tyr Gly Asn Ala Asn Gly Ile Ser Asp Tyr Ile Asn Lys Trp Ile Phe
            980                 985                 990

gtg aca ata act aat gat cgg ctg ggg gac agc aag ctc tat atc aac     3024
Val Thr Ile Thr Asn Asp Arg Leu Gly Asp Ser Lys Leu Tyr Ile Asn
        995                 1000                1005

ggg aac ctg att gat cag aag tcc att ttg aac ctg gga aat att cat     3072
Gly Asn Leu Ile Asp Gln Lys Ser Ile Leu Asn Leu Gly Asn Ile His
    1010                1015                1020

gtg tca gac aat atc ctt ttt aag ata gtc aac tgc agc tac acg cgt     3120
Val Ser Asp Asn Ile Leu Phe Lys Ile Val Asn Cys Ser Tyr Thr Arg
1025                1030                1035                1040

tac atc ggt att cga tat ttc aac att ttt gat aag gaa ttg gac gaa     3168
Tyr Ile Gly Ile Arg Tyr Phe Asn Ile Phe Asp Lys Glu Leu Asp Glu
                1045                1050                1055

acg gag atc cag aca ctg tat tca aac gag cct aac act aac att ctg     3216
Thr Glu Ile Gln Thr Leu Tyr Ser Asn Glu Pro Asn Thr Asn Ile Leu
            1060                1065                1070

aaa gat ttc tgg ggg aac tat ctt ctg tat gat aaa gag tat tac ctt     3264
Lys Asp Phe Trp Gly Asn Tyr Leu Leu Tyr Asp Lys Glu Tyr Tyr Leu
        1075                1080                1085

ctg aac gtc ctg aaa cct aat aac ttc atc gat cgc aga aag gat tcc     3312
Leu Asn Val Leu Lys Pro Asn Asn Phe Ile Asp Arg Arg Lys Asp Ser
    1090                1095                1100

acc ttg tct atc aat aac att agg tcc acc ata ctt ctg gca aat cga     3360
Thr Leu Ser Ile Asn Asn Ile Arg Ser Thr Ile Leu Leu Ala Asn Arg
1105                1110                1115                1120

ctt tat tct gga ata aag gtc aag atc cag agg gtg aac aat tcc tca     3408
Leu Tyr Ser Gly Ile Lys Val Lys Ile Gln Arg Val Asn Asn Ser Ser
                1125                1130                1135

acc aat gac aac ctg gtg cgt aaa aac gat cag gtg tat att aac ttt     3456
Thr Asn Asp Asn Leu Val Arg Lys Asn Asp Gln Val Tyr Ile Asn Phe
            1140                1145                1150

gtg gca tcc aag act cat ctg ttc ccc ctc tat gct gac acc gct aca     3504
Val Ala Ser Lys Thr His Leu Phe Pro Leu Tyr Ala Asp Thr Ala Thr
        1155                1160                1165

acc aat aag gaa aaa acc att aag att agc tca tct ggt aat aga ttt     3552
```

-continued

```
Thr Asn Lys Glu Lys Thr Ile Lys Ile Ser Ser Ser Gly Asn Arg Phe
    1170                1175                1180

aat caa gta gtc gta atg aat agc gtt ggc aac aat tgc acc atg aac     3600
Asn Gln Val Val Val Met Asn Ser Val Gly Asn Asn Cys Thr Met Asn
1185                1190                1195                1200

ttc aaa aac aac aac ggt aac aac atc ggc ctg ctg gga ttt aag gca     3648
Phe Lys Asn Asn Asn Gly Asn Asn Ile Gly Leu Leu Gly Phe Lys Ala
                1205                1210                1215

gac acc gtt gtg gcc tcc acc tgg tat tac aca cac atg cgg gac cac     3696
Asp Thr Val Val Ala Ser Thr Trp Tyr Tyr Thr His Met Arg Asp His
            1220                1225                1230

act aac agc aac ggt tgc ttt tgg aac ttc atc tcc gaa gag cat ggt     3744
Thr Asn Ser Asn Gly Cys Phe Trp Asn Phe Ile Ser Glu Glu His Gly
        1235                1240                1245

tgg cag gag aag tga                                                 3759
Trp Gln Glu Lys  *
    1250
```

```
<210> SEQ ID NO 81
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, C. griseus-modified 2

<400> SEQUENCE: 81

atgcctaaga tcaactcctt caactacaac gaccctgtga acgacagaac catcctgtac     60

atcaagcctg gcggctgtca ggagttctac aagtccttca acatcatgaa gaacatctgg    120

atcatccctg agagaaacgt gatcggcacc acccctcagg acttccaccc tcctacctcc    180

ctgaagaacg gcgactcctc ctactacgac cctaactacc tgcagtccga cgaggagaag    240

gacagattcc tgaagatcgt gaccaagatc ttcaacagaa tcaacaacaa cctgtccggc    300

ggcatcctgc tggaggagct gtccaaggcc aacccttacc tgggcaacga caacacccct    360

gacaaccagt tccacatcgg cgacgcctcc gccgtggaga tcaagttctc caacggctcc    420

caggacatcc tgctgcctaa cgtgatcatc atgggcgccg agcctgacct gttcgagacc    480

aactcctcca acatctccct gagaaacaac tacatgcctt ccaaccacgg cttcggctcc    540

atcgccatcg tgaccttctc ccctgagtac tccttcagat tcaacgacaa ctccatgaac    600

gagttcatcc aggaccctgc cctgaccctg atgcacgagc tgatccactc cctgcacggc    660

ctgtacggcg ccaagggcat caccaccaag tacaccatca cccagaagca gaaccctctg    720

atcaccaaca tcagaggcac caacatcgag gagttcctga ccttcggcgg caccgacctg    780

aacatcatca cctccgccca gtccaacgac atctacacca acctgctggc cgactacaag    840

aagatcgcct ccaagctgtc caaggtgcag gtgtccaacc ctctgctgaa cccttacaag    900

gacgtgttcg aggccaagta cggcctggac aaggacgcct ccggcatcta ctccgtgaac    960

atcaacaagt tcaacgacat cttcaagaag ctgtactcct tcaccgagtt cgacctggcc   1020

accaagttcc aggtgaagtg tagacagacc tacatcggcc agtacaagta cttcaagctg   1080

tccaacctgc tgaacgactc catctacaac atctccgagg gctacaacat caacaacctg   1140

aaggtgaact tcagaggcca gaacgccaac ctgaacccta gaatcatcac ccctatcacc   1200

ggcagaggcc tggtgaagaa gatcatcaga ttctgtaaga acatcgtgtc cgtgaagggc   1260

atcagaaagt ccatctgtat cgagatcaac aacggcgagc tgttcttcgt ggcctccgag   1320
```

-continued aactcctaca acgacgacaa catcaacacc cctaaggaga tcgacgacac cgtgacctcc 1380
aacaacaact acgagaacga cctggaccag gtgatcctga acttcaactc cgagtccgcc 1440
cctggcctgt ccgacgagaa gctgaacctg accatccaga acgacgccta catccctaag 1500
tacgactcca acggcacctc cgacatcgag cagcacgacg tgaacgagct gaacgtgttc 1560
ttctacctgg acgcccagaa ggtgcctgag ggcgagaaca acgtgaacct gacctcctcc 1620
atcgacaccg ccctgctgga gcagcctaag atctacacct tcttctcctc cgagttcatc 1680
aacaacgtga acaagcctgt gcaggccgcc ctgttcgtgt cctggatcca gcaggtgctg 1740
gtggacttca ccaccgaggc caaccagaag tccaccgtgg acaagatcgc cgacatctcc 1800
atcgtggtgc cttacatcgg cctggccctg aacatcggca acgaggccca gaagggcaac 1860
ttcaaggacg ccctggagct gctgggcgcc ggcatcctgc tggagttcga gcctgagctg 1920
ctgatcccta ccatcctggt gttcaccatc aagtccttcc tgggctcctc cgacaacaag 1980
aacaaggtga tcaaggccat caacaacgcc ctgaaggaga gagacgagaa gtggaaggag 2040
gtgtactcct tcatcgtgtc caactggatg accaagatca acacccagtt caacaagaga 2100
aaggagcaga tgtaccaggc cctgcagaac caggtgaacg ccatcaagac catcatcgag 2160
tccaagtaca actcctacac cctggaggag aagaacgagc tgaccaacaa gtacgacatc 2220
aagcagatcg agaacgagct gaaccagaag gtgtccatcg ccatgaacaa catcgacaga 2280
ttcctgaccg agtcctccat ctcctacctg atgaagctga tcaacgaggt gaagatcaac 2340
aagctgagag agtacgacga gaacgtgaag acctacctgc tgaactacat catccagcac 2400
ggctccatcc tgggcgagtc ccagcaggag ctgaactcca tggtgaccga caccctgaac 2460
aactccatcc ctttcaagct gtcctcctac accgacgaca agatcctgat ctcctacttc 2520
aacaagttct tcaagagaat caagtcctcc tccgtgctga acatgagata caagaacgac 2580
aagtacgtgg acacctccgg ctacgactcc aacatcaaca tcaacggcga cgtgtacaag 2640
taccctacca acaagaacca gttcggcatc tacaacgaca agctgtccga ggtgaacatc 2700
tcccagaacg actacatcat ctacgacaac aagtacaaga acttctccat ctccttctgg 2760
gtgagaatcc ctaactacga caacaagatc gtgaacgtga acaacgagta caccatcatc 2820
aactgtatga gagacaacaa ctccggctgg aaggtgtccc tgaaccacaa cgagatcatc 2880
tggaccctgc aggacaacgc cggcatcaac cagaagctgg ccttcaacta cggcaacgcc 2940
aacggcatct ccgactacat caacaagtgg atcttcgtga ccatcaccaa cgacagactg 3000
ggcgactcca agctgtacat caacggcaac ctgatcgacc agaagtccat cctgaacctg 3060
ggcaacatcc acgtgtccga caacatcctg ttcaagatcg tgaactgttc ctacaccaga 3120
tacatcggca tcagatactt caacatcttc gacaaggagc tggacgagac cgagatccag 3180
accctgtact ccaacgagcc taacaccaac atcctgaagg acttctgggg caactacctg 3240
ctgtacgaca aggagtacta cctgctgaac gtgctgaagc ctaacaactt catcgacaga 3300
agaaaggact ccaccctgtc catcaacaac atcagatcca ccatcctgct ggccaacaga 3360
ctgtactccg gcatcaaggt gaagatccag agagtgaaca actcctccac caacgacaac 3420
ctggtgagaa agaacgacca ggtgtacatc aacttcgtgg cctccaagac ccacctgttc 3480
cctctgtacg ccgacaccgc caccaccaac aaggagaaga ccatcaagat ctcctcctcc 3540
ggcaacagat tcaaccaggt ggtggtgatg aactccgtgg gcaacaactg taccatgaac 3600
ttcaagaaca acaacggcaa caacatcggc ctgctgggct tcaaggccga caccgtggtg 3660
gcctccacct ggtactacac ccacatgaga gaccacacca actccaacgg ctgtttctgg 3720

-continued aacttcatct ccgaggagca cggctggcag gagaagtga 3759

<210> SEQ ID NO 82
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, C. griseus-modified 3

<400> SEQUENCE: 82
atgcctaaaa ttaactcctt caattacaat gaccctgtaa acgaccgcac catcttatac 60
atcaaacctg gagggtgcca agaattctat aaatctttca atatcatgaa aaacatttgg 120
atcattccag agcggaatgt gatcggtacc acaccccagg acttccatcc tcccacgtca 180
ttgaagaacg gcgactcgag ttattacgat cctaactacc tgcagagcga cgaggaaaag 240
gacaggttcc tcaaaattgt gaccaagatc tttaacagaa tcaacaataa cctttcagga 300
ggcatccttt tggaggaact ctccaaggcc aacccatacc tgggcaacga taacacgcct 360
gataaccaat ttcacattgg cgatgctagc gctgtggaga tcaagttttc taatggatct 420
caggatattt tgctgccgaa tgtgatcatt atgggggcag agccagatct gttcgaaact 480
aattctagca atatctcact ccggaacaat tacatgccta gcaatcatgg tttcggaagc 540
attgcaatcg tcacctttag tccggagtac tcattcaggt tcaatgataa ctctatgaat 600
gaatttattc aggaccccgc cctcactctc atgcatgaat taatccatag cctgcatggg 660
ctttatggcg ctaagggaat tacaaccaag tacacaatta ctcagaagca aaatcccctg 720
ataaccaaca tcagaggaac taatatcgaa gagtttctga ctttcggggg aacggacctc 780
aacatcataa cctcggccca atccaacgat atctatacca atttgctggc agactacaag 840
aaaatagcat cgaagctgag caaggtgcag gtgagcaatc ctctactcaa cccctacaaa 900
gatgtcttcg aggccaaata tggcctggat aaagacgcct ctggaatcta ttctgtgaac 960
attaataagt ttaacgacat ctttaagaaa ctgtactcat ttactgagtt cgaccttgcc 1020
accaaattcc aggtcaaatg caggcagaca tacattggtc agtacaagta ttttaagctt 1080
tccaatctgc tcaatgactc aatttacaac atctccgaag gatacaacat aaacaatctg 1140
aaagtcaact tccgcggcca gaatgccaat ctgaaccccc ggataattac ccccatcacc 1200
ggtaggggcc tagtgaaaaa gattatcaga ttttgcaaaa atatcgtttc agtaaaaggt 1260
attcggaaga gtatatgtat tgaaattaat aacggggagc tatttttcgt agcaagtgaa 1320
aattcctaca acgatgacaa tatcaacact ccaaaagaga tcgacgatac cgtcacaagc 1380
aataacaatt acgagaatga tttggatcag gtgattttga actttaacag cgaaagtgct 1440
ccaggtctga gcgatgaaaa gttgaatctg actattcaga atgacgccta tatccctaag 1500
tatgatagca acggtacaag tgatatcgag cagcacgacg tgaacgaact taacgtgttc 1560
ttttacttag acgctcagaa agttcctgag ggcgaaaaca atgtgaattt gacctcctcg 1620
atagatacag ctttgctgga acagcctaaa atttacacct tcttttccag cgagttcatt 1680
aacaatgtga ataaaccagt tcaggctgcg ttgtttgttt cttggataca gcaagtcctt 1740
gtcgacttta ctaccgaggc taaccagaag agtacggtcg acaaaaatagc cgacattagc 1800 attgtggtcc cctacatagg actcgctctc aatattggca acgaagctca gaagggaaac 1860
tttaaggatg cactggagct gctaggcgca ggtatcctgt tagaattcga gccagagctg 1920

-continued

```
ttgataccca ccattttggt ttttactata aagtccttcc tgggatcttc ggacaacaag   1980

aataaagtga tcaaagccat caataacgct ctgaaagaac gagacgagaa gtggaaagag   2040

gtatactctt tcatcgtgtc aaattggatg acaaagatca acacccagtt taacaaacga   2100

aaggagcaga tgtatcaagc gctccagaac caggttaatg ctatcaagac tatcattgag   2160

tctaagtaca actcctacac cctggaggaa aagaatgagc tgactaacaa gtacgatatc   2220

aagcaaattg agaacgaact gaaccagaag gttagcatcg ccatgaacaa tattgatcgc   2280

tttctgaccg agagctcaat cagttaccta atgaagctga tcaatgaagt aaaaatcaac   2340

aagctgagag agtacgacga gaatgtgaag acctacctac tcaactatat catacagcac   2400

ggttccatcc ttggcgaaag tcagcaagag ctgaattcca tggttacaga tacccttaac   2460

aattctatcc cgtttaagct aagttcatat acagatgaca aaatactcat ttcttatttc   2520

aataagttct ttaagcgtat caagagttcc tctgtgctta acatgcgcta caagaacgac   2580

aagtatgtcg acacgtccgg gtatgacagc aacatcaata ttaacgggga cgtgtataaa   2640

tatcccacta acaaaaacca gttcggcata tataatgata aactgtcaga ggtgaatatc   2700

agtcaaaatg actacattat ctatgataac aaatacaaga atttttctat ctctttttgg   2760

gtaaggattc caaattacga caacaaaatc gtgaatgtga ataacgagta tactatcatt   2820

aactgcatga gggacaacaa tagtggctgg aaggtgtcac taaatcacaa cgagatcatt   2880

tggacactgc aggataacgc aggtattaac cagaagcttg cattcaatta cggcaatgcc   2940

aacgggatct ccgactacat taataagtgg atctttgtca ccataacaaa cgaccggctg   3000

ggtgattcta aattgtatat taatggcaat cttatcgatc agaagtcaat cttaaatctg   3060

ggcaacattc atgtaagtga caacatcctc ttcaaaatag tgaattgtag ctatactcga   3120

tatattggca tccgttattt caacatcttc gataaagaat tggacgagac agaaatacaa   3180

actctctact ccaacgagcc aaacacaaac atcctgaagg atttttgggg gaactattta   3240

ctgtatgata aagaatatta cctcctgaat gtgcttaagc caaacaattt cattgaccgc   3300

cgaaaggatt ccacactgtc catcaataac attcgttcca ctatcctgtt ggcgaacaga   3360

ctctactccg gcattaaggt taagatccag cgtgtgaaca attccagcac caatgataac   3420

ctggtgcgca agaacgacca ggtgtatatc aacttcgtgg cttctaagac acaccttttt   3480

cccctctacg ccgataccgc caccacaaat aaagagaaga ctatcaagat ctctagctct   3540

gggaacagat tcaatcaggt cgttgtcatg aacagcgtcg ggaacaattg tacgatgaac   3600

tttaagaaca ataacggaaa caatatcggg ctgctcggat tcaaggcaga caccgtcgtt   3660

gccagtacat ggtattacac acacatgcgg gatcacacaa actctaacgg atgtttctgg   3720

aacttcattt ccgaggaaca cggttggcag gagaagtga                          3759
```

<210> SEQ ID NO 83
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, S. scrofa-modified 1

<400> SEQUENCE: 83

```
atgcccaaga ttaactcctt taactacaat gatccagtta atgaccgcac cattctgtac     60

atcaagcctg gggctgcca ggaattctac aagtctttta acatcatgaa gaacatttgg    120

atcattccgg agaggaacgt gatcgggact acaccgcaag acttccatcc cccaacatcc    180
```

-continued

```
ctcaaaaatg gggactcaag ctactatgac cccaactacc tgcagtccga cgaagagaaa    240
gatagattcc tgaaaatcgt gaccaaaata ttcaatagaa tcaacaataa cttgagtggg    300
ggaattctcc tagaggaact cagcaaggcc aacccctatc tgggtaacga taacaccccc    360
gacaatcagt tccatatcgg agatgccagt gcagtggaaa tcaaattttc taatgggtcc    420
caggacattt tacttccgaa cgtgatcata atgggtgccg aaccagatct attcgagaca    480
aactcctcta acatctccct ccggaataac tacatgccta gcaatcacgg cttcgggtcc    540
atagcgattg tgaccttctc tcccgagtat tcattccgat tcaacgacaa ctccatgaac    600
gagtttatcc aggaccctgc acttacattg atgcacgaac ttatccatag tctccacggc    660
ctgtatggag ccaagggaat tactaccaaa tacaccataa cccagaagca gaacccactg    720
attactaaca tccgaggcac gaacatcgaa gagtttctga cctttggggg caccgacctt    780
aacatcataa catcagctca atcaaacgac atctacacaa acctgctcgc cgactacaaa    840
aagatagcta gcaaactctc taaggtgcaa gtaagtaatc cgttactcaa cccctacaag    900
gatgtcttcg aggccaagta tgggctggat aaggacgcgt ctgggatcta ctctgtcaat    960
atcaacaagt tcaacgatat cttcaaaaag ctttactcct tcaccgagtt tgacctggca   1020
acaaaattcc aggtgaaatg caggcagacc tacatcggcc agtacaagta ctttaaactg   1080
agcaacctgt tgaatgacag catctataac atcagtgaag ggtacaacat taacaatctg   1140
aaagtgaatt ttcggggaca aaacgctaat ctcaacccta gaatcattac tcccatcacc   1200
ggtcgtggcc tcgtaaagaa aattataagg ttctgtaaga atatcgtgtc cgtcaagggc   1260
atccgcaagt ctatatgtat agagatcaat aacggcgagt tattctttgt agcgagcgag   1320
aactcgtaca atgacgataa catcaacacc ccaaaggaga tcgacgatac cgtgacttcg   1380
aataacaatt atgagaatga tctggaccaa gtgatcttaa acttcaacag tgaatcagcc   1440
cctggtctaa gcgatgagaa actgaattta accatccaga atgatgccta tatccccaag   1500
tatgacagca atggcacgag cgatattgag cagcacgatg ttaacgaact aaatgtgttc   1560
ttttaccttg acgctcagaa agtccctgag ggcgaaaaca atgtgaatct gacctctagc   1620
attgacaccg cgctcctgga gcaacctaaa atttatacgt tcttttcctc agagttcatt   1680
aacaatgtaa ataagcccgt ccaggccgct ctgtttgtgt cctggatcca gcaagtcctg   1740
gtggacttca caaccgaggc aaatcagaaa tcaacagtcg ataaaatcgc cgacatctcc   1800
atagtggttc cttatatcgg actcgccctg aatattggta atgaggccca gaagggtaac   1860
ttcaaggacg ctcttgaatt gctcggcgct ggcatcctgt tagagtttga gccagagctg   1920
ctcatcccga ccattctggt ttttactata aagtcgttcc tggggagctc cgataacaaa   1980
aacaaggtca tcaaggccat aaataacgca ctcaaagaga gggacgaaaa gtggaaggag   2040
gtgtattcct ttatcgtgtc caactggatg actaagatca atacgcagtt caacaagcgc   2100
aaggagcaga tgtaccaggc cctgcaaaac caagtcaacg caattaagac tatcattgag   2160
tctaaataca actcctatac cttggaggaa aaaaacgaac tcactaacaa gtatgatatc   2220
aagcaaattg agaacgaact gaaccagaaa gtttcaattg ccatgaataa catcgatagg   2280
ttcctgacag aaagttccat aagctatctc atgaaactga tcaacgaagt caagattaac   2340
aagctgcggg agtatgacga gaacgtcaaa acgtacctac tgaattatat catacagcac   2400
ggctcaattc ttggcgaaag ccagcaggag ttgaatagta tggtcaccga caccttgaat   2460
aacagtattc cctttaagct gtcgtcttac accgacgata agatcctgat ctcctacttt   2520
```

-continued

```
aacaaattct ttaaacgaat caagagtagc tccgtcttga acatgagata caagaacgat   2580

aaatacgtgg acacgtctgg gtacgacagt aatatcaaca tcaatggtga tgtgtacaag   2640

tacccaacta ataagaacca gtttggaatt tataacgaca agctcagcga agtgaatatt   2700

tcacagaacg attatatcat ttacgacaat aagtacaaga acttcagcat cagcttctgg   2760

gtcagaatcc ccaattacga taacaagatt gtaaacgtta ataacgagta caccatcata   2820

aattgcatgc gggacaataa ctcggggtgg aaggtgtctc tgaaccacaa tgaaatcatt   2880

tggacccttc aggacaacgc tggcatcaat cagaagctgg cctttaatta cggaaatgct   2940

aacggaatct cagattacat caataagtgg atcttcgtca caattacgaa cgaccgcctg   3000

ggggactcta agctgtatat taacggtaat ctaatcgatc agaaatccat cctgaacctt   3060

ggcaacatcc atgtgtccga caatatcctc ttcaaaatcg tgaactgctc ctacacacgg   3120

tatatcggaa ttaggtattt caatatcttc gacaaagagc tggatgagac cgagatacag   3180

acactgtaca gcaatgagcc taacacgaac attctgaagg acttctgggg caactatctg   3240

ttgtacgata aggagtacta tctccttaac gtcctgaagc caaacaattt cattgaccgc   3300

agaaaggact ccactctgag cattaataac atccgtagta ccatcctgct cgccaatcgc   3360

ctctactctg gcattaaggt taaaatccag agggtgaata acagctctac aaacgacaat   3420

ttggttcgga agaacgatca ggtgtacatt aacttcgtgg caagcaagac tcatctcttt   3480

cccttgtacg ccgacacagc gaccactaac aaggagaaga caatcaaaat ctccagctcg   3540

ggcaatcggt ttaaccaggt ggtcgtgatg aatagcgtgg gcaacaattg cacgatgaat   3600

ttcaaaaaca acaacggaaa caacatcgga ctgctggggt tcaaggccga cacggttgtg   3660

gcttcaacct ggtactacac tcacatgcgc gaccacacca acagcaacgg atgtttttgg   3720

aacttcataa gcgaagagca cggctggcag gaaaaatga                          3759
```

<210> SEQ ID NO 84
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, S. scrofa-modified 2

<400> SEQUENCE: 84

```
atgcctaaaa tcaactcctt taactacaac gaccccgtaa acgaccgaac catcttgtat     60

ataaaacccg gcgggtgcca ggagttctac aagagcttca acattatgaa aaatatctgg    120

attatcccgg agcggaacgt cattgggact acaccccagg acttccatcc cccaacctcc    180

ttaaagaatg gagattcctc ttattacgac ccgaactatc tgcagagcga tgaggaaaag    240

gacaggttcc ttaagattgt gaccaagatt ttcaatcgga tcaacaataa cttatctggg    300

ggcatactcc tggaagagtt aagtaaagcc aacccatatc tcgggaatga taatacccct    360

gacaaccaat tccatattgg cgacgcgtcc gccgttgaga tcaagttttc gaacggatcc    420

caagatatac tgctcccaaa cgtgatcatt atgggcgcgg aacctgatct gttcgagact    480

aactccagca atatttcctt gcgcaacaat tacatgccct ctaatcacgg tttcggctca    540

atcgctatcg tcactttcag ccccgagtac agttttcgct tcaacgataa ctccatgaac    600

gagtttatcc aagacccagc cttaacactg atgcacgagc tgatccacag cctgcacggc    660

ctgtacggcg ctaagggcat tacgacaaaa tacaccatca cccaaaaaca gaatccactc    720

attactaaca tcaggggcac caacatcgag gaatttctga ctttcggggg cacggatctc    780
```

-continued

```
aacatcataa cctcggctca gagtaatgat atctacacta acctgctcgc cgactacaag    840
aaaattgcat ccaagctttc taaggtgcag gtgtccaacc cgctgctaaa cccttataag    900
gacgtcttcg aggccaagta cggccttgac aaagacgcta gcgggatcta tagcgtgaat    960
atcaataagt ttaatgacat cttcaagaaa ctttactcat tcacagagtt cgacctggcc   1020
accaaattcc aagtgaagtg ccgacagacg tatatcgggc agtacaaata tttcaaactg   1080
agtaatctgt tgaacgattc aatttacaac atctccgaag gatacaacat taataacctg   1140
aaagtgaact ttcgcggcca gaatgcaaac ctgaatccac gaattatcac tcccataaca   1200
ggcaggggcc tcgtaaaaaa gatcatacgc ttttgtaaaa acatcgtgtc cgttaaaggt   1260
atccggaagt ccatttgcat tgagatcaat aacggagagc tattctttgt ggcgagcgag   1320
aactcataca atgacgataa tatcaacacc ccaaaagaga ttgatgacac cgtcacatct   1380
aacaataact atgagaatga tcttgaccag gttattctca atttcaactc cgagtcagct   1440
ccgggcctaa gtgacgagaa gctgaacctg acaatccaga acgatgccta cattcccaag   1500
tatgattcca atggtacatc tgacattgag cagcacgacg tgaacgagct caacgtgttc   1560
ttttacctcg acgcccagaa ggtccctgag ggtgagaata acgtcaattt aacctcgtct   1620
atcgacaccg ctctgctcga acagcctaag atctacacgt tttcagtag cgaatttatc    1680
aacaatgtga ataagccagt tcaagctgcc ctgttcgtga gctggatcca gcaagtgctc   1740
gtggatttca ccacggaggc caatcagaaa agtaccgtgg acaagatagc agacatctca   1800
atcgtcgtgc cttatatcgg cctcgccctg aacattggga acgaggccca gaagggcaat   1860
tttaaagacg cactggaatt gctgggggct gggatcctcc tggagtttga acctgagctg   1920
cttataccca caatcctggt gtttactatt aaatcttttc ttgggagctc tgataacaag   1980
aacaaggtga taaaggccat caacaatgca ctcaaggaga gggatgaaaa atggaaagaa   2040
gtgtactcgt tcatcgttag taattggatg accaagatca acacgcagtt caataaacgc   2100
aaggagcaga tgtaccaggc cctccagaat caggtcaacg ccatcaaaac catcatagag   2160
agcaaataca acagctatac cctggaggaa aagaatgaac tgactaacaa gtacgacatc   2220
aagcagatcg agaacgaact taatcagaaa gtcagcatag ctatgaacaa tatcgacaga   2280
tttctgacag aaagtagcat tagctatctc atgaagctga tcaatgaagt taagatcaac   2340
aagctcaggg aatacgatga aaatgtgaag acttacttgc tgaactacat cattcagcat   2400
ggatctatcc tcggagaaag ccagcaagag ctgaattcta tggtgacgga cacactgaat   2460
aactccatcc ccttcaagtt gtcaagctac accgatgaca agattcttat ctcctacttc   2520
aataaatttt tcaagcggat caagagctcg agcgttctga atatgcggta taaaaacgat   2580
aagtatgtag atacgtccgg atatgacagc aacatcaata ttaatgggga cgtgtacaag   2640
taccccacaa acaagaacca attcggcatt tacaacgaca agctgtcgga agtgaacatc   2700
tcacagaatg actacattat atacgacaac aaatacaaaa atttttcaat ctcattttgg   2760
gtccgcatcc ccaactacga taataagatc gtgaacgtga acaatgagta taccattata   2820
aattgtatga gagacaacaa tagcggatgg aaggtctccc ttaatcacaa cgagatcata   2880
tggacgctcc aggacaatgc cggtatcaac cagaagttgg cgtttaacta tggtaacgcc   2940
aatggaatct cagactatat taacaagtgg atctttgtga caatcaccaa cgataggctg   3000
ggtgactcta agctgtacat taacggaaac cttatcgacc aaaagtctat attgaatttg   3060
gggaacatcc acgtgagtga taacattctg ttcaagattg tgaactgctc ctacaccaga   3120
```

-continued

```
tacatcggca tccgttactt caacattttc gacaaagagc tcgatgagac cgaaattcag   3180

accttgtaca gcaatgaacc caacacgaat atcctgaaag atttctgggg caactacctg   3240

ctatacgaca aggagtatta cctgctcaac gtgctgaagc ctaacaattt catcgaccgc   3300

agaaaggatt ctacactgag cattaacaat atcagaagca ctattctact cgcaaacagg   3360

ttgtatagtg gaatcaaggt caaaatacag cgtgtcaaca attcctcaac caatgacaac   3420

ctggttcgga aaaacgatca ggtttatatc aacttcgtag caagcaaaac tcacctattt   3480

ccgttatatg ccgacaccgc cacaaccaac aaggagaaga ctatcaagat ctcttcctct   3540

ggaaaccggt tcaaccaggt cgtagtgatg aacagtgtcg gcaacaattg cactatgaat   3600

ttcaaaaaca ataacggtaa caacataggg ctgctggggt tcaaggctga caccgtcgtc   3660

gcgtccacct ggtactatac ccatatgaga gatcacacaa actccaacgg atgtttctgg   3720

aactttattt ccgaagagca tggctggcag gagaagtga                          3759
```

<210> SEQ ID NO 85
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, S. scrofa-modified 3

<400> SEQUENCE: 85

```
atgcccaaaa tcaatagctt taattacaat gaccccgtga atgacaggac tatcctgtac     60

atcaagccag gcggttgcca ggagttctac aagagcttta atatcatgaa aaacatctgg    120

atcattccgg agcggaacgt gatcggtact accccgcagg actttcaccc acccacaagt    180

ctgaaaaatg gcgactcctc atattacgat ccgaactacc tgcagtccga cgaagagaag    240

gatcgcttcc tgaaaatcgt cacaaagatc ttcaatagaa tcaacaataa cctttccggc    300

gggatcctgc tcgaagagct gtccaaggcc aacccttact tggggaacga taatacgcca    360

gacaatcagt tccatattgg cgacgccagc gccgtcgaaa ttaaattcag taatggcagc    420

caggacatcc tgcttcccaa cgtgatcatt atgggtgcag agcctgattt gttcgaaacc    480

aactctagca atatctctct gcggaacaat tacatgccta gcaatcatgg cttcggaagc    540

atcgccatcg tgacctttag cccagagtac agcttcagat tcaatgacaa ctcaatgaat    600

gagtttatcc aggatccggc cctgaccctg atgcatgaac tcattcactc actccacgga    660

ctctacgggg ctaagggtat taccacgaag tacaccatca ctcagaagca gaatcccctg    720

atcaccaaca ttaggggcac taacatcgag gaatttctga cctttggagg gacagatctg    780

aatatcatta catccgccca gtctaacgat atctacacca atctcctggc cgattataag    840

aaaatcgcca gcaagttgag caaagtgcag gtttccaacc ctctcctgaa tccttataaa    900

gacgtgtttg aggccaagta cgggctggac aaagatgcca gtggcatcta tagcgtcaat    960

attaataagt tcaatgacat cttcaagaaa ctttactcat tcaccgaatt cgacctcgca   1020

actaagtttc aggtgaagtg cagacagacc tacatcggac agtacaaata cttcaaactg   1080

agcaacctgc tcaacgattc catttacaat atctccgaag gctataatat taacaatctc   1140

aaggttaact ttcggggaca gaacgctaac ctgaaccccc ggatcattac acccatcacc   1200

ggtcggggcc tggtcaagaa aattatccga ttctgtaaga acatcgtctc cgttaaaggg   1260

atccggaaat caatttgcat cgagatcaac aatggcgagc tgttctttgt ggcaagcgag   1320

aactcctaca acgacgataa tatcaacaca cctaaggaaa tcgatgacac ggtgaccagc   1380
```

-continued

```
aataacaatt atgagaatga tttggaccag gttatcttga acttcaatag cgagtccgcc   1440
ccaggcctgt ccgatgagaa gctgaacctg accatccaga acgatgccta catccccaag   1500
tacgactcaa atggcacctc tgacattgaa cagcacgacg tgaacgagct gaacgtgttc   1560
ttttaccttg atgcccagaa agtccccgag ggagaaaata acgtgaacct cactagttcc   1620
atcgacacag ctctgctcga gcagcctaag atttacactt tctttagtag cgagttcatc   1680
aataacgtga acaagcctgt tcaggccgca ttgtttgttt cttggatcca gcaggtgctt   1740
gtcgacttca caacggaagc caatcagaaa tctacagtgg ataaaatcgc tgacattagc   1800
attgtcgtgc catacatcgg cctggcactg aatatcggaa acgaggccca gaaagggaac   1860
ttcaaggacg cactggaact gctcggcgca gggatcctgc tcgagttcga gcccgaactt   1920
ctgattccaa ccatcctcgt gttcactatt aagagctttc ttggatcaag tgataataag   1980
aacaaggtga tcaaggctat caacaatgcc ctgaaagaga gagatgagaa gtggaaggaa   2040
gtgtacagct tcattgtctc taattggatg accaagatca acacccagtt caacaagaga   2100
aaagaacaga tgtaccaggc tctgcagaac caggtgaatg ccatcaaaac catcattgag   2160
agcaaatata acagctatac cctcgaagag aaaaacgagc tgacgaacaa gtatgacatc   2220
aagcagatcg agaatgaact gaatcagaag gtgtctatcg ctatgaacaa tattgaccga   2280
ttcctgaccg agagcagtat ctcttatctg atgaagttga ttaacgaagt gaagatcaac   2340
aaactgcggg aatacgatga gaacgttaag acttatctgt tgaactatat cattcagcac   2400
gggtctatcc tcggggagtc ccagcaggag ctgaactcca tggtgacaga cacactgaac   2460
aattcaattc ctttcaagct gtccagctat acagatgaca agatcctcat ctcttacttt   2520
aacaagtttt tcaagaggat taaaagctct agtgtgctga atatgaggta caagaacgac   2580
aaatatgtcg atacctctgg atacgactcc aacatcaaca tcaacggtga cgtctataag   2640
tatcccacca ataagaacca gttcggcatc tacaacgaca agttgtccga agtgaacatt   2700
tctcagaacg actatattat ctacgacaat aagtataaaa atttctccat ctctttctgg   2760
gtccgcattc cgaactacga caacaagatt gtgaatgtga acaatgagta cactatcatt   2820
aactgcatgc gcgacaacaa tagcggctgg aaagtgtccc ttaaccacaa cgagatcatt   2880
tggaccctcc aggacaacgc cggcatcaat cagaagctcg cctttaacta tggtaacgct   2940
aatggaattt ccgattatat caacaaatgg atcttcgtca ccatcacgaa cgacaggctg   3000
ggggactcaa agttgtacat caacgggaac cttatcgatc agaaatcaat cctgaacttg   3060
ggaaacatcc atgtcagcga caacattctg ttcaaaatcg tgaactgtag ttatacaagg   3120
tatatcggca tccgatattt taacattttc gacaaggagc tggatgaaac agagatccag   3180
accctgtact ccaatgaacc caataccaac atcctgaaag atttttgggg gaactacctg   3240
ctctacgata aggagtacta tctgctcaac gtgcttaagc ccaataactt tatcgacaga   3300
cgcaaggatt ccaccctgag tatcaacaat atccgcagca ccattctgct cgctaacagg   3360
ctctactcag gcatcaaggt gaagatccag agggtgaaca attcttccac gaacgacaac   3420
ctggttcgca agaacgacca ggtttacatc aactttgtgg ccagtaaaac ccacctgttc   3480
ccactgtacg ccgatacggc cactacaaat aaggagaaaa ctattaagat cagctccagt   3540
ggaaacaggt tcaaccaggt ggtcgtgatg aactcagtcg gcaataactg tactatgaat   3600
tttaagaaca ataacggaaa caatatcggg cttctggggt tcaaggccga cacggtggtc   3660
gctagcacgt ggtactacac tcacatgcgc gaccatacaa atagcaacgg ctgcttctgg   3720
```

-continued

```
aactttatca gcgaggagca cggttggcag gagaaatga                        3759


<210> SEQ ID NO 86
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, B. tarsus-modified 1

<400> SEQUENCE: 86

atgcccaaaa taaactcctt taactacaac gatccagtga acgacaggac tatactgtac     60

atcaagcccg gcgggtgcca agagttttat aagtcattta atatcatgaa aaacatctgg    120

ataatccctg agagaaatgt gattggaaca actccccagg attttcaccc cccaacctca    180

ctaaaaaatg gtgacagcag ttattacgat cccaactacc tgcagtctga cgaggaaaag    240

gatcggttct taaaaatcgt caccaaaatc tttaaccgga taaataacaa tctctctggc    300

gggatcctgc ttgaggaact gagcaaagct aatccttatc tcggaaacga caacacacca    360

gataatcagt ttcacattgg ggacgcatct gctgtggaga ttaagttctc caacggcagc    420

caggatatcc tgctccccaa cgtcatcata atgggagccg agcctgactt gtttgagacg    480

aactccagta acataagcct tagaaacaat tacatgccct cgaaccacgg atttggttca    540

atcgccatag tgaccttcag tccagaatac agcttccgct ttaatgataa ctcaatgaac    600

gaattcattc aggacccagc tctgacattg atgcatgagc tgattcactc cctccacggt    660

ctgtacggag ccaagggcat aactacaaag tataccatca cccaaaagca gaacccgctc    720

attaccaata tccgcggaac gaacatcgag gaatttctca cctttggtgg aaccgatctg    780

aacattataa caagtgccca gtcgaacgac atctacacca atttgctggc cgactataaa    840

aagatcgcta gcaagctgtc aaaggtgcag gtgagcaacc ccctcttgaa tccttacaag    900

gatgtgtttg aagctaaata cgggttagac aaggacgctt ccggaatcta cagcgtgaac    960

atcaacaagt tcaacgatat ctttaagaaa ctgtactctt tcaccgagtt tgatctggca   1020

actaaatttc aggtcaagtg ccgccagact tacatcggtc aatataagta ttttaaactc   1080

agcaacctgc ttaacgacag catttacaat atcagcgaag ggtataacat caacaatctg   1140

aaggtcaatt tccgagggca gaacgcaaac ctgaatccaa ggatcattac ccctatcaca   1200

ggccgtggcc tggtcaagaa aattatcagg ttctgtaaga acatcgtctc tgtaaagggc   1260

atccgaaagt ccatctgtat cgaaattaat aacggggagc tgtttttcgt tgccagcgaa   1320

aacagctaca acgatgacaa catcaacacg cccaaggaaa ttgacgatac cgtcacttcc   1380

aacaataact atgagaacga tctcgatcag gttatcctga atttcaatag cgagtcagca   1440

ccagggctaa gtgatgagaa gctcaatctg actatacaga acgatgcgta cattcccaaa   1500

tacgatagca acggcaccag cgacattgaa cagcatgatg ttaatgagct caacgtgttc   1560

ttttatctgg acgcccagaa agttccggag ggtgagaaca atgtcaatct gacttcctct   1620

atcgatacag ccctgcttga gcagcctaag atctacactt tctttagctc ggaattcatc   1680

aacaatgtga ataagccggt tcaggccgca ctgttcgtct cttggataca gcaagtgctg   1740

gtggacttca ccactgaggc caatcagaag tctacggtcg acaagattgc tgacatctct   1800

atcgtagttc cttatattgg cctcgccctc aacatcggca acgaggcaca gaagggcaac   1860

ttcaaagatg ccctggagct tctgggtgct ggaattctgc ttgagttcga accagagctc   1920

ctgatcccta ccatccttgt attcaccatc aagtcctttc tcggcagctc tgataataag   1980
```

-continued

```
aacaaggtca tcaaggccat taataacgcg ctgaaagaga gggacgagaa atggaaagag   2040

gtgtactcct tcattgtcag caattggatg accaagatta atacacagtt caacaaaagg   2100

aaggagcaga tgtatcaggc actccagaac caggtgaatg caataaagac cataatcgag   2160

tccaaatata attcgtacac tcttgaagag aaaaacgaac ttacgaacaa gtatgacatt   2220

aaacagatag agaacgagct gaatcagaaa gtctcaattg cgatgaacaa tatcgaccgt   2280

ttcctgacag agagctccat aagctacctc atgaaactaa tcaatgaggt gaagatcaac   2340

aagttgcggg agtatgacga aaacgtaaag acataccttt tgaattatat cattcaacat   2400

ggcagtatct taggcgaaag ccagcaagaa ttgaactcaa tggtgaccga caccttgaac   2460

aatagtattc cgttcaagct cagttcctac acagacgata agatactgat ttcatatttc   2520

aacaagttct ttaaacgaat taagtccagt tctgtgctga atatgcggta caagaacgac   2580

aaatacgtgg acacctctgg ctacgactct aatatcaaca ttaacgggga tgtgtataaa   2640

tatcctacca acaagaacca gtttggtatc tataacgaca agttgtccga agtgaatatc   2700

agtcagaacg attacattat ctacgataac aagtacaaga atttctccat ctccttttgg   2760

gtgcggatac ccaactacga caataagatc gtgaacgtga ataacgaata cacaatcatt   2820

aactgcatga gagacaataa ctcgggatgg aaggtttccc tcaaccacaa tgagattatc   2880

tggacactgc aggacaacgc tggcattaac caaaaattgg ccttcaacta tgggaatgcg   2940

aacgggatta gcgactacat caataagtgg attttcgtaa ctatcactaa cgatcggctc   3000

ggcgacagta agctgtatat caatggaaac ctgattgacc aaaaatctat tttaaaccta   3060

ggtaacatcc atgtctcgga caacatcctc ttcaagatcg tgaactgttc ttacacaaga   3120

tatattggga tccgatactt caatattttc gataaggagc tcgacgagac cgaaattcaa   3180

acactgtaca gcaacgaacc taacaccaat atccttaaag atttttgggg gaactactta   3240

ctttacgaca aagagtacta tttactaaat gtgctgaagc ccaacaattt tatagatcgc   3300

agaaaagaca gtacgctgag catcaacaat atccgttcca caatcctgct agccaacagg   3360

ctgtactcag gcattaaggt taaaatccag agggtgaata actcctcaac caacgacaat   3420

ctggtcagaa aaaatgacca ggtgtacatt aatttcgtgg ctagtaagac tcacttgttc   3480

ccactgtatg ccgacactgc cacgacaaat aaggaaaaaa cgatcaaaat cagttccagt   3540

ggcaaccgct ttaaccaagt cgtggttatg aattctgtgg gaaacaattg caccatgaac   3600

ttcaagaaca ataacggaaa caatatcggt ttgctcggct tcaaggccga cacagtagtg   3660

gcttcaacct ggtattacac ccacatgcgc gaccacacga actctaacgg atgcttctgg   3720

aatttcattt ccgaagagca tgggtggcag gaaaaatga                          3759
```

<210> SEQ ID NO 87
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, B. tarsus-modified 2

<400> SEQUENCE: 87

```
atgcccaaga tcaacagctt caactacaac gaccccgtga acgacaggac catcctgtac     60

atcaagcccg gcggctgcca ggagttctac aagagcttca acatcatgaa gaacatctgg    120

atcatccccg agaggaacgt gatcggcacc accccccagg acttccaccc ccccaccagc    180
```

-continued

```
ctgaagaacg gcgacagcag ctactacgac cccaactacc tgcagagcga cgaggagaag    240
gacaggttcc tgaagatcgt gaccaagatc ttcaacagga tcaacaacaa cctgagcggc    300
ggcatcctgc tggaggagct gagcaaggcc aacccctacc tgggcaacga caacaccccc    360
gacaaccagt tccacatcgg cgacgccagc gccgtggaga tcaagttcag caacggcagc    420
caggacatcc tgctgcccaa cgtgatcatc atgggcgccg agcccgacct gttcgagacc    480
aacagcagca acatcagcct gaggaacaac tacatgccca gcaaccacgg cttcggcagc    540
atcgccatcg tgaccttcag ccccgagtac agcttcaggt tcaacgacaa cagcatgaac    600
gagttcatcc aggaccccgc cctgaccctg atgcacgagc tgatccacag cctgcacggc    660
ctgtacggcg ccaagggcat caccaccaag tacaccatca cccagaagca gaacccccctg    720
atcaccaaca tcaggggcac caacatcgag gagttcctga ccttcggcgg caccgacctg    780
aacatcatca ccagcgccca gagcaacgac atctacacca acctgctggc cgactacaag    840
aagatcgcca gcaagctgag caaggtgcag gtgagcaacc ccctgctgaa cccctacaag    900
gacgtgttcg aggccaagta cggcctggac aaggacgcca gcggcatcta cagcgtgaac    960
atcaacaagt tcaacgacat cttcaagaag ctgtacagct tcaccgagtt cgacctggcc   1020
accaagttcc aggtgaagtg caggcagacc tacatcggcc agtacaagta cttcaagctg   1080
agcaacctgc tgaacgacag catctacaac atcagcgagg gctacaacat caacaacctg   1140
aaggtgaact tcaggggcca gaacgccaac ctgaacccca ggatcatcac cccccatcacc   1200
ggcaggggcc tggtgaagaa gatcatcagg ttctgcaaga acatcgtgag cgtgaagggc   1260
atcaggaaga gcatctgcat cgagatcaac aacggcgagc tgttcttcgt ggccagcgag   1320
aacagctaca acgacgacaa catcaacacc cccaaggaga tcgacgacac cgtgaccagc   1380
aacaacaact acgagaacga cctggaccag gtgatcctga acttcaacag cgagagcgcc   1440
cccggcctga gcgacgagaa gctgaacctg accatccaga acgacgccta catccccaag   1500
tacgacagca acggcaccag cgacatcgag cagcacgacg tgaacgagct gaacgtgttc   1560
ttctacctgg acgcccagaa ggtgcccgag ggcgagaaca acgtgaacct gaccagcagc   1620
atcgacaccg ccctgctgga gcagcccaag atctacacct tcttcagcag cgagttcatc   1680
aacaacgtga acaagcccgt gcaggccgcc ctgttcgtga gctggatcca gcaggtgctg   1740
gtggacttca ccaccgaggc caaccagaag agcaccgtgg acaagatcgc cgacatcagc   1800
atcgtggtgc cctacatcgg cctggccctg aacatcggca acgaggccca gaagggcaac   1860
ttcaaggacg ccctggagct gctgggcgcc ggcatcctgc tggagttcga gcccgagctg   1920
ctgatcccca ccatcctggt gttcaccatc aagagcttcc tgggcagcag cgacaacaag   1980
aacaaggtga tcaaggccat caacaacgcc ctgaaggaga gggacgagaa gtggaaggag   2040
gtgtacagct tcatcgtgag caactggatg accaagatca acacccagtt caacaagagg   2100
aaggagcaga tgtaccaggc cctgcagaac caggtgaacg ccatcaagac catcatcgag   2160
agcaagtaca acagctacac cctggaggag aagaacgagc tgaccaacaa gtacgacatc   2220
aagcagatcg agaacgagct gaaccagaag gtgagcatcg ccatgaacaa catcgacagg   2280
ttcctgaccg agagcagcat cagctacctg atgaagctga tcaacgaggt gaagatcaac   2340
aagctgaggg agtacgacga gaacgtgaag acctacctgc tgaactacat catccagcac   2400
ggcagcatcc tgggcgagag ccagcaggag ctgaacagca tggtgaccga caccctgaac   2460
aacagcatcc ccttcaagct gagcagctac accgacgaca agatcctgat cagctacttc   2520
aacaagttct tcaagaggat caagagcagc agcgtgctga acatgaggta caagaacgac   2580
```

-continued aagtacgtgg acaccagcgg ctacgacagc aacatcaaca tcaacggcga cgtgtacaag 2640
taccccacca acaagaacca gttcggcatc tacaacgaca agctgagcga ggtgaacatc 2700
agccagaacg actacatcat ctacgacaac aagtacaaga acttcagcat cagcttctgg 2760
gtgaggatcc ccaactacga caacaagatc gtgaacgtga acaacgagta caccatcatc 2820
aactgcatga gggacaacaa cagcggctgg aaggtgagcc tgaaccacaa cgagatcatc 2880
tggaccctgc aggacaacgc cggcatcaac cagaagctgg ccttcaacta cggcaacgcc 2940
aacggcatca gcgactacat caacaagtgg atcttcgtga ccatcaccaa cgacaggctg 3000
ggcgacagca agctgtacat caacggcaac ctgatcgacc agaagagcat cctgaacctg 3060
ggcaacatcc acgtgagcga caacatcctg ttcaagatcg tgaactgcag ctacaccagg 3120
tacatcggca tcaggtactt caacatcttc gacaaggagc tggacgagac cgagatccag 3180
accctgtaca gcaacgagcc caacaccaac atcctgaagg acttctgggg caactacctg 3240
ctgtacgaca aggagtacta cctgctgaac gtgctgaagc ccaacaactt catcgacagg 3300
aggaaggaca gcaccctgag catcaacaac atcaggagca ccatcctgct ggccaacagg 3360
ctgtacagcg gcatcaaggt gaagatccag agggtgaaca acagcagcac caacgacaac 3420
ctggtgagga agaacgacca ggtgtacatc aacttcgtgg ccagcaagac ccacctgttc 3480
cccctgtacg ccgacaccgc caccaccaac aaggagaaga ccatcaagat cagcagcagc 3540
ggcaacaggt tcaaccaggt ggtggtgatg aacagcgtgg gcaacaactg caccatgaac 3600
ttcaagaaca acaacggcaa caacatcggc ctgctgggct tcaaggccga caccgtggtg 3660
gccagcacct ggtactacac ccacatgagg gaccacacca acagcaacgg ctgcttctgg 3720
aacttcatca gcgaggagca cggctggcag gagaagtga 3759

<210> SEQ ID NO 88
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, B. tarsus-modified 3

<400> SEQUENCE: 88
atgcctaaga tcaactcttt taattataac gatccagtaa atgacagaac aatcctgtac 60
attaagcccg gtgggtgcca ggaattttac aagagtttta acattatgaa aaacatttgg 120
attataccag aacgcaacgt tatcggcacc acaccccagg actttcaccc tccgacttcg 180
ctgaaaaacg gtgatagctc ttattacgac cccaactatc tgcagtccga cgaggaaaaa 240
gacagatttc tgaagattgt cactaagatc ttcaacagaa tcaataacaa tctgtctggg 300
ggaatcctcc tggaggaact ttcaaaggcc aacccttact tgggtaacga caacactccc 360
gataatcaat tccatatagg cgacgcctct gctgtggaga taaagttctc aaacggaagt 420
caggacatcc tgcttcctaa cgtaatcata atgggagccg aaccagatct cttcgagacc 480
aatagctcaa acatcagtct taggaataac tacatgccta gcaaccacgg gtttggctct 540
attgccatag tgactttctc gcccgagtat tcctttcgat ttaatgataa cagcatgaac 600
gagttcatcc aagatcccgc acttaccctg atgcacgagc tgattcactc tctgcacggg 660
ctctatggag ccaaaggcat tacaaccaag tacaccatca ctcaaaaaca gaacccactt 720
atcacaaata tcaggggcac aaacatcgaa gagtttttga ccttcggagg cacagacctg 780

-continued

```
aacattatca cctccgctca atcaaacgac atctacacca atctcctggc cgactacaag    840
aaaatcgcat caaagctcag caaggttcag gtttccaatc ctctgttgaa tccatataag    900
gatgtcttcg aagcaaaata cggcctagac aaggacgcca gtggaattta cagtgtgaat    960
atcaataagt tcaatgatat cttcaaaaag ctgtactcct ttaccgagtt tgacttagcg   1020
acgaagttcc aagtaaaatg caggcagaca tacatcggcc agtacaaata tttcaagctg   1080
tccaatcttt taaacgactc gatttataat atcagtgagg gctacaatat taacaatttg   1140
aaagtaaatt tccgggggca gaacgctaac ctgaacccgc gaattatcac gcccataacc   1200
gggcggggtc tggtgaagaa aattatacgc ttttgcaaaa acatcgtgag cgtgaagggg   1260
attaggaaaa gcatctgtat cgaaatcaac aatggggagc tcttctttgt ggcctctgag   1320
aactcgtata atgatgacaa tatcaacaca cccaaggaga ttgacgatac tgtgacctct   1380
aacaataact acgagaatga cctagaccag gtgatcctca actttaacag tgaaagtgcc   1440
cccggcctta gtgatgagaa gttgaactta accattcaga atgacgcgta tataccgaag   1500
tatgacagca atggtacgag tgatatcgaa cagcatgacg tgaatgaatt gaacgtgttt   1560
ttctacctgg atgctcaaaa agtgcccgag ggcgaaaaca atgtcaatct taccagctcc   1620
attgacacag cactgctcga gcaaccaaag atttacacct tttctcctc tgagtttatt    1680
aacaatgtga acaagcctgt ccaggctgcc ctcttcgtta gttggatcca gcaagtgctg   1740
gtggacttca caacggaagc taaccagaaa tcgaccgtgg ataaaattgc cgacatctcc   1800
atcgtcgtgc cttacattgg actcgctctg aacatcggga atgaagcaca gaagggcaac   1860
tttaaagatg ctttagagct tctgggagcc gggatcctcc tggagttcga acccgagcta   1920
ctgatcccca ctatcctcgt cttcaccatc aaatcctttc tgggttcctc tgacaataag   1980
aataaggtca taaaggcaat caataacgct ttgaaagagc gggatgagaa gtggaaagag   2040
gtctatagct tcatagtcag caactggatg actaagatta atacccagtt caacaaacgg   2100
aaggagcaaa tgtaccaggc cctccagaat caagtcaatg ccatcaagac catcatagag   2160
agcaagtaca actcctatac tttggaagag aagaatgagc tcaccaacaa atacgacatc   2220
aaacagatcg agaacgaact gaaccagaag gtgtcaatcg ctatgaacaa tatcgaccgt   2280
ttcctgacag agtcatccat ctcatacttg atgaagctga ttaacgaggt gaagatcaat   2340
aagctgcgtg agtacgatga aaacgtcaaa acatatttgc taaactatat aattcagcac   2400
ggatccattt taggtgagag ccagcaggaa ctgaactcta tggttaccga caccttgaac   2460
aatagcatac cattcaagct gtctagctat acagatgaca aaatactgat cagctacttc   2520
aataaattct ttaaaagaat caagtccagc agtgtgctga atatgcgcta caagaacgat   2580
aaatacgtgg atacctccgg atacgattca aacattaaca tcaatggcga cgtatacaag   2640
tacccaacta ataagaacca gtttggaatt tataatgata aacttagcga agtgaacatc   2700
tcccagaacg actacatcat ttacgataac aagtataaga acttttcgat ctcctttttgg  2760
gtcaggattc ctaattacga caacaaaata gttaacgtca acaatgagta cacgatcatt   2820
aactgcatgc gagacaataa ctccggctgg aaggtgtcac tgaaccataa tgaaatcatt   2880
tggacgctcc aggataacgc cgggatcaac cagaaacttg cgttcaacta cggaaacgcc   2940
aatggtattt ccgactatat taacaagtgg attttcgtga cgatcacgaa tgacagactc   3000
ggtgactcta aactgtacat caacggcaac ctcatcgacc agaagagcat tcttaacctg   3060
ggcaatattc atgtttccga taacatcctg ttcaagatcg tgaactgttc ttacacacgc   3120
tacattggga tccgatactt taacattttc gataaagagc tggatgagac cgaaatccag   3180
```

-continued

```
accctgtaca gtaacgaacc gaacaccaac atcttaaaag acttctgggg taactatcta   3240

ctgtatgata aggaatacta tctgctcaac gtcctcaagc caaacaattt catagacagg   3300

agaaaagaca gcactctgtc aatcaacaat atccgtagca cgatcttgct cgccaatcgc   3360

ctctactctg gcataaaggt gaagatccag cgggtgaaca attctagcac taacgataac   3420

ctggtccgga agaatgatca ggtttatatt aatttcgtgg cttccaagac acatctgttt   3480

cctctctatg ccgacaccgc gactaccaac aaggagaaaa caatcaagat aagctctagc   3540

gggaatcgct tcaaccaggt tgtagtgatg aactcagtcg gaaataactg cactatgaac   3600

ttcaagaata acaatggcaa caacattggc ctcctaggct tcaaggcaga cacagtggtg   3660

gcaagtactt ggtattatac acacatgagg gaccacacca acagtaacgg atgtttctgg   3720

aactttatca gcgaggaaca cgggtggcag gagaagtga                          3759
```

<210> SEQ ID NO 89
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, E. caballus-modified 1

<400> SEQUENCE: 89

```
atgcccaaga taaactcttt caattacaac gatcccgtta atgacagaac catactgtac     60

atcaagcctg gaggctgcca ggagttttac aaaagcttca acataatgaa gaacatctgg    120

atcattcctg agaggaatgt aatagggaca accccgcaag acttccaccc ccctactagt    180

cttaaaaacg gtgactcaag ttactatgat cccaactact tgcagagcga cgaggaaaag    240

gacaggttcc ttaaaattgt cacaaagata ttcaatagga tcaataacaa tctctccggc    300

ggtattctac tcgaggaact gtcaaaggcc aacccttacc tgggcaatga taacacccct    360

gacaatcagt ttcatatcgg cgatgccagc gccgtcgaaa tcaagttcag taacggcagc    420

caggatattc tgctccctaa cgtgatcatt atgggcgcag aacctgactt attcgagaca    480

aatagttcta acatctcact gagaaataac tacatgccta gtaatcacgg tttcggctcc    540

atagcaattg tgactttctc ccctgagtat agctttcgct ttaacgacaa ctcaatgaat    600

gagtttattc aagacccagc cctaactctg atgcacgaac tgatccattc gttacacgga    660

ttatatggcg ctaaaggaat cactacgaag tatactatta cccagaaaca gaacccacta    720

atcaccaaca taaggggcac taacatcgaa gagtttctta ccttcggggg aaccgatttg    780

aatattatca cctccgccca gtcaaacgac atttacacaa acctgttggc cgactataag    840

aaaatcgcgt ccaaactgtc caaggtccag gtgagtaatc cactgttgaa cccatacaaa    900

gatgtcttcg aagctaaata cggattggat aaggacgcct ccggcatata cagcgtgaat    960

attaataagt ttaacgatat ttttaaaaag ctctactcct tcactgagtt cgatctggcc   1020

actaagtttc aggtgaagtg ccggcagacc tacatagggc aatataaata tttcaagctc   1080

tcaaatctcc tgaacgatag tatctacaac atcagcgagg gatataacat caataacctg   1140

aaggtgaact ttcgcgggca gaacgccaac ctaaatccgc gaatcattac tccaatcaca   1200

ggtagaggac tggttaaaaa gataatccgg ttctgcaaga acattgtcag cgtgaaggga   1260

atcaggaaaa gcatttgtat cgagatcaat aacggagaat tatttttcgt ggcatcagaa   1320

aacagctaca atgatgacaa catcaacacc cccaaggaga tcgatgacac tgtgacgtct   1380
```

-continued

```
aacaataact acgagaatga tttggatcag gtcatcttaa acttcaacag cgagtcagcc   1440
cccgggctca gcgacgagaa attgaacctg accatacaaa atgacgccta catacccaaa   1500
tatgattcaa acggcacctc tgacatcgag cagcatgatg tgaatgagct gaacgtcttc   1560
ttttatctgg acgcccaaaa ggtcccagaa ggagagaaca atgtcaatct cacttctagt   1620
atcgataccg ccctgctcga acagccgaaa atttatacct tctttagctc cgaattcatc   1680
aataacgtca acaagcccgt gcaggctgca cttttcgtga gttggattca gcaagtgctc   1740
gtagacttta ccactgaggc caatcagaaa tccaccgttg ataaaattgc tgatatctct   1800
atcgtggtcc cctacatcgg cctggctctt aacataggca acgaggcaca gaaagggaac   1860
ttcaaggacg cgctggagct gctcggagcc gggatcctgc tcgaattcga gccagaactg   1920
ttaataccga cgatccttgt attcacaatt aagtcatttc tcggctcctc tgacaataaa   1980
aataaggtga tcaaagccat caataacgca ctcaaggaga gagatgagaa gtggaaggaa   2040
gtctactcgt ttatcgtgtc caactggatg accaagatta acacacagtt taacaagcgc   2100
aaggaacaga tgtaccaggc tctgcagaac caggtcaacg ctattaagac tatcattgag   2160
tcaaagtaca acagctacac cctggaggaa aagaacgaac tcacgaacaa gtacgatatc   2220
aagcaaattg agaatgagct gaatcaaaag gtttccatcg ctatgaacaa tatagaccgg   2280
ttcctcaccg aatcctctat ttcctatctg atgaagttga ttaatgaagt taagattaac   2340
aagctgcggg agtatgacga gaacgtgaag acatatctgc ttaattatat tatccaacat   2400
gggagtattc tgggggaatc acaacaggag ctgaattcta tggtaacaga caccctgaac   2460
aatagtatcc catttaagct cagctcctat acagatgaca agattcttat ctcttacttt   2520
aacaagtttt tcaagcgtat caagagcagt tcagttctaa acatgcgcta caagaacgac   2580
aagtatgtgg acacaagtgg ttatgactcg aacatcaata tcaacggcga cgtgtacaaa   2640
taccccacga acaagaacca gttcggcatt tacaacgaca aactgagcga ggtgaatatc   2700
agccagaatg actacattat ctatgacaat aaatataaaa acttctccat tagcttttgg   2760
gttagaatcc ccaattatga taataaaata gtgaacgtta acaatgagta caccatcatt   2820
aattgcatga gggataacaa ttctgggtgg aaggtgtctt tgaatcacaa cgagatcatt   2880
tggactctgc aggacaacgc aggaatcaac cagaagctgg ctttcaatta tgggaatgct   2940
aatggcatat ctgactacat taacaaatgg atcttcgtga caatcaccaa cgacagactg   3000
ggggattcta aactctacat caacgggaac cttatcgatc agaagtcgat tctgaacctt   3060
ggaaacatcc acgtgtccga caacatactg ttcaagatcg tgaattgtag ctacacgcgt   3120
tacatcggca tcaggtactt caatatcttc gacaaagagc tcgacgagac cgagatccag   3180
acgctctact ccaatgaacc taacaccaat atcctgaagg acttctgggg aaactacttg   3240
ctgtatgaca aggagtacta tctcttgaat gtgctgaaac ccaacaattt catcgaccga   3300
cggaaagaca gcacgctctc tatcaataac atccgctcta ccattctgct agcgaaccgt   3360
ctgtactccg gcatcaaagt aaagatccag cgggtgaata acagtagcac aaacgataac   3420
ctggtcagaa aaaacgatca ggtgtacatc aacttcgtcg ccagcaaaac acatcttttt   3480
cctctttatg cggacactgc gactaccaat aaagaaaaga ccattaaaat ctcctcttcc   3540
ggcaaccgat ttaatcaagt ggtcgtgatg aatagcgtgg gtaataactg tactatgaat   3600
tttaagaata acaatggtaa taacattggt ttgctggggt ttaaggcaga tacggttgta   3660
gcctcaacat ggtactacac acacatgcgc gaccacacca attccaatgg ctgtttctgg   3720
aactttatct cggaagagca tggttggcag gagaaatga                          3759
```

-continued

<210> SEQ ID NO 90
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, E. caballus-modified 2

<400> SEQUENCE: 90

```
atgcccaaga tcaacagctt caactacaac gaccccgtga acgacagaac catcctgtac     60

atcaagcccg gcggctgtca ggagttctac aagagcttca acatcatgaa gaacatctgg    120

atcatccccg agagaaacgt gatcggcacc accccccagg acttccaccc ccccaccagc    180

ctgaagaacg gcgacagcag ctactacgac cccaactacc tgcagagcga cgaggagaag    240

gacagattcc tgaagatcgt gaccaagatc ttcaacagaa tcaacaacaa cctgagcggc    300

ggcatcctgc tggaggagct gagcaaggcc aacccctacc tgggcaacga caacaccccc    360

gacaaccagt tccacatcgg cgacgccagc gccgtggaga tcaagttcag caacggcagc    420

caggacatcc tgctgcccaa cgtgatcatc atgggcgccg agcccgacct gttcgagacc    480

aacagcagca acatcagcct gagaaacaac tacatgccca gcaaccacgg cttcggcagc    540

atcgccatcg tgaccttcag ccccgagtac agcttcagat tcaacgacaa cagcatgaac    600

gagttcatcc aggaccccgc cctgaccctg atgcacgagc tgatccacag cctgcacggc    660

ctgtacggcg ccaagggcat caccaccaag tacaccatca cccagaagca gaaccccctg    720

atcaccaaca tcagaggcac caacatcgag gagttcctga ccttcggcgg caccgacctg    780

aacatcatca ccagcgccca gagcaacgac atctacacca acctgctggc cgactacaag    840

aagatcgcca gcaagctgag caaggtgcag gtgagcaacc ccctgctgaa cccctacaag    900

gacgtgttcg aggccaagta cggcctggac aaggacgcca gcggcatcta cagcgtgaac    960

atcaacaagt tcaacgacat cttcaagaag ctgtacagct tcaccgagtt cgacctggcc   1020

accaagttcc aggtgaagtg tagacagacc tacatcggcc agtacaagta cttcaagctg   1080

agcaacctgc tgaacgacag catctacaac atcagcgagg gctacaacat caacaacctg   1140

aaggtgaact tcagaggcca gaacgccaac ctgaacccca gaatcatcac ccccatcacc   1200

ggcagaggcc tggtgaagaa gatcatcaga ttctgtaaga acatcgtgag cgtgaagggc   1260

atcagaaaga gcatctgtat cgagatcaac aacggcgagc tgttcttcgt ggccagcgag   1320

aacagctaca acgacgacaa catcaacacc cccaaggaga tcgacgacac cgtgaccagc   1380

aacaacaact acgagaacga cctggaccag gtgatcctga acttcaacag cgagagcgcc   1440

cccggcctga gcgacgagaa gctgaacctg accatccaga acgacgccta catccccaag   1500

tacgacagca acggcaccag cgacatcgag cagcacgacg tgaacgagct gaacgtgttc   1560

ttctacctgg acgcccagaa ggtgcccgag ggcgagaaca acgtgaacct gaccagcagc   1620

atcgacaccg ccctgctgga gcagcccaag atctacacct tcttcagcag cgagttcatc   1680

aacaacgtga acaagcccgt gcaggccgcc ctgttcgtga gctggatcca gcaggtgctg   1740

gtggacttca ccaccgaggc caaccagaag agcaccgtgg acaagatcgc cgacatcagc   1800

atcgtggtgc cctacatcgg cctggccctg aacatcggca acgaggccca gaagggcaac   1860

ttcaaggacg ccctggagct gctgggcgcc ggcatcctgc tggagttcga gcccgagctg   1920

ctgatcccca ccatcctggt gttcaccatc aagagcttcc tgggcagcag cgacaacaag   1980
```

-continued aacaaggtga tcaaggccat caacaacgcc ctgaaggaga gagacgagaa gtggaaggag 2040
gtgtacagct tcatcgtgag caactggatg accaagatca acacccagtt caacaagaga 2100
aaggagcaga tgtaccaggc cctgcagaac caggtgaacg ccatcaagac catcatcgag 2160
agcaagtaca acagctacac cctggaggag aagaacgagc tgaccaacaa gtacgacatc 2220
aagcagatcg agaacgagct gaaccagaag gtgagcatcg ccatgaacaa catcgacaga 2280
ttcctgaccg agagcagcat cagctacctg atgaagctga tcaacgaggt gaagatcaac 2340
aagctgagag agtacgacga gaacgtgaag acctacctgc tgaactacat catccagcac 2400
ggcagcatcc tgggcgagag ccagcaggag ctgaacagca tggtgaccga caccctgaac 2460
aacagcatcc ccttcaagct gagcagctac accgacgaca agatcctgat cagctacttc 2520
aacaagttct tcaagagaat caagagcagc agcgtgctga acatgagata caagaacgac 2580
aagtacgtgg acaccagcgg ctacgacagc aacatcaaca tcaacggcga cgtgtacaag 2640
taccccacca acaagaacca gttcggcatc tacaacgaca agctgagcga ggtgaacatc 2700
agccagaacg actacatcat ctacgacaac aagtacaaga acttcagcat cagcttctgg 2760
gtgagaatcc ccaactacga caacaagatc gtgaacgtga acaacgagta caccatcatc 2820
aactgtatga gagacaacaa cagcggctgg aaggtgagcc tgaaccacaa cgagatcatc 2880
tggaccctgc aggacaacgc cggcatcaac cagaagctgg ccttcaacta cggcaacgcc 2940
aacggcatca gcgactacat caacaagtgg atcttcgtga ccatcaccaa cgacagactg 3000
ggcgacagca agctgtacat caacggcaac ctgatcgacc agaagagcat cctgaacctg 3060
ggcaacatcc acgtgagcga caacatcctg ttcaagatcg tgaactgtag ctacaccaga 3120
tacatcggca tcagatactt caacatcttc gacaaggagc tggacgagac cgagatccag 3180
accctgtaca gcaacgagcc caacaccaac atcctgaagg acttctgggg caactacctg 3240
ctgtacgaca aggagtacta cctgctgaac gtgctgaagc ccaacaactt catcgacaga 3300
agaaaggaca gcaccctgag catcaacaac atcagaagca ccatcctgct ggccaacaga 3360
ctgtacagcg gcatcaaggt gaagatccag agagtgaaca acagcagcac caacgacaac 3420
ctggtgagaa agaacgacca ggtgtacatc aacttcgtgg ccagcaagac ccacctgttc 3480
cccctgtacg ccgacaccgc caccaccaac aaggagaaga ccatcaagat cagcagcagc 3540
ggcaacagat tcaaccaggt ggtggtgatg aacagcgtgg gcaacaactg taccatgaac 3600
ttcaagaaca acaacggcaa caacatcggc ctgctgggct tcaaggccga caccgtggtg 3660
gccagcacct ggtactacac ccacatgaga gaccacacca acagcaacgg ctgtttctgg 3720
aacttcatca gcgaggagca cggctggcag gagaagtga 3759

<210> SEQ ID NO 91
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, E. caballus-modified 3

<400> SEQUENCE: 91
atgcccaaga taaactcctt taactataac gatcccgtga acgaccgaac gatattgtac 60
attaagccag gcgggtgtca ggagttctac aaatcattca acataatgaa aaacatctgg 120
attatccccg agagaaacgt gattggcact acacctcagg acttccatcc cccaacgagt 180
cttaagaacg gagacagctc ttattacgac cccaattacc tgcaatcgga cgaggaaaaa 240

-continued

```
gatagatttc tgaagatcgt gacgaagatt tttaatcgga tcaataacaa tttatctgga    300
gggatcctcc tggaggaact tagtaaggca aatccatatt tggggaacga taacacccct    360
gataaccaat tccatatcgg cgatgccagt gccgtggaga ttaagttcag taacggatcc    420
caggatatcc tcttgcccaa cgtaatcatt atgggtgcgg agccagacct gttcgagact    480
aacagttcta acatttcact gagaaacaat tacatgcctt ccaatcacgg atttgggagc    540
attgccatcg ttaccttctc gcccgaatat tccttccgat ttaacgacaa tagtatgaac    600
gagttcattc aggaccccgc tttgactctc atgcatgagc ttatccactc tctgcacgga    660
ctctacggcg ctaagggtat taccactaag tacaccatca cccagaagca gaacccccctg    720
attacaaata tacggggaac aaatattgag gaattcctga cgttcggggg cacagatctc    780
aacatcatta ccagcgctca gagcaatgac atttatacca atctgctcgc agattacaaa    840
aagatagcct ccaagctgtc taaggtccag gtgtccaatc cgcttctaaa tccttataag    900
gatgtcttcg aggccaagta cggtctggac aaagacgcca gcggcattta tagcgtgaac    960
attaacaagt ttaacgacat cttcaagaaa ctctactcct tcaccgagtt tgaccttgct   1020
acaaaattcc aggtgaagtg tagacagaca tacatcgggc aatataagta ttttaagtta   1080
agcaatcttc tgaacgactc aatttacaac atctccgagg ggtacaatat taacaatctg   1140
aaggtgaact ttcgcggcca aaacgcgaat cttaaccctc gtatcataac tccgattacc   1200
ggtcgcggcc tggtgaaaaa gataatcagg ttctgcaaaa acatcgtgtc tgtgaagggc   1260
atccgaaaat ccatttgcat cgagattaac aatggcgaat tgtttttcgt ggcgagtgaa   1320
aattcttata acgacgataa tatcaacact cctaaagaaa tcgacgatac tgttacatct   1380
aacaataact acgagaatga cctcgaccag gtcatcctga acttcaactc cgagagtgcc   1440
ccaggactct ccgatgaaaa actcaacctg accatccaga acgatgcata catccctaaa   1500
tatgattcta acggcacaag tgacatcgag caacacgatg tgaacgagct gaatgtgttt   1560
ttctacctag atgcgcagaa agtccccgag gggaaaaaca atgtgaactt gacctcttca   1620
atcgacacgg cactcttaga gcagcccaaa atctacacct tctttagctc agagtttatc   1680
aacaatgtta acaagcccgt ccaggccgca ttattcgtca gctggattca acaggtactg   1740
gtcgatttta ccacagaggc caaccagaag tctacggtgg acaaaattgc cgacatctcc   1800
atcgtcgtac catacatcgg cttggcactg aacatcggga acgaggccca aaaaggtaac   1860
ttcaaggatg cgttggagtt gttaggtgca ggaatcctgc tagaatttga accggaactc   1920
ctgatcccta ccatactcgt cttcactatc aaatctttcc tagggtcatc cgacaacaag   1980
aataaggtga taaaggccat caataacgct ctgaaagagc gtgacgagaa atggaaagag   2040
gtgtacagct tcatagtctc gaactggatg accaaaatta acacgcaatt caacaagagg   2100
aaagaacaga tgtatcaggc cctgcagaac caggtaaacg ccataaagac aataatcgaa   2160
tccaaataca attcctacac cctcgaagag aagaacgagc tgactaacaa gtacgacatc   2220
aaacagatcg agaatgaact gaatcaaaag gtgagcatcg ctatgaacaa tattgatcgg   2280
tttctgaccg aatcttccat ctcctacctg atgaagctca tcaatgaggt taagataaat   2340
aaactgcggg agtatgacga gaacgtgaag acgtacctgc tcaattatat cattcagcat   2400
ggatcaatcc tcggcgagtc ccagcaagaa ctgaactcaa tggtaaccga cactcttaat   2460
aacagcatac cgttcaagct cagctcatac accgacgata aaatcttgat cagttatttt   2520
aacaagtttt tcaagcgcat taagagctca tccgtcctta atatgagata caaaaatgac   2580
```

-continued

```
aaatacgtgg acacaagtgg gtacgactcc aacatcaata ttaatggtga cgtttataag   2640

tatcctacaa ataagaacca gtttgggatc tataatgaca agctctccga agtcaatata   2700

tcacagaacg actacatcat ttacgacaat aaatataaaa acttctcgat ttcattttgg   2760

gtgcgcatcc caaactacga taataagatc gttaacgtga ataacgagta taccattata   2820

aactgtatgc gcgataacaa tagcggatgg aaggtgagcc tcaatcacaa cgagatcatt   2880

tggacactgc aggataatgc cggtattaat cagaagctgg ccttcaacta tggaaacgct   2940

aacgggatta gcgactacat caataagtgg atctttgtga caataaccaa cgaccggctt   3000

ggagacagta agctgtatat taatggcaat ctgatcgacc agaaatctat cctgaatctg   3060

ggcaacattc atgtcagcga taatatccta ttcaaaatag tgaactgttc ttacacgaga   3120

tacattggta tcaggtactt caacatcttc gataaggaac tggacgagac tgaaatccag   3180

accttgtaca gcaatgaacc taatactaat atcctgaagg acttttgggg caactaccta   3240

ctttacgata aggaatacta tctcttaaac gtgctcaaac ctaataactt tatcgatagg   3300

cgtaaggaca gcacactgtc aatcaataac atcaggagta ccatcctgtt ggctaataga   3360

ctgtatagcg gcatcaaagt gaagatccag cgcgtcaaca attcatcgac taacgacaac   3420

ctggtgagga aaaacgatca ggtttacatc aacttcgtcg ccagtaagac tcatctgttc   3480

ccactgtacg cagatactgc taccactaat aaggagaaaa ccattaagat ctccagctct   3540

gggaataggt ttaatcaggt ggttgtaatg aacagcgtgg gcaataactg caccatgaac   3600

tttaagaaca ataacggcaa taacattgga cttctgggat ttaaggctga taccgtcgtt   3660

gcctccactt ggtactatac acacatgcgg gaccacacca acagcaatgg ctgcttctgg   3720

aatttcatct ctgaggaaca cggctggcaa gagaagtga                          3759
```

```
<210> SEQ ID NO 92
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, C. aethiops-modified 1

<400> SEQUENCE: 92
```

```
atgccaaaaa ttaatagctt caactataat gacccggtaa acgaccgtac catcttgtat     60

atcaaacccg gggctgcca ggagttttac aagagtttta atatcatgaa aaacatctgg    120

atcattcctg aacggaacgt gattgggaca accccgcagg acttccaccc cccaacaagt    180

cttaagaacg gtgacagttc ctattacgat cccaactacc tgcagtcaga tgaagagaaa    240

gatagattcc tgaagatcgt tacaaagatc tttaatagga tcaacaataa cttatctggc    300

gggatactcc tggaggaact atccaaggcc aatccatact tggggaacga caataccccc    360

gacaatcaat ttcacattgg tgatgcgagt gctgtggaga taaagtttag taatggaagc    420

caagacatac tactgcctaa tgtgatcata atgggggcgg aaccggatct gttcgagact    480

aactctagca acatcagctt gagaaacaat tacatgcctt ctaatcacgg ctttgggtcc    540

attgctatcg tgactttctc gccggaatac tcatttcgct ttaacgacaa ttcaatgaac    600

gagtttatac aggatccagc cttaactctg atgcatgaac ttatccactc gctgcatggt    660

ctgtacggag caaaaggcat tacaaccaaa tacacgatca cacaaaagca aaacccactc    720

attaccaaca tccgtgggac gaacattgag gaattcctca cattcggcgg aacggatctg    780

aatatcataa caagtgccca gtcgaatgat atctatacca atcttctggc tgattacaag    840
```

-continued

```
aaaatcgcaa gcaagctctc caaggtgcaa gtctctaacc ctttacttaa cccttataag    900
gacgtctttg aagccaagta cggactcgac aaggatgctt ccggcattta ttctgtcaac    960
atcaataaat tcaacgatat ctttaaaaag ctgtattcct ttacagagtt cgatctggcc   1020
accaagttcc aggttaaatg ccggcagacc tacatcggcc agtacaagta tttcaagctt   1080
agtaatcttt tgaatgacag tatttacaac atcagcgagg gctataacat taacaatctg   1140
aaggtgaact tcagaggaca aaatgctaac cttaacccaa ggatcattac accaatcacg   1200
ggcagaggct tggtgaagaa aattatcaga ttttgcaaaa acatcgtcag tgtgaaaggg   1260
atccggaagt caatttgcat cgaaatcaat aacggcgagc tgttctttgt ggcttccgaa   1320
aactcgtata acgacgataa cattaacaca cccaaggaga tcgacgatac ggtcactagc   1380
aacaataact atgagaatga tctggatcag gtgattctga atttcaacag tgaaagcgcc   1440
cccggcctct ctgatgagaa attgaatctc acgatccaga acgacgccta catcccaaag   1500
tatgattcca acgggactag cgacatagaa cagcatgacg tgaatgagct caatgtgttc   1560
ttttatctgg atgcccagaa agtacctgag gggaaaata acgttaatct tacttcttca   1620
attgatacgg ccctcctgga acagcccaag atttatacct tcttttcctc tgagttcatc   1680
aataacgtga acaagcctgt ccaggcggcc ctgttcgtct cttggattca gcaagtgctc   1740
gtcgacttca ccacagaagc aaaccagaag agcaccgttg ataagatagc tgatatctct   1800
attgtggtac cctacatagg cttggcgctg aatattggaa atgaggccca aaaaggaaac   1860
ttcaaagacg cactggagct gttgggggca ggcatcctac tcgaattcga gcctgagttg   1920
ctgatcccta ctatcctggt tttcacaatt aaaagttttc tgggttcttc agacaacaag   1980
aacaaagtga tcaaagcaat caataacgcc ctgaaggaac gagacgagaa atggaaagaa   2040
gtgtatagct tcattgtttc caattggatg accaaaataa acacccagtt taacaaaagg   2100
aaagaacaga tgtaccaggc tctgcagaat caggttaatg ccattaaaac tattatcgag   2160
tctaaatata acagttatac cctggaggaa aagaacgagt tgaccaataa atacgacatc   2220
aagcaaatcg agaacgagct gaaccagaag gtttctatcg caatgaataa catagatcgc   2280
tttcttactg agagctccat tagttatctc atgaagctaa tcaacgaggt caaaatcaac   2340
aaactgaggg agtatgatga gaatgtgaag acttacttgc tgaattacat aatccagcat   2400
ggctccattc tgggtgagtc ccagcaagaa ctaaattcca tggtaacgga caccctgaac   2460
aattccatcc cattcaagct tagtagctac acagacgata agattcttat tagctacttt   2520
aataaattct ttaagcggat caagtcctca agcgttctca acatgcgata caaaaacgat   2580
aagtacgtag acacatccgg atacgactca aacattaata taaacggtga cgtgtataag   2640
taccccacga acaagaacca gtttggaatc tataatgata aacttagcga agtgaacatc   2700
tctcaaaacg actacatcat ttatgacaat aaatacaaaa atttctcaat ctcattttgg   2760
gtacggattc ccaactatga taacaaaatc gtcaatgtga acaatgaata cactatcatt   2820
aattgtatgc gagataataa cagcggctgg aaagtgagcc tcaaccacaa cgagataatt   2880
tggaccctgc aagacaacgc aggaatcaac caaaagttag cttttaatta tggcaacgcc   2940
aacggtattt ctgactacat caataaatgg atattcgtta ccataacaaa cgaccgcctc   3000
ggagactcca agctgtacat caatggaaac ctcattgacc agaagagcat actcaatctg   3060
gggaacattc atgtgagcga caacatcctt ttcaagatcg tcaattgctc atacacaaga   3120
tacataggta tccgttactt caacattttc gataaggagt tagacgagac ggaaatccag   3180
```

-continued actctttatt ccaatgagcc aaacactaac atcttaaaag acttctgggg aaattacctc 3240
ttgtatgaca aagaatatta cttacttaac gtcctgaagc ccaacaattt catcgaccgc 3300
cggaaggatt ccaccctgtc tattaataac atcagatcta ctattctcct ggccaatcgc 3360
ctttattctg gcataaaggt caaaattcag cgagtgaata actcatcgac gaacgataac 3420
ctcgttagga agaacgacca ggtgtatatc aacttcgtgg cttctaagac gcatctattt 3480
ccactgtacg ctgataccgc tactacaaac aaggagaaga ccatcaagat tagctcaagc 3540
ggaaatcgct ttaaccaggt cgtggtcatg aattccgttg gcaacaattg tacaatgaat 3600
tttaagaaca ataacgggaa taatattggt ttgctagggt tcaaagccga caccgtcgtc 3660
gcaagcactt ggtattatac acacatgagg gatcacacaa attctaatgg gtgtttctgg 3720
aatttcatct cagaggaaca cggctggcag gagaaatga 3759

<210> SEQ ID NO 93
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, C. aethiops-modified 2

<400> SEQUENCE: 93
atgccaaaga tcaacagctt caactacaac gacccagtga acgacagaac catcctgtac 60
atcaagccag gcggctgcca ggagttctac aagagcttca acatcatgaa gaacatctgg 120
atcatcccag agagaaacgt gatcggcacc accccacagg acttccaccc accaaccagc 180
ctgaagaacg gcgacagcag ctactacgac ccaaactacc tgcagagcga cgaggagaag 240
gacagattcc tgaagatcgt gaccaagatc ttcaacagaa tcaacaacaa cctgagcggc 300
ggcatcctgc tggaggagct gagcaaggcc aacccatacc tgggcaacga caacacccca 360
gacaaccagt tccacatcgg cgacgccagc gccgtggaga tcaagttcag caacggcagc 420
caggacatcc tgctgccaaa cgtgatcatc atgggcgccg agccagacct gttcgagacc 480
aacagcagca acatcagcct gagaaacaac tacatgccaa gcaaccacgg cttcggcagc 540
atcgccatcg tgaccttcag cccagagtac agcttcagat tcaacgacaa cagcatgaac 600
gagttcatcc aggacccagc cctgaccctg atgcacgagc tgatccacag cctgcacggc 660
ctgtacggcg ccaagggcat caccaccaag tacaccatca cccagaagca gaacccactg 720
atcaccaaca tcagaggcac caacatcgag gagttcctga ccttcggcgg caccgacctg 780
aacatcatca ccagcgccca gagcaacgac atctacacca acctgctggc cgactacaag 840
aagatcgcca gcaagctgag caaggtgcag gtgagcaacc cactgctgaa cccatacaag 900
gacgtgttcg aggccaagta cggcctggac aaggacgcca gcggcatcta cagcgtgaac 960
atcaacaagt tcaacgacat cttcaagaag ctgtacagct tcaccgagtt cgacctggcc 1020
accaagttcc aggtgaagtg cagacagacc tacatcggcc agtacaagta cttcaagctg 1080
agcaacctgc tgaacgacag catctacaac atcagcgagg gctacaacat caacaacctg 1140
aaggtgaact tcagaggcca gaacgccaac ctgaacccaa gaatcatcac cccaatcacc 1200
ggcagaggcc tggtgaagaa gatcatcaga ttctgcaaga acatcgtgag cgtgaagggc 1260
atcagaaaga gcatctgcat cgagatcaac aacggcgagc tgttcttcgt ggccagcgag 1320
aacagctaca acgacgacaa catcaacacc ccaaaggaga tcgacgacac cgtgaccagc 1380
aacaacaact acgagaacga cctggaccag gtgatcctga acttcaacag cgagagcgcc 1440

-continued

```
ccaggcctga gcgacgagaa gctgaacctg accatccaga acgacgccta catcccaaag   1500
tacgacagca acggcaccag cgacatcgag cagcacgacg tgaacgagct gaacgtgttc   1560
ttctacctgg acgcccagaa ggtgccagag ggcgagaaca acgtgaacct gaccagcagc   1620
atcgacaccg ccctgctgga gcagccaaag atctacacct tcttcagcag cgagttcatc   1680
aacaacgtga acaagccagt gcaggccgcc ctgttcgtga gctggatcca gcaggtgctg   1740
gtggacttca ccaccgaggc caaccagaag agcaccgtgg acaagatcgc cgacatcagc   1800
atcgtggtgc catacatcgg cctggccctg aacatcggca acgaggccca gaagggcaac   1860
ttcaaggacg ccctggagct gctgggcgcc ggcatcctgc tggagttcga gccagagctg   1920
ctgatcccaa ccatcctggt gttcaccatc aagagcttcc tgggcagcag cgacaacaag   1980
aacaaggtga tcaaggccat caacaacgcc ctgaaggaga gagacgagaa gtggaaggag   2040
gtgtacagct tcatcgtgag caactggatg accaagatca acacccagtt caacaagaga   2100
aaggagcaga tgtaccaggc cctgcagaac caggtgaacg ccatcaagac catcatcgag   2160
agcaagtaca acagctacac cctggaggag aagaacgagc tgaccaacaa gtacgacatc   2220
aagcagatcg agaacgagct gaaccagaag gtgagcatcg ccatgaacaa catcgacaga   2280
ttcctgaccg agagcagcat cagctacctg atgaagctga tcaacgaggt gaagatcaac   2340
aagctgagag agtacgacga gaacgtgaag acctacctgc tgaactacat catccagcac   2400
ggcagcatcc tgggcgagag ccagcaggag ctgaacagca tggtgaccga caccctgaac   2460
aacagcatcc cattcaagct gagcagctac accgacgaca agatcctgat cagctacttc   2520
aacaagttct tcaagagaat caagagcagc agcgtgctga acatgagata caagaacgac   2580
aagtacgtgg acaccagcgg ctacgacagc aacatcaaca tcaacggcga cgtgtacaag   2640
tacccaacca acaagaacca gttcggcatc tacaacgaca agctgagcga ggtgaacatc   2700
agccagaacg actacatcat ctacgacaac aagtacaaga acttcagcat cagcttctgg   2760
gtgagaatcc caaactacga caacaagatc gtgaacgtga acaacgagta caccatcatc   2820
aactgcatga gagacaacaa cagcggctgg aaggtgagcc tgaaccacaa cgagatcatc   2880
tggaccctgc aggacaacgc cggcatcaac cagaagctgg ccttcaacta cggcaacgcc   2940
aacggcatca gcgactacat caacaagtgg atcttcgtga ccatcaccaa cgacagactg   3000
ggcgacagca agctgtacat caacggcaac ctgatcgacc agaagagcat cctgaacctg   3060
ggcaacatcc acgtgagcga caacatcctg ttcaagatcg tgaactgcag ctacaccaga   3120
tacatcggca tcagatactt caacatcttc gacaaggagc tggacgagac cgagatccag   3180
accctgtaca gcaacgagcc aaacaccaac atcctgaagg acttctgggg caactacctg   3240
ctgtacgaca aggagtacta cctgctgaac gtgctgaagc caaacaactt catcgacaga   3300
agaaaggaca gcaccctgag catcaacaac atcagaagca ccatcctgct ggccaacaga   3360
ctgtacagcg gcatcaaggt gaagatccag agagtgaaca acagcagcac caacgacaac   3420
ctggtgagaa agaacgacca ggtgtacatc aacttcgtgg ccagcaagac ccacctgttc   3480
ccactgtacg ccgacaccgc caccaccaac aaggagaaga ccatcaagat cagcagcagc   3540
ggcaacagat tcaaccaggt ggtggtgatg aacagcgtgg gcaacaactg caccatgaac   3600
ttcaagaaca acaacggcaa caacatcggc ctgctgggct tcaaggccga caccgtggtg   3660
gccagcacct ggtactacac ccacatgaga gaccacacca acagcaacgg ctgcttctgg   3720
aacttcatca gcgaggagca cggctggcag gagaagtga                          3759
```

-continued

<210> SEQ ID NO 94
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, C. aethiops-modified 3

<400> SEQUENCE: 94

```
atgccaaaaa ttaactcatt taattacaac gatccggtga atgacaggac aattttgtac     60

attaagccag gcgggtgcca ggagttctac aaatccttca acattatgaa gaacatctgg    120

attatccccg aaagaaatgt gattggcacg acaccacagg acttccaccc acctacttcc    180

ctgaaaaacg gggatagttc ttactatgat cccaactatc tgcagtctga cgaagagaaa    240

gacagatttt tgaagatagt gacaaagatt tttaaccgaa ttaataacaa tctgtccggc    300

ggaatacttc tagaggaact gtcaaaagcc aacccctatt tggggaatga taatactccc    360

gacaaccagt tccacatcgg tgatgcctct gctgtagaga ttaagttttc taacggcagc    420

caagatattc tgctccccaa tgtcattatc atgggcgcag aacctgacct gttcgagaca    480

aacagcagta atatctctct cagaaataac tatatgccaa gtaaccacgg ctttgggtca    540

attgctatcg ttacgttctc ccctgaatat tcatttcgat tcaatgacaa tagcatgaac    600

gagttcatac aagatcccgc tcttacgctg atgcacgagc tgatccactc actccatggt    660

ctgtatgggg ccaaaggtat aactacgaag tacaccataa cccaaaagca gaacccccctc    720

ataacgaaca tccgaggcac caacatcgag gaattcctga ccttcggggg caccgatctg    780

aacatcatta cgagcgctca gagcaacgac atttacacaa acctcctggc cgattataaa    840

aagatcgcga gcaagctaag taaggtccag gtgtccaatc ccctttttaaa tccttacaaa    900

gatgtgttcg aagccaagta cggcttggat aaagatgcgt caggcattta cagcgttaac    960

ataaacaagt tcaatgatat cttcaagaaa ctttatagtt ttacagagtt tgaccttgct   1020

actaaattcc aggttaaatg taggcaaact tacatcggcc agtataaata cttcaaactg   1080

tccaatctgt tgaatgattc aatttacaat atcagcgaag gttacaacat aaacaatttg   1140

aaagtgaatt tcaggggcca aaatgcaaac ttgaatccaa ggatcataac tccaattacc   1200

gggcggggcc tggttaaaaa gattatccga ttttgcaaga atatcgtgtc tgtgaaagga   1260

attagaaaat ctatatgcat cgagatcaac aatggcgagt tatttttcgt ggcaagcgag   1320

aactcttata acgacgataa tattaacacc cctaaggaga ttgatgacac cgtgacgtcg   1380

aataacaatt acgagaatga tttggaccag gtgatcctta attttaactc cgagtctgcc   1440

ccaggactta gtgacgagaa gctgaaccta acaatccaga atgacgcata tattcccaag   1500

tatgattcaa atggaacatc tgacatcgag cagcacgatg taaatgagct aaacgttttc   1560

ttttacctgg acgcccagaa ggttccggag ggcgagaaca atgtcaatct gactagctcc   1620

atcgacactg ctctcctgga acaacccaaa atctatactt ttttctcaag tgagttcatc   1680

aacaatgtta ataagcctgt ccaggccgca ctcttcgtct cgtggattca gcaagttctc   1740

gttgacttca ctacagaagc aaaccagaag tcgaccgtcg acaagattgc cgacattagc   1800

atcgtagtcc cttacatagg gctggcgctg aatatcggaa acgaggccca gaaggggaac   1860

tttaaagacg cgctagaact gctcggggcc ggaatactct tggagttcga gcccgaactc   1920

ctgataccga ccatcctggt gtttacaatc aagagcttcc tgggtagctc cgataataag   1980

aataaggtga tcaaggctat taataacgca cttaaggaac gggacgagaa gtggaaagag   2040
```

-continued gtttacagct tcattgtgag taactggatg acaaaaatca acactcagtt taacaagcgt 2100
aaagagcaaa tgtatcaggc actccagaac caggtaaatg caattaaaac tatcattgaa 2160
agcaagtata atagctatac actggaggaa aagaatgagc tgaccaacaa gtacgacatc 2220
aaacaaatag aaaacgaatt gaaccagaaa gtctctatcg ccatgaacaa tattgaccgg 2280
ttcttaaccg aatcctctat tagctacctc atgaagctca tcaatgaggt caagatcaat 2340
aagctgcgtg agtacgatga gaacgtcaaa acatatttac tgaactatat cattcagcat 2400
ggttcaatcc tcggcgaatc ccagcaagaa ctgaattcta tggtcacgga cactcttaat 2460
aactccatac ctttcaagct cagcagttac accgatgaca aaatcctcat ctcctacttt 2520
aacaaatttt tcaagcgcat taagagtagc tctgtgctga atatgagata taagaatgac 2580
aagtacgtgg atacctctgg gtacgattct aacataaata tcaatggaga cgtgtacaag 2640
taccctacaa ataagaatca gtttggtatc tataatgata aactcagtga ggttaacatc 2700
tcccaaaacg attacattat ctatgataac aaatacaaga attttagcat ctccttttgg 2760
gtacggatcc cgaattatga caataaaatt gttaacgtaa acaatgaata tacgatcatt 2820
aactgcatgc gcgataataa ctcgggatgg aaggtgtctc ttaaccacaa tgagatcatt 2880
tggactctgc aggacaatgc tggcattaac caaaaactgg cttttaacta tggaaacgct 2940
aacggaatct cagattatat taacaaatgg atctttgtga ctatcaccaa cgatcggctg 3000
ggagacagca agctatacat taatggcaat ttaatcgatc aaaagagcat cctaaatttg 3060
ggaaacatcc atgtcagtga caacatcctt ttcaaaatcg tgaactgttc gtataccagg 3120
tacatcggga tccgctactt taacattttc gataaagaac tggacgagac ggagatacag 3180
acactttact ccaacgaacc aaataccaac atcctcaagg acttttgggg gaattatctt 3240
ctctatgaca aagaatatta ccttttaaac gtgctgaagc caaacaattt catcgaccgt 3300
agaaaggaca gcacactgag tataaataac atccgctcta ccatcttgct ggccaaccgc 3360
ctttactccg gtatcaaagt gaagattcag agagtcaaca attcatccac aaacgacaac 3420
ttagtgcgca aaaacgacca ggtgtatatc aatttcgtgg cctccaaaac acacttgttt 3480
ccactgtatg ctgataccgc cacgaccaac aaggagaaga ccataaagat ctcctcatct 3540
ggaaacaggt tcaaccaggt cgtggtcatg aacagtgtgg ggaacaattg caccatgaat 3600
ttcaaaaaca acaacggtaa caacatcggc ctgcttggct ttaaagctga tacagtcgtc 3660
gcctccactt ggtactacac gcatatgcgg gaccatacaa actctaacgg atgtttctgg 3720
aacttcattt cagaagagca tgggtggcag gaaaaatga 3759

<210> SEQ ID NO 95
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, H. sapiens-modified 1

<400> SEQUENCE: 95
atgccaaaga taaacagctt taattacaac gatcccgtga acgaccgtac catcctgtat 60
atcaagcccg gcgggtgtca agagttctat aagagcttta atatcatgaa aaacatttgg 120
atcatacccg aaaggaacgt gatcggaaca accccccaag atttccatcc cccgacaagc 180
ctgaagaacg gagatagcag ctattacgat cccaactatc tgcagagcga cgaggaaaag 240

-continued

```
gatcggtttc tgaagatagt tacgaagatt ttcaatagga ttaacaataa cctgagcgga    300
gggattctgc tggaggaact gagcaaggca aacccatatc tgggtaatga taacaccccg    360
gataaccagt tccatatcgg tgatgccagc gcagtcgaaa taaaatttag caatggcagc    420
caggatatcc tgctgccaaa tgtaatcatt atgggggcag agcctgacct gttcgaaacg    480
aacagcagca acattagcct gcggaataac tacatgccaa gcaatcacgg atttggtagc    540
attgcgattg tcacctttag ccctgaatat agcttcagat ttaatgacaa cagcatgaac    600
gagtttatcc aggatcctgc tctgactctg atgcacgagc tgatccatag cctgcacggc    660
ctgtacggcg ccaaaggtat cacgacaaag tacaccatta cacagaaaca gaatcctctg    720
atcaccaaca tccgcgggac caacatcgag gaattcctga cattcggcgg gaccgatctg    780
aatattatca ctagcgctca gagcaatgac atctacacca atctgctggc tgactacaaa    840
aagattgcca gcaagctgag caaagtgcag gtgagcaacc cactgctgaa cccctataag    900
gatgtgtttg aggccaaata cggctggac aaagacgcca gcggcattta tagcgtgaac    960
atcaacaaat tcaacgatat tttcaagaaa ctgtacagct ttacggagtt tgacctggca   1020
acaaaatttc aggtcaagtg tcggcagacg tacataggcc agtacaaata ttttaagctg   1080
agcaatctgc tgaatgatag catctacaat atcagcgagg gctacaatat caataacctg   1140
aaagttaatt ttcgcggcca aaatgcaaac ctgaaccctc ggattatcac ccctatcaca   1200
gggcgcggtc tggttaagaa aattatcagg ttttgcaaga acatcgttag cgttaagggc   1260
attagaaaaa gcatttgtat agagatcaac aatggagagc tgttctttgt ggctagcgaa   1320
aatagctata atgacgataa catcaacacc ccaaaggaga tagacgatac cgtcactagc   1380
aataacaatt acgagaatga cctggaccaa gtcatcctga attttaacag cgagagcgct   1440
ccaggcctga gcgacgagaa gctgaacctg accatccaaa acgatgccta tatccctaag   1500
tatgatagca atggcactag cgatattgaa cagcacgacg taaacgaact gaatgtcttt   1560
ttctatctgg acgcacaaaa agtgccagaa ggagagaaca atgtgaatct gactagcagc   1620
atcgatactg ccctgctgga gcagcctaag atctacacct tctttagcag cgagttcatt   1680
aacaatgtta acaagcccgt tcaggccgct ctgttcgtga gctggattca gcaagtgctg   1740
gtcgacttta caactgaggc taatcaaaag agcacggttg ataaaatagc agatatcagc   1800
attgttgtgc cgtatatcgg actggctctg aacatcggca atgaggccca gaaaggaaac   1860
ttcaaggacg ccctggaact gctgggggcg ggcatcctgc tggagttcga acccgaactg   1920
ctgatcccaa cgattctggt gttcactatt aagagctttc tgggaagcag cgacaacaag   1980
aacaaggtca ttaaggcaat aaataacgcc ctgaaagaaa gggatgaaaa gtggaaggag   2040
gtgtacagct tcattgtcag caactggatg accaagatca atacacagtt caataagcgg   2100
aaagaacaga tgtaccaggc cctgcagaac caggtgaatg cgattaagac tattatcgag   2160
agcaaataca acagctacac cctggaagag aagaacgaac tgactaataa atatgacatt   2220
aagcagattg agaacgagct gaaccagaaa gtgagcatcg caatgaataa catagaccga   2280
ttcctgacag agagcagcat aagctatctg atgaaactga tcaacgaggt gaaaatcaat   2340
aagctgcgtg aatatgacga gaacgtgaag acttatctgc tgaactatat catacagcac   2400
ggcagcattc tgggagaaag ccaacaggag ctgaacagca tggtgaccga taccctgaat   2460
aacagcatac cctttaagct gagcagctac actgacgata aaatactgat aagctacttt   2520
aacaaattct ttaagagaat aaaaagcagc agcgttctga atatgcgcta caaaaatgat   2580
aagtatgtgg atacaagcgg ttacgacagc aatattaata ttaatggcga cgtgtataag   2640
```

-continued

```
tacccgacaa acaaaaatca attcggtatc tataatgaca aactgagcga agtgaacatc   2700

agccagaacg actatatcat atatgacaat aaatacaaga atttcagcat cagcttctgg   2760

gtgagaatac ctaactacga caataagatt gtaaacgtga ataacgagta cacaatcatt   2820

aactgcatga gagacaacaa tagcgggtgg aaagtcagcc tgaaccataa tgagattatc   2880

tggactctgc aagacaacgc cggaatcaat cagaaactgg ccttcaacta cggaaacgct   2940

aatggtatta gcgattatat caataaatgg atatttgtaa ccatcacaaa tgatcgactg   3000

ggggacagca agctgtacat taacggtaac ctgatcgacc agaagagcat actgaacctg   3060

ggaaacatcc acgtaagcga taacatcctg tttaaaattg tcaactgcag ctacactagg   3120

tatatcggga tcagatactt caatattttc gacaaagaac tggatgagac agaaattcag   3180

accctgtaca gcaacgagcc aaacaccaac atcctgaaag acttctgggg caattatctg   3240

ctgtacgaca aggaatacta tctgctgaac gtactgaagc ctaataactt tatcgacagg   3300

cgtaaggaca gcactctgag catcaataac attaggagca ctattctgct ggctaaccgc   3360

ctgtacagcg gcattaaagt aaagattcag cgggtgaaca atagcagcac aaatgacaat   3420

ctggtgcgaa aaaacgatca ggtctatatt aatttcgtcg ccagcaagac acatctgttc   3480

cccctgtacg ccgacacagc tacaaccaat aaggaaaaaa ccattaagat aagcagcagc   3540

gggaaccgct tcaatcaggt cgttgtgatg aacagcgtcg ggaataactg tacaatgaat   3600

tttaaaaata acaatggaaa taacatcggc ctgctgggct ttaaggccga taccgtggtg   3660

gcgagcactt ggtactacac gcatatgaga gatcacacca atagcaatgg ttgcttctgg   3720

aatttcatca gcgaggaaca cgggtggcag gagaagtga                          3759
```

<210> SEQ ID NO 96
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, H. sapiens-modified 2

<400> SEQUENCE: 96

```
atgccgaaga tcaacagctt taactataat gacccagtta acgacagaac aattctgtac     60

attaagcctg gggatgtca ggagttctac aaaagcttta acattatgaa gaatatttgg    120

ataatccccg aaaggaatgt gattgggact acaccacaag acttccatcc acccaccagc    180

ctgaaaaatg gcgatagcag ctattacgac cctaattatc tgcaaagcga tgaggaaaaa    240

gacaggttcc tgaagattgt gacaaagatc ttcaacagaa ttaacaataa cctgagcgga    300

ggcatactgc tggaggaact gagcaaggca aatccctacc tgggcaatga caacacgcca    360

gataatcagt ttcatatcgg agatgccagc gctgtggaga tcaaatttag caacgggagc    420

caggatatcc tgctgccaaa tgtaattatc atgggtgctg agcctgacct gtttgaaacc    480

aatagcagca acataagcct gaggaacaat tacatgccca gcaaccacgg gtttggtagc    540

attgccattg tcaccttcag ccctgagtat agctttcgct tcaacgataa cagcatgaat    600

gaattcattc aggaccctgc tctgaccctg atgcacgagc tgatacacag cctgcacggg    660

ctgtatggcg ctaagggaat cacaaccaaa tacactatta cacaaaagca gaatccactg    720

ataaccaata ttcgcgggac aaatatcgag gaattcctga cttttggcgg aaccgacctg    780

aacatcataa caagcgccca gagcaatgac atctatacta atctgctggc cgattataaa    840
```

-continued

```
aagattgcga gcaagctgag caaagtgcag gtgagcaacc ctctgctgaa tccatataaa     900
gacgtcttcg aagctaagta cggtctggac aaagacgcta gcggcatcta cagcgtgaac     960
attaacaaat tcaacgatat ctttaaaaag ctgtacagct ttactgagtt cgacctggcc    1020
accaagtttc aggttaagtg tcgccagact tacattggac agtacaagta tttcaagctg    1080
agcaacctgc tgaacgacag catttataac atcagcgagg ggtacaacat taacaatctg    1140
aaagtgaact tcagaggcca gaacgctaac ctgaaccctc gaatcattac tccaatcaca    1200
ggccgcggcc tggtgaaaaa gattatacgc ttctgtaaaa acattgttag cgtaaaagga    1260
atccgtaaga gcatatgcat tgagatcaac aatggggaac tgtttttcgt ggccagcgag    1320
aatagctaca atgatgacaa tatcaacacc cccaaagaaa tcgatgacac cgtcaccagc    1380
aataacaatt acgagaacga tctggatcag gtgatcctga atttcaacag cgagagcgca    1440
cccggactga gcgatgaaaa gctgaacctg acaatccaga atgacgcata cattccaaaa    1500
tatgacagca atggaactag cgatatcgaa cagcacgacg taaatgagct gaacgtcttc    1560
ttttacctgg atgcccagaa ggtgccggag ggtgagaaca atgtgaatct gactagcagc    1620
atcgacaccg ctctgctgga acagcccaaa atctacactt ttttcagcag cgagttcatt    1680
aataacgtga acaagcccgt tcaagccgct ctgttcgtta gctggattca gcaagtgctg    1740
gtagatttca ctacagaggc gaaccagaaa agcaccgttg ataagatcgc cgacatcagc    1800
attgtcgtgc cttacatcgg gctggccctg aatattggta acgaggcaca gaagggtaat    1860
tttaaagacg ccctggaact gctgggcgcc ggcatcctgc tggagtttga gcccgaactg    1920
ctgattccga caatcctggt gttcacaatc aaaagcttcc tgggcagcag cgataacaag    1980
aacaaggtca taaaagcaat caataacgct ctgaaggaac gggatgagaa gtggaaagaa    2040
gtgtatagct tcatcgtgag caattggatg accaaaataa atacacagtt caataagaga    2100
aaggagcaaa tgtaccaggc cctgcaaaac caggtgaatg ccataaaaac aataatcgaa    2160
agcaagtata atagctacac actggaagag aagaatgagc tgaccaataa atatgacata    2220
aaacaaattg agaacgagct gaatcagaag gtcagcatcg caatgaataa catagacagg    2280
ttcctgaccg agagcagcat cagctacctg atgaagctga tcaatgaagt gaaaattaat    2340
aagctgagag agtatgacga gaatgtcaaa acttacctgc tgaactatat tatccagcac    2400
ggcagcatcc tgggtgaaag ccagcaagag ctgaatagca tggtgacgga tacgctgaat    2460
aacagcattc cctttaagct gagcagctac acagacgata aaattctgat cagctacttc    2520
aacaagtttt tcaagcgaat caagagcagc agcgtgctga acatgcggta caaaaatgat    2580
aaatacgtcg acaccagcgg ctacgacagc aatatcaaca tcaatggcga cgtgtacaag    2640
tatcccacaa acaaaaatca atttggcata tacaacgaca agctgagcga ggtgaacatt    2700
agccagaacg attatattat ctacgacaac aagtataaaa attttagcat cagcttttgg    2760
gtgcgtattc ctaattacga taacaagata gttaatgtaa acaatgagta taccattatc    2820
aactgcatga gggacaacaa tagcgggtgg aaggtgagcc tgaatcataa cgaaattatc    2880
tggaccctgc aggacaacgc aggaatcaac cagaagctgg catttaacta cggcaacgcg    2940
aatggtataa gcgattatat caacaaatgg atattcgtca ctattacgaa tgatcgtctg    3000
ggagatagca aactgtatat caatggcaac ctgatcgatc agaagagcat cctgaacctg    3060
ggcaacatcc acgtcagcga taatattctg ttcaagattg tgaactgcag ctacactcgg    3120
tatatcggga tcaggtattt taacatcttc gataaggaac tggacgaaac cgaaatccaa    3180
accctgtata gcaacgagcc taatacgaat atactgaagg acttttgggg gaattacctg    3240
```

-continued ctgtatgaca aggagtatta cctgctgaat gtcctgaagc cgaataactt tatagatcgg 3300
cgcaaggata gcacgctgag catcaataac attcggagca ctatcctgct ggcaaatcgg 3360
ctgtacagcg ggattaaagt gaaaattcag cgagtcaata acagcagcac caacgataac 3420
ctggttagaa agaacgacca ggtctacatt aattttgttg ccagcaaaac acatctgttt 3480
ccactgtacg ccgatactgc gaccacgaat aaggaaaaga ccatcaagat aagcagcagc 3540
ggaaatagat tcaaccaggt agtggtcatg aacagcgttg gaaacaattg cacaatgaac 3600
tttaaaaaca ataacggaaa taacatcggt ctgctggggt tcaaagctga cacggtagtt 3660
gccagcactt ggtattatac acatatgagg gaccatacca acagcaacgg ctgtttctgg 3720
aactttatta gcgaagagca cggttggcag gaaaaatga 3759

<210> SEQ ID NO 97
<211> LENGTH: 3759
<212> TYPE: DNA
<213> ORGANISM: Artificial Sequence
<220> FEATURE:
<221> NAME/KEY: mat_peptide
<222> LOCATION: (1)...(3756)
<223> OTHER INFORMATION: BoNT/E, H. sapiens-modified 3

<400> SEQUENCE: 97
atgcctaaaa ttaacagttt caattacaac gatccagtga acgataggac cattctgtac 60
atcaaacccg gcgggtgtca ggagttctat aaaagcttta atatcatgaa aaacatctgg 120
atcataccag aaaggaatgt cattggcact acccctcagg actttcaccc acctacttca 180
ctcaaaaatg gggacagctc atattacgat cctaattacc tacaatccga cgaggaaaag 240
gaccgcttcc tgaagatcgt gacgaaaatt tttaacagga ttaacaataa cttgtctggc 300
ggaatcctgc tcgaagagct ttccaaagct aatccttatc ttggtaatga caacactcca 360
gacaaccagt ttcatattgg tgatgcttct gctgtcgaga taaaattttc gaacggtagt 420
caagatatcc tgctcccaaa cgttatcata atgggtgcgg aaccggactt gttcgagacc 480
aacagcagta atatatccct gaggaacaat tatatgccgt caaatcacgg ctttggatcc 540
attgccattg ttacatttag ccccgagtat tcctttcgtt tcaacgacaa tagcatgaat 600
gagtttatcc aggatcccgc actgacctta atgcatgaac ttatacatag ccttcatgga 660
ctgtacggcg ccaagggtat caccacaaaa tatacaatca cccagaaaca aaatcccctt 720
atcaccaaca ttaggggcac aaatatagag gaattcttga catttggtgg gacagatctt 780
aacatcataa cctccgccca gagcaatgac atttatacca acttgttagc ggattacaag 840
aaaattgcct caaagttgtc aaaggttcag gtgagtaacc ccctgcttaa cccgtataag 900
gacgtgttcg aggctaagta tggcttagac aaggacgctt ctgggatata ctctgtgaac 960
atcaataaat ttaatgatat ttttaagaaa ctgtattcct tcactgaatt cgacttggct 1020
accaagttcc aggtgaaatg cagacagact tatatcggcc agtataagta tttcaagctg 1080
agcaatctcc taaacgacag catctacaat atttctgagg gatacaacat caataaccta 1140
aaagtaaatt tccgtggcca gaatgctaat ctcaacccaa ggatcattac cccccataacc 1200 gggagaggcc tcgttaagaa aatcattcgg ttttgtaaga acatcgtcag tgtgaaggga 1260
atccgaaaaa gcatttgtat tgagatcaat aacggtgagc tgtttttcgt ggcctctgag 1320
aattcttata atgatgacaa catcaatacg cctaaagaaa ttgatgacac cgtcacatcg 1380
aataacaatt acgagaacga tttggaccag gtgatcctaa atttcaactc agaatccgcc 1440

-continued

```
cctggcctga gtgatgaaaa actgaacctg acaattcaga acgatgccta tattccgaag   1500
tatgactcca atgggacgtc ggacatcgaa cagcacgatg tgaatgaact aaacgttttc   1560
ttttacctcg acgcccaaaa ggtccctgag ggcgaaaaca atgttaatct gacatcttcc   1620
atagatactg ctttactgga gcagcctaag atttacacct tcttttcgag tgagttcatc   1680
aacaatgtca acaaacccgt tcaagccgca ctgtttgtca gctggataca gcaagtgctg   1740
gtggacttca ccacagaagc caatcaaaag tcaacagtgg acaagatcgc ggatatcagc   1800
atcgtggttc cctacatagg acttgccctg aacatcggaa acgaggcaca gaaagggaac   1860
tttaaagatg cacttgaact gctaggagca gggatccttc tcgagtttga gccagagctc   1920
ctgatcccta cgattctggt tttcactatt aagtctttcc tgggcagttc cgataacaag   1980
aacaaagtca ttaaggccat taataacgct ctgaaagagc gcgatgaaaa gtggaaggaa   2040
gtgtactctt tcatcgtgtc caattggatg actaagatca atacacagtt taataagcga   2100
aaagagcaga tgtaccaggc cttgcagaat caggtgaatg ccattaaaac catcattgaa   2160
agcaaataca atagttacac actcgaagag aaaaacgaac tgactaataa gtatgatatc   2220
aagcaaatcg agaacgagct caaccagaag gtcagtattg caatgaacaa tattgaccgc   2280
tttctaacag agagctccat tagttacctg atgaaactga tcaatgaggt aaaaataaac   2340
aagctgagag aatacgatga gaacgtgaaa acctacctct tgaactacat cattcagcat   2400
gggtcaatcc tgggagaatc tcaacaggag cttaattcga tggtcacaga cacccttaac   2460
aattccatcc cattcaagct ttctagttac acggacgata aaatcctgat atcctatttc   2520
aacaagttct ttaaacggat taagagttcc agtgtcttaa acatgagata taaaaatgat   2580
aagtacgtgg acacctctgg gtatgactct aatatcaata tcaatggcga tgtctacaag   2640
taccccacaa acaaaaacca gttcggaatc tataacgata agctctccga agtaaacatc   2700
agccagaatg actacataat ctacgacaac aagtacaaga actttagcat ttcattctgg   2760
gtgcggattc ccaattatga caacaagatt gtcaacgtaa ataacgagta tacaatcatt   2820
aattgcatgc gagataataa ctccggttgg aaggtgtccc tgaaccacaa tgagataatt   2880
tggactctgc aagacaacgc gggtattaac cagaaactgg catttaacta tggaaacgcc   2940
aatgggatta gcgactacat caataagtgg atatttgtga ctatcacaaa tgaccgcctc   3000
ggcgatagca agctgtacat caatggaaac ctgatcgatc agaagtccat tctgaatttg   3060
ggtaacattc acgtatcaga caatattctg tttaagattg tgaactgttc ttatactcgg   3120
tacatcggaa tacggtattt caacatattt gacaaagagc tggatgagac agaaatccag   3180
accttgtact ccaacgagcc caataccaac atcctgaagg atttctgggg gaactacttg   3240
ctctatgaca aggaatacta tttactcaac gttctgaagc caaataactt cattgataga   3300
cgcaaggatt caaccctctc tattaataac atccgttcta ccatccttct cgccaacaga   3360
ttgtactctg ggatcaaagt gaaaatacag agagtcaaca atagctcaac gaacgacaat   3420
ttggttagga agaacgacca ggtgtatatc aacttcgtgg cttctaaaac tcacttgttt   3480
ccactctacg ccgatactgc taccacgaat aaggagaaaa ccataaagat ttcaagttct   3540
ggcaaccgct tcaatcaggt ggtcgtaatg aactctgtag gcaataactg cacgatgaat   3600
ttcaaaaaca ataacggcaa caatatcgga ctactgggct ttaaggcaga cactgtggtg   3660
gcaagcactt ggtactacac tcatatgcgg gaccacacaa attccaatgg ctgcttctgg   3720
aacttcatca gcgaagagca cgggtggcaa gaaaagtga                         3759
```

-continued

<210> SEQ ID NO 98
<211> LENGTH: 3811
<212> TYPE: DNA
<213> ORGANISM: Artificial Sequence
<220> FEATURE:
<221> NAME/KEY: mat_peptide
<222> LOCATION: (1)...(3811)
<223> OTHER INFORMATION: BoNT/E, E. coli-modified inactive
<400> SEQUENCE: 98
gatatcggat ccgaattcga gctcccatat gcctaaaatc aattcgttca actataatga 60
cccggttaac gatcgcacga tcctgtatat caagccaggt ggatgtcaag aattttataa 120
atcattcaac atcatgaaaa atatttggat tatcccggaa cgcaacgtga tcggcacgac 180
gcctcaagat tttcacccgc cgacctccct gaaaaatggc gacagttcct actatgaccc 240
gaattattta caatcggatg aagaaaaaga tcgtttcctc aagatcgtca cgaaaatttt 300
caaccgcatc aataacaatc tgtccggtgg catcttactt gaggaattat ctaaagctaa 360
tccgtatctg gggaacgata ataccccgga taatcagttc cacattggcg atgcgagcgc 420
tgtggaaatt aaattcagca acggcagtca agatattctt ctcccaaacg tgattatcat 480
gggggctgaa cctgatcttt tcgaaactaa tagttccaat atttcactgc gcaataatta 540
tatgccgtcg aaccatcgct ttggctcaat cgcaattgtg acgttctcac ctgaatatag 600
ttttcgtttt aacgacaact gcatgaatga atttatccaa gacccggcgc tgactttgat 660
gcatgaactg atccatagct tgcacggcct gtatggcgct aaaggcatca ctaccaaata 720
cacgattacg caaaaacaaa atcccttaat caccaacatc cgcggcacca acattgaaga 780
atttctgacc ttcggcggaa cggatctgaa catcattaca tctgcccaaa gcaacgacat 840
ctataccaat ctgttagcag attataagaa aatcgccagc aaattatcta aagttcaggt 900
cagcaatccg ctgttaaacc cgtataaaga tgtgttcgaa gcgaaatacg gcttggacaa 960
agacgctagt ggcatctatt ccgtcaatat taataaattt aacgatattt tcaaaaaatt 1020
atattccttc accgaatttg atttgcgcac caaattccag gtcaaatgtc gtcaaaccta 1080
tattggccaa tacaaatatt ttaaactgag caacctgctt aatgattcca tctacaatat 1140
tagtgaaggt tacaatatta ataacctgaa agttaacttt cgtgggcaaa atgcgaatct 1200
gaacccccgc atcattacac ccatcacggg ccgtgggttg gtcaaaaaaa ttattcgctt 1260
ttgtaagaat atcgtgagcg tgaagggtat tcgcaaaagt atctgtatcg aaatcaataa 1320
tggcgaactg tttttcgtcg catctgaaaa ctcgtataac gatgacaata tcaacacacc 1380
gaaagaaatt gatgacactg tcacttctaa caacaattac gaaaacgacc tggaccaggt 1440
gatcctcaat ttcaatagcg aaagcgcacc cggcctgagc gatgaaaaac ttaatctcac 1500
gattcagaac gacgcctaca ttccaaaata cgatagtaat ggtacatctg atattgaaca 1560
gcatgatgtc aacgaattaa atgttttctt ttacctcgat gcccagaaag tgccggaagg 1620
tgagaacaac gtaaatctga cctcttcgat tgatacggca ttattagaac agccgaaaat 1680
ttatactttc ttttcgtccg aatttattaa caatgttaac aaaccggttc aagcggcgtt 1740
attcgtttcc tggattcagc aagttcttgt agattttaca accgaggcta atcagaagag 1800
cacggtggat aagatcgccg acatcagcat cgtcgtgccc tacattggtt tggcattaaa 1860
cattggtaat gaggcgcaaa aggggaactt taaagacgcc ctggaattat taggagcagg 1920
tattctgctg gagttcgaac ctgagctgct gattccgact attttagtgt tcaccattaa 1980
atccttctta ggctctagtg acaacaaaaa taaagtgatt aaagcgatca ataatgccct 2040

-continued

```
taaagaacgt gatgagaaat ggaaagaagt ctactccttc attgtctcaa attggatgac   2100

gaaaatcaac acgcagttta ataaacgcaa agaacagatg tatcaggcgc tgcaaaacca   2160

ggttaatgcg atcaagacaa ttattgaatc taagtacaac tcgtacaccc tggaggagaa   2220

aaatgaactg actaataagt acgatattaa acaaatcgaa aacgaattga atcagaaagt   2280

ctccatcgct atgaacaata tcgatcgctt tctgaccgaa agctctattt cctatttgat   2340

gaaaattatc aatgaagtca aaatcaacaa acttcgcgaa tatgatgaga acgtaaaaac   2400

gtacctgctc aattatatta ttcaacatgg gtcgattctg ggcgagtctc aacaagaatt   2460

gaactcgatg gtgacggata ctttgaataa ctcgattccg tttaaattat cgtcatacac   2520

cgatgataaa attcttatct cgtacttcaa caaattcttt aagcggatca aaagcagcag   2580

cgtccttaat atgcgctata aaacgataa gtacgtagat acgtctggat acgacagtaa   2640

cattaatatt aatggggacg tctataaata tccgacaaat aaaaaccaat tcgggattta   2700

taatgataaa ctttcggagg tgaacatcag ccagaacgat tatattattt acgataataa   2760

atacaaaaac ttcagcattt ctttttgggt gcgtatccca aattacgaca acaaaattgt   2820

gaacgtgaat aacgaataca cgatcattaa ttgcatgcgc gataacaatt ctggttggaa   2880

agttagcctg aatcacaatg agattatctg gacttttgag gacaatcgtg gtatcaacca   2940

aaaattagcg ttcaactacg gtaatgccaa cggtatttct gactacatca ataagtggat   3000

ctttgtgacc atcaccaatg accgcctcgg cgatagcaag ctgtacatta acggtaacct   3060

gatcgaccag aaatctattc tgaacctggg taacattcac gtaagtgaca acatcctttt   3120

taaaattgtc aattgctcgt atactcgtta tatcggcatt cgctatttca atattttcga   3180

caaagaactg gatgagacgg aaatccagac tctgtattct aacgaaccga acaccaacat   3240

cctgaaggac ttttgggggga attatcttct ctacgataaa gagtactacc ttcttaacgt   3300

gttgaagccg aacaacttca ttgatcgtcg taaggatagc accttgagca ttaacaacat   3360

tcgtagcacc attttactgg caaaccgcct gtacagcggc attaaagtca aaattcagcg   3420

tgtcaataac tccagtacga atgacaatct ggtgcggaaa aatgaccaag tctatattaa   3480

ctttgtcgca agcaaaactc acctctttcc attatatgcg gatacagcta ccaccaataa   3540

agaaaaaact attaaaatct cctcttccgg gaaccgcttt aatcaggtgg tagttatgaa   3600

ctcggtcggc aattgtacta tgaattttaa aaataataac ggcaataaca tcggcctgct   3660

gggcttcaaa gctgatacag ttgtggccag cacctggtat tacacccaca tgcgtgatca   3720

taccaatagt aatggctgct tttggaattt tatttctgaa gagcacggct ggcaagaaaa   3780

ataagtcgac aagcttgcgg ccgcactcga g                                 3811
```

<210> SEQ ID NO 99
<211> LENGTH: 40
<212> TYPE: DNA
<213> ORGANISM: Artificial Sequence
<220> FEATURE:
<221> NAME/KEY: primer_bind
<222> LOCATION: (1)...(40)
<223> OTHER INFORMATION: Synthetic DNA oligonucleotide used as sense primer for R177G site-directed mutagenesis

<400> SEQUENCE: 99

```
tatatgccgt cgaaccatgg ctttggctca atcgcaattg                        40
```

<210> SEQ ID NO 100
<211> LENGTH: 40
<212> TYPE: DNA

-continued

<213> ORGANISM: Artificial Sequence
<220> FEATURE:
<221> NAME/KEY: primer_bind
<222> LOCATION: (1)...(40)
<223> OTHER INFORMATION: Synthetic DNA oligonucleotide used as antisense primer for R177G site-directed mutagenesis

<400> SEQUENCE: 100
caattgcgat tgagccaaag ccatggttcg acggcatata 40

<210> SEQ ID NO 101
<211> LENGTH: 34
<212> TYPE: DNA
<213> ORGANISM: Artificial Sequence
<220> FEATURE:
<221> NAME/KEY: primer_bind
<222> LOCATION: (1)...(34)
<223> OTHER INFORMATION: Synthetic DNA oligonucleotide used as sense primer for C198S site-directed mutagenesis

<400> SEQUENCE: 101
cgttttaacg acaacagcat gaatgaattt atcc 34

<210> SEQ ID NO 102
<211> LENGTH: 34
<212> TYPE: DNA
<213> ORGANISM: Artificial Sequence
<220> FEATURE:
<221> NAME/KEY: primer_bind
<222> LOCATION: (1)...(34)
<223> OTHER INFORMATION: Synthetic DNA oligonucleotide used as antisense primer for C198S site-directed mutagenesis

<400> SEQUENCE: 102
ggataaattc attcatgctg ttgtcgttaa aacg 34

<210> SEQ ID NO 103
<211> LENGTH: 40
<212> TYPE: DNA
<213> ORGANISM: Artificial Sequence
<220> FEATURE:
<221> NAME/KEY: primer_bind
<222> LOCATION: (1)...(40)
<223> OTHER INFORMATION: Synthetic DNA oligonucleotide used as sense primer for R340A site-directed mutagenesis

<400> SEQUENCE: 103
ccttcaccga atttgatttg gccaccaaat tccaggtcaa 40

<210> SEQ ID NO 104
<211> LENGTH: 40
<212> TYPE: DNA
<213> ORGANISM: Artificial Sequence
<220> FEATURE:
<221> NAME/KEY: primer_bind
<222> LOCATION: (1)...(40)
<223> OTHER INFORMATION: Synthetic DNA oligonucleotide used as antisense primer for R340A site-directed mutagenesis

<400> SEQUENCE: 104
ttgacctgga atttggtggc caaatcaaat tcggtgaagg 40

<210> SEQ ID NO 105
<211> LENGTH: 38
<212> TYPE: DNA
<213> ORGANISM: Artificial Sequence
<220> FEATURE:
<221> NAME/KEY: primer_bind
<222> LOCATION: (1)...(38)

<223> OTHER INFORMATION: Synthetic DNA oligonucleotide used as sense
primer for I773L site-directed mutagenesis

<400> SEQUENCE: 105
ctatttccta tttgatgaaa cttatcaatg aagtcaaa 38

<210> SEQ ID NO 106
<211> LENGTH: 38
<212> TYPE: DNA
<213> ORGANISM: Artificial Sequence
<220> FEATURE:
<221> NAME/KEY: primer_bind
<222> LOCATION: (1)...(38)
<223> OTHER INFORMATION: Synthetic DNA oligonucleotide used as antisense
primer for I773L site-directed mutagenesis

<400> SEQUENCE: 106
tttgacttca ttgataagtt tcatcaaata ggaaatag 38

<210> SEQ ID NO 107
<211> LENGTH: 45
<212> TYPE: DNA
<213> ORGANISM: Artificial Sequence
<220> FEATURE:
<221> NAME/KEY: primer_bind
<222> LOCATION: (1)...(45)
<223> OTHER INFORMATION: Synthetic DNA oligonucleotide used as sense
primer for F963L/E964Q/R967A site-directed mutagenesis

<400> SEQUENCE: 107
tatctggact cttcaggaca atgctggtat caaccaaaaa ttagc 45

<210> SEQ ID NO 108
<211> LENGTH: 45
<212> TYPE: DNA
<213> ORGANISM: Artificial Sequence
<220> FEATURE:
<221> NAME/KEY: primer_bind
<222> LOCATION: (1)...(45)
<223> OTHER INFORMATION: Synthetic DNA oligonucleotide used as antisense
primer for F963L/E964Q/R967A site-directed
mutagenesis

<400> SEQUENCE: 108
gctaattttt ggttgatacc agcattgtcc tgaagagtcc agata 45

<210> SEQ ID NO 109
<211> LENGTH: 36
<212> TYPE: DNA
<213> ORGANISM: Artificial Sequence
<220> FEATURE:
<221> NAME/KEY: primer_bind
<222> LOCATION: (1)...(36)
<223> OTHER INFORMATION: Synthetic DNA oligonucleotide used as sense
primer for +N1196 site-directed mutagenesis

<400> SEQUENCE: 109
gttatgaact cggtcggcaa caattgtact atgaat 36

<210> SEQ ID NO 110
<211> LENGTH: 36
<212> TYPE: DNA
<213> ORGANISM: Artificial Sequence
<220> FEATURE:
<221> NAME/KEY: primer_bind
<222> LOCATION: (1)...(36)
<223> OTHER INFORMATION: Synthetic DNA oligonucleotide used as antisense
primer for +N1196 site-directed mutagenesis -continued

<400> SEQUENCE: 110
attcatagta caattgttgc cgaccgagtt cataac 36

<210> SEQ ID NO 111
<211> LENGTH: 43
<212> TYPE: DNA
<213> ORGANISM: Artificial Sequence
<220> FEATURE:
<221> NAME/KEY: primer_bind
<222> LOCATION: (1)...(43)
<223> OTHER INFORMATION: Synthetic DNA oligonucleotide used as sense primer for H216Y site-directed mutagenesis

<400> SEQUENCE: 111
gctgactttg atgcatgaac tgatctatag cttgcacggc ctg 43

<210> SEQ ID NO 112
<211> LENGTH: 43
<212> TYPE: DNA
<213> ORGANISM: Artificial Sequence
<220> FEATURE:
<221> NAME/KEY: primer_bind
<222> LOCATION: (1)...(43)
<223> OTHER INFORMATION: Synthetic DNA oligonucleotide used as antisense primer for H216Y site-directed mutagenesis

<400> SEQUENCE: 112
caggccgtgc aagctataga tcagttcatg catcaaagtc agc 43

<210> SEQ ID NO 113
<211> LENGTH: 43
<212> TYPE: DNA
<213> ORGANISM: Artificial Sequence
<220> FEATURE:
<221> NAME/KEY: primer_bind
<222> LOCATION: (1)...(43)
<223> OTHER INFORMATION: Synthetic DNA oligonucleotide used as sense primer for E213Q site-directed mutagenesis

<400> SEQUENCE: 113
gctgactttg atgcatcaac tgatccatag cttgcacggc ctg 43

<210> SEQ ID NO 114
<211> LENGTH: 43
<212> TYPE: DNA
<213> ORGANISM: Artificial Sequence
<220> FEATURE:
<221> NAME/KEY: primer_bind
<222> LOCATION: (1)...(43)
<223> OTHER INFORMATION: Synthetic DNA oligonucleotide used as antisense primer for E213Q site-directed mutagenesis

<400> SEQUENCE: 114
caggccgtgc aagctatgga tcagttgatg catcaaagtc agc 43

<210> SEQ ID NO 115
<211> LENGTH: 43
<212> TYPE: DNA
<213> ORGANISM: Artificial Sequence
<220> FEATURE:
<221> NAME/KEY: primer_bind
<222> LOCATION: (1)...(43)
<223> OTHER INFORMATION: Synthetic DNA oligonucleotide used as sense primer for Q213E site-directed mutagenesis

<400> SEQUENCE: 115
gctgactttg atgcatgaac tgatccatag cttgcacggc ctg 43

-continued

<210> SEQ ID NO 116
<211> LENGTH: 43
<212> TYPE: DNA
<213> ORGANISM: Artificial Sequence
<220> FEATURE:
<221> NAME/KEY: primer_bind
<222> LOCATION: (1)...(43)
<223> OTHER INFORMATION: Synthetic DNA oligonucleotide used as antisense primer for Q213E site-directed mutagenesis
<400> SEQUENCE: 116
caggccgtgc aagctatgga tcagttcatg catcaaagtc agc 43

<210> SEQ ID NO 117
<211> LENGTH: 3814
<212> TYPE: DNA
<213> ORGANISM: Artificial Sequence
<220> FEATURE:
<221> NAME/KEY: mat_peptide
<222> LOCATION: (1)...(3814)
<223> OTHER INFORMATION: BoNT/E, E. coli-modified active
<400> SEQUENCE: 117
gatatcggat ccgaattcga gctcccatat gcctaaaatc aattcgttca actataatga 60
cccggttaac gatcgcacga tcctgtatat caagccaggt ggatgtcaag aattttataa 120
atcattcaac atcatgaaaa atatttggat tatcccggaa cgcaacgtga tcggcacgac 180
gcctcaagat tttcacccgc cgacctccct gaaaaatggc gacagttcct actatgaccc 240
gaattattta caatcggatg aagaaaaaga tcgtttcctc aagatcgtca cgaaaatttt 300
caaccgcatc aataacaatc tgtccggtgg catcttactt gaggaattat ctaaagctaa 360
tccgtatctg gggaacgata ataccccgga taatcagttc cacattggcg atgcgagcgc 420
tgtggaaatt aaattcagca acggcagtca agatattctt ctcccaaacg tgattatcat 480
gggggctgaa cctgatcttt tcgaaactaa tagttccaat atttcactgc gcaataatta 540
tatgccgtcg aaccatggct ttggctcaat cgcaattgtg acgttctcac ctgaatatag 600
ttttcgtttt aacgacaaca gcatgaatga atttatccaa gacccggcgc tgactttgat 660
gcatgaactg atccatagct tgcacggcct gtatggcgct aaaggcatca ctaccaaata 720
cacgattacg caaaaacaaa atcccttaat caccaacatc cgcggcacca acattgaaga 780
atttctgacc ttcggcggaa cggatctgaa catcattaca tctgcccaaa gcaacgacat 840
ctataccaat ctgttagcag attataagaa aatcgccagc aaattatcta aagttcaggt 900
cagcaatccg ctgttaaacc cgtataaaga tgtgttcgaa gcgaaatacg gcttggacaa 960
agacgctagt ggcatctatt ccgtcaatat taataaattt aacgatattt tcaaaaaatt 1020
atattccttc accgaatttg atttggccac caaattccag gtcaaatgtc gtcaaaccta 1080
tattggccaa tacaaatatt ttaaactgag caacctgctt aatgattcca tctacaatat 1140
tagtgaaggt tacaatatta ataacctgaa agttaacttt cgtgggcaaa atgcgaatct 1200
gaacccccgc atcattacac ccatcacggg ccgtgggttg gtcaaaaaaa ttattcgctt 1260
ttgtaagaat atcgtgagcg tgaagggtat tcgcaaaagt atctgtatcg aaatcaataa 1320
tggcgaactg tttttcgtcg catctgaaaa ctcgtataac gatgacaata tcaacacacc 1380
gaaagaaatt gatgacactg tcacttctaa caacaattac gaaaacgacc tggaccaggt 1440
gatcctcaat ttcaatagcg aaagcgcacc cggcctgagc gatgaaaaac ttaatctcac 1500
gattcagaac gacgcctaca ttccaaaata cgatagtaat ggtacatctg atattgaaca 1560

-continued

```
gcatgatgtc aacgaattaa atgttttctt ttacctcgat gcccagaaag tgccggaagg   1620
tgagaacaac gtaaatctga cctcttcgat tgatacggca ttattagaac agccgaaaat   1680
ttatactttc ttttcgtccg aatttattaa caatgttaac aaaccggttc aagcggcgtt   1740
attcgtttcc tggattcagc aagttcttgt agattttaca accgaggcta atcagaagag   1800
cacggtggat aagatcgccg acatcagcat cgtcgtgccc tacattggtt tggcattaaa   1860
cattggtaat gaggcgcaaa aggggaactt taaagacgcc ctggaattat taggagcagg   1920
tattctgctg gagttcgaac ctgagctgct gattccgact attttagtgt tcaccattaa   1980
atccttctta ggctctagtg acaacaaaaa taaagtgatt aaagcgatca ataatgccct   2040
taaagaacgt gatgagaaat ggaaagaagt ctactccttc attgtctcaa attggatgac   2100
gaaaatcaac acgcagttta ataaacgcaa agaacagatg tatcaggcgc tgcaaaacca   2160
ggttaatgcg atcaagacaa ttattgaatc taagtacaac tcgtacaccc tggaggagaa   2220
aaatgaactg actaataagt acgatattaa acaaatcgaa aacgaattga atcagaaagt   2280
ctccatcgct atgaacaata tcgatcgctt tctgaccgaa agctctattt cctatttgat   2340
gaaacttatc aatgaagtca aaatcaacaa acttcgcgaa tatgatgaga acgtaaaaac   2400
gtacctgctc aattatatta ttcaacatgg gtcgattctg ggcgagtctc aacaagaatt   2460
gaactcgatg gtgacggata ctttgaataa ctcgattccg tttaaattat cgtcatacac   2520
cgatgataaa attcttatct cgtacttcaa caaattcttt aagcggatca aaagcagcag   2580
cgtccttaat atgcgctata aaaacgataa gtacgtagat acgtctggat acgacagtaa   2640
cattaatatt aatggggacg tctataaata tccgacaaat aaaaaccaat tcgggattta   2700
taatgataaa ctttcggagg tgaacatcag ccagaacgat tatattattt acgataataa   2760
atacaaaaac ttcagcattt ctttttgggt gcgtatccca aattacgaca acaaaattgt   2820
gaacgtgaat aacgaataca cgatcattaa ttgcatgcgc gataacaatt ctggttggaa   2880
agttagcctg aatcacaatg agattatctg gactcttcag gacaatgctg gtatcaacca   2940
aaaattagcg ttcaactacg gtaatgccaa cggtatttct gactacatca ataagtggat   3000
ctttgtgacc atcaccaatg accgcctcgg cgatagcaag ctgtacatta acggtaacct   3060
gatcgaccag aaatctattc tgaacctggg taacattcac gtaagtgaca acatcctttt   3120
taaaattgtc aattgctcgt atactcgtta tatcggcatt cgctatttca atattttcga   3180
caaagaactg gatgagacgg aaatccagac tctgtattct aacgaaccga acaccaacat   3240
cctgaaggac ttttggggga attatcttct ctacgataaa gagtactacc ttcttaacgt   3300
gttgaagccg aacaacttca ttgatcgtcg taaggatagc accttgagca ttaacaacat   3360
tcgtagcacc attttactgg caaaccgcct gtacagcggc attaaagtca aaattcagcg   3420
tgtcaataac tccagtacga atgacaatct ggtgcggaaa aatgaccaag tctatattaa   3480
ctttgtcgca agcaaaactc acctctttcc attatatgcg gatacagcta ccaccaataa   3540
agaaaaaact attaaaatct cctcttccgg gaaccgcttt aatcaggtgg tagttatgaa   3600
ctcggtcggc aacaattgta ctatgaattt taaaaataat aacggcaata acatcggcct   3660
gctgggcttc aaagctgata cagttgtggc cagcacctgg tattacaccc acatgcgtga   3720
tcataccaat agtaatggct gcttttggaa ttttatttct gaagagcacg gctggcaaga   3780
aaaataagtc gacaagcttg cggccgcact cgag                               3814
```

<210> SEQ ID NO 118
<211> LENGTH: 3814

-continued

<212> TYPE: DNA
<213> ORGANISM: Artificial Sequence
<220> FEATURE:
<221> NAME/KEY: mat_peptide
<222> LOCATION: (1)...(3814)
<223> OTHER INFORMATION: BoNT/E, E.coli-modified, H216

<400> SEQUENCE: 118
gatatcggat ccgaattcga gctcccatat gcctaaaatc aattcgttca actataatga 60
cccggttaac gatcgcacga tcctgtatat caagccaggt ggatgtcaag aattttataa 120
atcattcaac atcatgaaaa atatttggat tatcccggaa cgcaacgtga tcggcacgac 180
gcctcaagat tttcacccgc cgacctccct gaaaaatggc gacagttcct actatgaccc 240
gaattattta caatcggatg aagaaaaaga tcgtttcctc aagatcgtca cgaaaatttt 300
caaccgcatc aataacaatc tgtccggtgg catcttactt gaggaattat ctaaagctaa 360
tccgtatctg gggaacgata ataccccgga taatcagttc cacattggcg atgcgagcgc 420
tgtggaaatt aaattcagca acggcagtca agatattctt ctcccaaacg tgattatcat 480
gggggctgaa cctgatcttt tcgaaactaa tagttccaat atttcactgc gcaataatta 540
tatgccgtcg aaccatggct ttggctcaat cgcaattgtg acgttctcac ctgaatatag 600
ttttcgtttt aacgacaaca gcatgaatga atttatccaa gacccggcgc tgactttgat 660
gcatgaactg atctatagct tgcacggcct gtatggcgct aaaggcatca ctaccaaata 720
cacgattacg caaaaacaaa atcccttaat caccaacatc cgcggcacca acattgaaga 780
atttctgacc ttcggcggaa cggatctgaa catcattaca tctgcccaaa gcaacgacat 840
ctataccaat ctgttagcag attataagaa aatcgccagc aaattatcta aagttcaggt 900
cagcaatccg ctgttaaacc cgtataaaga tgtgttcgaa gcgaaatacg gcttggacaa 960
agacgctagt ggcatctatt ccgtcaatat taataaattt aacgatattt tcaaaaaatt 1020
atattccttc accgaatttg atttggccac caaattccag gtcaaatgtc gtcaaaccta 1080
tattggccaa tacaaatatt ttaaactgag caacctgctt aatgattcca tctacaatat 1140
tagtgaaggt tacaatatta ataacctgaa agttaacttt cgtgggcaaa atgcgaatct 1200
gaacccccgc atcattacac ccatcacggg ccgtgggttg gtcaaaaaaa ttattcgctt 1260
ttgtaagaat atcgtgagcg tgaagggtat tcgcaaaagt atctgtatcg aaatcaataa 1320
tggcgaactg tttttcgtcg catctgaaaa ctcgtataac gatgacaata tcaacacacc 1380
gaaagaaatt gatgacactg tcacttctaa caacaattac gaaaacgacc tggaccaggt 1440
gatcctcaat ttcaatagcg aaagcgcacc cggcctgagc gatgaaaaac ttaatctcac 1500
gattcagaac gacgcctaca ttccaaaata cgatagtaat ggtacatctg atattgaaca 1560
gcatgatgtc aacgaattaa atgttttctt ttacctcgat gcccagaaag tgccggaagg 1620
tgagaacaac gtaaatctga cctcttcgat tgatacggca ttattagaac agccgaaaat 1680
ttatactttc ttttcgtccg aatttattaa caatgttaac aaaccggttc aagcggcgtt 1740
attcgtttcc tggattcagc aagttcttgt agattttaca accgaggcta atcagaagag 1800
cacggtggat aagatcgccg acatcagcat cgtcgtgccc tacattggtt tggcattaaa 1860
cattggtaat gaggcgcaaa aggggaactt taaagacgcc ctggaattat taggagcagg 1920
tattctgctg gagttcgaac ctgagctgct gattccgact attttagtgt tcaccattaa 1980
atccttctta ggctctagtg acaacaaaaa taaagtgatt aaagcgatca ataatgccct 2040
taaagaacgt gatgagaaat ggaaagaagt ctactccttc attgtctcaa attggatgac 2100

-continued gaaaatcaac acgcagttta ataaacgcaa agaacagatg tatcaggcgc tgcaaaacca 2160
ggttaatgcg atcaagacaa ttattgaatc taagtacaac tcgtacaccc tggaggagaa 2220
aaatgaactg actaataagt acgatattaa acaaatcgaa aacgaattga atcagaaagt 2280
ctccatcgct atgaacaata tcgatcgctt tctgaccgaa agctctattt cctatttgat 2340
gaaacttatc aatgaagtca aaatcaacaa acttcgcgaa tatgatgaga acgtaaaaac 2400
gtacctgctc aattatatta ttcaacatgg gtcgattctg ggcgagtctc aacaagaatt 2460
gaactcgatg gtgacggata ctttgaataa ctcgattccg tttaaattat cgtcatacac 2520
cgatgataaa attcttatct cgtacttcaa caaattcttt aagcggatca aaagcagcag 2580
cgtccttaat atgcgctata aaaacgataa gtacgtagat acgtctggat acgacagtaa 2640
cattaatatt aatggggacg tctataaata tccgacaaat aaaaaccaat tcgggattta 2700
taatgataaa ctttcggagg tgaacatcag ccagaacgat tatattattt acgataataa 2760
atacaaaaac ttcagcattt ctttttgggt gcgtatccca aattacgaca acaaaattgt 2820
gaacgtgaat aacgaataca cgatcattaa ttgcatgcgc gataacaatt ctggttggaa 2880
agttagcctg aatcacaatg agattatctg gactcttcag gacaatgctg gtatcaacca 2940
aaaattagcg ttcaactacg gtaatgccaa cggtatttct gactacatca ataagtggat 3000
ctttgtgacc atcaccaatg accgcctcgg cgatagcaag ctgtacatta acggtaacct 3060
gatcgaccag aaatctattc tgaacctggg taacattcac gtaagtgaca acatcctttt 3120
taaaattgtc aattgctcgt atactcgtta tatcggcatt cgctatttca atattttcga 3180
caaagaactg gatgagacgg aaatccagac tctgtattct aacgaaccga acaccaacat 3240
cctgaaggac ttttggggga attatcttct ctacgataaa gagtactacc ttcttaacgt 3300
gttgaagccg aacaacttca ttgatcgtcg taaggatagc accttgagca ttaacaacat 3360
tcgtagcacc attttactgg caaaccgcct gtacagcggc attaaagtca aaattcagcg 3420
tgtcaataac tccagtacga atgacaatct ggtgcggaaa aatgaccaag tctatattaa 3480
ctttgtcgca agcaaaactc acctctttcc attatatgcg gatacagcta ccaccaataa 3540
agaaaaaact attaaaatct cctcttccgg gaaccgcttt aatcaggtgg tagttatgaa 3600
ctcggtcggc aacaattgta ctatgaattt taaaaataat aacggcaata acatcggcct 3660
gctgggcttc aaagctgata cagttgtggc cagcacctgg tattacaccc acatgcgtga 3720
tcataccaat agtaatggct gcttttggaa ttttatttct gaagagcacg gctggcaaga 3780
aaaataagtc gacaagcttg cggccgcact cgag 3814

<210> SEQ ID NO 119
<211> LENGTH: 3814
<212> TYPE: DNA
<213> ORGANISM: Artificial Sequence
<220> FEATURE:
<221> NAME/KEY: mat_peptide
<222> LOCATION: (1)...(3814)
<223> OTHER INFORMATION: BoNT/E E.coli-modified, E213

<400> SEQUENCE: 119
gatatcggat ccgaattcga gctcccatat gcctaaaatc aattcgttca actataatga 60
cccggttaac gatcgcacga tcctgtatat caagccaggt ggatgtcaag aattttataa 120
atcattcaac atcatgaaaa atatttggat tatcccggaa cgcaacgtga tcggcacgac 180
gcctcaagat tttcacccgc cgacctccct gaaaaatggc gacagttcct actatgaccc 240
gaattattta caatcggatg aagaaaaaga tcgtttcctc aagatcgtca cgaaaatttt 300

-continued

```
caaccgcatc aataacaatc tgtccggtgg catcttactt gaggaattat ctaaagctaa    360
tccgtatctg gggaacgata ataccccgga taatcagttc cacattggcg atgcgagcgc    420
tgtggaaatt aaattcagca acggcagtca agatattctt ctcccaaacg tgattatcat    480
gggggctgaa cctgatcttt tcgaaactaa tagttccaat atttcactgc gcaataatta    540
tatgccgtcg aaccatggct ttggctcaat cgcaattgtg acgttctcac ctgaatatag    600
ttttcgtttt aacgacaaca gcatgaatga atttatccaa gacccggcgc tgactttgat    660
gcatcaactg atccatagct tgcacggcct gtatggcgct aaaggcatca ctaccaaata    720
cacgattacg caaaaacaaa atcccttaat caccaacatc cgcggcacca acattgaaga    780
atttctgacc ttcggcggaa cggatctgaa catcattaca tctgcccaaa gcaacgacat    840
ctataccaat ctgttagcag attataagaa aatcgccagc aaattatcta aagttcaggt    900
cagcaatccg ctgttaaacc cgtataaaga tgtgttcgaa gcgaaatacg gcttggacaa    960
agacgctagt ggcatctatt ccgtcaatat taataaattt aacgatattt tcaaaaaatt   1020
atattccttc accgaatttg atttggccac caaattccag gtcaaatgtc gtcaaaccta   1080
tattggccaa tacaaatatt ttaaactgag caacctgctt aatgattcca tctacaatat   1140
tagtgaaggt tacaatatta ataacctgaa agttaacttt cgtgggcaaa atgcgaatct   1200
gaaccccgc atcattacac ccatcacggg ccgtgggttg gtcaaaaaaa ttattcgctt   1260
ttgtaagaat atcgtgagcg tgaagggtat tcgcaaaagt atctgtatcg aaatcaataa   1320
tggcgaactg tttttcgtcg catctgaaaa ctcgtataac gatgacaata tcaacacacc   1380
gaaagaaatt gatgacactg tcacttctaa caacaattac gaaaacgacc tggaccaggt   1440
gatcctcaat ttcaatagcg aaagcgcacc cggcctgagc gatgaaaaac ttaatctcac   1500
gattcagaac gacgcctaca ttccaaaata cgatagtaat ggtacatctg atattgaaca   1560
gcatgatgtc aacgaattaa atgttttctt ttacctcgat gcccagaaag tgccggaagg   1620
tgagaacaac gtaaatctga cctcttcgat tgatacggca ttattagaac agccgaaaat   1680
ttatactttc ttttcgtccg aatttattaa caatgttaac aaaccggttc aagcggcgtt   1740
attcgtttcc tggattcagc aagttcttgt agattttaca accgaggcta atcagaagag   1800
cacggtggat aagatcgccg acatcagcat cgtcgtgccc tacattggtt tggcattaaa   1860
cattggtaat gaggcgcaaa aggggaactt taaagacgcc ctggaattat taggagcagg   1920
tattctgctg gagttcgaac ctgagctgct gattccgact attttagtgt tcaccattaa   1980
atccttctta ggctctagtg acaacaaaaa taaagtgatt aaagcgatca ataatgccct   2040
taaagaacgt gatgagaaat ggaaagaagt ctactccttc attgtctcaa attggatgac   2100
gaaaatcaac acgcagttta ataaacgcaa agaacagatg tatcaggcgc tgcaaaacca   2160
ggttaatgcg atcaagacaa ttattgaatc taagtacaac tcgtacaccc tggaggagaa   2220
aaatgaactg actaataagt acgatattaa acaaatcgaa aacgaattga atcagaaagt   2280
ctccatcgct atgaacaata tcgatcgctt tctgaccgaa agctctattt cctatttgat   2340
gaaacttatc aatgaagtca aaatcaacaa acttcgcgaa tatgatgaga acgtaaaaac   2400
gtacctgctc aattatatta ttcaacatgg gtcgattctg ggcgagtctc aacaagaatt   2460
gaactcgatg gtgacggata ctttgaataa ctcgattccg tttaaattat cgtcatacac   2520
cgatgataaa attcttatct cgtacttcaa caaattcttt aagcggatca aaagcagcag   2580
cgtccttaat atgcgctata aaaacgataa gtacgtagat acgtctggat acgacagtaa   2640
```

-continued

```
cattaatatt aatggggacg tctataaata tccgacaaat aaaaaccaat tcgggattta   2700

taatgataaa ctttcggagg tgaacatcag ccagaacgat tatattattt acgataataa   2760

atacaaaaac ttcagcattt ctttttgggt gcgtatccca aattacgaca acaaaattgt   2820

gaacgtgaat aacgaataca cgatcattaa ttgcatgcgc gataacaatt ctggttggaa   2880

agttagcctg aatcacaatg agattatctg gactcttcag gacaatgctg gtatcaacca   2940

aaaattagcg ttcaactacg gtaatgccaa cggtatttct gactacatca ataagtggat   3000

ctttgtgacc atcaccaatg accgcctcgg cgatagcaag ctgtacatta acggtaacct   3060

gatcgaccag aaatctattc tgaacctggg taacattcac gtaagtgaca acatcctttt   3120

taaaattgtc aattgctcgt atactcgtta tatcggcatt cgctatttca atattttcga   3180

caaagaactg gatgagacgg aaatccagac tctgtattct aacgaaccga acaccaacat   3240

cctgaaggac ttttggggga attatcttct ctacgataaa gagtactacc ttcttaacgt   3300

gttgaagccg aacaacttca ttgatcgtcg taaggatagc accttgagca ttaacaacat   3360

tcgtagcacc attttactgg caaaccgcct gtacagcggc attaaagtca aaattcagcg   3420

tgtcaataac tccagtacga atgacaatct ggtgcggaaa aatgaccaag tctatattaa   3480

ctttgtcgca agcaaaactc acctctttcc attatatgcg gatacagcta ccaccaataa   3540

agaaaaaact attaaaatct cctcttccgg gaaccgcttt aatcaggtgg tagttatgaa   3600

ctcggtcggc aacaattgta ctatgaattt taaaaataat aacggcaata acatcggcct   3660

gctgggcttc aaagctgata cagttgtggc cagcacctgg tattacaccc acatgcgtga   3720

tcataccaat agtaatggct gcttttggaa ttttatttct gaagagcacg gctggcaaga   3780

aaaataagtc gacaagcttg cggccgcact cgag                               3814
```

```
<210> SEQ ID NO 120
<211> LENGTH: 35
<212> TYPE: DNA
<213> ORGANISM: Artificial Sequence
<220> FEATURE:
<221> NAME/KEY: primer_bind
<222> LOCATION: (1)...(35)
<223> OTHER INFORMATION: Synthetic DNA oligonucleotide used as sense
      primer for CtermHis

<400> SEQUENCE: 120

ccgccagctt gtcgactttt tcttgccagc cgtgc                              35


<210> SEQ ID NO 121
<211> LENGTH: 35
<212> TYPE: DNA
<213> ORGANISM: Artificial Sequence
<220> FEATURE:
<221> NAME/KEY: primer_bind
<222> LOCATION: (1)...(35)
<223> OTHER INFORMATION: Synthetic DNA oligonucleotide used as antisense
      primer for CtermHis

<400> SEQUENCE: 121

gcacggctgg caagaaaaag tcgacaagct ggcgg                              35


<210> SEQ ID NO 122
<211> LENGTH: 3819
<212> TYPE: DNA
<213> ORGANISM: Artificial Sequence
<220> FEATURE:
<221> NAME/KEY: mat_peptide
<222> LOCATION: (1)...(3816)
<223> OTHER INFORMATION: Active His-BoNT/E
```

-continued

<400> SEQUENCE: 122
atgggcagca gccatcatca tcatcatcac agcagcggcc tggtgccgcg cggcagccat 60
atgcctaaaa tcaattcgtt caactataat gacccggtta acgatcgcac gatcctgtat 120
atcaagccag gtggatgtca agaattttat aaatcattca acatcatgaa aaatatttgg 180
attatcccgg aacgcaacgt gatcggcacg acgcctcaag attttcaccc gccgacctcc 240
ctgaaaaatg gcgacagttc ctactatgac ccgaattatt tacaatcgga tgaagaaaaa 300
gatcgtttcc tcaagatcgt cacgaaaatt ttcaaccgca tcaataacaa tctgtccggt 360
ggcatcttac ttgaggaatt atctaaagct aatccgtatc tggggaacga taataccccg 420
gataatcagt tccacattgg cgatgcgagc gctgtggaaa ttaaattcag caacggcagt 480
caagatattc ttctcccaaa cgtgattatc atgggggctg aacctgatct tttcgaaact 540
aatagttcca atatttcact gcgcaataat tatatgccgt cgaaccatgg ctttggctca 600
atcgcaattg tgacgttctc acctgaatat agttttcgtt ttaacgacaa cagcatgaat 660
gaatttatcc aagacccggc gctgactttg atgcatgaac tgatccatag cttgcacggc 720
ctgtatggcg ctaaaggcat cactaccaaa tacacgatta cgcaaaaaca aaatccctta 780
atcaccaaca tccgcggcac caacattgaa gaatttctga ccttcggcgg aacggatctg 840
aacatcatta catctgccca aagcaacgac atctatacca atctgttagc agattataag 900
aaaatcgcca gcaaattatc taaagttcag gtcagcaatc cgctgttaaa cccgtataaa 960
gatgtgttcg aagcgaaata cggcttggac aaagacgcta gtggcatcta ttccgtcaat 1020
attaataaat ttaacgatat tttcaaaaaa ttatattcct tcaccgaatt tgatttggcc 1080
accaaattcc aggtcaaatg tcgtcaaacc tatattggcc aatacaaata ttttaaactg 1140
agcaacctgc ttaatgattc catctacaat attagtgaag gttacaatat taataacctg 1200
aaagttaact ttcgtgggca aaatgcgaat ctgaaccccc gcatcattac acccatcacg 1260
ggccgtgggt tggtcaaaaa aattattcgc ttttgtaaga atatcgtgag cgtgaagggt 1320
attcgcaaaa gtatctgtat cgaaatcaat aatggcgaac tgtttttcgt cgcatctgaa 1380
aactcgtata acgatgacaa tatcaacaca ccgaaagaaa ttgatgacac tgtcacttct 1440
aacaacaatt acgaaaacga cctggaccag gtgatcctca atttcaatag cgaaagcgca 1500
cccggcctga gcgatgaaaa acttaatctc acgattcaga acgacgccta cattccaaaa 1560
tacgatagta atggtacatc tgatattgaa cagcatgatg tcaacgaatt aaatgttttc 1620
ttttacctcg atgcccagaa agtgccggaa ggtgagaaca acgtaaatct gacctcttcg 1680
attgatacgg cattattaga acagccgaaa atttatactt tcttttcgtc cgaatttatt 1740
aacaatgtta acaaaccggt tcaagcggcg ttattcgttt cctggattca gcaagttctt 1800
gtagatttta caaccgaggc taatcagaag agcacggtgg ataagatcgc cgacatcagc 1860
atcgtcgtgc cctacattgg tttggcatta aacattggta atgaggcgca aaaggggaac 1920
tttaaagacg ccctggaatt attaggagca ggtattctgc tggagttcga acctgagctg 1980
ctgattccga ctattttagt gttcaccatt aaatccttct taggctctag tgacaacaaa 2040
aataaagtga ttaaagcgat caataatgcc cttaaagaac gtgatgagaa atggaaagaa 2100
gtctactcct tcattgtctc aaattggatg acgaaaatca acacgcagtt taataaacgc 2160
aaagaacaga tgtatcaggc gctgcaaaac caggttaatg cgatcaagac aattattgaa 2220
tctaagtaca actcgtacac cctggaggag aaaaatgaac tgactaataa gtacgatatt 2280

-continued

```
aaacaaatcg aaaacgaatt gaatcagaaa gtctccatcg ctatgaacaa tatcgatcgc   2340

tttctgaccg aaagctctat ttcctatttg atgaaactta tcaatgaagt caaaatcaac   2400

aaacttcgcg aatatgatga gaacgtaaaa acgtacctgc tcaattatat tattcaacat   2460

gggtcgattc tgggcgagtc tcaacaagaa ttgaactcga tggtgacgga tactttgaat   2520

aactcgattc cgtttaaatt atcgtcatac accgatgata aaattcttat ctcgtacttc   2580

aacaaattct ttaagcggat caaaagcagc agcgtcctta atatgcgcta taaaaacgat   2640

aagtacgtag atacgtctgg atacgacagt aacattaata ttaatgggga cgtctataaa   2700

tatccgacaa ataaaaacca attcgggatt tataatgata aactttcgga ggtgaacatc   2760

agccagaacg attatattat ttacgataat aaatacaaaa acttcagcat ttctttttgg   2820

gtgcgtatcc caaattacga caacaaaatt gtgaacgtga ataacgaata cacgatcatt   2880

aattgcatgc gcgataacaa ttctggttgg aaagttagcc tgaatcacaa tgagattatc   2940

tggactcttc aggacaatgc tggtatcaac caaaaattag cgttcaacta cggtaatgcc   3000

aacggtattt ctgactacat caataagtgg atctttgtga ccatcaccaa tgaccgcctc   3060

ggcgatagca agctgtacat taacggtaac ctgatcgacc agaaatctat tctgaacctg   3120

ggtaacattc acgtaagtga caacatcctt tttaaaattg tcaattgctc gtatactcgt   3180

tatatcggca ttcgctattt caatattttc gacaaagaac tggatgagac ggaaatccag   3240

actctgtatt ctaacgaacc gaacaccaac atcctgaagg acttttgggg gaattatctt   3300

ctctacgata aagagtacta ccttcttaac gtgttgaagc cgaacaactt cattgatcgt   3360

cgtaaggata gcaccttgag cattaacaac attcgtagca ccattttact ggcaaaccgc   3420

ctgtacagcg gcattaaagt caaaattcag cgtgtcaata actccagtac gaatgacaat   3480

ctggtgcgga aaaatgacca agtctatatt aactttgtcg caagcaaaac tcacctcttt   3540

ccattatatg cggatacagc taccaccaat aaagaaaaaa ctattaaaat ctcctcttcc   3600

gggaaccgct ttaatcaggt ggtagttatg aactcggtcg gcaacaattg tactatgaat   3660

tttaaaaata ataacggcaa taacatcggc ctgctgggct tcaaagctga tacagttgtg   3720

gccagcacct ggtattacac ccacatgcgt gatcatacca atagtaatgg ctgcttttgg   3780

aattttattt ctgaagagca cggctggcaa gaaaaataa                          3819
```

```
<210> SEQ ID NO 123
<211> LENGTH: 1272
<212> TYPE: PRT
<213> ORGANISM: Artificial Sequence
<220> FEATURE:
<221> NAME/KEY: PEPTIDE
<222> LOCATION: (1)...(1272)
<223> OTHER INFORMATION: Active His-BoNT/E

<400> SEQUENCE: 123

Met Gly Ser Ser His His His His His His Ser Ser Gly Leu Val Pro
 1               5                  10                  15

Arg Gly Ser His Met Pro Lys Ile Asn Ser Phe Asn Tyr Asn Asp Pro
            20                  25                  30

Val Asn Asp Arg Thr Ile Leu Tyr Ile Lys Pro Gly Gly Cys Gln Glu
        35                  40                  45

Phe Tyr Lys Ser Phe Asn Ile Met Lys Asn Ile Trp Ile Ile Pro Glu
    50                  55                  60

Arg Asn Val Ile Gly Thr Thr Pro Gln Asp Phe His Pro Pro Thr Ser
65                  70                  75                  80
```

-continued

```
Leu Lys Asn Gly Asp Ser Ser Tyr Tyr Asp Pro Asn Tyr Leu Gln Ser
                85                  90                  95

Asp Glu Glu Lys Asp Arg Phe Leu Lys Ile Val Thr Lys Ile Phe Asn
            100                 105                 110

Arg Ile Asn Asn Asn Leu Ser Gly Gly Ile Leu Leu Glu Glu Leu Ser
        115                 120                 125

Lys Ala Asn Pro Tyr Leu Gly Asn Asp Asn Thr Pro Asp Asn Gln Phe
    130                 135                 140

His Ile Gly Asp Ala Ser Ala Val Glu Ile Lys Phe Ser Asn Gly Ser
145                 150                 155                 160

Gln Asp Ile Leu Leu Pro Asn Val Ile Ile Met Gly Ala Glu Pro Asp
                165                 170                 175

Leu Phe Glu Thr Asn Ser Ser Asn Ile Ser Leu Arg Asn Asn Tyr Met
            180                 185                 190

Pro Ser Asn His Gly Phe Gly Ser Ile Ala Ile Val Thr Phe Ser Pro
        195                 200                 205

Glu Tyr Ser Phe Arg Phe Asn Asp Asn Ser Met Asn Glu Phe Ile Gln
    210                 215                 220

Asp Pro Ala Leu Thr Leu Met His Glu Leu Ile His Ser Leu His Gly
225                 230                 235                 240

Leu Tyr Gly Ala Lys Gly Ile Thr Thr Lys Tyr Thr Ile Thr Gln Lys
                245                 250                 255

Gln Asn Pro Leu Ile Thr Asn Ile Arg Gly Thr Asn Ile Glu Glu Phe
            260                 265                 270

Leu Thr Phe Gly Gly Thr Asp Leu Asn Ile Ile Thr Ser Ala Gln Ser
        275                 280                 285

Asn Asp Ile Tyr Thr Asn Leu Leu Ala Asp Tyr Lys Lys Ile Ala Ser
    290                 295                 300

Lys Leu Ser Lys Val Gln Val Ser Asn Pro Leu Leu Asn Pro Tyr Lys
305                 310                 315                 320

Asp Val Phe Glu Ala Lys Tyr Gly Leu Asp Lys Asp Ala Ser Gly Ile
                325                 330                 335

Tyr Ser Val Asn Ile Asn Lys Phe Asn Asp Ile Phe Lys Lys Leu Tyr
            340                 345                 350

Ser Phe Thr Glu Phe Asp Leu Ala Thr Lys Phe Gln Val Lys Cys Arg
        355                 360                 365

Gln Thr Tyr Ile Gly Gln Tyr Lys Tyr Phe Lys Leu Ser Asn Leu Leu
    370                 375                 380

Asn Asp Ser Ile Tyr Asn Ile Ser Glu Gly Tyr Asn Ile Asn Asn Leu
385                 390                 395                 400

Lys Val Asn Phe Arg Gly Gln Asn Ala Asn Leu Asn Pro Arg Ile Ile
                405                 410                 415

Thr Pro Ile Thr Gly Arg Gly Leu Val Lys Lys Ile Ile Arg Phe Cys
            420                 425                 430

Lys Asn Ile Val Ser Val Lys Gly Ile Arg Lys Ser Ile Cys Ile Glu
        435                 440                 445

Ile Asn Asn Gly Glu Leu Phe Phe Val Ala Ser Glu Asn Ser Tyr Asn
    450                 455                 460

Asp Asp Asn Ile Asn Thr Pro Lys Glu Ile Asp Asp Thr Val Thr Ser
465                 470                 475                 480

Asn Asn Asn Tyr Glu Asn Asp Leu Asp Gln Val Ile Leu Asn Phe Asn
                485                 490                 495

Ser Glu Ser Ala Pro Gly Leu Ser Asp Glu Lys Leu Asn Leu Thr Ile
```

```
                500                 505                 510

Gln Asn Asp Ala Tyr Ile Pro Lys Tyr Asp Ser Asn Gly Thr Ser Asp
            515                 520                 525

Ile Glu Gln His Asp Val Asn Glu Leu Asn Val Phe Phe Tyr Leu Asp
    530                 535                 540

Ala Gln Lys Val Pro Glu Gly Glu Asn Asn Val Asn Leu Thr Ser Ser
545                 550                 555                 560

Ile Asp Thr Ala Leu Leu Glu Gln Pro Lys Ile Tyr Thr Phe Phe Ser
                565                 570                 575

Ser Glu Phe Ile Asn Asn Val Asn Lys Pro Val Gln Ala Ala Leu Phe
            580                 585                 590

Val Ser Trp Ile Gln Gln Val Leu Val Asp Phe Thr Thr Glu Ala Asn
        595                 600                 605

Gln Lys Ser Thr Val Asp Lys Ile Ala Asp Ile Ser Ile Val Val Pro
    610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
                645                 650                 655

Glu Pro Glu Leu Leu Ile Pro Thr Ile Leu Val Phe Thr Ile Lys Ser
            660                 665                 670

Phe Leu Gly Ser Ser Asp Asn Lys Asn Lys Val Ile Lys Ala Ile Asn
        675                 680                 685

Asn Ala Leu Lys Glu Arg Asp Glu Lys Trp Lys Glu Val Tyr Ser Phe
    690                 695                 700

Ile Val Ser Asn Trp Met Thr Lys Ile Asn Thr Gln Phe Asn Lys Arg
705                 710                 715                 720

Lys Glu Gln Met Tyr Gln Ala Leu Gln Asn Gln Val Asn Ala Ile Lys
                725                 730                 735

Thr Ile Ile Glu Ser Lys Tyr Asn Ser Tyr Thr Leu Glu Glu Lys Asn
            740                 745                 750

Glu Leu Thr Asn Lys Tyr Asp Ile Lys Gln Ile Glu Asn Glu Leu Asn
        755                 760                 765

Gln Lys Val Ser Ile Ala Met Asn Asn Ile Asp Arg Phe Leu Thr Glu
    770                 775                 780

Ser Ser Ile Ser Tyr Leu Met Lys Leu Ile Asn Glu Val Lys Ile Asn
785                 790                 795                 800

Lys Leu Arg Glu Tyr Asp Glu Asn Val Lys Thr Tyr Leu Leu Asn Tyr
                805                 810                 815

Ile Ile Gln His Gly Ser Ile Leu Gly Glu Ser Gln Gln Glu Leu Asn
            820                 825                 830

Ser Met Val Thr Asp Thr Leu Asn Asn Ser Ile Pro Phe Lys Leu Ser
        835                 840                 845

Ser Tyr Thr Asp Asp Lys Ile Leu Ile Ser Tyr Phe Asn Lys Phe Phe
    850                 855                 860

Lys Arg Ile Lys Ser Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                885                 890                 895

Asp Val Tyr Lys Tyr Pro Thr Asn Lys Asn Gln Phe Gly Ile Tyr Asn
            900                 905                 910

Asp Lys Leu Ser Glu Val Asn Ile Ser Gln Asn Asp Tyr Ile Ile Tyr
        915                 920                 925
```

-continued

Asp Asn Lys Tyr Lys Asn Phe Ser Ile Ser Phe Trp Val Arg Ile Pro
    930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
            980                 985                 990

Leu Ala Phe Asn Tyr Gly Asn Ala Asn Gly Ile Ser Asp Tyr Ile Asn
        995                 1000                1005

Lys Trp Ile Phe Val Thr Ile Thr Asn Asp Arg Leu Gly Asp Ser Lys
    1010                1015                1020

Leu Tyr Ile Asn Gly Asn Leu Ile Asp Gln Lys Ser Ile Leu Asn Leu
1025                1030                1035                1040

Gly Asn Ile His Val Ser Asp Asn Ile Leu Phe Lys Ile Val Asn Cys
                1045                1050                1055

Ser Tyr Thr Arg Tyr Ile Gly Ile Arg Tyr Phe Asn Ile Phe Asp Lys
            1060                1065                1070

Glu Leu Asp Glu Thr Glu Ile Gln Thr Leu Tyr Ser Asn Glu Pro Asn
        1075                1080                1085

Thr Asn Ile Leu Lys Asp Phe Trp Gly Asn Tyr Leu Leu Tyr Asp Lys
    1090                1095                1100

Glu Tyr Tyr Leu Leu Asn Val Leu Lys Pro Asn Asn Phe Ile Asp Arg
1105                1110                1115                1120

Arg Lys Asp Ser Thr Leu Ser Ile Asn Asn Ile Arg Ser Thr Ile Leu
                1125                1130                1135

Leu Ala Asn Arg Leu Tyr Ser Gly Ile Lys Val Lys Ile Gln Arg Val
            1140                1145                1150

Asn Asn Ser Ser Thr Asn Asp Asn Leu Val Arg Lys Asn Asp Gln Val
        1155                1160                1165

Tyr Ile Asn Phe Val Ala Ser Lys Thr His Leu Phe Pro Leu Tyr Ala
    1170                1175                1180

Asp Thr Ala Thr Thr Asn Lys Glu Lys Thr Ile Lys Ile Ser Ser Ser
1185                1190                1195                1200

Gly Asn Arg Phe Asn Gln Val Val Val Met Asn Ser Val Gly Asn Asn
                1205                1210                1215

Cys Thr Met Asn Phe Lys Asn Asn Asn Gly Asn Asn Ile Gly Leu Leu
            1220                1225                1230

Gly Phe Lys Ala Asp Thr Val Val Ala Ser Thr Trp Tyr Tyr Thr His
        1235                1240                1245

Met Arg Asp His Thr Asn Ser Asn Gly Cys Phe Trp Asn Phe Ile Ser
    1250                1255                1260

Glu Glu His Gly Trp Gln Glu Lys
1265                1270

<210> SEQ ID NO 124
<211> LENGTH: 3804
<212> TYPE: DNA
<213> ORGANISM: Artificial Sequence
<220> FEATURE:
<221> NAME/KEY: mat_peptide
<222> LOCATION: (1)...(3801)
<223> OTHER INFORMATION: Active BoNT/E-His

<400> SEQUENCE: 124

-continued atgcctaaaa tcaattcgtt caactataat gacccggtta acgatcgcac gatcctgtat 60
atcaagccag gtggatgtca agaattttat aaatcattca acatcatgaa aaatatttgg 120
attatcccgg aacgcaacgt gatcggcacg acgcctcaag attttcaccc gccgacctcc 180
ctgaaaaatg gcgacagttc ctactatgac ccgaattatt tacaatcgga tgaagaaaaa 240
gatcgtttcc tcaagatcgt cacgaaaatt ttcaaccgca tcaataacaa tctgtccggt 300
ggcatcttac ttgaggaatt atctaaagct aatccgtatc tggggaacga taatacccg 360
gataatcagt tccacattgg cgatgcgagc gctgtggaaa ttaaattcag caacggcagt 420
caagatattc ttctcccaaa cgtgattatc atgggggctg aacctgatct tttcgaaact 480
aatagttcca atatttcact gcgcaataat tatatgccgt cgaaccatgg ctttggctca 540
atcgcaattg tgacgttctc acctgaatat agttttcgtt ttaacgacaa cagcatgaat 600
gaatttatcc aagacccggc gctgactttg atgcatgaac tgatccatag cttgcacggc 660
ctgtatggcg ctaaaggcat cactaccaaa tacacgatta cgcaaaaaca aaatccctta 720
atcaccaaca tccgcggcac caacattgaa gaatttctga ccttcggcgg aacggatctg 780
aacatcatta catctgccca aagcaacgac atctatacca atctgttagc agattataag 840
aaaatcgcca gcaaattatc taaagttcag gtcagcaatc cgctgttaaa cccgtataaa 900
gatgtgttcg aagcgaaata cggcttggac aaagacgcta gtggcatcta ttccgtcaat 960
attaataaat ttaacgatat tttcaaaaaa ttatattcct tcaccgaatt tgatttggcc 1020
accaaattcc aggtcaaatg tcgtcaaacc tatattggcc aatacaaata ttttaaactg 1080
agcaacctgc ttaatgattc catctacaat attagtgaag gttacaatat taataacctg 1140
aaagttaact ttcgtgggca aaatgcgaat ctgaaccccc gcatcattac acccatcacg 1200
ggccgtgggt tggtcaaaaa aattattcgc ttttgtaaga atatcgtgag cgtgaagggt 1260
attcgcaaaa gtatctgtat cgaaatcaat aatggcgaac tgtttttcgt cgcatctgaa 1320
aactcgtata acgatgacaa tatcaacaca ccgaaagaaa ttgatgacac tgtcacttct 1380
aacaacaatt acgaaaacga cctggaccag gtgatcctca atttcaatag cgaaagcgca 1440
cccggcctga gcgatgaaaa acttaatctc acgattcaga acgacgccta cattccaaaa 1500
tacgatagta atggtacatc tgatattgaa cagcatgatg tcaacgaatt aaatgttttc 1560
ttttacctcg atgcccagaa agtgccggaa ggtgagaaca acgtaaatct gacctcttcg 1620
attgatacgg cattattaga acagccgaaa atttatactt tcttttcgtc cgaatttatt 1680
aacaatgtta acaaaccggt tcaagcggcg ttattcgttt cctggattca gcaagttctt 1740
gtagatttta caaccgaggc taatcagaag agcacggtgg ataagatcgc cgacatcagc 1800
atcgtcgtgc cctacattgg tttggcatta aacattggta atgaggcgca aaaggggaac 1860
tttaaagacg ccctggaatt attaggagca ggtattctgc tggagttcga acctgagctg 1920
ctgattccga ctattttagt gttcaccatt aaatccttct taggctctag tgacaacaaa 1980
aataaagtga ttaaagcgat caataatgcc cttaaagaac gtgatgagaa atggaaagaa 2040
gtctactcct tcattgtctc aaattggatg acgaaaatca acacgcagtt taataaacgc 2100
aaagaacaga tgtatcaggc gctgcaaaac caggttaatg cgatcaagac aattattgaa 2160
tctaagtaca actcgtacac cctggaggag aaaaatgaac tgactaataa gtacgatatt 2220
aaacaaatcg aaaacgaatt gaatcagaaa gtctccatcg ctatgaacaa tatcgatcgc 2280
tttctgaccg aaagctctat ttcctatttg atgaaactta tcaatgaagt caaaatcaac 2340
aaacttcgcg aatatgatga gaacgtaaaa acgtacctgc tcaattatat tattcaacat 2400

-continued

```
gggtcgattc tgggcgagtc tcaacaagaa ttgaactcga tggtgacgga tactttgaat   2460

aactcgattc cgtttaaatt atcgtcatac accgatgata aaattcttat ctcgtacttc   2520

aacaaattct ttaagcggat caaaagcagc agcgtcctta atatgcgcta taaaaacgat   2580

aagtacgtag atacgtctgg atacgacagt aacattaata ttaatgggga cgtctataaa   2640

tatccgacaa ataaaaacca attcgggatt tataatgata aactttcgga ggtgaacatc   2700

agccagaacg attatattat ttacgataat aaatacaaaa acttcagcat ttctttttgg   2760

gtgcgtatcc caaattacga caacaaaatt gtgaacgtga ataacgaata cacgatcatt   2820

aattgcatgc gcgataacaa ttctggttgg aaagttagcc tgaatcacaa tgagattatc   2880

tggactcttc aggacaatgc tggtatcaac caaaaaattag cgttcaacta cggtaatgcc   2940

aacggtattt ctgactacat caataagtgg atctttgtga ccatcaccaa tgaccgcctc   3000

ggcgatagca agctgtacat taacggtaac ctgatcgacc agaaatctat tctgaacctg   3060

ggtaacattc acgtaagtga caacatcctt tttaaaattg tcaattgctc gtatactcgt   3120

tatatcggca ttcgctattt caatattttc gacaaagaac tggatgagac ggaaatccag   3180

actctgtatt ctaacgaacc gaacaccaac atcctgaagg acttttgggg gaattatctt   3240

ctctacgata aagagtacta ccttcttaac gtgttgaagc cgaacaactt cattgatcgt   3300

cgtaaggata gcaccttgag cattaacaac attcgtagca ccattttact ggcaaaccgc   3360

ctgtacagcg gcattaaagt caaaattcag cgtgtcaata actccagtac gaatgacaat   3420

ctggtgcgga aaaatgacca agtctatatt aactttgtcg caagcaaaac tcacctcttt   3480

ccattatatg cggatacagc taccaccaat aaagaaaaaa ctattaaaat ctcctcttcc   3540

gggaaccgct ttaatcaggt ggtagttatg aactcggtcg gcaacaattg tactatgaat   3600

tttaaaaata ataacggcaa taacatcggc ctgctgggct tcaaagctga tacagttgtg   3660

gccagcacct ggtattacac ccacatgcgt gatcatacca atagtaatgg ctgcttttgg   3720

aattttattt ctgaagagca cggctggcaa gaaaaagtcg acaagcttgc ggccgcactc   3780

gagcaccacc accaccacca ctga                                          3804
```

```
<210> SEQ ID NO 125
<211> LENGTH: 1267
<212> TYPE: PRT
<213> ORGANISM: Artificial Sequence
<220> FEATURE:
<221> NAME/KEY: PEPTIDE
<222> LOCATION: (1)...(1267)
<223> OTHER INFORMATION: Active BoNT/E-His

<400> SEQUENCE: 125

Met Pro Lys Ile Asn Ser Phe Asn Tyr Asn Asp Pro Val Asn Asp Arg
 1               5                  10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95
```

-continued

```
Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
```

-continued

```
        515                 520                 525

Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Leu Ile Asn Glu Val Lys Ile Asn Lys Leu Arg Glu
    770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
    930                 935                 940
```

-continued

Asp Asn Asn Ser Gly Trp Lys Val Ser Leu Asn His Asn Glu Ile Ile
945 950 955 960

Trp Thr Leu Gln Asp Asn Ala Gly Ile Asn Gln Lys Leu Ala Phe Asn
965 970 975

Tyr Gly Asn Ala Asn Gly Ile Ser Asp Tyr Ile Asn Lys Trp Ile Phe
980 985 990

Val Thr Ile Thr Asn Asp Arg Leu Gly Asp Ser Lys Leu Tyr Ile Asn
995 1000 1005

Gly Asn Leu Ile Asp Gln Lys Ser Ile Leu Asn Leu Gly Asn Ile His
1010 1015 1020

Val Ser Asp Asn Ile Leu Phe Lys Ile Val Asn Cys Ser Tyr Thr Arg
1025 1030 1035 1040

Tyr Ile Gly Ile Arg Tyr Phe Asn Ile Phe Asp Lys Glu Leu Asp Glu
1045 1050 1055

Thr Glu Ile Gln Thr Leu Tyr Ser Asn Glu Pro Asn Thr Asn Ile Leu
1060 1065 1070

Lys Asp Phe Trp Gly Asn Tyr Leu Leu Tyr Asp Lys Glu Tyr Tyr Leu
1075 1080 1085

Leu Asn Val Leu Lys Pro Asn Asn Phe Ile Asp Arg Arg Lys Asp Ser
1090 1095 1100

Thr Leu Ser Ile Asn Asn Ile Arg Ser Thr Ile Leu Leu Ala Asn Arg
1105 1110 1115 1120

Leu Tyr Ser Gly Ile Lys Val Lys Ile Gln Arg Val Asn Asn Ser Ser
1125 1130 1135

Thr Asn Asp Asn Leu Val Arg Lys Asn Asp Gln Val Tyr Ile Asn Phe
1140 1145 1150

Val Ala Ser Lys Thr His Leu Phe Pro Leu Tyr Ala Asp Thr Ala Thr
1155 1160 1165

Thr Asn Lys Glu Lys Thr Ile Lys Ile Ser Ser Ser Gly Asn Arg Phe
1170 1175 1180

Asn Gln Val Val Val Met Asn Ser Val Gly Asn Asn Cys Thr Met Asn
1185 1190 1195 1200

Phe Lys Asn Asn Asn Gly Asn Asn Ile Gly Leu Leu Gly Phe Lys Ala
1205 1210 1215

Asp Thr Val Val Ala Ser Thr Trp Tyr Tyr Thr His Met Arg Asp His
1220 1225 1230

Thr Asn Ser Asn Gly Cys Phe Trp Asn Phe Ile Ser Glu Glu His Gly
1235 1240 1245

Trp Gln Glu Lys Val Asp Lys Leu Ala Ala Ala Leu Glu His His His
1250 1255 1260

His His His
1265

<210> SEQ ID NO 126
<211> LENGTH: 9
<212> TYPE: DNA
<213> ORGANISM: Artificial Sequence
<220> FEATURE:
<223> OTHER INFORMATION: Open reading frame

<400> SEQUENCE: 126 aaatactta 9

<210> SEQ ID NO 127
<211> LENGTH: 9

-continued

<212> TYPE: DNA
<213> ORGANISM: Artificial Sequence
<220> FEATURE:
<223> OTHER INFORMATION: Synonymous codon open reading frame

<400> SEQUENCE: 127 aagtatctg 9

<210> SEQ ID NO 128
<211> LENGTH: 9
<212> TYPE: DNA
<213> ORGANISM: Artificial Sequence
<220> FEATURE:
<223> OTHER INFORMATION: Open reading frame

<400> SEQUENCE: 128 aaatattta 9

<210> SEQ ID NO 129
<211> LENGTH: 9
<212> TYPE: DNA
<213> ORGANISM: Artificial Sequence
<220> FEATURE:
<223> OTHER INFORMATION: G+C content open reading frame

<400> SEQUENCE: 129 aagtacctg 9

<210> SEQ ID NO 130
<211> LENGTH: 9
<212> TYPE: DNA
<213> ORGANISM: Artificial Sequence
<220> FEATURE:
<223> OTHER INFORMATION: Open reading frame

<400> SEQUENCE: 130 aaaaaaaaa 9

<210> SEQ ID NO 131
<211> LENGTH: 9
<212> TYPE: DNA
<213> ORGANISM: Artificial Sequence
<220> FEATURE:
<223> OTHER INFORMATION: polyA region open reading frame

<400> SEQUENCE: 131 aagaagaag 9

<210> SEQ ID NO 132
<211> LENGTH: 12
<212> TYPE: DNA
<213> ORGANISM: Artificial Sequence
<220> FEATURE:
<223> OTHER INFORMATION: Open reading frame

<400> SEQUENCE: 132
acaaccaaaa tg 12

<210> SEQ ID NO 133
<211> LENGTH: 4
<212> TYPE: PRT
<213> ORGANISM: Artificial Sequence
<220> FEATURE:
<223> OTHER INFORMATION: Open reading frame

<400> SEQUENCE: 133

-continued

Thr Thr Lys Met
 1

<210> SEQ ID NO 134
<211> LENGTH: 12
<212> TYPE: DNA
<213> ORGANISM: Artificial Sequence
<220> FEATURE:
<223> OTHER INFORMATION: translational start site open reading frame

<400> SEQUENCE: 134
acgactaaga tg 12

<210> SEQ ID NO 135
<211> LENGTH: 9
<212> TYPE: DNA
<213> ORGANISM: Artificial Sequence
<220> FEATURE:
<223> OTHER INFORMATION: Open reading frame

<400> SEQUENCE: 135 ggtaattgc 9

<210> SEQ ID NO 136
<211> LENGTH: 9
<212> TYPE: DNA
<213> ORGANISM: Artificial Sequence
<220> FEATURE:
<223> OTHER INFORMATION: RNase cleavage site open reading frame

<400> SEQUENCE: 136 ggcaactgc 9

<210> SEQ ID NO 137
<211> LENGTH: 9
<212> TYPE: DNA
<213> ORGANISM: Artificial Sequence
<220> FEATURE:
<223> OTHER INFORMATION: Open reading frame

<400> SEQUENCE: 137 ggcaactgc 9

<210> SEQ ID NO 138
<211> LENGTH: 9
<212> TYPE: DNA
<213> ORGANISM: Artificial Sequence
<220> FEATURE:
<223> OTHER INFORMATION: Out of frame stop codon open reading frame

<400> SEQUENCE: 138 ggtaactgc 9

<210> SEQ ID NO 139
<211> LENGTH: 12
<212> TYPE: DNA
<213> ORGANISM: Artificial Sequence
<220> FEATURE:
<223> OTHER INFORMATION: Open reading frame

<400> SEQUENCE: 139
gcttggccaa gc 12

<210> SEQ ID NO 140
<211> LENGTH: 12
<212> TYPE: DNA

-continued

```
<213> ORGANISM: Artificial Sequence
<220> FEATURE:
<223> OTHER INFORMATION: hairpin-loop structure open reading frame

<400> SEQUENCE: 140

gcatggccta gc                                                        12
```